(12) United States Patent
Bernasconi et al.

(10) Patent No.: US 9,029,080 B2
(45) Date of Patent: May 12, 2015

(54) SCREENING ASSAY FOR INSECTICIDES

(75) Inventors: Paul Bernasconi, Chapel Hill, NC (US);
John Dorsch, Raleigh, NC (US); Lynn Stam, Raleigh, NC (US); Scott Zitko, Hillsborough, NC (US); Nancy B. Rankl, Cary, NC (US); Mike Griswold, Cary, NC (US); Franz-Josef Braun, Durham, NC (US); Gang Lu, Durham, NC (US); Robert D. Kirkton, Morrisville, NC (US); Barbara Wedel, Durham, NC (US); Joachim Dickhaut, Heidelberg (DE); Angela Hofhine, Durham, NC (US); Jennifer Zink, Apex, NC (US); Fae Malone, Cary, NC (US); Daniel Houtz, Durham, NC (US); Steffen Groβ, Ludwigshafen (DE); Ramani Kandasamy, Chapel Hill, NC (US); Damian O' Brecht London, Wake Forest, NC (US); Thomas M. Gurganus, Durham, NC (US)

(73) Assignee: BASF SE, Ludwigshafen (DE)

( * ) Notice: Subject to any disclaimer, the term of this patent is extended or adjusted under 35 U.S.C. 154(b) by 208 days.

(21) Appl. No.: 13/127,505

(22) PCT Filed: Nov. 5, 2009

(86) PCT No.: PCT/EP2009/064700
§ 371 (c)(1),
(2), (4) Date: Jun. 21, 2011

(87) PCT Pub. No.: WO2010/052276
PCT Pub. Date: May 14, 2010

(65) Prior Publication Data
US 2011/0263585 A1    Oct. 27, 2011

Related U.S. Application Data

(60) Provisional application No. 61/111,870, filed on Nov. 6, 2008, provisional application No. 61/139,667, filed on Dec. 22, 2008, provisional application No. 61/139,676, filed on Dec. 22, 2008, provisional application No. 61/139,686, filed on Dec. 22, 2008.

(51) Int. Cl.
| | | |
|---|---|---|
| G01N 33/68 | (2006.01) | |
| A01N 61/00 | (2006.01) | |
| C12Q 1/00 | (2006.01) | |
| C12Q 1/68 | (2006.01) | |
| C12N 5/07 | (2010.01) | |
| A01N 43/38 | (2006.01) | |
| A01N 43/40 | (2006.01) | |
| A01N 43/42 | (2006.01) | |
| A01N 43/54 | (2006.01) | |
| A01N 43/80 | (2006.01) | |
| A01N 43/88 | (2006.01) | |
| C07K 14/435 | (2006.01) | |

(52) U.S. Cl.
CPC ............ *G01N 33/6872* (2013.01); *A01N 43/38* (2013.01); *A01N 43/40* (2013.01); *A01N 43/42* (2013.01); *A01N 43/54* (2013.01); *A01N 43/80* (2013.01); *A01N 43/88* (2013.01); *A01N 61/00* (2013.01); *C07K 14/43577* (2013.01); *G01N 2500/10* (2013.01); *Y10S 530/858* (2013.01)

(58) Field of Classification Search
CPC .......... G01N 33/5008; G01N 2500/04; G01N 2500/10; G01N 33/6872; C07K 14/43577; A01N 61/00
See application file for complete search history.

(56) References Cited

FOREIGN PATENT DOCUMENTS

| WO | WO 98/16185 | 4/1998 |
|---|---|---|
| WO | WO 2007/056043 | 5/2007 |

OTHER PUBLICATIONS

Kunjilwar, K. et al., *KChIP3 rescues the functional expression of Shal channel tetramerization mutants*, Journal of Biological Chemistry, vol. 279, No. 52, Dec. 24, 2004, pp. 54542-54551, XP002571448.
Tsunoda, S. et al., "Genetic analysis of Drosophila neurons: Shal, Shaw, and Shab encode most embryonic potassium currents", The Journal of Neuroscience: The Official Journal of the Society for Neuroscience, vol. 15, No. 3, Mar. 1995, pp. 1741-1754, XP002571447.
Wei, A. et al., "K+ Current diversity is produced by extended gene family conserved in Drosophila and mouse", Science, vol. 248, No. 4955, May 4, 1990, pp. 599-603, XP002571446.
International Preliminary Report on Patentability, PCT/EP2009/064700.

*Primary Examiner* — Ruixiang Li
(74) *Attorney, Agent, or Firm* — Brinks Gilson & Lione

(57) ABSTRACT

The present invention relates to polypeptides, preferably from *Drosophila melanogaster* (DmShal) as target for insecticides.

5 Claims, 66 Drawing Sheets

Clone#6 P5
Patched 5 cells, 5 of 5 expressed Shal/KChIP.

Clone#20 P7
Patched 5 cells, 5 of 5 expressed Shal/KChIP.

Example of Shaker+Hkvβ A subunit clones

Example of Shaker+Hkvβ C subunit clones

Example of a mock clone: 30, 60, 60, 120, 150, 180 mM KCl stimulation

Example of Shaker+Hkvβ A subunit clones: 1.5, 3.7, 7.5, 15, 30, 60, 90, 120 mM KCl stimulation Example of Shaker+Hkvβ C subunit clones: 1.5, 3.7, 7.5, 15, 30, 60, 90, 120 mM KCl stimulation

SCREENING ASSAY FOR INSECTICIDES

This application is a National Stage application of International Application No. PCT/EP2009/064700, filed Nov. 5, 2009, which claims the benefit of U.S. Provisional Application No. 61/111,870, filed Nov. 6, 2008; U.S. Provisional Application No. 61/139,667, filed Dec. 22, 2008; U.S. Provisional Application No. 61/139,676, filed Dec. 22, 2008; and U.S. Provisional Application No. 61/139,686, filed Dec. 22, 2008; the entire contents of which are hereby incorporated herein by reference.

The present invention relates to a potassium channel with the activity of a voltage-gated potassium channel ShaI (Shaker cognate I or Shaker-like), preferably from *Drosophila melanogaster* (DmShaI) as target for insecticides. In one embodiment the voltage-gated potassium channel ShaI is co-expressed with its accessory protein KChIP (potassium channel-interacting protein), preferably its putative accessory protein CG5890, the *Drosophila* KChIP (potassium channel-interacting protein) ortholog. The present invention provides polypeptides with the activity of an insect voltage-gated potassium channel ShaI (Shaker cognate I or Shaker-like), preferably from *Drosophila melanogaster* (DmShaI) and its accessory protein KChIP (potassium channel-interacting protein), preferably its putative accessory protein CG5890, the *Drosophila* KChIP (potassium channel-interacting protein) ortholog as targets for insecticides, provides novel nucleic acid sequences encoding a polypeptide with the activity of an insect voltage-gated potassium channel ShaI (Shaker cognate I or Shaker-like) and its accessory protein KChIP (potassium channel-interacting protein) and functional equivalents of the aforementioned nucleic acid sequences.

The present invention relates further to the use of a polypeptide with the activity of an insect voltage-gated potassium channel ShaI and/or its accessory protein KChIP (potassium channel-interacting protein) in a method and in an assay for identifying insecticidally active compound that reduces the activity of an insect voltage-gated potassium channel ShaI (Shaker cognate I or Shaker-like) and/or its accessory protein KChIP (potassium channel-interacting protein). Furthermore, the invention relates to insecticidal compounds identified by the above mentioned method and the use of these compounds as insecticides.

In another embodiment, the present invention relates to a potassium channel with the activity of a Shaker potassium channel, preferably from *Drosophila melanogaster* as target for insecticides. In one embodiment the Shaker channel is co-expressed with a Hyperkinetic beta subunit, preferably H-kv beta subunit A or C subtype, preferably from *Drosophila melanogaster*.

The present invention further provides polypeptides with the activity of an insect Shaker channel, preferably from *Drosophila melanogaster* and a Hyperkinetic beta subunit, preferably H-kv beta subunit A or C subtype in an screening assay for insecticides, provides novel nucleic acid sequences encoding a polypeptide with the activity of an insect Shaker channel and a Hyperkinetic beta subunit, preferably H-kv beta subunit A or C subtype and functional equivalents of the aforementioned nucleic acid sequences.

The present invention furthermore relates further to the use of a polypeptide with the activity of an insect Shaker channel and/or a Hyperkinetic beta subunit, preferably H-kv beta subunit A or C subtype respectively in a method and in an assay for identifying insecticidally active compound that reduces the activity of an insect Shaker channel and a Hyperkinetic beta subunit, preferably H-kv beta subunit A or C subtype respectively. Furthermore, the invention relates to insecticidal compounds identified by the above mentioned method and the use of these compounds as insecticides.

In another embodiment, the present invention relates to a G-protein coupled receptor (GPCR) with the activity of an octopamine receptor, preferably from *Drosophila melanogaster* as target for insecticides.

The present invention further provides polypeptides with the activity of an an octopamine receptor, preferably from *Drosophila melanogaster* in an screening assay for insecticides, provides novel nucleic acid sequences encoding a polypeptide with the activity of an octopamine receptor, preferably from *Drosophila melanogaster* and functional equivalents of the aforementioned nucleic acid sequences.

The present invention relates further to the use of a polypeptide with the activity of an octopamine receptor selected from the group consisting of oa2, preferably from *Drosophila melanogaster*, Oamb, Oct-beta-2R and Oct-beta-3R in a method and in an assay for identifying insecticidally active compound that reduces the activity of an octopamine receptor selected from the group consisting of oa2, preferably from *Drosophila melanogaster*, Oamb, Oct-beta-2R and Oct-beta-3R. Furthermore, the invention relates to insecticidal compounds identified by the above mentioned method and the use of these compounds as insecticides.

In another embodiment, the present invention relates to a SK-channel as target for insecticides.

The present invention furthermore provides polypeptides with the activity of an insect small-conductance Ca2+-activated potassium channel as targets for insecticides, provides novel nucleic acid sequences encoding a polypeptide with the activity of an insect small-conductance Ca2+-activated potassium channel and functional equivalents of the aforementioned nucleic acid sequences.

The present invention relates further to the use of a polypeptide with the activity of an insect small-conductance Ca2+-activated potassium channel in a method and in an assay for identifying insecticidally active compound that reduces the activity of an insect small-conductance Ca2+-activated potassium channel. Furthermore, the invention relates to insecticidal compounds identified by the above mentioned method and the use of these compounds as insecticides.

Insects cause many human and animal diseases. Insects are also responsible for substantial agricultural and property damage resulting in economic loss. In spite of all the pesticide poison's used but also misused, insects still destroy over 30% of the world's food crops each year.

Many approaches have been developed in order to limit the damages caused by insects.

One approach is the use of chemicals for insect control. The problem of many insecticides, for example like DDT, is the fact that they require a application in high concentrations and they have a unspecific, broad spectrum of activity. Chemical pesticides generally affect beneficial as well as nonbeneficial species. Many of them are persistent in the environment and accumulate therefore in the food chain.

Another approach are transgenic crops that express insecticidal toxins, such as protein toxins from the bacterium *Bacillus thuringiensis*.

Insect pests tend to acquire resistance to all kinds of insecticides because they have an exceptional ability to adapt to their environment, due to a mechanisms which leads to the rapid development of resistance in an insect population, such as short life cycles, a high reproductive rate and the ability to travel long distances. At the moment pests exhibiting insecticide resistance is increasing.

Therefore, there is still a need to find effective and economic insecticides with a very specific effect against insect pests. The more effective an insecticide is the less environmental hazard it creates.

This can be achieved by identification and isolation of a gene that codes for a protein which will control insect development and/or surviving.

Figure 1:
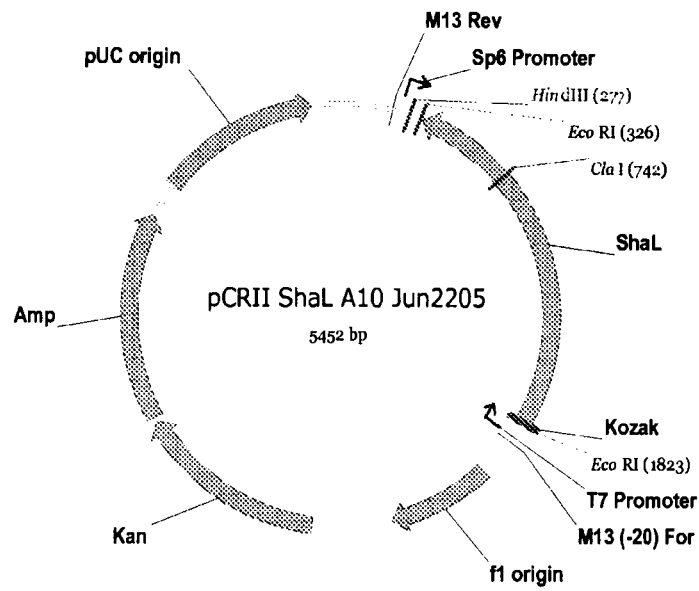
FIG. 1: Vector NTI-generated map of the primary Sha1 clone showing the major features of the construct.

The present invention provides a insect voltage-gated potassium channel ShaI (Shaker cognate I or Shaker-like) and/or its accessory protein KChIP (potassium channel-interacting protein) as new target for insecticides. The present invention puts further a method and an assay at disposal for identifying insecticidally active compounds that reduce the activity of a insect voltage-gated potassium channel ShaI (Shaker cognate I or Shaker-like) and/or its accessory protein KChIP (potassium channel-interacting protein).

The outward voltage-dependent K+ currents found in many *Drosophila* embryonic and larval neurons arise from a mix of currents generated from the Shaker family members Shaw, Shab and ShaI (Tsunoda, S. & L. Salkoll (1995) J Neuroscience. March; 15(3):1741-1754). ShaI generates the transient component (the "A-type" current) of these macroscopic K+ currents and modulates these currents by, for example, causing a delayed current spike in certain neurons (Yu, D., Feng, C. & A. Guo (1999) J Neurobiology. August; 40(2):158-70). Alternative splicing, post-translational modifications and other ShaI-associated processes are likely responsible in part for the large repertoire of modulations seen in these neurons (Choi, J. C., Park, D. & L. C. Griffith (2004) J Neurophysiology. 91:2353-2365).

KChIP, a Kv4.x (ShaI) accessory protein, has been shown to dramatically increase the trafficking of ShaI to the cell membrane, probably by promoting tetrameric channel assembly, and to cause distinct changes in ShaI channel gating properties (Kunjilwar, K., Strang, C., DeRubeis, D. & P. J. Pfaffinger (2004) J Biological Chemistry. December; 279 (52): 54542-54551).

Despite ShaI's role in neuronal transmission, the validation case for this target remains to be established. Our in situ data indicate low-levels of expression in the embryonic ventral nerve cord and visceral musculature. In situs at the Berkeley *Drosophila* Genome Project show staining in embryonic/larval visceral muscle, longitudinal visceral muscle fibers, ventral midline, and embryonic central nervous system including the ventral nerve cord. DmShaI mRNA is a rare transcript with an expression peak at mid-embryonic stages (in-house Lynx data). There are two intronic transposon insertion lines at the Harvard Medical School *Drosophila* Stock Collection, but no viability data is associated with these, and no other ShaI mutants are available. There is no microarray or northern data in the public domain.

No insecticide on the market has been identified as having modulation of ShaI potassium channels as its primary mode of action, meaning that a compound does not merely contribute by a "side effect" to a insecticidal activity, but its activity is the key lethal effect.

In another embodiment, the present invention provides a insect Shaker channel and/or a Hyperkinetic beta subunit, preferably H-kv beta subunit A or C subtype respectively as new target for insecticides. The present invention puts further a method and an assay at disposal for identifying insecticidally active compounds that reduce the activity of a insect Shaker channel and/or a Hyperkinetic beta subunit, preferably H-kv beta subunit A or C subtype respectively.

The *Drosophila* Hyperkinetic (Hk) mutations alter a gene encoding a homolog of the mammalian K+ channel P subunit. Wang et al. (Biophysical Journal Volume 71, December 1996, 3167-3176) have shown that the Hk P subunit modulates a wide range of the Shaker (Sh) K+ current properties. Coexpression of Hk with Sh in *Xenopus oocytes* is also known from CHOUINARD et al. (Proc. Natl. Acad. Sci. USA, Vol. 92, pp. 6763-6767, July 1995 Neurobiology) which demonstrated that this coexpression increases current amplitudes and changes the voltage dependence and kinetics of activation and inactivation.

Surprisingly it was found, that the coexpression Shaker channel and a Hyperkinetic beta subunit, preferably H-kv beta subunit A or C subtype respectively leads to a new screening assay for insecticides.

No insecticide on the market has been identified as having modulation of Shaker channel and/or a Hyperkinetic beta subunit, preferably H-kv beta subunit A or C subtype respectively as its primary mode of action, meaning that a compound does not merely contribute by a "side effect" to a insecticidal activity, but its activity is the key lethal effect.

In another embodiment, the present invention provides a insect octopamine receptor selected from the group consisting of oa2, preferably from *Drosophila melanogaster*, Oamb, Oct-beta-2R and Oct-beta-3R as new target for insecticides. The present invention puts further a method and an assay at disposal for identifying insecticidally active compounds that reduce the activity of a insect octopamine receptor selected from the group consisting of oa2, preferably from *Drosophila melanogaster*, Oamb, Oct-beta-2R and Oct-beta-3R.

Octopamine, a biogenic monoamine structurally related to noradrenaline, is a major neurotransmitter, neuromodulator and neurohormone, mediating diverse physiological processes in peripheral and central nervous system of invertebrates. Together with tyramine, octopamine is the only neuroactive non-peptide transmitter whose physiological role is restricted to invertebrates.

The action of octopamine is mediated through various receptor classes like oa2, Oamb, Oct-beta-2R or Oct-beta-3R.

The fact that octopamine receptors can only/mainly be found in invertebrates makes them a significant target for insecticides. Compounds that specifically modulate octopamine receptors should therefore have low vertebrate toxicity. In addition to selectivity, octopamine receptors are a good target for insecticides due to its neuronal expression. Together with tyramine, octopamine is the only neuroactive non-peptide transmitter whose physiological role is restricted to invertebrates.

Although octopamine is a principal neuromediator in insects, its receptors have proven to be difficult to clone. To date, only a few octopamine receptors have been cloned. The present invention puts a method at disposal for cloning octopamine receptors and for introducing them in membranes, preferably of cells. Preferably additionally linked proteins are introduced in the membrane.

Octopamine receptors can modulate their action through cyclic AMP production or intracellular calcium release, dependent on the receptor isoform. Octopamine receptors, preferably oa2 endogenously signals though cAMP. A detection of the activity of the receptor is difficult.

Therefore the present invention puts a method at disposal to force coupling to calcium, which leads to calcium release upon its activation. The calcium release is measurable by fluorescent calcium sensing dyes.

Surprisingly it was found, that the expression of octopamine receptor selected from the group consisting of oa2, preferably from *Drosophila melanogaster*, Oamb, Oct-beta-2R and Oct-beta-3R and expression of a promiscuous G-alpha protein leads to a new screening assay for insecticides.

GPCRs mediate signal transduction across a cell membrane upon the binding of a ligand to an extracellular portion of a GPCR. The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydolyzes GTP, and a dimeric βγ subunit. Certain G-proteins are considered "promiscuous" G-proteins because their G subunits allow them to couple with GPCRs that normally couple with G-proteins of other families.

No insecticide on the market has been identified as having modulation of octopamine receptor selected from the group consisting of oa2, preferably from *Drosophila melanogaster*, Oamb, Oct-beta-2R and Oct-beta-3R as its primary mode of action, meaning that a compound does not merely contribute by a "side effect" to a insecticidal activity, but its activity is the key lethal effect.

In another embodiment, the present invention provides a small-conductance calcium-activated potassium channel as new target for insecticides. The present invention puts further a method and an assay at disposal for identifying insecticidally active compounds that reduce the activity of an insect small-conductance Ca2+-activated potassium channel.

Calcium-activated potassium channels are a functionally diverse group of ion channels activated by an increase in intracellular calcium. In mammals they are found in a majority of nerve cells where they contribute to the shaping of action potentials and regulate neuronal excitability. More specifically, their currents underlie the after hyper-polarization that follows an action potential; they also appear to be involved in neuronal firing frequency precision (for review see: Stocker et al., Nature Reviews Neuroscience 5, 2004).

This class of potassium channel exists in three general types based on single channel conductances. The large-, intermediate- and small-conductance channels are termed BK, IK and SK, respectively. In *Drosophila*, the genes are termed slo, slack and SK, respectively.

Each type of potassium ion channel shows a distinct pharmacological profile. Potassium ion channels have been associated with a number of physiological processes, including regulation of heartbeat, dilation of arteries, release of insulin, excitability of nerve cells, and regulation of renal electrolyte transport. Therefore potassium ion channels are already known as a therapeutic target in the treatment of a number of diseases as disclosed in WO 2005 099711 and US 2005 0239800.

Specifically, SK channels have been shown to have distinct pharmacological profiles. As disclosed in WO 2005 100349, different compounds were found with clinically relevant psycho activity using patch clamp techniques. The evaluated compounds are structurally related to tricyclic antidepressants and include amitriptyline, carbamazepine, chlorpromazine, cyproheptadine, imipramine, tacrine and trifluperazine. Each of the compounds tested was found to block SK2 channel currents with micro-molar affinity. A number of neuromuscular inhibiting agents exist that affect SK channels, e. g. apamin, atracurium, pancuronium and tubocurarine (Shah et al., Br J Pharmacol 129: 627-30 (2000)).

Assays which use SK channels as target for pharmacological active compounds for treatment of diseases are also described:

Recombinant rat brain SK2 channels were expressed in HEK293 mammalian cells to study by patch clamp technique the effect of centrally acting muscle relaxant compounds, like chlorzoxazone (Cao et al., J. Pharmacol. Exp. Ther. 296: 683-689, 2001). The effect of metal ions on the activation of recombinant human SK4 channels has also been studied by patch clamp technique with transformed HEK293 cells (Cao et al., FEBS, 446: 137-141, 1999).

A method of identifying a compound which increases or decreases the potassium ion flux through a calcium-activated potassium SK channel is described in WO 98/11139. Until now, classical molecular targets in insects were acetylcholinesterase, voltage-dependent sodium channels, ionotropic receptors such as nicotinic acetylcholine and GABA receptors. Gautier et al. (J. Pharm. Exp. Therapeutics, jpet.107.128694, 2007) have brought evidence for the participation of calcium-activated potassium channel as an indirect target in insecticide neurotoxicity. They demonstrated by knockdown of DUM (dorsal unpaired median) neuron BK channels by antisense oligonucleotides treatment in DUM neurons from cockroaches (*Periplaneta americana*) that DMDS (di-methyl disulfide) inhibits calcium-activated potassium currents.

Further specific toxins, which inhibit the activity Ca2+-activated potassium channels, have been identified from several organisms, the most well-known being apamin from bee venom as disclosed for example in U.S. Pat. No. 5,607,843.

Nevertheless, at the moment no insecticide on the market has been identified that has modulation of Ca2+-activated potassium channels, preferably of an SK channel, as its primary mode of action, meaning that a compound does not merely contribute by a "side effect" to a insecticidal activity, but its activity is the key lethal effect.

In general, there is a great demand for the detection of polypeptides which might constitute novel targets for insecticides. The reasons are the above mentioned resistance problems and the ongoing endeavor to identify novel insecticidal active ingredients which are distinguished by a wide as possible spectrum of action, ecological and toxicological acceptability and/or low application rates.

The present invention now provides an insect voltage-gated potassium channel ShaI (Shaker cognate I or Shaker-like) and/or its accessory protein KChIP (potassium channel-interacting protein) as targets for insecticides and a method and an assay for identifying insecticidally active compound that reduces the activity of an insect voltage-gated potassium channel ShaI (Shaker cognate I or Shaker-like) and/or its accessory protein KChIP (potassium channel-interacting protein).

The present invention also provides an Shaker channel and/or a Hyperkinetic beta subunit, preferably H-kv beta subunit A or C subtype respectively as targets for insecticides and a method and an assay for identifying insecticidally active compound that reduces the activity of Shaker channel and/or a Hyperkinetic beta subunit, preferably H-kv beta subunit A or C subtype respectively.

The present invention further provides an octopamine receptor selected from the group consisting of oa2, preferably from *Drosophila melanogaster*, Oamb, Oct-beta-2R and Oct-beta-3R as targets for insecticides and a method and an assay for identifying insecticidally active compound that reduces the activity of octopamine receptor selected from the group consisting of oa2, preferably from *Drosophila melanogaster*, Oamb, Oct-beta-2R and Oct-beta-3R.

The present invention furthermore provides an insect small-conductance Ca2+-activated potassium channel as targets for insecticides and a method and an assay for identifying insecticidally active compound that reduces the activity of an insect small-conductance Ca2+-activated potassium channel.

In practice, the detection of novel targets entails great difficulties since the inhibition of the activity of a polypeptide frequently has no further effect on the survival of insects. This may be attributed to the fact that insects may switches to alternative activities, hence the number of protein-encoding genes is at least 3 fold higher than that of microorganisms.

Furthermore, in the case of the SK-channel, with regard to the research results in human medicine, e.g. WO 2005 100349, which teaches that even a inhibition of the potassium ion flow through the potassium ion channels is useful in the treatment of diseases, it was surprisingly that the SK channels of the invention are targets for insecticides as thy influence their survival.

It is an object of the present invention to identify novel targets which are essential for the development or survival of insects, and to provide methods which are suitable for identifying insecticidal active compounds.

We have found that this object is achieved by the use of a polypeptide with the activity of an insect voltage-gated potassium channel ShaI (Shaker cognate I or Shaker-like) and/or its accessory protein KChIP (potassium channel-interacting protein).

One embodiment of the present invention is directed to a method for identifying an insecticidal active compound that reduces the activity of a polypeptide with the activity of an insect voltage-gated potassium channel ShaI (Shaker cognate I or Shaker-like) and/or its accessory protein KChIP (potassium channel-interacting protein) which method comprises:
a) assembling in a membrane a polypeptide with the activity of an insect voltage-gated potassium channel ShaI (Shaker cognate I or Shaker-like) and/or its accessory protein KChIP (potassium channel-interacting protein), which is originally not present in said membrane,
b) applying at one side of the membrane the compound suspected of having the ability to inhibit the activity of said polypeptide which is originally not present said membrane,
c) determining the activity of said polypeptide and
d) identifying a compound applied in (b) that reduces the activity of said polypeptide.

In another embodiment, we have found that this object is achieved by the use of a polypeptide with the activity of an insect Shaker channel and/or a Hyperkinetic beta subunit, preferably H-kv beta subunit A or C subtype respectively.

One embodiment of the present invention is directed to a method for identifying an insecticidal active compound that reduces the activity of a polypeptide with the activity of an insect Shaker channel and/or a Hyperkinetic beta subunit, preferably H-kv beta subunit A or C subtype respectively which method comprises:
a) assembling in a membrane a polypeptide with the activity of an insect Shaker channel and/or a Hyperkinetic beta subunit, preferably H-kv beta subunit A or C subtype respectively, which is originally not present in said membrane,
b) applying at one side of the membrane the compound suspected of having the ability to inhibit the activity of said polypeptide which is originally not present said membrane,
c) determining the activity of said polypeptide and
d) identifying a compound applied in (b) that reduces the activity of said polypeptide.

In another embodiment, we have found that this object is achieved by the use of a polypeptide with the activity of an insect octopamine receptor selected from the group consisting of oa2, preferably from *Drosophila melanogaster*, Oamb, Oct-beta-2R and Oct-beta-3R.

One embodiment of the present invention is directed to a method for identifying an insecticidal active compound that reduces the activity of a polypeptide with the activity of an insect octopamine receptor selected from the group consisting of oa2, preferably from *Drosophila melanogaster*, Oamb, Oct-beta-2R and Oct-beta-3R which method comprises:
a) assembling in a membrane a polypeptide with the activity of an insect octopamine receptor selected from the group consisting of oa2, preferably from *Drosophila*

*melanogaster*, Oamb, Oct-beta-2R and Oct-beta-3R, which is originally not present in said membrane, b) applying at one side of the membrane the compound suspected of having the ability to inhibit the activity of said polypeptide which is originally not present said membrane, c) determining the activity of said polypeptide and d) identifying a compound applied in (b) that reduces the activity of said polypeptide.

In another embodiment, we have found that this object is achieved by the use of a polypeptide with the activity of an insect small-conductance Ca2+-activated potassium channel.

One embodiment of the present invention is directed to a method for identifying a insecticidally active compound that reduces the activity of an insect small-conductance Ca2+-activated potassium channel which method comprises:

a) assembling in a membrane a polypeptide with the activity of an insect small-conductance Ca2+-activated potassium channel, which is originally not present in said membrane, b) applying at one side of the membrane the compound suspected of having the ability to inhibit the activity of said polypeptide which is originally not present said membrane, c) determining the activity of said polypeptide and d) identifying a compound applied in (b) that reduces the activity of said polypeptide.

According to the present invention, a membrane is a structure like a semipermeable sheet or layer which acts as a barrier between two phases or solutions, whereby the membrane is solvent permeable, preferably water permeable. In one embodiment the membrane is a biological membrane, biomembrane or a lipid layer or lipid bilayer. The membrane is preferably composed of a fluid lipid bilayer. In one embodiment the membrane is the outer surface of a cell, cell compartment, vesicle, liposomes (vesicles made of phospholipids which are amphiphilic molecules), polymer vesicles or synthosomes.

Polymer vesicles are often referred as "polymersomes", which have been studied in detail and progress has been summarized in reviews [Discher et al., Science 2002, 297; 967 973]. Polymersomes or polymer vesicles consist of self-assembled di- or triblock copolymers.

The Synthosome, which is a functionalized nanocompartment system, has been developed for putative biotechnological applications [Nardin et al., Chem. Commun. 2000, 1433 1434]. A Synthosome is a hollow sphere consisting of a mechanically stable vesicle with a block copolymer membrane and an engineered transmembrane protein acting as the selective gate.

The, preferably insect, voltage-gated potassium channel Shal (Shaker cognate I or Shaker-like) and/or its accessory protein KChIP (potassium channel-interacting protein) of the invention is assembled or intercalated, embedded or integrated, terms which are synonymously and interchangeable, in the membrane.

The, preferably insect, Shaker channel and/or a Hyperkinetic beta subunit, preferably H-kv beta subunit A or C subtype respectively of the invention is assembled or intercalated, embedded or integrated, terms which are synonymously and interchangeable, in the membrane.

The, preferably insect, octopamine receptor selected from the group consisting of oa2, preferably from *Drosophila melanogaster*, Oamb, Oct-beta-2R and Oct-beta-3R of the invention is assembled or intercalated, embedded or integrated, terms which are synonymously and interchangeable, in the membrane.

The insect small-conductance Ca2+-activated potassium channel is assembled or intercalated, embedded or integrated, terms which are synonymously and interchangeable, in the membrane.

For the purposes of the invention, as a rule the plural is intended to encompass the singular and vice versa.

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or de-oxyribonucleotides. The terms refer only to the primary structure of the molecule.

Thus, the terms "gene(s)", "polynucleotide", "nucleic acid sequence", "nucleotide sequence", or "nucleic acid molecule(s)" as used herein include double- and single-stranded DNA and RNA. They also include known types of modifications, for example, methylation, "caps", substitutions of one or more of the naturally occurring nucleotides with an analog. Preferably, the DNA or RNA sequence comprises a coding sequence encoding the herein defined polypeptide.

A "coding sequence" is a nucleotide sequence, which is transcribed into a RNA, e.g. a regulatory RNA, such as a miRNA, a ta-siRNA, cosuppression molecule, a RNAi, a ribozyme, etc. or into a mRNA which is translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

As used in the present context a nucleic acid molecule may also encompass the untranslated sequence located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. In the event for example the antisense, RNAi, snRNA, dsRNA, siRNA, miRNA, ta-siRNA, cosuppression molecule, ribozyme etc. technology is used coding regions as well as the 5'- and/or 3'-regions can advantageously be used.

However, it is often advantageous only to choose the coding region for cloning and expression purposes.

"Polypeptide" refers to a polymer of amino acid (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The terms "comprise" or "comprising" and grammatical variations thereof when used in this specification are to be taken to specify the presence of stated features, integers, steps or components or groups thereof, but not to preclude the presence or addition of one or more other features, integers, steps, components or groups thereof.

The terms "reduction", "repression", "decrease" or "inhibition" relate to a corresponding change of a property in an organism, a part of an organism such as a tissue, or in a cell. Under "change of a property" it is understood that the activity is changed in a specific volume or in a specific amount of protein relative to a corresponding volume or amount of protein of a control, reference or wild type.

The terms "reduction", "repression", "decrease" or "inhibition" include the change of said property in only parts of the subject of the present invention, for example, the modification can be found in compartment of a cell, like an organelle, or in a part of a organism, like tissue, wing, leg, trunk etc. Preferably, the "reduction", "repression", "decrease" or "inhibition" is found cellular, thus the term "reduction, decrease or inhibition of an activity" relates to the cellular reduction, decrease or inhibition compared to the wild type cell or to the control cell.

Accordingly, the term "reduction", "repression", "decrease" or "inhibition" means that the specific activity of a gene product, a protein or a regulatory RNA as well as the amount of a compound or metabolite, e.g. of a polypeptide, a nucleic acid molecule, a ion or an encoding mRNA or DNA, can be reduced, decreased or inhibited in a specific volume. The terms "reduction", "repression", "decrease" or "inhibition" include that the reason for said "reduction", "repression", "decrease" or "inhibition" can be a chemical compound that is administered to the organism or part thereof.

The terms "reduction", "repression", or "decrease" are exchangeable. The term "reduction" shall include the terms "repression", "decrease" or "inhibition" if not otherwise specified.

Reduction is also understood as meaning the modification of the activity. In this context, the function or activity, e.g. the "functional activity" or the "biological activity", is reduced by at least 10%, advantageously 20%, preferably 30%, especially preferably 40%, 50% or 60%, very especially preferably 70%, 80%, 85% or 90% or more, very especially preferably are 95%, more preferably are 99% or more in comparison to the control, reference or wild type. Most preferably the reduction, decrease or deletion in activity amounts to essentially 100%. Thus, a particularly advantageous embodiment is the inactivation, e.g. inhibition of the function of a compound, e.g. a polypeptide or a nucleic acid molecule.

The terms "wild type", "control" or "reference" are exchangeable and can be a cell or a part of organisms such as an organelle or a tissue, or an organism, in particular an insect, which was not modified or treated according to the herein described process according to the invention. Accordingly, the cell or a part of organisms such as an organelle or a tissue, or an organism, in particular an insect used as wild type, control or reference corresponds to the cell, organism or part thereof as much as possible and is in any other property but in the result of the process of the invention as identical to the subject matter of the invention as possible. Thus, the wild type, control, or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular an insect, which was not modified or treated according to the herein described process of the invention and is in any other property as similar to the subject matter of the invention as possible. The reference, control, or wild type is in its genome, transcriptome, proteome or metabolome as similar as possible to the subject of the present invention. Preferably, the term "reference-" "control-" or "wild type-"-organelle, -cell, -tissue or -organism, relates to an organelle, cell, tissue or organism, which is nearly genetically identical to the organelle, cell, tissue or organism, of the present invention or a part thereof preferably 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, which is genetically identical to the organism, cell or organelle used according to the process of the invention except that the responsible or activity conferring nucleic acid molecules or the gene product encoded by them are amended, manipulated, exchanged or introduced according to the inventive process.

Preferably, the reference, control or wild type differs form the subject of the present invention only in the activity of the polypeptide of the invention or the polypeptide used in the method of the invention.

"Significant decrease": referring to the activity of the polypeptide encoded by a nucleic acid sequence according to the invention, this is understood as meaning a decrease in activity of the polypeptide treated with a test compound in comparison with the control. e.g. in comparison with the activity of the polypeptide which has not been incubated with the test compound, with a magnitude outside a measurement error.

Reference to the "functional activity" of an ion channel should be understood as a reference to any one or more of the functions and/or traits which an ion channel performs or is involved in.

Reference to the "functional activity" of an octopamine receptor should be understood as a reference to any one or more of the functions and/or traits which an octopamine receptor performs or is involved in.

In one embodiment the term "functional activity" or "biological activity" of a polypeptide with the activity of an insect voltage-gated potassium channel ShaI (Shaker cognate I or Shaker-like) and/or its accessory protein KChIP (potassium channel-interacting protein) is defined by the transport of potassium ions across membranes.

In another embodiment the term "functional activity" or "biological activity" of a polypeptide with the activity of an insect Shaker channel and/or a Hyperkinetic beta subunit, preferably H-kv beta subunit A or C subtype respectively is defined by the transport of potassium ions across membranes.

In another embodiment the term "functional activity" or "biological activity" of a polypeptide with the activity of an octopamine receptor selected from the group consisting of oa2, preferably from *Drosophila melanogaster*, Oamb, Oct-beta-2R and Oct-beta-3R is defined by the fact, that octopamine receptors are selectively blocked by α-adrenergic antagonists and activated by α-adrenergic agonists.

In another embodiment the term "functional activity" or "biological activity" of a polypeptide with the activity of an insect small-conductance Ca2+-activated potassium channel is defined by the transport of potassium ions across membranes. This transport is activated by calcium ions, with a half maximal activation or Ca2+ sensitivity K0.5 selected from the group of intervals 200-1000 nM, 300-900 nM, 300-800 nM and 400-800 nM. The SK channels of the invention have a single-channel conductance selected from the group of intervals 2-20 pS, 3-20 pS, 4-15 pS, 5-12 pS and 5-10 pS. The biological activity of a polypeptide of the invention is apamine-insensitive.

The term "activity" of a compound refers to the function of a compound in a biological system such as a cell, an organ or an organism. For example, the term "activity" of a compound refers to the enzymatic function, regulatory function or its function as binding partner, transporter, regulator, or carrier, etc of a compound.

Insecticidal activity of a compound refers to the ability of said compound to kill or paralyze insects, or to inhibit the insect development or growth in such a manner that the insects provide less damage. Compounds having insecticidal activity are also referred to as toxic to insects. Insecticidal activity of a compound induce not just to death of insects, but also include other detrimental effects on insects such as sickness, anti-feedant activity, growth retardation, reduced reproductive ability and reduced fecundity.

A compound with a insecticidal activity as used herein is a "insecticide". The term "insecticide" generally refers to chemicals, biological agents, and other compounds that adversely affect insect viability, e.g., that kill, paralyze, sterilize or otherwise disable insect species in the areas of agricultural crop protection, human and animal health.

In one embodiment the method of the invention is implemented with a membrane which comprises at least one polypeptide encoded by a nucleic acid molecule selected from the group consisting of:
a) a nucleic acid molecule encoding the polypeptide shown in SEQ ID NO: 2, 6, 10, 14, 18, 22, 26 and/or 30;
b) a nucleic acid molecule shown in SEQ ID NO: 1, 5, 9, 13, 17, 21, 25 and/or 29;
c) a nucleic acid molecule, which, as a result of the degeneracy of the genetic code, can be derived from a polypeptide sequence according to SEQ ID NO: 2, 6, 10, 14, 18, 22, 26 and/or 30;
d) a nucleic acid molecule having at least 50% identity with the nucleic acid molecule sequence of a polynucleotide comprising the nucleic acid molecule shown in SEQ ID NO: 1, 5, 9, 13, 17, 21, 25 and/or 29;
e) a nucleic acid molecule encoding a polypeptide having at least 50% identity with the amino acid sequence of the polypeptide encoded by the nucleic acid molecule of (a) to (c) and having the activity of an insect voltage-gated potassium channel ShaI (Shaker cognate I or Shaker-like) and/or its accessory protein KChIP (potassium channel-interacting protein) respectively;
f) nucleic acid molecule which hybridizes with a nucleic acid molecule of (a) to (c) under stringent hybridization conditions;
g) a nucleic acid molecule encoding a polypeptide which can be isolated with the aid of monoclonal or polyclonal antibodies made against a polypeptide encoded by one of the nucleic acid molecules of (a) to (e) and having the activity of a an insect voltage-gated potassium channel ShaI (Shaker cognate I or Shaker-like) and/or its accessory protein KChIP (potassium channel-interacting protein) respectively;
h) a nucleic acid molecule encoding a polypeptide comprising the consensus sequence as depicted in SEQ ID NO: 33 and/or 34 respectively or one or more motifs as depicted in SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;
i) nucleic acid molecule which comprises a polynucleotide, which is obtained by amplifying a cDNA library or a genomic library using the primers in SEQ ID NO: 3, 4; 7, 8; 11, 12; 15, 16; 19, 20; 23, 24; 27, 28 and/or 31, 32 respectively;
and
j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a an insect voltage-gated potassium channel ShaI (Shaker cognate I or Shaker-like) and/or its accessory protein KChIP (potassium channel-interacting protein) respectively.

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j), for example a ShaI_delN mutant, which has an N-terminal deletion for the 2-40 amino acid coding region.

In one embodiment the method of the invention is implemented with a membrane which comprises at least a functional equivalent or homologue of a polypeptide with the activity of a voltage-gated potassium channel ShaI as depicted in SEQ ID NO: 2, 6, 10, 14, 18 and/or 22 or homolog thereof and/or a ShaI_delN mutant, which has an N-terminal deletion for the 2-40 amino acid coding region linked to a polypeptide with the activity of its accessory protein KChIP as depicted in SEQ ID NO: 26 and/or 30 or homolog thereof.

In another embodiment the method of the invention is implemented with a membrane which comprises at least one polypeptide encoded by a nucleic acid molecule selected from the group consisting of:
a) a nucleic acid molecule encoding a polypeptide comprising the polypeptide shown in SEQ ID NO: 73, 75, 77, 79, 81, 83, 85 and/or 87;
b) a nucleic acid molecule comprising the nucleic acid molecule shown in SEQ ID NO: 72, 74, 76, 78, 80, 82, 84 and/or 86;
c) a nucleic acid molecule, which, as a result of the degeneracy of the genetic code, can be derived from a polypeptide comprising a polypeptide sequence according to SEQ ID NO: 73, 75, 77, 79, 81, 83, 85 and/or 87;
d) a nucleic acid molecule having at least 50% identity with the nucleic acid molecule sequence of a polynucleotide comprising the nucleic acid molecule shown in SEQ ID NO: 72, 74, 76, 78, 80, 82, 84 and/or 86;
e) a nucleic acid molecule encoding a polypeptide having at least 50% identity with the amino acid sequence of the polypeptide encoded by the nucleic acid molecule of (a) to (c) and having the activity of an insect Shaker channel and/or a Hyperkinetic beta subunit, preferably H-kv beta subunit A or C subtype respectively;
f) nucleic acid molecule which hybridizes with a nucleic acid molecule of (a) to (c) under stringent hybridization conditions;
g) a nucleic acid molecule encoding a polypeptide which can be isolated with the aid of monoclonal or polyclonal antibodies made against a polypeptide encoded by one of the nucleic acid molecules of (a) to (e) and having the activity of a an insect Shaker channel and/or a Hyperkinetic beta subunit, preferably H-kv beta subunit A or C subtype respectively;

h) a nucleic acid molecule encoding a polypeptide comprising the consensus sequence as depicted in SEQ ID NO: 102 and/or 103 respectively or one or more motifs as depicted in SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;

i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively; and j a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a an insect Shaker channel and/or a Hyperkinetic beta subunit, preferably H-kv beta subunit A or C subtype respectively.

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j), whereby the nucleic acid molecule comprises a Kozak sequence (e.g. ACCATG).

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j), whereby the nucleic acid molecule comprises a sequence coding for a 400 bp or 500 bp 5'-fragment of the Shaker channel, preferably comprising the Shaker ATG codon, preferably together with a proper Kozak, and/or 1770 bp fragment of the Shaker channel and/or for a Hyperkinetic beta subunit, preferably H-kv beta subunit A or C subtype.

In one embodiment the method of the invention is implemented with a membrane which comprises any combination of at least a polypeptide selected from the group consisting of SEQ ID NO: 73, 75, 77, 79, 81 and 83 or a functional equivalent or homologue thereof and a polypeptide selected from the group consisting of SEQ ID NO: 85 and 87 or a functional equivalent or homologue thereof.

In another embodiment the method of the invention is implemented with a membrane which comprises at least one polypeptide encoded by a nucleic acid molecule selected from the group consisting of:

a) a nucleic acid molecule encoding the polypeptide shown in SEQ ID NO: 130, 134, 138, 142, 146, 150, 154, 158, 162, 166, 170 and/or 174;

b) a nucleic acid molecule shown in SEQ ID NO: 129, 133, 137, 141, 145, 149, 153, 157, 161, 165, 169 and/or 173;

a nucleic acid molecule, which, as a result of the degeneracy of the genetic code, can be derived from a polypeptide sequence according to SEQ ID NO: 130, 134, 138, 142, 146, 150, 154, 158, 162, 166, 170 and/or 174;

d) a nucleic acid molecule having at least 50% identity with the nucleic acid molecule sequence of a polynucleotide comprising the nucleic acid molecule shown in SEQ ID NO: 129, 133, 137, 141, 145, 149, 153, 157, 161, 165, 169 and/or 173;

e) a nucleic acid molecule encoding a polypeptide having at least 50% identity with the amino acid sequence of the polypeptide encoded by the nucleic acid molecule of (a) to (c) and having the activity of an insect octopamine receptor selected from the group consisting of oa2, preferably from *Drosophila melanogaster*, Oamb, Oct-beta-2R and Oct-beta-3R;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a an insect octopamine receptor selected from the group consisting of oa2, preferably from *Drosophila melanogaster*, Oamb, Oct-beta-2R and Oct-beta-3R;

h) a nucleic acid molecule encoding a polypeptide comprising the consensus sequence as depicted in SEQ ID NO: 177, 178 and/or 179 respectively or one or more motifs as depicted in SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively;

i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156, 159, 160; 163, 164; 167, 168; 171, 172 and/or 175, 176; and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a an insect octopamine receptor selected from the group consisting of oa2, preferably from *Drosophila melanogaster*, Oamb, Oct-beta-2R and Oct-beta-3R.

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j) and additionally a marker protein, e.g. GFP, whereby it is preferably linked with the polypeptide of the invention, e.g. encoded by a nucleic acid molecule selected from the group as depicted above under item a), b), c), d), e), f), g), h), i) or j).

In one embodiment the method of the invention is implemented with a membrane which comprises at least a functional equivalent or homologue of a polypeptide as shown in SEQ ID NO: 46 encoded by a nucleic acid molecule as depicted in SEQ ID NO: 173 or a homolog thereof.

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j) and additionally a "promiscuous" G-protein, whose G subunits allow the G-proteins to couple with GPCRs that normally couple with G-proteins of other families, whereby the "promiscuous" G-protein is preferably linked with the polypeptide of the invention, e.g. encoded by a nucleic acid molecule selected from the group as depicted above under item a), b), c), d), e), f), g), h), i) or j).

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j) and additionally a marker protein, e.g. GFP, and/or additionally a "promiscuous" G-protein, whereby marker protein and/or the "promiscuous" G-protein is preferably linked with the polypeptide of the invention, e.g. encoded by a nucleic acid molecule selected from the group as depicted above under item a), b), c), d), e), f), g), h), i) or j).

In one embodiment the method of the invention is implemented with a membrane which comprises at least a functional equivalent or homologue of a polypeptide as shown in SEQ ID NO: 46 encoded by a nucleic acid molecule as depicted in SEQ ID NO: 173 or a homolog thereof and additionally a "promiscuous" G-protein whereby the protein is preferably linked with the.

In one embodiment the "promiscuous" G-protein is a promiscuous G-alpha-16-protein or a homolog thereof.

In another embodiment the method of the invention is implemented with a membrane which comprises at least one polypeptide encoded by a nucleic acid molecule selected from the group consisting of:

a) a nucleic acid molecule encoding the polypeptide shown in SEQ ID NO: 228, 230, 232;

b) a nucleic acid molecule shown in SEQ ID NO: 227, 229, 231;

c) a nucleic acid molecule, which, as a result of the degeneracy of the genetic code, can be derived from a polypeptide sequence according to SEQ ID NO: 228, 230, 232;

d) a nucleic acid molecule having at least 50% identity with the nucleic acid molecule sequence of a polynucleotide comprising the nucleic acid molecule shown in SEQ ID NO: 227, 229, 231;

e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;

h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;

i) nucleic acid molecule which comprises a polynucleotide, which is obtained by amplifying a cDNA library or a genomic library using the primers in SEQ ID NO: 233, 234, 235, 236; and 237, 238 respectively;

and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel.

In one embodiment the method of the invention is implemented with a membrane which comprises at least a functional equivalent or homologue of a polypeptide encoded by a nucleic acid molecule selected from the group as depicted above under item a), b), c), d), e), f), g), h), i) or j).

The term "functional equivalent" of a polypeptide as depicted above is a polypeptide which confers essentially the activity of a polypeptide as depicted in SEQ ID NO: 2, 6, 10, 14, 18, 22, 26 and/or 30, in the case of the shaker channel and/or a Hyperkinetic beta subunit SEQ ID NO:73, 75, 77, 79, 81, 83, 85 and/or 87, in the case of the G-protein coupled receptor SEQ ID NO: 130, 134, 138, 142, 146, 150, 154, 158, 162, 166, 170 and/or 174 and in the case of the SK-channel SEQ ID NO: 228, 230, 232.

The term "functional equivalent" of a nucleic acid molecule as depicted above is a polynucleotide which confers essentially the activity of a nucleic acid molecule as depicted in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173 and in the case of the SK-channel SEQ ID NO: 227, 229, 231.

In accordance with the invention, a protein or polypeptide has the activity of a polypeptide as depicted in SEQ ID NO: 2, 6, 10, 14, 18, 22, 26 and/or 30, in the case of the shaker channel and/or a Hyperkinetic beta subunit SEQ ID NO: 73, 75, 77, 79, 81, 83, 85 and/or 87, in the case of the G-protein coupled receptor SEQ ID NO: 130, 134, 138, 142, 146, 150, 154, 158, 162, 166, 170 and/or 174 and in the case of the SK-channel SEQ ID NO:228, 230, 232 if the reduction, repression, decrease or inhibition of its activity mediates a decrease of potassium flux through the membrane.

In accordance with the invention, a nucleic acid molecule or polynucleotide has the activity of a nucleic acid molecule as depicted in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173 and in the case of the SK-channel SEQ ID NO: 227, 229, 231 if the reduction, repression, decrease or inhibition of its expression mediates a decrease of potassium flux through the membrane.

Homologues (=homologs) of the polypeptide of the present invention, in particular homologues of a polypeptide which is encoded by or which is comprising a nucleic acid molecule as shown in SEQ ID NO: 1, 5, 9, 13, 17, 21, 25 and/or 29, or a polypeptide comprising the polypeptide, the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively, can be derived from any organisms as long as the homologue confers the herein mentioned activity, i.e. it is a functional equivalent of said molecules.

In the case of the shaker channel and/or a Hyperkinetic beta subunit, homologues (=homologs) of the polypeptide of the present invention, in particular homologues of a polypeptide which is encoded by or which is comprising a nucleic acid molecule as shown in SEQ ID NO: 72, 74, 76, 78, 80, 82, 84 and/or 86, or a polypeptide comprising the polypeptide, the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively, can be derived from any organisms as long as the homologue confers the herein mentioned activity, i.e. it is a functional equivalent of said molecules.

In the case of the G-protein coupled receptor, homologues (=homologs) of the polypeptide of the present invention, in particular homologues of a polypeptide which is encoded by or which is comprising a nucleic acid molecule as shown in SEQ ID NO: 129, 133, 137, 141, 145, 149, 153, 157, 161, 165, 169 and/or 173, or a polypeptide comprising the polypeptide, the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively, can be derived from any organisms as long as the homologue confers the herein mentioned activity, i.e. it is a functional equivalent of said molecules.

In the case of the SK-channel, homologues (=homologs) of the polypeptide of the present invention, in particular homologues of a polypeptide which is encoded by or which is comprising a nucleic acid molecule as shown in SEQ ID NO: 227, 229, 231, or a polypeptide comprising the polypeptide, the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253, can be derived from any organisms as long as the homologue confers the herein mentioned activity, i.e. it is a functional equivalent of said molecules.

Further, according to the present invention, the term "homologue" relates to the sequence of an organism having preferably the highest or essentially the highest sequence homology to the herein mentioned or listed sequences of all expressed sequences of said organism.

The person skilled in the art knows how to find, identify and confirm, that a putative homologue has the same activity as described herein. If known, the biological function or activity in an organism essentially relates or corresponds to the activity or function as described for the genes mentioned in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231.

Accordingly, in one embodiment, the homologue or the functional equivalent comprises the sequence of a polypeptide encoded by a nucleic acid molecule comprising a sequence indicated in SEQ ID NO: 1, 5, 9, 13, 17, 21, 25 and/or 29 or a polypeptide sequence as depicted in SEQ ID NO: 2, 6, 10, 14, 18, 22, 26 and/or 30, a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively or it is the expression product of a nucleic acid molecule comprising a polynucleotide indicated in SEQ ID NO: 2, 6, 10, 14, 18, 22, 26 and/or 30.

In the case of the shaker channel and/or a Hyperkinetic beta subunit, accordingly, in one embodiment, the homologue or the functional equivalent comprises the sequence of a polypeptide encoded by a nucleic acid molecule comprising a sequence indicated in SEQ ID NO: 72, 74, 76, 78, 80, 82, 84 and/or 86 or a polypeptide sequence as depicted in SEQ ID NO: 73, 75, 77, 79, 81, 83, 85 and/or 87, a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively or it is the expression product of a nucleic acid molecule comprising a polynucleotide indicated in SEQ ID NO: 73, 75, 77, 79, 81, 83, 85 and/or 87.

In the case of the G-protein coupled receptor, accordingly, in one embodiment, the homologue or the functional equivalent comprises the sequence of a polypeptide encoded by a nucleic acid molecule comprising a sequence indicated in SEQ ID NO: 129, 133, 137, 141, 145, 149, 153, 157, 161, 165, 169 and/or 173 or a polypeptide sequence as depicted in SEQ ID NO: 130, 134, 138, 142, 146, 150, 154, 158, 162, 166, 170 and/or 174, a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively or it is the expression product of a nucleic acid molecule comprising a polynucleotide indicated in SEQ ID NO: 130, 134, 138, 142, 146, 150, 154, 158, 162, 166, 170 and/or 174.

In the case of the SK-channel, accordingly, in one embodiment, the homologue or the functional equivalent comprises the sequence of a polypeptide encoded by a nucleic acid molecule comprising a sequence indicated in SEQ ID NO: 227, 229, 231 or a polypeptide sequence as depicted in SEQ ID NO: 228, 230, 232, a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253 or it is the expression product of a nucleic acid molecule comprising a polynucleotide indicated in SEQ ID NO: 228, 230, 232.

The herein disclosed information about sequence, activity, consensus sequence, polypeptide motifs and tests leads the person skilled in the art to the respective homologous or functional equivalent expression product in an organism.

In one embodiment, the homolog of any one of the polypeptides of the invention is derived from an insect and has a sequence identity of at least 50% and preferably has essentially the same or a similar activity of an insect voltage-gated potassium channel ShaI (Shaker cognate I or Shaker-like) and/or its accessory protein KChIP (potassium channel-interacting protein) respectively.

In another embodiment, the homolog of any one of the polypeptides of the invention is derived from an insect and has a sequence identity of at least 50% and preferably has essentially the same or a similar activity of a Shaker channel and/or a Hyperkinetic beta subunit, preferably H-kv beta subunit A or C subtype respectively.

In another embodiment, the homolog of any one of the polypeptides of the invention is derived from an insect and has a sequence identity of at least 50% and preferably has essentially the same or a similar activity of a octopamine receptor selected from the group consisting of oa2, preferably from *Drosophila melanogaster*, Oamb, Oct-beta-2R and Oct-beta-3R.

In a further embodiment, the homolog of any one of the polypeptides of the invention is derived from an insect and has a sequence identity of at least 50% and preferably has essentially the same or a similar activity of an insect small-conductance Ca2+-activated potassium channel.

In one embodiment, the homolog of any one of the polypeptides of the invention is derived from a insect, preferably from a insect selected from the group consisting of *Pterygota, Neopetra, Hemiptera, Lepidoptera, Coleoptera, Diptera, Homoptera, Tenebrionoidea, Tenebrionidae, Tenebrio, Sternorrhyncha, Aphidina, Brachycera, Drosophilidae, Drosophilinae* and *Drosophila* and has a sequence identity of at least 50% and preferably has essentially the same or a essentially similar activity of i) an insect voltage-gated potassium channel ShaI (Shaker cognate I or Shaker-like) and/or its accessory protein KChIP (potassium channel-interacting protein) respectively, or ii) a Shaker channel and/or a Hyperkinetic beta subunit, preferably H-kv beta subunit A or C subtype respectively, or iii) a octopamine receptor selected from the group consisting of oa2, preferably from *Drosophila melanogaster*, Oamb, Oct-beta-2R and Oct-beta-3R, or iv) an insect small-conductance Ca2+-activated potassium channel.

In one embodiment, the homolog of any one of the polypeptides of the invention is derived from i) *Drosophila melanogaster*, southern armyworm, tribolium, brown plant hopper, or ii) *Drosophila melanogaster*, southern armyworm, tribolium, green peach aphid, cotton aphid and/or black bean aphid, or iii) *Drosophila melanogaster*, southern armyworm (*Spodoptera eridania*), Red Fluor Beetle (*Tribolium castaneum*), Green Peach Aphid (*Myzus persicae*), and Silverleaf Whitefly (*Bemisia argentifolii*), or iv) a insect, preferably from a insect selected from the group consisting of *Pterygota, Neopetra, Hemiptera, Lepidoptera, Coleoptera, Diptera, Homoptera, Tenebrionoidea, Tenebrionidae, Tenebrio, Sternorrhyncha, Aphidina, Brachycera, Drosophilidae, Drosophilinae* and *Drosophila* and has a sequence identity of at least 50% and preferably has essentially the same or a essentially similar activity of an insect small-conductance Ca2+-activated potassium channel.

The functional equivalent or homologs of the polypeptide of the invention have the activity of i) an insect voltage-gated potassium channel ShaI (Shaker cognate I or Shaker-like) and/or its accessory protein KChIP (potassium channel-interacting protein) respectively, or ii) an insect Shaker channel and/or a Hyperkinetic beta subunit, preferably H-kv beta subunit A or C subtype respectively, or iii) an insect octopamine receptor selected from the group consisting of oa2, preferably from *Drosophila melanogaster*, Oamb, Oct-beta-2R and Oct-beta-3R, or iv) an insect small-conductance Ca2+-activated potassium channel and an amino acid sequence that has at least an identity of 55%, 56%, 57%, 58%, 59%, 60%, 61%, 62% or 63% preferably at least 64%, 65%, 66%, 67%, 68% or 69% more preferably at least 70%, 71%, 72%, 73%, 74%, 75%, 76%, 77%, 78%, 79%, 80%, 81%, 82%, 83%, 84% or 85% most preferably 86%, 87%, 88%, 89% or 90% especially preferably at least 91%, 92%, 93%, 94%, 95%, 96%, 97%, 98% or 99% identity with a polypeptide as shown in the sequences selected from the group consisting of SEQ ID NO: 2, 6, 10, 14, 18, 22, 26 and/or 30, in the case of the shaker channel and/or a Hyperkinetic beta subunit SEQ ID NO: 73, 75, 77, 79, 81, 83, 85 and/or 87, in the case of the G-protein coupled receptor SEQ ID NO: 130, 134, 138, 142, 146, 150, 154, 158, 162, 166, 170 and/or 174, and in the case of the SK-channel SEQ ID NO: 228, 230, 232.

"Functional equivalents" describe, in the present context, nucleic acid sequences which hybridize under standard conditions with the nucleic acid sequence encoding a polypeptide with the biological activity of i) an insect voltage-gated potassium channel ShaI (Shaker cognate I or Shaker-like) and/or its accessory protein KChIP (potassium channel-interacting protein) respectively, or ii) an insect Shaker channel and/or a Hyperkinetic beta subunit, preferably H-kv beta subunit A or C subtype respectively, or iii) an octopamine receptor selected from the group consisting of oa2, preferably from *Drosophila melanogaster*, Oamb, Oct-beta-2R and Oct-beta-3R, or iv) an insect small-conductance Ca2+-activated potassium channel or parts of the aforementioned nucleic acid sequence, which are capable of bringing about the expression, in a cell or an organism, of a polypeptide with the biological activity of a of i) an insect voltage-gated potassium channel ShaI (Shaker cognate I or Shaker-like) and/or its accessory protein KChIP (potassium channel-interacting protein) respectively, or ii) an insect Shaker channel and/or a Hyperkinetic beta subunit, preferably H-kv beta subunit A or C subtype respectively, or iii) an insect octopamine receptor selected from the group consisting of oa2, preferably from *Drosophila melanogaster*, Oamb, Oct-beta-2R and Oct-beta-3R, or iv) an insect small-conductance Ca2+-activated potassium channel.

To carry out the hybridization, it is advantageous to use short oligonucleotides with a length of approximately 10-50 bp, preferably 15-40 bp, for example of the conserved or other regions, which can be determined in the manner with which the skilled worker is familiar by comparisons with other related genes. However, longer fragments of the nucleic acids according to the invention with a length of 100-500 bp, or the complete sequences, may also be used for hybridization. Depending on the nucleic acid/oligonucleotide used, the length of the fragment or the complete sequence, or depending on which type of nucleic acid, i.e. DNA or RNA, is being used for the hybridization, these standard conditions vary. Thus, for example, the melting temperatures for DNA:DNA hybrids are approximately 10° C. lower than those of DNA:RNA hybrids of the same length.

Standard hybridization conditions are to be understood as meaning, depending on the nucleic acid, for example temperatures of between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids are advantageously 0.1×SSC and temperatures of between approximately 20° C. and 65° C., preferably between approximately 30° C. and 45° C. In the case of DNA:RNA hybrids, the hybridization conditions are advantageously 0.1×SSC and temperatures of between approximately 30° C. and 65° C., preferably between approximately 45° C. and 55° C. These hybridization temperatures which have been stated are melting temperature values which have been calculated by way of example for a nucleic acid with a length of approx. 100 nucleotides and a G+C content of 50% in the absence of formamide. The experimental conditions for DNA hybridization are described in specialist textbooks of genetics such as, for example, in Sambrook et al., "Molecular Cloning", Cold Spring Harbor Laboratory, 1989, and can be calculated using formulae with which the skilled worker is familiar, for example as a function of the length of the nucleic acids, the type of the hybrids or the G+C content. The skilled worker will find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

A functional equivalent is furthermore also understood as meaning in particular natural or artificial mutations of the respective nucleic acid sequences of the protein encoded by the nucleic acid sequences according to the invention and their homologs from other organisms.

Thus, the present invention also encompasses, for example, those nucleotide sequences which are obtained by modification of the nucleic acid sequence of SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231. For example, such modifications can be generated by techniques with which the skilled worker is familiar, such as "Site Directed Mutagenesis", "Error Prone PCR", "DNA shuffling" (Nature 370, 1994, pp. 389-391) or "Staggered Extension Process" (Nature Biotechnol. 16, 1998, pp. 258-261). The purpose of such a modification can be, for example, the insertion of further cleavage sites for restriction enzymes, the removal of DNA in order to truncate the sequence, the substitution of nucleotides to optimize the codons, or the addition of further sequences. Proteins which are encoded via modified nucleic acid sequences must retain the desired functions despite a deviating nucleic acid sequence, which is the biological activity of i) an insect voltage-gated potassium channel ShaI (Shaker cognate I or Shaker-like) and/or its accessory protein KChIP (potassium channel-interacting protein) respectively, or ii) an insect Shaker channel and/or a Hyperkinetic beta subunit, preferably H-kv beta subunit A or C subtype respectively, or iii) an insect octopamine receptor selected from the group consisting of oa2, preferably from *Drosophila melanogaster*, Oamb, Oct-beta-2R and Oct-beta-3R, or iv) an insect small-conductance Ca2+-activated potassium channel.

Functional equivalents thus comprise naturally occurring variants of the herein-described sequences and artificial nucleic acid sequences, for example those which have been obtained by chemical synthesis and which are adapted to the codon usage, and also the amino acid sequences derived from them.

Nucleic acid molecules corresponding to natural variant homologues of the nucleic acid molecule comprising a polynucleotide shown in SEQ ID NO: 2, 6, 10, 14, 18, 22, 26 and/or 30, in the case of the shaker channel and/or a Hyperkinetic beta subunit SEQ ID NO: 73, 75, 77, 79, 81, 83, 85 and/or 87, in the case of the G-protein coupled receptor SEQ ID NO: 130, 134, 138, 142, 146, 150, 154, 158, 162, 166, 170 and/or 174, and in the case of the SK-channel SEQ ID NO: 228, 230, 232, such as the nucleic acid molecule of the invention, and which can also be a cDNA, can be isolated based on their homology to the nucleic acid molecules disclosed herein using the nucleic acid molecule shown in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231, e.g. the nucleic acid molecule of the invention, or a fragment thereof, as a hybridization probe according to standard hybridization techniques under stringent hybridization conditions.

Nucleic acid molecules which are advantageously for the process according to the invention can be isolated based on their homology to the nucleic acid molecules disclosed herein using the sequences or part thereof as hybridization probe and following standard hybridization techniques under stringent hybridization conditions.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structural equivalents can for example be identified by testing the binding of said polypeptide to antibodies or computer based predictions. Structural equivalents have the similar immunological characteristic, e.g. comprise similar epitopes.

By "hybridizing" it is meant that such nucleic acid molecules hybridize under conventional hybridization conditions, preferably under stringent conditions such as described by, e.g., Sambrook (Molecular Cloning; A Laboratory Manual, $2^{nd}$ Edition, Cold Spring Harbor Laboratory Press, Cold Spring Harbor, N.Y. (1989)) or in Current Protocols in Molecular Biology, John Wiley & Sons, N.Y. (1989), 6.3.1-6.3.6.

According to the invention, DNA as well as RNA molecules of the nucleic acid of the invention can be used as probes. Further, as template for the identification of functional homologues Northern blot assays as well as Southern blot assays can be performed. The Northern blot assay advantageously provides further information about the expressed gene product: e.g. expression pattern, occurrence of processing steps, like splicing and capping, etc. The Southern blot assay provides additional information about the chromosomal localization and organization of the gene encoding the nucleic acid molecule of the invention.

A preferred, nonlimiting example of stringent Southern blot hybridization conditions are hybridizations in 6× sodium chloride/sodium citrate (=SSC) at approximately 45° C., followed by one or more wash steps in 0.2×SSC, 0.1% SDS at 50 to 65° C., for example at 50° C., 55° C. or 60° C. The skilled worker knows that these hybridization conditions differ as a function of the type of the nucleic acid and, for example when organic solvents are present, with regard to the temperature and concentration of the buffer. The temperature under "standard hybridization conditions" differs for example as a function of the type of the nucleic acid between 42° C. and 58° C., preferably between 45° C. and 50° C. in an aqueous buffer with a concentration of 0.1×0.5×, 1×, 2×, 3×, 4× or 5×SSC (pH 7.2). If organic solvent(s) is/are present in the abovementioned buffer, for example 50% formamide, the temperature under standard conditions is approximately 40° C., 42° C. or 45° C. The hybridization conditions for DNA:DNA hybrids are preferably for example 0.1×SSC and 20° C., 25° C., 30° C., 35° C., 40° C. or 45° C., preferably between 30° C. and 45° C. The hybridization conditions for DNA:RNA hybrids are preferably for example 0.1×SSC and 30° C., 35° C., 40° C., 45° C., 50° C. or 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows to determine the hybridization conditions required with the aid of textbooks, for example the ones mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A further example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2× SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65° C.

Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Relevant factors like i) length of treatment, ii) salt conditions, iii) detergent conditions, iv) competitor DNAs, v) temperature and vi) probe selection can combined case by case so that not all possibilities can be mentioned herein.

Some examples of conditions for DNA hybridization (Southern blot assays) and wash step are shown hereinbelow:

(1) Hybridization conditions can be selected, for example, from the following conditions:
 a) 4×SSC at 65° C.,
 b) 6×SSC at 45° C.,
 c) 6×SSC, 100 mg/ml denatured fragmented fish sperm DNA at 68° C.,
 d) 6×SSC, 0.5% SDS, 100 mg/ml denatured salmon sperm DNA at 68° C.,
 e) 6×SSC, 0.5% SDS, 100 mg/ml denatured fragmented salmon sperm DNA, 50% formamide at 42° C.,
 f) 50% formamide, 4×SSC at 42° C.,
 g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
 h) 2× or 4×SSC at 50° C. (low-stringency condition), or
 i) 30 to 40% formamide, 2× or 4×SSC at 42° C. (low-stringency condition).

(2) Wash steps can be selected, for example, from the following conditions:
 a) 0.015 M NaCl/0.0015 M sodium citrate/0.1% SDS at 50° C.
 b) 0.1×SSC at 65° C.
 c) 0.1×SSC, 0.5% SDS at 68° C.
 d) 0.1×SSC, 0.5% SDS, 50% formamide at 42° C.
 e) 0.2×SSC, 0.1% SDS at 42° C.
 f) 2×SSC at 65° C. (low-stringency condition).
 g) 0.2×SSC, 0.1% SDS at 60° C. (medium-high stringency conditions), or
 h) 0.1×SSC, 0.1% SDS at 60° C. (medium-high stringency conditions), or
 i) 0.2×SSC, 0.1% SDS at 65° C. (high stringency conditions), or
 h) 0.1×SSC, 0.1% SDS at 65° C. (high stringency conditions).

In one embodiment, the term "hybridizes under stringent conditions" is intended to describe conditions for hybridization and washing under which nucleotide sequences of at least 30%, 40%, 50% or 65% identical to each other typically remain hybridized to each other. Preferably, the conditions are such that sequences of at least about 70%, more preferably at least about 75% or 80%, and even more preferably of at least about 85%, 90% or 95% or more identical to each other typically remain hybridized to each other.

In one embodiment the nucleic acid molecule of the invention hybridizes under stringent conditions to a sequence shown in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231 and corresponds to a naturally-occurring nucleic acid molecule. As used herein, a "naturally-occurring" nucleic acid molecule refers to a RNA or DNA molecule having a nucleotide sequence that occurs in nature (e.g., encodes a natural protein).

In addition to naturally-occurring variants of the nucleic acid or protein sequence that may exist in the population, the skilled artisan will further appreciate that changes can be introduced by mutation into a nucleotide sequence of the nucleic acid molecule encoding the polypeptide, thereby leading to changes in the amino acid sequence of the encoded polypeptide and thereby altering the functional ability of the polypeptide, meaning preferably reducing, decreasing or deleting said activity. For example, nucleotide substitutions leading to amino acid substitutions at "essential" amino acid residues can be made in a sequence of the nucleic acid molecule to be reduced in the process of the invention, e.g. comprising the corresponding nucleic acid molecule as shown in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231. An "essential" amino acid residue is a residue that if altered from the wild-type sequence of one of the polypeptide lead to an altered activity of said polypeptide, whereas a "non-essential" amino acid residue is not required for the activity of the protein for example for the activity as an enzyme or channel. The alteration of "essential" residues often lead to a reduced, decreased or deleted activity of the polypeptides. Preferably amino acid of the polypeptide are changed in such a manner that the activity is reduced, decreased or deleted that means preferably essential amino acid residues and/or more nonessential residues are changed and thereby the activity is reduced after decreasing the expression or activity of the polypeptide. Other amino acid residues, however, (e.g., those that are not conserved or only semi-conserved in the domain having said activity) may not be essential for activity and thus are likely to be amenable to alteration without altering said activity are less preferred.

Preferably, the protein encoded by the nucleic acid molecule is at least about 60%, 70% or 80% identical to the sequence shown in SEQ ID NO: 2, 6, 10, 14, 18, 22, 26 and/or 30 or to a sequence comprising a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively, more preferably at least about 85% identical to one of the sequences shown in SEQ ID NO: 2, 6, 10, 14, 18, 22, 26 and/or 30 or to a sequence comprising a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively, even more preferably at least about 90%, 91%, 92%, 93%, 94%, 95% homologous to the sequence shown in SEQ ID NO: 2, 6, 10, 14, 18, 22, 26 and/or 30 or to a sequence comprising a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively, and most preferably at least about 96%, 97%, 98%, or 99% identical to the sequence shown in SEQ ID NO: 2, 6, 10, 14, 18, 22, 26 and/or 30 or to a sequence comprising a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively.

In the case of the shaker channel and/or a Hyperkinetic beta subunit, preferably, the protein encoded by the nucleic acid molecule is at least about 60%, 70% or 80% identical to the sequence shown in SEQ ID NO: 73, 75, 77, 79, 81, 83, 85 and/or 87 or to a sequence comprising a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively, more preferably at least about 85% identical to one of the sequences shown in SEQ ID NO: 73, 75, 77, 79, 81, 83, 85 and/or 87 or to a sequence comprising a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively, even more preferably at least about 90%, 91%, 92%, 93%, 94%, 95% homologous to the sequence shown in SEQ ID NO: 73, 75, 77, 79, 81, 83, 85 and/or 87 or to a sequence comprising a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively, and most preferably at least about 96%, 97%, 98%, or 99% identical to the sequence shown in SEQ ID NO: 73, 75, 77, 79, 81, 83, 85 and/or 87 or to a sequence comprising a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively.

In the case of the G-protein coupled receptor, preferably, the protein encoded by the nucleic acid molecule is at least about 60%, 70% or 80% identical to the sequence shown in SEQ ID NO: 130, 134, 138, 142, 146, 150, 154, 158, 162, 166, 170 and/or 174 or to a sequence comprising a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively, more preferably at least about 85% identical to one of the sequences shown in SEQ ID NO: 130, 134, 138, 142, 146, 150, 154, 158, 162, 166, 170 and/or 174 or to a sequence comprising a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively, even more preferably at least about 90%, 91%, 92%, 93%, 94%, 95% homologous to the sequence shown in SEQ ID NO: 130, 134, 138, 142, 146, 150, 154, 158, 162, 166, 170 and/or 174 or to a sequence comprising a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively, and most preferably at least about 96%, 97%, 98%, or 99% identical to the sequence shown in SEQ ID NO: 130, 134, 138, 142, 146, 150, 154, 158, 162, 166, 170 and/or 174 or to a sequence comprising a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively.

In the case of the SK-channel, preferably, the protein encoded by the nucleic acid molecule is at least about 60%, 70% or 80% identical to the sequence shown in SEQ ID NO: 228, 230, 232 or to a sequence comprising a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253, more preferably at least about 85% identical to one of the sequences shown in SEQ ID NO: 228, 230, 232 or to a sequence comprising a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253, even more preferably at least about 90%, 91%, 92%, 93%, 94%, 95% homologous to the sequence shown in SEQ ID NO: 228, 230, 232 or to a sequence comprising a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253, and most preferably at least about 96%, 97%, 98%, or 99% identical to the sequence shown in SEQ ID NO: 228, 230, 232 or to a sequence comprising a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253.

To determine the percentage homology (=identity) of two amino acid sequences or of two nucleic acid molecules, the sequences are written one underneath the other for an optimal comparison. Gaps may be inserted into the sequence of a protein or of a nucleic acid molecule in order to generate an optimal alignment with the other protein or the other nucleic acid. The amino acid residue or nucleotide at the corresponding amino acid position or nucleotide position is then compared between both polymers. If a position in one sequence is occupied by the same amino acid residue or the same nucleotide as in the corresponding position of the other sequence, the molecules are identical at this position. Amino acid or nucleotide "identity" as used in the present context corresponds to amino acid or nucleic acid "homology". Generally the percentage homology between the two sequences is a function of the number of identical positions shared by the sequences (i.e. % homology=number of identical positions/total number of positions×100). The terms "homology" and "identity" are thus to be considered as synonyms for this description.

For the determination of the percentage homology (=identity) of two or more amino acid or of two or more nucleotide sequences several computer software programs have been developed. The homology of two or more sequences can be calculated with for example the software fasta, which presently has been used in the version fasta 3 (W. R. Pearson and D. J. Lipman (1988), Improved Tools for Biological Sequence Comparison. PNAS 85:2444-2448; W. R. Pearson (1990) Rapid and Sensitive Sequence Comparison with FASTP and FASTA, Methods in Enzymology 183:63-98; W. R. Pearson and D. J. Lipman (1988) Improved Tools for Biological Sequence Comparison. PNAS 85:2444-2448; W. R. Pearson (1990); Rapid and Sensitive Sequence Comparison with FASTP and FASTAMethods in Enzymology 183: 63-98). Another useful program for the calculation of homologies of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences: -p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast[nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -l Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default= 0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351-360, 1987, Higgins et al., CABIOS, 5 1989: 151-153) or preferably with the programs Gap and BestFit, which are respectively based on the algorithms of Needleman and Wunsch [J. Mol. Biol. 48; 443-453 (1970)] and Smith and Waterman [Adv. Appl. Math. 2; 482-489 (1981)]. Both programs are part of the GCG software-package [Genetics Computer Group, 575 Science Drive, Madison, Wis., USA 53711 (1991); Altschul et al. (1997) Nucleic Acids Res. 25:3389 et seq.]. Therefore preferably the calculations to determine the perentages of sequence homology are done with the program Gap over the whole range of the sequences. The following standard adjustments for the comparison of nucleic acid sequences were used: gap weight: 50, length weight: 3, average match: 10.000, average mismatch: 0.000.

For example a sequence which has a 80% homology with sequence shown in SEQ ID NO.: 1 at the nucleic acid level is understood as meaning a sequence which, upon comparison with the sequence SEQ ID NO: 1 by the above Gap program algorithm with the above parameter set, has 80% homology.

Homology between two polypeptides is understood as meaning the identity of the amino acid sequence over in each case the entire sequence length which is calculated by comparison with the aid of the program algorithm Gap (Wisconsin Package Version 10.0, University of Wisconsin, Genetics Computer Group (GCG), Madison, USA), setting the following parameters: gap weight: 8; length weight: 2; average match: 2.912; average mismatch: −2.003.

For example a sequence which has a 80% homology with sequence SEQ ID NO: 2 at the protein level is understood as meaning a sequence which, upon comparison with the sequence SEQ ID NO: 2 by the above Gap program algorithm with the above parameter set, has 80% homology.

Functional equivalents derived from one of the polypeptides as shown in SEQ ID NO: 2, 6, 10, 14, 18, 22, 26 and/or 30 or comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2, 6, 10, 14, 18, 22, 26 and/or 30 or with one of the polypeptides comprising a consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively and are distinguished by essentially the same properties as the polypeptide as shown in SEQ ID NO: 2, 6, 10, 14, 18, 22, 26 and/or 30.

Functional equivalents derived from the nucleic acid sequence as shown in SEQ ID NO: 1, 5, 9, 13, 17, 21, 25 and/or 29 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the nucleic acids as shown in SEQ ID NO: 1, 5, 9, 13, 17, 21, 25 and/or 29 according to the invention and encode polypeptides having essentially the same properties as the polypeptide as shown in SEQ ID NO: 2, 6, 10, 14, 18, 22, 26 and/or 30.

In the case of the shaker channel and/or a Hyperkinetic beta subunit, functional equivalents derived from one of the polypeptides as shown in SEQ ID NO: 73, 75, 77, 79, 81, 83, 85 and/or 87 or comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 73, 75, 77, 79, 81, 83, 85 and/or 87 or with one of the polypeptides comprising a consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively and are distinguished by essentially the same properties as the polypeptide as shown in SEQ ID NO: 73, 75, 77, 79, 81, 83, 85 and/or 87.

In the case of the shaker channel and/or a Hyperkinetic beta subunit, functional equivalents derived from the nucleic acid sequence as shown in SEQ ID NO: 72, 74, 76, 78, 80, 82, 84 and/or 86 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the nucleic acids as shown in SEQ ID NO: 72, 74, 76, 78, 80, 82, 84 and/or 86 according to the invention and encode polypeptides having essentially the same properties as the polypeptide as shown in SEQ ID NO: 73, 75, 77, 79, 81, 83, 85 and/or 87.

In the case of the G-protein coupled receptor, functional equivalents derived from one of the polypeptides as shown in SEQ ID NO: 130, 134, 138, 142, 146, 150, 154, 158, 162, 166, 170 and/or 174 or comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 130, 134, 138, 142, 146, 150, 154, 158, 162, 166, 170 and/or 174 or with one of the polypeptides comprising a consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively and are distinguished by essentially the same properties as the polypeptide as shown in SEQ ID NO: 130, 134, 138, 142, 146, 150, 154, 158, 162, 166, 170 and/or 174.

In the case of the G-protein coupled receptor, functional equivalents derived from the nucleic acid sequence as shown in SEQ ID NO: 129, 133, 137, 141, 145, 149, 153, 157, 161, 165, 169 and/or 173 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the nucleic acids as shown in SEQ ID NO: 129, 133, 137, 141, 145, 149, 153, 157, 161, 165, 169 and/or 173 according to the invention and encode polypeptides having essentially the same properties as the polypeptide as shown in SEQ ID NO: 130, 134, 138, 142, 146, 150, 154, 158, 162, 166, 170 and/or 174.

In the case of the SK-channel, functional equivalents derived from one of the polypeptides as shown in SEQ ID NO: 228, 230, 232 or comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 228, 230, 232 or with one of the polypeptides comprising a consensus sequence as shown in SEQ ID NO: 239 or one or more motifs selected from the group consisting of SEQ ID NO: 240, 241, 242, 243, 244, 245, 246, 247, 248, 249, 250, 251, 252 and 253 and are distinguished by essentially the same properties as the polypeptide as shown in SEQ ID NO: 228, 230, 232.

In the case of the SK-channel, functional equivalents derived from the nucleic acid sequence as shown in SEQ ID NO: 227, 229, 231 according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the nucleic acids as shown in SEQ ID NO: 227, 229, 231 according to the invention and encode polypeptides having essentially the same properties as the polypeptide as shown in SEQ ID NO: 228, 230, 232.

In one embodiment "homology" or "identity" between two nucleic acid sequences or polypeptide sequences is defined by the identity of the nucleic acid sequence/polypeptide sequence over in each case the entire sequence length, which is calculated by alignment with the aid of the program algorithm GAP (Wisconsin Package Version 10.0, University of Wisconsin, Genetics Computer Group (GCG), Madison, USA), setting the following parameters:

Gap Weight: 8 Length Weight: 2
Average Match: 2,912 Average Mismatch: −2,003

In the following text, the term identity is also used synonymously instead of the term "homologous" or "homology".

"Mutations" comprise substitutions, additions, deletions, inversions or insertions of one or more nucleotide residues, which may also bring about changes in the corresponding amino acid sequence of the target protein by substitution, insertion or deletion of one or more amino acids.

In one embodiment the present invention is directed to an isolated nucleic acid molecule selected from the group consisting of:

a) a nucleic acid molecule encoding the polypeptide shown in SEQ ID NO: 2, 6, 10, 14, 18, 22, 26 and/or 30;

b) a nucleic acid molecule shown in SEQ ID NO: 1, 5, 9, 13, 17, 21, 25 and/or 29;

c) a nucleic acid molecule, which, as a result of the degeneracy of the genetic code, can be derived from a polypeptide sequence according to SEQ ID NO: 2, 6, 10, 14, 18, 22, 26 and/or 30;

d) a nucleic acid molecule having at least 50% identity with the nucleic acid molecule sequence of a polynucleotide comprising the nucleic acid molecule shown in SEQ ID NO: 1, 5, 9, 13, 17, 21, 25 and/or 29;

e) a nucleic acid molecule encoding a polypeptide having at least 50% identity with the amino acid sequence of the polypeptide encoded by the nucleic acid molecule of (a) to (c) and having the activity of a voltage-gated potassium channel Shal (Shaker cognate I or Shaker-like) and/or its accessory protein KChIP (potassium channel-interacting protein) respectively;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a voltage-gated potassium channel Shal (Shaker cognate I or Shaker-like) and/or its accessory protein KChIP (potassium channel-interacting protein) respectively;

h) a nucleic acid molecule encoding a polypeptide comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;

i) nucleic acid molecule which comprises a polynucleotide, which is obtained by amplifying a cDNA library or a genomic library using the primers in SEQ ID NO: 7, 8; 9, 10; 11, 12; respectively
and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a voltage-gated potassium channel Shal (Shaker cognate I or Shaker-like) and/or its accessory protein KChIP (potassium channel-interacting protein) respectively.

In the case of theshaker channel and/or a Hyperkinetic beta subunit, in one embodiment the present invention is directed to an isolated nucleic acid molecule selected from the group consisting of:

a) a nucleic acid molecule encoding a polypeptide comprising the polypeptide shown in SEQ ID NO: 73, 75, 77, 79, 81, 83, 85 and/or 87;

b) a nucleic acid molecule comprising the nucleic acid molecule shown in SEQ ID NO: 72, 74, 76, 78, 80, 82, 84 and/or 86;

c) a nucleic acid molecule, which, as a result of the degeneracy of the genetic code, can be derived from a polypeptide comprising a polypeptide sequence according to SEQ ID NO: 73, 75, 77, 79, 81, 83, 85 and/or 87;

d) a nucleic acid molecule having at least 50% identity with the nucleic acid molecule sequence of a polynucleotide comprising the nucleic acid molecule shown in SEQ ID NO: 72, 74, 76, 78, 80, 82, 84 and/or 86;

e) a nucleic acid molecule encoding a polypeptide having at least 50% identity with the amino acid sequence of the polypeptide encoded by the nucleic acid molecule of (a) to (c) and having the activity of a Shaker channel and/or a Hyperkinetic beta subunit, preferably H-kv beta subunit A or C subtype respectively;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a Shaker channel and/or a Hyperkinetic beta subunit, preferably H-kv beta subunit A or C subtype respectively;

h) a nucleic acid molecule encoding a polypeptide comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;

i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a Shaker channel and/or a Hyperkinetic beta subunit, preferably H-kv beta subunit A or C subtype respectively.

In the case of the G-protein coupled receptor, in one embodiment the present invention is directed to an isolated nucleic acid molecule selected from the group consisting of:

a) a nucleic acid molecule encoding the polypeptide shown in SEQ ID NO: 130, 134, 138, 142, 146, 150, 154, 158, 162, 166, 170 and/or 174;

b) a nucleic acid molecule shown in SEQ ID NO: 129, 133, 137, 141, 145, 149, 153, 157, 161, 165, 169 and/or 173;

c) a nucleic acid molecule, which, as a result of the degeneracy of the genetic code, can be derived from a polypeptide comprising a polypeptide sequence according to SEQ ID NO: 130, 134, 138, 142, 146, 150, 154, 158, 162, 166, 170 and/or 174;

d) a nucleic acid molecule having at least 50% identity with the nucleic acid molecule sequence of a polynucleotide comprising the nucleic acid molecule shown in SEQ ID NO: 129, 133, 137, 141, 145, 149, 153, 157, 161, 165, 169 and/or 173;

e) a nucleic acid molecule encoding a polypeptide having at least 50% identity with the amino acid sequence of the polypeptide encoded by the nucleic acid molecule of (a) to (c) and having the activity of a octopamine receptor selected from the group consisting of oa2, preferably from *Drosophila melanogaster*, Oamb, Oct-beta-2R and Oct-beta-3R;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a octopamine receptor selected from the group consisting of oa2, preferably from *Drosophila melanogaster*, Oamb, Oct-beta-2R and Oct-beta-3R;

h) a nucleic acid molecule encoding a polypeptide comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively, i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156, 159, 160; 163, 164; 167, 168; 171, 172 and/or 175, 176 and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a octopamine receptor selected from the group consisting of oa2, preferably from *Drosophila melanogaster*, Oamb, Oct-beta-2R and Oct-beta-3R.

In the case of the SK-channel, in one embodiment the present invention is directed to an isolated nucleic acid molecule selected from the group consisting of:

a) a nucleic acid molecule encoding the polypeptide shown in SEQ ID NO: 230, 232;

b) a nucleic acid molecule shown in SEQ ID NO: 229, 231;

c) a nucleic acid molecule, which, as a result of the degeneracy of the genetic code, can be derived from a polypeptide sequence according to SEQ ID NO: 230, 232;

d) a nucleic acid molecule having at least 50% identity with the nucleic acid molecule sequence of a polynucleotide comprising the nucleic acid molecule shown in SEQ ID NO: 229, 231;

e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;

h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;

i) nucleic acid molecule which comprises a polynucleotide, which is obtained by amplifying a cDNA library or a genomic library using the primers in SEQ ID NO: 233, 234, 235, 236; and 237, 238; respectively and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel.

In one embodiment the present invention is directed to nucleic acid construct comprising the isolated nucleic acid molecule of the invention.

In one embodiment the present invention is directed to a vector comprising the nucleic acid construct or the isolated nucleic acid molecule of the invention.

In one embodiment the present invention is directed to a transgenic host cell, comprising the vector, the nucleic acid construct or the isolated nucleic acid molecule of the invention by way of transfection/transformation.

An "isolated" polynucleotide or nucleic acid molecule is separated from other polynucleotides or nucleic acid molecules, which are present in the natural source of the nucleic acid molecule. An isolated nucleic acid molecule may be a chromosomal fragment of several kb, or preferably, a molecule only comprising the coding region of the gene. Accordingly, an isolated nucleic acid molecule may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). In various embodiments, the isolated nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

The nucleic acid molecules used in the process or a part thereof can be isolated using molecular-biological standard techniques and the sequence information provided herein. Also, for example a homologous sequence or homologous, conserved sequence regions at the DNA or amino acid level can be identified with the aid of comparison algorithms. The former can be used as hybridization probes under standard hybridization techniques (for example those described in Sambrook et al., Molecular Cloning: A Laboratory Manual. 2nd Ed., Cold Spring Harbor Laboratory, Cold Spring Harbor Laboratory Press, Cold Spring Harbor, N.Y., 1989) for isolating further nucleic acid sequences useful in this process.

A nucleic acid molecule encompassing a complete sequence of a molecule which activity is to be reduced in the process of the present invention or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this every sequence. For example, mRNA can be isolated from cells, for example by means of the guanidinium thiocyanate extraction method of Chirgwin et al. (1979) Biochemistry 18:5294-5299, and cDNA can be generated by means of reverse transcriptase (for example Moloney MLV reverse transcriptase, available from Gibco/BRL, Bethesda, Md., or AMV reverse transcriptase, obtainable from Seikagaku America, Inc., St. Petersburg, Fla.).

Synthetic oligonucleotide primers for the amplification by means of polymerase chain reaction can be generated on the basis of a sequence shown herein. Such primers can be used to amplify nucleic acids sequences for example from cDNA libaries or from genomic libraries and identify nucleic acid molecules, which are useful in the inventive process.

Moreover, it is possible to identify conserved regions from various organisms by carrying out protein sequence alignments with the polypeptide encoded by the nucleic acid molecule to be reduced according to the process of the invention, in particular with the sequences encoded by the nucleic acid molecule shown in SEQ ID NO: 1, 5, 9, 13, 17, 21, 25 and/or 29, in the case of the shaker channel and/or a Hyperkinetic beta subunit SEQ ID NO: 72, 74, 76, 78, 80, 82, 84 and/or 86, in the case of the G-protein coupled receptor SEQ ID NO: 129, 133, 137, 141, 145, 149, 153, 157, 161, 165, 169 and/or 173, and in the case of the SK-channel SEQ ID NO: 227, 229, 231, from which conserved regions, and in turn, degenerate primers can be derived.

Conserved regions are those, which show a very little variation in the amino acid in one particular position of several homologs from different origin. The consensus sequence and polypeptide motifs shown herein are derived from said alignments. Moreover, it is possible to identify conserved regions from various organisms by carrying out protein sequence alignments with the polypeptide encoded by the nucleic acid molecule to be reduced according to the process of the invention, in particular with the sequences encoded by the polypeptide molecule shown in SEQ ID NO: 2, 6, 10, 14, 18, 22, 26 and/or 30, in the case of the shaker channel and/or a Hyperkinetic beta subunit SEQ ID NO: 73, 75, 77, 79, 81, 83, 85 and/or 87, in the case of the G-protein coupled receptor SEQ ID NO: 130, 134, 138, 142, 146, 150, 154, 158, 162, 166, 170 and/or 174, and in the case of the SK-channel SEQ ID NO: 228, 230, 232 from which conserved regions, and in turn, degenerate primers can be derived.

Conserved regions are those, which show a very little variation in the amino acid in one particular position of several homologs from different origin. The consensus sequences and polypeptide motifs shown herein are derived from said alignments. In one advantageous embodiment, in the method of the present invention the activity of a polypeptide is decreased comprising or consisting of a consensus sequence as shown in SEQ ID NO: 33 and/or 34, in the case of the shaker channel and/or a Hyperkinetic beta subunit SEQ ID NO: 102 and/or 103, in the case of the G-protein coupled receptor SEQ ID NO: 177, 178 and/or 179, and in the case of the SK-channel SEQ ID NO: 239 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71, in the case of the shaker channel and/or a Hyperkinetic beta subunit SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128, in the case of the G-protein coupled receptor SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226, and in the case of the SK-channel SEQ ID NO: 240, 241, 242, 243, 244, 245, 246, 247, 248, 249, 250, 251, 252 and 253 respectively and in one another embodiment, the present invention relates to a polypeptide comprising or consisting of the consensus sequence as shown in SEQ ID NO: 33 and/or 34, in the case of the shaker channel and/or a Hyperkinetic beta subunit SEQ ID NO: 102 and/or 103, in the case of the G-protein coupled receptor SEQ ID NO: 177, 178 and/or 179, and in the case of the SK-channel SEQ ID NO: 239 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71, in the case of the shaker channel and/or a Hyperkinetic beta subunit SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128, in the case of the G-protein coupled receptor SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226, and in the case of the SK-channel SEQ ID NO: 240, 241, 242, 243, 244, 245, 246, 247, 248, 249, 250, 251, 252 and 253 respectively whereby 20 or less, preferably 15 or 10, preferably 9, 8, 7, or 6, more preferred 5 or 4, even more preferred 3, even more preferred 2, even more preferred 1, most preferred 0 of the amino acids positions indicated can be replaced by any amino acid. In one embodiment not more than 15%, preferably 10%, even more preferred 5%, 4%, 3%, or 2%, most preferred 1% or 0% of the amino acid position indicated by a letter are/is replaced another amino acid. In one embodiment 20 or less, preferably 15 or 10, preferably 9, 8, 7, or 6, more preferred 5 or 4, even more preferred 3, even more preferred 2, even more preferred 1, most preferred 0 amino acids are inserted into a consensus sequence or protein motif.

The consensus sequence was derived from a multiple alignment of the sequences as shown in SEQ ID NO 2, 6, 10, 14, 18, 22, 26 and/or 30, in the case of the shaker channel and/or a Hyperkinetic beta subunit SEQ ID NO 73, 75, 77, 79, 81, 83, 85 and/or 87, in the case of the G-protein coupled receptor SEQ ID NO 130, 134, 138, 142, 146, 150, 154, 158, 162, 166, 170 and/or 174, and in the case of the SK-channel SEQ ID NO 228, 230, 232. The letters represent the one letter amino acid code and indicate that the amino acids are conserved in all aligned proteins. The letter X stands for amino acids, which are not conserved in all sequences.

Conserved domains were identified from all sequences and are described using a subset of the standard Prosite notation, e.g the pattern Y-x(21,23)-[FW] means that a conserved tyrosine is separated by minimum 21 and maximum 23 amino acid residues from either a phenylalanine or tryptophane.

Conserved patterns were identified with the software tool MEME version 3.5.1 or manually. MEME was developed by Timothy L. Bailey and Charles Elkan, Dept. of Computer Science and Engeneering, University of California, San Diego, USA and is described by Timothy L. Bailey and Charles Elkan [Fitting a mixture model by expectation maximization to discover motifs in biopolymers, Proceedings of the Second International Conference on Intelligent Systems for Molecular Biology, pp. 28-36, AAAI Press, Menlo Park, Cali., 1994]. The source code for the stand-alone program is public available from the San Diego Supercomputer center (http://meme.sdsc.edu).

For identifying common motifs in all sequences with the software tool MEME, the following settings were used: -maxsize 500000, -nmotifs 15, -evt 0.001, -maxw 60, -distance 1e-3, -minsites number of sequences used for the analysis. Input sequences for MEME were non-aligned sequences in Fasta format. Other parameters were used in the default settings in this software version.

Prosite patterns for conserved domains were generated with the software tool Pratt version 2.1 or manually. Pratt was developed by Inge Jonassen, Dept. of Informatics, University of Bergen, Norway and is described by Jonassen et al. [I. Jonassen, J. F. Collins and D. G. Higgins, Finding flexible patterns in unaligned protein sequences, Protein Science 4 (1995), pp. 1587-1595; I. Jonassen, Efficient discovery of conserved patterns using a pattern graph, Submitted to CABIOS February 1997]. The source code (ANSI C) for the stand-alone program is public available, e.g. at establisched Bioinformatic centers like EBI (European Bioinformatics Institute).

For generating patterns with the software tool Pratt, following settings were used: PL (max Pattern Length): 100, PN (max Nr of Pattern Symbols): 100, PX (max Nr of consecutive x's): 30, FN (max Nr of flexible spacers): 5, FL (max Flexibility): 30, FP (max Flex.Product): 10, ON (max number patterns): 50. Input sequences for Pratt were distinct regions of the protein sequences exhibiting high similarity as identified from software tool MEME. The minimum number of sequences, which have to match the generated patterns (CM, min Nr of Seqs to Match) was set to at least 80% of the provided sequences. Parameters not mentioned here were used in their default settings.

The Prosite patterns of the conserved domains can be used to search for protein sequences matching this pattern. Various establisched Bioinformatic centers provide public internet portals for using those patterns in database searches (e.g. PIR [Protein Information Resource, located at Georgetown University Medical Center] or ExPASy [Expert Protein Analysis System]). Alternatively, stand-alone software is available, like the program Fuzzpro, which is part of the EMBOSS software package. For example, the program Fuzzpro not only allows to search for an exact pattern-protein match but also allows to set various ambiguities in the performed search.

The alignment was performed with the software ClustalW (version 1.83) and is described by Thompson et al. [Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680]. The source code for the stand-alone program is public available from the European Molecular Biology Laboratory; Heidelberg, Germany. The analysis was performed using the default parameters of ClustalW v1.83 (gap open penalty: 10.0; gap extension penalty: 0.2; protein matrix: Gonnet; pprotein/DNA endgap: −1; protein/DNA gapdist: 4).

Degenerate primers, designed as described above, can then be utilized by PCR for the amplification of fragments of novel coding regions coding for proteins having above-mentioned activity.

These fragments can then be utilized as hybridization probe for isolating the complete gene sequence. As an alternative, the missing 5' and 3' sequences can be isolated by means of RACE-PCR. A nucleic acid molecule according to the invention can be amplified using cDNA or, as an alternative, genomic DNA as template and suitable oligonucleotide primers, following standard PCR amplification techniques. The nucleic acid molecule amplified thus can be cloned into a suitable vector and characterized by means of DNA sequence analysis. Oligonucleotides, which correspond to one of the nucleic acid molecules used in the process, can be generated by standard synthesis methods, for example using an automatic DNA synthesizer.

Nucleic acid molecules which are advantageously for the process according to the invention can be isolated based on their homology to the nucleic acid molecules disclosed herein using the sequences or part thereof as hybridization probe and following standard hybridization techniques under stringent hybridization conditions.

In one embodiment the present invention is directed to a polypeptide encoded by a nucleic acid molecule selected from the group consisting of:
 a) a nucleic acid molecule encoding the polypeptide shown in SEQ ID NO: 2, 6, 10, 14, 18, 22, 26 and/or 30;
 b) a nucleic acid molecule shown in SEQ ID NO: 1, 5, 9, 13, 17, 21, 25 and/or 29;
 c) a nucleic acid molecule, which, as a result of the degeneracy of the genetic code, can be derived from a polypeptide sequence according to SEQ ID NO: 2, 6, 10, 14, 18, 22, 26 and/or 30;

d) a nucleic acid molecule having at least 50% identity with the nucleic acid molecule sequence of a polynucleotide comprising the nucleic acid molecule shown in SEQ ID NO: 1, 5, 9, 13, 17, 21, 25 and/or 29;

e) a nucleic acid molecule encoding a polypeptide having at least 50% identity with the amino acid sequence of the polypeptide encoded by the nucleic acid molecule of (a) to (c) and having the activity of a voltage-gated potassium channel ShaI (Shaker cognate I or Shaker-like) and/or its accessory protein KChIP (potassium channel-interacting protein) respectively;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a voltage-gated potassium channel ShaI (Shaker cognate I or Shaker-like) and/or its accessory protein KChIP (potassium channel-interacting protein) respectively;

h) a nucleic acid molecule encoding a polypeptide comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;

i) nucleic acid molecule which comprises a polynucleotide, which is obtained by amplifying a cDNA library or a genomic library using the primers in SEQ ID NO: 7, 8; 9, 10; 11, 12; respectively and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a voltage-gated potassium channel ShaI (Shaker cognate I or Shaker-like) and/or its accessory protein KChIP (potassium channel-interacting protein) respectively.

In the case of theshaker channel and/or a Hyperkinetic beta subunit, in one embodiment the present invention is directed to a polypeptide encoded by a nucleic acid molecule selected from the group consisting of:

a) a nucleic acid molecule encoding the polypeptide shown in SEQ ID NO: 73, 75, 77, 79, 81, 83, 85 and/or 87;

b) a nucleic acid molecule shown in SEQ ID NO: 72, 74, 76, 78, 80, 82, 84 and/or 86;

c) a nucleic acid molecule, which, as a result of the degeneracy of the genetic code, can be derived from a polypeptide sequence according to SEQ ID NO: 73, 75, 77, 79, 81, 83, 85 and/or 87;

d) a nucleic acid molecule having at least 50% identity with the nucleic acid molecule sequence of a polynucleotide comprising the nucleic acid molecule shown in SEQ ID NO: 72, 74, 76, 78, 80, 82, 84 and/or 86;

e) a nucleic acid molecule encoding a polypeptide having at least 50% identity with the amino acid sequence of the polypeptide encoded by the nucleic acid molecule of (a) to (c) and having the activity of a Shaker channel and/or a Hyperkinetic beta subunit, preferably H-kv beta subunit A or C subtype respectively;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a Shaker channel and/or a Hyperkinetic beta subunit, preferably H-kv beta subunit A or C subtype respectively;

h) a nucleic acid molecule encoding a polypeptide comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;

i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a Shaker channel and/or a Hyperkinetic beta subunit, preferably H-kv beta subunit A or C subtype respectively.

In the case of the G-protein coupled receptor, in one embodiment the present invention is directed to a polypeptide encoded by a nucleic acid molecule selected from the group consisting of:

a) a nucleic acid molecule encoding the polypeptide shown in SEQ ID NO: 130, 134, 138, 142, 146, 150, 154, 158, 162, 166, 170 and/or 174;

a nucleic acid molecule shown in SEQ ID NO: 129, 133, 137, 141, 145, 149, 153, 157, 161, 165, 169 and/or 173 a nucleic acid molecule, which, as a result of the degeneracy of the genetic code, can be derived from a polypeptide sequence according to SEQ ID NO: 130, 134, 138, 142, 146, 150, 154, 158, 162, 166, 170 and/or 174;

d) a nucleic acid molecule having at least 50% identity with the nucleic acid molecule sequence of a polynucleotide comprising the nucleic acid molecule shown in SEQ ID NO: 129, 133, 137, 141, 145, 149, 153, 157, 161, 165, 169 and/or 173;

e) a nucleic acid molecule encoding a polypeptide having at least 50% identity with the amino acid sequence of the polypeptide encoded by the nucleic acid molecule of (a) to (c) and having the activity of a octopamine receptor selected from the group consisting of oa2, preferably from *Drosophila melanogaster*, Oamb, Oct-beta-2R and Oct-beta-3R;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a octopamine receptor selected from the group consisting of oa2, preferably from *Drosophila melanogaster*, Oamb, Oct-beta-2R and Oct-beta-3R;
h) a nucleic acid molecule encoding a polypeptide comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively;
i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156, 159, 160; 163, 164; 167, 168; 171, 172 and/or 175, 176 and
j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a octopamine receptor selected from the group consisting of oa2, preferably from *Drosophila melanogaster*, Oamb, Oct-beta-2R and Oct-beta-3R.

In the case of the SK-channel, in one embodiment the present invention is directed to a polypeptide encoded by a nucleic acid molecule selected from the group consisting of:
a) a nucleic acid molecule encoding the polypeptide shown in SEQ ID NO: 230, 232;
b) a nucleic acid molecule shown in SEQ ID NO: 229, 231;
c) a nucleic acid molecule, which, as a result of the degeneracy of the genetic code, can be derived from a polypeptide sequence according to SEQ ID NO: 230, 232;
d) a nucleic acid molecule having at least 50% identity with the nucleic acid molecule sequence of a polynucleotide comprising the nucleic acid molecule shown in SEQ ID NO: 229, 231;
e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;
f) nucleic acid molecule which hybridizes with a nucleic acid molecule of (a) to (c) under stringent hybridization conditions;
g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;
h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;
i) nucleic acid molecule which comprises a polynucleotide, which is obtained by amplifying a cDNA library or a genomic library using the primers in SEQ ID NO: 233, 234, 235, 236; and 237, 238; respectively and
j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel.

In one embodiment the present invention is directed to a membrane comprising the polypeptide of the invention, whereby the membrane has not shown endogenous activity of the polypeptide of the invention.

In one embodiment the present invention is directed to a host cell comprising the polypeptide of the invention, whereby the membrane of the host has not shown endogenous activity of the polypeptide of the invention.

The wording "the membrane has not shown originally the activity of the polypeptide of the invention" means, that a polypeptide of the invention is not part of the natural occuring membrane, but it was assembled into the membrane according to a method of the invention.

In one embodiment the method of the present invention comprise the expression of a gene coding for a polypeptide with the activity of
i) an insect voltage-gated potassium channel ShaI (Shaker cognate I or Shaker-like) and/or its accessory protein KChIP (potassium channel-interacting protein) respectively in the membrane of a host cell, or
ii) an insect Shaker channel and/or a Hyperkinetic beta subunit, preferably H-kv beta subunit A or C subtype respectively in the membrane of a host cell, or
iii) an insect octopamine receptor selected from the group consisting of oa2, preferably from *Drosophila melanogaster*, Oamb, Oct-beta-2R and Oct-beta-3R in the membrane of a host cell, or
iv) an insect small-conductance Ca2+-activated potassium channel in the membrane of a host cell.

In one embodiment the host cell is a mammalian cell.

In one embodiment the host cell is a cell that in its native state has low or uninteresting electric activity. In contrast, a host cell expressing the polypeptide of the invention shows conductivity selected from the group of intervals 2-20 pS, 3-20 pS, 4-15 pS, 5-12 pS and 5-10 pS.

In one embodiment the host cell is selected from the group consisting of CHO-cells, HEK293, COS, HeLa, NIH3T3, BAK21, Jurkat, CV-1, HepC-2-, *Xenopus* oocyte; Sf9, S2, Sf21, Hi5, Pc12, U2OS.

For the production of the host cell of the invention comprising the polypeptide of the invention with the activity of
i) a ion channel and/or its accessory protein, a nucleotide sequence encoding the polypeptide, or
ii) a ion channel and/or a Hyperkinetic beta subunit, preferably H-kv beta subunit A or C subtype, a nucleotide sequence encoding the polypeptide, or
iii) an octopamine receptor and preferably additionally a marker protein, e.g. GFP, and/or additionally a "promiscuous" G-protein at least one nucleotide sequence encoding the polypeptides, or
iv) a ion channel a nucleotide sequence encoding the polypeptide is introduced into the host cell where it is recombinantly produced.
is introduced into the host cell where it is recombinantly produced.

In one embodiment the host cell is a microorganism in which the nucleotide sequence encoding the polypeptide with the activity of i) a potassium ion channel of the invention and/or its accessory protein, or ii) a potassium ion channel of the invention and/or a Hyperkinetic beta subunit, preferably H-kv beta subunit A or C subtype, or iii) an octopamine receptor of the invention and preferably additionally a marker protein, e.g. GFP, and/or additionally a "promiscuous" G-protein, or iv) a channel of the invention is introduce in order to manifold said nucleotide sequence according to the general cloning techniques as are described, for example, in T. Maniatis, E. F. Fritsch and J. Sambrook, "Molecular Cloning: A Laboratory Manual", Cold Spring Harbor Laboratory, Cold Spring Harbor, N.Y. (1989).

The above mentioned nucleic acid molecules can be cloned into a nucleic acid constructs or vectors according to the invention in combination together with further genes, or else different genes are introduced by transforming several nucleic acid constructs or vectors (including plasmids) into a host cell.

Accordingly, the invention also relates to a nucleic acid construct, preferably to an expression construct, comprising the nucleic acid molecule or molecules used in the process of the present invention or a fragment thereof functionally linked to one or more regulatory elements or signals. Furthermore the invention also relates to a nucleic acid constructs for the production of homologous recombination events, comprising the nucleic acids molecule used in the process of the present invention or parts thereof.

The nucleic acid construct can also comprise further genes, which are to be introduced into the host cells.

As described herein, regulator sequences or factors can have a positive effect on preferably the expression of the constructs introduced, thus increasing it. Thus, an enhancement of the regulator elements may advantageously take place at the transcriptional level by using strong transcription signals such as promoters and/or enhancers. In addition, however, an enhancement of translation is also possible, for example by increasing RNA stability.

Thus, the nucleic acid construct of the invention can be used as expression cassette and thus can be used directly for introduction into the host cell, or else they may be introduced into a vector. Accordingly in one embodiment the nucleic acid construct is an expression cassette comprising a microorganism promoter or a microorganism terminator or both. In another embodiment the expression cassette encompasses a eukaryotic promoter or a eukaryotic terminator or both.

If it is intended to transform the host cell with several constructs or vectors, the marker of a preceding transformation must be removed or a further marker employed in a following transformation. The markers can be removed from the host cell as described in the state of art via methods with which the skilled worker is familiar.

In one embodiment, the nucleic acid sequences used in the method according to the invention can be advantageously linked operably to one or more regulatory signals in order to increase gene expression.

These regulatory sequences are intended to enable the specific expression of nucleic acid molecules, e.g. the genes or gene fragments or of the gene products or the nucleic acid used in the process of the invention. Depending on the host organism for example eukaryotic cell or microorganism, this may mean, for example, that the gene or gene constructs is expressed and/or overexpressed after induction only, or that it is expressed and/or overexpressed constitutive. These regulatory sequences are, for example, sequences to which the inductors or repressors bind and which thus regulate the expression of the nucleic acid. Moreover, the gene construct can advantageously also comprise one or more of what are known as enhancer sequences in operable linkage with the promoter, and these enable an increased expression of the nucleic acid sequence. Also, it is possible to insert additional advantageous sequences at the 3' end of the DNA sequences, such as, for example, further regulatory elements or terminators.

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest.

In the case of theshaker channel and/or a Hyperkinetic beta subunit, in one embodiment of the invention a Kozak sequence is used.

The nucleic acid molecules, which encode proteins according to the invention and nucleic acid molecules, which encode other polypeptides may be present in one nucleic acid construct or vector or in several ones. In one embodiment, only one copy of the nucleic acid molecule for use in the process of the invention or its encoding genes is present in the nucleic acid construct or vector. Several vectors or nucleic acid construct or vector can be expressed together in the host organism. The nucleic acid molecule or the nucleic acid construct according to the invention can be inserted in a vector and be present in the cell in a free form. If a stable transformation is preferred, a vector is used, which is stably duplicated over several generations or which or a part of which is else be inserted into the genome. In the case of mammalian cells, integration into the nuclear genome may have taken place. For the insertion of more than one constructs in the host genome the constructs to be expressed might be present together in one vector, for example in above-described vectors bearing a plurality of constructs.

As a rule, regulatory sequences for the expression rate of a constructs are located upstream (5'), within, and/or downstream (3') relative to the sequence of the nucleic acid molecule to be regulated. They control in particular transcription and/or translation and/or the transcript stability. The expression level is dependent on the conjunction of further cellular regulatory systems, such as the protein biosynthesis and degradation systems of the cell.

Regulatory sequences include transcription and translation regulating sequences or signals, e.g. sequences located upstream (5'), which concern in particular the regulation of transcription or translation initiation, such as promoters or start codons, and sequences located downstream (3'), which concern in particular the regulation of transcription or translation termination and transcript stability, such as polyadenylation signals or stop codons.

Promoters, which are particularly advantageous, are constitutive, tissue or compartment specific and inducible promoters. In general, "promoter" is understood as meaning, in the present context, a regulatory sequence in a nucleic acid molecule, which mediates the expression of a coding sequence segment of a nucleic acid molecule. In principle, it is possible to use natural promoters together with their regulatory sequences. Some promoters for mammalian cells are for example CMV, SV40, TK, Beta-actin.

The nucleic acid construct is advantageously constructed in such a way that a promoter is followed by a suitable cleavage site for insertion of the nucleic acid to be expressed, advantageously in a polylinker, followed, if appropriate, by a terminator located behind the polylinker. If appropriate, this order is repeated several times so that several genes are combined in one construct and thus can be introduced into the transgenic plant in order to be expressed. The sequence is a for example repeated up to three times. For the expression, the nucleic acid sequences are inserted via the suitable cleavage site, for example in the polylinker behind the promoter. It is advantageous for each nucleic acid sequence to have its own promoter and, if appropriate, its own terminator, as mentioned above. However, it is also possible to insert several nucleic acid sequences behind a promoter and, if appropriate, before a terminator, in particular, if a polycistronic transcription is possible in the host or target cells. In this context, the insertion site, or the sequence of the nucleic acid molecules inserted, in the nucleic acid construct is not decisive, that is to say a nucleic acid molecule can be inserted in the first or last position in the cassette without this having a substantial effect on the expression. However, it is also possible to use only one promoter type in the construct.

One embodiment of the present invention also relates to a method for generating a vector, which comprises the insertion, into a vector, of the nucleic acid molecule characterized herein, the nucleic acid molecule according to the invention or the expression cassette according to the invention. The vector can, for example, be introduced into a cell, e.g. a microorganism or a mammalian cell, as described herein for the nucleic acid construct, or below under transformation or transfection or shown in the examples. A transient or stable transformation of the host or target cell is possible, however, a stable transformation is preferred.

The vector according to the invention is preferably a vector, which is suitable for expressing the polypeptide according to the invention in a cell, preferable a mammalian cell. The method can thus also encompass one or more steps for integrating regulatory signals into the vector, in particular signals, which mediate the expression in an organism such as a microorganism or mammalian cell.

Accordingly, the present invention also relates to a vector comprising the nucleic acid molecule characterized herein as part of a nucleic acid construct suitable for plant expression or the nucleic acid molecule according to the invention.

A advantageous vector used in the process of the invention, e.g. the vector of the invention, comprises a nucleic acid molecule which encodes a nucleic acid molecule which is used in the method of the invention, or a nucleic acid construct suitable for the expression in a cell comprising the nucleic acid molecules usable in the method of the invention as described above, either alone or in combination with further genes such as marker or selection genes.

Accordingly, the recombinant expression vectors which are advantageously used in the method of the invention comprise the nucleic acid molecules used in the method according to the invention or the nucleic acid construct according to the invention in a form which is suitable for expressing a nucleic acid molecule comprising a polynucleotide as shown in SEQ ID NO 2, 6, 10, 14, 18, 22, 26 and/or 30, in the case of the shaker channel and/or a Hyperkinetic beta subunit SEQ ID NO 73, 75, 77, 79, 81, 83, 85 and/or 87, in the case of the G-protein coupled receptor SEQ ID NO 130, 134, 138, 142, 146, 150, 154, 158, 162, 166, 170 and/or 174, and in the case of the SK-channel SEQ ID NO 228, 230, 232, or a homologue thereof and/or in the same time expressing, in a host cell, additional genes, which are accompanied by the nucleic acid molecules according to the invention or described herein. Accordingly, the recombinant expression vectors comprise one or more regulatory signals selected on the basis of the host cells to be used for the expression, in operable linkage with the nucleic acid sequence to be expressed.

In accordance with the invention, the term "vector" refers to a nucleic acid molecule, which is capable of transporting another nucleic acid to which it is linked. One type of vector is a "plasmid", which means a circular double-stranded DNA loop into which additional DNA segments can be ligated. A further type of vector is a viral vector, it being possible to ligate additional DNA segments into the viral genome. Certain vectors are capable of autonomous replication in a host cell into which they have been introduced (for example bacterial vectors with bacterial replication origin). Other preferred vectors are advantageously completely or partly integrated into the genome of a host cell when they are introduced into the host cell and thus replicate together with the host genome. Moreover, certain vectors are capable of controlling the expression of genes with which they are in operable linkage. In the present context, these vectors are referred to as "expression vectors". As mentioned above, they are capable of autonomous replication or may be integrated partly or completely into the host genome. Expression vectors, which are suitable for DNA recombination techniques usually, take the form of plasmids. In the present description, "plasmid" and "vector" can be used interchangeably since the plasmid is the most frequently used form of a vector. However, the invention is also intended to encompass these other forms of expression vectors, such as viral vectors, which exert similar functions. The term vector is furthermore also to encompass other vectors which are known to the skilled worker, such as phages, viruses such as SV40, CMV, TMV, transposons, IS elements, phasmids, phagemids, cosmids, and linear or circular DNA.

In a recombinant expression vector, "operable linkage" means that the nucleic acid molecule of interest is linked to the regulatory signals in such a way that expression of the genes is possible: they are linked to one another in such a way that the two sequences fulfill the predicted function assigned to the sequence (for example in an in-vitro transcription/translation system, or in a host cell if the vector is introduced into the host cell).

The term "regulatory sequence" is intended to comprise promoters, enhancers and other expression control elements (for example polyadenylation signals). These regulatory sequences are described, for example, in Goeddel: Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., Ed.: Glick and Thompson, chapter 7, 89-108, including the references cited therein. Regulatory sequences encompass those, which control the constitutive expression of a nucleotide sequence in many types of host cells and those which control the direct expression of the nucleotide sequence in specific host cells only, and under specific conditions. The skilled worker knows that the design of the expression vector may depend on factors such as the selection of the host cell to be transformed, the extent to which the protein amount is reduced, and the like. A preferred selection of regulatory sequences is described above, for example promoters, terminators, enhancers and the like. The term regulatory sequence is to be considered as being encompassed by the term regulatory signal. Several advantageous regulatory sequences, in particular promoters and terminators are described above. In general, the regulatory sequences described as advantageous for nucleic acid construct suitable for expression are also applicable for vectors.

As an alternative, the nucleic acid sequences can be expressed in insect cells using baculovirus expression vectors. Baculovirus vectors which are available for expressing proteins in cultured insect cells (for example Sf9 cells) encompass the pAc series (Smith et al. (1983) Mol. Cell Biol. 3:2156-2165) and the pVL series (Lucklow and Summers (1989) Virology 170:31-39). The abovementioned vectors are only a small overview of potentially suitable vectors. Further plasmids are known to the skilled worker and are described, for example, in: Cloning Vectors (Ed. Pouwels, P. H., et al., Elsevier, Amsterdam-New York-Oxford, 1985, ISBN 0 444 904018). Further suitable expression systems for prokaryotic and eukaryotic cells, see the chapters 16 and 17 by Sambrook, J., Fritsch, E. F., and Maniatis, T., Molecular Cloning: A Laboratory Manual, 2nd Edition, Cold Spring Harbor Laboratory, Cold Spring Harbor Laboratory Press, Cold Spring Harbor, N.Y., 1989.

Accordingly, one embodiment of the invention relates to a vector comprising a nucleic acid molecule for use in the process according to the invention or a nucleic acid construct for use in the method of the invention, e.g. the nucleic acid molecule or the nucleic acid construct of the invention. Said vector is useful for the transfection or transformation of host cells in order to provide the expression of the polypeptide according to the invention. Advantageously said nucleic acid molecule is in an operable linkage with regulatory sequences for the expression in a prokaryotic or eukaryotic, or in a prokaryotic and an eukaryotic host. Furthermore vectors which are suitable for homologous recombination are also within the scope of the invention.

Accordingly, one embodiment of the invention relates to a host cell, which has been transformed stably or transiently with the vector usable in the process of the invention, in particular with the vector according to the invention or the nucleic acid molecule according to the invention or the nucleic acid construct according to the invention, whereby the membrane of the host has not shown endogenously the activity of the polypeptide of the invention.

A further embodiment of the invention also relates to a method for the generation of a transgenic host cell, e.g. a eukaryotic or prokaryotic host or host cell, preferably a transgenic mammalian cell which comprises introducing, into the host cell, the nucleic acid construct according to the invention, the vector according to the invention, or the nucleic acid molecule according to the invention, whereby the membrane of the host has not shown endogenously the activity of the polypeptide of the invention.

Vector DNA can be introduced into prokaryotic or eukaryotic cells via conventional transformation or transfection techniques. The terms "transformation" and "transfection" include conjugation and transduction and, as used in the present context, are intended to encompass a multiplicity of prior-art methods for introducing foreign nucleic acid molecules (for example DNA) into a host cell, including calcium phosphate coprecipitation or calcium chloride coprecipitation, DEAE-dextran-mediated transfection, PEG-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., $2^{nd}$ Ed., Cold Spring Harbor Laboratory, Cold Spring Harbor Laboratory Press, Cold Spring Harbor, N.Y., 1989) and in other laboratory handbooks such as Methods in Molecular Biology, 1995, Vol. 44, Agrobacterium protocols, Ed.: Gartland and Davey, Humana Press, Totowa, N.J.

To select for the successful transfer of a nucleic acid molecule, vector or nucleic acid construct into a host organism, it is advantageous to use marker genes as have already been described above in detail. It is known of the stable or transient integration of nucleic acids into plant cells that only a minority of the cells takes up the foreign DNA and, if desired, integrates it into its genome, depending on the expression vector used and the transfection technique used. To identify and select these integrants, a gene encoding for a selectable marker (as described above, for example resistance to antibiotics) is usually introduced into the host cells together with the gene of interest. Preferred selectable markers are, for example, markers, which encode genes involved in a resistance, preferably gene for resistance to antibiotics, or in biosynthetic pathways of, for example, sugars or amino acids, such as 1-galactosidase, ura3 or ilv2. Markers, which encode genes such as luciferase, gfp or other fluorescence genes, are likewise suitable. These markers and the aforementioned markers can be used in mutants in whom these genes are not functional since, for example, they have been deleted by conventional methods. Furthermore, nucleic acid molecules, which encode a selectable marker, can be introduced into a host cell on the same vector as those, which encode the nucleotide acid molecule used in the process or else in a separate vector. Cells which have been transfected stably with the nucleic acid molecule introduced can be identified for example by selection (for example, cells which have integrated the selectable marker survive whereas the other cells die).

"Reporter genes" encode readily quantifiable proteins, as the above mentioned marker genes. The transformation efficacy or the expression site or timing can be assessed by means of these genes via growth assay, fluorescence assay, chemoluminescence assay, bioluminescence assay or resistance assay or via a photometric measurement (intrinsic color) or enzyme activity. Very especially preferred in this context are reporter proteins (Schenborn E, Groskreutz D. Mol Biotechnol. 1999; 13(1):29-44) such as the "green fluorescent protein" (GFP) (Gerdes H H and Kaether C, FEBS Lett. 1996; 389(1):44-47; Chui W L et al., Curr Biol 1996, 6:325-330; Leffel S M et al., Biotechniques. 23(5):912-8, 1997), chloramphenicol acetyltransferase, a luciferase (Giacomin, Plant Sci 1996, 116:59-72; Scikantha, J Bact 1996, 178:121; Millar et al., Plant Mol Biol Rep 1992 10:324-414), and luciferase genes in general, beta-galactosidase or beta-glucuronidase (Jefferson et al., EMBO J. 1987, 6, 3901-3907) or the Ura3 gene.

"Selection markers" confer resistance to antibiotics or other toxic compounds: examples which may be mentioned in this context are the neomycin phosphotransferase gene, which confers resistance to the aminoglycoside antibiotics neomycin (G 418), kanamycin, paromycin (Deshayes A et al., EMBO J. 4 (1985) 2731-2737), the sul gene encoding a mutated dihydropteroate synthase (Guerineau F et al., Plant Mol Biol. 1990; 15(1):127-136), the hygromycin B phosphotransferase gene (Gen Bank Accession NO: K 01193) and the she ble resistance gene, which confers resistance to the bleomycin antibiotics, e.g. zeocin. Further examples of selection marker genes are genes which confer resistance to 2-deoxyglucose-6-phosphate (WO 98/45456) or phosphinothricin and the like, or those which confer a resistance to antimetabolites, for example the dhfr gene (Reiss, Plant Physiol. (Life Sci. Adv.) 13 (1994) 142-149). Examples of other genes which are suitable are trpB or hisD (Hartman S C and Mulligan R C, Proc Natl Acad Sci USA. 85 (1988) 8047-8051).

Another suitable gene is the mannose phosphate isomerase gene (WO 94/20627), the ODC (ornithine decarboxylase) gene (McConlogue, 1987 in: Current Communications in Molecular Biology, Cold Spring Harbor Laboratory, Ed.) or the Aspergillus terreus deaminase (Tamura K et al., Biosci Biotechnol Biochem. 59 (1995) 2336-2338).

In one embodiment the vector or nucleic acid construct of the invention comprises a nucleic acid sequence coding fo an affinity tag. "Affinity tag": this refers to a peptide or polypeptide whose coding nucleic acid sequence can be fused to the nucleic acid sequence encoding the polypeptide of the invention either directly or by means of a linker, using customary cloning techniques. The affinity tag serves for the isolation, concentration and/or specific purification of the recombinant target protein by means of affinity chromatography from total cell extracts. The abovementioned linker can advantageously contain a protease cleavage site (for example for thrombin or factor Xa), whereby the affinity tag can be cleaved from the target protein when required. Examples of usual affinity tags are the "His tag" for example from Quiagen, Hilden, "Strep tag", the "Myc tag" (Invitrogen, Carlsberg), the tag from New England Biolabs which consists of a chitin-binding domain and an intein, the maltose-binding protein (pMal) from New England Biolabs, and what is known as the CBD tag from Novagen. In this context, the affinity tag can be attached to the 5' or the 3' end of the coding nucleic acid sequence with the sequence encoding the target protein.

The nucleic acid molecules of the invention can be used for generating hybridization probes via which functional equivalents of the nucleic acid sequences according to the invention can be isolated. The generation of these probes and the experimental procedure are known. For example, this involves the specific generation of radioactive or nonradioactive probes by means of PCR and the use of suitably labeled oligonucleotides, followed by hybridization experiments. The techniques required for this purpose are mentioned, for example, in T. Maniatis, E. F. Fritsch and J. Sambrook, Molecular Cloning: A Laboratory Manual, Cold Spring Harbor Laboratory, Cold Spring Harbor, N.Y. (1989). The probes in question can furthermore be modified by standard techniques (Lit. SDM or random mutagenesis) in such a way that they can be employed for further purposes, for example as probe which hybridizes specifically with mRNA and the corresponding coding sequences, in order to analyze the corresponding sequences in other organisms. The probe can be used for example for screening a genomic library or a cDNA library of the insect in question or in a computer search for analogous sequences in electronic databases.

"Genetic control sequence": the term "genetic control sequence" is considered as equivalent to the term "regulatory sequence" and describes sequences which have an effect on the transcription and, if appropriate, translation of the nucleic acids according to the invention in prokaryotic or eukaryotic organisms. Examples are promoters, terminators or what are known as "enhancer" sequences. In addition to these control sequences, or instead of these sequences, the natural regulation of these sequences may still be present before the actual structural genes and may, if appropriate, have been genetically modified in such a way that the natural regulation is switched off and the expression of the target gene has been modified, that is to say increased or reduced. The choice of the control sequence depends on the host organism or starting organism. Genetic control sequences furthermore also comprise the 5'-untranslated region, introns or the noncoding 3' region of genes. Control sequences are furthermore understood as meaning those which make possible homologous recombination or insertion into the genome of a host organism or which permit removal from the genome.

"Knock-out transformants" refers to individual transgenic organism in which a specific gene has been inactivated, respectively the activity of a specific gene has been decreased, doew regulated, reduced or deleted in a targeted fashion by means of transformation.

"Natural genetic environment" refers to the natural chromosomal locus in the organism of origin. In the case of a genomic library, the natural genetic environment of the nucleic acid sequence is preferably retained at least in part. The environment flanks the nucleic acid sequence at least 5' or 3' and has a sequence length of at least 50 bp, preferably at least 100 bp, especially preferably at least 500 bp, very especially preferably at least 1 000 bp, and most preferably at least 5 000 bp.

"Reaction time" refers to the time required for carrying out an activity assay until a significant finding regarding an activity is obtained; it depends both on the specific activity of the protein employed in the assay and on the method used and the sensitivity of the apparatus used. The skilled worker is familiar with the determination of the reaction times. In the case of methods for identifying fungicidally active compounds which are based on photometry, the reaction times are generally between >0 and 360 minutes.

"Recombinant DNA" describes a combination of DNA sequences which can be generated by recombinant DNA technology.

"Recombinant DNA technology": generally known techniques for fusing DNA sequences (for example described in Sambrook et al., 1989, Cold Spring Harbor, N.Y., Cold Spring Harbor Laboratory Press).

"Origin of Replication" ensure the multiplication of the expression cassettes or vectors according to the invention in microorganisms and yeasts, for example the pBR322 ori, ColE1 or the P15A on in E. coli (Sambrook et al.: Molecular Cloning. A Laboratory Manual, 2nd ed. Cold Spring Harbor Laboratory Press, Cold Spring Harbor, N.Y., 1989) and the ARS1 on in yeast (Nucleic Acids Research, 2000, 28(10): 2060-2068).

"Target/target protein": the polypeptide of the invention, a protein, with the activity of
i) a potassium ion channel and/or its accessory protein respectively, or
ii) a potassium ion channel and/or a Hyperkinetic beta subunit, preferably H-kv beta subunit A or C subtype, or
iii) a protein, with the activity of an octopamine receptor, or
iv) a potassium ion channel.

All of the targets or sites of action share the characteristic that the functional presence of the target protein is essential for the survival of the insect.

"Transformation" describes a process for introducing heterologous DNA into a prokaryotic or eukaryotic cell. A transformed cell describes not only the product of the transformation process per se, but also all of the transgenic progeny of the transgenic organism generated by the transformation process.

"Transgenic": referring to a nucleic acid sequence, an expression cassette or a vector comprising a nucleic acid sequence according to the invention or an organism transformed with a nucleic acid sequence according to the invention, expression cassette or vector, the term transgenic describes all those constructs which have been generated by genetic engineering methods in which either the nucleic acid sequence of the target protein or a genetic control sequence linked operably to the nucleic acid sequence of the target protein or a combination of the abovementioned possibilities are not in their natural genetic environment or have been modified by recombinant methods. In this context, the modification can be achieved, for example, by mutating one or more nucleotide residues of the nucleic acid sequence in quest.

In one embodiment the present invention is directed to the use of the polypeptide, the membrane or the host cell of the invention as insecticidal target.

The deletion of the gene coding for insect voltage-gated potassium channel ShaI (Shaker cognate I or Shaker-like) and/or its accessory protein KChIP (potassium channel-interacting protein) respectively in *Drosophila melanogaster*, or the inhibition of the activity of the voltage-gated potassium channel ShaI (Shaker cognate I or Shaker-like) and/or its accessory protein KChIP (potassium channel-interacting protein) respectively is lethal for *Drosophila melanogaster*.

Accordingly, in one embodiment the present invention is directed to the use of a polypeptide encoded by a nucleic acid molecule selected from the group consisting of:
  a) a nucleic acid molecule encoding the polypeptide shown in SEQ ID NO: 2, 6, 10, 14, 18, 22, 26 and/or 30;
  b) a nucleic acid molecule shown in SEQ ID NO: 1, 5, 9, 13, 17, 21, 25 and/or 29;
  c) a nucleic acid molecule, which, as a result of the degeneracy of the genetic code, can be derived from a polypeptide sequence according to SEQ ID NO: 2, 6, 10, 14, 18, 22, 26 and/or 30;
  d) a nucleic acid molecule having at least 50% identity with the nucleic acid molecule sequence of a polynucleotide comprising the nucleic acid molecule shown in SEQ ID NO: 2, 6, 10, 14, 18, 22, 26 and/or 30;
  e) a nucleic acid molecule encoding a polypeptide having at least 50% identity with the amino acid sequence of the polypeptide encoded by the nucleic acid molecule of (a) to (c) and having the activity of a voltage-gated potassium channel ShaI (Shaker cognate I or Shaker-like) and/or its accessory protein KChIP (potassium channel-interacting protein) respectively;
  f) nucleic acid molecule which hybridizes with a nucleic acid molecule of (a) to (c) under stringent hybridization conditions;
  g) a nucleic acid molecule encoding a polypeptide which can be isolated with the aid of monoclonal or polyclonal antibodies made against a polypeptide encoded by one of the nucleic acid molecules of (a) to (e) and having the activity of a voltage-gated potassium channel ShaI (Shaker cognate I or Shaker-like) and/or its accessory protein KChIP (potassium channel-interacting protein) respectively;
  h) a nucleic acid molecule encoding a polypeptide comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;
  i) nucleic acid molecule which comprises a polynucleotide, which is obtained by amplifying a cDNA library or a genomic library using the primers in SEQ ID NO: 7, 8; 9, 10; 11, 12; respectively; and
  j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a voltage-gated potassium channel ShaI (Shaker cognate I or Shaker-like) and/or its accessory protein KChIP (potassium channel-interacting protein) respectively, or a homologue thereof as insecticidal target.

In the case of the shaker channel and/or a Hyperkinetic beta subunit, the deletion of the gene coding for insect Shaker channel and/or a Hyperkinetic beta subunit, preferably H-kv beta subunit A or C subtype respectively in *Drosophila melanogaster*, or the inhibition of the activity of the Shaker channel and/or a Hyperkinetic beta subunit, preferably H-kv beta subunit A or C subtype respectively is lethal for *Drosophila melanogaster*.

Accordingly, in one embodiment the present invention is directed to the use of a polypeptide encoded by a nucleic acid molecule selected from the group consisting of:
  a) a nucleic acid molecule encoding a polypeptide comprising the polypeptide shown in SEQ ID NO: 73, 75, 77, 79, 81, 83, 85 and/or 87;
  b) a nucleic acid molecule comprising the nucleic acid molecule shown in SEQ ID NO: 72, 74, 76, 78, 80, 82, 84 and/or 86;
  c) a nucleic acid molecule, which, as a result of the degeneracy of the genetic code, can be derived from a polypeptide comprising a polypeptide sequence according to SEQ ID NO: 73, 75, 77, 79, 81, 83, 85 and/or 87;
  d) a nucleic acid molecule having at least 50% identity with the nucleic acid molecule sequence of a polynucleotide comprising the nucleic acid molecule shown in SEQ ID NO: 73, 75, 77, 79, 81, 83, 85 and/or 87;
  e) a nucleic acid molecule encoding a polypeptide having at least 50% identity with the amino acid sequence of the polypeptide encoded by the nucleic acid molecule of (a) to (c) and having the activity of a Shaker channel and/or a Hyperkinetic beta subunit, preferably H-kv beta subunit A or C subtype respectively;
  f) nucleic acid molecule which hybridizes with a nucleic acid molecule of (a) to (c) under stringent hybridization conditions;
  g) a nucleic acid molecule encoding a polypeptide which can be isolated with the aid of monoclonal or polyclonal antibodies made against a polypeptide encoded by one of the nucleic acid molecules of (a) to (e) and having the activity of a Shaker channel and/or a Hyperkinetic beta subunit, preferably H-kv beta subunit A or C subtype respectively;
  h) a nucleic acid molecule encoding a polypeptide comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;
  i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively;
  and
  j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a Shaker channel and/or a Hyperkinetic beta subunit, preferably H-kv beta subunit A or C subtype respectively, or a homologue thereof as insecticidal target.

In the case of the G-protein coupled receptor, the deletion of the gene coding for insect octopamine receptor selected from the group consisting of oa2, preferably from *Drosophila melanogaster*, Oamb, Oct-beta-2R and Oct-beta-3R in *Drosophila melanogaster* or othe insects, or the inhibition of the activity of the octopamine receptor selected from the group consisting of oa2, preferably from *Drosophila melanogaster*, Oamb, Oct-beta-2R and Oct-beta-3R is lethal for *Drosophila melanogaster* or other insect respectively.

Accordingly, in one embodiment the present invention is directed to the use of a polypeptide encoded by a nucleic acid molecule selected from the group consisting of:

a) a nucleic acid molecule encoding the polypeptide shown in SEQ ID NO: 130, 134, 138, 142, 146, 150, 154, 158, 162, 166, 170 and/or 174;

b) a nucleic acid molecule shown in SEQ ID NO: 129, 133, 137, 141, 145, 149, 153, 157, 161, 165, 169 and/or 173;

c) a nucleic acid molecule, which, as a result of the degeneracy of the genetic code, can be derived from a polypeptide comprising a polypeptide sequence according to SEQ ID NO: 130, 134, 138, 142, 146, 150, 154, 158, 162, 166, 170 and/or 174;

d) a nucleic acid molecule having at least 50% identity with the nucleic acid molecule sequence of a polynucleotide comprising the nucleic acid molecule shown in SEQ ID NO: 130, 134, 138, 142, 146, 150, 154, 158, 162, 166, 170 and/or 174;

e) a nucleic acid molecule encoding a polypeptide having at least 50% identity with the amino acid sequence of the polypeptide encoded by the nucleic acid molecule of (a) to (c) and having the activity of a octopamine receptor selected from the group consisting of oa2, preferably from *Drosophila melanogaster*, Oamb, Oct-beta-2R and Oct-beta-3R;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a octopamine receptor selected from the group consisting of oa2, preferably from *Drosophila melanogaster*, Oamb, Oct-beta-2R and Oct-beta-3R;

h) a nucleic acid molecule encoding a polypeptide comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively;

i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156, 159, 160; 163, 164; 167, 168; 171, 172 and/or 175, 176;

and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a octopamine receptor selected from the group consisting of oa2, preferably from *Drosophila melanogaster*, Oamb, Oct-beta-2R and Oct-beta-3R, or a homologue thereof as insecticidal target.

In the case of the SK-channel, the deletion of the gene coding for insect small-conductance Ca2+-activated potassium channel in *Drosophila melanogaster*, or the inhibition of the activity of the insect small-conductance Ca2+-activated potassium channel is lethal for *Drosophila melanogaster*.

Accordingly, in one embodiment the present invention is directed to the use of a polypeptide encoded by a nucleic acid molecule selected from the group consisting of:

a) a nucleic acid molecule encoding the polypeptide shown in SEQ ID NO: 228, 230, 232;

b) a nucleic acid molecule shown in SEQ ID NO: 227, 229, 231;

c) a nucleic acid molecule, which, as a result of the degeneracy of the genetic code, can be derived from a polypeptide sequence according to SEQ ID NO: 228, 230, 232;

d) a nucleic acid molecule having at least 50% identity with the nucleic acid molecule sequence of a polynucleotide comprising the nucleic acid molecule shown in SEQ ID NO: 228, 230, 232;

e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;

h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;

i) nucleic acid molecule which comprises a polynucleotide, which is obtained by amplifying a cDNA library or a genomic library using the primers in SEQ ID NO: 233, 234, 235, 236; and 237, 238; respectively;

and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel, or a homologue thereof as insecticidal target.

The invention furthermore relates to nucleic acid construct or expression cassettes comprising a) genetic control sequences in operable linkage with a nucleic acid sequence encompassing i) a nucleic acid sequence with the nucleic acid sequence shown in SEQ ID NO 1, 5, 9, 13, 17, 21, 25 and/or 29, in the case of the shaker channel and/or a Hyperkinetic beta subunit SEQ ID NO 72, 74, 76, 78, 80, 82, 84 and/or 86, in the case of the G-protein coupled receptor SEQ ID NO 129, 133, 137, 141, 145, 149, 153, 157, 161, 165, 169 and/or 173, and in the case of the SK-channel SEQ ID NO 227, 229, 231; or ii) a nucleic acid sequence which, on the basis of the degeneracy of the genetic code, can be derived from the amino acid sequence shown in SEQ ID NO 2, 6, 10, 14, 18, 22, 26 and/or 30, in the case of the shaker channel and/or a Hyperkinetic beta subunit SEQ ID NO 73, 75, 77, 79, 81, 83, 85 and/or 87, in the case of the G-protein coupled receptor SEQ ID NO 130, 134, 138, 142, 146, 150, 154, 158, 162, 166, 170 and/or 174, and in the case of the SK-channel SEQ ID NO 228, 230, 232 by back translation; or iii) a functional equivalent of the nucleic acid sequence SEQ ID NO 1, 5, 9, 13, 17, 21, 25 and/or 29, in the case of the shaker channel and/or a Hyperkinetic beta subunit SEQ ID NO 72, 74, 76, 78, 80, 82, 84 and/or 86, in the case of the G-protein coupled receptor SEQ ID NO 129, 133, 137, 141, 145, 149, 153, 157, 161, 165, 169 and/or 173, and in the case of the SK-channel SEQ ID NO 227, 229, 231; and b) additional functional elements; or c) a combination of a) and b)

and to the use of the nucleic acid construct or the expression cassettes comprising a) genetic control sequences in operable linkage with a nucleic acid sequence according to the invention;

b) additional functional elements; or c) a combination of a) and b) in "in vitro" or "in vivo" assay systems.

The invention furthermore relates to the use of the above-mentioned embodiments of the nucleic acid construct or the expression cassettes for expressing the polypeptide of the invention for in-vitro or in-vivo assay systems.

In one embodiment the present invention is directed to the use of the polypeptide, the membrane or the host cell of the invention for identifying compounds with insecticidal activity.

The present invention furthermore relates to the use of a polypeptide of the invention in a method for identifying insecticidal compounds.

A preferred embodiment of the method according to the invention comprises the following steps:

i. bringing a polypeptide of the invention into contact with one or more test compounds under conditions which permit the test compound(s) to bind to the polypeptide of the invention, ii. detecting whether the test compound binds the polypeptide of the invention set forth in i); or iii. detecting whether the test compound reduces or inhibits or blocks the activity of the polypeptide of the invention set forth in i); or iv. detecting whether the test compound reduces or inhibits or blocks the transcription, translation or expression of the polypeptide with the activity of 1. the voltage-gated potassium channel ShaI (Shaker cognate I or Shaker-like) and/or its accessory protein KChIP (potassium channel-interacting protein) respectively set forth in I), or 2. the Shaker channel and/or a Hyperkinetic beta subunit, preferably H-kv beta subunit A or C subtype respectively set forth in i), or 3. the octopamine receptor selected from the group consisting of oa2, preferably from *Drosophila melanogaster*, Oamb, Oct-beta-2R and Oct-beta-3R set forth in i), or 4. the insect small-conductance Ca2+-activated potassium channel set forth in i).

The detection in accordance with step ii or iii of the above method regarding the activity of the polypeptide of the invention can be assessed using a variety of in vitro and in vivo assays, e. g., measuring current, measuring membrane potential, measuring ion flow, e. g., potassium or rubidium, measuring potassium concentration, measuring second messengers and transcription levels, using potassium-dependent yeast growth assays, and using e. g., voltage-sensitive dyes, radioactive tracers, and patch-clamp electrophysiology.

In the case of the G-protein coupled receptor, the detection in accordance with step ii or iii of the above method regarding the activity of the polypeptide of the invention can be assessed using a variety of in vitro and in vivo assays, e. g., measuring current, measuring membrane potential, measuring ion flow, e. g., calcium, preferably measuring calcium concentration, measuring second messengers and transcription levels, using potassium-dependent yeast growth assays, and using e. g., calcium concentration sensitive dyes or radioactive tracers.

The detection in accordance with step ii or iii of the above method can be effected using techniques which identify the interaction between protein and ligand. In this context, either the test compound or the polypeptide can contain a detectable label such as, for example, a fluorescent label, a radioisotope, a chemiluminescent label or an membrane or potentiometric label. Examples of labels are selected from the group consisting blue membrane potential dye from Molecular Devices, ANEP (AminoNaphthylEthenylPyridinium) dyes like di-4-ANEPPS, di-8-ANEPPS, di-2-ANEPEQ+, di-8-ANEPPQ, di-12-ANEPPQ; RH dyes (originally synthesized by Rina Hildesheim), including a serie of dialkylaminophenylpolyenylpyridinium dyes from Molecular Probes like RH 414 (T-1111), RH 795 (R-649) and RH 237 (S-1109). RH 421 (S-1108), or other dyes from Molecular Probes based on Carbocyanine and Oxonol as described in the Seventh Edition of Molecular Probes' Handbook of Fluorescent Probes and Research Chemicals published in 1999.

In the case of the shaker channel and/or a Hyperkinetic beta subunit, in one embodiment of the invention the method of detection whether the test compound reduces or inhibits or blocks the activity of the polypeptide of the invention comprises subjecting CHO-cells stably transfected with a insect Shaker channel and/or a Hyperkinetic beta subunit, preferably H-kv beta subunit A or C subtype respectively, preferably selected from the group consisting of SEQ ID NOs: 72, 74, 76, 78, 80, 82, 84 and/or 86, to loading with at least one of the above mentioned dyes, preferably blue membrane potential dye from Molecular Devices, for 0.1-3 hours, preferably 0.5-1 hours, preferably 0.45 hours, activating the Shaker channel and/or a Hyperkinetic beta subunit, preferably H-kv beta subunit A or C subtype respectively by increasing the extrcellular level of KCl, in a concentration of the EC50 value of 1-120 mM, preferably 10-60 mM, more preferably 50 mM KCl, adding the compound suspected to have the ability to inhibit the activity of the channel, preferably in a concentration of 1 µM-100 mM, 10-10000 µM, preferably 100-1000 µM measuring the luminescence, fluorescence, comparing the data of the luminescence/fluorescence of the dye with a control and determining whether the tested compound has the ability to inhibit the activity of the channel.

In the case of the G-protein coupled receptor, the detection in accordance with step ii or iii of the above method can be effected using techniques which identify the interaction between protein and ligand. In this context, either the test compound or the polypeptide can contain a detectable label such as, for example, a fluorescent label, a radioisotope, a chemiluminescent label or an membrane or potentiometric label. Examples of labels are selected from the group of calcium concentration sensitive dyes, e.g. Fluo-4 Calcium Crimson™, Calcium Green™, Calcium Orange™, Calcium Yellow™, Fura Red™, Oregon Green®, Rhod-3, X-rhod-5F, Fura-2, bis-fura-2, fluo-5F, fluo-5N, fura dextran, fura-4F, fura-5F, fura-6F, fura-FF, fura-FF, quin-2, rhod dextran, rhod-2, rhod-5N or rhod-FF or other dyes from Molecular Probes based on Carbocyanine and Oxonol as described in the Seventh Edition of Molecular Probes' Handbook of Fluorescent Probes and Research Chemicals published in 1999.

In the case of the SK-channel, in one embodiment of the invention the method of detection whether the test compound reduces or inhibits or blocks the activity of the polypeptide of the invention comprises subjecting CHO-cells stably transfected with a insect small-conductance Ca2+-activated potassium channel, preferably selected from the group consisting of SEQ ID NOs: 227, 229, 231, to loading with at least one of the above mentioned dyes, preferably blue membrane potential dye from Molecular Devices, for 2-6 hours, preferably −5 hours, preferably 4 hours, activating the small-conductance Ca2+-activated potassium channel with a ionophore, preferably ionomycin, in a concentration of the EC50 value of 100-500 nM, more preferably 200 nM, meaning incubation the cells in a concentration of 1-5 µM, adding the compound suspected to have the ability to inhibit the activity of the channel in a concentration of 5-50 pM, 5-20 µM, preferably 10 µM measuring the luminescence, fluorescence comparing the data the luminescence/fluorescence of the dye with a control and determining whether the tested compound has the ability to inhibit the activity of the channel.

In one embodiment of the invention the method of detection whether the test compound reduces or inhibits or blocks the activity of the polypeptide of the invention comprises subjecting CHO-cells stably transfected with a insect voltage-gated potassium channel Shal (Shaker cognate I or Shaker-like) and/or its accessory protein KChIP (potassium channel-interacting protein) respectively, preferably selected from the group consisting of SEQ ID NOs: 1, 5, 9, 13, 17, 21, 25 and/or 29, to loading with at least one of the above mentioned dyes, preferably blue membrane potential dye from Molecular Devices, for 0.5-3 hours, preferably 1.5 hours, preferably 2-2.5 hours, activating the voltage-gated potassium channel Shal (Shaker cognate I or Shaker-like) and/or its accessory protein KChIP (potassium channel-interacting protein) respectively by increasing the extrcellular level of KCl, in a concentration of the EC50 value of 10-120 mM, preferably 10-60 mM, more preferably 30 mM KCl, adding the compound suspected to have the ability to inhibit the activity of the channel in a concentration of 1-200 µM, 5-100 µM, preferably 25-30 µM measuring the luminescence, fluorescence comparing the data the luminescence/fluorescence of the dye with a control and determining whether the tested compound has the ability to inhibit the activity of the channel.

The compound suspected of having the ability to inhibit the activity of the polypeptide of the invention is added directly to the bath solution.

Alternatively the detection in accordance with step ii or iii of the above method can be effected using the patch clamp technique.

Several variations of the basic technique can be applied selected from the group consisting of inside-out, outside-out, cell-attached, both excised patch, whole-cell patch and perforated patch techniques.

The subsequent detection depends on the label and is known to the skilled worker.

In one embodiment of the invention the method of detection whether the test compound reduces or inhibits or blocks the activity of the polypeptide of the invention comprises subjecting CHO-cells stably transfected with a insect voltage-gated potassium channel Shal (Shaker cognate I or Shaker-like) and/or its accessory protein KChIP (potassium channel-interacting protein) respectively, preferably selected from the group consisting of SEQ ID NOs: 2, 6, 10, 14, 18, 22, 26 and/or 30, to the whole-cell configuration of the patch-clamp technique at room temperature (22-25° C.), using borosilicate glass capillaries with a resistances of 2-3 MOhm when filled with pipette solution and measured in bath solution, preferably compensating liquid junction potential between bath and pipette solution, measuring membrane current under whole-cell clamp, sampled at 2 kHz and filtered at 1 kHz, holding the cells at −70 mV and applying a family of 400 ms test voltage pulses starting from −100 to +130 mV in 10 mV increments every 2 sec, measuring the amplitude, as measured for the current-voltage relationship, and defining as the maximal outward current at a given depolarizing potential.

In the case of theshaker channel and/or a Hyperkinetic beta subunit, in one embodiment of the invention the method of detection whether the test compound reduces or inhibits or blocks the activity of the polypeptide of the invention comprises subjecting CHO-cells stably transfected with a insect Shaker channel and/or a Hyperkinetic beta subunit, preferably H-kv beta subunit A or C subtype respectively, preferably selected from the group consisting of SEQ ID NOs: 73, 75, 77, 79, 81, 83, 85 and/or 87, to the whole-cell configuration of the patch-clamp technique at room temperature (22-25° C.). The whole-cell voltage-clamp method of the invention comprises for data acquisition and further analysis, using the EPC10 digitally controlled amplifier in combination with PATCHMASTER software (HEKA Electronics, Lambrect, Germany). The EPC10 provides automatic subtraction of capacitance and leakage currents by mean of prepulse. The data are filtered at 66.7 KHz (−3 dB, 8-pole Bessel lowpass) and digitized at 5 µs per point. The input resistance of the patch pipettes is 2.0-4.0 MS/and the capacitances of the cells were 15.3±2.1 pF (n=45); the residual series resistances (after up to 80% compensation) are 4.2±0.4 MΩ. Correction for liquid junction potential is routinely applied. Membrane potential is clamped at −100 mV and currents are elicited by 50 ms depolarization pulses (0.1 Hz) from −60 mV to +100 mV (or +60 mV).

The compound suspected of having the ability to inhibit the activity of the polypeptide of the invention is added directly to the bath solution.

In one embodiment the subtraction of residual capacitance and leak current is performed with an on-line P/4 protocol by pClamp.

In the case of the G-protein coupled receptor, in one embodiment of the invention the method of detection whether the test compound reduces or inhibits or blocks the activity of the polypeptide of the invention comprises subjecting CHO-cells stably expressing the G-alpha-16 promiscuous G protein and stably or transiently expressing a octopamine receptor selected from the group consisting of oa2, preferably from *Drosophila melanogaster*, Oamb, Oct-beta-2R and Oct-beta-3R, preferably selected from the group consisting of SEQ ID NOs: 129, 133, 137, 141, 145, 149, 153, 157, 161, 165, 169 and/or 173, to loading with at least one of the above mentioned dyes, preferably Fluo-4, for 0.1-3 hours, preferably 0.5-2 hours, preferably 1 hour, placing into the FLIPR and run using a two-addition protocol, whereby the test compounds, the compound suspected to have the ability to block or to activate the octopamine receptor, is to be added in the first addition and allowed to incubate for three minutes, the activator octopamine is then to be introduced in the second addition at an EC80 concentration and the fluorescence read for two minutes. Controls will to be run for both additions. An increase in fluorescence above baseline in the first addition will indicate a possible activator and a reduced response or no increase in the second addition may indicate a possible inhibitor.

The subsequent detection depends on the label and is known to the skilled worker.

In the case of the SK-channel, in one embodiment of the invention the method of detection whether the test compound reduces or inhibits or blocks the activity of the polypeptide of the invention comprises subjecting CHO-cells stably transfected with a insect small-conductance Ca2+-activated potassium channel, preferably selected from the group consisting of SEQ ID NOs: 228, 230, 232, to the whole-cell configuration of the patch-clamp technique at room temperature (22-25° C.), using borosilicate glass capillaries with a resistances of 2-3 MOhm when filled with pipette solution and measured in bath solution, preferably compensating liquid junction potential between bath and pipette solution, measuring membrane current under whole-cell clamp, sampled at 2 kHz and filtered at 1 kHz, holding the cells at −70 mV and applying a family of 400 ms test voltage pulses starting from −100 to +130 mV in 10 mV increments every 2 sec, measuring the amplitude, as measured for the current-voltage relationship, and defining as the maximal outward current at a given depolarizing potential.

It is also possible, in the method according to the invention, to employ a plurality of test compounds in a method according to the invention. If a group of test compounds affects the target, then it is either possible directly to isolate the individual test compounds or to divide the group of test compounds into a variety of subgroups, for example when it consists of a multiplicity of different components, in order to reduce the number of the different test compounds in the method according to the invention. The method according to the invention is then repeated with the individual test compound or the relevant subgroup of test compounds. Depending on the complexity of the sample, the above-described steps can be carried out repeatedly, preferably until the subgroup identified in accordance with the method according to the invention only comprises a small number of test compounds, or indeed just one test compound.

The method according to the invention can advantageously be carried out as an HTS procedure.

HTS makes possible the simultaneous testing of a multiplicity of different compounds.

The quality of a high throughput screen is determined by two factors, the relative size of the assay window and the stability of this assay window from control experiment to control experiment (i.e. stability of assay signal across ~20 assay screening plates of controls). This is expressed as the z' factor for the screen and the equation:

$$Z'=1-((3\sigma_{max}+3\sigma_{min})/(I\mu_{max}-\mu_{min}I)).$$

In the case of the SK-channel, the quality of a high throughput screen is determined by two factors, the relative size of the assay window, in this case signal from a fully activated channel minus a the signal from an unactivated channel (usually expressed in arbitrary units). The second factor is the stability of this assay window from control experiment to control experiment (i.e. stability of assay signal across ~20 assay screening plates of controls). This is expressed as the z' factor for the screen and the equation:

$$Z'=1-[3*(\sigma_{max}+\sigma_{min})/\text{Abs}(\text{Ave}(\text{MAX})-\text{Ave}(\text{MIN}))].$$

A calculated Z'>0.5 is considered an excellent assay.

In the case of theshaker channel and/or a Hyperkinetic beta subunit, alternatively for the calculation of the Z' factor the following formula is used:

$$Z' = 1 - \left(\frac{3*(ST.DEV \text{ agonist} + ST.DEV \text{ Tyrode})}{\text{MEAN agonist} - \text{MEAN Tyrode}}\right)$$

In this context preferred embodiments which are also suitable for high-throughput screening methods (HTS) in connection with the present invention, must be mentioned in particular:

1. In accordance with a preferred embodiment, the detection of step ii (and in the case of the SK-channel, variant 3) of the method according to the invention encompasses the following steps: Fluorescent resonance energy transfer (FRET) is based on the irradiation-free energy transfer between two spatially adjacent fluorescent molecules under suitable conditions. A prerequisite is that the emission spectrum of the donor molecule overlaps with the excitation spectrum of the acceptor molecule. By fluorescently labeling UGP and the test compounds, the binding can be measured by means of FRET (Cytometry 34, 1998, pp. 159-179). As an alternative, the method according to the invention may also take the form of the "displacement assay" described under 1. An especially suitable embodiment of FRET technology is "Homogeneous Time Resolved Fluorescence" (HTRF) as can be obtained from Packard BioScience. The compounds which are identified in this manner may be suitable as inhibitors.

2. In accordance with a preferred embodiment, the detection of step ii (and in the case of the SK-channel, variant 3) of the method according to the invention comprises the following steps: The measurement of surface plasmon resonance is based on the change in the refractive index at a surface when a chemical compound binds to a protein which is immobilized to said surface. Since the change in the refractive index is identical for virtually all proteins and polypeptides for a defined change in the mass concentration at the surface, this method can be applied to any protein in principle (Lindberg et al. Sensor Actuators 4 (1983) 299-304; Malmquist Nature 361 (1993) 186-187). The measurement can be carried out for example with the automatic analyzer based on surface plasmon resonance which is available from Biacore (Freiburg) at a throughput of, currently, up to 384 samples per day. A method according to the invention can be designed directly for measuring the binding of the test compound to the UGP. As an alternative, the method according to the invention may also take the form of the "displacement assay" described under 1. The compounds identified in this manner may be suitable as inhibitors.

3. In accordance with a preferred embodiment, the detection of step ii of the method according to the invention comprises the use of FLIPR Membrane Potential Assay Kits from Molecular Devices as disclosed in the examples. The method is based on the application of voltage-sensitive dyes on the FLIPR Fluorometric Imaging Plate Reader system, while showing good correlation with manual patch clamping data.

4. In accordance with a preferred embodiment, the detection of step ii of the method according to the invention comprises the use of BIOMOL Compound Screening or the BioFocus compound screening, using two fluid addition method to permit the detection of activators and antagonists in a single experiment, or subsequent BIOMOL and BioFocus validation screening as disclosed in the examples.

In the case of theshaker channel and/or a Hyperkinetic beta subunit, the method of the invention puts a functional cellular-based assay for the *Drosophila melanogaster* Shaker channel at disposal, preferably developed in CHO-K1 cells by stable pure clone selection and functional characterization with Membrane Potential sensitive dye at FLIPR, preferably for FLIPR384 and/or FLIPRTETRA or both experiments, and electrophysiological techniques.

The generated assay completely fulfil the HTS requirements showing very high signal quality and reproducibility.

For the purposes of high-throughput screening, the following parameters are to be mentioned:
Activator KCl concentration: 50 mM (~EC80) in Activation buffer
Reference Z': 0.60
Minimal acceptable Z' for single assay plate: 0.45
% Inhibition Threshold for Hit: 40%

All of the substances identified via the above mentioned methods can subsequently be checked for their insecticidal action in another embodiment of the method according to the invention.

Furthermore, there exists the possibility of detecting further candidates for insecticidal active ingredients by molecular modeling via elucidation of the three-dimensional structure of the polypeptide of the invention by x-ray structure analysis. The preparation of protein crystals required for x-ray structure analysis, and the relevant measurements and subsequent evaluations of these measurements, the detection of a binding site in the protein, and the prediction of potential inhibitor structures are known to the skilled worker. In principle, an optimization of the active compounds identified by the abovementioned methods is also possible via molecular modeling.

In one embodiment the activity of the polypeptide of the invention incubated with the test compound is compared with the activity of a control a wild type cell or a polypeptide of the invention which has not been incubated with a test compound in step iii.

In this context, compounds are selected in step (iii) which result in a significant decrease in the activity of the polypeptide of the invention, a reduction of at least 10%, advantageously at least 20%, 25%, 29% preferably at least 30%, especially preferably at least 50% and very especially preferably at least 70%, 80%, 90%, 95% 96%, 97%, 98%, 995, or 100% reduction (inhibition), being achieved.

The invention furthermore relates to compounds identified by the methods according to the invention. These compounds are hereinbelow referred to as "selected compounds". They have a molecular weight of less than 1 000 g/mol, advantageously less than 500 g/mol, preferably less than 400 g/mol, especially preferably less than 300 g/mol. Insecticidal active compounds have a Ki value of less than 1 µM, preferably less than 1 µM, especially preferably less than 0.1 µM, very especially preferably less than 0.01 µM.

Substances identified via the above mentioned methods and/or as shown in the examples are depicted in table I:

| Structure | % inhibition | Mol Formula | Mol Weight |
|---|---|---|---|
| 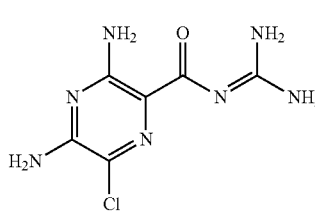<br>Amiloride, 3,5-diamino-6-chloro-N-(diaminomethylene)pyrazine-2-carboxamide<br>CAS number 2016-88-8 | 80-100% | C6H8ClN7O | 229.627 g/mol |
| 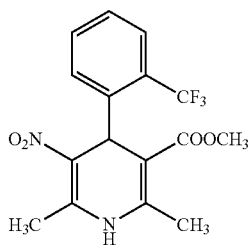 [SMILES: COC(=O)C1=C(C)NC(C)=C([N+](=O)[O-])C1c1ccccc1C(F)(F)F]<br>Bay K8644 | | C16H15F3N2O4 | 356.3 g/mol |

-continued
| Structure | % inhibition | Mol Formula | Mol Weight |
|---|---|---|---|
| 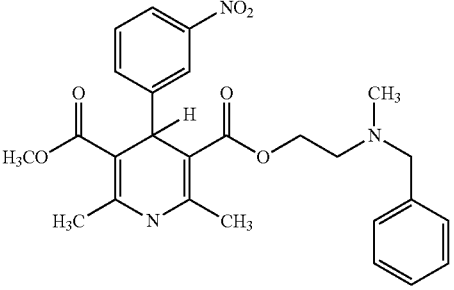 [SMILES: COC(=O)C1=C(C)NC(C)=C(C(=O)OCCN(C)Cc2ccccc2)C1c1cccc([N+](=O)[O-])c1] Nicardipine | | C26H29N3O6 | 479.525 g/mol |
| 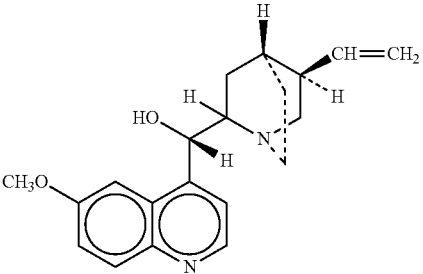 Quinidine, Synonyms (2-ethenyl-4-azabicyclo[2.2.2]oct-5-yl)-(6-methoxyquinolin-4-yl)-methanol 6'-methoxycinchonan-9-ol 6'-methoxy-a-(5-vinyl-2-quinuclidinyl)-4-quinolinemethanol | | C20H24N2O2 | 324.417 g/mol |
| 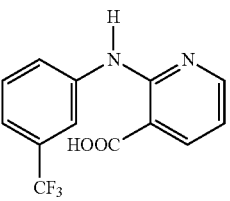 [SMILES: O=C(O)c1cccnc1Nc1cccc(C(F)(F)F)c1] Niflumic acid | | C13H9F3N2O2 | 282.21797 g/mol |
| 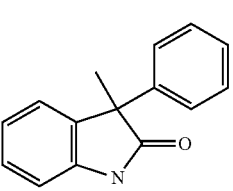 [SMILES: CC1(c2ccccc2)C(=O)Nc2ccccc21] | 42.6 | C15H13NO | 223.28 |
| 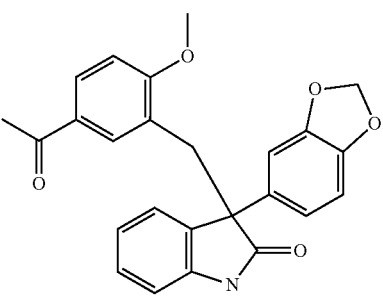 [SMILES: COc1ccc(C(C)=O)cc1CC1(c2ccc3c(c2)OCO3)C(=O)Nc2ccccc21] | 35.2 | C25H21NO5 | 415.45 |

-continued

| Structure | % inhibition | Mol Formula | Mol Weight |
|---|---|---|---|
| 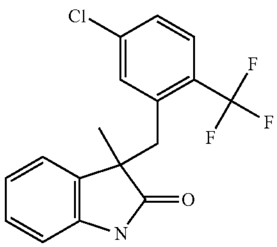 [SMILES: CC1(Cc2cc(Cl)ccc2C(F)(F)F)C(=O)Nc2ccccc21] | 32.5 | C17H13ClF3NO | 339.75 |
| 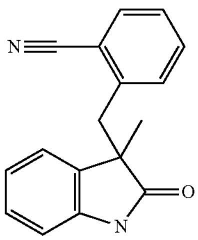 [SMILES: CC1(Cc2ccccc2C#N)C(=O)Nc2ccccc21] | 39.7 | C17H14N2O | 262.31 |
| | 56.8 | C14H13NOS | 243.33 |
| 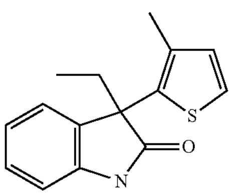 [SMILES: CCC1(c2sccc2C)C(=O)Nc2ccccc21] | 52.0 | C15H15NOS | 257.36 |
| 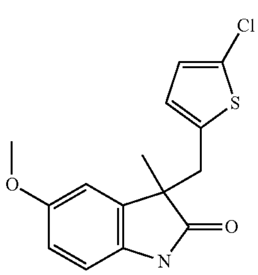 [SMILES: COc1ccc2c(c1)C(C)(Cc1ccc(Cl)s1)C(=O)N2] | 38.3 | C15H14ClNO2S | 307.8 |
| | 56.8 | C20H14ClFN2O | 352.8 |

| Structure | % inhibition | Mol Formula | Mol Weight |
|---|---|---|---|
| 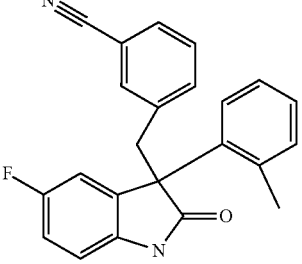 | 55.5 | C23H17FN2O | 356.4 |
| 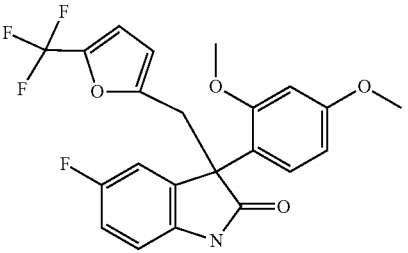 [SMILES: COc1ccc(C2(Cc3ccc(C(F)(F)F)o3)C(=O)Nc3ccc(F)cc32)c(OC)c1] | 60.3 | C22H17F4NO4 | 435.38 |
| 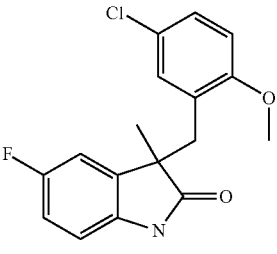 [SMILES: COc1ccc(Cl)cc1CC1(C)C(=O)Nc2ccc(F)cc21] | 32.0 | C17H15ClFNO2 | 319.77 |
| 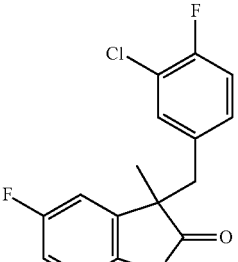 | 52.6 | C16H12ClF2NO | 307.73 |
| 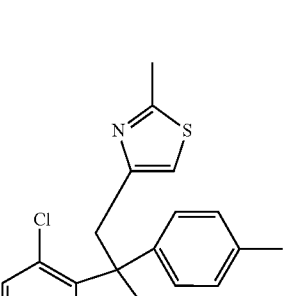 | 46.0 | C20H17ClN2OS | 368.89 |

-continued
| Structure | % inhibition | Mol Formula | Mol Weight |
|---|---|---|---|
| 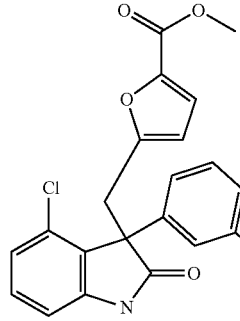 | 41.5 | C21H15ClFNO4 | 399.81 |
| 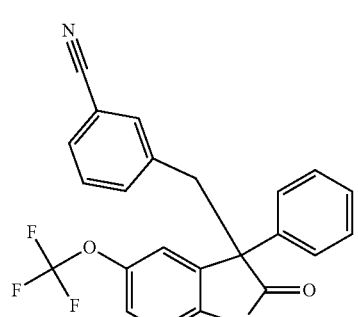 | 32.1 | C23H15F3N2O2 | 408.38 |
| 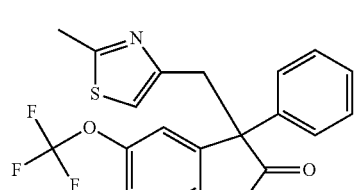 | 31.4 | C20H15F3N2O2S | 404.41 |
| 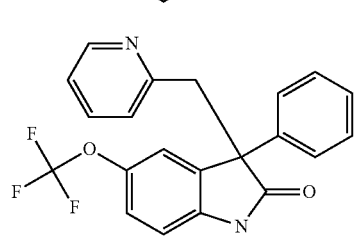 | 39.1 | C21H15F3N2O2 | 384.36 |
| 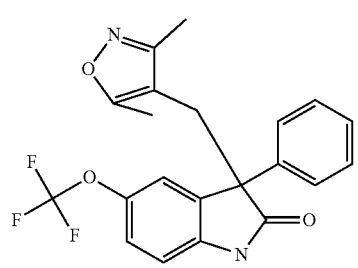 [SMILES: Cc1noc(C)c1CC1(c2ccccc2)C(=O)Nc2ccc(OC(F)(F)F)cc21] | 50.4 | C21H17F3N2O3 | 402.38 |
| 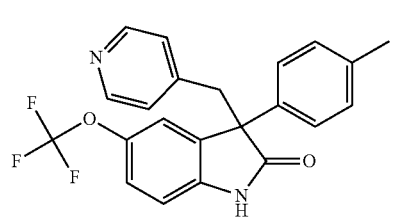 [SMILES: Cc1ccc(C2(Cc3ccncc3)C(=O)Nc3ccc(OC(F)(F)F)cc32)cc1] | 29.1 | C22H17F3N2O2 | 398.39 |

-continued

| Structure | % inhibition | Mol Formula | Mol Weight |
|---|---|---|---|
| 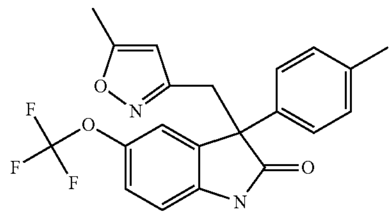 [SMILES: Cc1ccc(C2(Cc3cc(C)on3)C(=O)Nc3ccc(OC(F)(F)F)cc32)cc1] | 40.1 | C21H17F3N2O3 | 402.38 |
| 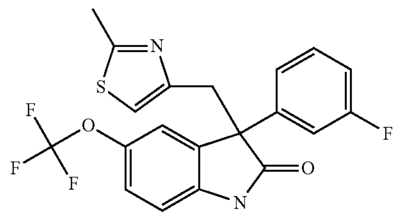 [SMILES: Cc1nc(CC2(c3cccc(F)c3)C(=O)Nc3ccc(OC(F)(F)F)cc32)cs1] | 34.0 | C20H14F4N2O2S | 422.4 |
| 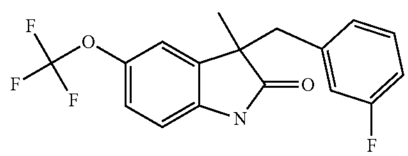 [SMILES: CC1(Cc2cccc(F)c2)C(=O)Nc2ccc(OC(F)(F)F)cc21] | 33.5 | C17H13F4NO2 | 339.29 |
| 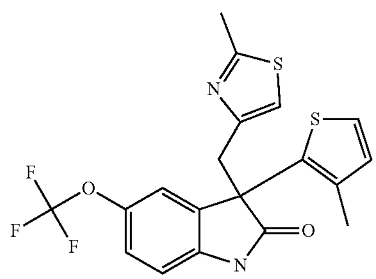 [SMILES: Cc1nc(CC2(c3sccc3C)C(=O)Nc3ccc(OC(F)(F)F)cc32)cs1] | 37.8 | C19H15F3N2O2S2 | 424.47 |
| 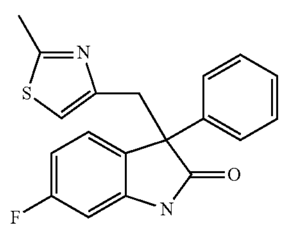 [SMILES: Cc1nc(CC2(c3ccccc3)C(=O)Nc3cc(F)ccc32)cs1] | 42.5 | C19H15FN2OS | 338.41 |
| 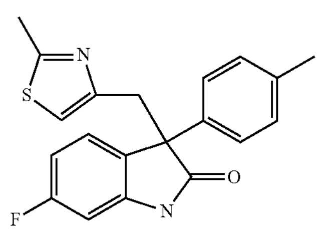 [SMILES: Cc1ccc(C2(Cc3csc(C)n3)C(=O)Nc3cc(F)ccc32)cc1] | 29.3 | C20H17FN2OS | 352.43 |
| 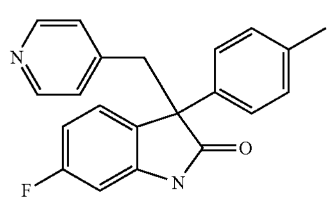 [SMILES: Cc1ccc(C2(Cc3ccncc3)C(=O)Nc3cc(F)ccc32)cc1] | 48.5 | C21H17FN2O | 332.38 |

-continued

| Structure | % inhibition | Mol Formula | Mol Weight |
|---|---|---|---|
| 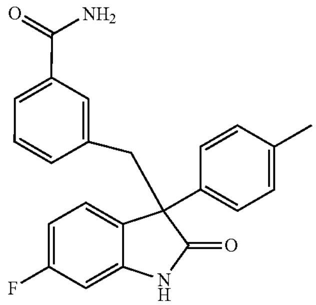 [SMILES: Cc1ccc(C2(Cc3cccc(C(N)=O)c3)C(=O)Nc3cc(F)ccc32)cc1] | 57.5 | C23H19FN2O2 | 374.42 |
| 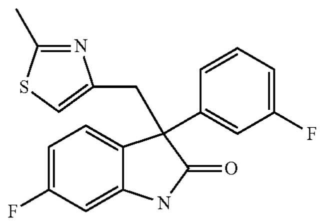 [SMILES: Cc1nc(CC2(c3cccc(F)c3)C(=O)Nc3cc(F)ccc32)cs1] | 37.5 | C19H14F2N2OS | 356.4 |
| 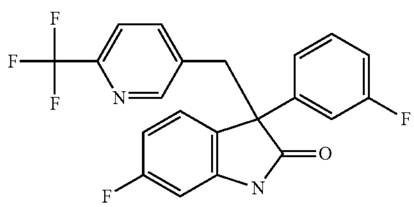 [SMILES: O=C1Nc2cc(F)ccc2C1(Cc1ccc(C(F)(F)F)nc1)c1cccc(F)c1] | 42.7 | C21H13F5N2O | 404.34 |
| 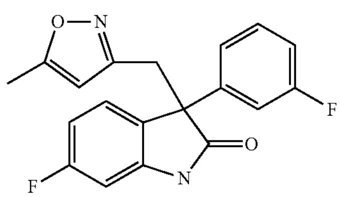 [SMILES: Cc1cc(CC2(c3cccc(F)c3)C(=O)Nc3cc(F)ccc32)no1] | 54.9 | C19H14F2N2O2 | 340.33 |
| 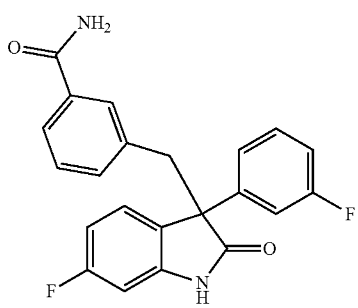 [SMILES: NC(=O)c1cccc(CC2(c3cccc(F)c3)C(=O)Nc3cc(F)ccc32)c1] | 54.1 | C22H16F2N2O2 | 378.38 |
| 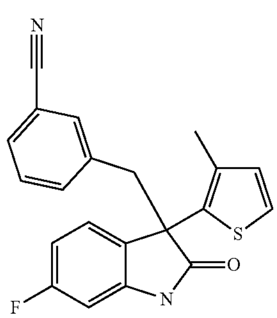 [SMILES: Cc1ccsc1C1(Cc2cccc(C#N)c2)C(=O)Nc2cc(F)ccc21] | 58.0 | C21H15FN2OS | 362.43 |

-continued
| Structure | % inhibition | Mol Formula | Mol Weight |
|---|---|---|---|
| 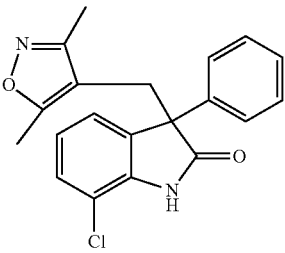 [SMILES: Cc1noc(C)c1CC1(c2ccccc2)C(=O)Nc2c(Cl)cccc21] | 33.0 | C20H17ClN2O2 | 352.82 |
| 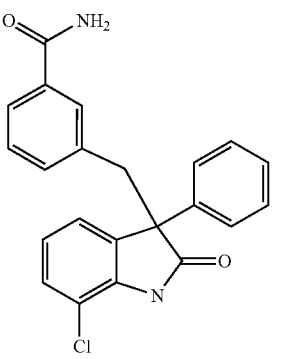 [SMILES: NC(=O)c1cccc(CC2(c3ccccc3)C(=O)Nc3c(Cl)cccc32)c1] | 33.3 | C22H17ClN2O2 | 376.85 |
| 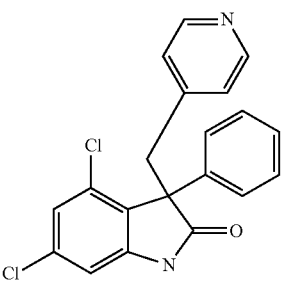 [SMILES: O=C1Nc2cc(Cl)cc(Cl)c2C1(Cc1ccncc1)c1ccccc1] | 36.4 | C20H14Cl2N2O | 369.25 |
| 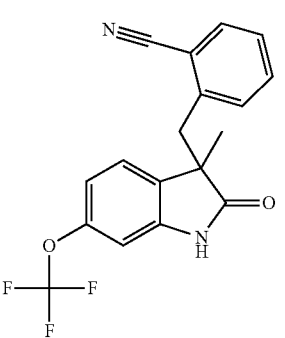 [SMILES: CC1(Cc2ccccc2C#N)C(=O)Nc2cc(OC(F)(F)F)ccc21] | 31.2 | C18H13F3N2O2 | 346.31 |
| 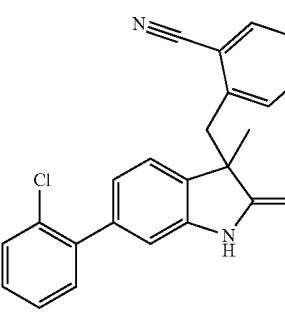 | 63.3 | C23H17ClN2O | 372.86 |

| Structure | % inhibition | Mol Formula | Mol Weight |
|---|---|---|---|
| | 38.7 | C18H16ClFN2O4 | 378.79 |
| 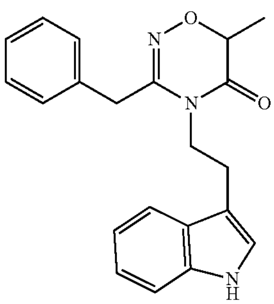 [SMILES: CC1ON=C(Cc2ccccc2)N(CCc2c[nH]c3ccccc23)C1=O] | 29.6 | C21H21N3O2 | 347.42 |
| 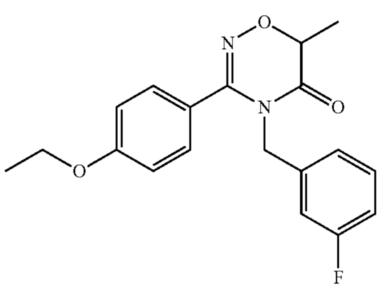 [SMILES: CCOc1ccc(C2=NOC(C)C(=O)N2Cc2cccc(F)c2)cc1] | 52.7 | C19H19FN2O3 | 342.37 |
| | 38.7 | C18H14ClN3O2 | 339.78 |
| 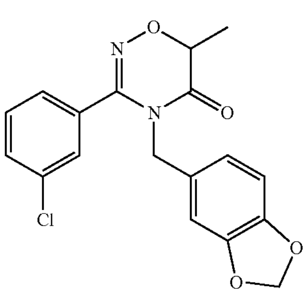 [SMILES: CC1ON=C(c2cccc(Cl)c2)N(Cc2ccc3c(c2)OCO3)C1=O] | 31.5 | C18H15ClN2O4 | 358.78 |

-continued
| Structure | % inhibition | Mol Formula | Mol Weight |
|---|---|---|---|
| 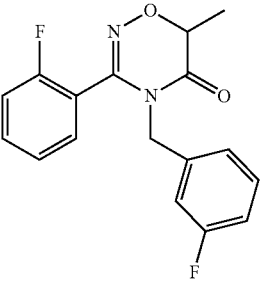 [SMILES: CC1ON=C(c2ccccc2F)N(Cc2cccc(F)c2)C1=O] | 30.2 | C17H14F2N2O2 | 316.31 |
| 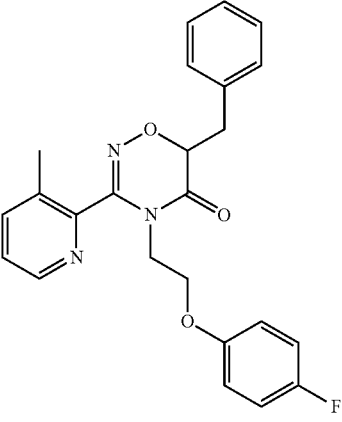 [SMILES: Cc1cccnc1C1=NOC(Cc2ccccc2)C(=O)N1CCOc1ccc(F)cc1] | 36.2 | C24H22FN3O3 | 419.46 |
| 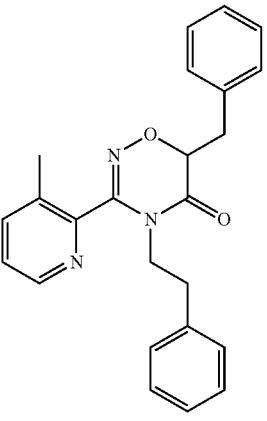 [SMILES: Cc1cccnc1C1=NOC(Cc2ccccc2)C(=O)N1CCc1ccccc1] | 33.3 | C24H23N3O2 | 385.47 |
| 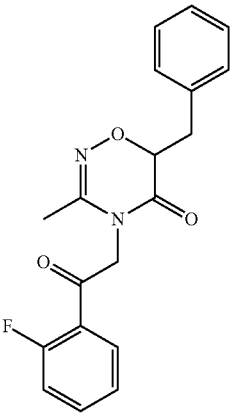 [SMILES: CC1=NOC(Cc2ccccc2)C(=O)N1CC(=O)c1ccccc1F] | 41.6 | C19H17FN2O3 | 340.36 |

| Structure | % inhibition | Mol Formula | Mol Weight |
|---|---|---|---|
| 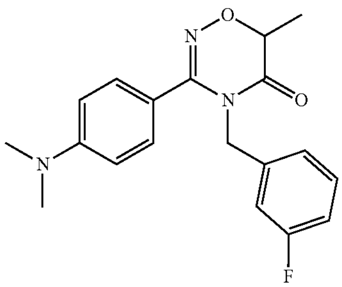 [SMILES: CC1ON=C(c2ccc(N(C)C)cc2)N(Cc2cccc(F)c2)C1=O] | 41.3 | C19H20FN3O2 | 341.39 |
| 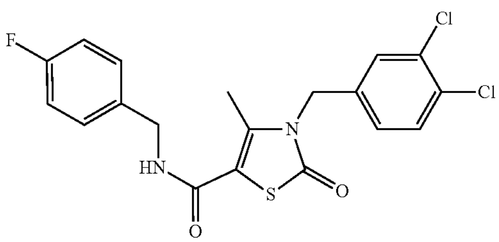 [SMILES: Cc1c(C(=O)NCc2ccc(F)cc2)sc(=O)n1Cc1ccc(Cl)c(Cl)c1] | 38.0 | C19H15Cl2FN2O2S | 425.31 |
| 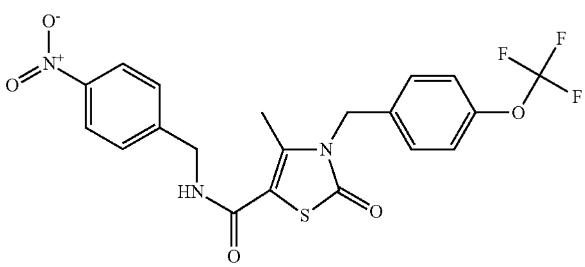 [SMILES: Cc1c(C(=O)NCc2ccc([N+](=O)[O-])cc2)sc(=O)n1Cc1ccc(OC(F)(F)F)cc1] | 30.2 | C20H16F3N3O5S | 467.43 |
| 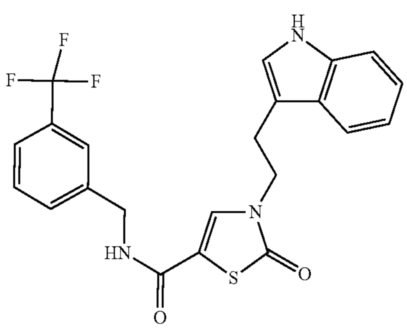 [SMILES: O=C(NCc1cccc(C(F)(F)F)c1)c1cn(CCc2c[nH]c3ccccc23)c(=O)s1] | 35.0 | C22H18F3N3O2S | 445.47 |
| 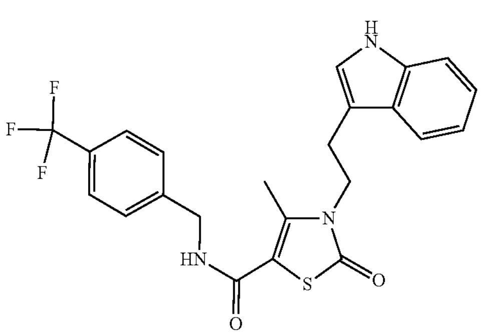 [SMILES: Cc1c(C(=O)NCc2ccc(C(F)(F)F)cc2)sc(=O)n1CCc1c[nH]c2ccccc12] | 33.3 | C23H20F3N3O2S | 459.49 |

-continued

| Structure | % inhibition | Mol Formula | Mol Weight |
|---|---|---|---|
| 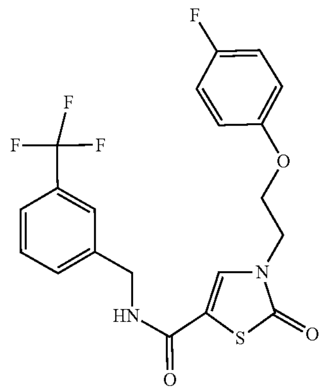 [SMILES: O=C(NCc1cccc(C(F)(F)F)c1)c1cn(CCOc2ccc(F)cc2)c(=O)s1] | 30.2 | C20H16F4N2O3S | 440.42 |
| 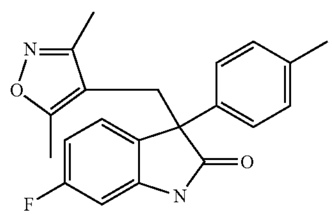 [SMILES: Cc1ccc(C2(Cc3c(C)noc3C)C(=O)Nc3cc(F)ccc32)cc1] | 35.2 | C21H19FN2O2 | 350.4 |

The selected compounds are suitable for controlling insect pests as those mentioned above. Examples of those insects are the selected from the group consisting of Pterygota, Neopetra, Hemiptera, Coleoptera, Diptera, Homoptera, Tenebrionoidea, Tenebrionidae, Tenebrio, Sternorrhyncha, Aphidina, Brachycera, Drosophilidae, Drosophilinae and *Drosophila*, preferably in the case of the SK-channel Green Peach Aphid (*Myzus persica*) and/or Red Flower Beetle (*Tribolium castaneum*).

The selected compounds are suitable for controlling insect pests in agriculture, for protection of crops, forests, urban trees, rangelands, postharvest systems (e.g. stored grains) and natural areas against insect pests as well as in storage of grains and/or food.

The selected compounds are suitable for preventing Infestation, meaning to impede the growth of a pest population that it becomes so large it becomes harmful or unpleasant.

According to the invention, a insect pest is any insect that is undesirable or causes harm to people, property, or the environment. An organism may be a pest in one place but not in another; for example, termites in a house vs. those that recycle dead trees in a forest.

The selected compounds can also be present in the form of their useful salts. Useful salts which are suitable are mainly the salts of those cations, or the acid addition salts of those acids, whose cations, or anions, do not adversely affect the insecticidal action of the insecticidal active compounds identified via the methods according to the invention.

All of the compounds identified via the above methods can, if they contain chiral centers, be subject matter of the present invention in the form of pure enantiomers or diastereomers or in the form of their mixtures and as racemates.

The selected compounds can be chemically synthesized substances or substances produced by microorganisms and can be found, for example, in cell extracts of, for example, plants, animals or microorganisms. The reaction mixture can be a cell-free extract or comprise a cell or cell culture. Suitable methods are known to the SKilled worker and are described generally for example in Alberts, Molecular Biology the cell, $3^{rd}$ Edition (1994), for example chapter 17.

Possible test compounds can be expression libraries such as, for example, cDNA expression libraries, peptides, proteins, nucleic acids, antibodies, small organic substances, hormones, PNAs or the like (Milner, Nature Medicin 1 (1995), 879-880; Hupp, Cell. 83 (1995), 237-245; Gibbs, Cell. 79 (1994), 193-198 and references cited therein).

Compounds with an insecticidal activity according to the invention are selected from the group consisting of TMB-8, Nifedipine, Nitrndipine, Tetrandrine, Verapamil, Methoxy Verapamil, YS035, Propafenone, Quinidine, Sulfonamides, Thiazolidinones, Indolones, Isoxazolylamides.

For use in a method according to the present invention, the compounds can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound identified according to the method of the invention can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:

1. Products for dilution with water. For seed treatment purposes, such products may be applied to the seed diluted or undiluted.

A) Water-soluble concentrates (SL, LS)

10 parts by weight of the active compound is dissolved in 90 parts by weight of water or a water-soluble solvent. As an alternative, wetters or other auxiliaries are added.

The active compound dissolves upon dilution with water, whereby a formulation with 10% (w/w) of active compound is obtained.

B) Dispersible concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-dispersible granules and water-soluble granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-dispersible powders and water-soluble powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds identified according to the method of the invention may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphates: acephate, azamethiphos, azinphos-ethyl, azinphosmethyl, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamates: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-, yfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium and AKD1022.

M.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula M6.1

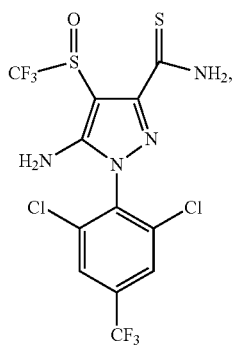

(M$^{6.1}$)

M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. octapaminergic agonsits: amitraz;

M.21. ryanodine receptor modulators: flubendiamide;

M.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, tartar emetic; pyrimidinyl alkynylether compounds M$^{22.1}$ or thiadiazolyl alkynylether compounds M$^{22.2}$:

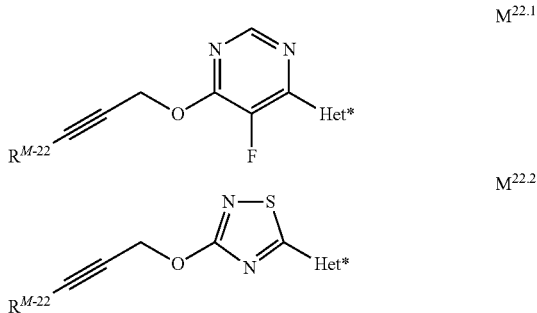

wherein RM-22 is methyl or ethyl and Het* is 3,3-dimethylpyrrolidin-1-yl, 3-methylpiperidin-1-yl, 3,5-dimethylpiperidin-1-yl, 3-trifluormethylpiperidin-1-yl, hexahydroazepin-1-yl, 2,6-dimethylhexahydroazepin-1-yl or 2,6-dimethylmorpholin-4-yl.

M.23. N—R'-2,2-dihalo-1-R"cyclo-propanecarboxamide-2-(2,6-dichloro-alpha, alpha, alpha-tri-fluoro-p-tolyl)hydrazone or N—R'-2,2-di(R''')propionamide-2-(2,6-dichloro-alpha, alpha, alpha-trifluoro-p-tolyl)-hydrazone, wherein R' is methyl or ethyl, halo is chloro or bromo, R" is hydrogen or methyl and R''' is methyl or ethyl;

M.24. Anthranilamides: chloranthraniliprole, the compound of formula M24 1

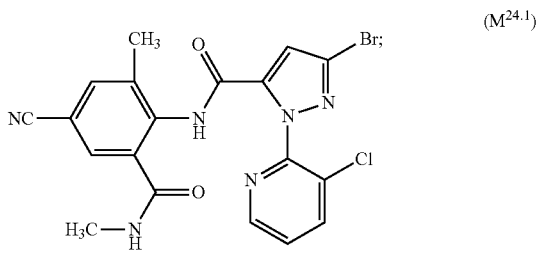 [SMILES: CNC(=O)c1cc(C#N)cc(C)c1NC(=O)c1cc(Br)nn1-c1ncccc1Cl]

(M$^{24.1}$)

M.25. Malononitrile compounds: $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2$ (CF$_2$)$_3$CF$_2$H, CF$_3$CF$_2$CH$_2$C(CN)$_2$CH$_2$(CF$_2$)$_3$CF$_2$H, 2-(2,2,3,3,4,4,5,5-octafluoropentyl)-2-(3,3,4,4,4-pentafluorobutyl)-malonodinitrile, and CF$_2$HCF$_2$CF$_2$CF$_2$CH$_2$C(CN)$_2$CH$_2$CH$_2$CF$_2$CF$_3$;

M.26. Microbial disruptors: *Bacillus thuringiensis* subsp. Israelensi, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

The commercially available compounds of the group A may be found in The Pesticide Manual, 13th Edition, British Crop Protection Council (2003) among other publications.

Thioamides of formula $M^{6.1}$ and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A 1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. AKD 1022 and its preparation have been described in U.S. Pat. No. 6,300,348. Chloranthraniliprole has been described in WO 01/70671, WO 03/015519 and WO 05/118552. Anthranilamide derivatives of formula $M^{24.1}$ have been described in WO 01/70671, WO 04/067528 and WO 05/118552. Cyflumetofen and its preparation have been described in WO 04/080180. The aminoquinazolinone compound pyrifluquinazon has been described in EPA 109 7932. The alkynylether compounds $M^{22.1}$ and $M^{22.2}$ are described e.g. in JP 2006131529. The malononitrile compounds CF$_3$(CH$_2$)$_2$C(CN)$_2$CH$_2$(CF$_2$)$_3$CF$_2$H, CF$_3$(CH$_2$)$_2$C(CN)$_2$CH$_2$(CF$_2$)$_5$CF$_2$H, CF$_3$(CH$_2$)$_2$C(CN)$_2$(CH$_2$)$_2$C(CF$_3$)$_2$F, CF$_3$(CH$_2$)$_2$C(CN)$_2$(CH$_2$)$_2$(CF$_2$)$_3$CF$_3$, CF$_2$H(CF$_2$)$_3$CH$_2$C(CN)$_2$CH$_2$(CF$_2$)$_3$CF$_2$H, CF$_3$(CH$_2$)$_2$C(CN)$_2$CH$_2$(CH$_2$)$_3$CF$_3$, CF$_3$(CF$_2$)$_2$CH$_2$C(CN)$_2$CH$_2$(CF$_2$)$_3$CF$_2$H, CF$_3$CF$_2$CH$_2$C(CN)$_2$CH$_2$(CF$_2$)$_3$CF$_2$H, 2-(2,2,3,3,4,4,5,5-octafluoropentyl)-2-(3,3,4,4,4-pentafluorobutyl)-malonodinitrile, and CF$_2$HCF$_2$CF$_2$CF$_2$CH$_2$C(CN)$_2$CH$_2$CH$_2$CF$_2$CF$_3$ have been described in WO 05/63694.

Fungicidal mixing partners are those selected from the group F consisting of

F.1 acylalanines such as benalaxyl, metalaxyl, ofurace, oxadixyl;

F.2 amine derivatives such as aldimorph, dodine, dodemorph, fenpropimorph, fenpropidin, guazatine, iminoctadine, spiroxamin, tridemorph;

F.3 anilinopyrimidines such as pyrimethanil, mepanipyrim or cyrodinyl;

F.4 antibiotics such as cycloheximid, griseofulvin, kasugamycin, natamycin, polyoxin or streptomycin;

F.5 azoles such as bitertanol, bromoconazole, cyproconazole, difenoconazole, dinitroconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol;

F.6 dicarboximides such as iprodion, myclozolin, procymidon, vinclozolin;

F.7 dithiocarbamates such as ferbam, nabam, maneb, mancozeb, metam, metiram, propineb, polycarbamate, thiram, ziram, zineb;

F.8 heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

F.9 copper fungicides such as Bordeaux mixture, copper acetate, copper oxychloride, basic copper sulfate;

F.10 nitrophenyl derivatives such as binapacryl, dinocap, dinobuton, nitrophthalisopropyl;

F.11 phenylpyrroles such as fenpiclonil or fludioxonil;

F.12 strobilurins such as azoxystrobin, dimoxystrobin, fluoxastrobin, kresoxim-methyl, metominostrobin, orysastrobin, picoxystrobin or trifloxystrobin;

F.13 sulfenic acid derivatives such as captafol, captan, dichlofluanid, folpet, tolylfluanid;

F.14 cinnemamides and analogs such as dimethomorph, flumetover or flumorph;

F.15 sulfur, and other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentinacetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid.

Applications

The animal pest, i.e. the insects, the plant, soil or water in which the plant is growing can be contacted with the present compound(s) identified according to the method of the invention or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula identified according to the method of the invention or the insecticidal compositions comprising them may be used to protect growing plants and crops from attack or infestation by animal pests, especially insects, acaridae or arachnids by contacting the plant/crop with a insecticidally effective amount of compounds identified according to the method of the invention. The term "crop" refers both to growing and harvested crops.

Moreover, animal pests may be controlled by contacting the target pest, its food supply, habitat, breeding ground or its locus with a insecticidally effective amount of compounds identified according to the method of the invention. As such, the application may be carried out before or after the infection of the locus, growing crops, or harvested crops by the pest.

The compounds of the invention can also be applied preventively to places at which occurrence of the pests is expected.

The compounds identified according to the method of the invention may be also used to protect growing plants from attack or infestation by pests by contacting the plant with a insecticidally effective amount of compounds identified according to the method of the invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "insecticidally effective amount" means the amount of active ingredient needed to achieve an observable effect on growth, death, retardation, prevention, and removal, destruction, or otherwise diminishing the occurrence and activity of the target organism. The insecticidally effective amount can vary for the various compounds/compositions used in the invention. A insecticidally effective amount of the compositions will also vary according to the prevailing conditions such as desired insecticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds identified according to the method of the invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, di-methyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds identified according to the method of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethyl-cyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculate, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds identified according to the method of the invention and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds identified according to the method of the invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds identified according to the method of the invention are also suitable for the treatment of seeds in order to protect the seed from insect pest, in particular from soil-living insect pests and the resulting plant's roots and shoots against soil pests and foliar insects.

The compounds identified according to the method of the invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred, specially Green Peach Aphid (*Myzus persica*) and/or Red Flower Beetle (*Tribolium castaneum*)

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound identified according to the method of the invention. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, egg-plants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds identified according to the method of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound identified according to the method of the invention, or an agriculturally useful salt of I, as defined herein. The amount of the compound identified according to the method of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

In one embodiment the invention relates to subject mater summarized as follows:

item a1. A method for identifying a insecticidally active compound that reduces the activity of an insect voltage-gated potassium channel ShaI (Shaker cognate I or Shaker-like) and/or its accessory protein KChIP (potassium channel-interacting protein) respectively which method comprises:
   a) assembling in a membrane a polypeptide with the activity of an insect voltage-gated potassium channel ShaI (Shaker cognate I or Shaker-like) and/or its accessory protein KChIP (potassium channel-interacting protein) respectively which is originally not present said membrane,
   b) applying at one side of the membrane the compound suspected of having the ability to inhibit the activity of said polypeptide which is originally not present said membrane,
   c) determining the activity of said polypeptide and
   d) identifying a compound applied in (b) that reduces the activity of said polypeptide.

item a2. A method according to item a1 whereby a gene coding for a polypeptide with the activity of an insect voltage-gated potassium channel ShaI (Shaker cognate I or Shaker-like) and/or its accessory protein KChIP (potassium channel-interacting protein) respectively is expressed in the membrane of a host cell.

item a3. A method of any one of the items 1 or 2 wherein the membrane comprises at least one polypeptide encoded by a nucleic acid molecule selected from the group consisting of:
   a) a nucleic acid molecule encoding the polypeptide shown in SEQ ID NO: 1, 5, 9, 13, 17, 21, 25 and/or 29;
   b) a nucleic acid molecule shown in SEQ ID NO: 1, 5, 9, 13, 17, 21, 25 and/or 29;
   c) a nucleic acid molecule, which, as a result of the degeneracy of the genetic code, can be derived from a polypeptide sequence according to SEQ ID NO: 2, 6, 10, 14, 18, 22, 26 and/or 30;
   d) a nucleic acid molecule having at least 50% identity with the nucleic acid molecule sequence of a polynucleotide comprising the nucleic acid molecule shown in SEQ ID NO: 1, 5, 9, 13, 17, 21, 25 and/or 29;
   e) a nucleic acid molecule encoding a polypeptide having at least 50% identity with the amino acid sequence of the polypeptide encoded by the nucleic acid molecule of (a) to (c) and having the activity of a voltage-gated potassium channel ShaI (Shaker cognate I or Shaker-like) and/or its accessory protein KChIP (potassium channel-interacting protein) respectively;
   f) nucleic acid molecule which hybridizes with a nucleic acid molecule of (a) to (c) under stringent hybridization conditions;
   g) a nucleic acid molecule encoding a polypeptide which can be isolated with the aid of monoclonal or polyclonal antibodies made against a polypeptide encoded by one of the nucleic acid molecules of (a) to (e) and having the activity of a voltage-gated potassium channel ShaI (Shaker cognate I or Shaker-like) and/or its accessory protein KChIP (potassium channel-interacting protein) respectively;
   h) a nucleic acid molecule encoding a polypeptide comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;
   i) nucleic acid molecule which comprises a polynucleotide, which is obtained by amplifying a cDNA library or a genomic library using the primers in SEQ ID NO: 3, 4; 7, 8; 11, 12; 15, 16, 19, 20; 23, 24; 27, 28 and/or 31, 32 respectively; and
   j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a voltage-gated potassium channel ShaI (Shaker cognate I or Shaker-like) and/or its accessory protein KChIP (potassium channel-interacting protein) respectively.

item a4. A method of item a1 whereby the activity of said polypeptide with the activity of insect voltage-gated potassium channel ShaI (Shaker cognate I or Shaker-like) and/or its accessory protein KChIP (potassium channel-interacting protein) respectively is determinated electrophysiologically.

item a5. A method of item a4 whereby the activity of said polypeptide with the activity of insect voltage-gated potassium channel ShaI (Shaker cognate I or Shaker-like) and/or its accessory protein KChIP (potassium channel-interacting protein) respectively is determinated by patch clamp or in a HTS assay.

item a6. A method of item a2 whereby a gene coding for a polypeptide with the activity of an insect voltage-gated potassium channel ShaI (Shaker cognate I or Shaker-like) and/or its accessory protein KChIP (potassium channel-interacting protein) respectively is expressed in a mammalian cell.

item a7. A method of item a2 whereby a gene coding for a polypeptide with the activity of an insect voltage-gated potassium channel ShaI (Shaker cognate I or Shaker-like) and/or its accessory protein KChIP (potassium channel-interacting protein) respectively is expressed in a mammalian cell selected from the group consisting of: CHO-cells and HEK293.

item a8. A method of item a1 which comprises:
- a) e) applying to an insect, to a population of insects or to the location wherein said insect is to be controlled an insect-controlling amount a compound identified according to item aa1 d) and
- b) f) determining of the growth or the viability of said treated insect or population of insects or of insects or population of insects on said location and untreated insect, population of insects or location and
- c) g) selecting of compounds, which reduces the growth or the viability of said treated insect or population of insects or of insects or population of insects on said location following application of the compound of step e).

item a9. An assay system comprising a host organism, tissue, cells or a cell digest thereof or a membrane, which has embedded, assembled, intercalated or incorporated a nucleic acid molecule selected from the group consisting of the nucleic acid molecule as depicted in item a3 a) to 3 j) and, based on the expression of this nucleic acid molecule, a polypeptide having the biological activity of a insect voltage-gated potassium channel ShaI (Shaker cognate I or Shaker-like) and/or its accessory protein KChIP (potassium channel-interacting protein) respectively, for identifying insecticidally active compound that reduces the activity of an insect voltage-gated potassium channel ShaI (Shaker cognate I or Shaker-like) and/or its accessory protein KChIP (potassium channel-interacting protein) respectively.

item a10. The assay system of item a9 whereby the host organism is a stably transfected mammalian cell which expresses a nucleic acid molecule selected from the group consisting of the nucleic acid molecule as depicted in item a3 a) to 3 j).

item a11. The assay system of item a10 whereby the mammalian cell is selected from the group consisting of: CHO-cells, HEK293, COS, HeLa, NIH3T3, BAK21, Jurkat, CV-1, HepC-2-, *Xenopus oocyte*, Sf9, S2, Sf21, Hi5, Pc12 and U2OS.

item a12. A method for killing or inhibiting the growth or viability of an insect, comprising applying to the insect a compound identified according to the method of item a1.

item a13. A nucleic acid molecule selected from the group consisting of:
- a) a nucleic acid molecule encoding the polypeptide shown in 2, 6, 10, 14, 18, 22, 26 and/or 30;
- b) a nucleic acid molecule shown in SEQ ID NO: 1, 5, 9, 13, 17, 21, 25 and/or 29;
- c) a nucleic acid molecule, which, as a result of the degeneracy of the genetic code, can be derived from a polypeptide sequence according to SEQ ID NO: 2, 6, 10, 14, 18, 22, 26 and/or 30;
- d) a nucleic acid molecule having at least 50% identity with the nucleic acid molecule sequence of a polynucleotide comprising the nucleic acid molecule shown in SEQ ID NO: 1, 5, 9, 13, 17, 21, 25 and/or 29;
- e) a nucleic acid molecule encoding a polypeptide having at least 50% identity with the amino acid sequence of the polypeptide encoded by the nucleic acid molecule of (a) to (c) and having the activity of a voltage-gated potassium channel ShaI (Shaker cognate I or Shaker-like) and/or its accessory protein KChIP (potassium channel-interacting protein) respectively;
- f) nucleic acid molecule which hybridizes with a nucleic acid molecule of (a) to (c) under stringent hybridization conditions;
- g) a nucleic acid molecule encoding a polypeptide which can be isolated with the aid of monoclonal or polyclonal antibodies made against a polypeptide encoded by one of the nucleic acid molecules of (a) to (e) and having the activity of a voltage-gated potassium channel ShaI (Shaker cognate I or Shaker-like) and/or its accessory protein KChIP (potassium channel-interacting protein) respectively;
- h) a nucleic acid molecule encoding a polypeptide comprising the consensus sequence as shown in SEQ ID NO: 33 and/or 34 respectively or one or more motifs selected from the group consisting of SEQ ID NO: 35, 36, 37, 38, 39, 40, 41, 42, 43, 44, 45, 46, 47, 48, 49, 50, 51, 52, 53, 54 and/or 55, and/or 56, 57, 58, 59, 60, 61, 62, 63, 64, 65, 66, 67, 68, 69, 70 and/or 71 respectively;
- i) nucleic acid molecule which comprises a polynucleotide, which is obtained by amplifying a cDNA library or a genomic library using the primers in SEQ ID NO: 3, 4; 7, 8; 11, 12; 15, 16; 19, 20; 23, 24; 27, 28 and/or 31, 32 respectively; and
- j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a potassium channel ShaI (Shaker cognate I or Shaker-like) and/or its accessory protein KChIP (potassium channel-interacting protein) respectively.

item a14. A nucleic acid construct comprising a nucleic acid molecule according to item a13.

item a15. A vector comprising a nucleic acid construct according to item a14 or a nucleic acid molecule according to item a13.

item a16. A transgenic cell comprising a vector according to item a15, a nucleic acid construct according to item a14 or a nucleic acid molecule according to item a13.

item a17. A polypeptide encoded by a nucleic acid molecule according to item a13.

item a18. Use of a polypeptide with the activity of an insect voltage-gated potassium channel ShaI (Shaker cognate I or Shaker-like) and/or its accessory protein KChIP (potassium channel-interacting protein) respectively as insecticidal target.

item a19. Use of a polypeptide encoded by a nucleic acid molecule selected from the group consisting of the nucleic acid molecule as depicted in item a3 a) to 3 j) as insecticidal target.

item a20. A method for controlling a insecticidal pest comprising the application of a composition comprising as insecticidal active ingredient at least one compound as depicted in table I or a derivate thereof.

Item b1. A method for identifying a insecticidally active compound that reduces the activity of an insect Shaker channel and/or a Hyperkinetic beta subunit, preferably H-kv beta subunit A or C subtype respectively which method comprises:
- a) assembling in a membrane a polypeptide with the activity of an insect Shaker channel and/or a Hyperkinetic beta subunit, preferably H-kv beta subunit A or C subtype respectively which is originally not present said membrane,
- b) applying at one side of the membrane the compound suspected of having the ability to inhibit the activity of said polypeptide which is originally not present said membrane,
- c) determining the activity of said polypeptide and
- d) identifying a compound applied in (b) that reduces the activity of said polypeptide.

Item b2. A method according to item b1 whereby a gene coding for a polypeptide with the activity of an insect Shaker channel and/or a Hyperkinetic beta subunit, preferably H-kv beta subunit A or C subtype respectively is expressed in the membrane of a host cell.

Item b3. A method of any one of the items b1 or b2 wherein the membrane comprises at least one polypeptide encoded by a nucleic acid molecule selected from the group consisting of:
- a) a nucleic acid molecule encoding a polypeptide comprising the polypeptide shown in SEQ ID NO: 73, 75, 77, 79, 81, 83, 85 and/or 87;
- b) a nucleic acid molecule comprising a nucleic acid molecule shown in SEQ ID NO: 72, 74, 76, 78, 80, 82, 84 and/or 86;
- c) a nucleic acid molecule, which, as a result of the degeneracy of the genetic code, can be derived from a polypeptide comprising a polypeptide sequence according to SEQ ID NO: 73, 75, 77, 79, 81, 83, 85 and/or 87;
- d) a nucleic acid molecule having at least 50% identity with the nucleic acid molecule sequence of a polynucleotide comprising the nucleic acid molecule shown in SEQ ID NO: 72, 74, 76, 78, 80, 82, 84 and/or 86;
- e) a nucleic acid molecule encoding a polypeptide having at least 50% identity with the amino acid sequence of the polypeptide encoded by the nucleic acid molecule of (a) to (c) and having the activity of a Shaker channel and/or a Hyperkinetic beta subunit, preferably H-kv beta subunit A or C subtype respectively;
- f) nucleic acid molecule which hybridizes with a nucleic acid molecule of (a) to (c) under stringent hybridization conditions;
- g) a nucleic acid molecule encoding a polypeptide which can be isolated with the aid of monoclonal or polyclonal antibodies made against a polypeptide encoded by one of the nucleic acid molecules of (a) to (e) and having the activity of a Shaker channel and/or a Hyperkinetic beta subunit, preferably H-kv beta subunit A or C subtype respectively;
- h) a nucleic acid molecule encoding a polypeptide comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;
- i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively; and
- j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a Shaker channel and/or a Hyperkinetic beta subunit, preferably H-kv beta subunit A or C subtype respectively.

Item b4. A method of item b1 whereby the activity of said polypeptide with the activity of insect Shaker channel and/or a Hyperkinetic beta subunit, preferably H-kv beta subunit A or C subtype respectively is determinated electrophysiologically.

Item b5. A method of item b4 whereby the activity of said polypeptide with the activity of insect Shaker channel and/or a Hyperkinetic beta subunit, preferably H-kv beta subunit A or C subtype respectively is determinated by patch clamp or FLIPR.

Item b6. A method of item b2 whereby a gene coding for a polypeptide with the activity of an insect Shaker channel and/or a Hyperkinetic beta subunit, preferably H-kv beta subunit A or C subtype respectively is expressed in a mammalian cell.

Item b7. A method of item b2 whereby a gene coding for a polypeptide with the activity of an insect Shaker channel and/or a Hyperkinetic beta subunit, preferably H-kv beta subunit A or C subtype respectively is expressed in a mammalian cell selected from the group consisting of: CHO-cells, HEK293.

Item b8. A method of item b1 which comprises:
- e) applying to an insect, to a population of insects or to the location wherein said insect is to be controlled an insect-controlling amount a compound identified according to item b1 d) and
- f) determining of the growth or the viability of said treated insect or population of insects or of insects or population of insects on said location and untreated insect, population of insects or location and
- g) selecting of compounds, which reduces the growth or the viability of said treated insect or population of insects or of insects or population of insects on said location following application of the compound of step e).

Item b9. An assay system comprising a host organism, tissue, cells or a cell digest thereof or a membrane, which has embedded, assembled, intercalated or incorporated a nucleic acid molecule selected from the group consisting of the nucleic acid molecule as depicted in item b3 a) to b3 j) and, based on the expression of this nucleic acid molecule, a polypeptide having the biological activity of a insect Shaker channel and/or a Hyperkinetic beta subunit, preferably H-kv beta subunit A or C subtype respectively, for identifying insecticidally active compound that reduces the activity of an insect Shaker channel and/or a Hyperkinetic beta subunit, preferably H-kv beta subunit A or C subtype respectively.

Item b10. The assay system of item b9 whereby the host organism is a stably transfected mammalian cell which expresses a nucleic acid molecule selected from the group consisting of the nucleic acid molecule as depicted in item b3 a) to b3 j).

Item b11. The assay system of item b10 whereby the mammalian cell is selected from the group consisting of: CHO-cells, HEK293, COS, HeLa, NIH3T3, BAK21, Jurkat, CV-1, HepC-2-, *Xenopus oocyte*, Sf9, S2, Sf21, Hi5, Pc12, U2O5.

Item b12. A method for killing or inhibiting the growth or viability of an insect, comprising applying to the insect a compound identified according to the method of item b1.

Item b13. A nucleic acid molecule selected from the group consisting of:
  a) a nucleic acid molecule encoding a polypeptide comprising the polypeptide shown in SEQ ID NO: 73, 75, 77, 79, 81, 83, 85 and/or 87;
  b) a nucleic acid molecule comprising a nucleic acid molecule shown in SEQ ID NO: 72, 74, 76, 78, 80, 82, 84 and/or 86;
  c) a nucleic acid molecule, which, as a result of the degeneracy of the genetic code, can be derived from a polypeptide comprising a polypeptide sequence according to SEQ ID NO: 73, 75, 77, 79, 81, 83, 85 and/or 87;
  d) a nucleic acid molecule having at least 50% identity with the nucleic acid molecule sequence of a polynucleotide comprising the nucleic acid molecule shown in SEQ ID NO: 72, 74, 76, 78, 80, 82, 84 and/or 86;
  e) a nucleic acid molecule encoding a polypeptide having at least 50% identity with the amino acid sequence of the polypeptide encoded by the nucleic acid molecule of (a) to (c) and having the activity of a Shaker channel and/or a Hyperkinetic beta subunit, preferably H-kv beta subunit A or C subtype respectively;
  f) nucleic acid molecule which hybridizes with a nucleic acid molecule of (a) to (c) under stringent hybridization conditions;
  g) a nucleic acid molecule encoding a polypeptide which can be isolated with the aid of monoclonal or polyclonal antibodies made against a polypeptide encoded by one of the nucleic acid molecules of (a) to (e) and having the activity of a Shaker channel and/or a Hyperkinetic beta subunit, preferably H-kv beta subunit A or C subtype respectively;
  h) a nucleic acid molecule encoding a polypeptide comprising the consensus sequence as shown in SEQ ID NO: 102 and/or 103 respectively or one or more motifs selected from the group consisting of SEQ ID NO: 104, 105, 106, 107, 108, 109, 110, 111, 112, 113, 114, 115, 116, 117, 118, 119, 120, 121, 122, 123, 124 and/or 125 and/or 126, 127 and/or 128 respectively;
  i) nucleic acid molecule which comprises a polynucleotide, which is obtained by amplifying a cDNA library or a genomic library using the primers in SEQ ID NO: 88, 89; 90, 91; 92, 93; 94, 95; 96, 97; 98, 99 and/or 100, 101 respectively; and
  j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a Shaker channel and a Hyperkinetic beta subunit, preferably H-kv beta subunit A or C subtype respectively.

Item b14. A nucleic acid construct comprising a nucleic acid molecule according to item b13.

Item b15. A vector comprising a nucleic acid construct according to item b14 or a nucleic acid molecule according to item b13.

Item b16. A transgenic cell comprising a vector according to item b15, a nucleic acid construct according to item b14 or a nucleic acid molecule according to item b13.

Item b17. A polypeptide encoded by a nucleic acid molecule according to item b13.

Item b18. Use of a polypeptide with the activity of an insect Shaker channel and a Hyperkinetic beta subunit, preferably H-kv beta subunit A or C subtype respectively as insecticidal target.

Item b19. Use of a polypeptide encoded by a nucleic acid molecule selected from the group consisting of the nucleic acid molecule as depicted in item b3 a) to b3 j) as insecticidal target.

Item c1. A method for identifying a insecticidal active compound that reduces the activity of an octopamine receptor selected from the group consisting of oa2, preferably from *Drosophila melanogaster*, Oamb, Oct-beta-2R and Oct-beta-3R which method comprises:
  a) assembling in a membrane a polypeptide with the activity of an octopamine receptor selected from the group consisting of oa2, preferably from *Drosophila melanogaster*, Oamb, Oct-beta-2R and Oct-beta-3R which is originally not present said membrane,
  b) applying at one side of the membrane the compound suspected of having the ability to inhibit the activity of said polypeptide which is originally not present said membrane,
  c) determining the activity of said polypeptide and
  d) identifying a compound applied in (b) that reduces the activity of said polypeptide.

Item c2. A method according to Item c1 whereby a gene coding for a polypeptide with the activity of an octopamine receptor selected from the group consisting of oa2, preferably from *Drosophila melanogaster*, Oamb, Oct-beta-2R and Oct-beta-3R is expressed in the membrane of a host cell.

Item c3. A method of any one of the Items c1 or c2 wherein the membrane comprises at least one polypeptide encoded by a nucleic acid molecule selected from the group consisting of:
  a) a nucleic acid molecule encoding the polypeptide shown in SEQ ID NO: 130, 134, 138, 142, 146, 150, 154, 158, 162, 166, 170 and/or 174;
  b) a nucleic acid molecule shown in SEQ ID NO: 129, 133, 137, 141, 145, 149, 153, 157, 161, 165, 169 and/or 173;
  c) a nucleic acid molecule, which, as a result of the degeneracy of the genetic code, can be derived from a polypeptide sequence according to SEQ ID NO: 130, 134, 138, 142, 146, 150, 154, 158, 162, 166, 170 and/or 174
  d) a nucleic acid molecule having at least 50% identity with the nucleic acid molecule sequence of a polynucleotide comprising the nucleic acid molecule shown in SEQ ID NO: 129, 133, 137, 141, 145, 149, 153, 157, 161, 165, 169 and/or 173;
  e) a nucleic acid molecule encoding a polypeptide having at least 50% identity with the amino acid sequence of the polypeptide encoded by the nucleic acid molecule of (a) to (c) and having the activity of an octopamine receptor selected from the group consisting of oa2, preferably from *Drosophila melanogaster*, Oamb, Oct-beta-2R and Oct-beta-3R;
  f) nucleic acid molecule which hybridizes with a nucleic acid molecule of (a) to (c) under stringent hybridization conditions;
  g) a nucleic acid molecule encoding a polypeptide which can be isolated with the aid of monoclonal or polyclonal antibodies made against a polypeptide encoded by one of the nucleic acid molecules of (a) to (e) and having the activity of an octopamine receptor selected from the group consisting of oa2, preferably from *Drosophila melanogaster*, Oamb, Oct-beta-2R and Oct-beta-3R;
  h) a nucleic acid molecule encoding a polypeptide comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively;

i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156; 159, 160; 163, 164; 167, 168; 171, 172 and/or 175, 176 respectively; and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of an octopamine receptor selected from the group consisting of oa2, preferably from *Drosophila melanogaster*, Oamb, Oct-beta-2R and Oct-beta-3R.

Item c4. A method of Item c1 whereby the activity of said polypeptide with the activity of an octopamine receptor selected from the group consisting of oa2, preferably from *Drosophila melanogaster*, Oamb, Oct-beta-2R and Oct-beta-3R is determinated by fluorescence measurement.

Item c5. A method of Item c2 whereby the activity of said polypeptide with the activity of an octopamine receptor selected from the group consisting of oa2, preferably from *Drosophila melanogaster*, Oamb, Oct-beta-2R and Oct-beta-3R is determinated with Calcium concentration sensitive dyes.

Item c6. A method of Item c2 whereby a gene coding for a polypeptide with the activity of an octopamine receptor selected from the group consisting of oa2, preferably from *Drosophila melanogaster*, Oamb, Oct-beta-2R and Oct-beta-3R is expressed in a mammalian cell.

Item c7. A method of Item c2 whereby a gene coding for a polypeptide with the activity of an octopamine receptor selected from the group consisting of oa2, preferably from *Drosophila melanogaster*, Oamb, Oct-beta-2R and Oct-beta-3R is expressed in a mammalian cell selected from the group consisting of: CHO-cells, HEK293.

Item c8. A method of Item c1 which comprises:

e) applying to an insect, to a population of insects or to the location wherein said insect is to be controlled an insect-controlling amount a compound identified according to Item c1 d) and f) determining of the growth or the viability of said treated insect or population of insects or of insects or population of insects on said location and untreated insect, population of insects or location and g) selecting of compounds, which reduces the growth or the viability of said treated insect or population of insects or of insects or population of insects on said location following application of the compound of step e).

Item c9. An assay system comprising a host organism, tissue, cells or a cell digest thereof or a membrane, which has embedded, assembled, intercalated or incorporated a nucleic acid molecule selected from the group consisting of the nucleic acid molecule as depicted in Item c3 a) to c3 j) and, based on the expression of this nucleic acid molecule, a polypeptide having the biological activity of an octopamine receptor selected from the group consisting of oa2, preferably from *Drosophila melanogaster*, Oamb, Oct-beta-2R and Oct-beta-3R, for identifying insecticidally active compound that reduces the activity of an octopamine receptor selected from the group consisting of oa2, preferably from *Drosophila melanogaster*, Oamb, Oct-beta-2R and Oct-beta-3R.

Item c10. The assay system of Item c9 whereby the host organism is a stably transfected mammalian cell which expresses a nucleic acid molecule selected from the group consisting of the nucleic acid molecule as depicted in Item c3 a) to c3 j).

Item c11. The assay system of Item c10 whereby the mammalian cell is selected from the group consisting of: CHO-cells, HEK293, COS, HeLa, NIH3T3, BAK21, Jurkat, CV-1, HepC-2-, *Xenopus oocyte*, Sf9, S2, Sf21, Hi5, Pc12, U2O5.

Item c12. A method for killing or inhibiting the growth or viability of an insect, comprising applying to the insect a compound identified according to the method of Item c1.

Item c13. A nucleic acid molecule selected from the group consisting of:

a) a nucleic acid molecule encoding the polypeptide shown in 2, 6, 10, 14, 18, 22, 26, 30, 34, 38, 42 and/or 46;

b) a nucleic acid molecule shown in SEQ ID NO: 129, 133, 137, 141, 145, 149, 153, 157, 161, 165, 169 and/or 173;

c) a nucleic acid molecule, which, as a result of the degeneracy of the genetic code, can be derived from a polypeptide sequence according to SEQ ID NO: 130, 134, 138, 142, 146, 150, 154, 158, 162, 166, 170 and/or 174;

d) a nucleic acid molecule having at least 50% identity with the nucleic acid molecule sequence of a polynucleotide comprising the nucleic acid molecule shown in SEQ ID NO: 129, 133, 137, 141, 145, 149, 153, 157, 161, 165, 169 and/or 173;

e) a nucleic acid molecule encoding a polypeptide having at least 50% identity with the amino acid sequence of the polypeptide encoded by the nucleic acid molecule of (a) to (c) and having the activity of an octopamine receptor selected from the group consisting of oa2, preferably from *Drosophila melanogaster*, Oamb, Oct-beta-2R and Oct-beta-3R;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of an octopamine receptor selected from the group consisting of oa2, preferably from *Drosophila melanogaster*, Oamb, Oct-beta-2R and Oct-beta-3R;

h) a nucleic acid molecule encoding a polypeptide comprising the consensus sequence as shown in SEQ ID NO: 177, 178 and/or 179 respectively or one or more motifs selected from the group consisting of SEQ ID NO: 180, 181, 182, 183, 184, 185, 186, 187, 188, 189 and/or 190, and/or 191, 192, 193, 194, 195, 196, 197, 198, 199, 200, 201, 202, 203, 204, 205, 206, 207 and/or 208, and/or 209, 210, 211, 212, 213, 214, 215, 216, 217, 218, 219, 220, 221, 222, 223, 224, 225 and/or 226 respectively;

i) nucleic acid molecule which comprises a polynucleotide, which is obtained by amplifying a cDNA library or a genomic library using the primers in SEQ ID NO: 131, 132; 135, 136; 139, 140; 143, 144; 147, 148; 151, 152; 155, 156; 159, 160; 163, 164; 167, 168; 171, 172 and/or 175, 176 respectively;

and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of an octopamine receptor selected from the group consisting of oa2, preferably from *Drosophila melanogaster*, Oamb, Oct-beta-2R and Oct-beta-3R.

Item c14. A nucleic acid construct comprising a nucleic acid molecule according to Item c13.

Item c15. A vector comprising a nucleic acid construct according to Item c14 or a nucleic acid molecule according to Item c13.

Item c16. A transgenic cell comprising a vector according to Item c15, a nucleic acid construct according to Item c14 or a nucleic acid molecule according to Item c13.

Item c17. A polypeptide encoded by a nucleic acid molecule according to Item c13.

Item c18. Use of a polypeptide with the activity of an octopamine receptor selected from the group consisting of oa2, preferably from *Drosophila melanogaster*, Oamb, Oct-beta-2R and Oct-beta-3R as insecticidal target.

Item c19. Use of a polypeptide encoded by a nucleic acid molecule selected from the group consisting of the nucleic acid molecule as depicted in Item c3 a) to c3 j) as insecticidal target.

Item c20. Use of manserin and/or cyproheptadine as insecticidal active ingredients.

Item d1. A method for identifying a insecticidally active compound that reduces the activity of an insect small-conductance Ca2+-activated potassium channel which method comprises:
  a) assembling in a membrane a polypeptide with the activity of an insect small-conductance Ca2+-activated potassium channel which is originally not present said membrane,
  b) applying at one side of the membrane the compound suspected of having the ability to inhibit the activity of said polypeptide which is originally not present said membrane,
  c) determining the activity of said polypeptide and
  d) identifying a compound applied in (b) that reduces the activity of said polypeptide.

Item d2. A method according to Item d1 whereby a gene coding for a polypeptide with the activity of an insect small-conductance Ca2+-activated potassium channel is expressed in the membrane of a host cell.

Item d3. A method of any one of the Items d1 or d2 wherein the membrane comprises at least one polypeptide encoded by a nucleic acid molecule selected from the group consisting of:
  a) a nucleic acid molecule encoding the polypeptide shown in SEQ ID NO: 228, 230, 232;
  b) a nucleic acid molecule shown in SEQ ID NO: 227, 229, 231;
  c) a nucleic acid molecule, which, as a result of the degeneracy of the genetic code, can be derived from a polypeptide sequence according to SEQ ID NO: 228, 230, 232;
  d) a nucleic acid molecule having at least 50% identity with the nucleic acid molecule sequence of a polynucleotide comprising the nucleic acid molecule shown in SEQ ID NO: 227, 229, 231;
  e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;
  f) nucleic acid molecule which hybridizes with a nucleic acid molecule of (a) to (c) under stringent hybridization conditions;
  g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;
  h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;
  i) nucleic acid molecule which comprises a polynucleotide, which is obtained by amplifying a cDNA library or a genomic library using the primers in SEQ ID NO: 233, 234; 235, 236; 237, 238 respectively;
  and
  j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel.

Item d4. A method of Item d1 whereby the activity of said polypeptide with the activity of insect small-conductance Ca2+-activated potassium channel is determinated electrophysiologically.

Item d5. A method of Item d4 whereby the activity of said polypeptide with the activity of insect small-conductance Ca2+-activated potassium channel is determinated by patch clamp.

Item d6. A method of Item d2 whereby a gene coding for a polypeptide with the activity of an insect small-conductance Ca2+-activated potassium channel is expressed in a mammalian cell.

Item d7. A method of Item d2 whereby a gene coding for a polypeptide with the activity of an insect small-conductance Ca2+-activated potassium channel is expressed in a mammalian cell selected from the group consisting of: CHO-cells, HEK293.

Item d8. A method of Item d1 which comprises:
  e) applying to an insect, to a population of insects or to the location wherein said insect is to be controlled an insect-controlling amount a compound identified according to Item d1 d) and
  f) determining of the growth or the viability of said treated insect or population of insects or of insects or population of insects on said location and untreated insect, population of insects or location and
  g) selecting of compounds, which reduces the growth or the viability of said treated insect or population of insects or of insects or population of insects on said location following application of the compound of step e).

Item d9. An assay system comprising a host organism, tissue, cells or a cell digest thereof or a membrane, which has embedded, assembled, intercalated or incorporated a nucleic acid molecule selected from the group consisting of the nucleic acid molecule as depicted in Item d3 a) to d3 j) and, based on the expression of this nucleic acid molecule, a polypeptide having the biological activity of a insect small-conductance Ca2+-activated potassium channel, for identifying insecticidally active compound that reduces the activity of an insect small-conductance Ca2+-activated potassium channel.

Item d10. The assay system of Item d9 whereby the host organism is a stably transfected mammalian cell which expresses a nucleic acid molecule selected from the group consisting of the nucleic acid molecule as depicted in Item d3 a) to d3 j).

Item d11. The assay system of Item d10 whereby the mammalian cell is selected from the group consisting of: CHO-cells, HEK293, COS, HeLa, NIH3T3, BAK21, Jurkat, CV-1, HepC-2-, *Xenopus oocyte* some more?. Sf9, S2, Sf21, Hi5, Pc12, U2O5.

Item d12. A method for killing or inhibiting the growth or viability of an insect, comprising applying to the insect a compound identified according to the method of Item d1.

Item d13. A nucleic acid molecule selected from the group consisting of:

a) a nucleic acid molecule encoding the polypeptide shown in SEQ ID NO: 230, 232;

b) a nucleic acid molecule shown in SEQ ID NO: 229, 231;

c) a nucleic acid molecule, which, as a result of the degeneracy of the genetic code, can be derived from a polypeptide sequence according to SEQ ID NO: 230, 232;

d) a nucleic acid molecule having at least 50% identity with the nucleic acid molecule sequence of a polynucleotide comprising the nucleic acid molecule shown in SEQ ID NO: 229, 231;

e) a nucleic acid molecule encoding a polypeptide having at least 50% identity with the amino acid sequence of the polypeptide encoded by the nucleic acid molecule of (a) to (c) and having the activity of a small-conductance Ca2+-activated potassium channel;

f) nucleic acid molecule which hybridizes with a nucleic acid molecule of (a) to (c) under stringent hybridization conditions;

g) a nucleic acid molecule encoding a polypeptide which can be isolated with the aid of monoclonal or polyclonal antibodies made against a polypeptide encoded by one of the nucleic acid molecules of (a) to (e) and having the activity of a small-conductance Ca2+-activated potassium channel;

h) a nucleic acid molecule encoding a polypeptide comprising the consensus sequence as shown in SEQ ID NO: 239 or one or more motifs selected from the group consisting of SEQ ID NO: 240, 241, 242, 243, 244, 245, 246, 247, 248, 249, 250, 251, 252 and 253;

i) nucleic acid molecule which comprises a polynucleotide, which is obtained by amplifying a cDNA library or a genomic library using the primers in SEQ ID NO: 233, 234; 235, 236; 237, 238 respectively;

and j) a nucleic acid molecule which is obtainable by screening a suitable nucleic acid library under stringent hybridization conditions with a probe comprising a complementary sequence of a nucleic acid molecule of (a) or (b) or with a fragment thereof, having at least 15 nt, preferably 20 nt, 30 nt, 50 nt, 100 nt, 200 nt or 500 nt of a nucleic acid molecule complementary to a nucleic acid molecule sequence characterized in (a) to (e) and encoding a polypeptide and having the activity of a small-conductance Ca2+-activated potassium channel.

Item d14. A nucleic acid construct comprising a nucleic acid molecule according to Item d13.

Item d15. A vector comprising a nucleic acid construct according to Item d14 or a nucleic acid molecule according to Item d13.

Item d16. A transgenic cell comprising a vector according to Item d15, a nucleic acid construct according to Item d14 or a nucleic acid molecule according to Item d13.

Item d17. A polypeptide encoded by a nucleic acid molecule according to Item d13.

Item d18. Use of a polypeptide with the activity of an insect small-conductance Ca2+-activated potassium channel as insecticidal target.

Item d19. Use of a polypeptide encoded by a nucleic acid molecule selected from the group consisting of the nucleic acid molecule as depicted in Item d3 a) to d3 j) as insecticidal target.

EXAMPLES

Cell Biology

Molecular Biology: The full-length ShaI CDS (coding sequence) was subcloned into the pcDNA3/Neo(−) expression vector using the EcoR1 restriction site. The ShaI_delN mutant has an N-terminal deletion for the 2-40 aa coding region. The deletion mutation was inserted into the pcDNA3_ShaI construct using ShaI_del_2-4aa_fwd (5' gca-gaattcgccctttgccaccatggagaagctcctga tcaacgtctccgg-3') and ShaI_del_2-4aa_rev (5'-ccggagacgttgatcaggagcttctc-catggtggcaagggc gaattctgc-3') primers and the XL Site-Directed Mutagenesis Kit (Stratagene). A unique AscI restriction site was inserted before the ATG start codon in pcDNA_ShaI and pcDNA_ShaI_delN constructs by site-directed mutagenesis. The full length ShaI and ShaI_delN inserts were subcloned into the pcDNA3_AcGFPC1 vector (AscI and HindIII restriction sites) to obtain an AcGFP chimera (FIG. 1) The AcGFP is thus tagged to the N-terminus of both these constructs. All constructs were double-stranded sequenced for the ShaI coding region to confirm sequence integrity. The dominant-negative ShaI_DelNW362F mutant was made by changing the tryptophan (W) to phenylalanine (F) at position 362 in the pore region. KChIP, a ShaI accessory protein, was cloned from *Drosophila* and subcloned into the pcDNA3.1/Zeo vector.

Figure 2:
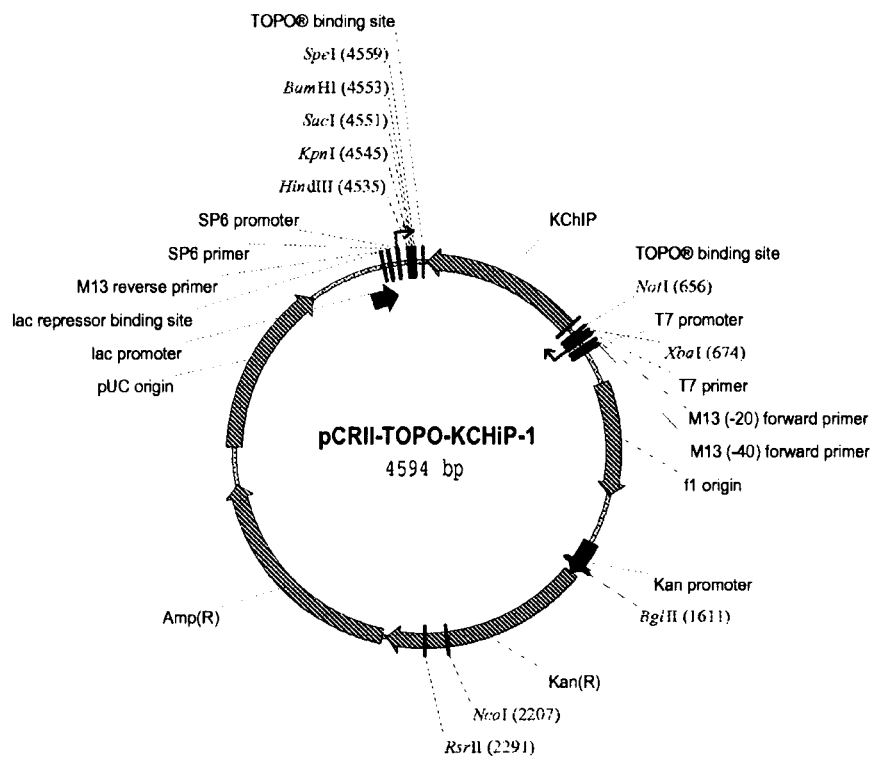
FIG. 2: Vector NTI-generated map of the primary KChIP clone showing the major features of the construct.

FIG. 1: Primary ShaI clone. Vector NTI-generated map of the primary ShaI clone showing the major features of the construct. The ShaI coding region is 1473 bp in length FIG. 2: Primary KChIP clone. Vector NTI-generated map of the primary KChIP clone showing the major features of the construct. The KChIP coding region is 621 bp in length. The expression construct, pcDNA3.1-Zeo-KChIP-intron1 (data not shown, notebook 1049294 #5) contains a ~700 bp intron to aid in cloning, and places the KChIP ORF downstream of a CMV promoter.

Figure 3:
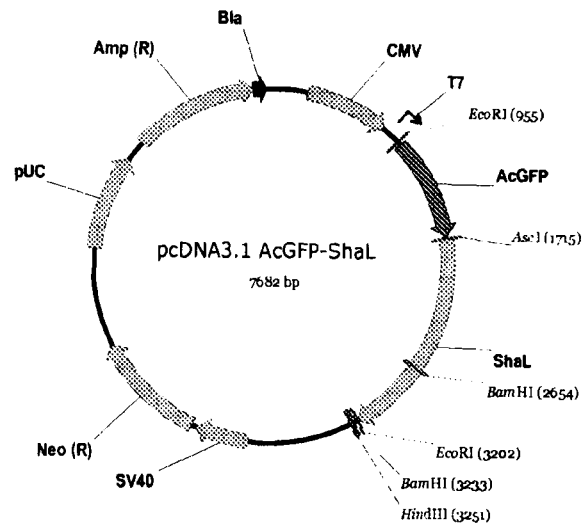
FIG. 3: Vector maps of pcDNA3/AcGFP-Sha1 and pcDNA3/AcGFP-Sha1delN2-40aa.
Figure 3:
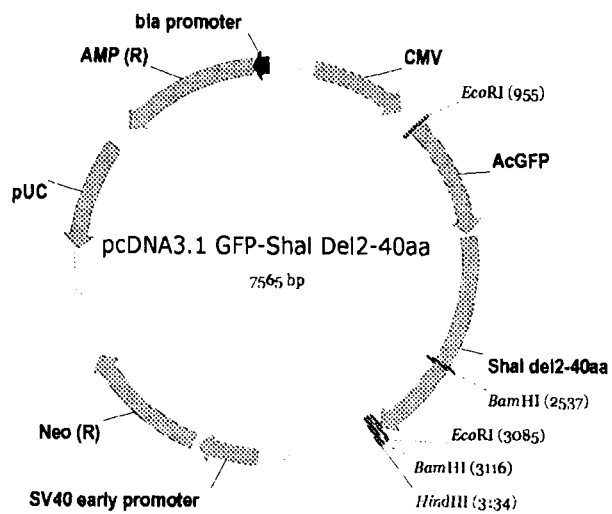

FIG. 3: ShaI and KChIP expression constructs. Maps of pcDNA3/AcGFP-ShaI and pcDNA3/AcGFP-ShaIdelN2-40aa and links to Vector NTI pcDNA3_ShaIDelN and pcDNA3_Zeo_KCHiP_intron1 constructs.

Figure 4:
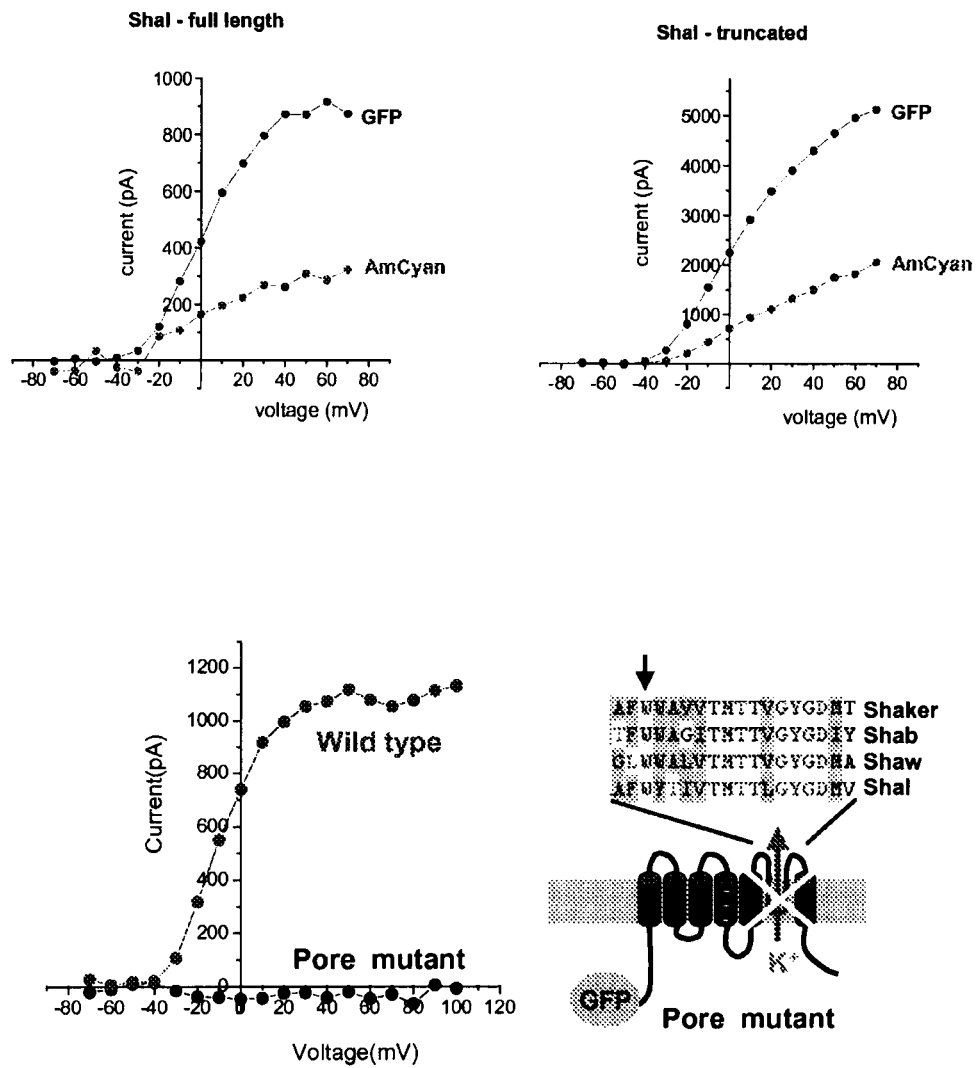
FIG. 4: Patch clamp data for full length and truncated constructs Sha1 and Sha1_delN when coexpressed with AmCyan as well as AcGFP-tagged versions (top); schematic representation of GFP-Sha1 pore mutant and patch clamp data for wild type and pore mutant.

FIG. 4: Patch clamp data for full length and truncated constructs ShaI and ShaI_delN when coexpressed with AmCyan as well as AcGFP-tagged versions (top). Schematic representation of GFP-ShaI pore mutant and patch clamp data for wild type and pore mutant, showing that the measured currents indeed arise from overexpressed ShaI and not an upregulated endogenous current (bottom).

Expression in mammalian cells: Wild type and mutant ShaI channels were transiently expressed in CHO cells and tested for function at 48 hrs by whole-cell voltage clamp recordings. The untagged ShaI constructs were cotransfected with pcDNA3_AmCyan. The full length ShaI and ShaI_delN mutant mediated functional channel activity. The GFP tag at the amino terminus did not alter channel function. The ShaI_delN-W362F mutant did not form functional channels.

Stable cell line generation: Wild type CHO cells were transfected with AcGFP-ShaI and AcGFP-ShaI_delN DNA using FuGene Transfection Reagent (Roche). Stable clonal lines were generated by selecting the cells with G418 (900 ug/ml) at 24 hrs post transfection. 25 colonies were picked for each construct and evaluated for GFP expression using a fluorescence microscope. 70-75% of the clonal lines had very weak or no GFP expression. Based on the fluorescence rating, some of the high and medium GFP expressing clonal lines were tested for ShaI activity by patch clamp (Table 1). The ShaI_delN clones (Clone 10 & 15) had higher current density than the full length ShaI clones. Thus, the development of an assay was proceeded with these 2 clones.

TABLE 1

Summary of ShaI clone screening showing relative fluorescent response and current density.

| Clone | Fluorescence rating | Current Density (pA/pF) |
| --- | --- | --- |
| ShaI C7 | ++ | 54 (58; 50) |
| ShaI C10 | ++ | 86 (89; 83) |
| ShaI C16 | ++ | 41 (60; 21) |
| ShaI C20 | ++ | 36 (37; 35) |
| ShaI C21 | +++ | 45 (41; 48) |
| ShaI_DelN C5 | ++ | n/a |
| ShaI_DelN C8 | ++ | no current |
| ShaI_DelN C10 | ++ | 337 (216; 457) |
| ShaI_DelN C11 | ++ | no current |
| ShaI_DelN C15 | +++ | 107 (38; 118; 166) |

Figure 5:
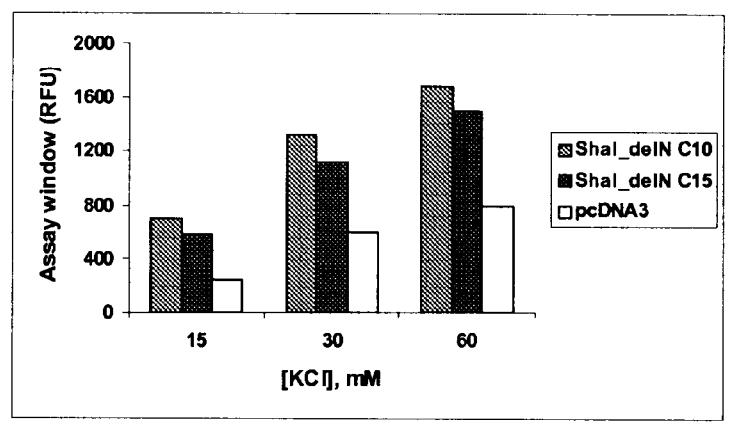
FIG. 5: Sha1_DelN clones tested on FLIPR with KCl depolarization.

ShaI_DelN C10 and C15 were tested for function on the FLIPR using the Molecular Devices blue membrane potential dye. The cells were seeded at 60K cells/well in 96-well Costar plates in complete media and assayed for function at 24 hrs. Depolarization with 15-60 mM KCl caused a 2-2.8 fold higher activity in the clonal line than the pcDNA control cell line (FIG. 5). Clone 10 had slightly higher activity than clone 15.

Figure 6:
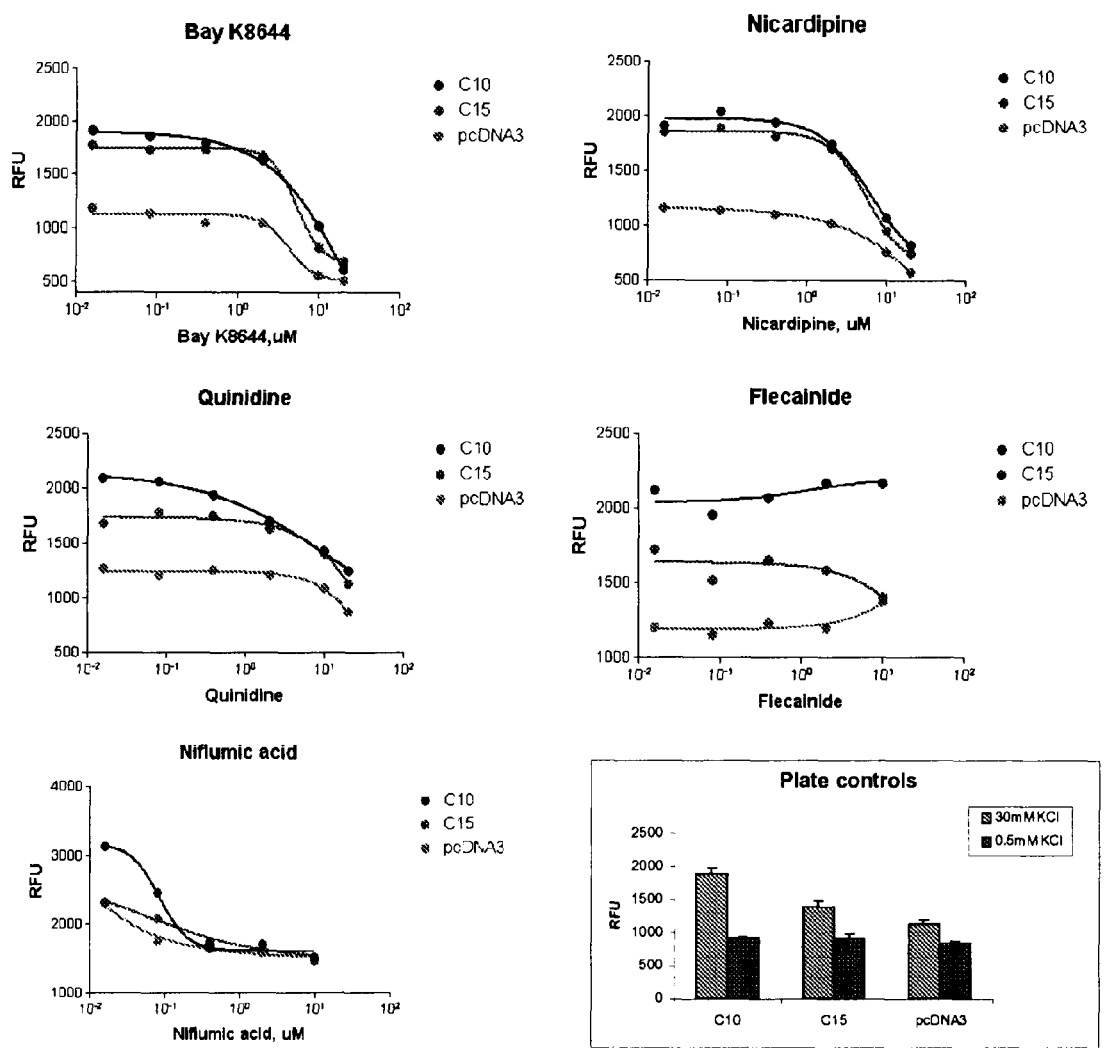
FIG. 6: K channel blocker inhibition curves of known K-channel blockers tested on FLIPR.

FIG. 5: ShaI_DelN clones tested on FLIPR with KCl depolarization. We also tested some known K-channel blockers on channel activity on the FLIPR (FIG. 6). Bay K8644, nicardipine, quinidine and niflumic acid showed dose dependent inhibition of KCl depolarization in both the ShaI_delN clonal lines and the control pcDNA3 cell line. Flecainide did not show any inhibition on the clones and control cell lines at the concentrations tested. The ShaI_delN clonal cell lines lost their GFP expression and assay window with cell passage. At passage 12, only 10-15% of the cell population was GFP positive.

FIG. 6: K channel blocker inhibition curves tested on the FLIPR. ShaI_delN C10 cells were subcloned by flow-sorting. The cells were flow-sorted into 96-well tissue culture plates to obtain GFP-positive single cells. Several clonal lines were expanded and tested for function using KCl depolarization on the FLIPR (FIG. 7).

Figure 7:
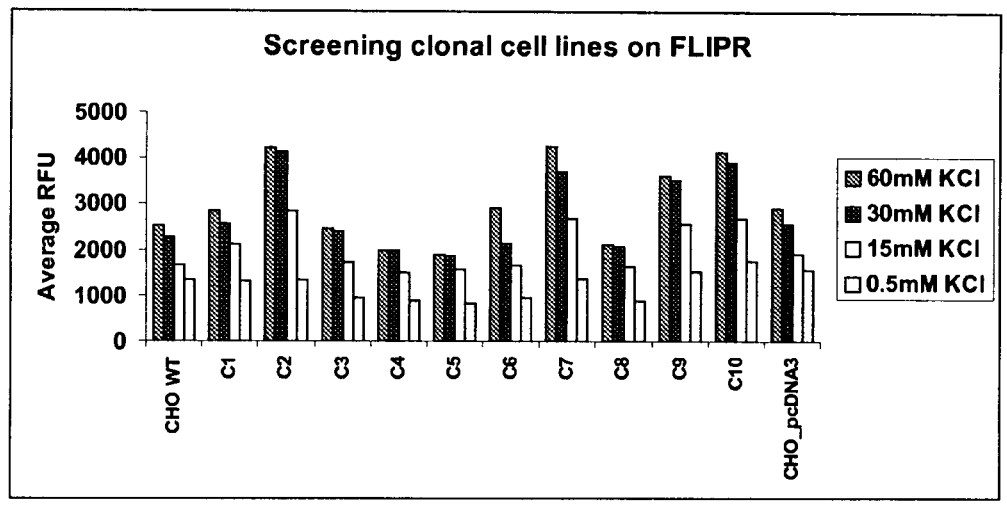
FIG. 7: Screening Sha1_delN Clone10 subclones by KCl depolarization on FLIPR.
Figure 8:
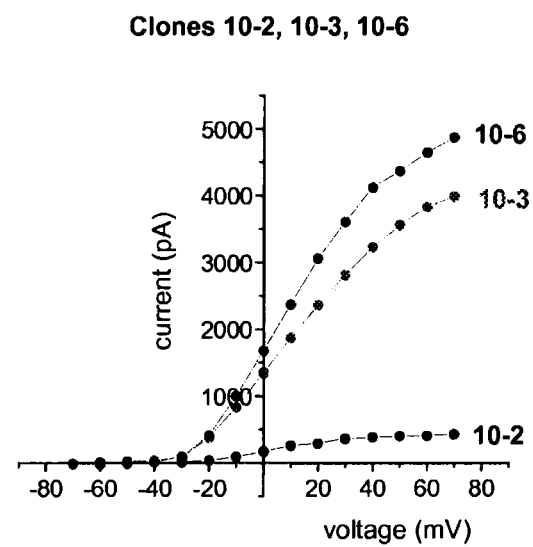
FIG. 8: Patch clamp data for clones 10-2, 10-3 and 10-6. IV curves showing the relationship of applied voltage to current.

FIG. 7: Screening ShaI_delN Clone10 subclones by KCl depolarization on FLIPR. Based on the FLIPR data, clones 10-2, 10-3 and 10-6 were further tested by patch clamp (FIG. 8). Clones 10-3 and 10-6 had high currents in the whole-cell patch clamp studies.

FIG. 8: Patch clamp data for clones 10-2, 10-3 and 10-6. IV curves showing the relationship of applied voltage to current.

A ShaI_delN clone 10-3 subclone maintained the GFP expression over several cell passages. At Passage12, about 80-85% of the cell population was GFP positive (FIG. 9).

Figure 9:
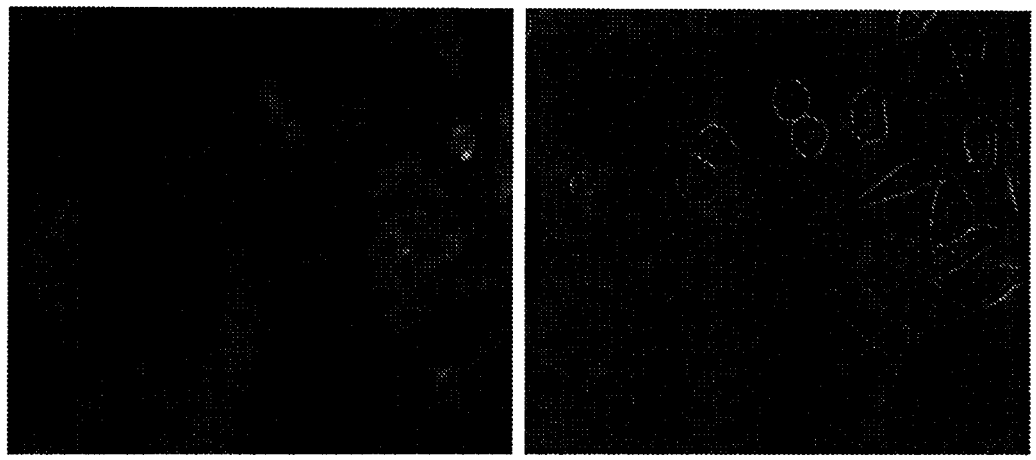
FIG. 9: Sha1_DelN C10-3 cells at passage 12. Left panel—fluorescence excitation, right panel—normal light.

FIG. 9: ShaI_DelN C10-3 cells at passage 12 showing stability of fluorescence over time. Left panel—fluorescence excitation, right panel—normal light.

Increase of Assay window:

The effects of barium (Ba2+) on ShaI_delN function were tested. Barium is known to inhibit some open rectifier and inward rectifier K-channel activities. Cells were dye loaded in the presence of BaCl2 for 1 hr at RT and assayed on the FLIPR using KCl depolarization for channel activation. Ba2+ at a concentration of 4-5 mM significantly reduced fluorescent responses in CHO_pcDNA3 control cells without any significant reduction in the ShaI_delN channel activity with KCl depolarization (FIG. 10).

Figure 10:
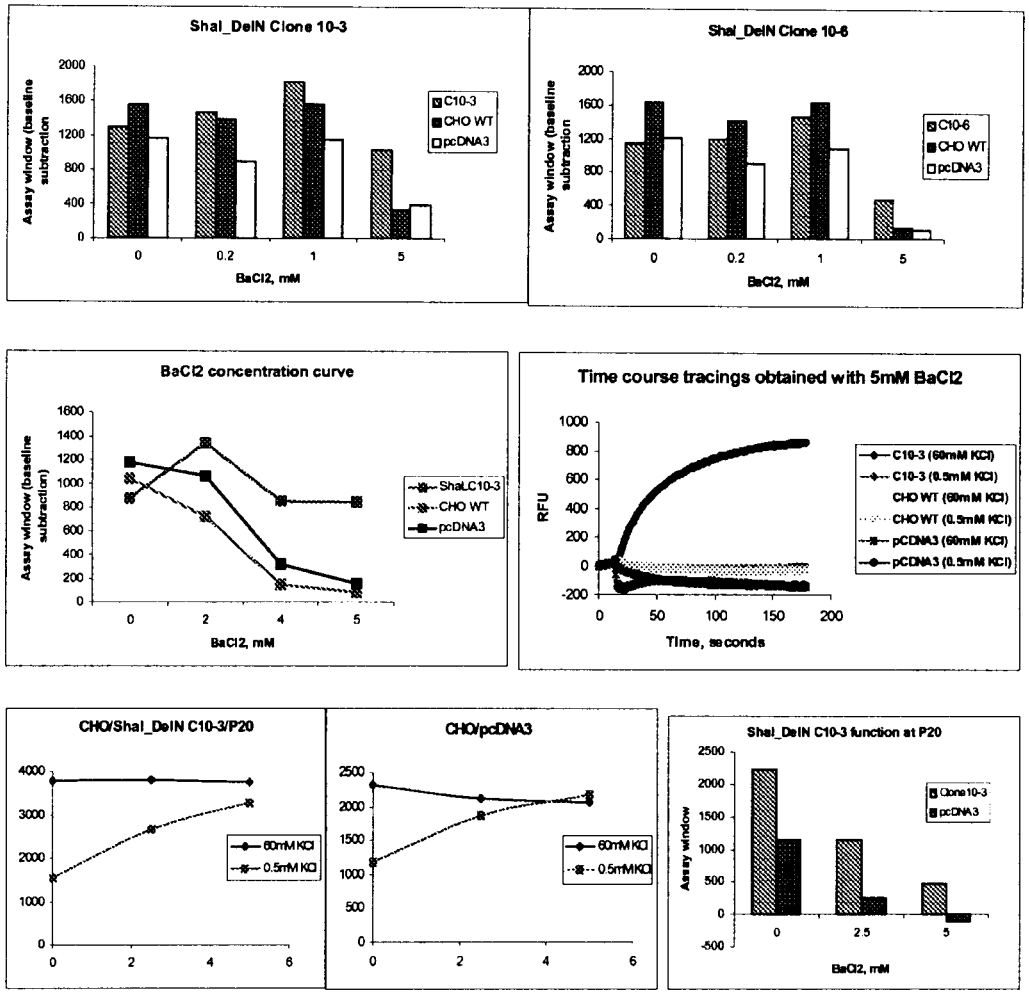
FIG. 10: Effect of BaCl2 on Sha1 channel activity on FLIPR.

FIG. 10: Effect of BaCl2 on ShaI channel activity on FLIPR.

Clone 10-3 had a higher assay window on FLIPR in the presence of Ba2+, than clone 10-6. ShaI outward currents were not inhibited by Ba2+ as shown by electrophysiology. The idea is that in pcDNA3 cells, Ba2+ inhibits the endogenous outward K+ currents leading to an accumulation in intracellular Potassium and therefore depolarization of the cells. Thus, with 0.5 mM KCl in the external solution and increasing Ba2+ concentration, the membrane potential is increased with complete collapse of the wild-type cell assay window at 5 mM BaCl2. In contrast the ShaI_delN clone 10-3 cell line still has significant ShaI outward K+ current activity at 5 mM Ba2+ resulting in an assay window. ShaI_delN clone 10-3 cells were tested for function on FLIPR up to passage 20 (P20, FIG. 11). The cells still had a significant assay window at passage window at P20. However, the size of the window is reduced with increase in cell passage.

Figure 11:
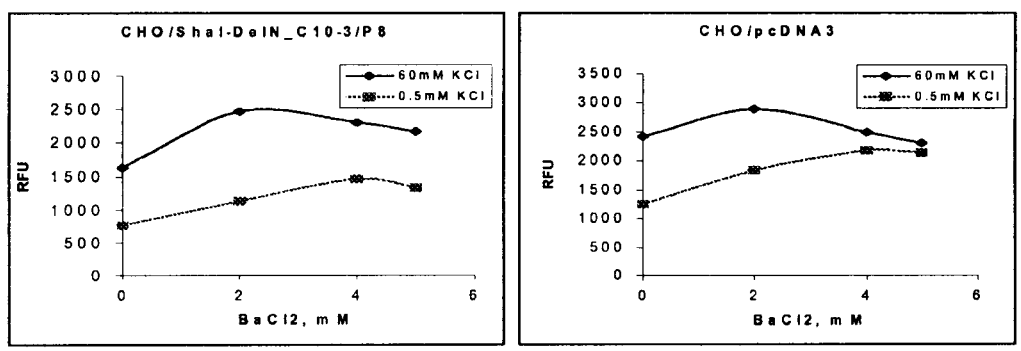
FIG. 11: Sha1_delN C10-3 function on FLIPR at passage 20.

FIG. 11: ShaI_delN C10-3 function on FLIPR at passage 20.

Increased Currents by Coexpression of an Accessory Protein: For some ion channels, currents can be increased by coexpression of accessory proteins, which is shown in FIG. 12.

Figure 12:
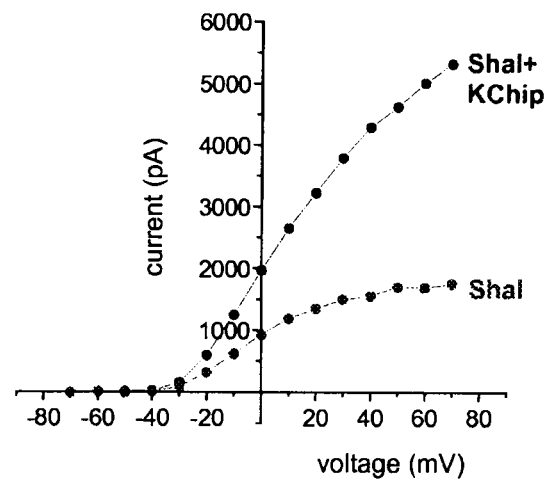
FIG. 12: CHO-K1 cells stably expressing Sha1_delN were either mock transfected (lower line) or cotransfected with KChIP (upper line).

FIG. 12: CHO-K1 cells stably expressing ShaI_delN were either mock transfected (red trace, lower line) or cotransfected with KChIP (blue trace, upper line).

Additional Electrophysiology

Chinese hamster ovary (CHO) cells transfected with (a) a *Drosophila* ShaI gene (b) a *Drosophila* ShaI pore mutant gene and (c) a *Drosophila* ShaI+KChIP gene, and were used for all measurements. Cells were plated in 35 mm Petri dishes 2-6 hours before the experiment.

Data were acquired and analyzed using pClamp software (version 9.0.1.16). The whole-cell configuration of the patch-clamp technique was used to voltage clamp cells at room temperature (22-25° C.). Pipettes were pulled from borosilicate glass capillaries (#8250, Garner Glass, Claremont, Calif.) using a DMZ Universal Puller (Zeitz, Munich, Germany) and had resistances of 1-2 MOhm when filled with pipette solution and measured in bath solution. The liquid junction potential between bath and pipette solution was always compensated before the formation of a gigaohm seal.

Membrane current was measured under whole-cell clamp, sampled at 2 kHz and filtered at 1 kHz by an Axoclamp 200B (Axon Instruments). Capacitance currents were electronically compensated at the beginning of each experiment. P/4 leak correction was applied.

To study ShaI currents on CHO cells, cells were held at −70 mV and a family of 500 ms test voltage pulses was applied starting from −70 to +70 mV, or +100 mV, in 10 mV increments. The amplitude, as measured for the current-voltage relationship, was defined as the maximal current at a given membrane potential.

Bath solution: NaCl (160 mM), KCl (2.5 mM), MgCl2 (1 mM), CaCl2 (2 mM), HEPES (10 mM) pH 7.4 (with NaOH)

Pipet solution: KCl (160 mM), MgCl2 (5 mM), EGTA (1 mM), CaCl2 (0.1 mM), NaGTP (0.1 mM), K2ATP (3 mM), HEPES (5 mM) pH 7.4 (with NaOH)

Additional Electrophysiology

By way of further assay validation, the presumptive ShaI blocker arachidonic acid (J. Neurosci. 1996, 16:2522) was tested on ShaI/KChIP 20 cells (FIG. 13).

Figure 13:
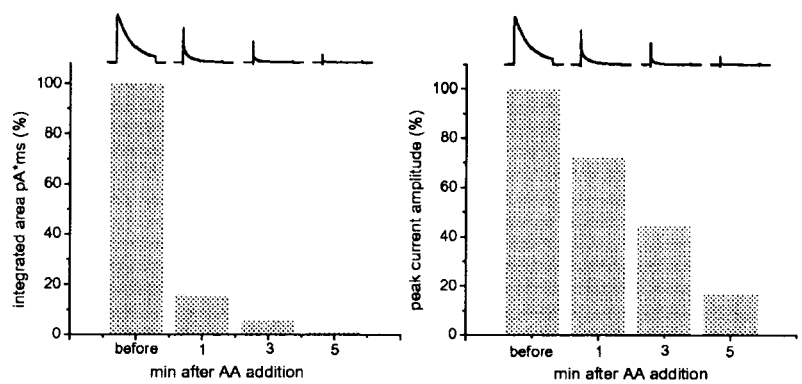
FIG. 13: Sha1/KChIP inhibition by arachidonic acid measured by whole cell patch-clamp; Right panel: Peak current amplitudes; Left panel: Integrated area.

FIG. 13: ShaI/KChIP inhibited by arachidonic acid. ShaI/KChIP 20 cells were perfused with a 100 uM [final] solution of arachidonic acid in bath solution. Pre- and post-compound currents were measured under whole-cell clamp. Left panel: Integrations of the areas under the curves (total current). Right panel: Peak current amplitudes.

Results and conclusions: Complete inhibition of total ShaI/KChIP current was obtained after incubation with arachidonic acid for five minutes, thus confirming a key indicator of this channel.

Figure 14:
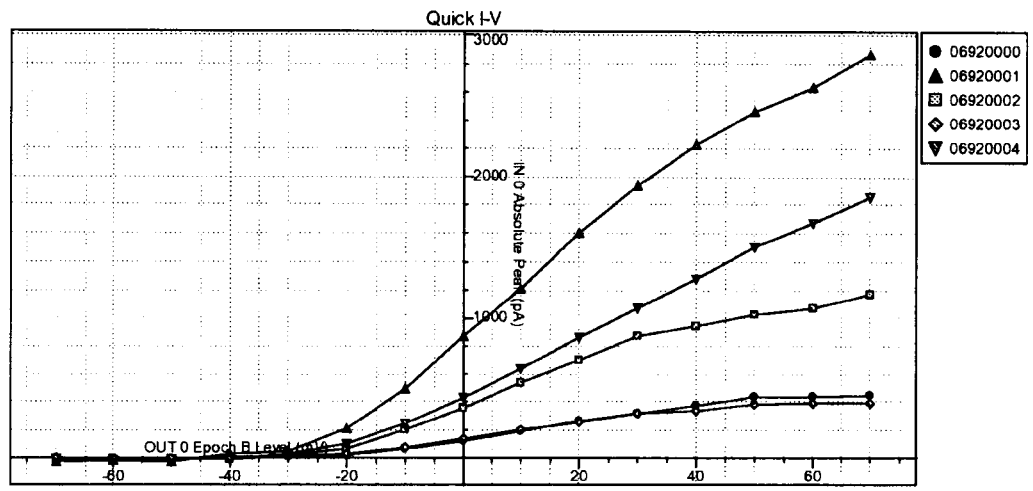
FIG. 14: I/V curves for clones 18-13-6 and 18-13-20.
Figure 14:
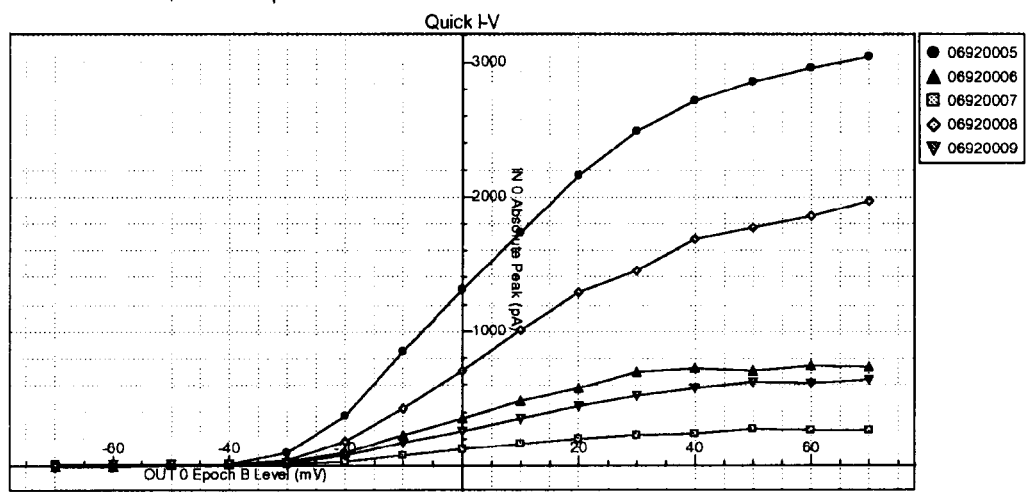

ShIP_GFP stable clones in CHO cell line, shown in FIG. 14.

FIG. 14: I/V curves for clones 18-13-6 and 18-13-20.

Buffer: KCNQ Int/Ext solution

Protocol: C:\FJB\patch clamp\Patch_parmeters\CHO cells_ShaI_IV 500 ms_to70 mV_Whole_cell.pro Clone Generation and Selection Transfection: ShaI_delN 10-3 cells were plated in a 35 mm 6-well plates at 2.5×105 cells/well and each well transfected 6 hours later with 1 ug pcDNA3.1/Zeo(+)KChIP DNA using FuGENE transfection reagent (Roche) and the manufacturer's recommendations. A mock transformation without KChIP DNA was also done to monitor antibiotic selection. For a "Neo/Zeo" control cell line, pcDNA3.1/Neo CHO cells at passage 44 were transfected with 1 ug pcDNA3.1/Zeo DNA. Cells were passaged 24 hr later to 175 cm2 flasks @750K cells/flask and placed under antibiotic selection (900 ug/ml G418; 1 mg/ml Zeocin). For the ShaI/KChIP transfection, once selection was complete (four days), cells were diluted to 12 cells/ml in complete culture medium and 250 ul was dispensed into each well of four 96-well culture plates. Wells containing a single colony were identified after one week's growth and picked for expansion and testing after an additional week. The Neo/Zeo control cells were propagated as a polyclonal pool.

Figure 15:
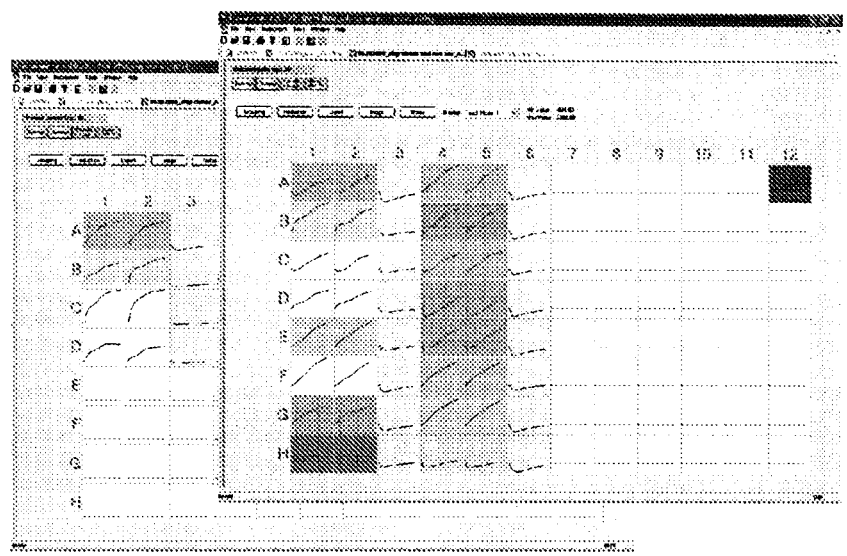
FIG. 15: Sha1/KChIP clone screening and Neo/Zeo control line. ScreenWorks screenshots showing primary FLIPR data and a reduced data table for the 19 clones and the Neo/Zeo pool (middle panel, wells H4-6).

Clone screening: 19 individual ShaI/KChIP clones were screened for function (FIG. 15). The amplitude and kinetic profile in response to depolarization with KCl was used to select clones for further evaluation.

FIG. 15: ShaI/KChIP clone screening and Neo/Zeo control line. ScreenWorks screenshots showing primary FLIPR data and a reduced data table for the 19 clones and the Neo/Zeo pool (middle panel, wells H4-6). Cells were plated at an estimated 5×104 cells/well into 96-well assay plates (TC-treated, BD Biosciences) and incubated overnight at 37° C./5% CO2. Culture medium was removed and replaced with 1× blue membrane potential dye in assay buffer and incubated for 0.5 hour at 25° C. The assay was read on a FLIPR Tetra by recording baseline fluorescence for 20 sec, and recording an additional 180 sec after activation with isometrically-substituted KCl (60 mM [final], columns 1, 2, 4 & 5). Columns 3 & 6 show the responses to normal assay buffer (0.5 mM KCl [final]). Subtract bias was set at 1 and negative control correction was OFF. For the data table, subtract bias was at 1 and negative control correction (from columns 3 & 6) was ON.

Results and conclusions: Seven ShaI/KChIP clones were identified for further testing (blue rows in data table). Clone 18 (left panel, row C) was ultimately selected for two rounds of subcloning in order to stabilize the response and reduce heterogeneity. Importantly, as the Neo/Zeo cell line was found to be essentially unresponsive to the activation method used (middle panel, wells H4 & 5), the requirement for it as a control line was effectively eliminated.

Intermediate subclone generation: ShaI/KChIP clones 17 & 18 were plated for subcloning as described previously. A combined total of 66 subclones were screened, and number 18-13 was selected as the source for final subclone generation (data not shown, notebook 1050115 #8).

Final subclone screening and selection: ShaI/KChIP subclone 18-13 was plated for final subcloning as described previously. Thirty-four subclones were evaluated for response to KCl depolarization (FIG. 16).

Figure 16:
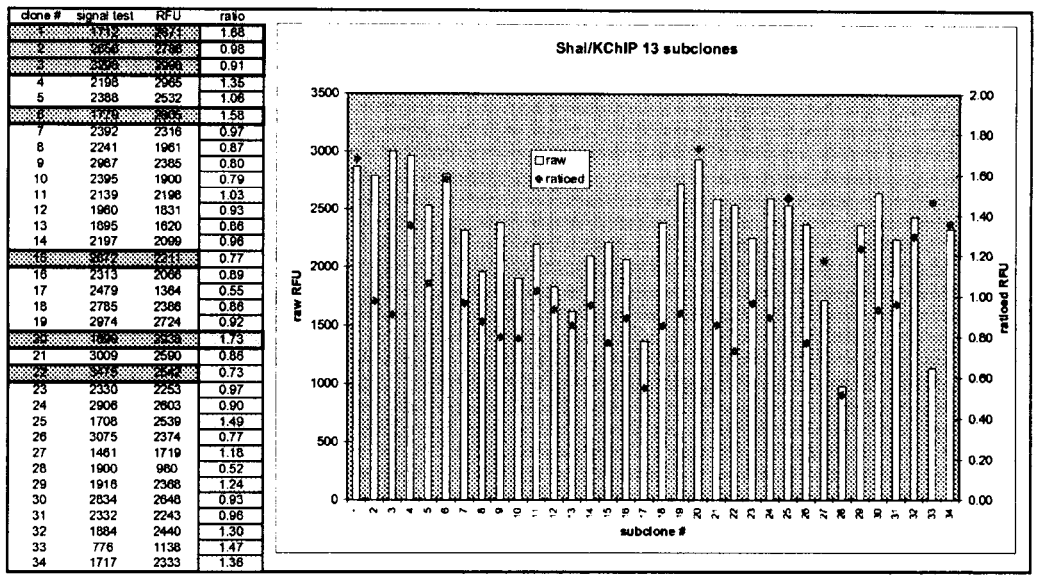
FIG. 16: Sha1/KChIP final subclone screening. Reduced FLIPR data from subclone screening resulting in the final cell line.

FIG. 16: ShaI/KChIP final subclone screening. Reduced FLIPR data from subclone screening resulting in the final cell line. Cells were plated at an estimated 5×104 cells/well into 96-well assay plates (TC-treated, BD Biosciences) and incubated overnight at 37° C./5% CO2. Culture medium was aspirated and replaced with 1× blue membrane potential dye in assay buffer and incubated for 0.5 hour at 25° C. The assay was read on a FLIPR Tetra by recording baseline fluorescence for 20 sec, and recording an additional 60 sec after activation with isometrically-substituted KCl (60 mM [final]). No data reductions were used during data export. Both the raw response (RFU, relative fluorescence units, blue bars) and ratioed responses (diamonds) are shown. The ratioed response is equal to the raw response divided by the signal test (i.e., baseline fluorescence)—this was done to compensate for variations in the number of cells plated for each clone. The green cells in the "ratio" column indicate clones with a raw/baseline ration >1. Clones were chosen for further evaluation by considering one and/or both reductions (indicated by marked lines).

Results and conclusions: Seven cell lines were chosen for further evaluation (marked in FIG. 15) on the FLIPR (data not shown) and in electrophysiology (see "Additional Electrophysiology" for examples). After testing clones via conventional patch clamp, it was decided to move forward with ShaI/KChIP 18-13-20. This cell line, known as ShaI/KChIP 20 (or ShIP 20), was used, unless indicated otherwise, in all subsequent HTS assay and screen development.

Assay & Screen Development

HTS Screening Strategy

Figure 17:
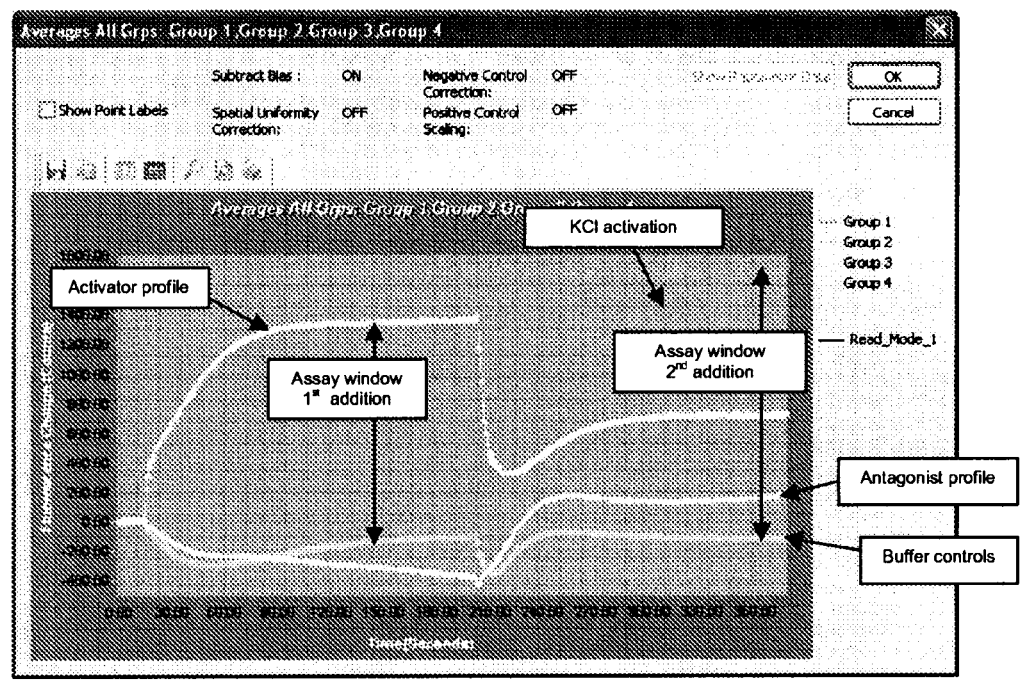
FIG. 17: Sha1/KChIP assay FLIPR response profiles.

This assay uses two fluid additions to permit the detection of activators and antagonists in a single experiment (FIG. 17). In screening, test compounds are added in the first addition and allowed to incubate for three minutes. An activating dose of KCl is then introduced in the second addition and the fluorescence read for an additional three minutes. Controls are run for both additions. A response (rise in fluorescence) significantly greater than that from buffer/DMSO in the first addition indicates that the compound may be an activator (green trace). A reduced response after the second addition indicates that the compound may be an antagonist (blue trace).

FIG. 17: ShaI/KChIP assay FLIPR response profiles. Sample control group averages from BioFocus compound screening showing first and second addition assay windows, and potential activator and antagonist profiles.

Basic Test Protocol

Cells were dispensed in a 50 μl volume containing 7,500 cells into 384-well TC clear/black assay plates (Greiner 781091) using a Multidrop 384 dispenser, incubated at ambient temperature for one hour (to reduce edge effects), and incubated overnight at 37° C./5% CO2. The cells were assayed 18-24 hours after seeding, at which point they were just approaching confluency in the wells. Culture medium was removed by flicking and tapping it out of the plate, and cells were loaded with 20 ul/well of 1× blue membrane potential dye in assay buffer for 30 minutes at 25° C. After 30 minutes the assay plate was placed into the FLIPR and run using a two-addition protocol. The first addition (5×, 5 ul) contained 2.5% DMSO in assay buffer. The pipetting height was set at 15 and the speed 20. The plate was read for three minutes after this addition. The second addition (2×, 25 ul) was either assay buffer or 120 mM isometrically-substituted KCl (i.e., KCl substituted for NaCl on a 1:1 molar basis). The height was 20 and the speed 25. Aspirate speeds were set at the lowest values and no hold or expel volumes applied. The plate was read for an additional three minutes after the second addition. The exported statistics were typically configured as stat1=average of 190-200 (the interval just before the first addition) and stat2=maximum of 260-maximum allowed. Subtract bias was set at 1 and negative control correction was OFF. Z' statistics (an index of "screenability", Z'>0.5=single-pass screen) were calculated using the following formula:

$$Z'=1-((3\sigma max+3\sigma min)/(I\mu max-\mu min I)).$$

Use of Membrane Potential Dye in Assay

The ShaI cell line assay used the addition of membrane potential dye in the activation buffer to increase the size of the assay window (data not shown). After the addition of KChIP to the ShaI cell line, we examined whether this requirement for dye could be dropped in order to simplify the protocol and reduce the cost of the assay for both development and HTS (FIG. 18).

Figure 18:
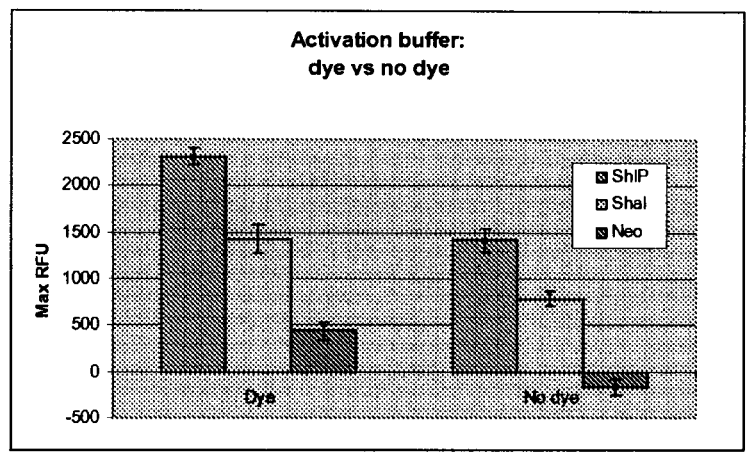
FIG. 18: Effect of dye in activation buffer measured on FLIPR Tetra.

FIG. 18: Use of dye in activation buffer. ShaI/KChIP (ShIP), ShaI and Neo (ShaI control) cell lines were plated at 5×10$^4$ cells/well into 96-well assay plates (TC-treated, BD Biosciences) and incubated overnight at 37° C./5% CO2. Culture medium was aspirated and replaced with 50 ul 1× blue membrane potential dye in assay buffer and incubated for 0.5 hour at 25° C. The assay was read on a FLIPR Tetra by recording baseline fluorescence for 20 sec, and recording an additional 60 sec after addition of 50 ul isometrically-substituted KCl (60 mM [final]) with and without membrane potential dye. For the data export, subtract bias was set at 1. Error bars are +/−1 SD.

Results and conclusions: The removal of membrane potential dye from the activation buffer resulted in a significantly reduced fluorescence change upon KCl activation for all three cell lines. The Z' statistic for ShaI/KChIP decreased from 0.77 to 0.59, which is still well above the single-pass screening cutoff of 0.5 (data not shown). As the addition of dye to the activation buffer would complicate the HTS protocol, and as the estimated potential cost savings over the course of development and screening was considerable, it was decided to progress without the use of dye in the activation buffer. The reduction in the Z' statistic was largely recovered during subsequent development.

Assay Plate Selection

An experiment was undertaken to compare the assay's performance between our standard BD Falcon 353962 plates and the less-expensive Greiner 781091 384-well tissue culture-treated assay plates (FIG. 19) Note: Greiner is the manufacturer of the BD Falcon plates.

Figure 19:
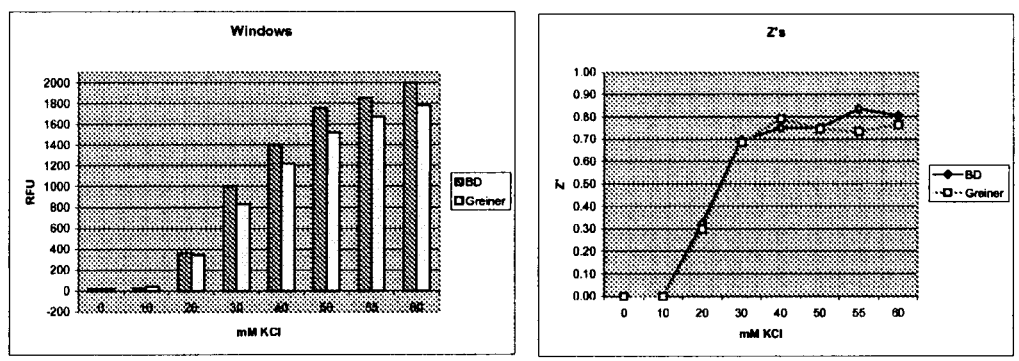
FIG. 19: Comparison of BD and Greiner 384-well assay plates.

FIG. 19: Comparison of BD and Greiner 384-well assay plates: ShaI/KChIP 20 cells were plated at 7500 cells/well into BD and Greiner 384-well assay plates and incubated overnight at 37° C./5% CO2. Culture medium was flicked out and replaced with 20 ul 1× blue membrane potential dye in assay buffer and incubated for 0.5 hour at 25° C. The assay was read on a FLIPR Tetra. The first addition (5×, 5 ul) contained 2.5% DMSO in assay buffer, and was read for three minutes. The second addition (2×, 25 ul) consisted of isometrically-substituted KCl at dose, and was also read for three minutes. Each condition was measured from 2×48 replicates to allow the calculation of Z's. The exported statistics were configured as stat1=average of 190-200 and stat2=maximum of 260-maximum allowed. Subtract bias was set at 1. Left panel: Window sizes (calculated as stat2-stat1) as a function of [KCl] for the two plate types. Right panel: Z' statistics calculated as a function of [KCl] for the two plate types.

Results and conclusions: There was a small but consistent decrease (~200 RFU) in the assay window size when using Greiner assay plates in this test. The Z' statistics, however, were nearly identical due to slightly lower CVs on the Greiner plates. As the estimated potential cost savings over the course of development and screening was substantial, it was decided to continue development using the Greiner plates, and all subsequent work was done with them.

Assay Buffer Preparation Method Testing

While experimental results during early assay development indicated the use of freshly-prepared assay buffers, this requirement was eventually dropped during screen development (data not shown). The preparation method (additions of stock solutions of KCl, NaCl and DMSO to base buffer) remained in use however, and a volume-compensated buffer preparation calculator is included in this document.

Cell Density Optimization

Figure 20:
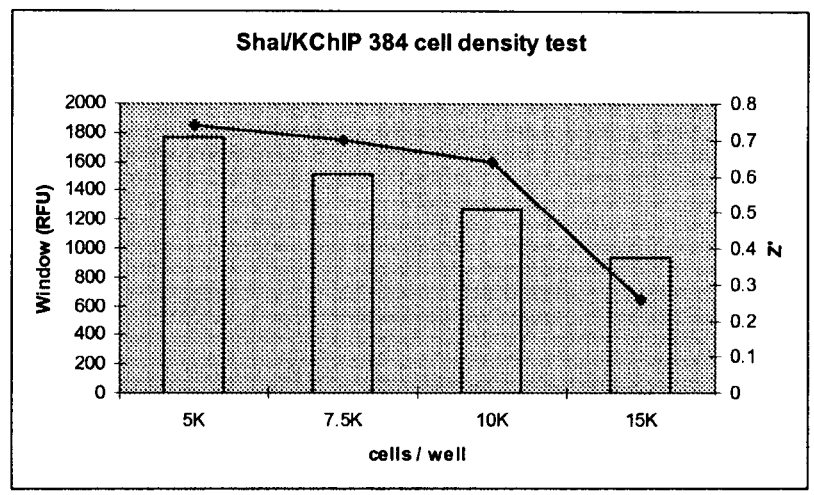
FIG. 20: Cell density optimization measured on FLIPR.

Plating densities from 5,000 to 15,000 cells/well were examined for mean response and standard deviation, and Z' statistics were calculated (FIG. 20).

FIG. 20: Cell density optimization. Reduced FLIPR data showing statistics for full plates at the indicated cell densities with resulting Z' statistics. Platings below 5000 cells/well did not yield a monolayer the next day and were not tested. ShaI/KChIP cells were plated at the indicated densities incubated at 37° C./5% CO2 and assayed the following day. Cells were loaded with 20 ul 1× dye/well for 0.5 hour at 25° C. A two-addition protocol was used. The first addition (5×) was 5 ul 2.5% DMSO in assay buffer (0.5% [final]) read for 180 sec, and the second (2×) was 25 ul isometrically-substituted KCl in assay buffer (60 mM [final]) read for an additional 180 sec. The statistics were calculated using the average of reads 190-200 (minimum response) and the maximum of reads 260-end (maximum response). Spatial uniformity correction was ON. The bars show response to activation, and the line shows the trend in Z' statistics Results and conclusions: This assay tended to perform better at lower cell densities. It was decided to move development forward with 7500 cells/well (rather than 5000 cells/well, as would seem indicated) to avoid potential problems due to variations in cell counting and plating.

Dye Concentration

Figure 21:
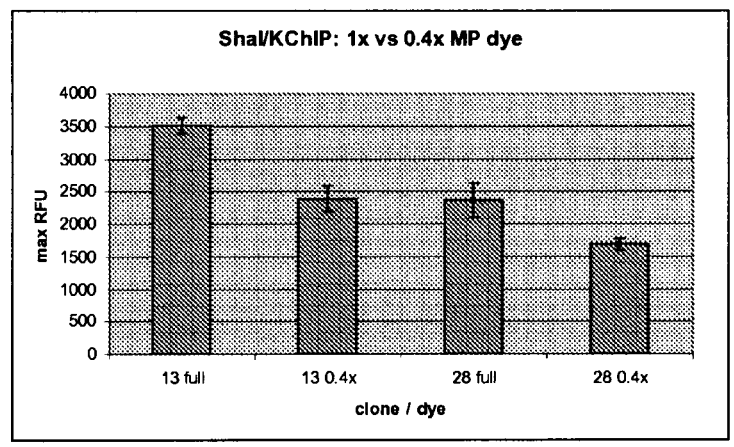
FIG. 21: Dye concentration evaluation for Sha1/KChIP clones 18-13 and 18-28.

The performance of ShaI/KChIP intermediate subclones 18-13 and 18-28 was examined using 0.4× membrane potential dye (vs. 1×) as a possible cost saving measure (FIG. 21).

FIG. 21: Dye concentration evaluation. ShaI/KChIP clones 18-13 and 18-28 were plated at 5×10$^4$ cells/well into 96-well assay plates (TC-treated, BD Biosciences) and incubated overnight at 37° C./5% CO2. Culture medium was removed and replaced with 50 ul 1× or 0.4× blue membrane potential dye in assay buffer and incubated for 0.5 hour at 25° C. The assay was read on a FLIPR Tetra by recording baseline fluorescence for 20 sec, and recording an additional 60 sec after addition of 50 ul isometrically-substituted KCl (60 mM [final]). Maximum RFU values are shown. For the data export, subtract bias was set at 1 and negative control correction was ON. Error bars are +/−1 SD.

Results and conclusions: Dye used at 0.4× resulted in an assay window reduced to 70% the size of that obtained with full (1×) dye for both clones tested. To preserve the full assay window it was decided to carry out all subsequent development using 1× dye.

DMSO Tolerance

A cell-based assay's sensitivity to DMSO in the first addition factors into calculations made about the ability to screen compounds at desired levels from particular DMSO stock concentrations. The effects of first addition DMSO on assay window size and variability, and the resulting Z' statistics were examined (FIG. 22).

Figure 22:
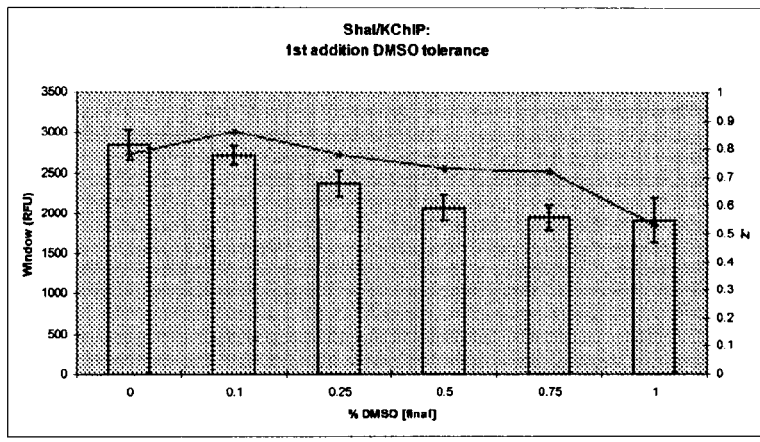
FIG. 22: Effect of DMSO on Sha1/KChIP assay window size, standard deviations and Z' statistics.

FIG. 22: ShaI/KChIP assay window size, standard deviations and Z' statistics. ShaI/KChIP18-13 cells were plated at 7500 cells/well into Greiner 384-well assay plates and incubated overnight at 37° C./5% CO2. Culture medium was flicked out and replaced with 20 ul 1× blue membrane potential dye in assay buffer and incubated for 0.5 hour at 25° C. The assay was run on a FLIPR Tetra using the following conditions: the first addition (5×, 5 ul) contained 5× [final] DMSO in assay buffer, and was read for three minutes. The second addition (2×, 25 ul) consisted of isometrically-substituted KCl (120 mM), and was read for an additional three minutes. Each condition was measured from 64 replicates to allow the calculation of Z's. The exported statistics were configured as stat1=average of 180-200 and stat2=maximum of 260-380. Subtract bias was set at 1 and negative control correction was OFF. Blue bars (stat2-stat1) show response to activation, and the red line shows the trend in Z' statistics. Error bars are +/−1 SD.

Results and conclusions: While standard deviations remained relatively constant, with the exception of 1% DMSO [final], window sizes decreased with increasing DMSO and, necessarily, there occurred a corresponding decrease in Z' statistics. As a practical matter, given the concentrations of the compound DMSO stocks available to us (usually 2 or 10 mM), we can limit the cells' exposure to 0.5% DMSO [final]. In this experiment, that condition yielded an assay window of >2000 RFUs and a Z' statistic of 0.73.

Dye Loading Time

Figure 23:
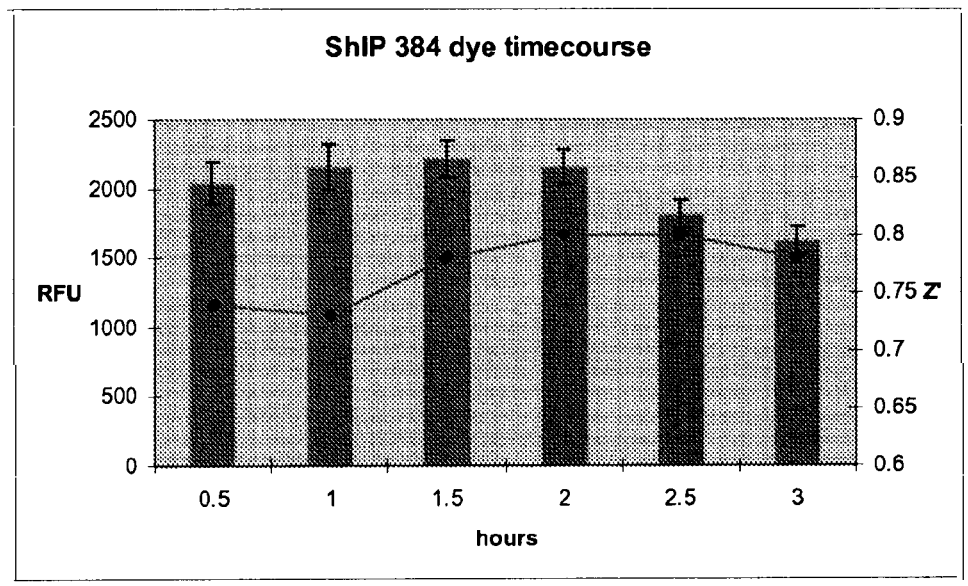
FIG. 23: Effect of dye loading time on Sha1/KChIP assay window size, standard deviation and resulting Z' statistic.

The effect of progressively longer dye loading times on assay window size, standard deviation and resulting Z' statistic was examined (FIG. 23).

FIG. 23: Effect of dye loading time on assay statistics. Filtered full-plate statistics showing the effect of dye loading times between 0.5 and 3 hours on window size, standard deviation and Z' statistics. ShaI/KChIP18-13 cells were plated at 7500 cells/well in 384-well assay plates and tested the following day. Culture medium was removed by flicking the plates and cells loaded with 20 ul 1× membrane potential dye per well for 0.5-3 hours at 25° C. A two-addition protocol was used. The first addition (5×) was 5 ul 2.5% DMSO in assay buffer (0.5% [final]) read for 180 sec, and the second (2×) was 25 ul 120 mM isometrically-substituted KCl in assay buffer (60 mM [final]) read for an additional 180 sec. Statistics were calculated using the average of reads 190-200 (minimum response) and the maximum of reads 260-end (maximum response). Subtract bias was set at 1 and negative control correction was OFF, green bars (stat2-stat1) show response to activation, and the blue line shows the trend in Z' statistics. Error bars are +/−1 SD. The data were minimally corrected for systematic artifacts.

Results and conclusions: Dye loading times between 0.5 and 3 hours all produced Z' statistics above 0.7. There was an assay window maximum at 1.5 hours and a Z' maximum at 2-2.5 hours. A visual inspection of the cells at three hours showed them to be in good condition. It was concluded that all dye loading times from 0.5-3 hours result in assays that perform well.

Cell Temperature for Dye Loading

Figure 24:
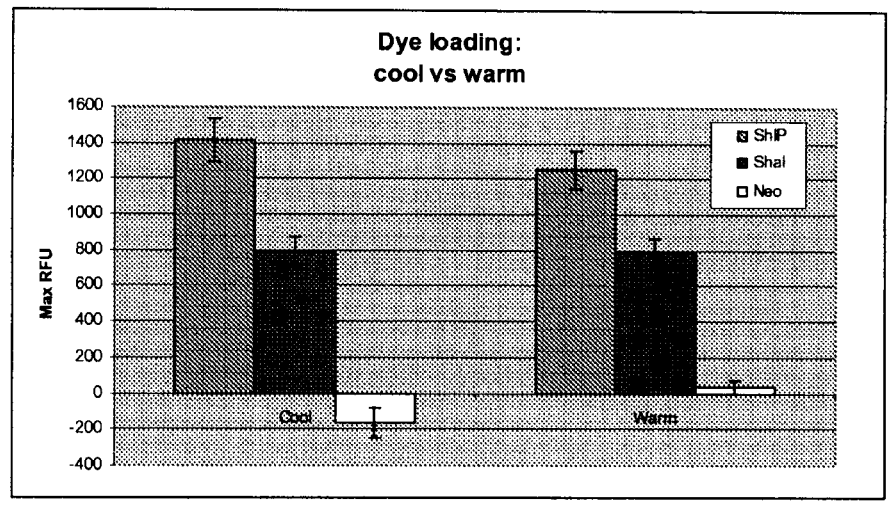
FIG. 24: The effects of pre-cooling cells to room temperature on the Sha1/KChIP assay prior to dye-loading.

A comparison was made regarding dye-loading temperature between cell plates allowed to cool at room temperature (25° C.) for one hour and those plates dye-loaded directly from 37° C. incubation (FIG. 24).

FIG. 24: The effects of pre-cooling cells to room temperature prior to dye-loading. ShaI/KChIP (ShIP), ShaI and Neo (ShaI control) cell lines were plated at 5×104 cells/well into 96-well assay plates (TC-treated, BD Biosciences) and incubated overnight at 37° C./5% CO2 for testing the following day. Culture medium was removed and replaced with 50 ul 1× blue membrane potential dye in assay buffer and incubated for 0.5 hour at 25° C. The assay was read on a FLIPR Tetra by recording baseline fluorescence for 20 sec, and recording an additional 60 sec after addition of 50 ul isometrically-substituted 120 mM KCl (60 mM [final]). For the data export, subtract bias was set at 1 and negative control correction was ON. Error bars are +/−1 SD. Results and conclusions: There was a statistically negligible difference between cool and warm cells for ShaI/KChIP, no difference for ShaI, and a significant reduction in response of the pre-cooled Neo control line. It was decided that subsequent development would be done by dye-loading assay plates that had been equilibrated at room temperature for one hour as the reduction of background response (as seen in the control line) was a desirable outcome. The requirement for pre-cooling assay plates places only a minor burden on the HTS protocol.

Activator EC50s

Figure 25:
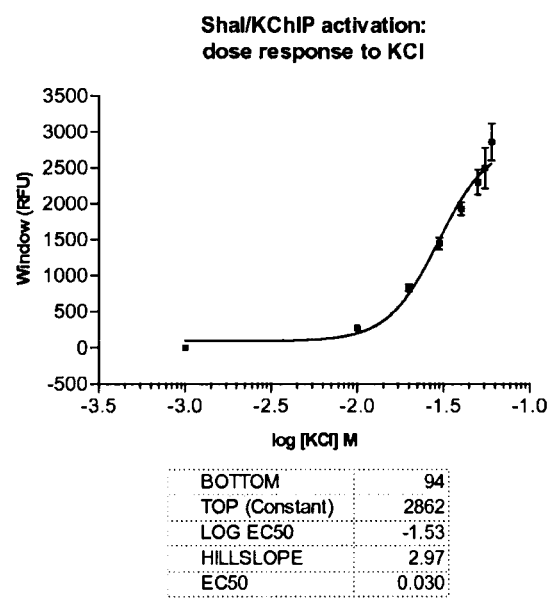
FIG. 25: Group-averaged primary FLIPR data and preliminary EC50 for Sha1/KChIP18-13 cell line.

A dose response was established for ShaI/KChIP 18-13 by isometric KCl activation (FIG. 25).

FIG. 25: Group-averaged primary FLIPR data and preliminary EC50. ShaI/KChIP18-13 cells were plated at 7500 cells/well in 384-well assay plates and tested the following day. Culture medium was removed by flicking the plates and cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second (2×) was 25 ul 1 isometrically-substituted KCl at dose in assay buffer (0-60 mM [final]) read for an additional 180 sec. Statistics were calculated using the average of reads 180-200 and the maximum of reads 260-maximum allowed. Subtract bias was set at 1 and negative control correction was OFF. Top panel: ScreenWorks screenshot of reduced FLIPR data showing group average responses to KCl dosing. Bottom panel: Non-linear regression/sigmoidal dose response showing calculated Hillslope and EC50.

Results and conclusions: The ShaI/KChIP cell line responded progressively and with low variability to activation by increasing levels of isometrically-substituted KCl. The highest achievable concentration of KCl using this method is 60 mM [final]. The EC50, using a fixed top response, was calculated to be 30 mM KCl in this experiment.

MDC vs Axygen FLIPR 384 Tips

Figure 26:
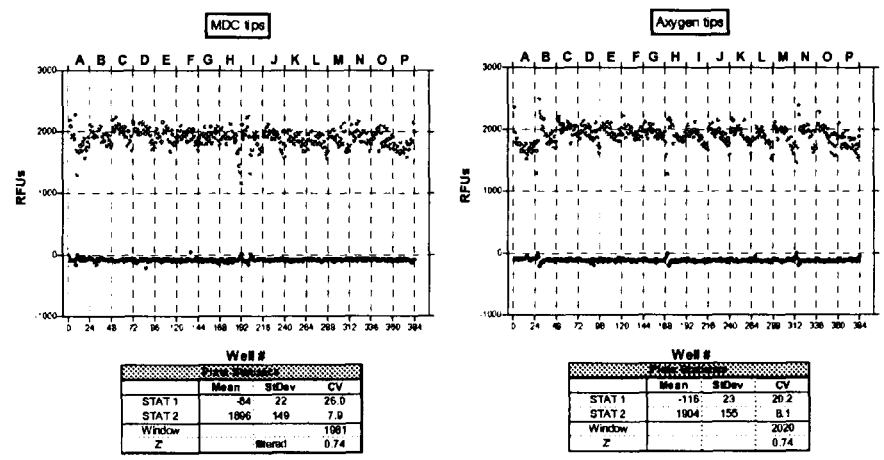
FIG. 26: Comparison of GraphPad Prism scatter plots showing maximum and minimum responses with resultant statistics of the Sha1/KChIP assay for MDC and Axygen FLIPR 384 tips.

A comparison was made between FLIPR 384 tips supplied by Molecular Devices Corporation (MDC) and those supplied by Axygen Scientific (FIG. 26). Note: Axygen is a former supplier of FLIPR 384 tips to MDC. The cost to us in RTP for Axygen tips is ⅔ that of MDC tips.

FIG. 26: Comparison of MDC and Axygen FLIPR 384 tips. GraphPad Prism scatter plots showing maximum and minimum responses with resultant statistics of the ShaI/KChIP assay. ShaI/KChIP18-13 cells were plated at 7500 cells/well in 384-well assay plates and tested the following day. Culture medium was removed by flicking the plates and cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second (2×) was 25 ul 120 mM isometrically-substituted KCl in assay buffer (60 mM [final]) read for an additional 180 sec. Statistics were exported using the average of reads 180-200 and the maximum of reads 260-maximum allowed. Subtract bias was set at 1 and negative control correction was OFF. Left panel: Molecular Devices FLIPR 384 tips. Right panel: Axygen FLIPR 384 tips.

Results and conclusions: The performance of the ShaI/KChIP assay was identical using either MDC or Axygen tips. As the cost savings over the course of assay development and HTS was calculated to be considerable, all subsequent protocols used Axygen Scientific FLIPR 384 tips.

Stability of Assay Buffer and Other Reagents

Figure 27:
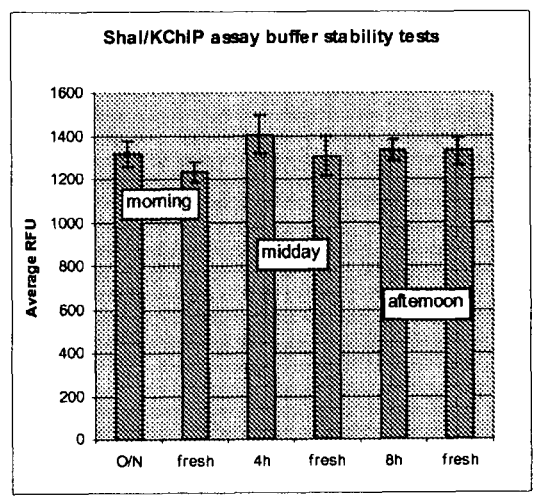
FIG. 27: Determination of stability of reagents used in the Sha1/KChIP 18-13 assay over time.

An assessment was made of the stability of the reagents used in the ShaI/KChIP assay, namely, the first addition assay buffer/DMSO, reconstituted dye and activation buffer (FIG. 27).

FIG. 27: Reagent stability. ShaI/KChIP 18-13 cells were plated at 7500 cells/well in 384-well assay plates and tested the following day. Culture medium was removed by flicking the plates and cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second (2×) was 25 ul 120 mM isometrically-substituted KCl in assay buffer (60 mM [final]) read for an additional 180 sec. Statistics were exported using the average of reads 180-200 and the maximum of reads 260-maximum allowed. Subtract bias was set at 1 and negative control correction was OFF. All reagents for the ShaI/KChIP assay were prepared the day prior (with the exception of the dye), early in the workday and freshly for each experiment. The assay was run at time points 0, 4 and 8 hrs and overnight (O/N) with both previously- and freshly-prepared reagents.

Results and conclusions: The performance of the ShaI/KChIP assay exhibited only minor fluctuations during the course of the day. It was concluded that the reagents were stable for at least one full day. Subsequently, it was found that the assay and activation buffers were stable over the course of at least one week (data not shown).

FLIPR Tetra Pipetting Optimization

A number of experiments (data not shown) were carried out to examine the effect of changes in pipetting heights, speeds, and hold and expel volumes on assay statistics (Table 2).

Results and conclusions: The following table shows the settings that consistently gave the best results, as measured by Z' statistics:

The parameters were established using the basic test protocol. Note: No hold volumes were used during aspiration and no pauses or mixing applied to dispensing.

3-Day Minimum/Midpoint/Maximum Response

Figure 28:
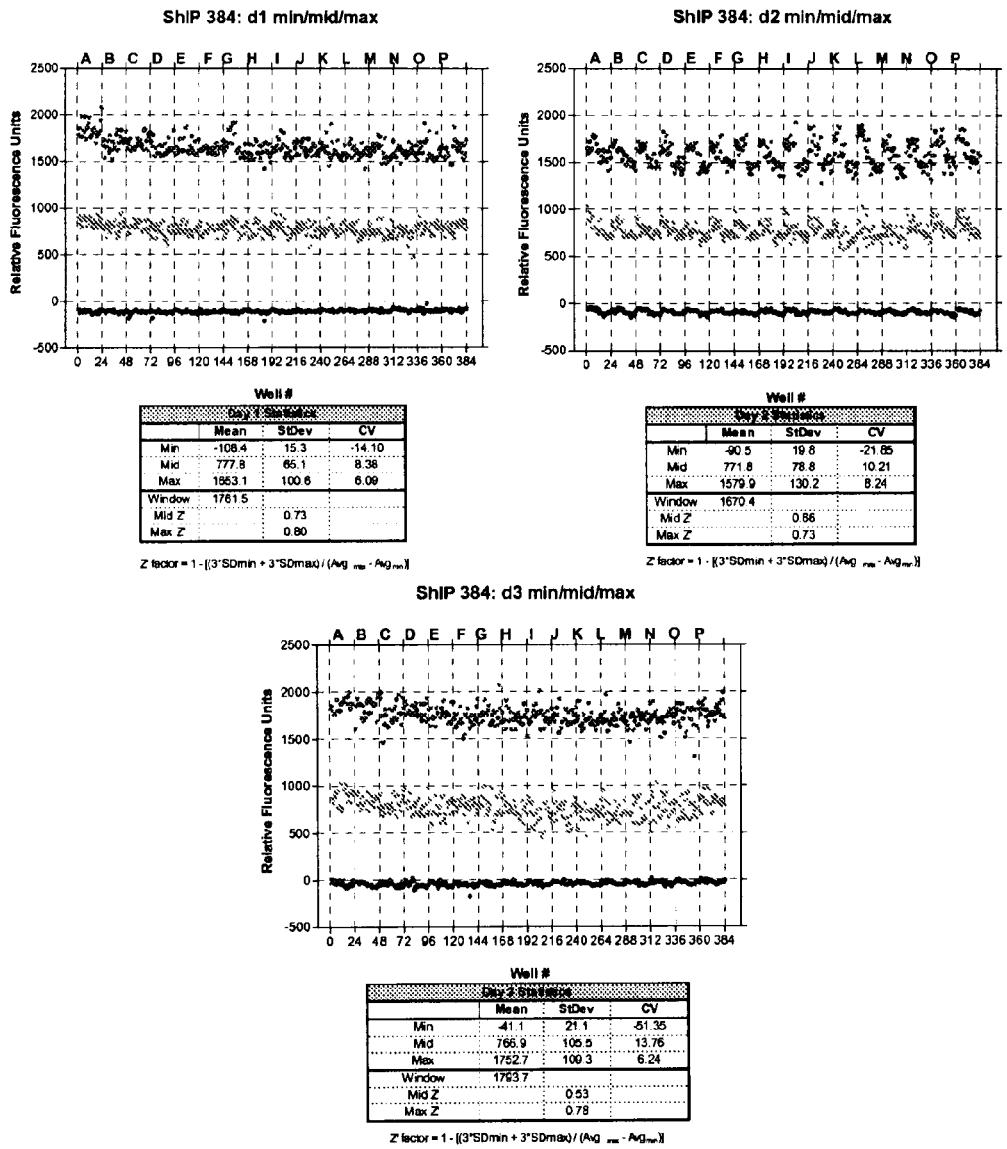
FIG. 28: Three-day minimum, midpoint and maximum statistics for Sha1/KChIP 20 assay cells.

ShaI/KChIP 20 cells were examined for stability of response three times over the course of five days to assess the variability that could be expected during a screen (FIG. 28).

FIG. 28: Three-day minimum, midpoint and maximum statistics. GraphPad Prism scatterplots showing duplicate half-plate assay data for three days with resulting window, CV and Z' statistics. ShaI/KChIP 20 cells were plated at 7500 cells/well in 384-well assay plates and tested the following day. Culture medium was removed by flicking the plates and the cells loaded with 20 ul 1× membrane potential dye per well for 0.5+ hours at 25° C. A two-addition protocol was used. The first addition (5×) was 5 ul 2.5% DMSO in assay buffer (0.5% [final]) read for 180 sec, and the second (2×) was 25 ul 60 mM (left-half of plate) or 120 mM (right-half of plate) isometrically-substituted KCl in assay buffer (30 and 60 mM [final], respectively) read for an additional 180 sec. Statistics were exported using the average of reads 180-200 and the maximum of reads 260-maximum allowed. Subtract bias was set at 1 and negative control correction was OFF. Statistics were compiled as follows: Min-left half of n001 stat1 & right half of n002 stat1; Mid-left half n001 stat2 & left half n002 stat2; Max-right half n001 stat2 & right half n002 stat2. The data were minimally corrected for systematic artifacts Results and conclusions: This assay performed well over the course of five days with a maximum Z' statistic range of 0.73 to 0.80, a mean of 0.77, and a standard deviation of 0.03. Note: Three-day single full-plate (three plates/day) experiments were also conducted (data not shown) with good results. The assay performed well over the course of six days with a maximum Z' statistic range of 0.69 to 0.74, a mean of 0.72, and a standard deviation of 0.03. Taken together, this assay could be expected to perform well over the course of a screening campaign.

3-Day Activator Dose Response Curves & EC50s

Figure 29:
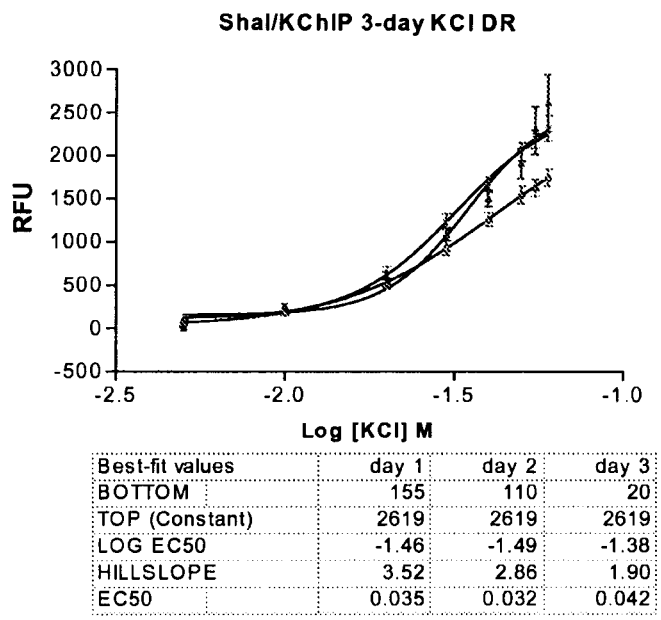
FIG. 29: Three-day KCl dose response curves and EC50s of Sha1/KChIP 20 assay cells.

The stability of response of ShaI/KChIP 20 to isometrically-substituted KCl dosing was measured three times across six days (FIG. 29).

FIG. 29: Three-day KCl dose response curves and EC50s. ShaI/KChIP 20 cells were plated at 7500 cells/well in 384-well assay plates and tested the following day. Culture medium was removed by flicking the plates and the cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second addition was 25 ul 2× isometrically-substituted KCl at dose in assay buffer (0-60 mM [final]) read for an additional 180 sec. Statistics were exported using the average of reads 180-200 and the maximum of reads 260-maximum allowed. Subtract bias was set at 1 and negative control correction was OFF. Analysis is non-

TABLE 2

Pipetting optimization. First and second addition pipetting tip heights, speeds, and expel volumes that consistently resulted in Z' statistics of 0.5 or better.

| initial vol | 1st add | vol | height | speed | tip up | expel | 2nd add | vol | height | speed | tip up | expel |
|---|---|---|---|---|---|---|---|---|---|---|---|---|
| 20 ul | 5× | 5 ul | 15 | 20 | 6 | 0 | 2× | 25 ul | 20 | 25 | 6 | 0 | linear regression, sigmoidal dose-response, top constant. Data are from single plates with 48 replicates for each dose.

Results and conclusions: The assay responded reasonably consistently to KCl dosing over three days with an EC50 range of 32 to 42 mM KCl, a mean of 36 mM, and a standard deviation of 5 mM.

3-Day Antagonist Dose Response Curves & IC50s

Figure 30:
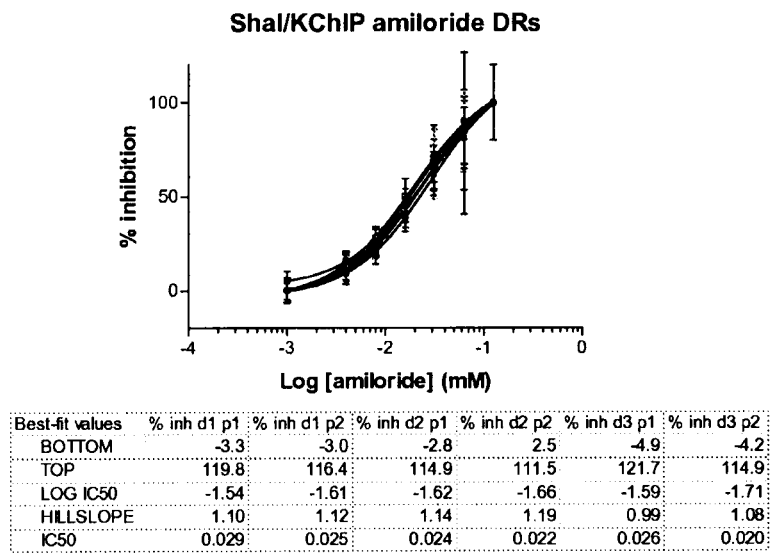
FIG. 30: Three-day amiloride dose response curves in Sha1/KChIP 20 cells.

The presumptive ShaI/KChIP antagonist amiloride, identified during BIOMOL compound screening at 25 uM, was used to generate duplicate dose responses over three consecutive days (FIG. 30).

FIG. 30: Three-day amiloride dose responses. ShaI/KChIP 20 cells were plated at 7500 cells/well in 384-well assay plates and tested the following day. Culture medium was removed by flicking the plates and the cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second addition was 25 ul 2× isometrically-substituted KCl at dose in assay buffer (0-60 mM [final]) read for an additional 180 sec. Statistics were exported using the average of reads 180-200 and the maximum of reads 260-maximum allowed. Subtract bias was set at 1 and negative control correction was OFF. Analysis is nonlinear regression, sigmoidal dose-response. The data were fixed to an extrapolated point at 55 mM KCl to compensate for first addition artifacts seen as inhibition approached 100%. Data are from duplicate plates each day with 48 replicates/plate for each dose. Results and conclusions: The assay responded consistently to inhibition by amiloride over three consecutive days with an IC50 range of 20 to 29 uM amiloride, a mean of 24 uM, and a standard deviation of 3 uM. It was concluded that this compound could reasonably be expected to perform well as an inhibition control for HTS.

Direct-to-Plate Assay

Figure 31:
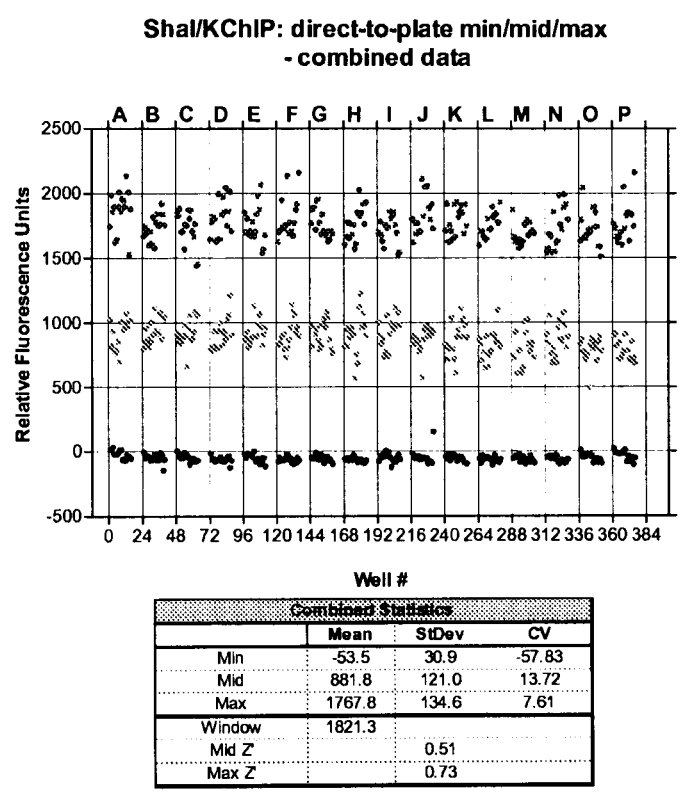
FIG. 31: Sha1/KChIP 20 direct-to-plate assay results.

Experiments were undertaken to determine the feasibility of plating cells directly from liquid nitrogen storage to assay plates without any intervening cell culture (FIG. 31).

FIG. 31: Direct-to-plate assay. Frozen ShaI/KChIP 20 cells (2 ml×106/ml) were thawed, added to 82 ml complete culture medium, and plated in a 50 ul volume (1.2×104 cells/well) in 384-well plates for testing the following day. Culture medium was removed by flicking the plates and the cells loaded with 20 ul 1× membrane potential dye per well for 0.5 hours at 25° C. A two-addition protocol was used. The first addition (5×) was 5 ul 2.5% DMSO in assay buffer (0.5% [final]) read for 180 sec, and the second addition was 25 ul 60 mM or 120 mM isometrically-substituted KCl in assay buffer (30 mM or 60 mM [final], respectively) read for an additional 180 sec. Statistics were exported using the average of reads 180-200 and the maximum of reads 260-maximum allowed. Subtract bias was set at 1 and negative control correction was OFF.

This strategy is widely-employed throughout the lead discovery sector and often results in decreased assay variability, significant time savings, and reduced labor costs.

Results and conclusions: The ShaI/KChIP assay responded well when plated directly from liquid nitrogen storage. The Z' achieved from the maximum response was 0.73. While this strategy will not be employed during the current campaign, it will be considered during future screen developments.

BIOMOL Compound Screening

Figure 32:
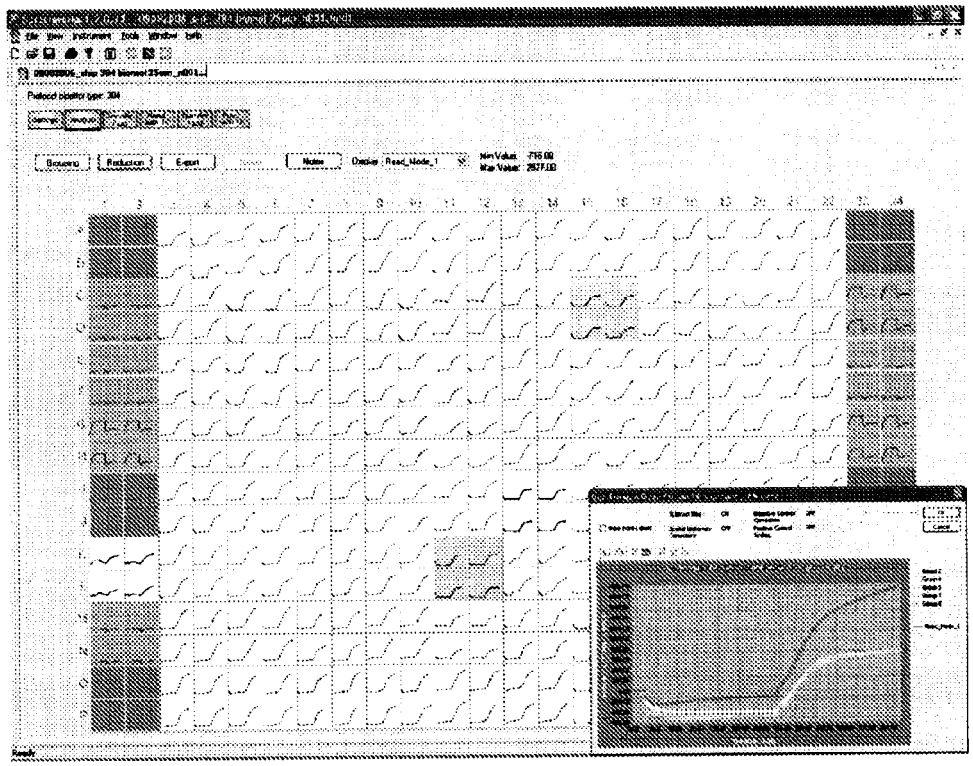
FIG. 32: ScreenWorks screenshots showing primary FLIPR data for BIOMOL compound screening in Sha1/KChIP 20 cells.
Figure 33:
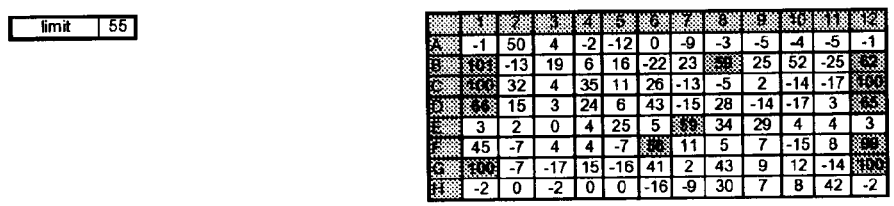
FIG. 33: Assay plate views showing percent inhibition of Sha1/KChIP response by BIOMOL compounds.

An Ion Channel Ligand Library (BIOMOL #2805), comprising 71 activators and inhibitors covering the major ion channel types, was twice measured against ShaI/KChIP 20 activity at 25 uM in 384-well four-pont mode (FIGS. 32 & 33).

FIG. 32: BIOMOL compounds—primary screening data. ScreenWorks screenshots showing primary FLIPR data for BIOMOL compound screening. ShaI/KChIP 20 cells were plated at 7500 cells/well in 384-well assay plates and screened the following day. Culture medium was removed by flicking the plates and the cells were loaded with 20 ul 1× membrane potential dye per well for 0.5 hours at 25° C. A two-addition protocol was used. The first addition was 5 ul 5× control or compound in 2.5% DMSO in assay buffer (0.5% [final]) read for 180 sec, and the second addition was 25 ul 2× control or 120 mM isometrically-substituted KCl in assay buffer (0-60 mM [final]) read for an additional 180 sec. Statistics were exported using the average of reads 180-200 and the maximum of reads 260-maximum allowed. Subtract bias was set at 1 and negative control correction was OFF. Control columns ½ and $^{23}\!/_{24}$ are described starting on pg. 53 of this document. Inset: Screenshot of group averages for the control and compound wells highlighted in the primary data screen.

FIG. 33: BIOMOL compounds—reduced screening data. Assay plate views showing percent inhibition of ShaI/KChIP response by BIOMOL compounds. Experimental conditions are described in the previous figure legend.

Results and conclusions: Using an arbitrary cutoff of 55% inhibition, three compounds showed reproducible inhibitory activity against the ShaI/KChIP response. Amiloride (B8) is a known calcium channel blocker. Both NS-1619 (E7) and flufenamic acid (F6) are known to stimulate KCa2+ channel activities. It was unlikely that these compounds would prove to be direct inhibitors of ShaI, and patch clamp measurements bore this out (data not shown). For screening purposes, amiloride proved to be consistent in its action, and so was used for subsequent BIOMOL and BioFocus validation screening, and is recommended for HTS.

BioFocus Compound Screening

Figure 34:
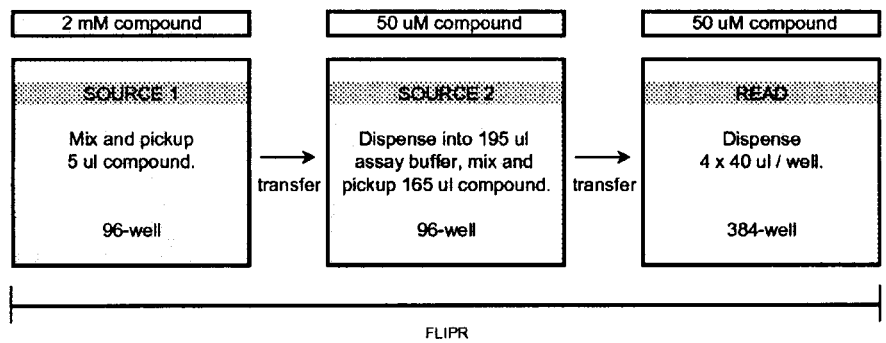
FIG. 34: Compound preparation protocol for BioFocus screening.

FIG. 34: Compound preparation protocol for BioFocus screening. Compound preparation was carried out on the FLIPR Tetra. Library plates at 2 mM were diluted 40× in assay buffer and dispensed into quadrants for 384-well screening.

The 3222 unique members of the BioFocus SoftFocus Ion Channel Libraries #1-4 (#SF101-04) were screened in 384-well four-point mode against ShaI/KChIP at 10 uM in a combined activator and antagonist screen. The same FLIPR protocol was used as for the BIOMOL screening and was carried out over four non-consecutive days. The following compound preparation protocol was used to prepare screening plates: Briefly, ShaI-KChIP cells were seeded in 384-well plates at 7500 cells/well in 50 ul and incubated overnight at 37° C./5% CO2. The next day, culture medium was removed, 20 ul of 1×FMP dye was added, and the cell plate was incubated at 27° C. for 30 minutes. After incubation, the cell plate was placed into the Tetra and a two-addition protocol was used. The 1st addition was 5 µl of 5× compound (50 µM) with a three minute read. If the compound showed a response in the 1st addition, it was flagged as an activator. The 2nd addition was 25 ul of 2× activation buffer (120 mM isometric KCl substitution for NaCl) and read for an additional two minutes. A depression of the KCl response indicated the compound was an antagonist. All data were exported as statistics files. For the 1st addition, the average from reads 190-200 was used and for the 2nd addition, the maximum from 260—maximum allowed was used.

The activation and inhibition percentages were calculated by the following formulas and all results were calculated based on controls:

% Activation (1st addition statistic)=(test sample−µmin$A$)/(µmax$A$−µmin$A$)×100 where µmax$A$=mean 100% activation, and µmin$A$=mean 0% activation.

% Inhibition (2nd addition statistic)=(µmin$I$−test sample)/(µmin$I$−µmax$I$)×100 where µmax$I$=mean 100% inhibition, and µmin$I$=mean 0% inhibition.

The Z' statistics for activation and inhibition were calculated using the following formula:

$Z' = 1 - ((3\sigma max + 3\sigma min)/(I\mu max - \sigma min I))$

Figure 35:
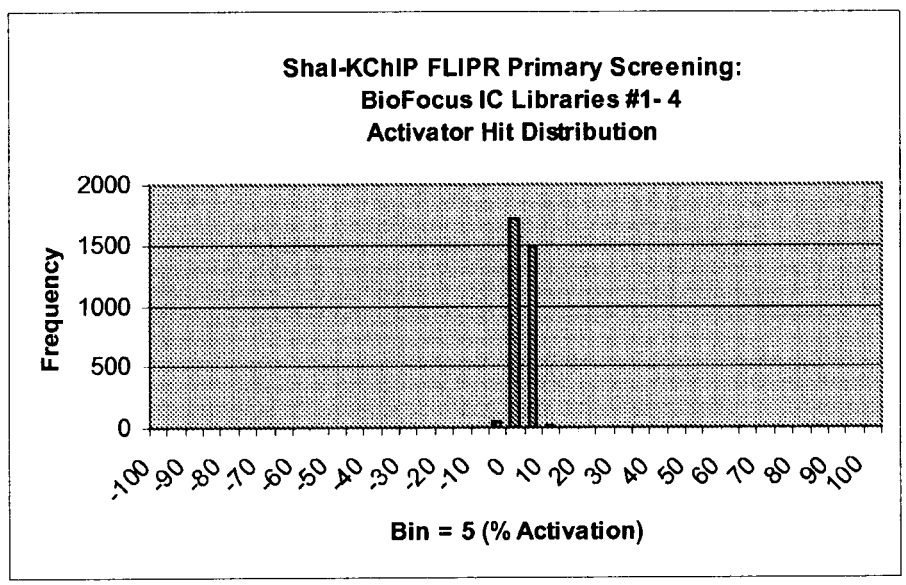
FIG. 35: Sha1/KChIP FLIPR BioFocus 1° screening—activation and distribution of actives on Sha1/KChIP.

BioFocus SoftFocus® Ion Channel Focused Libraries #1-4: 1° Screening Activator Hits The percent activity relative to control is plotted as a histogram for the BioFocus ion channel library activator screen (FIG. 35).

FIG. 35: ShaI/KChIP FLIPR BioFocus 1° screening—activation. Distribution of actives on ShaI/KChIP.

The activity was based on the mean and standard deviation of the compound set (minus controls and outliers, such as fluorescent compounds). Because the mean and standard deviation were so low, we chose to use a 6 σ cut-off of 12% activation to select compounds for follow-up. As shown in Table 3, there were no compounds that showed activation over the 6 σ cut-off of 12%.

TABLE 3

Summary of ShaI/KChIP activation. Summary table showing results from ShaI/KChIP activator screening.

|  | ShaI-KChIP Activation |
|---|---|
| Total compounds | 3222 |
| Mean of Data set | −0.3 |
| SD of Data set | 1.98 |
| 6-Sigma | 12% |
| Total Actives | 0 |
| % Hit Rate | 0.00% |

BioFocus SoftFocus® Ion Channel Focused Libraries #1-4: 1° Screening Antagonist Hits The percent activity relative to control is plotted as a histogram for the BioFocus ion channel library antagonist screen. The activity was calculated based on the mean and standard deviation of the compound set (minus controls and outliers, such as fluorescent compounds). The distribution of the antagonist activity shows a normal distribution; however, it is centered at 10-15% inhibition, which we have seen previously with this compound set. We chose to use a 3 σ cut-off of 29% inhibition to select the compounds for follow-up (Table 4). Because the compounds were tested in quadruplicate in the FLIPR screen and did not show strong inhibition at 10 µM, and because the amount of compound available is limiting, IC50s will not be performed on the FLIPR. All follow-up for antagonist hits will be performed on the QPatch. Table I details the antagonist actives with inhibition >/=29%.

TABLE 4

Summary of ShaI/KChIP inhibition. Summary table showing results from ShaI/KChIP inhibitor screening.

|  | ShaI-KChIP Antagonist |
|---|---|
| Total compounds | 3222 |
| Mean of Data set | 5.9 |
| SD of Data set | 825 |
| 3-Sigma | 29% |
| Total Actives | 53 |
| % Hit Rate | 1.60% |

Molecular Validation of ShaI/KChIP Cell Line

Experiments were undertaken to assess the integrity of the ShaI and KChIP coding sequences incorporated into the ShaI/KChIP stable cell line (Table A1). The strategy employed was to isolate genomic DNA (gDNA) from ShaI/KChIP 20 and control cell lines and to use these DNAs as templates for informative PCRs (polymerase chain reactions). Amplification primers were selected to generate products across the 5' and 3' ends of the ShaI and KChIP coding regions. Additional primers were chosen to verify the overall length of each coding region.

TABLE A1

Overview of primer pairs and PCR parameters used in molecular validation of ShaI/KChIP cell line.

| ShaI/KChIP: molecular validation | | | | | | |
|---|---|---|---|---|---|---|
|  |  | 5' primer | Tm | 3' primer | Tm | expected size |
| ShaI |  |  |  |  |  |  |
| 1 | ShaI 5' end | T7 | 48 | Inside GFP +40 Reverse | 52 | 180 bp |
| 2 | ShaI 3' end | ShaI 5'2 | 54 | BGH rev | 50 | 1.1 kb |
| 3 | ShaI full length | AcGFP_ATG_F | 66 | ShaI_1451R | 57 | 2.1 kb |
| KChIP |  |  |  |  |  |  |
| 4 | KChIP 5' end | T7 | 48 | KChIP-r | 62 | 1.4 kb |
| 5 | KChIP 3' end | KCHiP-INTRON-2F | 70 | BGH rev | 50 | 260 bp |
| 6 | KChIP full length | KChIP-f | 66 | KChIP-r | 62 | 1.3 |
| ShaI/KChIP gDNA | 635 ng/ul |  |  | 300 ulw/1.4 ug gDNA |  | 2.2 ul |
| PCR | DNA/H2O GoTaq 2x |  |  | 23 ul 25 ul |  | (100 ng gDNA) |

TABLE A1-continued

Overview of primer pairs and PCR parameters used in molecular validation of ShaI/KChIP cell line.

| | | |
|---|---|---|
| Primer1- 5', 25 uM | 1 ul | |
| Primer2- 3', 25 uM | 1 ul | |
| | 50 ul | |

| Cycling parameters | Ends | Full-length |
|---|---|---|
| initial denature | 94 2' | 94 2' |
| denature | 94 30" | 94 30" |
| touchdown anneal | 10× 65, 55; 20× 45 30" | 10× 60, 55; 20× 50 30" |
| extension | 72 30" | 72 3' |
| final extension | 72 5' | 72 5' |
| hold | 4 end | 4 end |

PCR products were generated across the 5' and 3' ends as well as the full-length coding sequences of ShaI and KChIP. Primer names, target regions, Tms (annealing temperatures) and expected fragment sizes are indicated. The ShaI/KChIP 20 gDNA prep is described, as is the 50 ul reaction setup. The cycling parameters include a modified "touchdown" protocol to reduce the generation of non-specific products, and were designed to accommodate differing predicted optimal annealing temperatures.

Figure 35A:
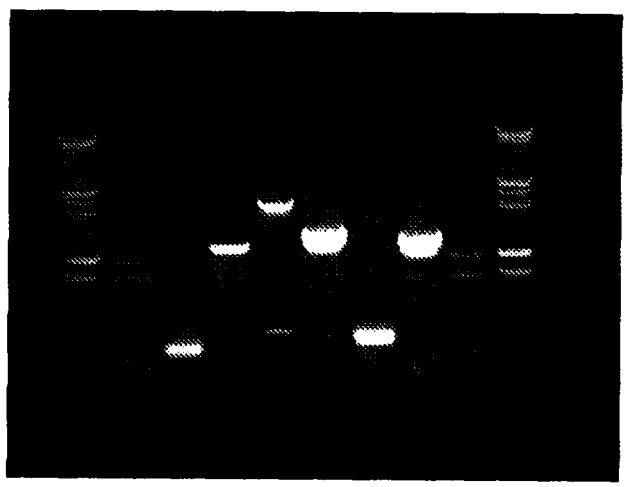
FIG. 35A: PCR products from the reactions described in Table A1.

Results and conclusions: All reactions yielded single products of the correct predicted size (FIG. 35A) with the exception of reaction #3 which produced a minor product of about 300 bp (FIG. 35A, lane 3). This product was also generated when amplifying control cell line gDNA (data not shown) and is presumed to be an artifact of the specific primer pair used. In conclusion, the coding sequences of ShaI and KChIP appear to be intact using this kind of molecular examination.

FIG. 35A: PCR products from the reactions described in Table A1. Each lane contains 20 ul of each 50 ul amplification reaction electrophoresed on a 1% agarose gel and stained with ethidium bromide. M1: BenchTop 1 kb DNA Ladder (Promega), M2: BenchTop PCR Markers (Promega), 1: ShaI 5' end (180 bp), 2: ShaI 3' end (1.1 kb), 3: ShaI full-length (2.1 kb), 4: KChIP 5' end (1.4 kb), 5: KChIP 3' end (260 bp), 6: KChIP full-length (1.3 kb).

The following examples are in connection with the shaker channel and/or a Hyperkinetic beta subunit:

Molecular Cloning and Vector Map

The pTriEx/Shaker plasmid we started with contains a Kozak sequence upstream 5' additional N-terminal amino acids (MAISR). In order to clone the Shaker full-length cDNA into different expression vectors, the following strategy was performed:

500 bp 5'-fragment amplification: two oligos have been designed for the amplification of the Shaker ATG codon together with a proper Kozak sequence without the additional 5' Nterminal amino acids.

```
Oligo SH-UPP, 5'-CCGGTACCATGGCCGCCGTTGCC-3'

Oligo SH-LOW, 5'-CCGGTCTCCGTAGTCGGCCACC-3'
```

In bold KpnI restriction site; in bold, underlined the Kozak sequence, in underlined Shaker annealing sequence.

SH-LOW oligo is located downstream the unique SalI restriction site on Shaker sequence.

The PCR fragment has been cloned into pCR-Blunt vector and the sequence has been verified.

The pCR-Blunt/5'-PCR clone has been digested with KpnI (in SH-UPP oligo) and SalI (in Shaker sequence) and the 400 bp 5'-fragmet was purified.

1770 bp 3'-fragment cloning: pTriEx/Shaker plasmid was digested with SalI and EcoR1 restriction enzymes and the 1770 bp fragment was purified.

Shaker wt cloning into pExSelect and pIRES2EGFP expression vectors via pcDNA3.1(+) vector: the 400 bp KpnI-SalI 5'-fragment and the 1770 bp SalI-EcoRI 3'-fragment obtained as described above have been cloned into the pcDNA3.1(+) vector.

Figure 36:
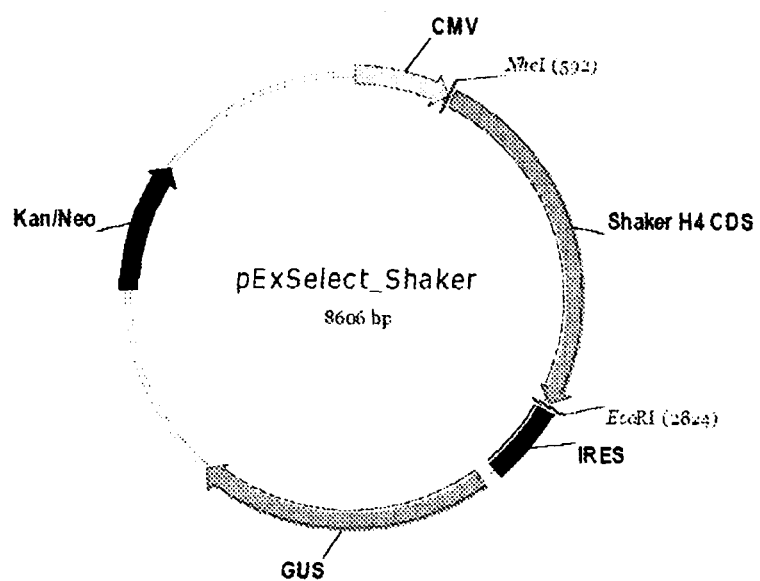
FIG. 36: VectorNTi map of the final pExSelect_Shaker construct.

The NheI-EcoRI Shaker fragment of this construct has been cut and then cloned into the pExSelect and pIRES2EGFP previously digested with NheI and EcoRI. The VectorNTi map of the final pExSelect_Shaker construct is shown in FIG. 36.

Cell Culture Conditions and Transfection

CHO-K1 cells were maintained in Dulbecco's MEM/Nutrient Mix F12 (1:1) (DME-F12 Euroclone cat.#ECM0090L) supplemented with 1.6 mM Sodium Pyruvate, (100 mM solution, Euroclone cat.#ECM0542D), 13 mM Hepes (1M solution, Euroclone cat. #ECM0180D), 0.2% Sodium Bicarbonate (7.5% solution, Euroclone cat. #ECM0980D), 2 mM Ultraglutamine (BioWhittaker cat. #BE17-605E/U1), 10% FBS (Fetal Bovine Serum, Euroclone cat. #ECS0180L), and 1% Penicillin/Streptomycin (100× solution Euroclone cat. #B3001 D).

Propagation conditions consist of seeding about 6×105 cells/T75 flask twice a week.

Recovering about 10-13×106 cells/T75 flask.

Transfection was performed by electroporating 1.0×106 cells in presence of 10 µg of DNA at 300 mV and 950 µF. Cells were then selected with medium containing 2 mg/ml G418 or 1 mg/ml Zeocin for 10-15 days. After antibiotic selection, resistant clones were maintained in 1 mg/ml G418 (Calbiochem cat. #345812) or 0.5 mg/ml Zeocin (InvivoGen cat. # ant-zn-5) medium.

All the cell lines are plated in complete medium without antibiotics for the FLIPR experiments.

Cellular Membrane Voltage Measurement by FLIPR

In order to detect the membrane depolarization elicited by KCl injection, the Membrane Potential sensitive dye was used both for FLIPR384 and FLIPRTETRA experiments. Cells were analyzed in 384 clear-bottom black MPTs (MATRIX cat. #4324) by seeding 5000, 7500, 10000 cells/well 24 hrs before experiment. Plates were incubated with 40 µl/w of 0.625× membrane potential dye for 45-60 minutes at 37° C. or room temperature and measured at FLIPR instrument by injecting 10 µl/w of 5× antagonist (in the presence of 0.5% DMSO, as indicated) followed by 3-5 minutes fluorescence reading; then a second injection of 25 µl/w of 3× KCl in Standard Tyrode solution) was performed and fluorescence measured for further 3-4 minutes. In experiments with a single injection (agonist), plates were incubated with 20 µl/w of 1× dye and injected with 20 µl/w of 2× KCl in Standard Tyrode solution.

Kinetic data obtained from different well replicates were analyzed with FLIPR, Excel and Spotfire software, by calculating the Integral or Maximum-Minimum RFU values after the injection; the obtained means and standard deviations were utilized to create sigmoidal dose-response fits by GraphPad PRISM® or Spotfire software and to calculate EC50-IC50 values and Z' factors.

EC80 value was calculated according to the following formula:

$$ECx = (x/100-x)1/\text{Hill Slope} * EC50$$

For the calculation of the Z' factor the following formula was used:

$$Z' = 1 - \frac{3*(ST.DEV \text{ agonist} + ST.DEV \text{ Tyrode})}{\text{MEAN agonist} - \text{MEAN Tyrode}}$$

Current detection by Patch clamp
Electrophysiological Recordings

Standard whole-cell voltage-clamp experiments were performed at room temperature. For data acquisition and further analysis, we used the EPC10 digitally controlled amplifier in combination with PATCHMASTER software (HEKA Electronics, Lambrect, Germany). The EPC10 provides automatic subtraction of capacitance and leakage currents by mean of prepulse. The data were filtered at 66.7 KHz (−3 dB, 8-pole Bessel lowpass) and digitized at 5 µs per point. The input resistance of the patch pipettes was 2.0-4.0 MΩ and the capacitances of the cells were 15.3±2.1 pF (n=45); the residual series resistances (after up to 80% compensation) were 4.2±0.4 MΩ. Correction for liquid junction potential was routinely applied. Membrane potential was clamped at −100 mV and currents were elicited by 50 ms depolarization pulses (0.1 Hz) from −60 mV to +100 mV (or +60 mV).

Cell Culture

For electrophysiology experiments, CHO—K1/DmShaker cells have been treated and maintained in culture with the standard protocol described above. 24 hrs (or four to six hrs in the second limiting dilution tests) before experiments CHO—K1/DmShaker cells were seeded onto poly-D-lysine coated glasses (200000 cells each) and placed in six well plates in antibiotic free medium. Immediately before experiments coated glasses, with seeded cells, have been washed five times with patch clamp extracellular solution and then put into the recording chamber.

Solutions

The pipette solution contained (mM): KMeSO3 128, HEPES 10, EGTA 12, MgCl2 3, CaCl2 0.7, K2ATP 5, pH 7.2 with KOH.

The bath solution contained (mM): NaCl 145, KCl 5, MgCl2 1, CaCl2 2, HEPES 10, Glucose 10, pH 7.4 with NaOH.

Ligand Storage
DMSO (Dimethyl sulfoxide SIGMA cat. #D-5879) was purchased from SIGMA®.
KCl was purchased from SIGMA® and stock solution was prepared 3 M in water.
TEA was purchased from SIGMA® and stock solution was prepared 1M in water.
Working solutions are prepared in the Standard Tyrode buffer (pH 7.4):
NaCl 130 mM, KCl 5 mM, CaCl2-2H2O 2 mM, MgCl2 1 mM, NaHCO3 5 mM, HEPES 20 mM.

Software

Data were analyzed using Excel, GraphPad Prism 4, FLIPR384 Control Software, ScreenWorks 1.2.0.

Stable Cell Line Generation

CHO—K1 cells have been stably transfected with pExSelect_Shaker or pExSelect vector alone (as mock control). 48 hrs after transfection cells have been cultured in complete medium supplemented with 2 mg/ml G418 to select a resistant pool. Antibiotic resistant DmShaker transfected cells (not FACSorted) have been further transfected with the H-kvβ subunit A or C subtype vectors received from BASF and 48 hrs later cells put on selection with 1 mg/ml Zeocin.

First Limiting Dilution Clone Selection

Figure 37:
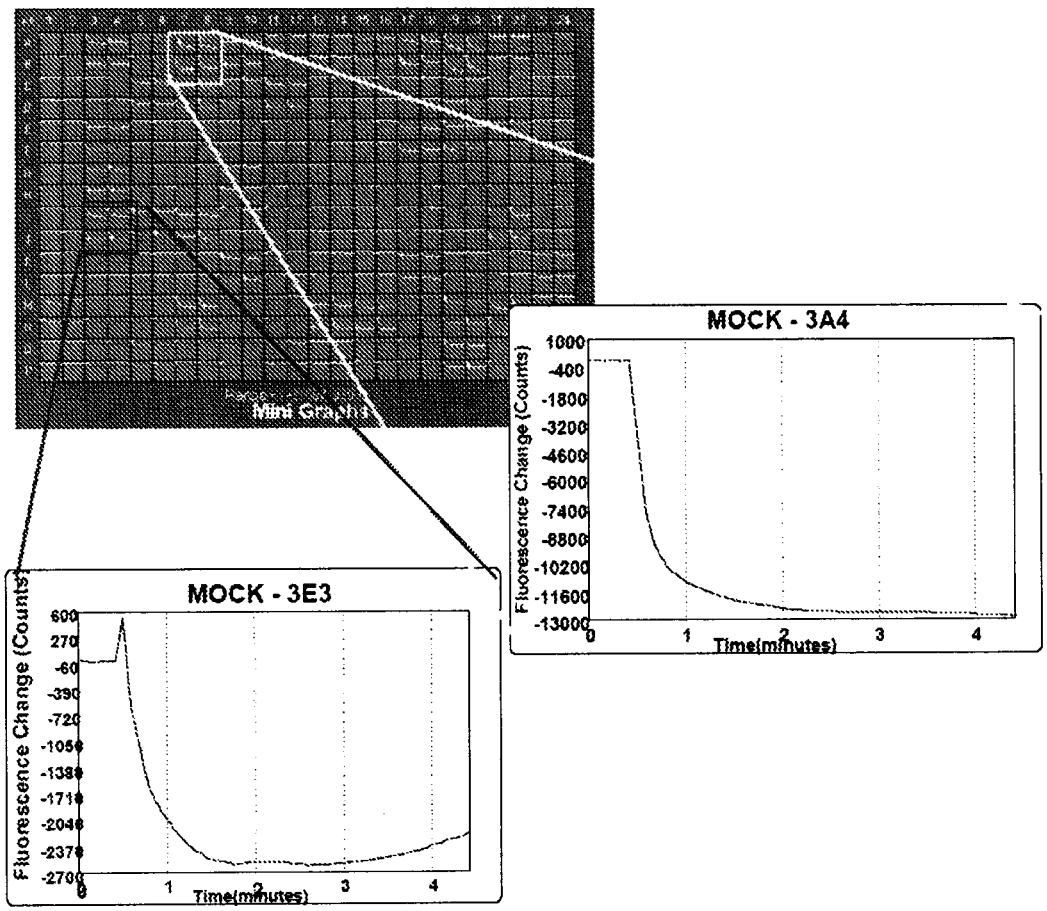
FIG. 37: Assay data for mock clones upon KCl injection.
Figure 38:
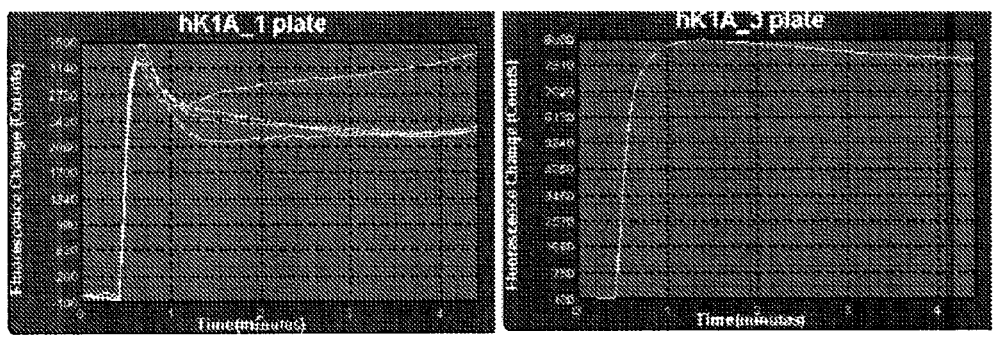
FIG. 38: Assay data for Shaker and Hkvβ clones upon KCl injection.
Figure 38:
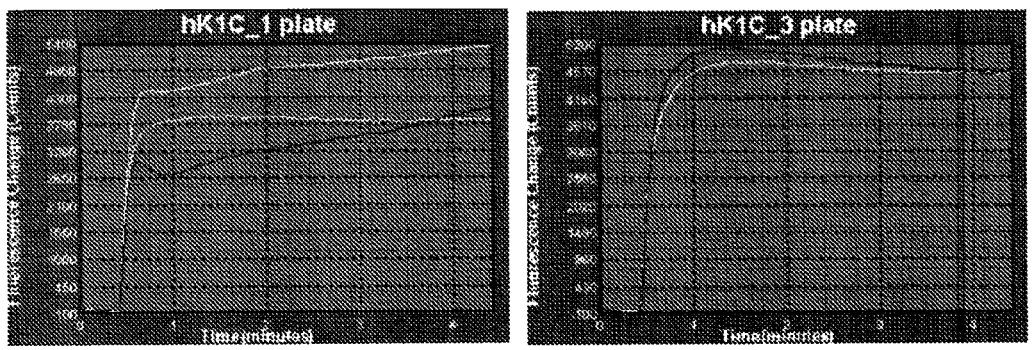

In order to obtain a pure Shaker and H-kvβ clone, a first limiting dilution step has been performed by diluting stable mock or Shaker transfected pools in 96 wp at a cell density of 1 cell/well (5×96 wp mock and 5×96 wp Shaker plus H-kvβ for each subunit). Confluent clones were replicated into clear bottom 384 wp and analyzed after 24 hrs at FLIPR384 by injecting 100 mM KCl. As shown in FIG. 37 the mock clones showed an hyperpolarization upon KCl injection while some of the Shaker and Hkvβ both A and C clones displayed a KCl response recorded as a sustained depolarization, as shown in FIG. 38.

FIG. 37. Mock I limiting dilution plate selection at FLIPR[384]: example of one plate FIG. 38. Shaker+Hkvβ A or C subunit I limiting dilution clone selction at FLIPR[384] Data were analyzed using the total integral RFU values after activator injection. On the basis of this data analysis, two mock clones and six clones each from both Shaker plus A or C subtype have been selected for re-test in a counted cells experiment: 10000 c/w have been plated and 24 hrs later a KCl dose-response at FLIPR384 has been performed. The resulting best clones are shown in FIG. 39.

Figure 39:
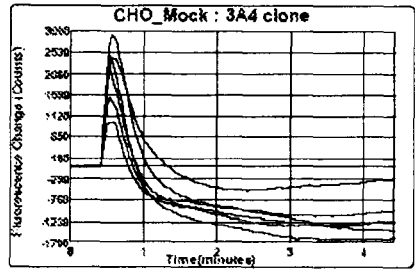
FIG. 39: Re-test assay data for two mock clones and six clones each from both Shaker plus A or C subtype.
Figure 39:
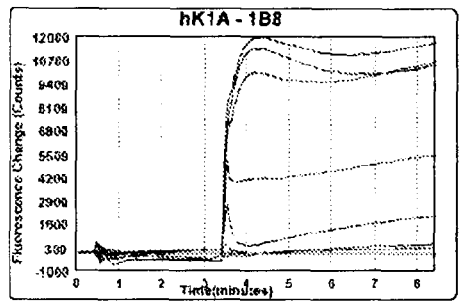
Figure 39:
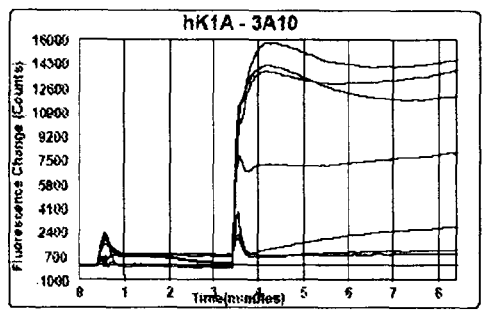
Figure 39:
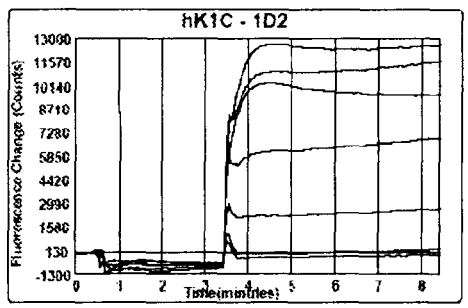
Figure 39:
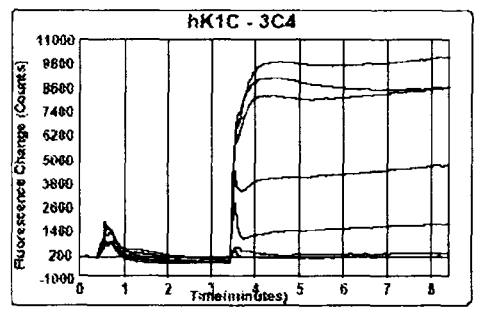

FIG. 39. I limiting dilution clone re-test as counted cells at FLIPR[384]

Protocol: 10000 c/w-24 h; MEM discarded; 45' incubation at 37° C. with 40 µl of blue MP dye according to the described procedure; 20 µl/w KCl injection at FLIPR384 (3× Tyrode solution).

Clone Stability at Different Passages in Culture and After Freezing/Thawing

A-3A10 has been selected as the best responding clone and maintained in culture for more than two months. A-3A10 has been analyzed at FLIPR384 for KCl response stability at different cell passages and after freezing/thawing as shown in FIGS. 40 and 41

Figure 40:
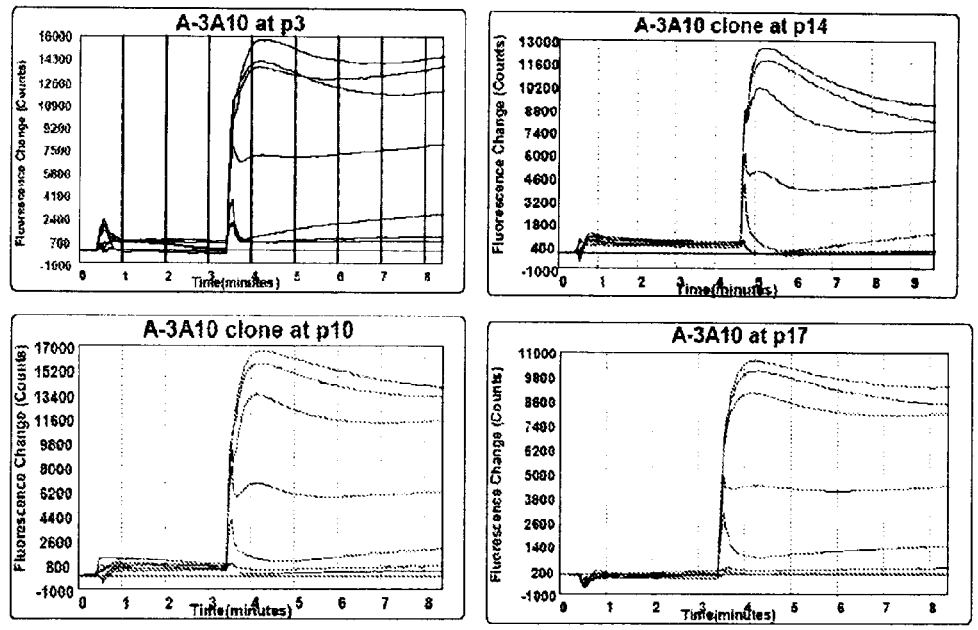
FIG. 40: A-3A10 signal stability at different cell passages.
Figure 41:
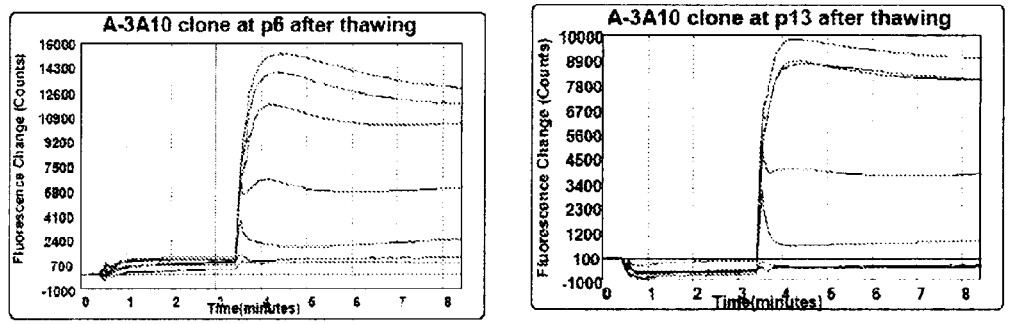
FIG. 41: A-3A10 signal stability after freezing and thawing.

FIG. 40. A-3A10 signal stability at different cell passages: 10000 c/w-24 h; MEM discarded; 45' incubation at 37° C. with 40 µl of blue MP dye according the described procedure; 10 µl/w 0.5% DMSO injection as 5× tyrode solutions; 3' later, 25 µl/w KCl injection at FLIPR384 (3× tyrode solution) 1.5, 3.7, 7.5, 15, 30, 60, 90, 120 mM FIG. 41. A-3A10 signal stability after freezing and thawing: 10000 c/w-24 h; MEM discarded; 45' incubation. at 37° C. with 40 µl of blue MP dye according to the described procedure; 10 µl/w 0.5% DMSO injection 5× Tyrode solutions; 3' later, 25 µl/w KCl injection at FLIPR384 (3× Tyrode solutions) 1.5, 3.7, 7.5, 15, 30, 60, 90, 120 mM TEA Effect on A-3A10 Clone TEA effect has been analyzed on A-3A10 clone by KCl stimulation upon 30, 60 or 90 mM TEA pre-injection by FLIPR 384. TEA blocking effect is visible in particular on 30 mM KCl stimulation as shown in FIG. 42.

Figure 42:
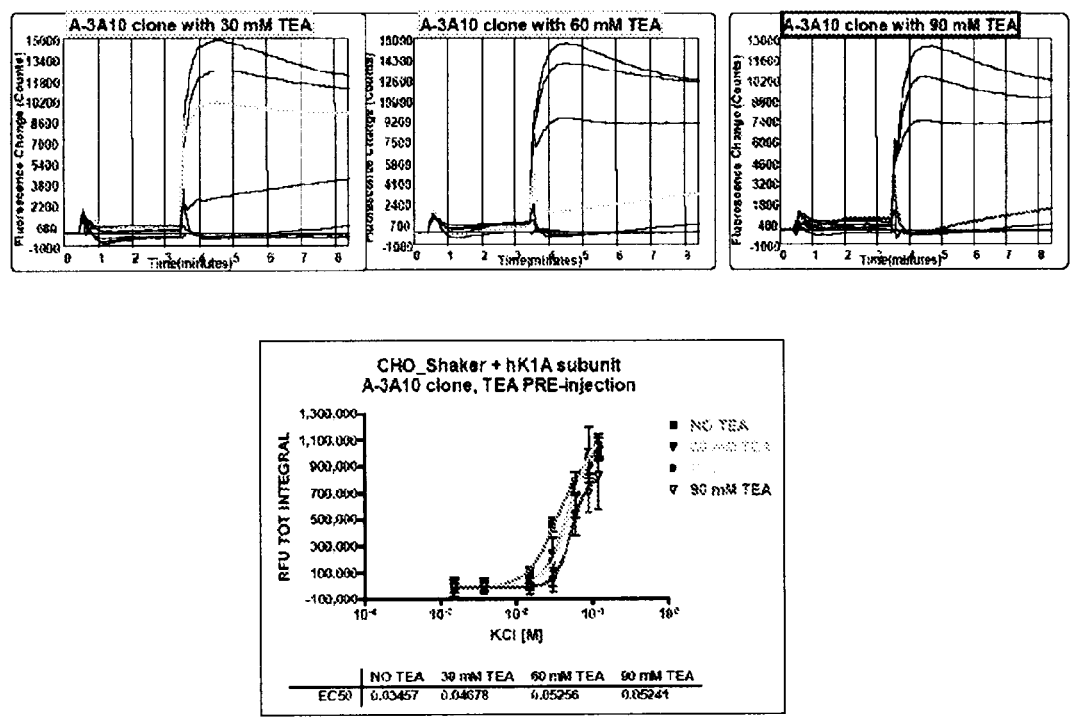
FIG. 42: TEA effect on A-3A10 clone.

FIG. 42. TEA effect on A-3A10 clone: 10000 c/w-24 h; MEM discarded; 45' incubation at 37° C. with 40 µl of blue MP dye according the described procedure; 10 µl/w 0.5%

Figure 43:
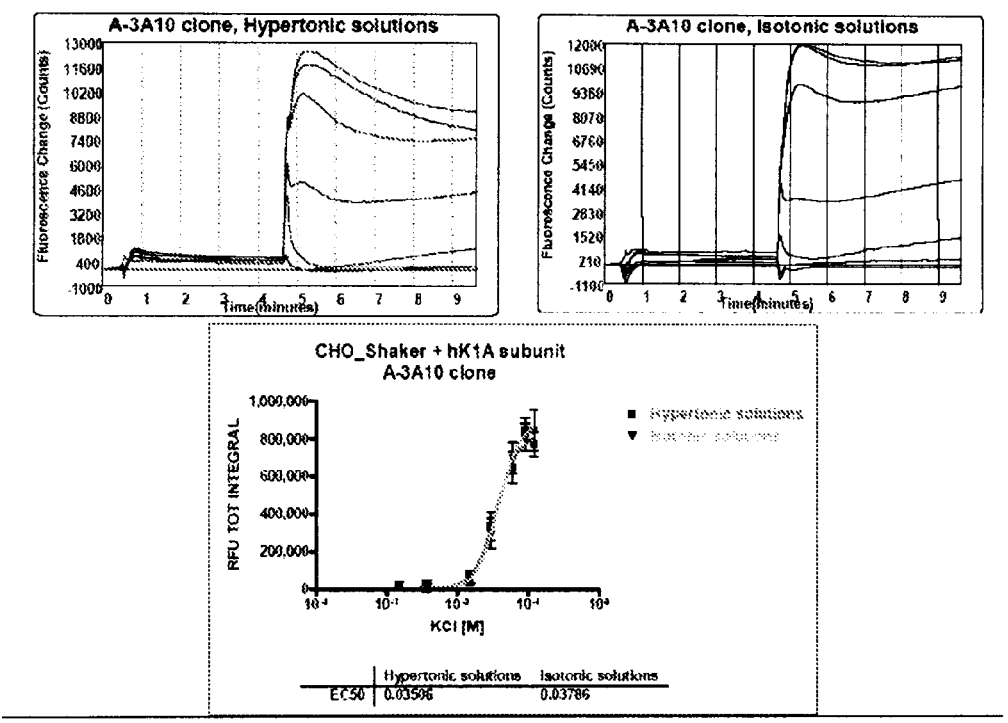
FIG. 43: Hypertonic and isotonic solutions analysis.

DMSO inj. in the presence of 30, 60 or 90 mM TEA 5× Tyrode solutions; 3' later, 25 µl/w KCl injection at FLIPR384 (3× tyrode solutions) 1.5, 3.7, 7.5, 15, 30, 60, 90, 120 mM KCl Hypertonic or Isotonic Solution Analysis Both KCl hypertonic or isotonic solutions have been analyzed on A-3A10 clone. Hypertonic solutions have been prepared starting from standard Tyrode buffer (135 mM NaCl+KCl) by adding the required volume of KCl stock solution (standard protocol). Isotonic solutions have been prepared starting from "Tyrode base" (0 M NaCl+KCl) and keeping NaCl+KCl salts concentration at 135 mM. No differences have been observed in the response of the tested clone both as RFU and as kinetic shape, when using the two solutions as shown in FIG. 43. So all validation experiments were performed in standard Tyrode.

FIG. 43. Hypertonic and isotonic solutions analysis: 10000 c/w-24 h; MEM discarded; 45' inc. at 37° C. with 40 µl of blue MP dye according the described procedure; 10 µl/w 0.5% DMSO inj. 5× tyrode solutions; 3' after, 25 µl/w KCl inj at FLIPR384 (3× tyrode solutions) 1.5, 3.7, 7.5, 15, 30, 60, 90, 120 mM Second Limiting Dilution Clone Selection The Shaker/H-kvβ A subunit best clone, A-3A10, has been put in second limiting dilution in 3×96 wp at a cell density of 1 cell/well. 30 clones have been picked-up and grown for testing. Ten clones have been tested first as counted cells using the standard loading and experimental protocols. KCl response of the best clones is shown in FIG. 44.

Figure 44:
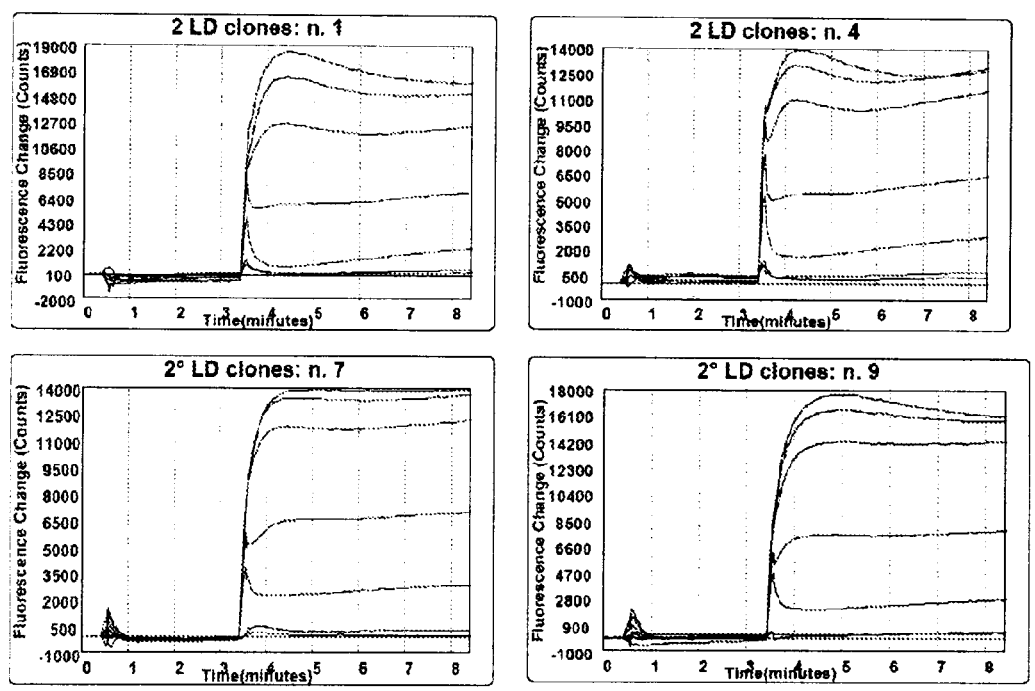
FIG. 44: A-3A10 II limiting dilution clone selection at FLIPR384.

FIG. 44. A-3A10 II limiting dilution clone selection at FLIPR384

Example of best clones: 10000 c/w-24 h; MEM discarded; 45' incubation at 37° C. with 40 µl of blue MP dye according the described procedure; 10 µl/w 0.5% DMSO injection 5× Tyrode solutions; 3' later, 25 µl/w KCl inj at FLIPR384 (3× Tyrode solutions) 1.5, 3.7, 7.5, 15, 30, 60, 90, 120 mM Two clones, n° 1 and n° 9, have been selected as the best responsive clones for further analysis at FLIPRTETRA. 10000, 7500, 5000 and 2500 c/w have been plated 24 hrs before experiment and KCl dose-response analysis has been performed. Data obtained are shown in FIG. 45

Figure 45:
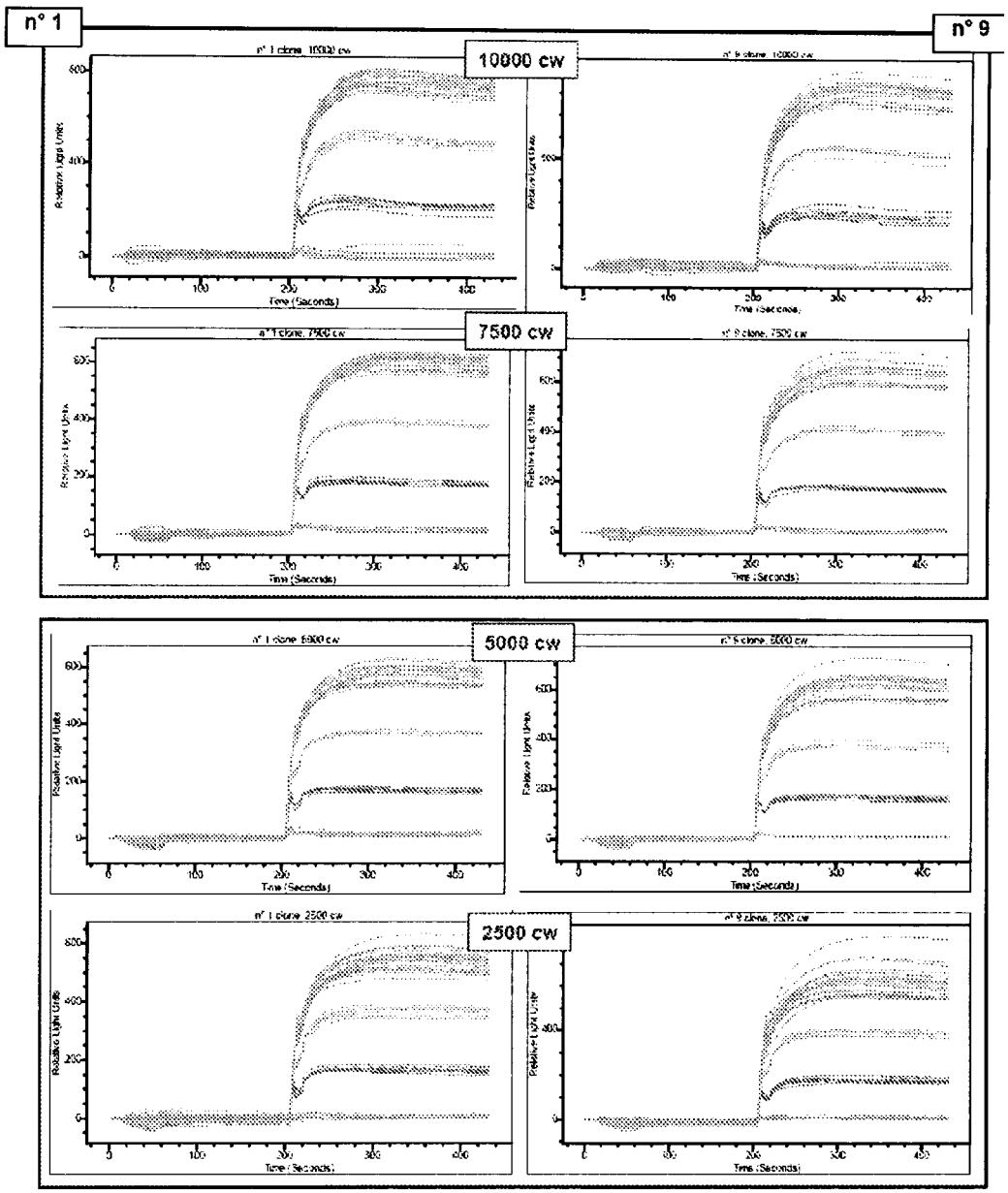
FIG. 45: n° 1 and n° 9 II limiting dilution clones analyzed at FLIPRTETRA.

FIG. 45. n° 1 and n° 9 II limiting dilution clones analyzed at FLIPRTETRA: 10000 c/w-24 h; MEM discarded; 45' incubation at 37° C. with 40 µl of blue MP dye according the described procedure; 10 µl/w 0.5% DMSO injection 5× Tyrode solutions; 3' later, 25 µl/w KCl injection at FLIPRTETRA (3× Tyrode solutions) 1.5, 3.7, 7.5, 15, 30, 60, 90, 120 mM Final Clone Optimization The Shaker n° 1 clone has been chosen for further characterization and final clone optimization.

Cell Density Dependency

Shaker n° 1 clone has been seeded 10000, 7500 and 5000 c/w 24 h before experiment in order to determine the optimal cell density. The day of experiment a KCl dose-response has been injected at FLIPRTETRA and the EC50 has been calculated. The results are shown in FIG. 46.

Figure 46:
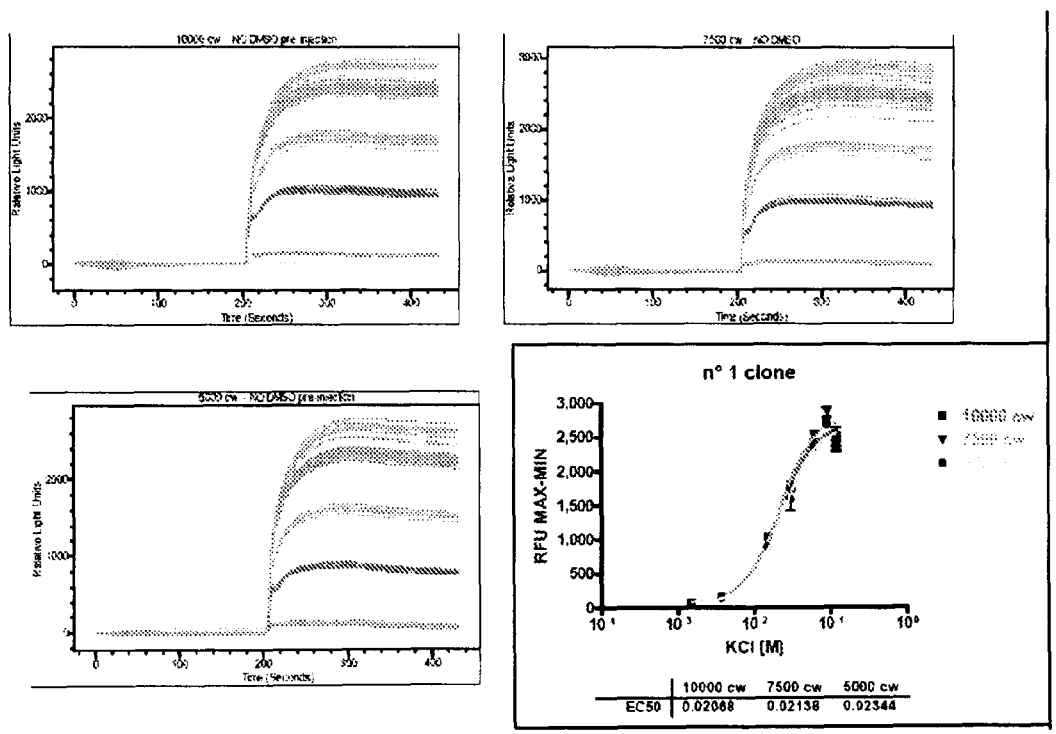
FIG. 46: Cell density dependency and KCl dose-response.

FIG. 46. Cell density dependency, KCl dose-response: 10000, 7500, 5000 c/w-24 h; MEM discarded; 45' incubation at RT with 40 µl of blue MP dye according the described procedure; 10 µl/w Tyrode injection; 3' later, 25 µl/w KCl injection at FLIPRTETRA (3× Tyrode solutions) 1.5, 3.7, 7.5, 15, 30, 60, 90, 120 mM.

To draw the curve the Max-Min value after KCl injection has been considered.

DMSO Sensitivity

In order to determine if DMSO causes any effect on the activator response, clone n° 1 has been plated at the cell density of 10000, 7500 or 5000 c/w and analyzed at FLIPRTETRA 24 h later, by injecting KCl dose-response, after a instrument pre-injection of 0.5-1-1.5-3% DMSO.

Figure 47:
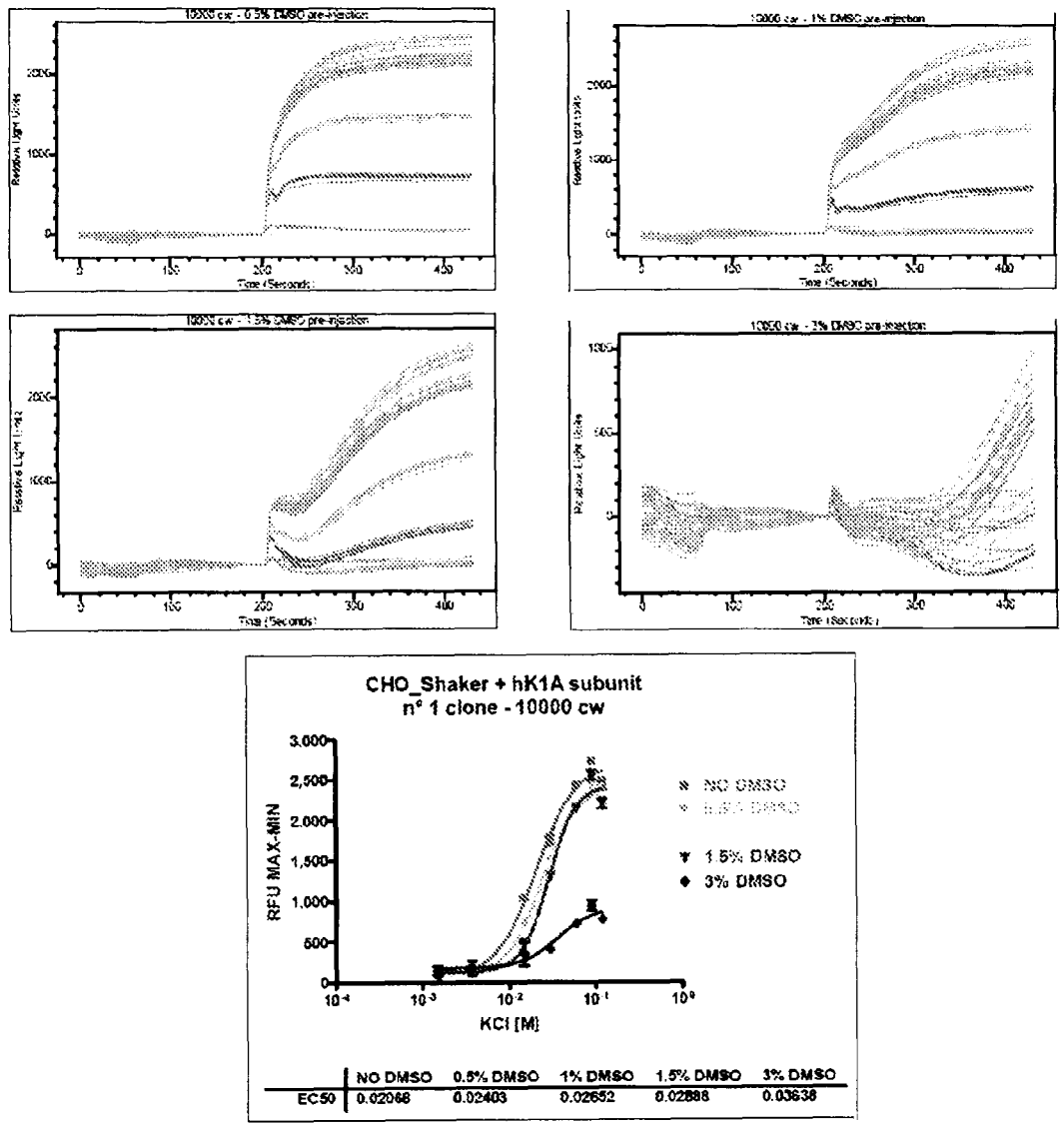
FIG. 47: DMSO sensitivity: 10000 c/w-24 h.
Figure 48:
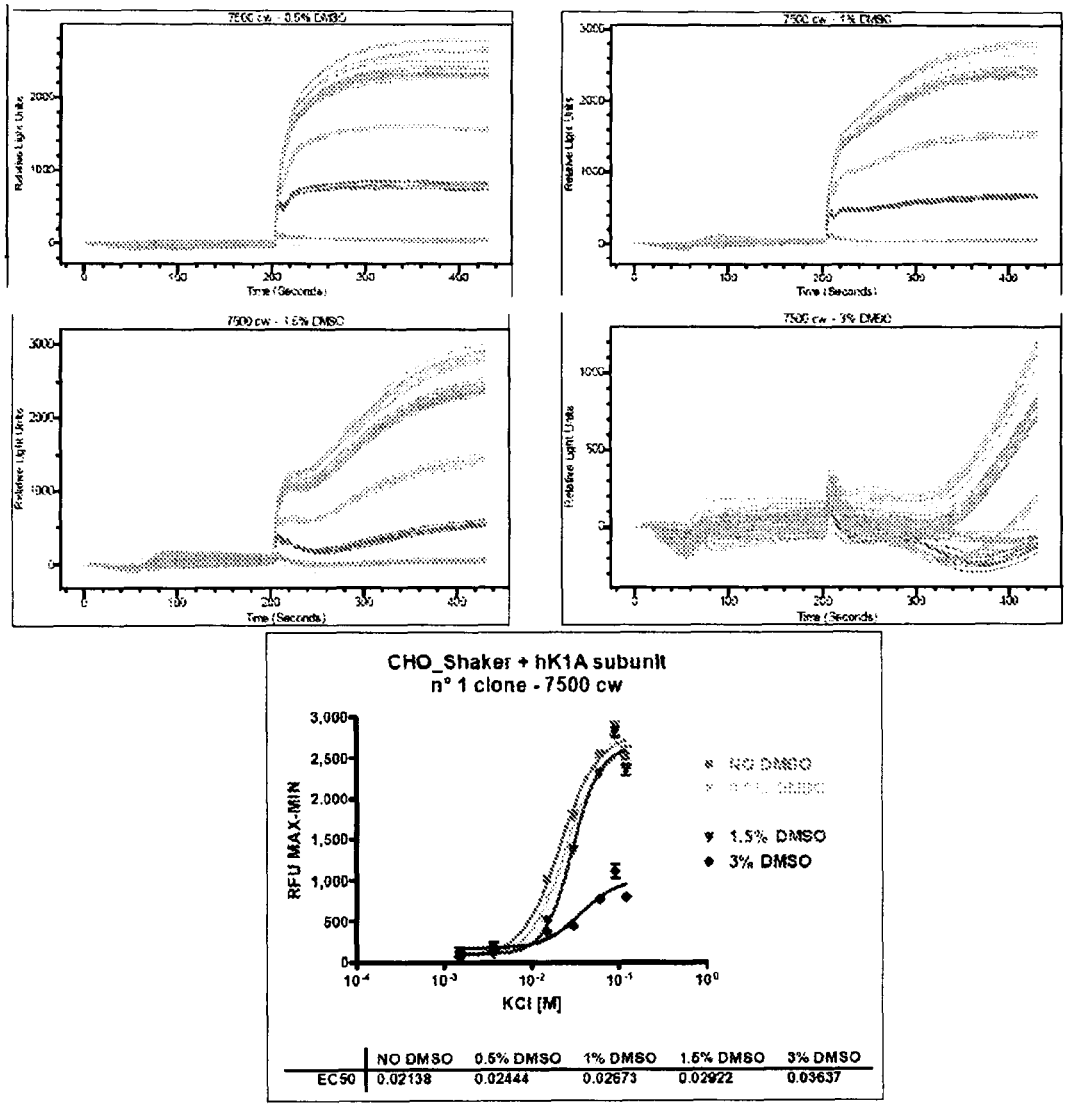
FIG. 48: DMSO sensitivity: 7500 c/w-24 h.
Figure 49:
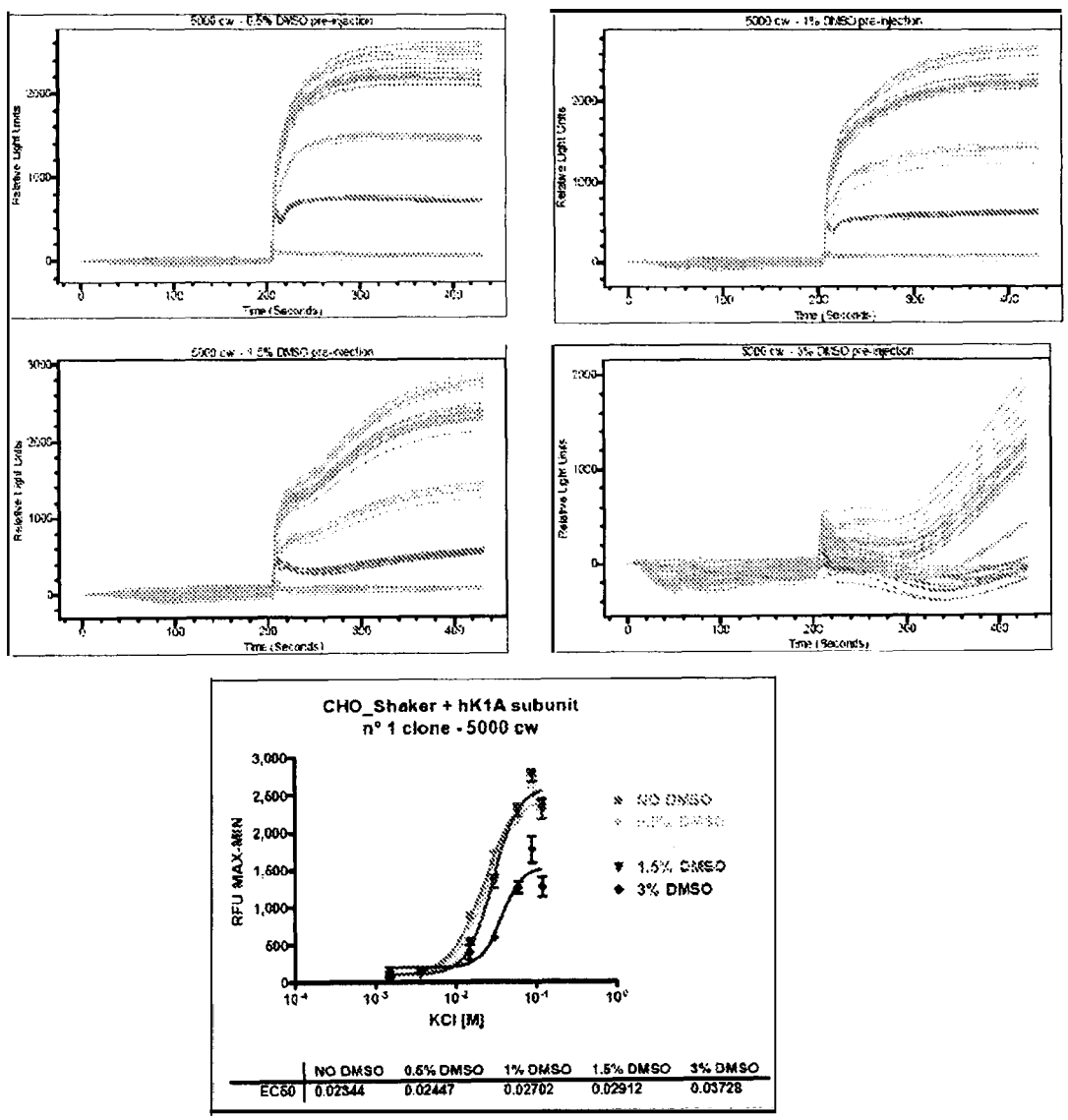
FIG. 49: DMSO sensitivity: 5000 c/w-24 h.

As shown in FIG. 47-48-49 DMSO concentrations up to 1.5% have no significant effect on the KCl response; 3% DMSO gives rise to a decrease in KCl dependent response.

FIG. 47 DMSO sensitivity: 10000 c/w-24 h; MEM discarded; 45' incubation at RT with 40 µl of blue MP dye according the described procedure; 10 µl/w 0.5, 1, 1.5, 3% DMSO injection 5× Tyrode solutions; 3' after, 25 µl/w KCl inj at FLIPRTETRA (3× tyrode solutions) 1.5, 3.7, 7.5, 15, 30, 60, 90, 120 mM.

To draw the curve the Max-Min value after KCl injection has been considered.

FIG. 48 DMSO sensitivity: 7500 c/w-24 h; MEM discarded; 45' incubation at RT with 40 µl of blue MP dye according the described procedure; 10 µl/w 0.5, 1, 1.5, 3% DMSO injection 5× Tyrode solutions; 3' later, 25 µl/w KCl inj at FLIPRTETRA (3× Tyrode solutions) 1.5, 3.7, 7.5, 15, 30, 60, 90, 120 mM.

To draw the curve the Max-Min value after KCl injection has been considered.

FIG. 49 DMSO sensitivity: 5000 c/w-24 h; MEM discarded; 45' incubation at RT with 40 µl of blue MP dye according the described procedure; 10 µl/w 0.5, 1, 1.5, 3% DMSO injection 5× Tyrode solutions; 3' later, 25 µl/w KCl injection at FLPIRTETRA (3× Tyrode solutions) 1.5, 3.7, 7.5, 15, 30, 60, 90, 120 mM.

To draw the curve the Max-Min value after KCl injection has been considered.

Clone Stability After Freezing/Thawing

Clone n° 1 has been analyzed after culturing (p 6) and freezing/thawing: cells have been plated at the cell density of 10000, 7500 or 5000 c/w and analyzed at FLIPRTETRA after 24 h by injecting KCl dose-response in the presence of 0.5% DMSO.

Figure 50:
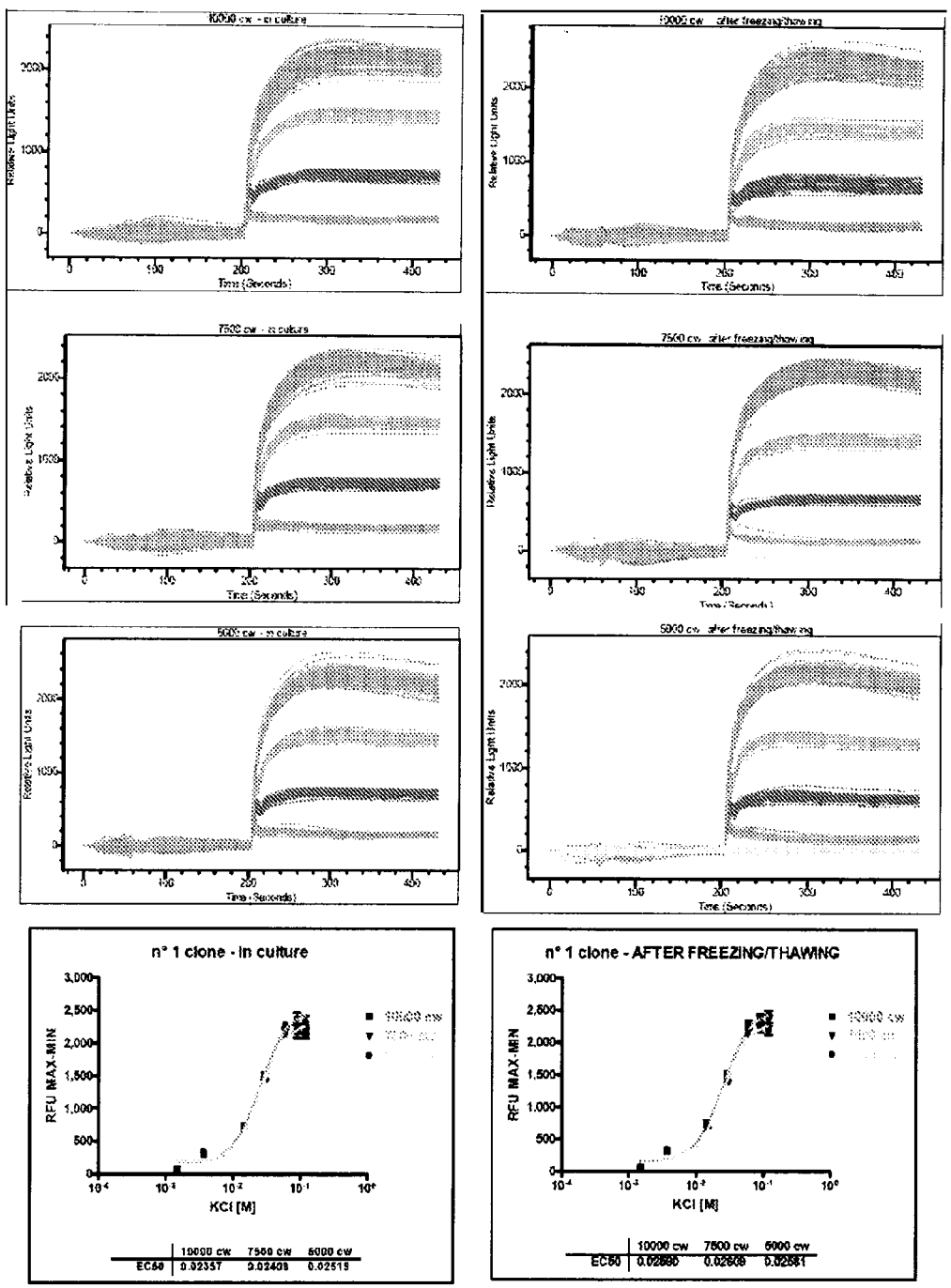
FIG. 50: Clone stability in culture and after freezing/thawing: 10000, 7500, 5000 c/w-24 h.

The results are shown in FIG. 50.

FIG. 50 Clone stability in culture and after freezing/thawing: 10000, 7500, 5000 c/w-24 h; MEM discarded; 45' incubation at RT with 40 µl of blue MP dye according the described procedure; 10 µl/w 0.5% DMSO injection 5× Tyrode solutions; 3' later, 25 µl/w KCl inj at FLPIRTETRA (3× Tyrode solutions) 1.5, 3.7, 7.5, 15, 30, 60, 90, 120 mM.

To draw the curve the Max-Min value after KCl injection has been considered.

EC50 Stability on Three Separate Days

Figure 51:
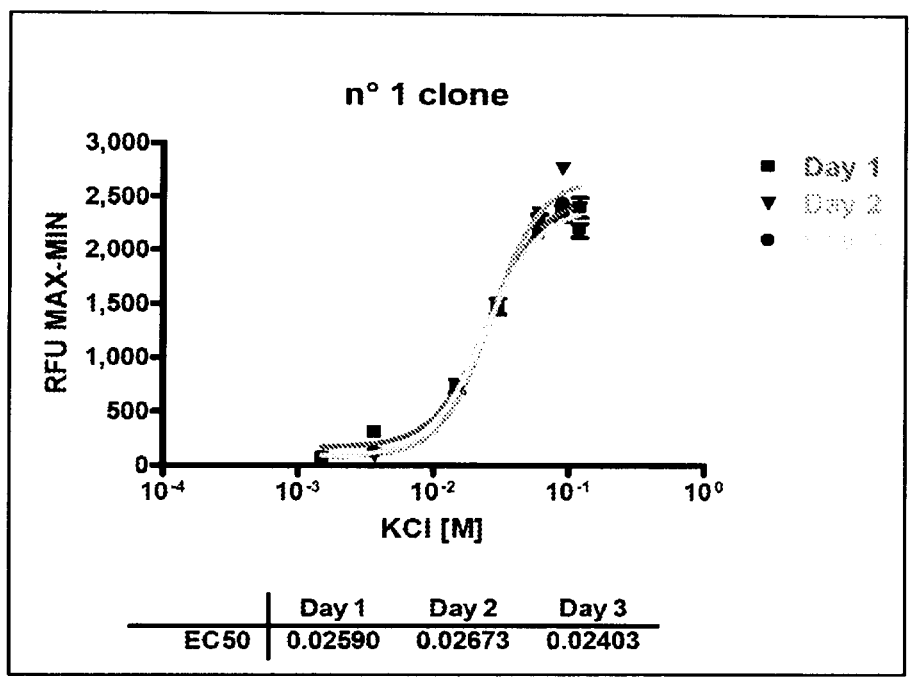
FIG. 51: EC50 reproducibility on three different days.

In order to verify the KCl response stability throughout different days of experiment, the final clone has been tested at FLIPR384 in three separate days by injecting a KCl dose-response. As shown in FIG. 51.

FIG. 51. EC50 reproducibility in three different days

Protocol: 10000 c/w-24 h; MEM discarded; 30' incubation at 37° C. with 40 µl of blue MP dye according the described procedure; 10 µl/w Tyrode 0.5% DMSO injection at FLIPR384; read for 2'; 25 µl/w KCl injection at FLIPR384 (3× Tyrode solutions). Values in the graph refer to the Max-Min after KCl injection.

Patch Clamp Analysis

Figure 52A:
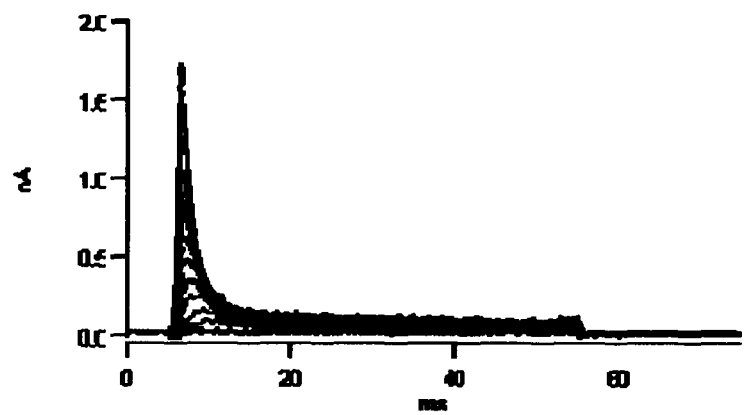
FIG. 52a: Patch clamp analysis of clone 3a10 subtype A.
Figure 52B:
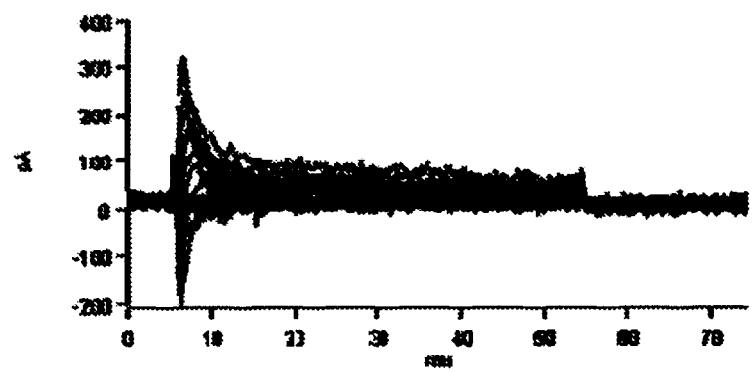
FIG. 52b: Patch clamp analysis of clone 7d1 subtype C.

The two best clones coming from the first limiting dilution were tested through whole cell patch clamp technique. As shown (FIGS. 52a and b) the application of depolarization pulses to up +100 mV induced a Dm-Shaker current with a typical fast activation and fast inactivation profile. In some experiments, a TTX-sensitive inward current was present as shown in FIG. 52b.

For each clone six experiments were performed and very promising results were obtained: 100% of the cells of clone 3a10 showed a Dm-Shaker current profile with a mean current density (at +60 mV) of 56.3±36 pA/pF, whereas five cells showed the potassium current for the clone 4d1 with a mean current densities of 13.4±18 pA/pF As the best electrophysiology results were obtained from the Dm-Shaker A-subtype clone, it was decided to put into limiting dilution only the cell transfected with the Shaker channel plus the H-kvp A subunit. In the meanwhile the activity of the 3a10 clone was routinely checked every two weeks; moreover the clone expression stability after cells thawing was also checked.

Figure 53:
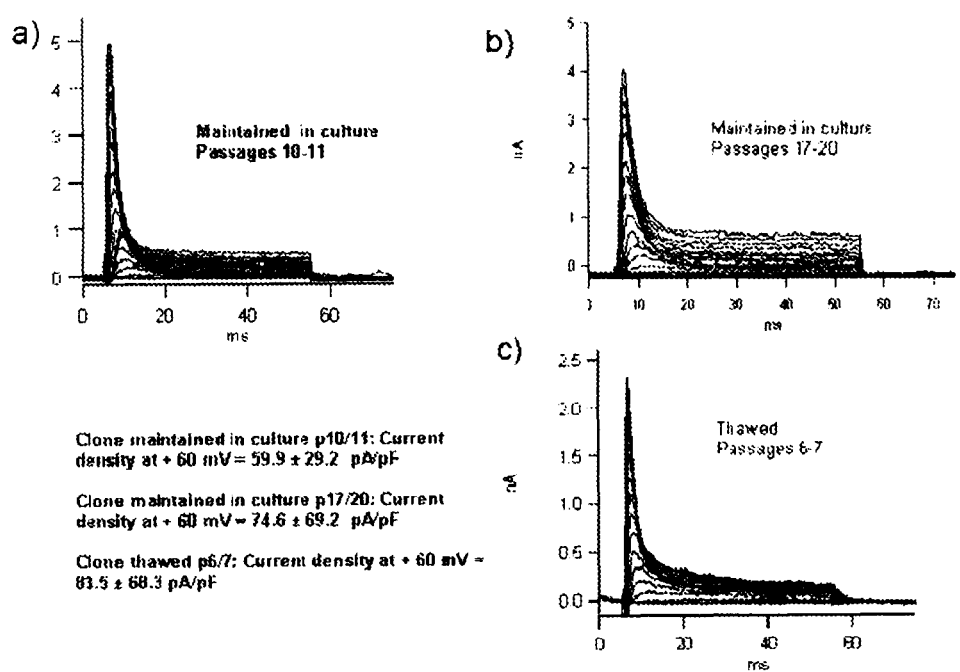
FIG. 53: Activation of Dm-Shaker in cells: a) Activation of Dm-Shaker in cells cultured for 10-11 passages; b) Activation of Dm-Shaker in cells cultured for 17-20 passages; c) Activation of Dm-Shaker in cells after thawing.

In FIG. 53 we can see that pulses of depolarization up to +60 mV (b) or to +100 mV (a and c) induced the activation of Dm-Shaker. In particular the stability of the functional channel expression was still very high when cells were maintained in culture at least up to five-six weeks (FIG. 53a) and after cells thawing (FIG. 53c). In this experiments 83.3% and 100% of the cells respectively showed Dm-Shaker current (n=6 and 7).

Figure 54:
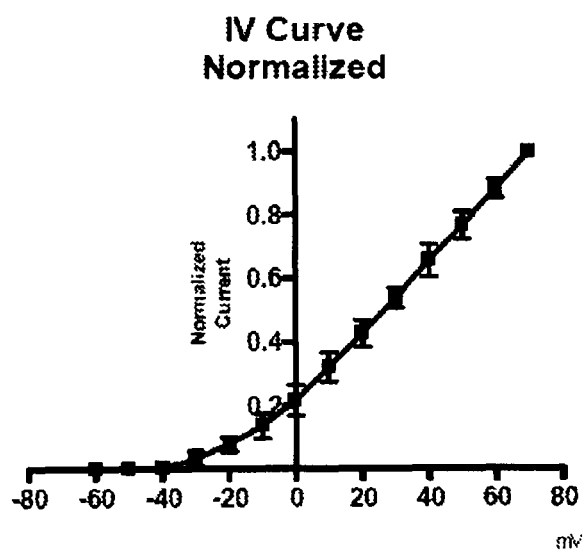
FIG. 54: The I-V relationship of voltage dependency of the activity of DM-Shaker.

After sub-culturing clone 3a10 for more than two months (passages 17-20), the expression of the channel was decreased and the cells showing Dm-Shaker current were 50% (n=8). In order to have kinetic informations about the voltage dependence of the activity of Dm-Shaker, the I-V relationship was plotted (FIG. 54). I-V plot was constructed by measuring peak currents and plotting the normalized values against membrane potential (n=8±SD).

Clone 1 coming from the second limiting dilution was then used for electrophysiology analysis and two compounds, were also tested on the selected clone. The two compounds affect the Dm-Shaker activity.

Screening Protocol

In the final assay adaptation for screening, several modifications of the protocols were done. The most substantial of these changes are:

Implementation of an automated procedure for dye loading
50 mM KCl: final concentration for screening (1:3 dilution of Activation buffer)
Automated process Where the activation buffer was prepared as follows:
150 mM KCl, 2 mM CaCl2*2H2O, 1 mM MgCl2, 5 mM NaHCO3, 20 mM HEPES, pH 7.4

The composition of the activation buffer represents a solution that is as close as possible to the physiological conditions in terms of osmolarity. That is the reason why it was decided to perform the screening adaptation and the full screening by using this buffer instead of standard tyrode.

Final FLIPR Protocol for Screening
The finalized FLIPR protocol has this setup:
Source Plate 1: Compound dilution plate
Source Plate 2: Activator plate
Read Position: Assay plate
Source Plate 3/Tips: not used (Tip box)
Filters: Excitation: 510-545; Emission: 565-625
Read settings (typical): Gain 60. Exp. Time 0.6; Excitation 60
Wash Buffer A: water
Wash Buffer B: water with 2.5% DMSO
The protocol (which is represented graphically above) includes these steps:
Mix the compound dilution plate
Transfer 10 µL from compound dilution plate to the assay plate
Start read 3.0 minutes
After 30 seconds, mix assay wells
Wash tips (while reading)
Transfer 25 µL from activator plate to the assay plate, mix immediately
Read 4.0 minutes
Wash tips (while reading)

The only substantial change in physical processing of the plate in the automated procedure versus the manual procedure is in the dye loading. In the manual process, this is accomplished by first dumping the medium out of the wells by "flicking" the liquid into a sink, and then aliquoting dye into the wells.

In the automated procedure, the dye loading is accomplished by the automated 384-well pipettor of our screening system. In order to remove the culture medium without disturbing the cell monolayer, we perform a cycle of aspiration/buffer dispense/aspiration in order to accomplish a "washing" of the well. In effect, our pipetting procedure resulted in a residual of 5% of the culture medium in the well with the dye. The final dye loading step involves removing the wash buffer, leaving 10 µL in the well, then adding 30 µL of 0.666× dye, for a final of 40 µL of 0.5× dye. We found that this resulted in an identical (or even better) performance of the assay as compared to manual emptying of the wells.

For the running of the automated process, an optimized schedule is compute to maximize plate throughput. An example of the optimized schedule for many plates is shown in FIG. 54. The throughput of this scheduled process is one plate each 13 minutes. This allows us to process 50-60 plates each day.

Overview of Automated Scheduled Process

The steps presented represent the processing of a single experiment. The scheduler system takes care of interlacing multiple assays in order to optimize throughout.

Figure 86:
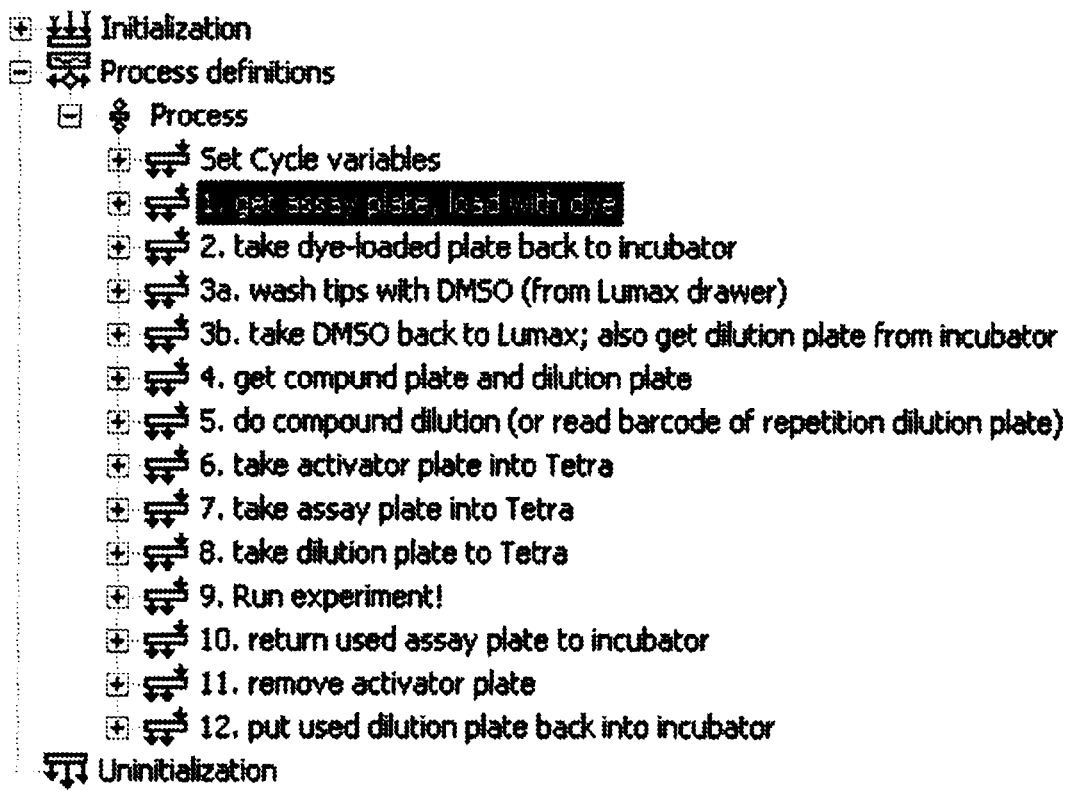
FIG. 86: Schematic of an automated scheduled process for a single assay experiment.

An overview of the automated scheduled process is depicted in FIG. 86.

Figure 55A:
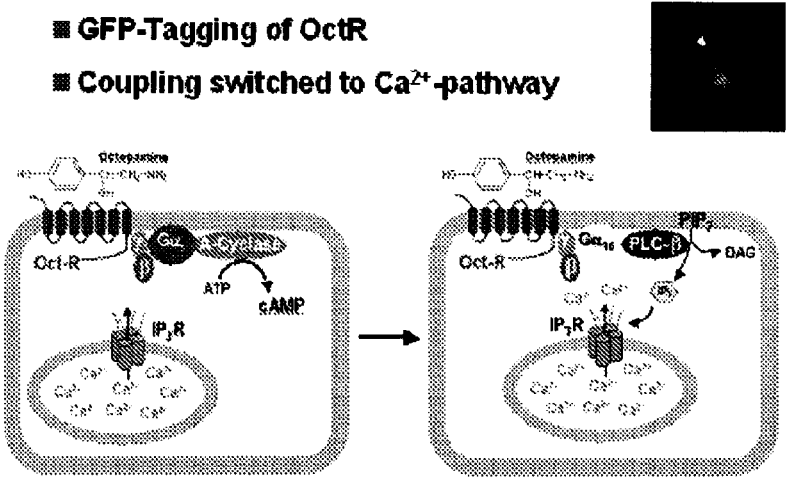
FIG. 55a: Schematic of calcium release from activation of G-alpha-16-protein.

The following examples are in connection with the G-protein coupled receptor:

Octopamine receptors can modulate their action through cyclic AMP production or intracellular calcium release, dependent on the receptor isoform. Although Oa2 endogenously signals though cAMP, we were able to force coupling to calcium via transfection of the receptor into a cell line expressing the promiscuous G-alpha-16-protein, which leads to calcium release upon its activation. The calcium release is measurable by fluorescent calcium sensing dyes (in this case Fluo-4). (FIG. 55A)

Cell Biology

Cell Line Construction

The OctR-pcDNA3.1(+)_zeo expression vector was created. This construct was used as a template for the creation of the fluorescently tagged pcDNA3.1-OctR-GFP plasmid. The pAcGFP sequence was inserted into the untagged OctR expression vector using a mega-primer strategy. The first step of this strategy was to use PCR to generate a gene fragment from the pAcGFP-N1-Asc1 plasmid, using primers specific for the pAcGFP vector with an additional overhang of approximately 20 base pairs specific to the OctR-pcDNA3.1 vector.

Figure 55B:
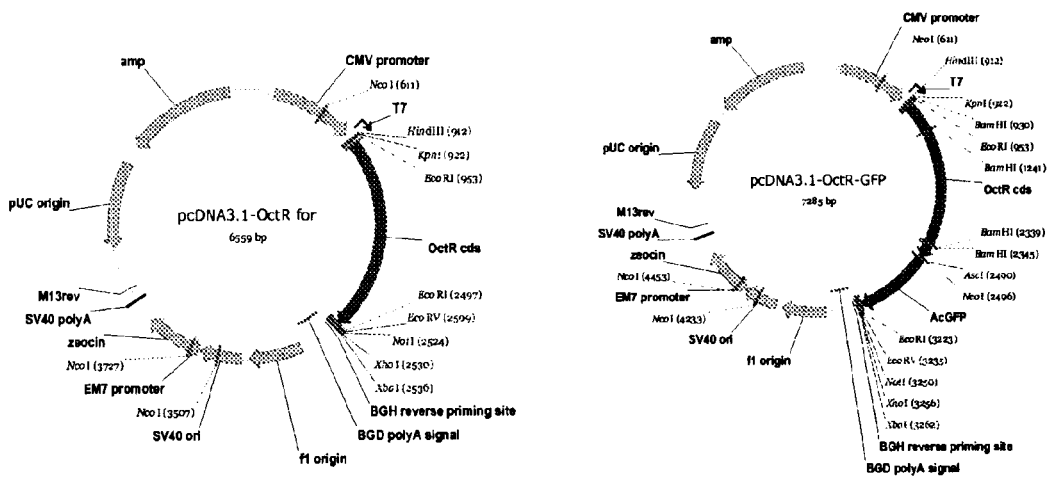
FIG. 55b: Vector maps of pcDNA3.1-OcrR for and pcDNA3.1-OcrR-GFP.

The primers used in this step were 6919-For (5' ctgcatccctgtacaccaacggcgcgcccatggtgagcaag 3') and 6919-Rev2 (5' ggatatctgcagaattcgcccttcacttgtacagctcatccatgc 3'). This 771 base-pair gene fragment was then purified from an agarose gel, concentration determined, and 125 ng of the purified PCR product was used as a mega-primer for a second PCR reaction, using the OctR-pcDNA3.1(+)_neo expression vector as the template and the QuickChange XL site-directed mutagenesis kit protocol. This PCR reaction generated pcDNA3.1-OctR-pAcGFP, which is the CG6919 dmOa2 octopamine receptor sequence with the AcGFP sequence attached to the C-terminus of the gene. The coding region of the construct was sequenced to confirm double-stranded sequence integrity. (FIG. 55B)

Transient Expression in Mammalian CHO Cells Coexpressing G 16

The untagged and GFP-tagged versions of OctR, which natively couples to cAMP, were transiently expressed in CHO cells stably expressing the G-alpha-16 promiscuous G protein, which signals through calcium. This allowed activation of the receptor to be measured by calcium-sensing fluorescent dyes.

In FIG. 55A, various amounts of untagged OctR-pcDNA3.1 DNA were transfected into CHO cells (6-well dish, 300,000 cells/well) and tested for function at 48 hours using Fluo-4 dye on the Discovery microscope. The graph shown below represents an average of all single-cell readings from cells expressing the cyan vector. It is assumed that the majority of cells expressing the cyan vector also express OctR. This experiment demonstrated that the OctR-pcDNA3.1 expression vector is fully functional, that the OctR receptor will couple to G-alpha16, and that a large assay window exists above control-transfected cells upon addition of a maximal dose of octopamine. In addition, it demonstrated that OctR is not toxic to the CHO cells, and increasing amounts of DNA yield greater expression and greater signals.

Figure 55C:
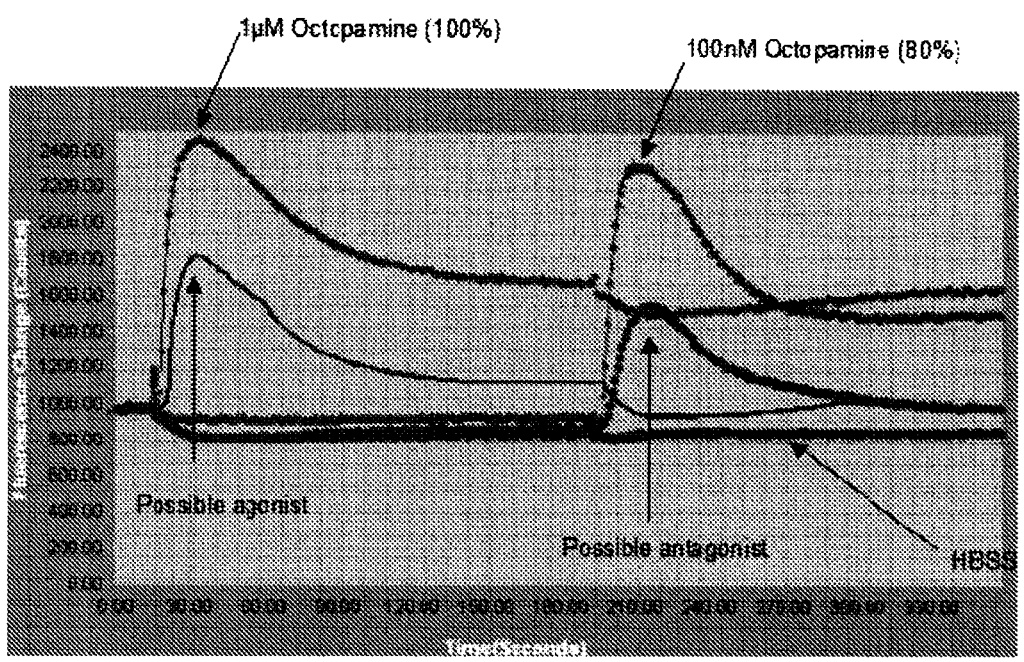
FIG. 55c: Fluorescence change in response to 1 μM and 100 nM octopamine.
Figure 55D:
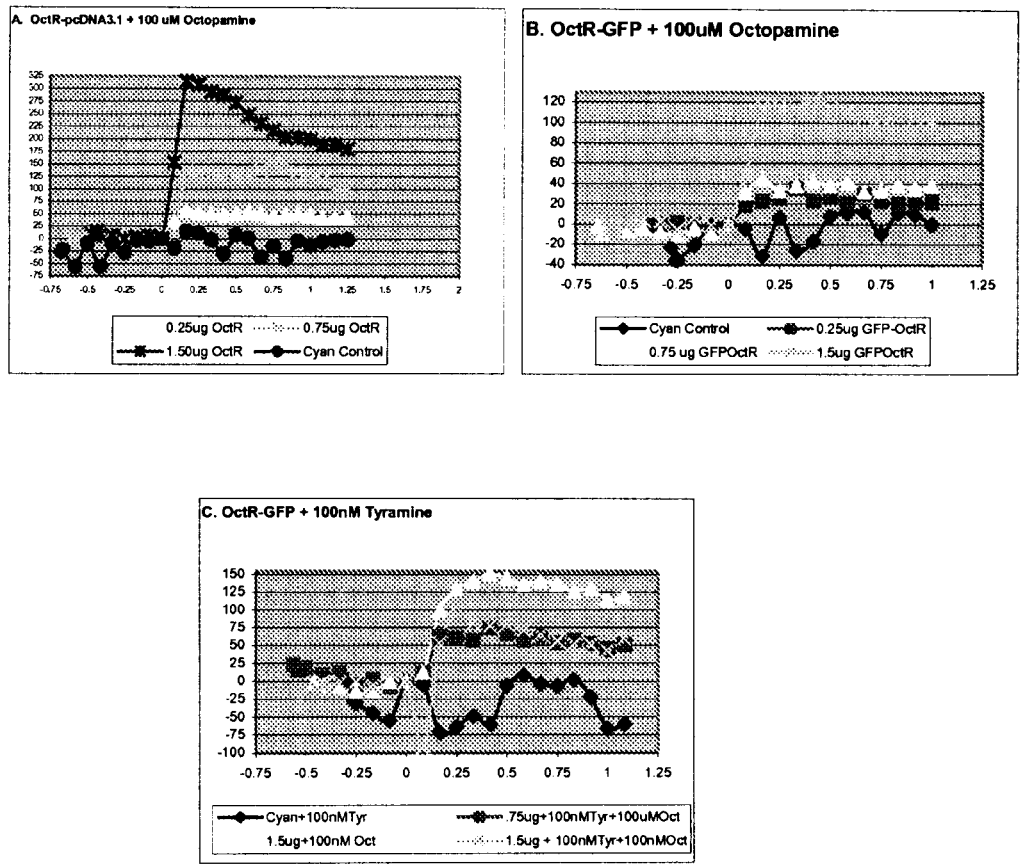
FIG. 55d: Calcium-sensing Fluo-4 fluorescent dye response to octopamine or tyramine stimulation in CHO cells stably expressing G-alpha-16 and transiently expressed tagged or untagged OctR-pcDNA3.1.

In FIG. 55B, a similar experiment is shown with the GFP-tagged OctR expression vector. Once again, the experiment demonstrates that the construct is fully functional and that the assay is capable of measuring calcium release specifically in response to stimulation with octopamine. FIG. 55C shows that the octopamine receptor is also activated by tyramine. Dose curves and competition studies were not performed, but preliminary data and published reports suggest that tyramine is only slightly less efficacious on the OctR than octopamine and has similar potency.

FIG. 55. Calcium-sensing Fluo-4 fluorescent dye response to octopamine or tyramine stimulation in CHO cells stably expressing G-alpha-16 and transiently expressing increasing amounts of untagged or GFP-tagged OctR-pcDNA3.1. Cells cotransfected with pAmCyan vector as a marker of transfected cells were stimulated with a maximal dose of octopamine or sub-maximal dose of tyramine. Well averages of single-cell response measured on the Discovery microscope are graphed above.

Stable Line Generation in Mammalian CHO Cells Coexpressing G-Alpha-16

Figure 56:
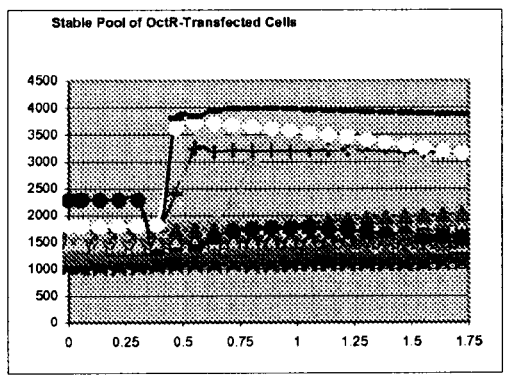
FIG. 56: Stable pool of zeocin-selected CHO-G-alpha-16 cells identified by green fluorescent protein expression.

A line of CHO cells stably co-expressing the pcDNA3(+)-OctR-AcGFP and G-alpha-16 was created. CHO cells stably expressing the G(16 construct (passage 20) were transiently transfected with 1.5 ug of pcDNA3(+)-OctR-AcGFP, the optimal amount of DNA as determined in FIG. 55. Forty-eight hours after transfection, the cells (already maintained under 4 ug/ml hygromycin selection) were put under zeocin selection (300 ug/ml). Cells were grown and passaged under selection for three weeks, then single-cell flow cytometry sorting by fluorescence was completed at Duke University to create monoclonal stable cell lines. FIG. 56 shows an experiment completed just prior to cell-sorting, demonstrating that about 10% of the stable pool population responded to octopamine. At the time of sorting, the G-alpha-16 CHO line was at passage 22.

FIG. 56. Following three weeks of zeocin selection, a stable pool of zeocin-resistant CHO-G-alpha-16 cells exists. Approximately 10% of the stable pool responded to octopamine at measurable levels. This pool was subsequently sorted into single-cell monoclonal colonies.

Monoclonal colonies were visually assessed for the expression of green fluorescent protein, and therefore by assumption, the fused OctR receptor. Colonies positive for green fluorescent protein expression were expanded and tested for response to octopamine.

Figure 57:
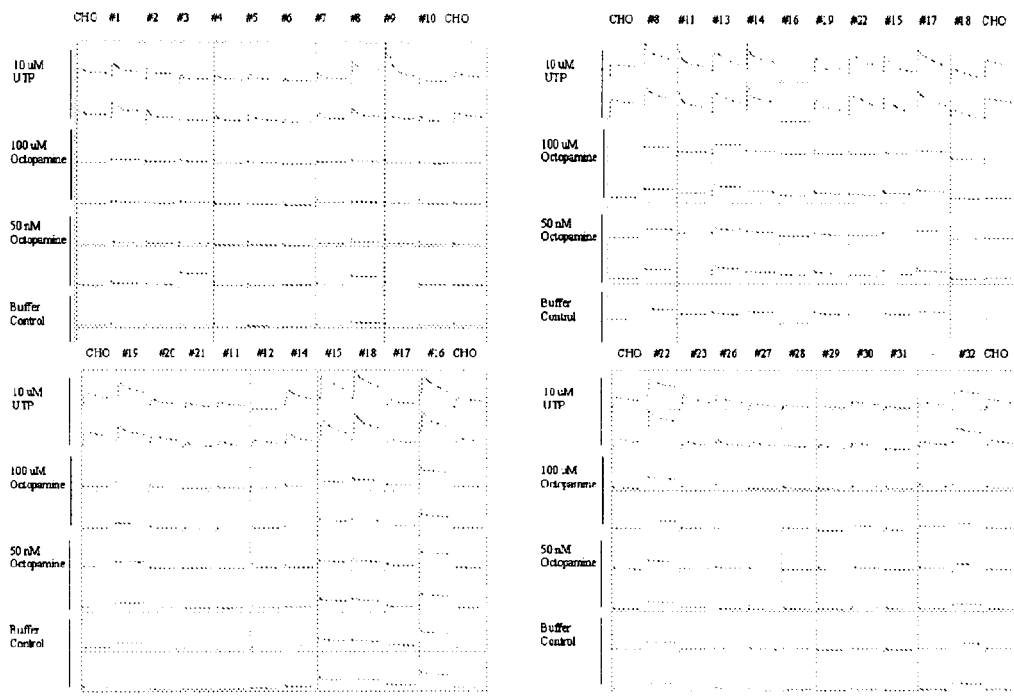
FIG. 57: Screening of all GFP-positive monoclonal cell lines for response to octopamine.
Figure 58:
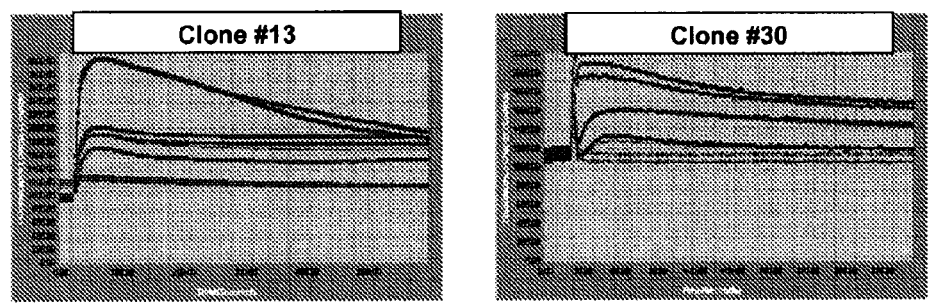
FIG. 58: Response of clones #13 and #30 to octopamine on FLIPR Tetra.

Approximately 30 monoclonal lines positive for green fluorescent protein expression were tested for response to octopamine on the FLIPR Tetra (FIG. 57). All clones were stimulated by UTP as the positive control and a measure of the maximal calcium response, two doses of octopamine, and by buffer for negative control. Cells were seeded at a density of 20,000 cells/well. Of the approximately 30 lines, only 2 clonal lines (#13 and #30) demonstrated a measurable response to octopamine (FIG. 58). These two lines were selected for further testing.

FIG. 57. Screening of all GFP-positive monoclonal cell lines for response to octopamine. All lines responded to the positive control (10 µM UTP) and no response to the negative control (buffer addition), but only clones #13 and #30 had a measurable response to a maximal dose of octopamine FIG. 58. Response of clones #13 and #30 on FLIPR Tetra. On each graph, top two lines are in response to maximal dose of UTP, followed in descending order by 10 uM octopamine, 50 nM octopamine, and buffer control.

Stable Lines #13 and #30 Show Best Response to Octopamine

Figure 59:
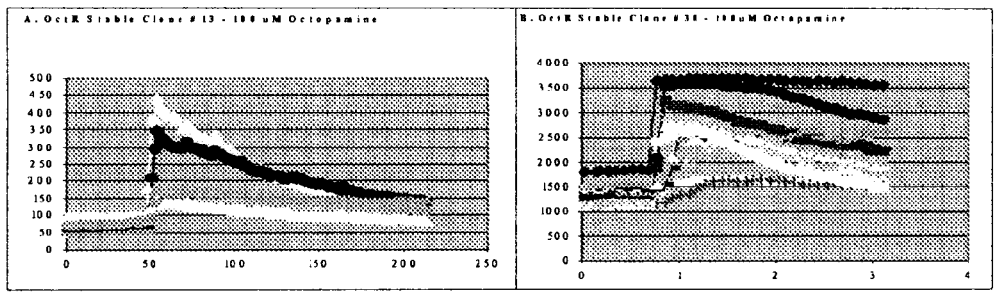
FIG. 59: Single-cell response to octopamine for clones #13 and #30.

After evaluation of approximately 30 GFP-positive monoclonal lines, clone #13 and #30 were selected for further analysis due to their measurable response to octopamine. The uniformity of each of these clonal lines was tested, by assessing single-cell response to octopamine. Clone #13 was assessed using Fura-2 fluorescent dye on the calcium imaging system, and Clone #30 was examined using Fluo-4 fluorescent dye on the Discovery microscope. FIG. 59 shows the results of these tests. Both clones appear to be comprised completely of cells expressing the OctR, as shown by their response to octopamine. However, a noticeable delineation exists between strong responders and weak responders. This may be due to a difference in receptor expression or in G 16 levels of expression from cell to cell. These experiments were performed following passage 7 after flow-sorting into monoclonal lines.

FIG. 59. Single-cell response to octopamine for clones #13 and #30. Clone #13 (A) was assessed by Fura-2 fluorescent dye on the calcium imaging system, and Clone #30 (B) was assessed by Fluo-4 fluorescent dye on the Discovery microscope.

Do to a shrinking of the signal over time in the FLIPR, further subcloning of both lines #13 and #30 were conducted. Single-cell flow cytometry sorting by fluorescence was completed at Duke University to create further subcloned monoclonal stable cell lines coexpressing the OctR-GFP and G(16. Single cells with medium or high expression of green fluorescent protein (and by assumption the fused OctR) were sorted into 96-well dishes and put under selection of hygromycin and zeocin.

Stable Cell Line Generation and Clone Selection

Over 50 subclones from the original #30 clonal line were evaluated on the FLIPR for several weeks looking for a maximum octopamine response above baseline. Clone 55 was chosen to move forward into assay development based on a good dynamic range in the FLIPR (FIG. 60: OCTR clone 55 selection) and over 82% homogeneity in the Discovery microscope (FIG. 61: Homogeneity of OCTR clone 55).

Figure 60:
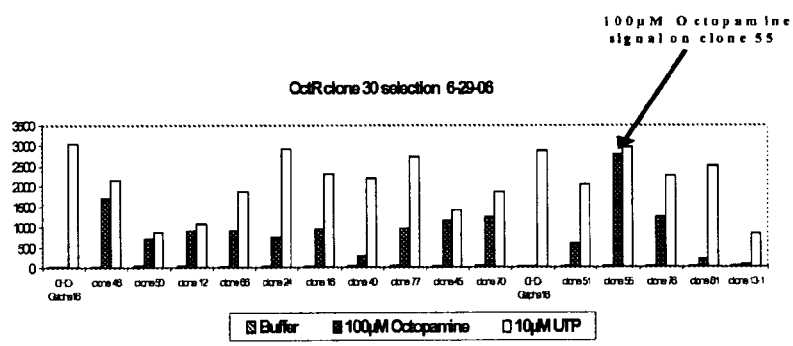
FIG. 60: OCTR clone 55 selection.

FIG. 60. OCTR clone 55 selection. OCTR clones were plated at 20K/well into black 96-well plates and assayed the next day. Culture medium was removed and cells were loaded with 50 ul of 2 μM Fluo-4 with probenecid per well for 1 hour at 25° C. Dye was removed and 50 μl of buffer with probenecid added. A single addition was performed in the Tetra. 50 μL of buffer or (2×) 200 μM Octopamine was added to cells while 10 μM UTP was used as a control for maximum intracellular calcium signal.

Figure 61:
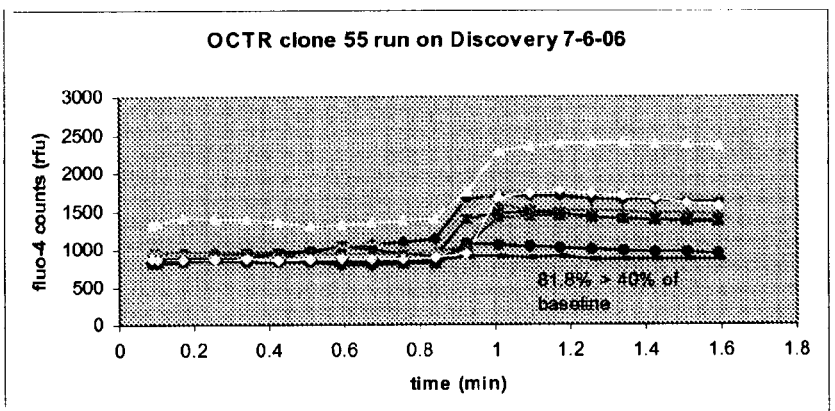
FIG. 61: Homogeneity assay of OCTR clone 55.

FIG. 61. Homogeneity of OCTR clone 55. OCTR cells were plated at 6K/well into a black 96-well plate and assayed the next day. Culture medium was removed and cells loaded with 50 ul Fluo-4 per well for 1 hour at 25° C. Dye was removed and 50 μl of buffer with probenecid added. 50 μl of 10 μM Octopamine or buffer was added and signal was recorded using the Discovery microscope. Well averages of single-cell response measured on the Discovery microscope are graphed above.

Pharmacology

Clone 55 was assessed for correct pharmacology and compared to published results based on a cAMP readout. As shown in FIGS. 62A&B, the agonists and antagonists showed the same rank order of potency as the published data, where in the case of the agonists, naphazoline>octopamine>amitraz>clonidine>tolazoline (Evans P, et al. 2005. Invertebrate Neuroscience 5: 111-118). In FIG. 62C, these same compounds had no effect on the parental cell line, showing the specificity of the ligands to the octopamine receptor.

Figure 62:
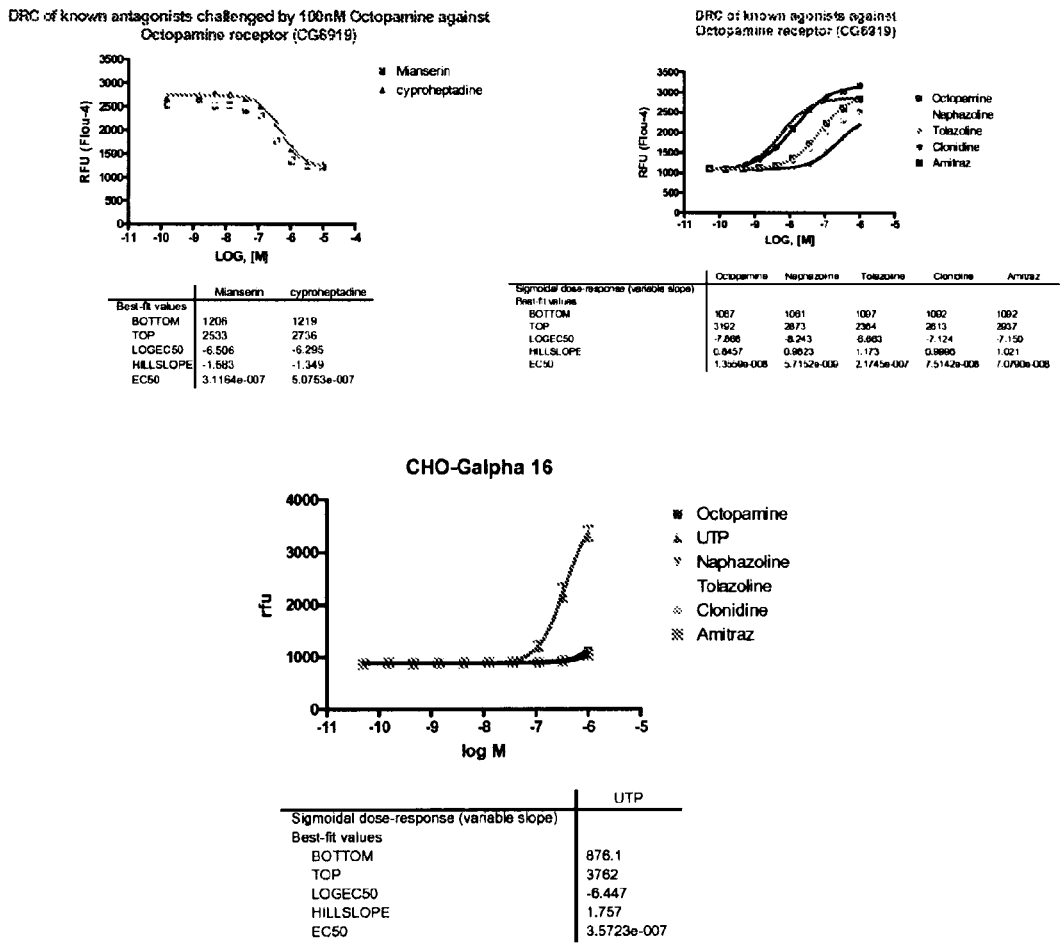
FIG. 62: Antagonist dose response curves and agonist dose response curves in transfected and parent cell lines analysed on FLIPR.

FIG. 62. Cells were plated at 10K/well in 384 well plates and allowed to incubate overnight at 370 C. The cells were assayed 18-24 hours after seeding. Media was removed and cells were dye loaded for 60 minutes with 2 μM Fluo-4. After 1 hour, dye was removed and 20 μl of buffer added to the plate and placed into FLIPR. The 1st addition was antagonist dose response curves and the 2nd addition was agonist dose response curves. Antagonists were challenged with 100 nM Octopamine. In addition, these compounds were tested in the parental cell line CHO-Galpha16.

Assay Development

HTS Screening Strategy

This assay uses two fluid additions to permit the detection of activators and inhibitors in a single experiment. In screening, test compounds will be added in the first addition and allowed to incubate for three minutes. The activator octopamine will then be introduced in the second addition at an EC80 concentration and the fluorescence read for two minutes. Controls will be run for both additions. An increase in fluorescence above baseline in the first addition will indicate a possible activator and a reduced response or no increase in the second addition may indicate a possible inhibitor. FIG. 55C

Basic Test Protocol

Cells were plated at 10,000 cells/well in 50 μl into 384-well black TC plates and allowed to incubate overnight at 37° C./5% CO2. The cells were assayed 18-24 hours after seeding. Culture medium was removed by flicking and cells were dye loaded for 60 minutes with 20 μl of 2 μM Fluo-4 in assay buffer plus probenecid at 25° C. After one hour dye was removed by flicking and 20 μL of assay buffer was added, wait 5 min prior to placing into the FLIPR and run using a two-addition protocol. The first addition (20 ul, 2×) was 0.5% DMSO final in assay buffer. The second addition (20 ul, 3×) was either assay buffer or 100 nM octopamine final.

Cell Plating Method

Experiments were conducted to examine manual vs. multidrop dispensing of cells into assay plates (data not shown). The data showed that the multidrop plating was more reproducible than hand plating. There are two critical points to remember when plating cells with the multidrop:

1. Cells need to stay in suspension during cell plating. We use a rotating plate or a rotomixer with a holder attached, where we can place a 500 ml conical bottom tube containing the cells.
2. Do not leave the cells sitting in multidrop tubing between plates. The cells will settle in the tubing, which will result in streaking patterns in the data. If the cells sit, you will need to empty the tubing and reprime.

DMSO Tolerance Study

Full octopamine dose response curves were performed in the 1st and 2nd additions to test the sensitivity of this assay to varying concentrations of DMSO. As shown in FIG. 63A, there was a significant shift in the EC50 for octopamine at 2% DMSO (final). For the 2nd addition (FIG. 63B), final DMSO concentrations greater than 0.67% showed a significant shift in the EC50. For this assay, we will be using final concentrations of 0.5% DMSO in the 1st addition and 0.33% in the second addition, which will have a minimal effect on the octopamine EC50.

Figure 63:
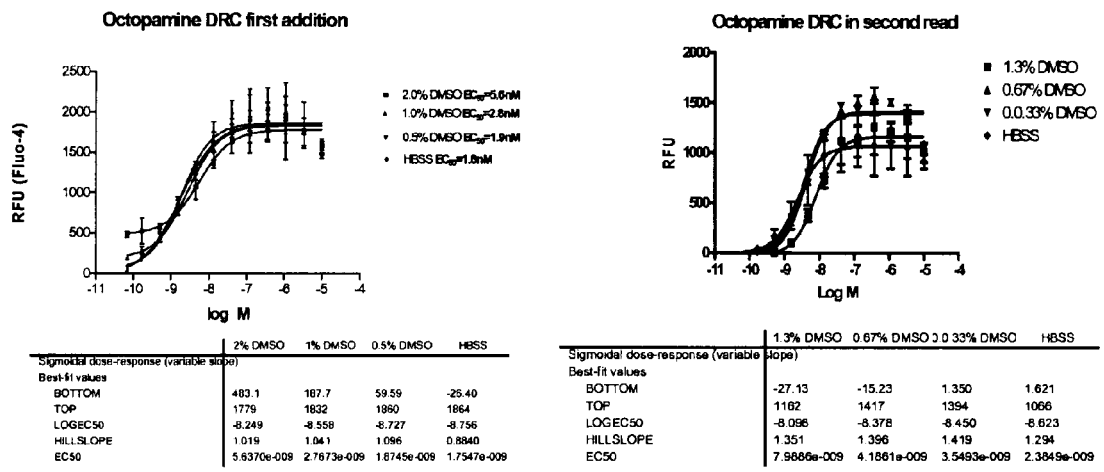
FIG. 63: Octopamine EC50 curves in different DMSO concentrations in 1st and 2nd additions.

FIG. 63: Octopamine EC50 curves in different DMSO concentrations in 1st and 2nd additions. OctR cells were plated at 10K cells/well and assayed the following day. Culture medium was removed and cells loaded with 20 ul of 2 μM Fluo-4 plus probenecid per well for 1 hour at 25° C. After one hour, dye was removed and 20 μl of buffer plus probenecid was added to plate and placed in Tetra. A two-addition protocol was used. The first addition (2×) was either 20 ul indicated % DMSO+octopamine DRC (FIG. 63A) or 20 ul indicated % DMSO in assay buffer (FIG. 63B) then read for 180 sec. The second addition, for FIG. 63B, was (2×) 20 μl of octopamine DRC and read for an additional 180 sec. Statistics were calculated using the maximum of reads 20-180 (1st addition) and the maximum of reads 200-360 (2nd addition).

Cell Density Optimization

Figure 64:
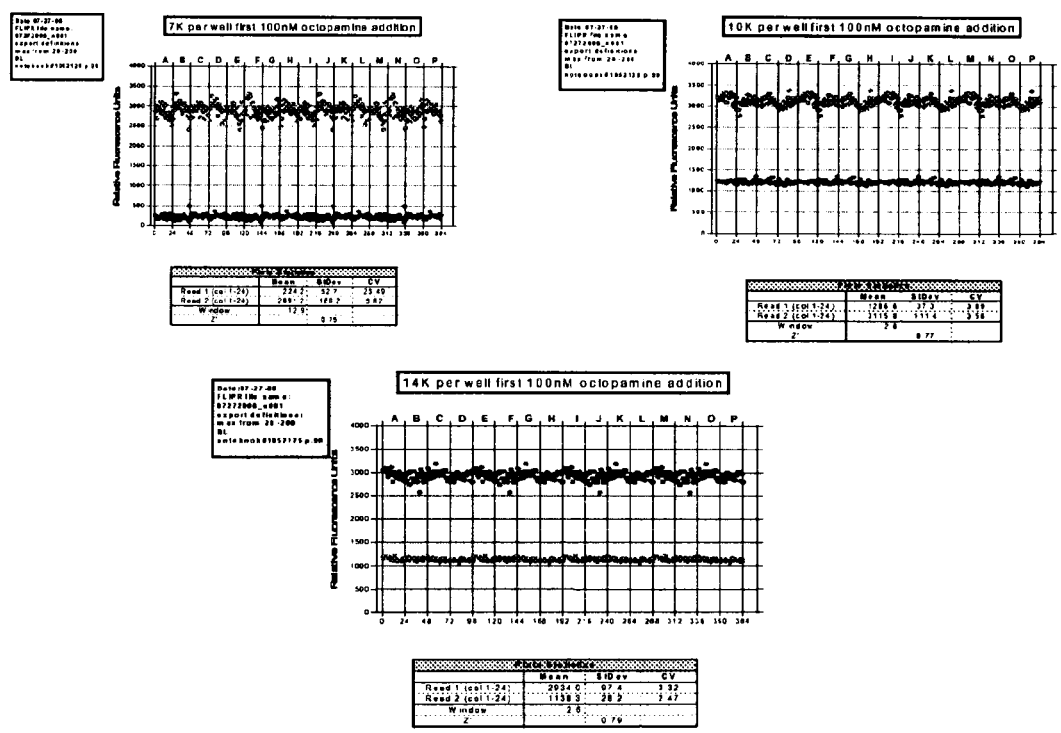
FIG. 64: Graphical representation of effect of cell density measured on FLIP.

Plating densities at 7K, 10K, and 14K per well were examined for variability and Z' statistics and data are shown in FIG. 64. All densities tested performed resulted in excellent Z' statistics. It was decided to move forward with 10K/well based on the low variability and cost reduction.

FIG. 64: Cell density optimization. FLIPR data showing maximum and minimum statistics for full plates at the indicated densities with resulting CV and Z' statistics. Platings below 4K cells/well did not yield a confluent monolayer the next day and were not tested. OCTR cells were plated by-hand at the appropriate densities and assayed the following day. Culture medium was removed and cells loaded with 20 ul/well of 2 μM Fluo-4 plus probenecid and incubated for 1 hour at 25° C. After one hour, dye was removed and 20 μl/well of buffer plus probenecid was added and placed in Tetra. A two-addition protocol was used. The first addition (2×) was 20 ul 1% DMSO in assay buffer (0.5% [final]) read for 180 sec, and the second (3×) was 20 ul 300 nM Octopamine in assay buffer (100 nM [final]) read for an additional 180 sec. The statistics were calculated using the maximum of reads 20-180 (minimum response) and the maximum of reads 200-360 (maximum response).

Dye Concentration

Figure 65:
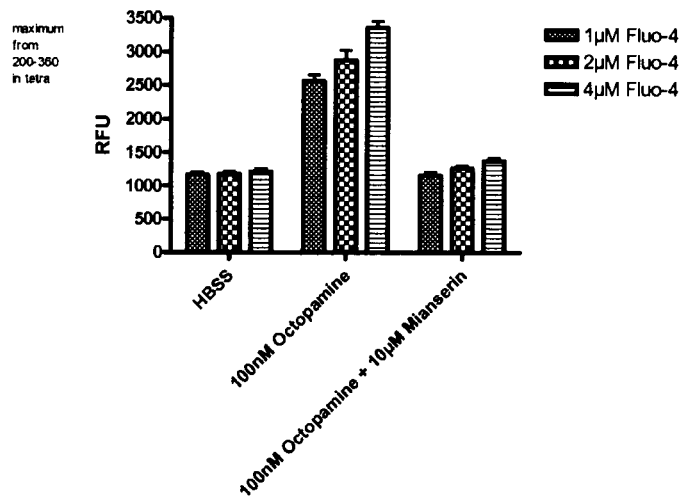
FIG. 65: Graphical representation of effect of dye concentration on assay window size.

An experiment comparing the response of cells loaded for one hour with 1 μM, 2 μM and 4 μM Fluo-4 dye (Notebook 1052125 #1 p. 102) is shown in FIG. 65. All concentrations of Fluo-4 tested resulted in acceptable window size and Z' statistics. It was decided to move forward with 2 μM Fluo-4 based on the good dynamic range and significant cost reduction.

FIG. 65: Dye concentration. Maximum statistics showing the effect of dye concentration on window size. OCTR cells were plated at 10K cells/well and assayed the following day.

Culture medium was removed and cells loaded with 20 ul of 1 μM, 2 μM or 4 μM Fluo-4 per well for 1 hour at 25° C. After one hour, dye was removed and 20 μl of buffer was added to plate and placed in Tetra. A two-addition protocol was used. The first addition (2×) was 20 ul 1% DMSO in assay buffer (0.5% [final]) read for 180 sec, and the second (3×) was 20 ul 300 nM octopamine in assay buffer (100 nM [final]) read for an additional 180 sec. The statistics were calculated using the maximum of reads 20-180 (minimum response) and the maximum of reads 200-360 (maximum response). (not shown Z' for 1 μM Fluo-4=0.73, 2 μM=0.70, and 4 μM=0.80)

Dye Loading Time

Figure 66:
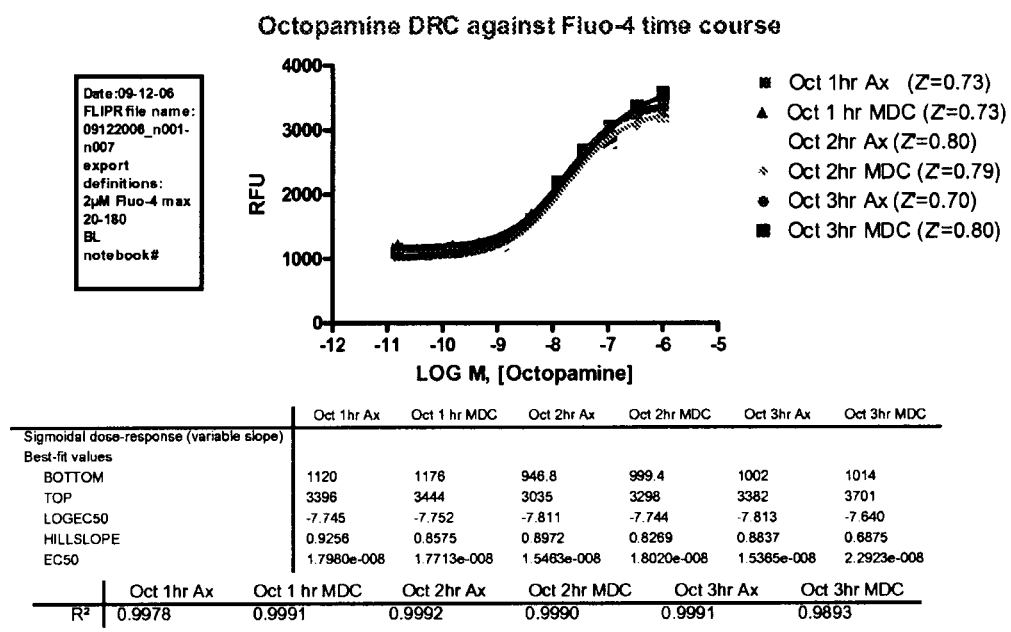
FIG. 66: Graphical results of time course experiment of effect of dye loading time.

The effect of dye loading time on variability and Z' statistics was examined in FIG. 66. In addition, we compared MDC tips versus Axygen Tetra tips. The results showed that dye loading times between 1.0 and 3.0 hours had no significant effect on EC50, window sizes or, as a consequence, Z' statistics. There was no difference between the MDC or the Axygen tips.

FIG. 66: Dye loading time. OctR cells were loaded for 1 hr, 2 hr and 3 hrs to determine if there would be a shift in the octopamine EC50 with increasing dye loading time. In addition, we compared MDC tips with Axygen tips over the same amount of time. OctR cells were plated at 10K cells/well and assayed the following day. Culture medium was removed and cells loaded with 20 ul of 2 μM Fluo-4/probenecid per well at 25° C. After one two, and three hours, dye was removed and 20 μl of buffer was added to plate and placed in Tetra. A two-addition protocol was used. The first addition (2×) was 20 μl DMSO (0.5% final) in assay buffer read for 180 sec, and the second (3×) was 20 μl of octopamine at given dose in assay buffer read for an additional 180 sec. Statistics were calculated using the maximum of reads 20-180 (minimum response) and the maximum of reads 200-360 (maximum response).

Dye Loading Temperature

The OctR cells loaded well at room temperature, so 37° C. was not examined.

Assay Buffer pH Optimization

Standard HBSS buffer at pH 7.4 was used throughout assay development.

Stability of Assay Buffer

Assay buffer stored at 4° C. was tested out to one week (data not shown) with no significant difference in performance.

Stability of Octopamine

Octopamine was tested comparing freshly diluted versus a 24-hour solution (data not shown). The response obtained with the 24-hour solution stored at room temperature was identical to that of the freshly diluted solution. We have repeatedly freeze-thawed 4° C. DMSO stocks of 10 mM octopamine with no reduction in activity.

Pipette Washing and Octopamine Carryover Assessment

In order to reduce the cost of the screen, tip washing experiments were performed to evaluate the ability to remove octopamine from the tips, so that the tips could be used multiple times. Octopamine is extremely sticky and is easily carried over on the tips to the next plate. The following DMSO wash protocol was evaluated:

4 cycles times 2 strokes @ 28 μL in 2.5% DMSO
   Mix 10 strokes @ 25 μL in 100% DMSO
   1 cycle times 2 strokes @ 28 μL in 2.5% DMSO
   1 cycle times 2 strokes @ 28 μL in water Based on the data shown in FIGS. 67A and B, the DMSO wash protocol did not eliminate octopamine from the tips and resulted in significant carryover into the 2nd plate (FIG. 67B). In addition, it should be noted that the length of the assay increased to over 11 minutes, which significantly impacted the number of plates that could be run per day (Notebook 1052125 #1 p124). Acetone was also tested once and worked very well to eliminate carryover (data not shown), but due to the low flash point, it would be a safety hazard to use acetone in the Tetra instrument. For this screen, tips will be changed in between plates.

Figure 67:
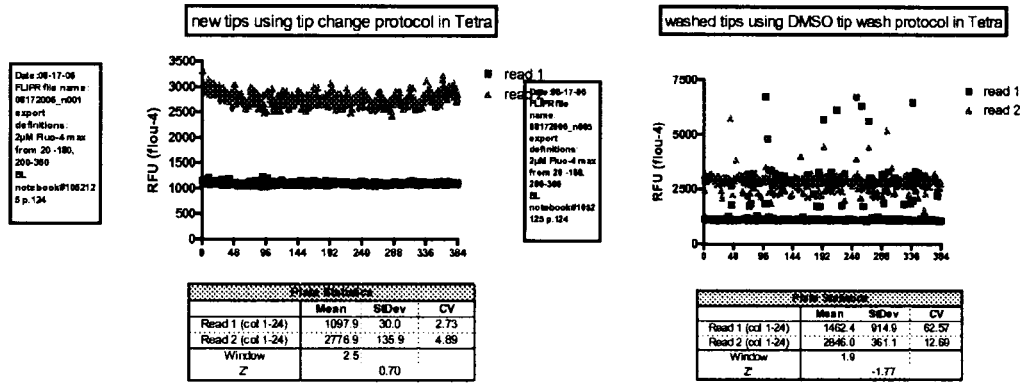
FIG. 67: Graphical results of effect of different tip washings measured on FLIPR.

FIG. 67: Tip washing assessment. FLIPR data showing maximum and minimum statistics for full plates with resulting CV and Z' statistics. OCTR cells were plated at 10K/well and assayed the following day. Culture medium was removed and cells loaded with 20 ul of 2 μM Fluo-4 plus probenecid per well for 1 hour at 25° C. After one hour, dye was removed and 20 μl of buffer plus probenecid was added to plate and placed in Tetra. A two-addition wash protocol was used. The first addition (2×) was 20 ul 1% DMSO in assay buffer (0.5% [final]) read for 180 sec, and the second (3×) was 20 ul 300 nM Octopamine in assay buffer (100 nM [final]) read for an additional 180 sec. The statistics were calculated using the maximum of reads 20-180 (minimum response) and the maximum of reads 200-360 (maximum response).

3-Day Variability Assessment

Three independent assays were performed on three different days to validate the appropriate concentrations of agonist (octopamine) or antagonist (mianserin) to be used during screening, and to validate the inter and intra plate variability of the assay. On each day, duplicate plates were run for each condition. The assay protocol was as follows: OctR cells were plated at 10K/well in 50 μl media and incubated at 370 C/5% CO2 for 18-24 hours prior to running in the Tetra. On the day of the assay, cells were dye loaded with 2 μl Fluo-4 for 1 hour at 250 C, dye removed, 20 μl buffer added to the plate, incubated at RT for 5 minutes, then run in the Tetra.

Figure 69:
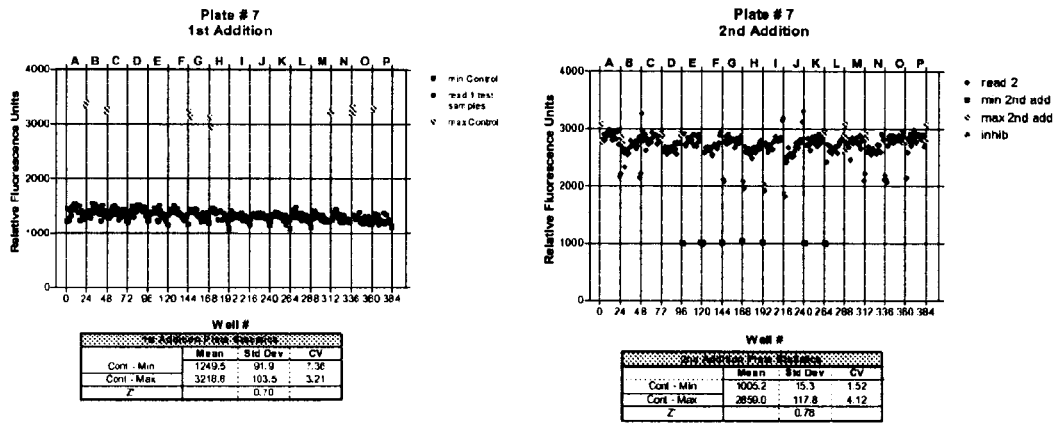
FIG. 69: A scatter plot of plate #7, showing the controls and test wells for the agonist portion of the screen (left) and antagonist portion of the screen (right).

For the 3-day variability assessment, the following concentrations of agonist and antagonist were used:
   100% Agonist=100 nM (day 1) and 1 μM (day 2 and 3)
   80% Agonist=40 nM (day 1) and 100 nM (day 2 and 3)
   50% Agonist=5 nM (all days)
   50% Antagonist=40 nM (all days)
   Time Cuts:
   Read 1=20-180 max stat
   Read 2=200-360 max stat
   1) Buffer+50% agonist+100% agonist. The following scatter plots show 3 days of duplicate plates in order to validate the ability of the assay to identify agonists. The 50% dose of octopamine was achieved on days 2 and 3
   2) Buffer+80% agonist+100% agonist. The following scatter plots show 3 days of duplicate plates in order to validate the 80% dose of octopamine, which will be used in the 2nd addition. As shown, the 80% dose was achieved on all three days.
   3) Buffer+50% antagonist+80% agonist. The following scatter plots show 3 days of duplicate plates in order to validate the ability of the assay to identify antagonists. Unfortunately, the incorrect dose of mianserin was used for all three days; however, the correct dose was achieved during the twenty-plate DMSO test run (FIG. 69B).

3-Day Agonist and Antagonist Dose Response Curves

Figure 68:
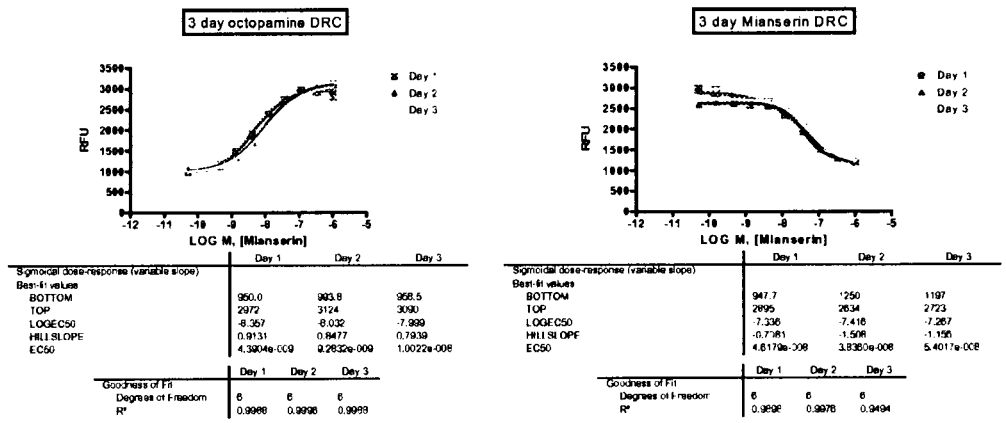
FIG. 68: Octopamine and mianserin dose response curves run on three separate days in OCTR cells.

Octopamine and mianserin dose response curves were run on three separate days to analyze EC50 shifts through time. The data in FIGS. 68A and B show that the EC50 for octopamine and the IC50 for mianserin were very reproducible over three days. FIG. 68. OCTR cells were plated at 10K/well and assayed the following day. Culture medium was removed and cells loaded with 20 ul of 2 μM Fluo-4 plus probenecid per well for 1 hour at 25° C. After one hour, dye was removed and 20 μl of buffer plus probenecid was added to plate and placed in Tetra. A two-addition wash protocol was used. The first addition (2×) was 20 ul DMSO or mianserin at given dose in assay buffer read for 180 sec, and the second (3×) was 20 μl of octopamine at given dose (FIG. 55A) or 100 nM final octopamine (FIG. 55B) and read for an additional 180 sec. Statistics were calculated using the maximum of reads 20-180 (minimum response) and the maximum of reads 200-360 (maximum response).

20-Plate DMSO Test Run

A 20 plate DMSO test run was performed in order to test the following:

Compound dilution scheme (page 30)

Reagent preparation volumes for 20-plate run (SOP page 30-31)

Dynamics of running: timing, equipment issues etc.

Table 5 shows the Z' for all 20 plates. All plates have acceptable Z', except for plate 6, which had a multidrop pipetting error that resulted in variable volumes of liquid being added across the plate. Plate 2 had one control well in the 1st addition (activation) that was low. Removing that point from the calculation resulted in the Z' activation=0.60.

TABLE 5

| Plate   | z' Activation | z' Inhibition |
|---------|---------------|---------------|
| Plate01 | 0.60          | 0.79          |
| Plate02 | 0.47          | 0.65          |
| Plate03 | 0.60          | 0.59          |
| Plate04 | 0.64          | 0.81          |
| Plate05 | 0.59          | 0.72          |
| Plate06 | 0.20          | 0.29          |
| Plate07 | 0.70          | 0.78          |
| Plate08 | 0.66          | 0.76          |
| Plate09 | 0.65          | 0.68          |
| Plate10 | 0.68          | 0.69          |
| Plate11 | 0.57          | 0.70          |
| Plate12 | 0.64          | 0.74          |
| Plate13 | 0.61          | 0.72          |
| Plate14 | 0.71          | 0.76          |
| Plate15 | 0.63          | 0.74          |
| Plate16 | 0.63          | 0.74          |
| Plate17 | 0.64          | 0.76          |
| Plate18 | 0.60          | 0.73          |
| Plate19 | 0.66          | 0.78          |
| Plate20 | 0.53          | 0.78          |

FIG. 69A is a scatter plot of plate #7, showing the controls and test wells for the agonist portion of the screen. The green squares are the 100% (1 μM) octopamine controls, the blue squares are the 0% or buffer controls, and the black diamonds are the test samples, in this case 0.5% final DMSO.

FIG. 69B is a scatter plot of plate #7, showing the controls and test wells for the antagonist portion of the screen. The green squares are the 80% (100 nM) octopamine controls, the blue squares are the 0% or buffer controls, and the black diamonds are the test samples, in this case 100 nM octpamine+0.33% final DMSO. The black diamonds with larger values than the green squares are a 100% dose of octopamine (1 μM). These wells are not used in data calculation, but are included in the assay to validate the 80% dose of octopamine. The black diamonds with lower values than the green squares are the 100% controls from the 1st addition that have decreased over time. They are not included in any data calculations. The red squared are the 50% antagonist control (267 nM mianserin) and are included to ensure that the cells are responding properly.

DATA CALCULATIONS

The % activation and % inhibition were calculated by the following formulas:

% Activation=((Test sample–ave 0% act)/(ave 100% act–ave 0% act))×100

% Inhibition=((Test sample–ave 0% inhib)/(ave 80% inhib–ave 0% inhib))×100

The Z' statistic for activation were calculated using the following formula:

1–((3×ave. STDEV min+3×ave STDEV max)/(abs ave 100%–ave 0%))

where min=0% activation and Max=100% activation

The Z' statistic for activation were calculated using the following formula:

1–((3×ave. STDEV min+3×ave STDEV max)/(abs ave 80%–ave 0%))

where min=0% activation and Max=80% activation
HTS SOP
1) Materials

|                                         | Vendor     | Catalog #   |
|-----------------------------------------|------------|-------------|
| Base media type                         |            |             |
| Ham's F12                               | Mediatech  | 010-080-cv  |
| FBS                                     | Hyclone    | Sh30071.02  |
| trypsin-EDTA (high Conc.)               | Mediatech  | 15400-054   |
| hygromycin (per 50 ml bottle)           | Calbiochem | 400052      |
| zeocin (per 1 g-10 ml-8 tubes/box)      | Invitrogen | 46-0509     |
| Pen/Strep (P/S/antimycotic)             | Mediatech  | bw17602e    |
| PBS                                     | Mediatech  | bw17512q    |
| Consumables (Plastics) Tissue Culture Treated |       |             |
| Flasks (T175)                           | Nunc       | 159910      |
| Plates (black/clear, 384 well)          | bd falcon  | 353962      |
| compound plates                         | NUNC       | 264573      |
| Tetra tips                              | axygen     |             |

Assay Buffer (HBSS):
20 mM Hepes; 11.1 mM Glucose; 1.8 mM CaCl2; 1 mM MgCl12; 125 mM NaCl; 2.5 mM KCl; 5 mM Probenecid; pH to 7.4 Osm 290
To make 1 L of HBSS, add 20 mls of 1M Hepes, 11.1 mls of 1M glucose, 1.8 mls of 1M CaCl2, 31.25 mls of 4M NaCl, 1 ml of 1M MgCl2 and 0.83 mls of 3M KCl to 935 mls of dH20. pH to 7.4 with NaOH. Store at 4° C.
Probenecid:
MW=285.4; ICN Biomedical (156370)
Add 14.2 grams of powder to 100 mls of 1M NaOH=500 mM
Add 10 ml of 500 mM stock to 1 L of HBSS and pH to 7.4 with HCL. Store at RT.
Fluo-4AM:
MW=1096.95; Molecular Probes (F-14202)
Add 912 μl of 100% DMSO to 1 mg vial=1 mM stock
20% Pluronic F-127:
MW-12500; Invitrogen (P3000MP)
20% solution in DMSO
Octopamine:
MW=189.64; Sigma (O-0250)
10 mM stock prepared in 100% DMSO
Mianserin:
MW=300.8; Sigma (M-2525)
10 mM stock prepared in 100% DMSO 2) Cell Culture A) Cell Culture Protocol This assay uses one cell line: OCTR clone 55

Complete culture medium: Prepared in biosafety cabinet/laminar flow hood.

1. 500 ml of Dulbecco's Modified Eagle's Medium/Ham's Nutrient Mixture F-12.
2. Add 50 ml ml fetal bovine serum.
3. Add 5 ml penicillin-streptomycin solution.
4. Add 2.2 ml Hygromycin
5. Add 1.5 ml Zeocin
6. Sterile filter through 0.2 um filter and store at 4° C.

Thawing frozen cells: It is best at first to thaw cells early in the day on Monday so that the cell growth can be monitored and numbers adjusted during the week. The cell numbers listed below can only be considered rough guides as the cells may grow at a different rate in your culture medium.

1. Remove a vial from liquid nitrogen storage and rapidly thaw the cells by immediately placing it in a 37° C. water bath and applying gentle agitation. Keep the O-ring and cap out of the water to reduce the possibility of contamination.
2. When the contents are nearly thawed, remove the vial from water bath, mix by inverting, and decontaminate by spraying with 70% ethanol. All operations from this point on are carried out under aseptic conditions.
3. Transfer the 1 ml of thawed cell suspension into a 50 ml conical bottom centrifuge tube containing 30 ml of complete medium.
4. Centrifuge the cells for 5-7 minutes at 150 g.
5. After centrifugation, remove medium by aspiration and resuspend the pellet in 5 ml of complete medium.
6. Transfer the 5 ml of resuspended cells into a 225 cm2 flask containing 25 ml of complete medium.
7. Inspect the culture flask the following morning and split for expansion or replace medium for further growth.

B) Subculture of Cells/Harvest Protocol

1. Remove flasks from incubator.
2. Aseptically aspirate old media from the flask in the hood.
3. Add 5-10 ml PBS per flask.
4. Rinse flask with the PBS briefly
5. Aspirate PBS
6. Add 3-5 ml RT trypsin
7. Wash trypsin over cells briefly.
8. Aspirate trypsin.
9. Allow cells to detach for 3 minutes and tap flask to loosen cells.
10. Add 8 ml media to the flask.
11. Pipette several times to break up any clumps and to wash cells from the bottom of the flask. Stand flask on end while next steps are completed.
12. If harvesting multiple flasks, then combine cells from all flasks into one flask and mix thoroughly.
13. Remove 20 ul cell suspension from the flask and place into a tube for counting.
14. Proceed to step C below.

C) Performing Cell and Viability Counts/Seeding of Flasks and Plates:

1. After harvesting cells, prepare cells for counting by diluting in trypan blue and PBS at a 1:1 dilution: 20 µl cell suspension+20 µl of 0.4% trypan blue solution NOTE: Trypan blue is available as a 0.4% solution and is used at a working concentration of 0.02%-0.04%, but works well at 0.2%. After being stained with trypan blue, the cells are counted within 3 minutes; after that time viable cells will begin to take up the dye.
2. Using a pipette, withdraw a small amount of the stained cell suspension and place the tip of the pipette onto the slot of a clean hemacytometer with the coverslip. The cell suspension will pass under the coverslip by capillary action. Fill the opposite chamber. Do not overfill. The cell distribution should be homogeneous in both chambers.
3. Place the hemacytometer on the stage of microscope and view one of the four large corner squares ruled by three lines. Viable cells will be slightly opalescent, round and pale with a darker outline. Nonviable cells will be dark, opaque blue.
4. Count the viable cells in the four squares. Count the cells that overlap outside borders of squares but not those overlapping inside borders. Calculate the average number of viable cells per square (total viable cells in the four squares, divided by four).
5. Record the cell counts from both chambers. If the counts differ by more than 20%, prepare a third sample to verify the count.
6. The viable cell number is calculated using the formula:

Viable cell number/ml=average number of viable cells×10$^4$×dilution factor % viability=number of viable cell counted/total number of cells×100

For seeding flasks, calculate the cells/ml of suspension and volume of cells needed.

For example,

Seed 10 flasks at 8.5e6 cells/flask using a cell suspension at 2.5e6 cells/ml

Pipette 25 ml of complete media into each flask.

Calculate the volume of cell suspension that needs to be added to each flask.

8.5e6/2.5e6=3.4 ml of cells added to each flask.

Pipette the cells into each flask.

Rock flasks gently to evenly coat the flask with cells and media.

Place flasks into 370 C/5% CO2 incubator.

The following table shows the seeding schedule and densities for T175 flasks.

| Cell Culture Schedule for 20 plates/day 4 days/week | | | | | | |
|---|---|---|---|---|---|---|
| # of vessels | Mon. | Tues. | Wed. | Thurs. | Fri. | |
| available for plating | 13 | 13 | 13 | 13 | 0 | # of flasks need |
| to make more vessels | 27 | 0 | 0 | 0 | 20 | # of flasks need |
| total | 40 | 13 | 13 | 13 | 20 | Total # of flasks |

| Splitting schedule | | |
|---|---|---|
| overnight | 10e6 c/f | |
| 2 days | 8.5e6 c/f | Cells need to be refed on second day ie. RF Th |
| 3 days | 5e6 c/f | |
| 4 days | 2-2.5e6 c/f | |

For seeding plates, calculate the number of cells per plate needed.

For example,

Seed 20 plates at 10K cells/well using a cell suspension at 2.5e6 cells/ml

Calculate the volume of cell suspension you will need.

10,000 cells/well×384 wells/plates=3.84e6 cells/plate 3.84e6 cells/plate×23 plates=8.832e7 cells total (Note: 23 plates is used in the calculation so that there is a dead volume for the multidrop)

8.83e7 cells total/2.5e6 cells/ml=35.3 ml of cell suspension

Figure 87:
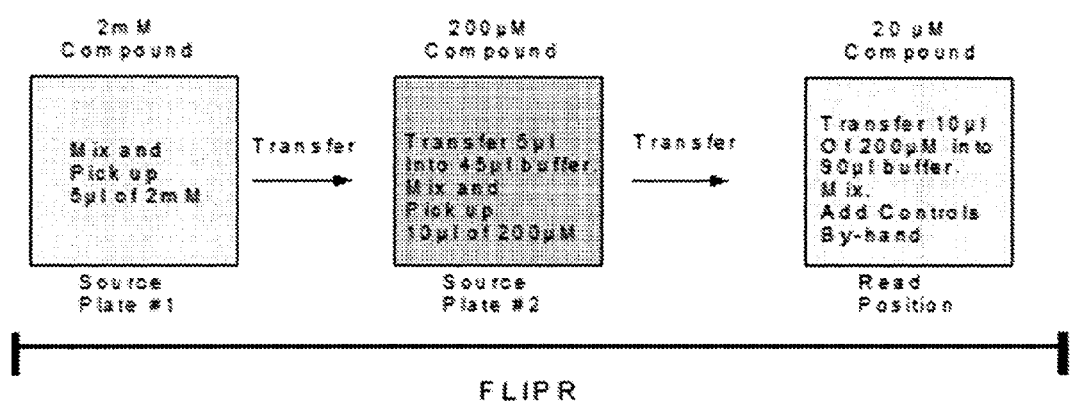
FIG. 87: Schematic of Tripos compound dilution file.
Figure 88:
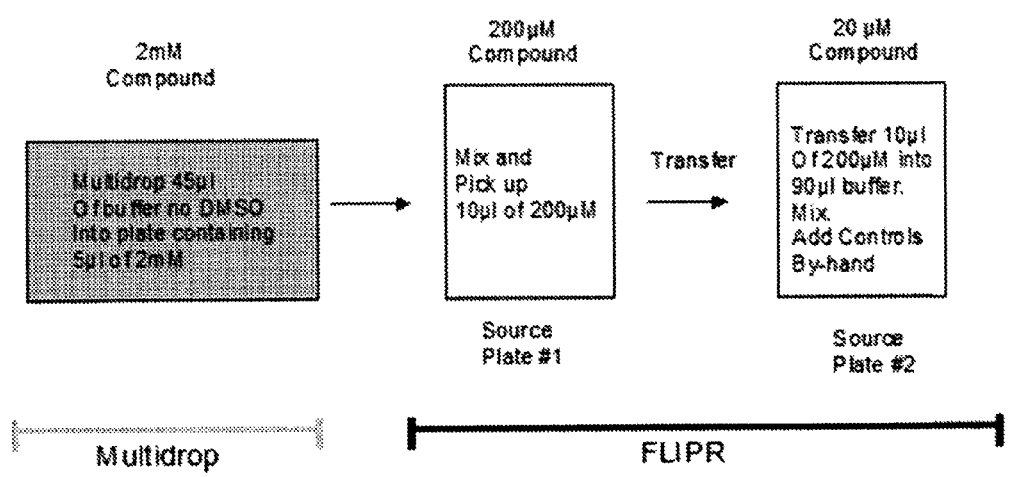
FIG. 88: Schematic of Divpick compound dilution control file.
Figure 89:
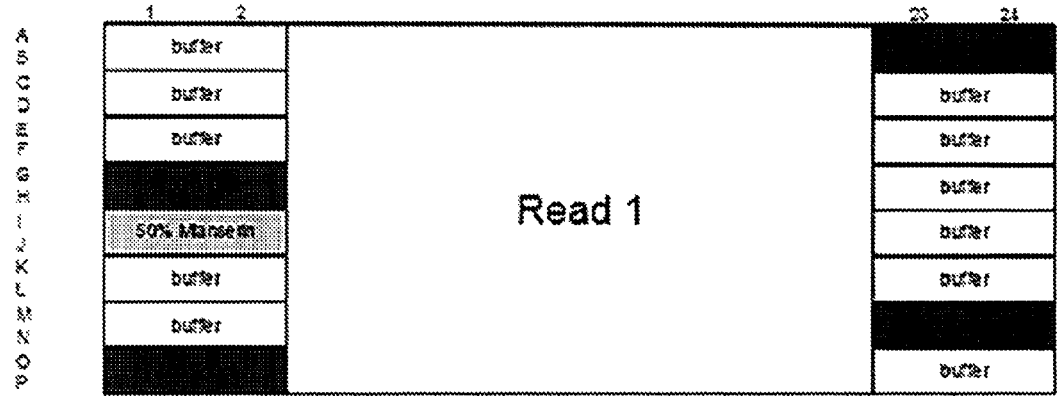
FIG. 89: Schematic of Read 1 plate map.
Figure 90:
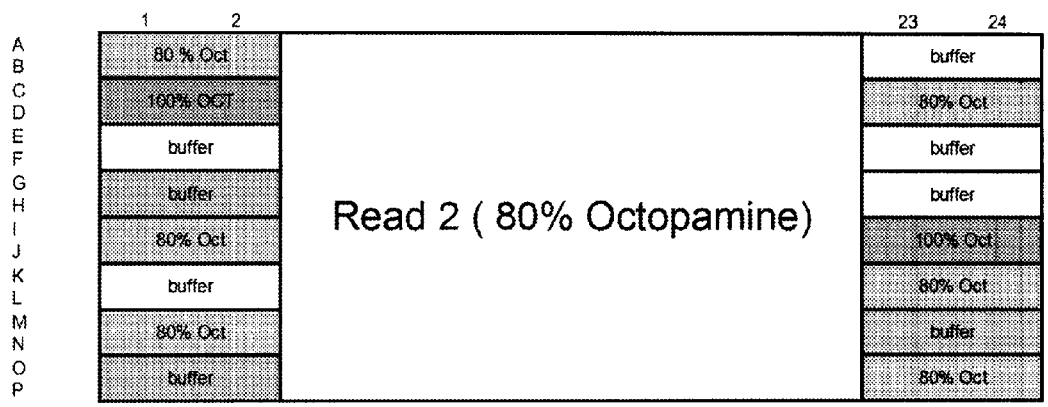
FIG. 90: Schematic of Read 2 plate map.
Figure 91:
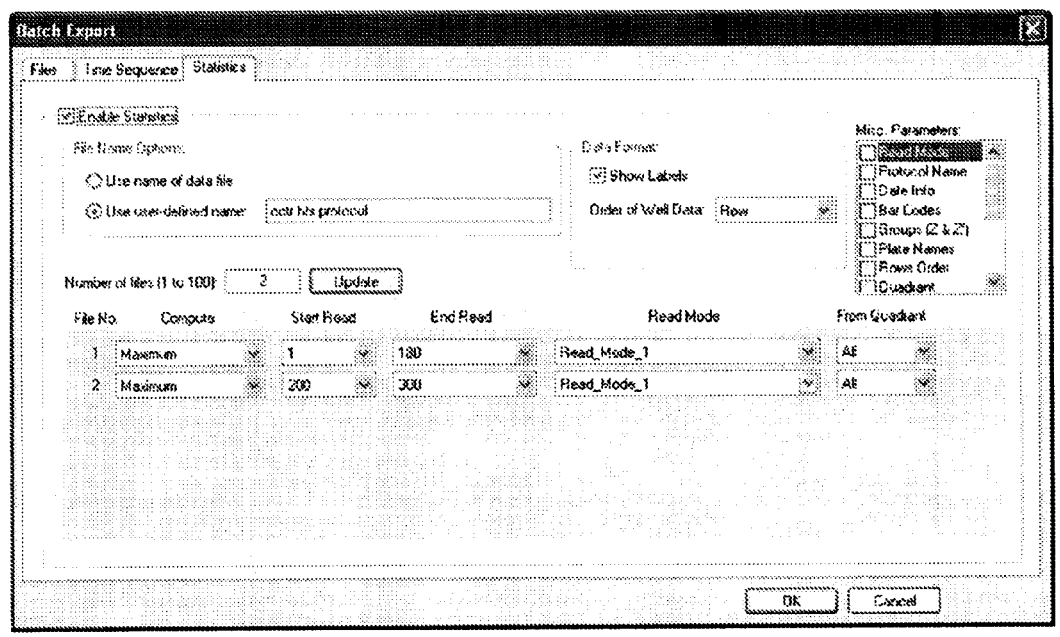
FIG. 91: Screenshot of Batch Export statistics interface.

Calculate the total volume that you will add the cells suspension to:
50 µl/well×384 wells/plates=19.2 ml/plate
19.2 ml/plate×23 plates=442 ml total
To the 35.3 ml cell suspension, add 406.3 ml media.
Mix thoroughly and take a sample to count.
The cell count should be 5e5 cells/ml or 2.5e4 cells/50 µl
Use the multidrop to dispense cells into the plates:
  Put multidrop head into the dispenser
  Flush the head with 50 ml 70% EtOH
  Flush with 70 ml sterile PBS
  Place the cell suspension in a 500 ml conical bottom tube on the rotomix table and place the multidrop tubing into the cell suspension.
  Prime the head with the cell suspension.
  Dispense 50 µl/well into each plate. Make certain to keep the cells in suspension while dispensing and that the cells do not sit in the tubing. Both will result in patterns in the data.
  Leave plates in a single layer at room temperature for at least 30 minutes, prior to placing into 370 C/5% CO2 incubator.
  Make certain that plates are in a single layer in the incubator.
  Clean multidrop tubing by flushing with 70 ml of 70% EtOH followed by 70 ml of dH2O.
3) HTS 20 Plate Screening Assay
A) One Day Prior to Assay:
Harvest cells from flasks. Seed 20× 384-well plates at 10 Kcells/well/50 µl per well. Leave plates at RT for at least 30 min to reduce edge effects (see page 29 for details).
Incubate at 37(C/5% CO2 overnight (16-24 hours, stacking no more than 1 plate high).
B) Day of the Assay:
1. Prepare Tripos Read 1:
Place the 45 µL 2 mM stock plate into source position #1 on Tetra
Place a new 384-well plate with 45 µl of HBSS (no DMSO) in columns 3-22 in source position #2
Place a new 384-well plate with 90 µl of HBSS (no DMSO) in columns 3-22 in read position
Run Tripos compound dilution control file
The Tripos compound dilution control file is depicted in FIG. 87.
Or,
1. Prepare Divpick Read 1:
Using multidrop, add 45 µl of HBSS to stock plate containing 5 µl of compound for a final stock of 200 µM.
Place the 50 µL 200 µM stock plate into source position #2 in Tetra
Place a new 384-well plate with 90 µl of HBSS (no DMSO) in columns 3-22 in read position
Run Divpick compound dilution control file
The Divpick compound dilution control file is depicted in FIG. 88.
2. Prepare Read plate 1 controls.
Make up HBSS 1% DMSO buffer by adding 750 µl of 100% DMSO to 75 mls of HBSS. Add 60 µl to appropriate wells according to READ 1 plate map below.
Make up 100% Octopamine by adding 5 µL of 10 mM stock to 25 ml of HBSS for a 2 µM (2×) concentration. Add 60 µl to appropriate wells according to READ 1 plate map below.
Make up 50% Mianserin by adding 50 µL of 100 µM stock to 6.25 ml of HBSS for a 800 nM (2×) concentration. Add 60 µl to appropriate wells according to READ 1 plate map below.
The Read 1 plate map is depicted in FIG. 89.
3. Prepare Read 2 Plates
Make up 80% octopamine by adding 165 µL of 1 mM stock to 550 ml of HBSS for a 300 nM (3×) concentration. Add 60 µls to appropriate wells according to READ 2 plate map below.
Make up 100% octopamine by adding 37.5 µL of 1 mM stock to 12.5 ml of HBSS for a 3 µM (3×) concentration. Add 60 µls to appropriate wells according to READ 2 plate map below.
Add 60 µLs of HBSS (no DMSO) to appropriate wells according to READ 2 plate map below.
The Read 2 plate map is depicted in FIG. 90.
4. Dye Load
Prepare dye by adding 0.5 ml of 1 mM Fluo-4 together with 0.5 ml of 20% pluronic into a tube, mix, then add mixture into 250 mls of HBSS/probenecid.
Remove media from cell plates by flicking plates into sink containing Clorox, tap gently on kimwipes to remove excess, and add 20 µl/well of dye using multidrop.
Place in RT incubator for 60 min.
5. Run the Assay
Remove dye from cell plate by flicking into sink containing bleach; tap gently on Kimwipes to remove excess dye.
Add 20 µl of HBSS using multidrop to cell plate; place in read position in FLIPR and wait 5 minutes prior to running in FLIPR. (***Failure to wait 5 minutes will increase the variability in the plate)
Place Read 1 compound plate into source #1
Place Read 2 compound plate into source #2
Run protocol: OCTR HTS screen on Tetra
FLIPR read settings:
1st addition=180 reads at 1 sec interval with 20 µl addition after 10 baseline reads
2nd addition=120 reads at 1 sec interval with 20 µl addition after 10 baseline reads
7. Data Export
After 20 plates have been run, manually batch export maximum statistics from read 1-180 as stat1 and reads 200-300 as stat2. These statistics are then copied into an excel spreadsheet to calculate the percent control for inhibition and activation.
A screenshot of the Batch Export statistics interface is depicted in FIG. 91.
The following examples are in connection with the SK-channel:
1.
The potassium channel is responsible for the survival of Dm. In transient RNAi experiments it was demonstrated that reduced viability and lethality effects are induced in Dm. In comparison to buffer control as-well-as injection of a known nonlethal RNAi, RNAi produced from SEQ ID NO: 227, shows measurable reduced viability in Dm.

| Construct | injected eggs | developing eggs | larvae hatched | dev E to L rate | Pupae | L to P rate | Adults | P to A rate | survival devE to A |
|---|---|---|---|---|---|---|---|---|---|
| Buffer only | 82 | 71 | 50 | 70.42% | 40 | 80.00% | 37 | 92.50% | 52.11% |
| Nonlethal Control | 99 | 92 | 79 | 85.87% | 74 | 93.67% | 63 | 85.14% | 68.48% |

| Construct | injected eggs | developing eggs | larvae hatched | dev E to L rate | Pupae | L to P rate | Adults | P to A rate | survival devE to A |
|---|---|---|---|---|---|---|---|---|---|
| Seq No: 1 RNAi | 87 | 74 | 50 | 67.57% | 33 | 66.00% | 31 | 93.94% | 41.89% |
| Lethal Control | 82 | 72 | 28 | 38.89% | 13 | 46.43% | 11 | 84.62% | 15.28% |

2. Expression of *Drosophila* SK Gene in CHO Cells

Gene name small conductance calcium-activated potassium channel

Synonyms CG10706

Species *Drosophila melanogaster*

Figure 70:
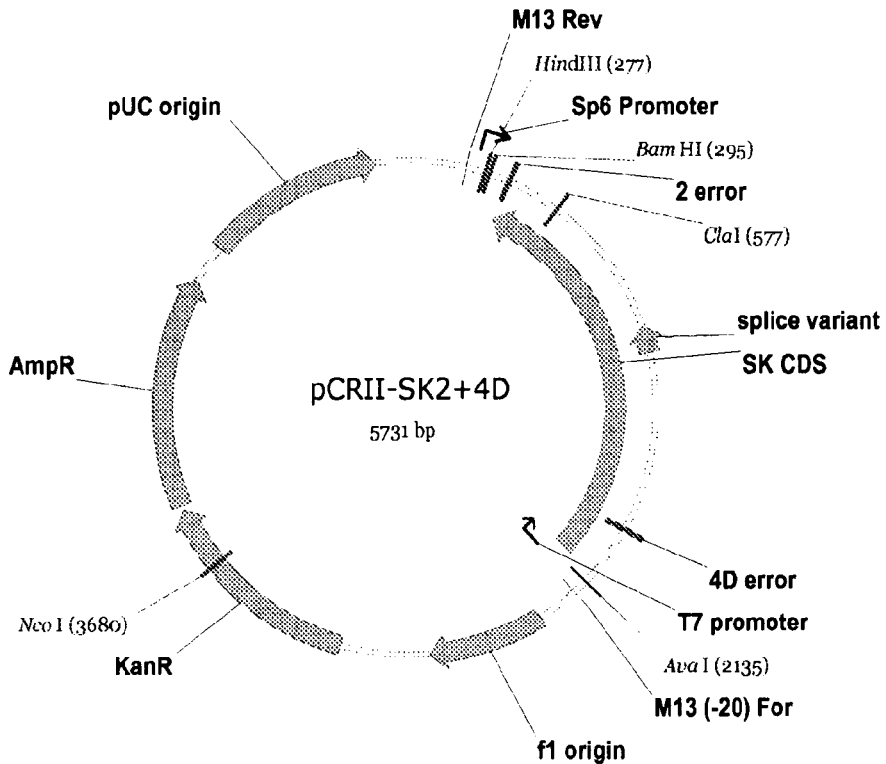
FIG. 70: Vector map of pCRII-SK2+4D

Final clone name pCRII-SK2+4D (coding sequence only) FIG. 70

Base vector pCRII-TOPO (Invitrogen)

Primers

```
                                              (SEQ ID NO: 233)
    Forward: SK 5'1 5'ATGAAAACACCTTCCATTGC 3'

(SEQ ID NO: 224)
    Reverse: SK 3'2 5'TCAGCTGCCGTATTTGTTGG 3'
```

Cloning strategy: Coding sequence from mixed fs-cDNA (head and 2nd instar) was PCR amplified using the above primers, and cloned into pCRII-TOPO vector. 2 independent clones were chosen for sequencing, 2 and 4D, and a perfect sequence was created by subcloning the AvrI/NdeI 498 bp fragment from 2 into the AvrI/NdeI 5233 bp vector fragment of 4D.

Figure 71:
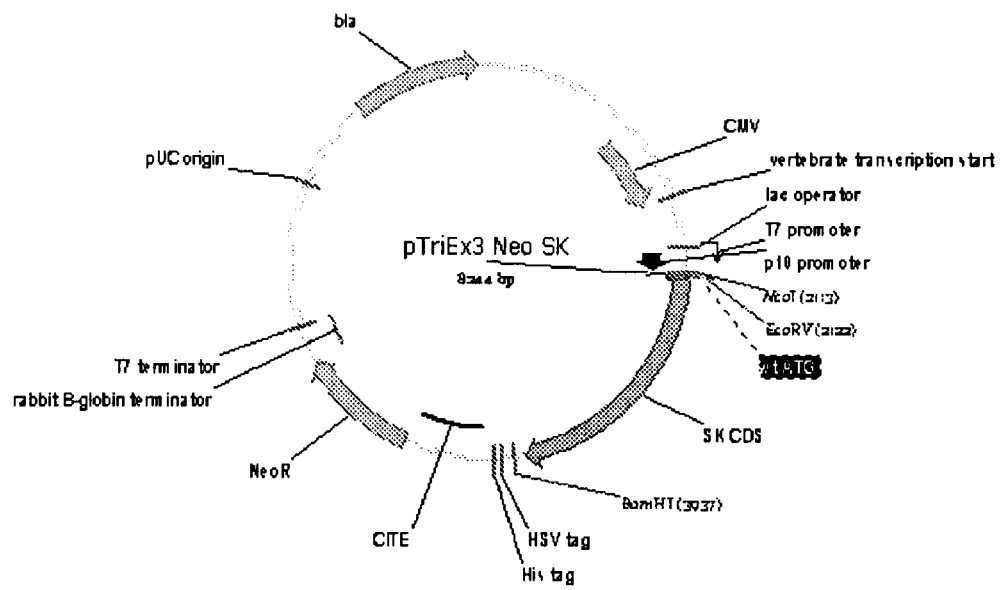
FIG. 71: Vector map of pTriEx3 Neo SK

Expression Construct pTriEx3 Neo SK was created by ligating the 1.8 kb EcoRV/BamHI fragment from pCRII-SK2+4D to the EcoRV and BamHI sites of pTriEx3-Neo. The resulting construct contains the SK CDS downstream of the CMV promoter and adds nine codons to the 5' end as a result being in-frame with the Kozak translation start consensus. FIG. 71 Transfection: CHO—K1 cells were plated in 35 mm 6-well plates at 2.5× 104 cells/well and transfected the following day with 1 ug pTriEx3 Neo SK DNA from each of three different bacterial clones using FuGENE 6 transfection reagent (Roche Diagnostics Corporation) and the manufacturer's recommendations. Cells were passaged 24 hr later into 75 cm2 flasks and placed under antibiotic selection (400 ug/ml G-418, Calbiochem).

3. Testing Functionality

Basic test protocol: Cells were plated at 5×104/well into 96-well poly-D-lysine assay plates (BD Biosciences) and placed at 37 C/5% CO2 the day before testing. Culture medium was aspirated and replaced with 0.4× blue membrane potential dye (Molecular Devices Corporation) in assay buffer and incubated for 1 hour at RT. The assay was run by reading baseline fluorescence for 20 sec, and reading an additional 60 or 180 sec after activation.

Figure 72:
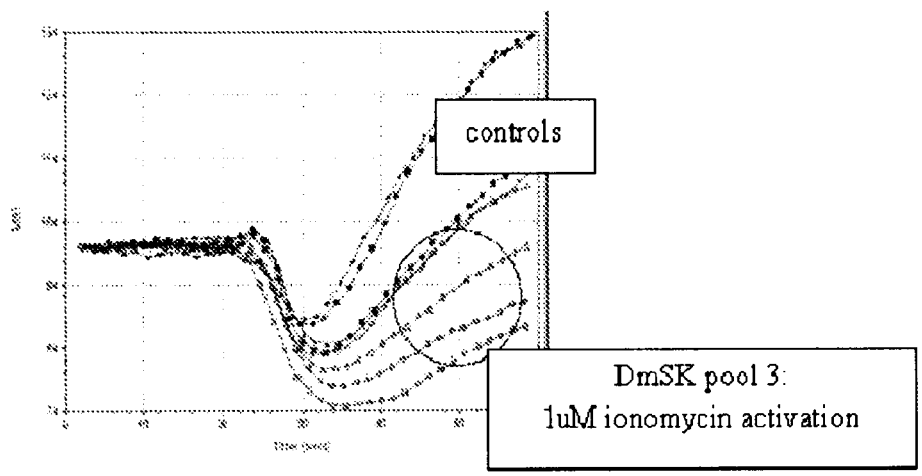
FIG. 72: Activation curves for CHO-K1 cells transfected with pTriEx3 Neo SK and activated with ionomycin.

Pool testing: Once selection was complete (about 10 days) the cells were passaged again into assay plates and culture vessels for expansion. The three transfection pools were tested for function using 1 uM [final] ionomycin (a Ca2+ ionophore) as an activator. Pool 3 (clone SK3) showed the expected hyperpolarization in response to presumptive Ca2+ influx. FIG. 72

4. Assay Protocol

Assay Buffer (Prepared Fresh Daily):

| Stock solution | Final concentration |
|---|---|
| 1M KCl | 1 mM |
| 1M CaCl2 | 2.3 mM |
| 0.5M NaHCO3 | 5 mM |
| 1M MgCl2 | 1 mM |
| 5M NaCl | 154 mM |
| 1M D(+) glucose | 5.5 mM |
| 1M HEPES pH 7.4 | 20 mM |

Stock solutions can be sterile-filtered and stored indefinitely at room temperature, with the exception of glucose, which is stored at 4° C. The assay buffer is prepared by starting with 0.8 volume of high-quality water; adding stock components to the final concentration, and adjusting the volume. The solution is sterile-filtered and the pH adjusted to 7.4 with 1N NaOH.

A 10 mM ionomycin (MW=709) stock is prepared by dissolving the powder in DMSO to a final concentration of 7.1 mg/ml. This solution is stored at 4° C. and is stable for one year.

Activation solution (5×) is prepared by adding 10 mM ionomycin to assay buffer to a final concentration of 5 uM (1:2000 dilution). This solution should be prepared fresh daily. We have heard reports of ionomycin sticking to certain types of polypropylene, but have not seen this with the tips, tubes and compound plates we are using, with the exception of the black FLIPR Tetra 96-well tips.

This assay was developed using the Molecular Devices blue membrane potential dye at 0.4× the normal concentration. It is important to vortex the dye upon hydration and rinse the vial repeatedly to ensure that all the dye has been recovered and that it is in solution. The dye can be stored during the day at 4°. Dye loading is carried out by flipping the culture medium from the 96-well poly-D-lysine plate, gently tapping the plate on Kimwipes to remove excess medium, replacing it with 180 ul 0.4× dye per well, and incubating in the dark at room temperature (25° C.-28° C.) for 3-5 hr. The assay plate is now ready for testing which comprises a 20 ul (10×) first addition and 50 ul (5×) second addition. 50 uM propafenone [final] is used as a control inhibitor. The assay is read for three minutes after activation to allow maximum window development relative to controls.

Special reagents: Ionomycin, free acid (Calbiochem #407950)

Propafenone hydrochloride (Sigma #P4670)

5. Cloning:

Cells from pool 3 were diluted to 12 cells/ml and 250 ul was dispensed into each well of two 96-well culture plates. Wells containing a single clone were identified after one week's growth and picked for expansion and testing the following week.

Clone screening: Fifteen individual clones were screened for function using the same conditions as pool testing. The time and extent of maximum hyperpolarization as well as a measurement of the sustainability of the hyperpolarization were used to select the best performing clones for further evaluation.

6. Functional Validation

Figure 73:
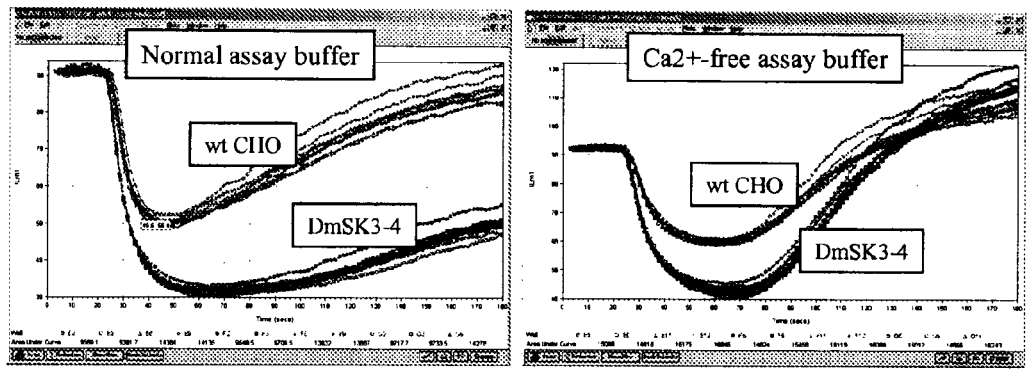
FIG. 73: Activation curves comparing normal assay buffer and Ca2+ free buffer.

An experiment was undertaken to examine the response to elimination of external Ca2+. If the channel is indeed activated by the import of Ca2+ by ionomycin, then removing Ca2+ from the outside of the cell should reduce the differential response. FIG. 73

Conclusion: Elimination of Ca2+ from the assay buffer reduced maximum hyperpolarization to within 20% of wild-type and abolished the differential response altogether by timepoint 120 sec. Therefore, the SK-expressing cells require Ca2+ for full response, indicating a Ca2+-dependent activation.

7. Activation Optimization/EC50

Tests were conducted to determine the optimal concentration of ionomycin in the activation buffer needed to produce a robust signal with a large response window relative to controls. The EC50 for ionomycin on SK3 was calculated in three separate experiments, yielding a value of 200 nM (SD=10). There was no increase in the size of the response window relative to controls above 800 nM ionomycin. These results correspond to literature values of 1 uM for full activation of Ca2+-dependent channels (Terstappen et al., 2001. Neuropharmacology 40).

Figure 74:
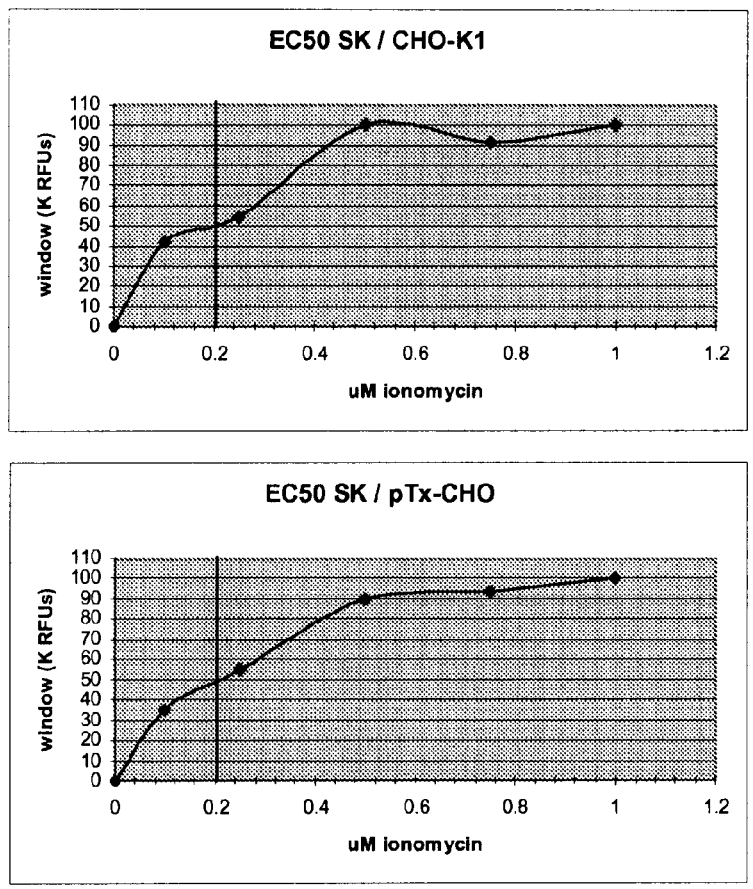
FIG. 74: EC50 curves for SK/CHO-K1 and SK/pTx-CHO cells activated with increasing amounts of ionomycin.

Sample data: FIG. 74 pTX-CHO is a mock transfected cell line, i.e. a cell line transfected with vector that does not contain the gene of interest to show any activity in screening is due to the gene of interest and not the vector.

8. Variability in Relation to Dye Loading Time

Figure 75:
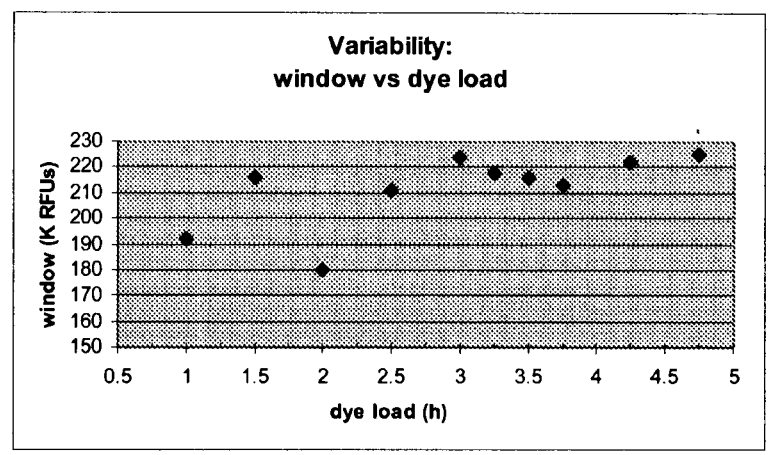
FIG. 75: Graphical representation of assay window size variability in relation to dye loading time.

Tests were conducted to examine the assay window size relative to dye loading time. 24 wells each SK3-9 and pTx-CHO were loaded at room temperature for the times indicated on the following chart, up to nearly five hours: FIG. 75

The window size stabilized at maximum after 3 hours and variability among wells was reduced (data not shown). Based on these results, a dye load time of 3-5 hours is recommended for screening.

9. DMSO Tolerance

Figure 76:
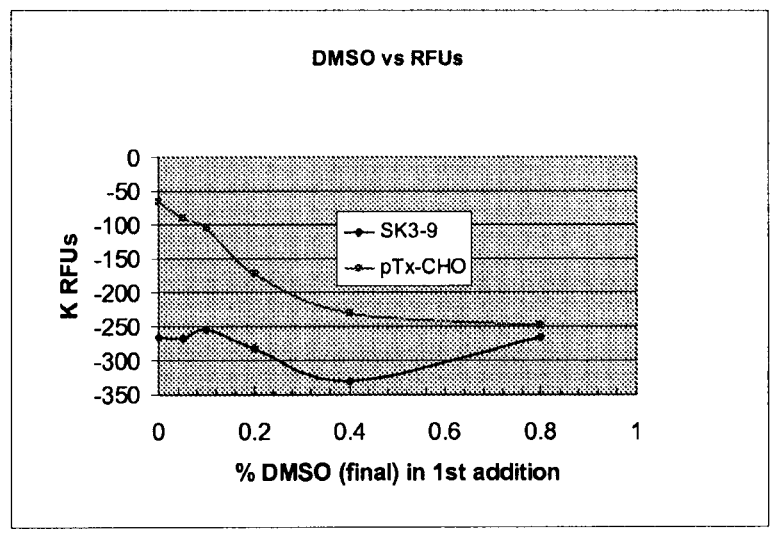
FIG. 76: Graphical representation of DMSO concentration effect on ionomycin activation.

Cells responded predictably to increasing levels of DMSO in the first (10×) addition with increased instability and a narrowing of the assay window. Additions resulting in DMSO levels above 0.2% showed severe perturbations after ionomycin activation. FIG. 76

10. Ionomycin Stability

An experiment was conducted (data not shown) to examine the stability of ionomycin in solution. Ionomycin was diluted to 5 uM in assay buffer, loaded into a compound plate and compared with freshly-prepared ionomycin for SK activation the following day. The freshly-prepared ionomycin yielded a statistically significant 6% increase in assay window size, so our recommendation is for freshly-prepared ionomycin.

11. Statistical Tests

Figure 77:
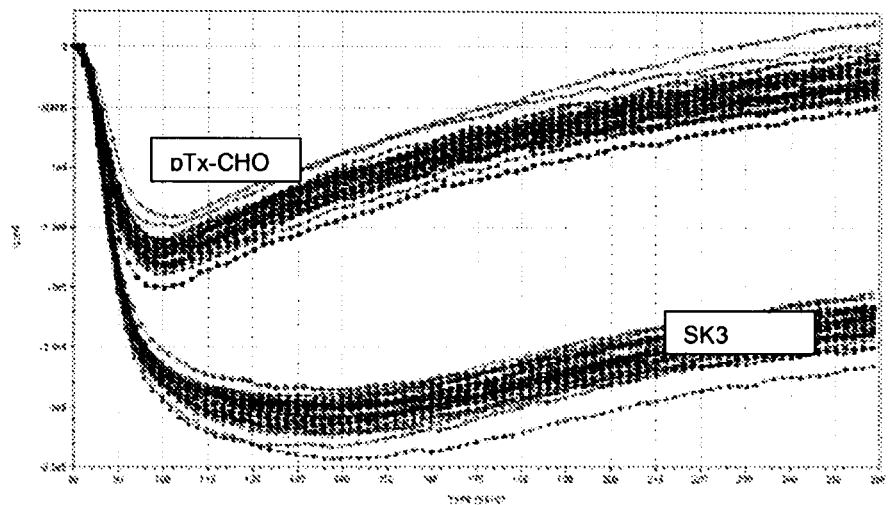
FIG. 77: Graphical representation of data used for statistically testing the probability of a differential response occurring by chance in the assay.

The following half-plate data (FIG. 77) was used to calculate two statistical parameters from timepoint 260 sec using zero baseline with a lag time of 80 sec.

t-test: The two-tailed P value is less than 0.0001. Therefore, the probability of the differential response occurring by chance is essentially zero.

Z'-factor data table (units are -K RFUs, n=24):

| SK3-9 | 220 | 205 | 217 | 218 | 215 | 208 |
|---|---|---|---|---|---|---|
|  | 239 | 227 | 223 | 224 | 217 | 224 |
|  | 250 | 236 | 238 | 228 | 224 | 237 |
|  | 250 | 240 | 266 | 243 | 233 | 239 |
|  | AVE | 230 | STD | 14 |  |  |
| pTx-CHO | 10 | −5 | 9 | 2 | 15 | −21 |
|  | 32 | 20 | 25 | 15 | 20 | 5 |
|  | 32 | 28 | 27 | 18 | 26 | 38 |
|  | 50 | 34 | 38 | 36 | 31 | 41 |
|  | AVE | 22 | STD | 16 |  |  |
|  |  |  |  |  | Z'-factor | 0.56 |

This statistic places the test in the "an excellent assay" category (Zhang et al., 1999. Journal of Biomolecular Screening 4. A Simple Statistical Parameter for Use in Evaluation and Validation of High Throughput Screening Assays).

12. Ion Channel Library Testing

The DmSK3 clone was tested at 10 uM on a set of 71 compounds comprised of known activators, agonists and inhibitors across the major ion channel types (BIOMOL #2805, Ion Channel Ligand Library). Cells were incubated with compound for 1 min before activation by 1 uM ionomycin.

Summary of Results

Seventeen of the 71 compounds (24%) had a clear effect on the response of the cells to ionomycin. Of these, nine (13%) appeared to be inhibitory to hyperpolarization and eight (11%) had an activator/agonist effect on response. In general terms, DmSK3 tended to respond to compounds involved in Ca2+ movements and were relatively insensitive to K+ and Na+ channel modulators (with some exceptions).

Selected Results (from SK3 Testing)

Figure 78:
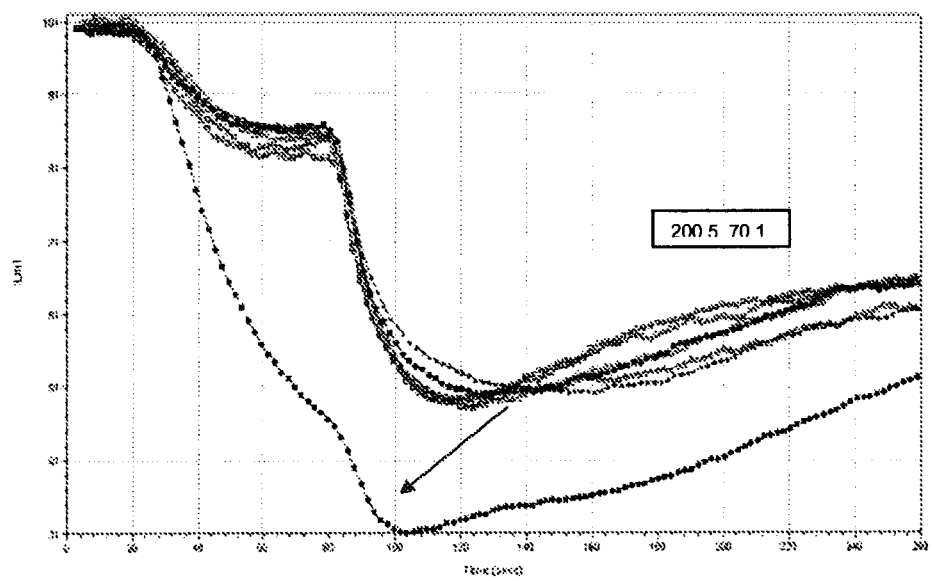
FIG. 78: Graphical result for BAY K-8644 L-type Ca2+ channel agonist.

BAY K-8644 L-type Ca2+ channel agonist FIG. 78

Figure 79:
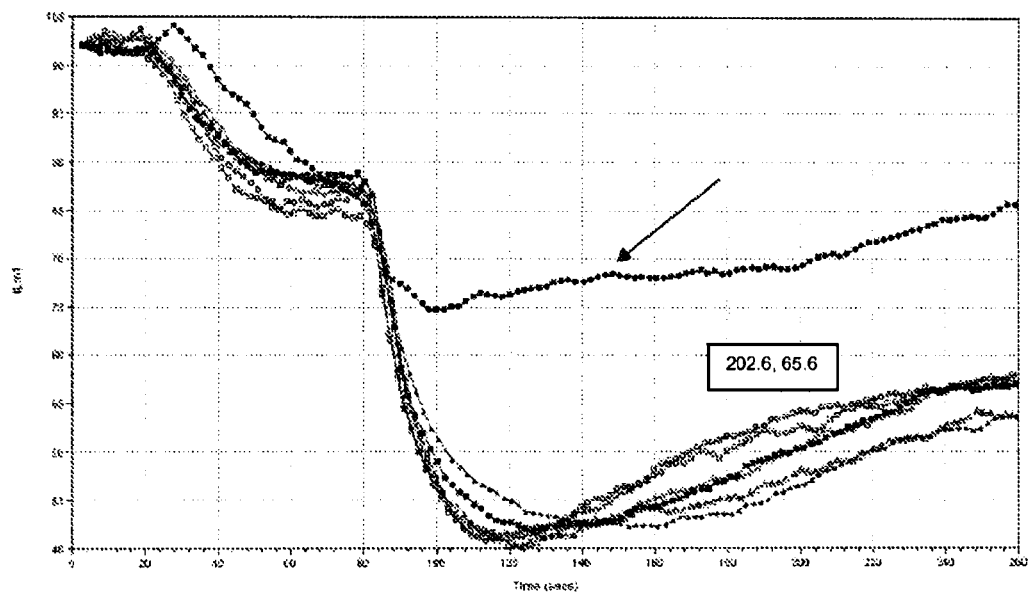
FIG. 79: Graphical result for Propafenone.

Propafenone Efficacious potassium channel blocker. FIG. 79

Figure 80:
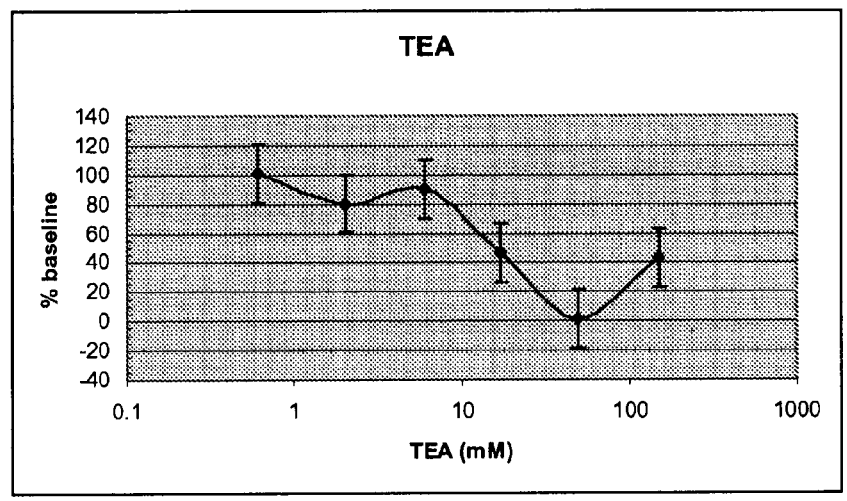
FIG. 80: Graphical result for tetraethylammonium (SK3) as percent baseline.

TEA (SK3) (Tetraethylammonium) FIG. 80

Figure 81:
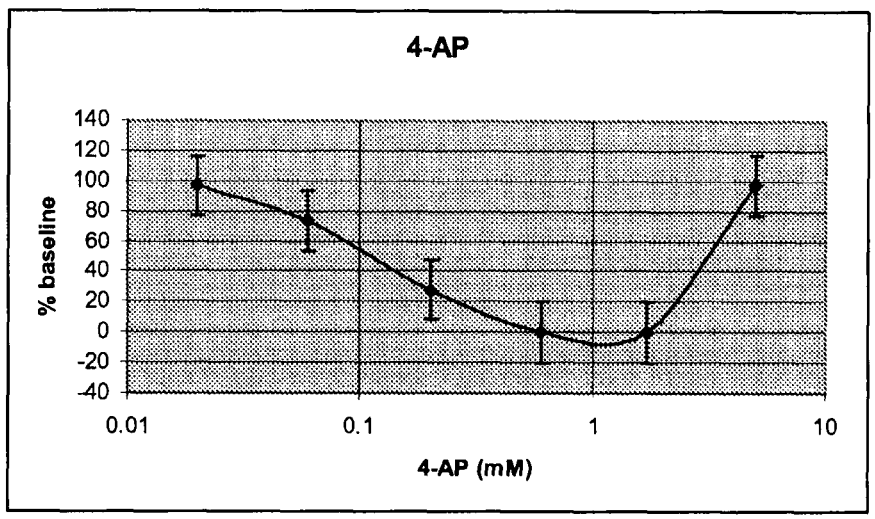
FIG. 81: Graphical EC50 result for 4-aminopyridine (SK3-4) as a percent baseline.
Figure 82:
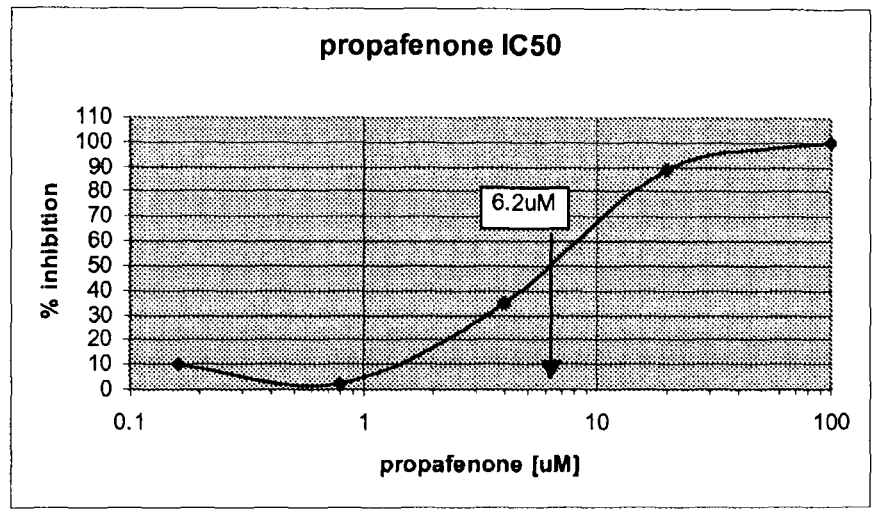
FIG. 82: Graphical EC50 results for propafenone (SK3).

4-AP (SK3-4) (4-aminopyridine) FIG. 81 propafenone (SK3) FIG. 82

13. Apamin Sensitivity

Mammalian SK channels are characterized by their sensitivity to the peptide toxin apamin, from bee venom. We found DmSK to be apamin-insensitive, even at high dose (10 uM, data not shown).

14. SK Expression in CHO Cells Tested with the Patch-Clamp Technique

Materials and Methods

Cells:

Chinese hamster ovary (CHO) cells stably transfected with a Drosophila SK gene were used for all measurements. Cells were plated in 35 mm Petri dishes 18-22 hours before the experiment.

Electrophysiology:

Data were acquired and analyzed using pClamp software (version 9.0.1.16). The whole-cell configuration of the patch-clamp technique was used to voltage clamp cells at room temperature (22-25° C.). Pipettes were pulled from borosilicate glass capillaries (8250, Garner Glass, Claremont, Calif.) using a DMZ Universal Puller (Zeitz, Munich, Germany) and had resistances of 2-3 MOhm when filled with pipette solution and measured in bath solution. The liquid junction potential between bath and pipette solution was always compensated before the formation of a gigaohm seal.

Membrane current was measured under whole-cell clamp, sampled at 2 kHz and filtered at 1 kHz by an Axoclamp 200B (Axon Instruments). Capacitance currents were electronically compensated at the beginning of each experiment. Due to the linear nature of the IV-curve, leak correction was not applied.

To study SK currents on CHO cells, cells were held at −40 mV and a family of 200 ms test voltage pulses were applied starting from −100 to +130 mV in 10 mV increments every 2 sec. The amplitude, as measured for the current-voltage relationship, was defined as the maximal outward current at a given depolarizing potential.

Inhibitors were added directly to the bath solution.

| Bath solution: | | pipette solution: | |
|---|---|---|---|
| | mM | | mM |
| KCl | 30 | KCl | 140 |
| NaCl | 110 | | |
| MgCl2 | 1 | MgCl2 | 1 |
| CaCl2 | 1 | CaCl2 | 0.1 |
| HEPES | 10 | HEPES | 10 |
| pH 7.2 (with NaOH) 295 mOsm | | pH 7.2 (with KOH) 280 mOsm | |

Results

Figure 83:
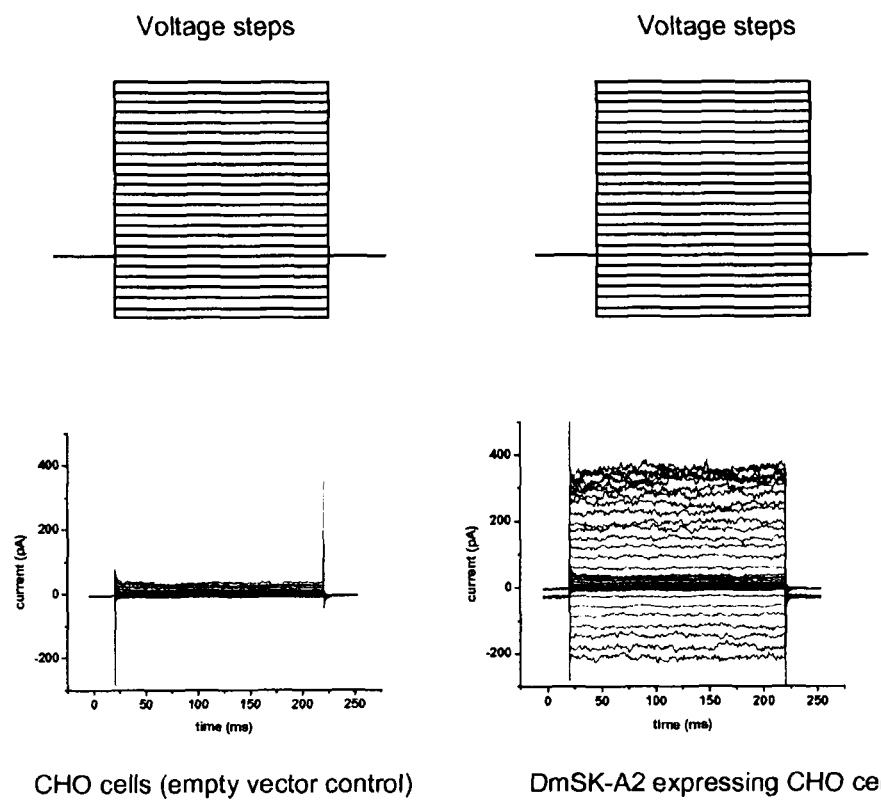
FIG. 83: Graphical representation of characterization of DmSK expression in CHO cells by functional expression assay.
Figure 84:
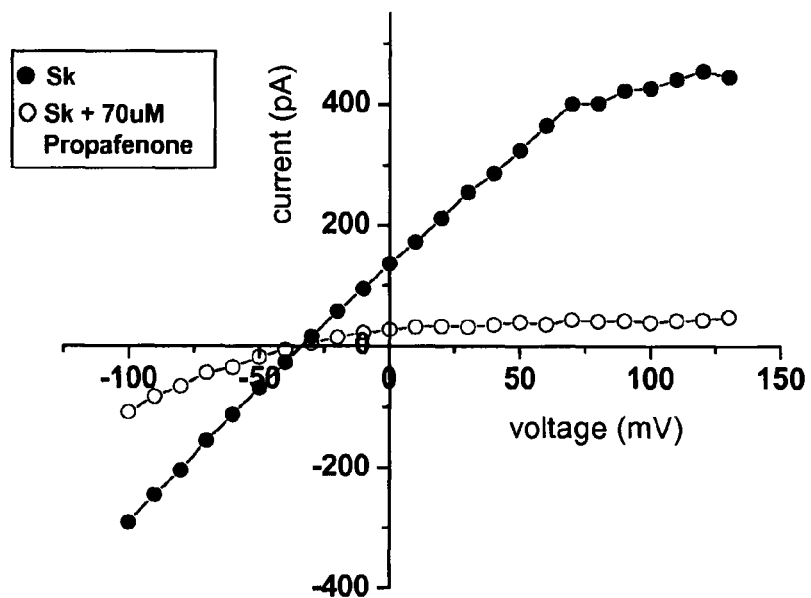
FIG. 84: Graphical representation of the effect of Propafenone on DmSK expressing CHO cells

Experiment: Test of DmSK expression in CHO cells (Clone SK) FIG. 83

Conclusion:

CHO cells transfected with the DmSK gene (clone SK) show functional expression of the channels.

Experiment: Effect of Propafenone on DmSK expressing CHO cells (Clone SK)

Figure 85:
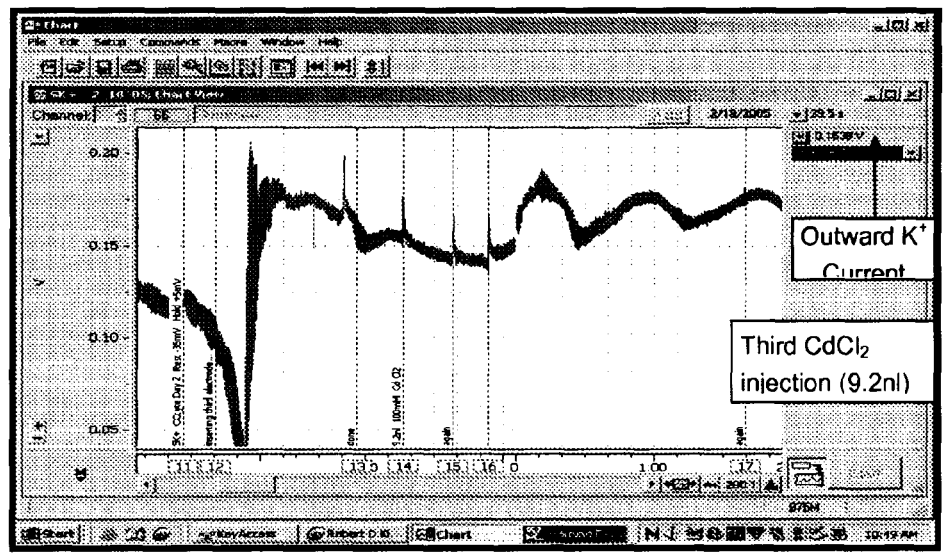
FIG. 85: Graphical results of whole cell patch-clamp assay for DmSK expressing CHO cells subjected to 70 μm propafenone.

Purpose: To confirm the results obtained with the plate-based FlexStation II and FLIPR experimental procedure, cells were subjected to 70 uM Propafenone, under whole-cell patch clamp conditions. FIG. 85 Conclusion:

The DmSK-A2 channels are completely blocked by the addition of 70 uM Propafenone.

15. *Xenopus laevis* Oocyte Expression of the DmSK Potassium Channel

Purpose: To utilize the oocyte two-electrode voltage clamp expression system to assay functional expression of the voltage-gated *Drosophila* melanogaster small-conductance calcium-activated potassium channel (SK) within *Xenopus laevis* oocytes.

Ovarian lobes freshly harvested from a *Xenopus laevis* frog were ordered from NASCO (Fort Atkinson, Wis.).

Oocytes were isolated with 1.5 mg/ml collagenase Type 1A in 20 ml of calcium-free OR-2 oocyte buffer at room temperature.

Stage V-VI oocytes were injected with 50 nl of in vitro transcribed DmSK RNA (1 ug/ul) using a Drummond Nanoject Injector (pCRII-SK2+4D plasmid linearized with HindIII and transcribed using the Ambion T7 mMessage mMachine transcription kit).

Oocytes were incubated at 18° C. for 2 days in supplemented ND-96.

Channel expression was assayed using two-electrode voltage clamp (borosilicate glass 1.5 mm×1.12 mm filled with 3M KCl) through a Turbo Tec 10C Amplifier (NPI Instruments) connected to an Apple PowerMac G3 via an ADInstruments PowerLab system.

Injected oocytes with resting potentials greater than −30 mV were clamped at +5 mV and perfused with ND-96 bath solution (96 mM NaCl, 2 mM KCl, 1 mM MgCl2, 0.3 mM CaCl2, 5 mM HEPES at pH 7.5 and 230 mOsm) Currents measured were filtered at 2 kHz and with a 50/60 Hz HumBug noise eliminator.

SK channels were activated with intracellular injection of 100 mM cadmium chloride (9.2 nl) using the nanoject while clamped. Measured currents were compared to published results of SK activation within oocytes (FIG. 85).

Results:

Initial evaluation of the functional expression of the DmSK Channel within the oocyte expression system produced outward currents activated by at least three 9.2 nl injections of cadmium chloride inside the oocytes. Compared to the results examined using expression of rat SK (ref. 4), this insect SK channel appears to require more calcium-like activation (28 nl of 100 mM CdCl2).

Figure 92:
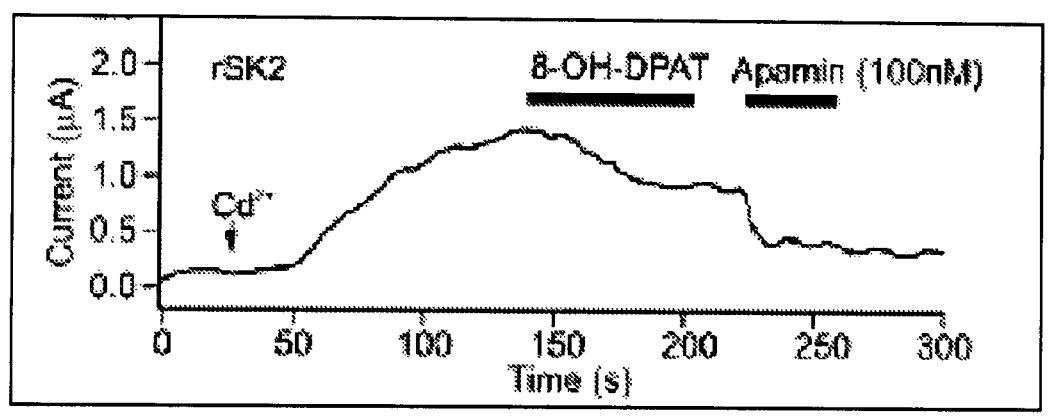
FIG. 92: Reference graph of activity of rat SK channel in oocyte expression system.

A reference graph of activity of rat SK channel in oocyte expression system from Grunnet et al. Journal of Neuroscience Methods 2004 is reproduced in FIG. 92.

The invention claimed is:

1. A method for identifying an insecticidal active compound that reduces the activity of an insect voltage-gated potassium channel Sha1 (Shaker cognate 1 or Shaker-like) and its accessory protein KChIP (potassium channel-interacting protein) which method comprises:
   a) assembling in a membrane polypeptides, originally not present in said membrane, having the activity of an insect voltage-gated potassium channel Sha1 (Shaker cognate 1 or Shaker-like) and its accessory protein KChIP (potassium channel-interacting protein),
   b) applying at one side of the membrane the compound suspected of having the ability to inhibit the activity of said polypeptides which are originally not present in said membrane,
   c) determining the activity of said polypeptides,
   d) identifying the compound applied in (b) that reduces the activity of said polypeptides as an insecticidal active compound; and
   e) selecting the compound identified in step d) as the insecticidal active compound;
   wherein said polypeptides having the activity of Sha1 are encoded by one or more nucleic acid molecules selected from the group consisting of:
   a) a nucleic acid molecule encoding the polypeptide shown in SEQ ID NO: 2, or a polypeptide of a ShaI_delN mutant which is a polypeptide with an N-terminal deletion of amino acids 2-40 of the polypeptide shown in SEQ ID NO: 2;
   b) a nucleic acid molecule shown in SEQ ID NO: 1 or a nucleic acid molecule which is a nucleic acid molecule with a deletion of the coding region in SEQ ID NO: 1 that encodes amino acids 2-40 of the polypeptide shown in SEQ ID NO: 2;
   c) a nucleic acid molecule encoding a polypeptide having at least 80% identity with the amino acid sequence of the polypeptide encoded by the nucleic acid molecule of (a) to (b) and having the activity of a voltage-gated potassium channel Sha1 (Shaker cognate 1 or Shaker-like); and
   wherein said polypeptides having the activity of KChIP are encoded by one or more nucleic acid molecules selected from the group consisting of:
   a) a nucleic acid molecule encoding a polypeptide with KChIP activity as shown in SEQ ID NO: 26;
   b) a nucleic acid molecule shown in SEQ ID NO: 25;
   (c) a nucleic acid molecule encoding a polypeptide having at least 80% identity with the amino acid sequence of the polypeptide encoded by the nucleic acid molecule of (a) to (b) and having the activity of a voltage-gated potassium channel accessory protein KChIP (potassium channel-interacting protein).

2. A method according to claim 1 wherein the polypeptides with the activity of an insect voltage-gated potassium channel Sha1 (Shaker cognate 1 or Shaker-like) and its accessory protein KChIP (potassium channel-interacting protein) are co-expressed in the membrane of a host cell.

3. A method of claim 1 whereby the activity of said polypeptides with the activity of insect voltage-gated potassium channel Sha1 (Shaker cognate 1 or Shaker-like) and its accessory protein KChIP (potassium channel-interacting protein) respectively is determinated electrophysiologically by patch clamp or in a HTS assay.

4. A method of claim 1 wherein the polypeptides with the activity of an insect voltage-gated potassium channel Sha1 (Shaker cognate 1 or Shaker-like) and its accessory protein KChIP (potassium channel-interacting protein) are expressed in a mammalian cell said mammalian cell selected from the group consisting of: CHO-cells and HEK293 cells.

5. A method of claim 1 which comprises:
   f) applying to an insect, to a population of insects or to the location wherein said insect is to be controlled an insect-controlling amount a compound identified according to the method of claim 1 and
   g) determining of the growth or the viability of said treated insect or population of insects or of insects or population of insects on said location and untreated insect, population of insects or location and
   h) selecting of compounds, which reduces the growth or the viability of said treated insect or population of insects or of insects or population of insects on said location following application of the compound of step f).

* * * * *

SEQUENCE LISTING

```
<160> NUMBER OF SEQ ID NOS: 253

<210> SEQ ID NO 1
<211> LENGTH: 1473
<212> TYPE: DNA
<213> ORGANISM: Drosophila melanogaster

<400> SEQUENCE: 1
atggcctcgg tcgccgcttg gctgcccttc gcccgggcgg cggccatcgg gtgggtgccg      60
atagccaccc acccactgcc accgccccg  atgcccaagg atcgccgcaa aacggacgac     120
gagaagctcc tgatcaacgt ctccgggcgg cgtttcgaga cgtggcggaa tactttggag     180
aagtatccgg acacccttt  aggttccaat gaaagggagt tcttctacga cgaggactgc     240
aaagaatact tcttcgatcg ggacccggac atcttccggc acatactgaa ctactaccgg     300
acgggcaagc tgcactaccc gaagcacgaa tgcctcacca gctacgacga ggagctggcc     360
ttctttggaa taatgccgga tgtcattggc gattgctgct acgaggacta ccgggaccgg     420
aagcgggaga acgcggagcg gctgatggac gacaagctgt cggagaacgg ggatcagaat     480
ctgcagcagc tgaccaacat gcgccagaag atgtggcggg ccttcgagaa tccgcacacg     540
```

```
tcgacgagcg ccctggtgtt ctactatgtt acgggtttct tcatcgccgt ctccgtgatg      600
gccaacgtgg tggagacggt gccgtgtggc caccggccgg gcagagcggg aactctgccc      660
tgcggcgagc gctacaagat cgtcttcttc tgcctggata ccgcctgcgt gatgatcttt      720
acggcggagt acctacttcg actcttcgcc gcccccgatc gctgcaagtt cgtgcgctcg      780
gtgatgagca ttattgatgt ggtggccatt atgccgtact acattggcct cgggatcacc      840
gacaacgacg acgtgagcgg tgctttcgtc acgctgcgcg tgttccgtgt cttccgcata      900
ttcaagttct cgcgccactc gcaaggactt cggatcctcg gctacacgct caagtcctgc      960
gccagcgaac tgggcttcct tgtcttctcg ctggccatgg ccattatcat ctttgccacc     1020
gtcatgttct acgccgagaa gaacgtcaat ggcaccaact tcacatcgat tccggcggcc     1080
ttctggtata ccatcgtcac aatgacgacg ctgggatatg cgacatggt gccagagaca     1140 atagctggca aaattgtggg cggcgtctgc tcgcttagcg gtgtgctggt catcgcctta     1200
cctgtacctg ttatcgtatc gaactttagt agaatctatc accagaacca gcgagcggac     1260
aagcgcaagg cgcagcggaa agctcgcctg gcgcgcatcc gcattgccaa ggcctcgtcc     1320
ggagccgcct tgttagcaa gaagaaggcc gccgaggccc ggtgggctgc ccaggagtcg     1380
ggcatcgagc tggatgacaa ctatcgggac gaggacatct tcgagctgca gcaccatcat     1440
ttgctgcgat gtctggagaa gacaacgatg tag                                  1473

<210> SEQ ID NO 2
<211> LENGTH: 490
<212> TYPE: PRT
<213> ORGANISM: Drosophila melanogaster

<400> SEQUENCE: 2

Met Ala Ser Val Ala Ala Trp Leu Pro Phe Ala Arg Ala Ala Ile
1               5                   10                  15

Gly Trp Val Pro Ile Ala Thr His Pro Leu Pro Pro Pro Met Pro
                20                  25                  30

Lys Asp Arg Arg Lys Thr Asp Asp Glu Lys Leu Leu Ile Asn Val Ser
            35                  40                  45

Gly Arg Arg Phe Glu Thr Trp Arg Asn Thr Leu Glu Lys Tyr Pro Asp
        50                  55                  60

Thr Leu Leu Gly Ser Asn Glu Arg Glu Phe Phe Tyr Asp Glu Asp Cys
65                  70                  75                  80

Lys Glu Tyr Phe Phe Asp Arg Asp Pro Asp Ile Phe Arg His Ile Leu
                85                  90                  95

Asn Tyr Tyr Arg Thr Gly Lys Leu His Tyr Pro Lys His Glu Cys Leu
            100                 105                 110

Thr Ser Tyr Asp Glu Glu Leu Ala Phe Phe Gly Ile Met Pro Asp Val
        115                 120                 125

Ile Gly Asp Cys Cys Tyr Glu Asp Tyr Arg Asp Arg Lys Arg Glu Asn
    130                 135                 140

Ala Glu Arg Leu Met Asp Asp Lys Leu Ser Glu Asn Gly Asp Gln Asn
145                 150                 155                 160

Leu Gln Gln Leu Thr Asn Met Arg Gln Lys Met Trp Arg Ala Phe Glu
                165                 170                 175

Asn Pro His Thr Ser Thr Ser Ala Leu Val Phe Tyr Tyr Val Thr Gly
            180                 185                 190

Phe Phe Ile Ala Val Ser Val Met Ala Asn Val Val Glu Thr Val Pro
        195                 200                 205
```

```
Cys Gly His Arg Pro Gly Arg Ala Gly Thr Leu Pro Cys Gly Glu Arg
210                 215                 220
Tyr Lys Ile Val Phe Phe Cys Leu Asp Thr Ala Cys Val Met Ile Phe
225                 230                 235                 240
Thr Ala Glu Tyr Leu Leu Arg Leu Phe Ala Ala Pro Asp Arg Cys Lys
                245                 250                 255
Phe Val Arg Ser Val Met Ser Ile Ile Asp Val Val Ala Ile Met Pro
            260                 265                 270
Tyr Tyr Ile Gly Leu Gly Ile Thr Asp Asn Asp Val Ser Gly Ala
        275                 280                 285
Phe Val Thr Leu Arg Val Phe Arg Val Phe Arg Ile Phe Lys Phe Ser
290                 295                 300
Arg His Ser Gln Gly Leu Arg Ile Leu Gly Tyr Thr Leu Lys Ser Cys
305                 310                 315                 320
Ala Ser Glu Leu Gly Phe Leu Val Phe Ser Leu Ala Met Ala Ile Ile
                325                 330                 335
Ile Phe Ala Thr Val Met Phe Tyr Ala Glu Lys Asn Val Asn Gly Thr
            340                 345                 350
Asn Phe Thr Ser Ile Pro Ala Ala Phe Trp Tyr Thr Ile Val Thr Met
        355                 360                 365
Thr Thr Leu Gly Tyr Gly Asp Met Val Pro Glu Thr Ile Ala Gly Lys
370                 375                 380
Ile Val Gly Gly Val Cys Ser Leu Ser Gly Val Leu Val Ile Ala Leu
385                 390                 395                 400
Pro Val Pro Val Ile Val Ser Asn Phe Ser Arg Ile Tyr His Gln Asn
                405                 410                 415
Gln Arg Ala Asp Lys Arg Lys Ala Gln Arg Lys Ala Arg Leu Ala Arg
            420                 425                 430
Ile Arg Ile Ala Lys Ala Ser Ser Gly Ala Ala Phe Val Ser Lys Lys
        435                 440                 445
Lys Ala Ala Glu Ala Arg Trp Ala Ala Gln Glu Ser Gly Ile Glu Leu
    450                 455                 460
Asp Asp Asn Tyr Arg Asp Glu Asp Ile Phe Glu Leu Gln His His His
465                 470                 475                 480
Leu Leu Arg Cys Leu Glu Lys Thr Thr Met
                485                 490

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gccaccatgg cctcggtcgc c                                         21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ctacatcgtt gtcttctcca                                           20
```

<210> SEQ ID NO 5
<211> LENGTH: 621
<212> TYPE: DNA
<213> ORGANISM: Drosophila melanogaster

<400> SEQUENCE: 5

```
atggcctcac caccggagag tcccatcgag gaggtggtct atgagttgga acacacacga      60
gtgcctaagc ccattcccgt tgccctcgag gatctgtgcc ggcagaccaa gttcaccaaa     120
caggaaatcc gcgtcatgta cagaggattc aaaacggaat gccccgaggg cgtggtacac     180
gaggattgtt ttaaggatat ctacgccaaa ttctttccac atggcaattc aagtttatac     240
gctcattatg tgttcaaagc gttcgatgtt aattgcaatg cgccattagt tttcgggat     300
ttactggtca ccttgtcgac cttgctgaga ggttctgtat atgagcgtct cgttggacc     360
ttcaagttgt acgatctgaa cggcgacgga aggatcagtc gcggcgaact gagtgaaatt     420
attttggcca ttcacgagct tatgggtcgg agaccacatc aacctgagga cgatcgcaag     480
gcgagggatc aggttgatcg tgtgtttcgc aaactggact tgaaccaaga tggcattata     540
acgatagagg agttttttgga ggcctgcctg aaggacgact tggtaactcg atcgctgcaa     600
atgttcgaca cgacctttg a                                                621
```

<210> SEQ ID NO 6
<211> LENGTH: 206
<212> TYPE: PRT
<213> ORGANISM: Drosophila melanogaster

<400> SEQUENCE: 6

Met Ala Ser Pro Pro Glu Ser Pro Ile Glu Glu Val Val Tyr Glu Leu
1               5                   10                  15

Glu His Thr Arg Val Pro Lys Pro Ile Pro Val Ala Leu Glu Asp Leu
            20                  25                  30

Cys Arg Gln Thr Lys Phe Thr Lys Gln Glu Ile Arg Val Met Tyr Arg
        35                  40                  45

Gly Phe Lys Thr Glu Cys Pro Glu Gly Val Val His Glu Asp Cys Phe
    50                  55                  60

Lys Asp Ile Tyr Ala Lys Phe Phe Pro His Gly Asn Ser Ser Leu Tyr
65                  70                  75                  80

Ala His Tyr Val Phe Lys Ala Phe Asp Val Asn Cys Asn Gly Ala Ile
                85                  90                  95

Ser Phe Arg Asp Leu Leu Val Thr Leu Ser Thr Leu Leu Arg Gly Ser
            100                 105                 110

Val Tyr Glu Arg Leu Arg Trp Thr Phe Lys Leu Tyr Asp Leu Asn Gly
        115                 120                 125

Asp Gly Arg Ile Ser Arg Gly Glu Leu Ser Glu Ile Ile Leu Ala Ile
    130                 135                 140

His Glu Leu Met Gly Arg Arg Pro His Gln Pro Glu Asp Asp Arg Lys
145                 150                 155                 160

Ala Arg Asp Gln Val Asp Arg Val Phe Arg Lys Leu Asp Leu Asn Gln
                165                 170                 175

Asp Gly Ile Ile Thr Ile Glu Glu Phe Leu Glu Ala Cys Leu Lys Asp
            180                 185                 190

Asp Leu Val Thr Arg Ser Leu Gln Met Phe Asp Asn Asp Leu
        195                 200                 205

<210> SEQ ID NO 7
<211> LENGTH: 27

```
<212> TYPE: DNA
<213> ORGANISM: Artificial Sequence
<220> FEATURE:
<223> OTHER INFORMATION: primer

<400> SEQUENCE: 7
atggcctcac caccggagag tcccatc                                              27

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
tcaaaggtcg ttgtcgaaca tttgcagcga t                                         31

<210> SEQ ID NO 9
<211> LENGTH: 1479
<212> TYPE: DNA
<213> ORGANISM: Drosophila melanogaster

<400> SEQUENCE: 9
gccaccatgg cctcggtcgc cgcttggctg cccttcgccc gggcggcggc catcgggtgg          60
gtgccgatag ccacccaccc actgccaccg ccccgatgc caaggatcg ccgcaaaacg           120 gacgacgaga agctcctgat caacgtctcc gggcggcgtt tcgagacgtg gcggaatact         180
ttggagaagt atccggacac cctttaggt tccaatgaaa gggagttctt ctacgacgag          240
gactgcaaag aatacttctt cgatcgggac ccggacatct tccggcacat actgaactac        300
taccggacgg gcaagctgca ctacccgaag cacgaatgcc tcaccagcta cgacgaggag         360
ctggccttct ttggaataat gccggatgtc attggcgatt gctgctacga ggactaccgg        420
gaccggaagc gggagaacgc ggagcggctg atggacgaca gctgtcgga gaacggggat         480 cagaatctgc agcagctgac caacatgcgc cagaagatgt ggcgggcctt cgagaatccg        540
cacacgtcga cgagcgccct ggtgttctac tatgttacgg gtttcttcat cgccgtctcc       600
gtgatggcca acgtggtgga gacggtgccg tgtggccacc ggccgggcag agcgggaact         660
ctgccctgcg cgagcgcta caagatcgtc ttcttctgcc tggataccgc ctgcgtgatg        720
atctttacgg cggagtacct acttcgactc ttcgccgccc ccgatcgctg caagttcgtg       780
cgctcggtga tgagcattat tgatgtggtg gccattatgc cgtactacat tggcctcggg        840
atcaccgaca acgacgacgt gagcggtgct ttcgtcacgc tgcgcgtgtt ccgtgtcttc        900
cgcatattca agttctcgcg ccactcgcaa ggacttcgga tcctcggcta cacgctcaag        960
tcctgcgcca cgaactggg cttccttgtc ttctcgctgg ccatggccat tatcatcttt      1020
gccaccgtca tgttctacgc cgagaagaac gtcaatggca ccaacttcac atcgattccg       1080
gcggccttct ggtataccat cgtcacaatg acgacgctgg gatatggcga catggtgcca       1140
gagacaatag ctggcaaaat tgtgggcggc gtctgctcgc ttagcggtgt gctggtcatc       1200
gccttacctg tacctgttat cgtatcgaac tttagtagaa tctatcacca gaaccagcga       1260
gcggacaagc gcaaggcgca gcggaaagct cgcctggcgc catccgcat tgccaaggcc        1320 tcgtccggag ccgcctttgt tagcaagaag aaggccgccg aggcccggtg ggctgcccag       1380
gagtcgggca tcgagctgga tgacaactat cgggacgagg acatcttcga gctgcagcac      1440
catcatttgc tgcgatgtct ggagaagaca acgatgtag                               1479
```

<210> SEQ ID NO 10
<211> LENGTH: 492
<212> TYPE: PRT
<213> ORGANISM: Drosophila melanogaster

<400> SEQUENCE: 10

```
Ala Thr Met Ala Ser Val Ala Trp Leu Pro Phe Ala Arg Ala Ala
 1               5                  10                  15

Ala Ile Gly Trp Val Pro Ile Ala Thr His Pro Leu Pro Pro Pro
             20                  25                  30

Met Pro Lys Asp Arg Arg Lys Thr Asp Asp Glu Lys Leu Leu Ile Asn
         35                  40                  45

Val Ser Gly Arg Arg Phe Glu Thr Trp Arg Asn Thr Leu Glu Lys Tyr
     50                  55                  60

Pro Asp Thr Leu Leu Gly Ser Asn Glu Arg Glu Phe Phe Tyr Asp Glu
 65                  70                  75                  80

Asp Cys Lys Glu Tyr Phe Phe Asp Arg Asp Pro Asp Ile Phe Arg His
                 85                  90                  95

Ile Leu Asn Tyr Tyr Arg Thr Gly Lys Leu His Tyr Pro Lys His Glu
            100                 105                 110

Cys Leu Thr Ser Tyr Asp Glu Glu Leu Ala Phe Phe Gly Ile Met Pro
        115                 120                 125

Asp Val Ile Gly Asp Cys Cys Tyr Glu Asp Tyr Arg Asp Arg Lys Arg
130                 135                 140

Glu Asn Ala Glu Arg Leu Met Asp Asp Lys Leu Ser Glu Asn Gly Asp
145                 150                 155                 160

Gln Asn Leu Gln Gln Leu Thr Asn Met Arg Gln Lys Met Trp Arg Ala
                165                 170                 175

Phe Glu Asn Pro His Thr Ser Thr Ser Ala Leu Val Phe Tyr Tyr Val
            180                 185                 190

Thr Gly Phe Phe Ile Ala Val Ser Val Met Ala Asn Val Val Glu Thr
        195                 200                 205

Val Pro Cys Gly His Arg Pro Gly Arg Ala Gly Thr Leu Pro Cys Gly
    210                 215                 220

Glu Arg Tyr Lys Ile Val Phe Phe Cys Leu Asp Thr Ala Cys Val Met
225                 230                 235                 240

Ile Phe Thr Ala Glu Tyr Leu Leu Arg Leu Phe Ala Ala Pro Asp Arg
                245                 250                 255

Cys Lys Phe Val Arg Ser Val Met Ser Ile Ile Asp Val Val Ala Ile
            260                 265                 270

Met Pro Tyr Tyr Ile Gly Leu Gly Ile Thr Asp Asn Asp Asp Val Ser
        275                 280                 285

Gly Ala Phe Val Thr Leu Arg Val Phe Arg Val Phe Arg Ile Phe Lys
    290                 295                 300

Phe Ser Arg His Ser Gln Gly Leu Arg Ile Leu Gly Tyr Thr Leu Lys
305                 310                 315                 320

Ser Cys Ala Ser Glu Leu Gly Phe Leu Val Phe Ser Leu Ala Met Ala
                325                 330                 335

Ile Ile Ile Phe Ala Thr Val Met Phe Tyr Ala Glu Lys Asn Val Asn
            340                 345                 350

Gly Thr Asn Phe Thr Ser Ile Pro Ala Ala Phe Trp Tyr Thr Ile Val
        355                 360                 365

Thr Met Thr Thr Leu Gly Tyr Gly Asp Met Val Pro Glu Thr Ile Ala
    370                 375                 380
```

```
Gly Lys Ile Val Gly Val Cys Ser Leu Ser Gly Val Leu Val Ile
385                 390                 395                 400

Ala Leu Pro Val Pro Val Ile Val Ser Asn Phe Ser Arg Ile Tyr His
                405                 410                 415

Gln Asn Gln Arg Ala Asp Lys Arg Lys Ala Gln Arg Lys Ala Arg Leu
            420                 425                 430

Ala Arg Ile Arg Ile Ala Lys Ala Ser Ser Gly Ala Ala Phe Val Ser
        435                 440                 445

Lys Lys Lys Ala Ala Glu Ala Arg Trp Ala Ala Gln Glu Ser Gly Ile
    450                 455                 460

Glu Leu Asp Asp Asn Tyr Arg Asp Glu Asp Ile Phe Glu Leu Gln His
465                 470                 475                 480

His His Leu Leu Arg Cys Leu Glu Lys Thr Thr Met
                485                 490

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
gccaccatgg cctcggtcgc c                                         21

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ctacatcgtt gtcttctcca                                           20

<210> SEQ ID NO 13
<211> LENGTH: 1623
<212> TYPE: DNA
<213> ORGANISM: Spodoptera eridania

<400> SEQUENCE: 13
atggcgtccg tcgccgcttg gctgcccttc gctcgagcag ccgccatcgg atgggttccc     60
atagccacac acccactacc gccaccccca gtcccaagg accggcgccg cgccgaagac    120
gagaagctcc ttataaacgt ctccggacga cgctttgaga catggcggaa caccctcgag    180
aaataccccg actcgctcct cggctccacc gagagagaat tcttctacga cgaggacagc    240
agagagtatt tcttcgacag agatccagat atattccgcc acatattaaa ctactacagg    300
actggcaagt tgcactatcc caaacacgag tgtctgacgg gttacgacga ggagttggct    360
ttctttggga tcctacctga tgtgatcgga gactgttgtt atgaggacta ccgtgatagg    420
aaacgtgaga atgccgaaag gctgatggac gataagttaa gtgaggcggg agatcagagc    480
ctgcctcaac tgacagactt gcggcagaag atgtggcgcg cgttcgagaa cccccacact    540
tcgactgctg ctctggtatt ttactatgtg actgggttct ttatcgcagt atcggtgatg    600
gcgaacgtag tggagacagt gccgtgcggc caccggcccg ccgcgctgg gaccctgcct    660 tgtggcgagc gatacaaaat cgtgttcttc tgcttagaca cagcgtgtgt gatgatattt    720
accgcggagt acctactccg actcttcgca gcgccggacc gctgcaagtt cgtgcgatcc    780
```

```
gtgatgtcga tcatagacgt ggtcgccatc cttccatact acattggact cgggatcacc    840
gacaatgatg atgtctccgg cgccttcgtg accctgagag tgttcagagt gttccgtatc    900
ttcaagttct ccaggcactc tcagggattg cggatcctgg ggtacacgtt gaagtcgtgc    960
gccagtgagc tgggtttcct ggtgttttcg ttggcgatgg ctataatcat cttcgccaca   1020
gtcatgttct acgctgagaa gaatgagcaa gatactaatt tcacatccat tcctgctgcc   1080
ttctggtaca ccattgtgac aatgacaacg ttggggtacg gtgacatggt accaggcacg   1140
atagctggta gatcgtggg aggagtgtgc tccctctccg gagtgctggt gatagccctc   1200
cctgtgcccg tcatcgtgtc taacttctca agaatctacc atcagaatca gcgcgctgac   1260
aagagaaagg ctcaaaggaa agcccgtctc gcgcggatcc gcatcgccaa agcctcatct   1320
ggggccgcat tcgtgtcaaa gaagaaggca gcagaagctc gactggctgc gcaggagtcg   1380
ggcgtagaac tagacgatgc tggaagagac gaggacattt tcgagttgca acaccaccac   1440
ctactgcgct gtcttgagcg cactacggtg ggtgaagtta gaccacatcc attatctaac   1500
gctttaattc cgtggcatgt ttggactttc atgtcatgtc ggtgtggtgt tgtgttagta   1560
gttctagact ctttttattg tatcgacgtt tgtatgtctg ttcgttcgtt tagtaaagcg   1620
tga                                                                 1623

<210> SEQ ID NO 14
<211> LENGTH: 540
<212> TYPE: PRT
<213> ORGANISM: Spodoptera eridania

<400> SEQUENCE: 14

Met Ala Ser Val Ala Ala Trp Leu Pro Phe Ala Arg Ala Ala Ile
1               5                   10                  15

Gly Trp Val Pro Ile Ala Thr His Pro Leu Pro Pro Pro Val Pro
                20                  25                  30

Lys Asp Arg Arg Ala Glu Asp Glu Lys Leu Leu Ile Asn Val Ser
            35                  40                  45

Gly Arg Arg Phe Glu Thr Trp Arg Asn Thr Leu Glu Lys Tyr Pro Asp
        50                  55                  60

Ser Leu Leu Gly Ser Thr Glu Arg Glu Phe Phe Tyr Asp Glu Asp Ser
65                  70                  75                  80

Arg Glu Tyr Phe Phe Asp Arg Asp Pro Asp Ile Phe Arg His Ile Leu
                85                  90                  95

Asn Tyr Tyr Arg Thr Gly Lys Leu His Tyr Pro Lys His Glu Cys Leu
            100                 105                 110

Thr Gly Tyr Asp Glu Glu Leu Ala Phe Phe Gly Ile Leu Pro Asp Val
        115                 120                 125

Ile Gly Asp Cys Cys Tyr Glu Asp Tyr Arg Asp Arg Lys Arg Glu Asn
    130                 135                 140

Ala Glu Arg Leu Met Asp Asp Lys Leu Ser Ala Gly Asp Gln Ser
145                 150                 155                 160

Leu Pro Gln Leu Thr Asp Leu Arg Gln Lys Met Trp Arg Ala Phe Glu
                165                 170                 175

Asn Pro His Thr Ser Thr Ala Ala Leu Val Phe Tyr Tyr Val Thr Gly
            180                 185                 190

Phe Phe Ile Ala Val Ser Val Met Ala Asn Val Val Glu Thr Val Pro
        195                 200                 205

Cys Gly His Arg Pro Gly Arg Ala Gly Thr Leu Pro Cys Gly Glu Arg
```

```
              210                 215                 220
Tyr Lys Ile Val Phe Phe Cys Leu Asp Thr Ala Cys Val Met Ile Phe
225                 230                 235                 240

Thr Ala Glu Tyr Leu Leu Arg Leu Phe Ala Ala Pro Asp Arg Cys Lys
                245                 250                 255

Phe Val Arg Ser Val Met Ser Ile Ile Asp Val Val Ala Ile Leu Pro
            260                 265                 270

Tyr Tyr Ile Gly Leu Gly Ile Thr Asp Asn Asp Val Ser Gly Ala
        275                 280                 285

Phe Val Thr Leu Arg Val Phe Arg Val Phe Arg Ile Phe Lys Phe Ser
290                 295                 300

Arg His Ser Gln Gly Leu Arg Ile Leu Gly Tyr Thr Leu Lys Ser Cys
305                 310                 315                 320

Ala Ser Glu Leu Gly Phe Leu Val Phe Ser Leu Ala Met Ala Ile Ile
                325                 330                 335

Ile Phe Ala Thr Val Met Phe Tyr Ala Glu Lys Asn Glu Gln Asp Thr
            340                 345                 350

Asn Phe Thr Ser Ile Pro Ala Ala Phe Trp Tyr Thr Ile Val Thr Met
        355                 360                 365

Thr Thr Leu Gly Tyr Gly Asp Met Val Pro Gly Thr Ile Ala Gly Lys
370                 375                 380

Ile Val Gly Gly Val Cys Ser Leu Ser Gly Val Leu Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Lys Ala Gln Arg Lys Ala Arg Leu Ala Arg
            420                 425                 430

Ile Arg Ile Ala Lys Ala Ser Ser Gly Ala Ala Phe Val Ser Lys Lys
        435                 440                 445

Lys Ala Ala Glu Ala Arg Leu Ala Ala Gln Glu Ser Gly Val Glu Leu
450                 455                 460

Asp Asp Ala Gly Arg Asp Glu Asp Ile Phe Glu Leu Gln His His His
465                 470                 475                 480

Leu Leu Arg Cys Leu Glu Arg Thr Thr Val Gly Glu Val Arg Pro His
                485                 490                 495

Pro Leu Ser Asn Ala Leu Ile Pro Trp His Val Trp Thr Phe Met Ser
            500                 505                 510

Cys Arg Cys Gly Val Val Leu Val Val Leu Asp Ser Phe Tyr Cys Ile
        515                 520                 525

Asp Val Cys Met Ser Val Arg Ser Phe Ser Lys Ala
530                 535                 540

<210> SEQ ID NO 15
<211> LENGTH: 30
<212> TYPE: DNA
<213> ORGANISM: Artificial sequence
<220> FEATURE:
<223> OTHER INFORMATION: Primer

<400> SEQUENCE: 15
gccaccatgg cgtccgtcgc cgcttggctg                                    30

<210> SEQ ID NO 16
<211> LENGTH: 23
<212> TYPE: DNA
<213> ORGANISM: Artificial sequence
```

<220> FEATURE:
<223> OTHER INFORMATION: Primer

<400> SEQUENCE: 16
tcacgcttta ctaaacgaac gaa                                                23

<210> SEQ ID NO 17
<211> LENGTH: 1722
<212> TYPE: DNA
<213> ORGANISM: Tribolium castaneum

<400> SEQUENCE: 17

| | | | | | |
|---|---|---|---|---|---|
| gccaccatgg | cctcggtcgc | cgcttggctg | ccatttgccc | gggcggcggc | catcggctgg | 60 |
| gtgcccatcg | ccacgcaccc | gctcccgccg | ccgccgatcc | ccaaggatcg | gcgcaaagcc | 120 |
| gacgacgaga | agctcctcat | caacgtctcg | ggacggcgct | tcgaaacgtg | gcggaacacc | 180 |
| ctcgagaagt | accccgacac | gctgctcggc | tccaacgagc | gcgagttctt | ctacgacgag | 240 |
| gagtgcaaag | agtactttt | tgaccgagat | ccggacatct | tccggcacat | cctcaactac | 300 |
| taccgcactg | gcaagctgca | ctatcccaag | cacgagtgcc | tcaccagcta | cgatgaagag | 360 |
| ctggcttct | tcgggatctt | gccggacgtt | atcggggact | gctgctacga | ggactacaga | 420 |
| gaccgcaaac | gtgagaacgc | cgaaagactc | atggacgata | aactttccga | aaacggtgac | 480 |
| caaaatctgc | agcaactgac | caacatacga | cagaaaatgt | ggcgcgcctt | cgaaaatcca | 540 |
| cacacttcaa | cggcggccct | agtcttctat | tacgttacag | gcttcttcat | tgctgtttct | 600 |
| gtgatggcga | atgtagtaga | gacggttcct | tgcggaagcc | gccgggggg | agctggctcc | 660 |
| ttaccgtgcg | gcgaaagata | caaaattgca | ttctcctgct | tagacaccgc | ttgtgttatg | 720 |
| attttcacag | ctgaatattt | attacggatg | tttgcagccc | cgaaccgata | caaatttgtt | 780 |
| cgctccgtga | tgagcattat | cgatgtcgtg | gccattctac | cttattacat | cggcctgggc | 840 |
| atcaccgaca | cgatgatgt | ttccggtgct | tttgttaccc | tgcgagtctt | ccgcgttttc | 900 |
| agaattttca | aattctcacg | tcactcccaa | ggtctccgca | tcttgggtta | cactctcaaa | 960 |
| tcgtgcgctt | ccgaacttgg | ttttctcgta | ttttcactag | ccatggctat | tatcatcttc | 1020 |
| gctaccgtaa | tgttctacgc | cgaaaagaac | gtcggcaaaa | caaatttcac | ttccatccct | 1080 |
| gctgccttct | ggtacaccat | cgtcacgatg | actacgctag | gttacggcga | catggttccg | 1140 |
| gccactatcg | caggaaaaat | cgttggcggc | gtctgctccc | tgagtggtgt | ccttgtgatc | 1200 |
| gcactacccg | tacctgttat | cgtttccaac | ttcagcagga | tctaccacca | gaaccaaagg | 1260 |
| gccgacaagc | gcaaagctca | aagaaaggct | cgcttggcgc | gcatccgcat | cgccaaagcg | 1320 |
| tcgtcggggg | cggcgttcgt | cagcaagaag | aaggcggcgg | aggcccgcct | ggccgcccaa | 1380 |
| gagtcgggca | tcgagctcga | cgacaactac | cgcgaggaag | acattttcga | gctgcagcac | 1440 |
| caccacttgc | tgcggtgtct | ggagaagacc | accgaccgcg | agttcgtgga | gctggaggtg | 1500 |
| ccgtacaacg | gccacccaa | gcggcccggc | tcgccgtcgc | ccatggccag | ccctgcccac | 1560 |
| tcggccgtct | ccatcggcct | gatccagtcc | tgctgcggcc | gctgctgccc | cgcaggtac | 1620 |
| cagcaggcct | gcgggaagta | catgccggcg | gcctcggcgg | cgcagtcgaa | ccaaactggc | 1680 |
| ggcggtatgg | acggcaccta | tctcgtggag | gcgtcatttt | ag | | 1722 |

<210> SEQ ID NO 18
<211> LENGTH: 573
<212> TYPE: PRT
<213> ORGANISM: Tribolium castaneum

```
<400> SEQUENCE: 18

Ala Thr Met Ala Ser Val Ala Ala Trp Leu Pro Phe Ala Arg Ala Ala
1               5                   10                  15

Ala Ile Gly Trp Val Pro Ile Ala Thr His Pro Leu Pro Pro Pro Pro
            20                  25                  30

Ile Pro Lys Asp Arg Arg Lys Ala Asp Asp Glu Lys Leu Leu Ile Asn
        35                  40                  45

Val Ser Gly Arg Arg Phe Glu Thr Trp Arg Asn Thr Leu Glu Lys Tyr
    50                  55                  60

Pro Asp Thr Leu Leu Gly Ser Asn Glu Arg Glu Phe Phe Tyr Asp Glu
65                  70                  75                  80

Glu Cys Lys Glu Tyr Phe Asp Arg Asp Pro Asp Ile Phe Arg His
                85                  90                  95

Ile Leu Asn Tyr Tyr Arg Thr Gly Lys Leu His Tyr Pro Lys His Glu
            100                 105                 110

Cys Leu Thr Ser Tyr Asp Glu Glu Leu Ala Phe Phe Gly Ile Leu Pro
        115                 120                 125

Asp Val Ile Gly Asp Cys Cys Tyr Glu Asp Tyr Arg Asp Arg Lys Arg
    130                 135                 140

Glu Asn Ala Glu Arg Leu Met Asp Asp Lys Leu Ser Glu Asn Gly Asp
145                 150                 155                 160

Gln Asn Leu Gln Gln Leu Thr Asn Ile Arg Gln Lys Met Trp Arg Ala
                165                 170                 175

Phe Glu Asn Pro His Thr Ser Thr Ala Ala Leu Val Phe Tyr Tyr Val
            180                 185                 190

Thr Gly Phe Phe Ile Ala Val Ser Val Met Ala Asn Val Val Glu Thr
        195                 200                 205

Val Pro Cys Gly Ser Arg Pro Gly Gly Ala Gly Ser Leu Pro Cys Gly
    210                 215                 220

Glu Arg Tyr Lys Ile Ala Phe Ser Cys Leu Asp Thr Ala Cys Val Met
225                 230                 235                 240

Ile Phe Thr Ala Glu Tyr Leu Leu Arg Met Phe Ala Ala Pro Asn Arg
                245                 250                 255

Tyr Lys Phe Val Arg Ser Val Met Ser Ile Ile Asp Val Val Ala Ile
            260                 265                 270

Leu Pro Tyr Tyr Ile Gly Leu Gly Ile Thr Asp Asn Asp Asp Val Ser
        275                 280                 285

Gly Ala Phe Val Thr Leu Arg Val Phe Arg Val Phe Arg Ile Phe Lys
    290                 295                 300

Phe Ser Arg His Ser Gln Gly Leu Arg Ile Leu Gly Tyr Thr Leu Lys
305                 310                 315                 320

Ser Cys Ala Ser Glu Leu Gly Phe Leu Val Phe Ser Leu Ala Met Ala
                325                 330                 335

Ile Ile Ile Phe Ala Thr Val Met Phe Tyr Ala Glu Lys Asn Val Gly
            340                 345                 350

Lys Thr Asn Phe Thr Ser Ile Pro Ala Ala Phe Trp Tyr Thr Ile Val
        355                 360                 365

Thr Met Thr Thr Leu Gly Tyr Gly Asp Met Val Pro Ala Thr Ile Ala
    370                 375                 380

Gly Lys Ile Val Gly Gly Val Cys Ser Leu Ser Gly Val Leu Val Ile
385                 390                 395                 400

Ala Leu Pro Val Pro Val Ile Val Ser Asn Phe Ser Arg Ile Tyr His
                405                 410                 415
```

```
Gln Asn Gln Arg Ala Asp Lys Arg Lys Ala Gln Arg Lys Ala Arg Leu
                420                 425                 430
Ala Arg Ile Arg Ile Ala Lys Ala Ser Ser Gly Ala Ala Phe Val Ser
            435                 440                 445
Lys Lys Lys Ala Glu Ala Arg Leu Ala Ala Gln Glu Ser Gly Ile
450                 455                 460
Glu Leu Asp Asp Asn Tyr Arg Glu Glu Asp Ile Phe Glu Leu Gln His
465                 470                 475                 480
His His Leu Leu Arg Cys Leu Glu Lys Thr Thr Asp Arg Glu Phe Val
                485                 490                 495
Glu Leu Glu Val Pro Tyr Asn Gly His Pro Lys Arg Pro Gly Ser Pro
                500                 505                 510
Ser Pro Met Ala Ser Pro Ala His Ser Ala Val Ser Ile Gly Leu Ile
                515                 520                 525
Gln Ser Cys Cys Gly Arg Cys Cys Pro Arg Arg Tyr Gln Gln Ala Cys
                530                 535                 540
Gly Lys Tyr Met Pro Ala Ala Ser Ala Ala Gln Ser Asn Gln Thr Gly
545                 550                 555                 560
Gly Gly Met Asp Gly Thr Tyr Leu Val Glu Ala Ser Phe
                565                 570

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
gccaccatgg cctcggtcgc cgcttggctg                                      30

<210> SEQ ID NO 20
<211> LENGTH: 35
<212> TYPE: DNA
<213> ORGANISM: Artificial sequence
<220> FEATURE:
<223> OTHER INFORMATION: Primer

<400> SEQUENCE: 20
ctaaaatgac gcctccacga gataggtgcc gtcca                                35

<210> SEQ ID NO 21
<211> LENGTH: 1665
<212> TYPE: DNA
<213> ORGANISM: Nilaparvata lugens

<400> SEQUENCE: 21
atggcctcgg tcaccgcttg gctgccgttt gcccgggcgg cggccatcgg ctgggtgccc     60
attgccagcc atcccctgcc tcctccgccc gtgcccaagg accgtcgcaa ggctgatgac    120
gagaaactgc ttatcaacgt gtctggtcgt cgcttcgaga cttggcgtaa cacgctcgaa    180
aagtatcctg acactttgct cggctccaat gagcgcgaat ttttcttcga cgaagaatgc    240
aaagagtact tcttcgaccg cgatcctgac atatttcgac acatcctcaa ctactaccgc    300
accggcaagt tgcattatcc gaagcatgag tgcctgacga gctatgatga ggagctggcc    360
ttcttcggta ttctgcccga tgtgattggt gactgctgct atgaggacta ccagaccgc     420 aagcgggaga acgccgaacg tctgatggac gacaagctct cggagaatgg cgatcagaat    480
```

-continued

```
ctgccacagc tgaccgacat ccgacagaag atgtggagag ccttcgagaa cccacacacg    540
tcgacagcgg cactggtgtt ctactatgtg acgggcttct tcatcgcggt gtcagtgatg    600
gcaaacgtgg tggagacggt gccgtgtggc accgaccgg gtcgtgctgg cacgctaccc     660
tgtggcgagc gctacaagat cgtgttcttc tgcttggaca cagcctgtgt gatgatcttc    720
acagcagagt acttgctgcg actgttcgcc gctcccgacc gctgcaagtt cgtgcgtagc    780
gtgatgtcga tcatcgacgt ggtggccatt ttgccgtact acattggcct cggcatcact    840
gacaacgacg acgtgtctgg ggcttttgtc acgctgcgag ttttcgcgt gttcagaatt     900
ttcaagttct cccgtcactc gcagggtctt cgaattctag ctacacact gaaatcgtgt     960
gcttccgaac tcggcttcct cgtgttctcg ttggccatgg ccatcattat ttttgccacg   1020
gtcatgttct acgcagaaaa gaatgtcgat ggcactaact tcacatcgat tccggccgcc   1080
ttctggtaca ccattgtcac tatgaccacc ttggggtacg gagacatggt accagaaaca   1140
atcgccggta aaatagtggg tggagtctgt tcattgtcag gagtgcttgt catagcattg   1200
cccgtacctg ttattgtgtc caacttcagc agaatatacc accagaatca aagggctgac   1260
aagcgcaaag ctcaaaggaa agcacgtctg gctcgcatca gaatcgcaaa agcgtcttct   1320
ggagcggcct tcgtcagcaa aaagaaagca gctgaagcca gactggctgc tcaagagtcc   1380
ggtatggaga tggacgagaa ctatcgcgaa gaggatatct tcgagttgca gcatcatcat   1440
ttattacgct gcctagagaa gaccacggac agggagtttg tggagctgga ggtgccgtac   1500
aatggtcagc cgaaaaggcc aggatcgcca tctccgctga tcagtccgac ccactcggcg   1560
gggagtcgga cagggctgct tcactcctgc tgtggtcgct gctgtgggca acgttaccag   1620
actgaccaag aggttccatc gagtatggag atggatgaat tatga                   1665
```

<210> SEQ ID NO 22
<211> LENGTH: 554
<212> TYPE: PRT
<213> ORGANISM: Nilaparvata lugens

<400> SEQUENCE: 22

Met Ala Ser Val Thr Ala Trp Leu Pro Phe Ala Arg Ala Ala Ile
1               5                   10                  15

Gly Trp Val Pro Ile Ala Ser His Pro Leu Pro Pro Pro Val Pro
                20                  25                  30

Lys Asp Arg Arg Lys Ala Asp Asp Glu Lys Leu Leu Ile Asn Val Ser
            35                  40                  45

Gly Arg Arg Phe Glu Thr Trp Arg Asn Thr Leu Glu Lys Tyr Pro Asp
        50                  55                  60

Thr Leu Leu Gly Ser Asn Glu Arg Glu Phe Phe Phe Asp Glu Glu Cys
65                  70                  75                  80

Lys Glu Tyr Phe Phe Asp Arg Asp Pro Asp Ile Phe Arg His Ile Leu
                85                  90                  95

Asn Tyr Tyr Arg Thr Gly Lys Leu His Tyr Pro Lys His Glu Cys Leu
            100                 105                 110

Thr Ser Tyr Asp Glu Glu Leu Ala Phe Phe Gly Ile Leu Pro Asp Val
        115                 120                 125

Ile Gly Asp Cys Cys Tyr Glu Asp Tyr Arg Asp Lys Arg Glu Asn
    130                 135                 140

Ala Glu Arg Leu Met Asp Asp Lys Leu Ser Glu Asn Gly Asp Gln Asn
145                 150                 155                 160

Leu Pro Gln Leu Thr Asp Ile Arg Gln Lys Met Trp Arg Ala Phe Glu

```
                165                 170                 175
Asn Pro His Thr Ser Thr Ala Ala Leu Val Phe Tyr Tyr Val Thr Gly
            180                 185                 190

Phe Phe Ile Ala Val Ser Val Met Ala Asn Val Val Glu Thr Val Pro
        195                 200                 205

Cys Gly His Arg Pro Gly Arg Ala Gly Thr Leu Pro Cys Gly Glu Arg
    210                 215                 220

Tyr Lys Ile Val Phe Phe Cys Leu Asp Thr Ala Cys Val Met Ile Phe
225                 230                 235                 240

Thr Ala Glu Tyr Leu Leu Arg Leu Phe Ala Ala Pro Asp Arg Cys Lys
                245                 250                 255

Phe Val Arg Ser Val Met Ser Ile Ile Asp Val Val Ala Ile Leu Pro
            260                 265                 270

Tyr Tyr Ile Gly Leu Gly Ile Thr Asp Asn Asp Val Ser Gly Ala
        275                 280                 285

Phe Val Thr Leu Arg Val Phe Arg Val Phe Arg Ile Phe Lys Phe Ser
    290                 295                 300

Arg His Ser Gln Gly Leu Arg Ile Leu Gly Tyr Thr Leu Lys Ser Cys
305                 310                 315                 320

Ala Ser Glu Leu Gly Phe Leu Val Phe Ser Leu Ala Met Ala Ile Ile
                325                 330                 335

Ile Phe Ala Thr Val Met Phe Tyr Ala Glu Lys Asn Val Asp Gly Thr
            340                 345                 350

Asn Phe Thr Ser Ile Pro Ala Ala Phe Trp Tyr Thr Ile Val Thr Met
        355                 360                 365

Thr Thr Leu Gly Tyr Gly Asp Met Val Pro Glu Thr Ile Ala Gly Lys
    370                 375                 380

Ile Val Gly Gly Val Cys Ser Leu Ser Gly Val Leu Val Ile Ala Leu
385                 390                 395                 400

Pro Val Pro Val Ile Val Ser Asn Phe Ser Arg Ile Tyr His Gln Asn
                405                 410                 415

Gln Arg Ala Asp Lys Arg Lys Ala Gln Arg Lys Ala Arg Leu Ala Arg
            420                 425                 430

Ile Arg Ile Ala Lys Ala Ser Ser Gly Ala Ala Phe Val Ser Lys Lys
        435                 440                 445

Lys Ala Ala Glu Ala Arg Leu Ala Ala Gln Glu Ser Gly Met Glu Met
    450                 455                 460

Asp Glu Asn Tyr Arg Glu Glu Asp Ile Phe Glu Leu Gln His His His
465                 470                 475                 480

Leu Leu Arg Cys Leu Glu Lys Thr Thr Asp Arg Glu Phe Val Glu Leu
                485                 490                 495

Glu Val Pro Tyr Asn Gly Gln Pro Lys Arg Pro Gly Ser Pro Ser Pro
            500                 505                 510

Leu Ile Ser Pro Thr His Ser Ala Gly Ser Arg Thr Gly Leu Leu His
        515                 520                 525

Ser Cys Cys Gly Arg Cys Cys Gly Gln Arg Tyr Gln Thr Asp Gln Glu
    530                 535                 540

Val Pro Ser Ser Met Glu Met Asp Glu Leu
545                 550

<210> SEQ ID NO 23
<211> LENGTH: 24
<212> TYPE: DNA
<213> ORGANISM: Artificial sequence
```

<220> FEATURE:
<223> OTHER INFORMATION: Primer

<400> SEQUENCE: 23
gccaccatgg cctcggtcac cgct                                           24

<210> SEQ ID NO 24
<211> LENGTH: 40
<212> TYPE: DNA
<213> ORGANISM: Artificial sequence
<220> FEATURE:
<223> OTHER INFORMATION: Primer

<400> SEQUENCE: 24
tcataattca tccatctcca tactcgatgg aacctcttgg                          40

<210> SEQ ID NO 25
<211> LENGTH: 621
<212> TYPE: DNA
<213> ORGANISM: Drosophila melanogaster

<400> SEQUENCE: 25
atggcctcac caccggagag tcccatcgag gaggtggtct atgagttgga acacacacga    60
gtgcctaagc ccattcccgt tgccctcgag gatctgtgcc ggcagaccaa gttcaccaaa   120
caggaaatcc gcgtcatgta cagaggattc aaaacggaat gccccgaggg cgtggtacac   180
gaggattgtt ttaaggatat ctacgccaaa ttctttccac atggcaattc aagtttatac   240
gctcattatg tgttcaaagc gttcgatgtt aattgcaatg cgccattagt tttcgggat    300 ttactggtca ccttgtcgac cttgctgaga ggttctgtat atgagcgtct gcgttggacc   360
ttcaagttgt acgatctgaa cggcgacgga aggatcagtc gcggcgaact gagtgaaatt   420
attttggcca ttcacgagct tatgggtcgg agaccacatc aacctgagga cgatcgcaag   480
gcgagggatc aggttgatcg tgtgtttcgc aaactggact tgaaccaaga tggcattata   540
acgatagagg agtttttgga ggcctgcctg aaggacgact tggtaactcg atcgctgcaa   600
atgttcgaca cgaccctttg a                                             621

<210> SEQ ID NO 26
<211> LENGTH: 206
<212> TYPE: PRT
<213> ORGANISM: Drosophila melanogaster

<400> SEQUENCE: 26

Met Ala Ser Pro Pro Glu Ser Pro Ile Glu Glu Val Val Tyr Glu Leu
1               5                   10                  15

Glu His Thr Arg Val Pro Lys Pro Ile Pro Val Ala Leu Glu Asp Leu
            20                  25                  30

Cys Arg Gln Thr Lys Phe Thr Lys Gln Glu Ile Arg Val Met Tyr Arg
        35                  40                  45

Gly Phe Lys Thr Glu Cys Pro Glu Gly Val Val His Glu Asp Cys Phe
    50                  55                  60

Lys Asp Ile Tyr Ala Lys Phe Phe Pro His Gly Asn Ser Ser Leu Tyr
65                  70                  75                  80

Ala His Tyr Val Phe Lys Ala Phe Asp Val Asn Cys Asn Gly Ala Ile
                85                  90                  95

Ser Phe Arg Asp Leu Leu Val Thr Leu Ser Thr Leu Leu Arg Gly Ser
            100                 105                 110

Val Tyr Glu Arg Leu Arg Trp Thr Phe Lys Leu Tyr Asp Leu Asn Gly

```
                115                 120                 125
Asp Gly Arg Ile Ser Arg Gly Glu Leu Ser Glu Ile Ile Leu Ala Ile
    130                 135                 140

His Glu Leu Met Gly Arg Arg Pro His Gln Pro Glu Asp Asp Arg Lys
145                 150                 155                 160

Ala Arg Asp Gln Val Asp Arg Val Phe Arg Lys Leu Asp Leu Asn Gln
                165                 170                 175

Asp Gly Ile Ile Thr Ile Glu Glu Phe Leu Glu Ala Cys Leu Lys Asp
            180                 185                 190

Asp Leu Val Thr Arg Ser Leu Gln Met Phe Asp Asn Asp Leu
            195                 200                 205

<210> SEQ ID NO 27
<211> LENGTH: 27
<212> TYPE: DNA
<213> ORGANISM: Artificial sequence
<220> FEATURE:
<223> OTHER INFORMATION: Primer

<400> SEQUENCE: 27
atggcctcac caccggagag tcccatc                                          27

<210> SEQ ID NO 28
<211> LENGTH: 31
<212> TYPE: DNA
<213> ORGANISM: Artificial sequence
<220> FEATURE:
<223> OTHER INFORMATION: Primer

<400> SEQUENCE: 28
tcaaaggtcg ttgtcgaaca tttgcagcga t                                     31

<210> SEQ ID NO 29
<211> LENGTH: 627
<212> TYPE: DNA
<213> ORGANISM: Tribolium castaneum

<400> SEQUENCE: 29
gccaccatgg caacgccgtc agacagccct atcgaggagg tcgtgttcga gatagagccg      60
tccagggtgc ccaagcccgt gcctgttgcc ctagaggacc tctgcaggct caccaagttc     120
acacgacagg aaattagaat catgtatcga ggattcaaaa cggaatgtcc agagggtgtt     180
gtccatgaag atagctttaa agaaatttat tcgaaatttt ttccacatgg aaattcgagt     240
ttgtatgcac actacgtgtt caaagccttc gatgtcaact gcaacggagc aattagtttc     300
agggacctgc tgataacctt atcgacgttg ctccgcggtt cggtgtacga gcgcctccga     360
tggaccttca aactgtatga cgtgaacggt gacggctgca tcagccgcgg cgaactgtcc     420
gaaatcgtgg tggcggtgca cgaactcatg gggcggcgcg cccaccaggt ggaggacgac     480
cgcaaggccc gcgagcaaat cgaccgagtc ttccggaagc tggacctcaa ccaggacggc     540
gtcatcacca tcgaggagtt catggaatcg tgcctcaaag acgatgtgat cactaggtct     600
ctgcagatgt tcgactcagt gctgtga                                         627

<210> SEQ ID NO 30
<211> LENGTH: 206
<212> TYPE: PRT
<213> ORGANISM: Tribolium castaneum

<400> SEQUENCE: 30
```

```
Met Ala Thr Pro Ser Asp Ser Pro Ile Glu Glu Val Val Phe Glu Ile
1               5                   10                  15

Glu Pro Ser Arg Val Pro Lys Pro Val Pro Val Ala Leu Glu Asp Leu
            20                  25                  30

Cys Arg Leu Thr Lys Phe Thr Arg Gln Glu Ile Arg Ile Met Tyr Arg
        35                  40                  45

Gly Phe Lys Thr Glu Cys Pro Glu Gly Val Val His Glu Asp Ser Phe
    50                  55                  60

Lys Glu Ile Tyr Ser Lys Phe Phe Pro His Gly Asn Ser Ser Leu Tyr
65                  70                  75                  80

Ala His Tyr Val Phe Lys Ala Phe Asp Val Asn Cys Asn Gly Ala Ile
                85                  90                  95

Ser Phe Arg Asp Leu Leu Ile Thr Leu Ser Thr Leu Leu Arg Gly Ser
            100                 105                 110

Val Tyr Glu Arg Leu Arg Trp Thr Phe Lys Leu Tyr Asp Val Asn Gly
            115                 120                 125

Asp Gly Cys Ile Ser Arg Gly Glu Leu Ser Glu Ile Val Val Ala Val
    130                 135                 140

His Glu Leu Met Gly Arg Arg Ala His Gln Val Glu Asp Asp Arg Lys
145                 150                 155                 160

Ala Arg Glu Gln Ile Asp Arg Val Phe Arg Lys Leu Asp Leu Asn Gln
                165                 170                 175

Asp Gly Val Ile Thr Ile Glu Glu Phe Met Glu Ser Cys Leu Lys Asp
            180                 185                 190

Asp Val Ile Thr Arg Ser Leu Gln Met Phe Asp Ser Val Leu
            195                 200                 205

<210> SEQ ID NO 31
<211> LENGTH: 37
<212> TYPE: DNA
<213> ORGANISM: Artificial sequence
<220> FEATURE:
<223> OTHER INFORMATION: Primer

<400> SEQUENCE: 31
gccaccatgg caacgccgtc agacagccct atcgagg                              37

<210> SEQ ID NO 32
<211> LENGTH: 40
<212> TYPE: DNA
<213> ORGANISM: Artificial sequence
<220> FEATURE:
<223> OTHER INFORMATION: Primer

<400> SEQUENCE: 32
tcacagcact gagtcgaaca tctgcagaga cctagtgatc                           40

<210> SEQ ID NO 33
<211> LENGTH: 491
<212> TYPE: PRT
<213> ORGANISM: Artificial sequence
<220> FEATURE:
<223> OTHER INFORMATION: Consensus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
```

```
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (39)..(41)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(83)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (250)..(250)
<223> OTHER INFORMATION: Xaa can be any naturally occurring amino acid
```

```
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (351)..(353)
<223> OTHER INFORMATION: Xaa can be any naturally occurring amino acid
<220> FEATURE:
<221> NAME/KEY: misc_feature
<222> LOCATION: (381)..(381)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (466)..(466)
<223> OTHER INFORMATION: Xaa can be any naturally occurring amino acid
<220> FEATURE:
<221> NAME/KEY: misc_feature
<222> LOCATION: (468)..(470)
<223> OTHER INFORMATION: Xaa can be any naturally occurring amino acid
<220> FEATURE:
<221> NAME/KEY: misc_feature
<222> LOCATION: (472)..(472)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid

<400> SEQUENCE: 33

Xaa Xaa Met Ala Ser Val Xaa Ala Trp Leu Pro Phe Ala Arg Ala Ala
1               5                   10                  15

Ala Ile Gly Trp Val Pro Ile Ala Xaa His Pro Leu Pro Pro Pro Pro
            20                  25                  30

Xaa Pro Lys Asp Arg Arg Xaa Xaa Xaa Asp Glu Lys Leu Leu Ile Asn
        35                  40                  45

Val Ser Gly Arg Arg Phe Glu Thr Trp Arg Asn Thr Leu Glu Lys Tyr
    50                  55                  60

Pro Asp Xaa Leu Leu Gly Ser Xaa Glu Arg Glu Phe Phe Xaa Asp Glu
65                  70                  75                  80

Xaa Xaa Xaa Glu Tyr Phe Phe Asp Arg Asp Pro Asp Ile Phe Arg His
                85                  90                  95

Ile Leu Asn Tyr Tyr Arg Thr Gly Lys Leu His Tyr Pro Lys His Glu
            100                 105                 110

Cys Leu Thr Xaa Tyr Asp Glu Glu Leu Ala Phe Phe Gly Ile Xaa Pro
        115                 120                 125

Asp Val Ile Gly Asp Cys Cys Tyr Glu Asp Tyr Arg Asp Arg Lys Arg
    130                 135                 140

Glu Asn Ala Glu Arg Leu Met Asp Asp Lys Leu Ser Glu Xaa Gly Asp
145                 150                 155                 160

Gln Xaa Leu Xaa Gln Leu Thr Xaa Xaa Arg Gln Lys Met Trp Arg Ala
                165                 170                 175
```

```
Phe Glu Asn Pro His Thr Ser Thr Xaa Ala Leu Val Phe Tyr Tyr Val
            180                 185                 190

Thr Gly Phe Phe Ile Ala Val Ser Val Met Ala Asn Val Val Glu Thr
        195                 200                 205

Val Pro Cys Gly Xaa Arg Pro Gly Xaa Ala Gly Xaa Leu Pro Cys Gly
210                 215                 220

Glu Arg Tyr Lys Ile Xaa Phe Xaa Cys Leu Asp Thr Ala Cys Val Met
225                 230                 235                 240

Ile Phe Thr Ala Glu Tyr Leu Leu Arg Xaa Phe Ala Ala Pro Xaa Arg
            245                 250                 255

Xaa Lys Phe Val Arg Ser Val Met Ser Ile Ile Asp Val Val Ala Ile
        260                 265                 270

Xaa Pro Tyr Tyr Ile Gly Leu Gly Ile Thr Asp Asn Asp Asp Val Ser
        275                 280                 285

Gly Ala Phe Val Thr Leu Arg Val Phe Arg Val Phe Arg Ile Phe Lys
        290                 295                 300

Phe Ser Arg His Ser Gln Gly Leu Arg Ile Leu Gly Tyr Thr Leu Lys
305                 310                 315                 320

Ser Cys Ala Ser Glu Leu Gly Phe Leu Val Phe Ser Leu Ala Met Ala
            325                 330                 335

Ile Ile Ile Phe Ala Thr Val Met Phe Tyr Ala Glu Lys Asn Xaa Xaa
        340                 345                 350

Xaa Thr Asn Phe Thr Ser Ile Pro Ala Ala Phe Trp Tyr Thr Ile Val
        355                 360                 365

Thr Met Thr Thr Leu Gly Tyr Gly Asp Met Val Pro Xaa Thr Ile Ala
        370                 375                 380

Gly Lys Ile Val Gly Gly Val Cys Ser Leu Ser Gly Val Leu Val Ile
385                 390                 395                 400

Ala Leu Pro Val Pro Val Ile Val Ser Asn Phe Ser Arg Ile Tyr His
            405                 410                 415

Gln Asn Gln Arg Ala Asp Lys Arg Lys Ala Gln Arg Lys Ala Arg Leu
        420                 425                 430

Ala Arg Ile Arg Ile Ala Lys Ala Ser Ser Gly Ala Ala Phe Val Ser
        435                 440                 445

Lys Lys Lys Ala Ala Glu Ala Arg Xaa Ala Ala Gln Glu Ser Gly Xaa
450                 455                 460

Glu Xaa Asp Xaa Xaa Xaa Arg Xaa Glu Asp Ile Phe Glu Leu Gln His
465                 470                 475                 480

His His Leu Leu Arg Cys Leu Glu Xaa Thr Thr
            485                 490

<210> SEQ ID NO 34
<211> LENGTH: 206
<212> TYPE: PRT
<213> ORGANISM: Artificial sequence
<220> FEATURE:
<223> OTHER INFORMATION: Consensus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (14)..(14)
```

```
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
```

```
<222> LOCATION: (186)..(186)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (194)..(195)
<223> OTHER INFORMATION: Xaa can be any naturally occurring amino acid
<220> FEATURE:
<221> NAME/KEY: misc_feature
<222> LOCATION: (204)..(205)
<223> OTHER INFORMATION: Xaa can be any naturally occurring amino acid

<400> SEQUENCE: 34

Met Ala Xaa Pro Xaa Xaa Ser Pro Ile Glu Glu Val Val Xaa Glu Xaa
1               5                   10                  15

Glu Xaa Xaa Arg Val Pro Lys Pro Xaa Pro Val Ala Leu Glu Asp Leu
            20                  25                  30

Cys Arg Xaa Thr Lys Phe Thr Xaa Gln Glu Ile Arg Xaa Met Tyr Arg
        35                  40                  45

Gly Phe Lys Thr Glu Cys Pro Glu Gly Val Val His Glu Asp Xaa Phe
    50                  55                  60

Lys Xaa Ile Tyr Xaa Lys Phe Phe Pro His Gly Asn Ser Ser Leu Tyr
65                  70                  75                  80

Ala His Tyr Val Phe Lys Ala Phe Asp Val Asn Cys Asn Gly Ala Ile
                85                  90                  95

Ser Phe Arg Asp Leu Leu Xaa Thr Leu Ser Thr Leu Leu Arg Gly Ser
            100                 105                 110

Val Tyr Glu Arg Leu Arg Trp Thr Phe Lys Leu Tyr Asp Xaa Asn Gly
        115                 120                 125

Asp Gly Xaa Ile Ser Arg Gly Glu Leu Ser Glu Ile Xaa Xaa Ala Xaa
    130                 135                 140

His Glu Leu Met Gly Arg Arg Xaa His Gln Xaa Glu Asp Asp Arg Lys
145                 150                 155                 160

Ala Arg Xaa Gln Xaa Asp Arg Val Phe Arg Lys Leu Asp Leu Asn Gln
                165                 170                 175

Asp Gly Xaa Ile Thr Ile Glu Glu Phe Xaa Glu Xaa Cys Leu Lys Asp
            180                 185                 190

Asp Xaa Xaa Thr Arg Ser Leu Gln Met Phe Asp Xaa Xaa Leu
        195                 200                 205

<210> SEQ ID NO 35
<211> LENGTH: 4
<212> TYPE: PRT
<213> ORGANISM: Artificial sequence
<220> FEATURE:
<223> OTHER INFORMATION: Motif

<400> SEQUENCE: 35

Met Ala Ser Val
1

<210> SEQ ID NO 36
<211> LENGTH: 17
<212> TYPE: PRT
<213> ORGANISM: Artificial sequence
<220> FEATURE:
<223> OTHER INFORMATION: Motif

<400> SEQUENCE: 36
```

```
Ala Trp Leu Pro Phe Ala Arg Ala Ala Ala Ile Gly Trp Val Pro Ile
1               5                   10                  15

Ala

<210> SEQ ID NO 37
<211> LENGTH: 7
<212> TYPE: PRT
<213> ORGANISM: Artificial sequence
<220> FEATURE:
<223> OTHER INFORMATION: Motif

<400> SEQUENCE: 37

His Pro Leu Pro Pro Pro Pro
1               5

<210> SEQ ID NO 38
<211> LENGTH: 5
<212> TYPE: PRT
<213> ORGANISM: Artificial sequence
<220> FEATURE:
<223> OTHER INFORMATION: Motif

<400> SEQUENCE: 38

Pro Lys Asp Arg Arg
1               5

<210> SEQ ID NO 39
<211> LENGTH: 25
<212> TYPE: PRT
<213> ORGANISM: Artificial sequence
<220> FEATURE:
<223> OTHER INFORMATION: Motif

<400> SEQUENCE: 39

Asp Glu Lys Leu Leu Ile Asn Val Ser Gly Arg Arg Phe Glu Thr Trp
1               5                   10                  15

Arg Asn Thr Leu Glu Lys Tyr Pro Asp
            20                  25

<210> SEQ ID NO 40
<211> LENGTH: 4
<212> TYPE: PRT
<213> ORGANISM: Artificial sequence
<220> FEATURE:
<223> OTHER INFORMATION: Motif

<400> SEQUENCE: 40

Leu Leu Gly Ser
1

<210> SEQ ID NO 41
<211> LENGTH: 5
<212> TYPE: PRT
<213> ORGANISM: Artificial sequence
<220> FEATURE:
<223> OTHER INFORMATION: Motif

<400> SEQUENCE: 41

Glu Arg Glu Phe Phe
1               5

<210> SEQ ID NO 42
<211> LENGTH: 32
<212> TYPE: PRT
<213> ORGANISM: Artificial sequence
<220> FEATURE:
```

<223> OTHER INFORMATION: Motif

<400> SEQUENCE: 42

Glu Tyr Phe Phe Asp Arg Asp Pro Asp Ile Phe Arg His Ile Leu Asn
1               5                   10                  15
Tyr Tyr Arg Thr Gly Lys Leu His Tyr Pro Lys His Glu Cys Leu Thr
            20                  25                  30

<210> SEQ ID NO 43
<211> LENGTH: 10
<212> TYPE: PRT
<213> ORGANISM: Artificial sequence
<220> FEATURE:
<223> OTHER INFORMATION: Motif

<400> SEQUENCE: 43

Tyr Asp Glu Glu Leu Ala Phe Phe Gly Ile
1               5                   10

<210> SEQ ID NO 44
<211> LENGTH: 30
<212> TYPE: PRT
<213> ORGANISM: Artificial sequence
<220> FEATURE:
<223> OTHER INFORMATION: Motif

<400> SEQUENCE: 44

Pro Asp Val Ile Gly Asp Cys Cys Tyr Glu Asp Tyr Arg Asp Arg Lys
1               5                   10                  15
Arg Glu Asn Ala Glu Arg Leu Met Asp Asp Lys Leu Ser Glu
            20                  25                  30

<210> SEQ ID NO 45
<211> LENGTH: 15
<212> TYPE: PRT
<213> ORGANISM: Artificial sequence
<220> FEATURE:
<223> OTHER INFORMATION: Motif

<400> SEQUENCE: 45

Arg Gln Lys Met Trp Arg Ala Phe Glu Asn Pro His Thr Ser Thr
1               5                   10                  15

<210> SEQ ID NO 46
<211> LENGTH: 27
<212> TYPE: PRT
<213> ORGANISM: Artificial sequence
<220> FEATURE:
<223> OTHER INFORMATION: Motif

<400> SEQUENCE: 46

Ala Leu Val Phe Tyr Tyr Val Thr Gly Phe Phe Ile Ala Val Ser Val
1               5                   10                  15
Met Ala Asn Val Val Glu Thr Val Pro Cys Gly
            20                  25

<210> SEQ ID NO 47
<211> LENGTH: 9
<212> TYPE: PRT
<213> ORGANISM: Artificial sequence
<220> FEATURE:
<223> OTHER INFORMATION: Motif

<400> SEQUENCE: 47

Leu Pro Cys Gly Glu Arg Tyr Lys Ile

<210> SEQ ID NO 48
<211> LENGTH: 17
<212> TYPE: PRT
<213> ORGANISM: Artificial sequence
<220> FEATURE:
<223> OTHER INFORMATION: Motif

<400> SEQUENCE: 48

Cys Leu Asp Thr Ala Cys Val Met Ile Phe Thr Ala Glu Tyr Leu Leu
1               5                   10                  15

Arg

<210> SEQ ID NO 49
<211> LENGTH: 4
<212> TYPE: PRT
<213> ORGANISM: Artificial sequence
<220> FEATURE:
<223> OTHER INFORMATION: Motif

<400> SEQUENCE: 49

Phe Ala Ala Pro
1

<210> SEQ ID NO 50
<211> LENGTH: 15
<212> TYPE: PRT
<213> ORGANISM: Artificial sequence
<220> FEATURE:
<223> OTHER INFORMATION: Motif

<400> SEQUENCE: 50

Lys Phe Val Arg Ser Val Met Ser Ile Ile Asp Val Val Ala Ile
1               5                   10                  15

<210> SEQ ID NO 51
<211> LENGTH: 77
<212> TYPE: PRT
<213> ORGANISM: Artificial sequence
<220> FEATURE:
<223> OTHER INFORMATION: Motif

<400> SEQUENCE: 51

Pro Tyr Tyr Ile Gly Leu Gly Ile Thr Asp Asn Asp Val Ser Gly
1               5                   10                  15

Ala Phe Val Thr Leu Arg Val Phe Arg Val Phe Arg Ile Phe Lys Phe
            20                  25                  30

Ser Arg His Ser Gln Gly Leu Arg Ile Leu Gly Tyr Thr Leu Lys Ser
        35                  40                  45

Cys Ala Ser Glu Leu Gly Phe Leu Val Phe Ser Leu Ala Met Ala Ile
    50                  55                  60

Ile Ile Phe Ala Thr Val Met Phe Tyr Ala Glu Lys Asn
65                  70                  75

<210> SEQ ID NO 52
<211> LENGTH: 27
<212> TYPE: PRT
<213> ORGANISM: Artificial sequence
<220> FEATURE:
<223> OTHER INFORMATION: Motif

<400> SEQUENCE: 52

Thr Asn Phe Thr Ser Ile Pro Ala Ala Phe Trp Tyr Thr Ile Val Thr

```
                1               5                   10                  15
Met Thr Thr Leu Gly Tyr Gly Asp Met Val Pro
                20                  25
```

<210> SEQ ID NO 53
<211> LENGTH: 75
<212> TYPE: PRT
<213> ORGANISM: Artificial sequence
<220> FEATURE:
<223> OTHER INFORMATION: Motif

<400> SEQUENCE: 53

```
Thr Ile Ala Gly Lys Ile Val Gly Gly Val Cys Ser Leu Ser Gly Val
1               5                   10                  15
Leu Val Ile Ala Leu Pro Val Pro Val Ile Val Ser Asn Phe Ser Arg
                20                  25                  30
Ile Tyr His Gln Asn Gln Arg Ala Asp Lys Arg Lys Ala Gln Arg Lys
                35                  40                  45
Ala Arg Leu Ala Arg Ile Arg Ile Ala Lys Ala Ser Ser Gly Ala Ala
            50                  55                  60
Phe Val Ser Lys Lys Lys Ala Ala Glu Ala Arg
65                  70                  75
```

<210> SEQ ID NO 54
<211> LENGTH: 6
<212> TYPE: PRT
<213> ORGANISM: Artificial sequence
<220> FEATURE:
<223> OTHER INFORMATION: Motif

<400> SEQUENCE: 54

```
Ala Ala Gln Glu Ser Gly
1               5
```

<210> SEQ ID NO 55
<211> LENGTH: 16
<212> TYPE: PRT
<213> ORGANISM: Artificial sequence
<220> FEATURE:
<223> OTHER INFORMATION: Motif

<400> SEQUENCE: 55

```
Glu Asp Ile Phe Glu Leu Gln His His His Leu Leu Arg Cys Leu Glu
1               5                   10                  15
```

<210> SEQ ID NO 56
<211> LENGTH: 7
<212> TYPE: PRT
<213> ORGANISM: Artificial sequence
<220> FEATURE:
<223> OTHER INFORMATION: Motif

<400> SEQUENCE: 56

```
Ser Pro Ile Glu Glu Val Val
1               5
```

<210> SEQ ID NO 57
<211> LENGTH: 5
<212> TYPE: PRT
<213> ORGANISM: Artificial sequence
<220> FEATURE:
<223> OTHER INFORMATION: Motif

<400> SEQUENCE: 57

```
Arg Val Pro Lys Pro
1               5

<210> SEQ ID NO 58
<211> LENGTH: 9
<212> TYPE: PRT
<213> ORGANISM: Artificial sequence
<220> FEATURE:
<223> OTHER INFORMATION: Motif

<400> SEQUENCE: 58

Pro Val Ala Leu Glu Asp Leu Cys Arg
1               5

<210> SEQ ID NO 59
<211> LENGTH: 4
<212> TYPE: PRT
<213> ORGANISM: Artificial sequence
<220> FEATURE:
<223> OTHER INFORMATION: Motif

<400> SEQUENCE: 59

Thr Lys Phe Thr
1

<210> SEQ ID NO 60
<211> LENGTH: 4
<212> TYPE: PRT
<213> ORGANISM: Artificial sequence
<220> FEATURE:
<223> OTHER INFORMATION: Motif

<400> SEQUENCE: 60

Gln Glu Ile Arg
1

<210> SEQ ID NO 61
<211> LENGTH: 17
<212> TYPE: PRT
<213> ORGANISM: Artificial sequence
<220> FEATURE:
<223> OTHER INFORMATION: Motif

<400> SEQUENCE: 61

Met Tyr Arg Gly Phe Lys Thr Glu Cys Pro Glu Gly Val Val His Glu
1               5                   10                  15

Asp

<210> SEQ ID NO 62
<211> LENGTH: 33
<212> TYPE: PRT
<213> ORGANISM: Artificial sequence
<220> FEATURE:
<223> OTHER INFORMATION: Motif

<400> SEQUENCE: 62

Lys Phe Phe Pro His Gly Asn Ser Ser Leu Tyr Ala His Tyr Val Phe
1               5                   10                  15

Lys Ala Phe Asp Val Asn Cys Asn Gly Ala Ile Ser Phe Arg Asp Leu
            20                  25                  30

Leu

<210> SEQ ID NO 63
<211> LENGTH: 22
<212> TYPE: PRT
```

```
<213> ORGANISM: Artificial sequence
<220> FEATURE:
<223> OTHER INFORMATION: Motif

<400> SEQUENCE: 63

Thr Leu Ser Thr Leu Leu Arg Gly Ser Val Tyr Glu Arg Leu Arg Trp
1               5                   10                  15

Thr Phe Lys Leu Tyr Asp
            20

<210> SEQ ID NO 64
<211> LENGTH: 4
<212> TYPE: PRT
<213> ORGANISM: Artificial sequence
<220> FEATURE:
<223> OTHER INFORMATION: Motif

<400> SEQUENCE: 64

Asn Gly Asp Gly
1

<210> SEQ ID NO 65
<211> LENGTH: 9
<212> TYPE: PRT
<213> ORGANISM: Artificial sequence
<220> FEATURE:
<223> OTHER INFORMATION: Motif

<400> SEQUENCE: 65

Ile Ser Arg Gly Glu Leu Ser Glu Ile
1               5

<210> SEQ ID NO 66
<211> LENGTH: 7
<212> TYPE: PRT
<213> ORGANISM: Artificial sequence
<220> FEATURE:
<223> OTHER INFORMATION: Motif

<400> SEQUENCE: 66

His Glu Leu Met Gly Arg Arg
1               5

<210> SEQ ID NO 67
<211> LENGTH: 7
<212> TYPE: PRT
<213> ORGANISM: Artificial sequence
<220> FEATURE:
<223> OTHER INFORMATION: Motif

<400> SEQUENCE: 67

Glu Asp Asp Arg Lys Ala Arg
1               5

<210> SEQ ID NO 68
<211> LENGTH: 13
<212> TYPE: PRT
<213> ORGANISM: Artificial sequence
<220> FEATURE:
<223> OTHER INFORMATION: Motif

<400> SEQUENCE: 68

Asp Arg Val Phe Arg Lys Leu Asp Leu Asn Gln Asp Gly
1               5                   10

<210> SEQ ID NO 69
```

<211> LENGTH: 6
<212> TYPE: PRT
<213> ORGANISM: Artificial sequence
<220> FEATURE:
<223> OTHER INFORMATION: Motif

<400> SEQUENCE: 69

Ile Thr Ile Glu Glu Phe
1               5

<210> SEQ ID NO 70
<211> LENGTH: 5
<212> TYPE: PRT
<213> ORGANISM: Artificial sequence
<220> FEATURE:
<223> OTHER INFORMATION: Motif

<400> SEQUENCE: 70

Cys Leu Lys Asp Asp
1               5

<210> SEQ ID NO 71
<211> LENGTH: 8
<212> TYPE: PRT
<213> ORGANISM: Artificial sequence
<220> FEATURE:
<223> OTHER INFORMATION: Motif

<400> SEQUENCE: 71

Thr Arg Ser Leu Gln Met Phe Asp
1               5

<210> SEQ ID NO 72
<211> LENGTH: 1971
<212> TYPE: DNA
<213> ORGANISM: Drosophila melanogaster

<400> SEQUENCE: 72
atggccgccg ttgccggcct ctatggcctt ggggaggatc gccagcaccg caagaagcag      60
cagcaacagc agcagcacca gaaggagcag ctcgagcaga aggaggagca aaagaagatc     120
gccgagcgga agctgcagct gcgggagcag cagctccagc gcaactccct cgatggttac     180
gggtctttgc ccaaattgag cagtcaagac gaagaagggg gggctggtca tggctttggt     240
ggcggaccgc aacactttga acccattcct cacgatcatg atttctgcga agagtcgtt      300
ataaatgtaa gcggattaag gtttgagaca caactacgta cgttaaatca attcccggac     360
acgctgcttg gggatccagc tcggagatta cggtactttg acccgcttag aaatgaatat     420
ttttttgacc gtagtcgacc gagcttcgat gcgattttat actattatca gagtggtggc     480
cgactacgga gaccggtcaa tgtccctta gacgtattta gtgaagaaat aaaattttat      540
gaattaggtg atcaagcaat taataaattc agagaggatg aaggctttat taagaggaa      600
gaaagaccat taccggataa tgagaaacag agaaaagtct ggctgctctt cgagtatcca     660
gaaagttcgc aagccgccag agttgtagcc ataattagtg tatttgttat attgctatca     720
attgttatat tttgtctaga aacattaccc gaatttaagc attacaaggt gttcaataca     780
acaacaaatg gcacaaaaat cgaggaagac gaggtgcctg acatcacaga tcctttcttc     840
cttatagaaa cgttatgcat tatttggttt acatttgaac taactgtcag gttcctcgca     900
tgtccgaaca attaaatttt ctgcagggat gtcatgaatg ttatcgacat aatcgccatc     960
attccgtact ttataacact agcgactgtc gttgccgaag aggaggatac gttaaatctt    1020

|  |  |  |
|---|---|---|
| ccaaaagcgc cagtcagtcc acaggacaag tcatcgaatc aggctatgtc cttggcaata | 1080 |
| ttacgagtga tacgattagt tcgagtattt cgaatattta agttatctag gcattcgaag | 1140 |
| ggtttacaaa tattaggacg aactctgaaa gcctcaatgc gggaattagg tttacttata | 1200 |
| tttttcttat ttataggcgt cgtactcttc tcatcggcgg tttattttgc ggaagctgga | 1260 |
| agcgaaaatt ccttcttcaa gtccataccc gatgcatttt ggtgggcggt cgttaccatg | 1320 |
| accaccgttg gatatggtga catgacaccc gtcggcgttt ggggcaagat tgtgggatca | 1380 |
| ctttgtgcca ttgctggcgt gctgaccatc gcactgccgg tgccggtcat cgtcagcaat | 1440 |
| ttcaactact␣tctatcaccg cgaaacggat caggaggaga tgcagagcca gaactttaat | 1500 |
| cacgttacta gttgtccata tttgccaggt acattagtag gtcaacacat gaagaaatca | 1560 |
| tcattgtctg agtcctcatc ggatatgatg gatttggacg atggtgtcga gtccacgccg | 1620 |
| ggattgacag aaacacatcc tggacgcagt gcggtggctc cattttttggg agcccagcag | 1680 |
| cagcagcaac aaccggtagc atcctcactg tcgatgtcga tcgacaaaca actgcagcac | 1740 |
| ccactgcagc agctgacgca gacgcaactg taccaacagc agcaacagca gcagcagcag | 1800 |
| cagcaaaacg gcttcaagca gcagcagcaa cagacgcagc agcagctgca acagcaacag | 1860 |
| tcccacacaa taaacgcaag tgcagcagcg gcgacgagcg gcagcggcag tagcggtctc | 1920 |
| accatgaggc acaataatgc cctggccgtt agtatcgaga ccgacgtttg a | 1971 |

<210> SEQ ID NO 73
<211> LENGTH: 656
<212> TYPE: PRT
<213> ORGANISM: Drosophila melanogaster

<400> SEQUENCE: 73

```
Met Ala Ala Val Ala Gly Leu Tyr Gly Leu Gly Glu Asp Arg Gln His
 1               5                  10                  15

Arg Lys Lys Gln Gln Gln Gln Gln His Gln Lys Glu Gln Leu Glu
                20                  25                  30

Gln Lys Glu Glu Gln Lys Lys Ile Ala Glu Arg Lys Leu Gln Leu Arg
            35                  40                  45

Glu Gln Gln Leu Gln Arg Asn Ser Leu Asp Gly Tyr Gly Ser Leu Pro
        50                  55                  60

Lys Leu Ser Ser Gln Asp Glu Glu Gly Gly Ala Gly His Gly Phe Gly
65                  70                  75                  80

Gly Gly Pro Gln His Phe Glu Pro Ile Pro His Asp His Asp Phe Cys
                85                  90                  95

Glu Arg Val Val Ile Asn Val Ser Gly Leu Arg Phe Glu Thr Gln Leu
            100                 105                 110

Arg Thr Leu Asn Gln Phe Pro Asp Thr Leu Leu Gly Asp Pro Ala Arg
        115                 120                 125

Arg Leu Arg Tyr Phe Asp Pro Leu Arg Asn Glu Tyr Phe Phe Asp Arg
    130                 135                 140

Ser Arg Pro Ser Phe Asp Ala Ile Leu Tyr Tyr Gln Ser Gly Gly
145                 150                 155                 160

Arg Leu Arg Arg Pro Val Asn Val Pro Leu Asp Val Phe Ser Glu Glu
                165                 170                 175

Ile Lys Phe Tyr Glu Leu Gly Asp Gln Ala Ile Asn Lys Phe Arg Glu
            180                 185                 190

Asp Glu Gly Phe Ile Lys Glu Glu Glu Arg Pro Leu Pro Asp Asn Glu
        195                 200                 205
```

```
Lys Gln Arg Lys Val Trp Leu Leu Phe Glu Tyr Pro Glu Ser Ser Gln
    210                 215                 220

Ala Ala Arg Val Val Ala Ile Ile Ser Val Phe Val Ile Leu Leu Ser
225                 230                 235                 240

Ile Val Ile Phe Cys Leu Glu Thr Leu Pro Glu Phe Lys His Tyr Lys
                245                 250                 255

Val Phe Asn Thr Thr Asn Gly Thr Lys Ile Glu Glu Asp Glu Val
            260                 265                 270

Pro Asp Ile Thr Asp Pro Phe Leu Ile Glu Thr Leu Cys Ile Ile
        275                 280                 285

Trp Phe Thr Phe Glu Leu Thr Val Arg Phe Leu Ala Cys Pro Asn Lys
    290                 295                 300

Leu Asn Phe Cys Arg Asp Val Met Asn Val Ile Asp Ile Ile Ala Ile
305                 310                 315                 320

Ile Pro Tyr Phe Ile Thr Leu Ala Thr Val Ala Glu Glu Glu Asp
                325                 330                 335

Thr Leu Asn Leu Pro Lys Ala Pro Val Ser Pro Gln Asp Lys Ser Ser
            340                 345                 350

Asn Gln Ala Met Ser Leu Ala Ile Leu Arg Val Ile Arg Leu Val Arg
                355                 360                 365

Val Phe Arg Ile Phe Lys Leu Ser Arg His Ser Lys Gly Leu Gln Ile
    370                 375                 380

Leu Gly Arg Thr Leu Lys Ala Ser Met Arg Glu Leu Gly Leu Leu Ile
385                 390                 395                 400

Phe Phe Leu Phe Ile Gly Val Val Leu Phe Ser Ser Ala Val Tyr Phe
                405                 410                 415

Ala Glu Ala Gly Ser Glu Asn Ser Phe Phe Lys Ser Ile Pro Asp Ala
            420                 425                 430

Phe Trp Trp Ala Val Val Thr Met Thr Thr Val Gly Tyr Gly Asp Met
    435                 440                 445

Thr Pro Val Gly Val Trp Gly Lys Ile Val Gly Ser Leu Cys Ala Ile
    450                 455                 460

Ala Gly Val Leu Thr Ile Ala Leu Pro Val Pro Val Ile Val Ser Asn
465                 470                 475                 480

Phe Asn Tyr Phe Tyr His Arg Glu Thr Asp Gln Glu Glu Met Gln Ser
                485                 490                 495

Gln Asn Phe Asn His Val Thr Ser Cys Pro Tyr Leu Pro Gly Thr Leu
            500                 505                 510

Val Gly Gln His Met Lys Lys Ser Ser Leu Ser Glu Ser Ser Ser Asp
                515                 520                 525

Met Met Asp Leu Asp Asp Gly Val Glu Ser Thr Pro Gly Leu Thr Glu
    530                 535                 540

Thr His Pro Gly Arg Ser Ala Val Ala Pro Phe Leu Gly Ala Gln Gln
545                 550                 555                 560

Gln Gln Gln Gln Pro Val Ala Ser Ser Leu Ser Met Ser Ile Asp Lys
                565                 570                 575

Gln Leu Gln His Pro Leu Gln Gln Leu Thr Gln Thr Gln Leu Tyr Gln
            580                 585                 590

Gln Gln Gln Gln Gln Gln Gln Gln Asn Gly Phe Lys Gln Gln
                595                 600                 605

Gln Gln Gln Thr Gln Gln Leu Gln Gln Gln Ser His Thr Ile
    610                 615                 620

Asn Ala Ser Ala Ala Ala Ala Thr Ser Gly Ser Gly Ser Ser Gly Leu
```

Thr Met Arg His Asn Asn Ala Leu Ala Val Ser Ile Glu Thr Asp Val
        645                 650                 655

<210> SEQ ID NO 74
<211> LENGTH: 1497
<212> TYPE: DNA
<213> ORGANISM: Spodoptera eridania

<400> SEQUENCE: 74

```
atgttcgctg gcggaggtgc cggcttccag aaacagtcaa agccgccgtg ggagagtacc      60
aacaccagct ccgagcagaa tatccctac aaccggtcac tgccaaaact gtgcaaccag     120
gaagaggagc ctggacgtcc accccagggc ggggtggtga cgttcgaacc catacaacac     180
gatcacgact tctgcgaaag agttgttatc aacgtaagtg gcctgaagtt tgagacccaa     240
ctacgaacac tgaatcaatt cccggaaacc ctactggggg acccaactcg gagaatacgc     300
tacttcgatc ccttgaggaa cgaatacttt tttgaccgca accgcccctc atttgacgca     360
atcctgtact actaccaaag cggcggccgc ctgcggcgcc ctgttaacgt tcccctagat     420
gtcttctccg aggagattaa attctacgaa ctcggagaac aagccacaaa caaattccgt     480
gaggatgagg gcttcatcaa ggaagaggaa aaaccccttc cgtccaacga gcgccagcgc     540
aaaatttggt tgctcttcga atacccagag agctctcagg ccgcacgtgt cgtggctatc     600
atctccgtgt ttgtcattct cctgtctatc gtcattttct gcctggagac cctgccagag     660
ttcaaacact acaaggtctt caacaccacc accaacggca ctaagatcga ggaagatgaa     720
gtccctgata tcaccgatcc attcttcttg atagagaccc tctgtattat atggtttacg     780
ttcgagttga tagtacggtt tctggcgtgt cccaacaagt tcaacttctt tagagatgtc     840
atgaatatta tagacatcat cgccattatt ccgtacttta tcaccctggc gacagtcgtg     900
gcagaggagg aagatactct caacttaccg cgtgccccag tgtctccgca agacaagtcg     960
actaaccaag cgatgagtct ggccatactg cgagtgatac gtctggtgcg tgtgttccgt    1020
atcttcaaac tgtcgcgaca ctccaaagga ttacagattt gggtcgtac gttaaaagca    1080
tcaatgaggg aacttggctt attgatattc ttcttgttca ttggtgtggt gctgttttca    1140
tccgcggtgt acttcgctga gcgggaagt gagaacagct tcttcaaatc catacctgat    1200
gcgttttggt gggcggtcgt gacaatgaca actgtgggat acggagacat gacgcccgtt    1260
ggagtatggg aaagatcgt cggatccctg tgtgctattg ccggagtgct caccattgca    1320
ttgcctgttc ctgtcatcgt gtcgaacttc aattacttct accatcggga gaccgaccag    1380
gaggagatgc aatcgcagaa cttcaaccac gtcaccagct gcccgtacct acctggcact    1440
atgggcgagc cttacctcag tgggaaagaa gatgacgagg tttgcagtga tcaatga       1497
```

<210> SEQ ID NO 75
<211> LENGTH: 498
<212> TYPE: PRT
<213> ORGANISM: Spodoptera eridania

<400> SEQUENCE: 75

Met Phe Ala Gly Gly Gly Ala Gly Phe Gln Lys Gln Ser Lys Pro Pro
1               5                   10                  15

Trp Glu Ser Thr Asn Thr Ser Ser Gly Ala Asp Ile Pro Tyr Asn Arg
            20                  25                  30

Ser Leu Pro Lys Leu Cys Asn Gln Glu Glu Glu Pro Gly Arg Pro Pro
        35                  40                  45

Gln Gly Gly Val Val Thr Phe Glu Pro Ile Gln His Asp His Asp Phe
 50                  55                  60

Cys Glu Arg Val Val Ile Asn Val Ser Gly Leu Lys Phe Glu Thr Gln
 65                  70                  75                  80

Leu Arg Thr Leu Asn Gln Phe Pro Glu Thr Leu Leu Gly Asp Pro Thr
                 85                  90                  95

Arg Arg Ile Arg Tyr Phe Asp Pro Leu Arg Asn Glu Tyr Phe Phe Asp
            100                 105                 110

Arg Asn Arg Pro Ser Phe Asp Ala Ile Leu Tyr Tyr Gln Ser Gly
            115                 120                 125

Gly Arg Leu Arg Arg Pro Val Asn Val Pro Leu Asp Val Phe Ser Glu
130                 135                 140

Glu Ile Lys Phe Tyr Glu Leu Gly Glu Gln Ala Thr Asn Lys Phe Arg
145                 150                 155                 160

Glu Asp Glu Gly Phe Ile Lys Glu Glu Lys Pro Leu Pro Ser Asn
                165                 170                 175

Glu Arg Gln Arg Lys Ile Trp Leu Leu Phe Glu Tyr Pro Glu Ser Ser
            180                 185                 190

Gln Ala Ala Arg Val Val Ala Ile Ile Ser Val Phe Val Ile Leu Leu
            195                 200                 205

Ser Ile Val Ile Phe Cys Leu Glu Thr Leu Pro Glu Phe Lys His Tyr
210                 215                 220

Lys Val Phe Asn Thr Thr Thr Asn Gly Thr Lys Ile Glu Glu Asp Glu
225                 230                 235                 240

Val Pro Asp Ile Thr Asp Pro Phe Phe Leu Ile Glu Thr Leu Cys Ile
                245                 250                 255

Ile Trp Phe Thr Phe Glu Leu Ile Val Arg Phe Leu Ala Cys Pro Asn
            260                 265                 270

Lys Phe Asn Phe Phe Arg Asp Val Met Asn Ile Ile Asp Ile Ile Ala
            275                 280                 285

Ile Ile Pro Tyr Phe Ile Thr Leu Ala Thr Val Val Ala Glu Glu Glu
290                 295                 300

Asp Thr Leu Asn Leu Pro Arg Ala Pro Val Ser Pro Gln Asp Lys Ser
305                 310                 315                 320

Thr Asn Gln Ala Met Ser Leu Ala Ile Leu Arg Val Ile Arg Leu Val
                325                 330                 335

Arg Val Phe Arg Ile Phe Lys Leu Ser Arg His Ser Lys Gly Leu Gln
            340                 345                 350

Ile Leu Gly Arg Thr Leu Lys Ala Ser Met Arg Glu Leu Gly Leu Leu
            355                 360                 365

Ile Phe Phe Leu Phe Ile Gly Val Val Leu Phe Ser Ser Ala Val Tyr
370                 375                 380

Phe Ala Glu Ala Gly Ser Glu Asn Ser Phe Phe Lys Ser Ile Pro Asp
385                 390                 395                 400

Ala Phe Trp Trp Ala Val Val Thr Met Thr Thr Val Gly Tyr Gly Asp
                405                 410                 415

Met Thr Pro Val Gly Val Trp Gly Lys Ile Val Gly Ser Leu Cys Ala
            420                 425                 430

Ile Ala Gly Val Leu Thr Ile Ala Leu Pro Val Pro Val Ile Val Ser
            435                 440                 445

Asn Phe Asn Tyr Phe Tyr His Arg Glu Thr Asp Gln Glu Glu Met Gln
450                 455                 460

Ser Gln Asn Phe Asn His Val Thr Ser Cys Pro Tyr Leu Pro Gly Thr
465                 470                 475                 480

Met Gly Glu Pro Tyr Leu Ser Gly Lys Glu Asp Asp Glu Val Cys Ser
                485                 490                 495

Asp Gln

<210> SEQ ID NO 76
<211> LENGTH: 1656
<212> TYPE: DNA
<213> ORGANISM: Tribolium castaneum

<400> SEQUENCE: 76

| | | | | | |
|---|---|---|---|---|---|
| gccaccatga | cgatgtggca | gagtgggatg | gggggggcccg | ggggcaagaa | caacgcgtgg | 60 |
| atgaagctga | tggggatcgt | ccacaaagag | cgccgacacc | acgactccgg | agccacttcc | 120 |
| acagatcgca | cacttagcca | gtcgctgccc | aagctcagca | gccaggaaga | ggacgggcac | 180 |
| acccccact | cccagttcac | tggcgtagcc | cactttgagc | ccatcccgca | cgaccacgac | 240 |
| ttttgcgaaa | gagttgtgat | aaacgtcagc | ggcctccggt | tcgagacgca | acttagaacg | 300 |
| ctaaatcagt | ttcctgacac | gctgctaggt | gatccagccc | gccgcatccg | ctacttcgac | 360 |
| ccgcttcgca | atgagtactt | cttcgaccgc | aaccggcccc | ccttcgacgc | catcctgtac | 420 |
| tactaccaga | gcggcggtcg | gctccggcgg | cccgtcaacg | tgccgctgga | cgtcttctcc | 480 |
| gaggagatca | agttctacga | gctgggggag | ctggcgatca | acaagttccg | cgaggacgag | 540 |
| ggcttcatca | aggaggagga | gaagccgcya | ccctcgcacg | agttccagcg | caacgtgtgg | 600 |
| ctgctgttcg | agtacccgga | gtcgtcgcag | gcggcgcgcg | tcgtcgccat | catctccgtg | 660 |
| ttcgttatcc | tgctctctat | cgttattttc | tgcctggaga | cgctgcccga | gttcaagcac | 720 |
| tacaaggtgt | tcaacacgac | taccaacggc | accaagatag | aggaggacga | ggtgccggac | 780 |
| atcacggacc | cgttcttcct | catcgagacc | atctgcatca | tctggttcac | gttcgaattg | 840 |
| tccgtgcgct | tcctggcgtg | tcccaacaag | ctacatttct | tccgggacgt | catgaacttt | 900 |
| atcgatatca | tcgccatcat | tccgtacttt | attacgttgg | ccaccgtcgt | ggccgaggag | 960 |
| gaggacacgt | tgaacctgcc | acgtgcgcct | gttagtccgc | aagwtaaaag | caccaaccag | 1020 |
| gccatgtcgc | tggccattct | tcgtgtcatt | cggctcgtgc | gagtcttccg | catcttcaaa | 1080 |
| cttagccggc | atagtaaggg | cctgcagatc | ctagggcgca | cgcttaaagc | cagcatgcgc | 1140 |
| gagttaggct | tgctcatctt | cttcctattc | ataggygtsg | tsctyttctc | gagcrycgtc | 1200 |
| tacttcgckg | argcgggckc | cgagmaktcs | ttcttcaagt | csatcccrga | cgcgttctgg | 1260 |
| tgggcmgtgg | tsaccatgac | sacygtgggc | tacggcgaca | tgasgccggt | cggcgtttgg | 1320 |
| ggcaagatcg | tgggttcgct | gtgtgcaatc | gctggtgtat | tgaccattgc | gctgccagtg | 1380 |
| ccagtcatag | tttcgaattt | caattacttt | tatcatcgtg | agacggatca | ggaagagatg | 1440 |
| cagtcgcaga | acttcaacca | cgtgaccagc | tgcccgtacc | tgccaggcac | cttaggccaa | 1500 |
| catatgaaga | gagctcgct | aagcgaatcc | tccagcgatc | tcgttgagct | ggaggagggc | 1560 |
| ctgctggtga | cgcgcgacca | gctggtccgg | aagcagaact | gcaatccgcg | ccacaacaac | 1620 |
| aacatcaacg | ccatgagcat | cgagactgac | gtttga | | | 1656 |

<210> SEQ ID NO 77
<211> LENGTH: 545
<212> TYPE: PRT
<213> ORGANISM: Tribolium

<400> SEQUENCE: 77

```
Ala Thr Met Thr Met Trp Gln Ser Gly Met Gly Pro Gly Gly Lys
1               5                   10                  15

Asn Asn Ala Trp Met Lys Leu Met Gly Ile Val His Lys Glu Arg Arg
            20                  25                  30

His His Asp Ser Gly Ala Thr Ser Thr Asp Arg Thr Leu Ser Gln Ser
        35                  40                  45

Leu Pro Lys Leu Ser Ser Gln Glu Glu Asp Gly His Thr Pro His Ser
50                  55                  60

Gln Phe Thr Gly Val Ala His Phe Glu Pro Ile Pro His Asp His Asp
65                  70                  75                  80

Phe Cys Glu Arg Val Val Ile Asn Val Ser Gly Leu Arg Phe Glu Thr
                85                  90                  95

Gln Leu Arg Thr Leu Asn Gln Phe Pro Asp Thr Leu Leu Gly Asp Pro
                100                 105                 110

Ala Arg Arg Ile Arg Tyr Phe Asp Pro Leu Arg Asn Glu Tyr Phe Phe
                115                 120                 125

Asp Arg Asn Arg Pro Ser Phe Asp Ala Ile Leu Tyr Tyr Tyr Gln Ser
        130                 135                 140

Gly Gly Arg Leu Arg Arg Pro Val Asn Val Pro Leu Asp Val Phe Ser
145                 150                 155                 160

Glu Glu Ile Lys Phe Tyr Glu Leu Gly Glu Leu Ala Ile Asn Lys Phe
                165                 170                 175

Arg Glu Asp Glu Gly Phe Ile Lys Glu Glu Lys Pro Pro Ser His
                180                 185                 190

Glu Phe Gln Arg Asn Val Trp Leu Leu Phe Glu Tyr Pro Glu Ser Ser
        195                 200                 205

Gln Ala Ala Arg Val Val Ala Ile Ile Ser Val Phe Val Ile Leu Leu
        210                 215                 220

Ser Ile Val Ile Phe Cys Leu Glu Thr Leu Pro Glu Phe Lys His Tyr
225                 230                 235                 240

Lys Val Phe Asn Thr Thr Asn Gly Thr Lys Ile Glu Glu Asp Glu
                245                 250                 255

Val Pro Asp Ile Thr Asp Pro Phe Phe Leu Ile Glu Thr Ile Cys Ile
            260                 265                 270

Ile Trp Phe Thr Phe Glu Leu Ser Val Arg Phe Leu Ala Cys Pro Asn
        275                 280                 285

Lys Leu His Phe Phe Arg Asp Val Met Asn Phe Ile Asp Ile Ile Ala
        290                 295                 300

Ile Ile Pro Tyr Phe Ile Thr Leu Ala Thr Val Val Ala Glu Glu Glu
305                 310                 315                 320

Asp Thr Leu Asn Leu Pro Arg Ala Pro Val Ser Pro Gln Lys Ser Thr
                325                 330                 335

Asn Gln Ala Met Ser Leu Ala Ile Leu Arg Val Ile Arg Leu Val Arg
            340                 345                 350

Val Phe Arg Ile Phe Lys Leu Ser Arg His Ser Lys Gly Leu Gln Ile
        355                 360                 365

Leu Gly Arg Thr Leu Lys Ala Ser Met Arg Glu Leu Gly Leu Leu Ile
370                 375                 380

Phe Phe Leu Phe Ile Gly Val Val Leu Phe Ser Ser Val Tyr Phe Ala
385                 390                 395                 400

Glu Ala Gly Glu Ser Phe Phe Lys Ser Ile Pro Asp Ala Phe Trp Trp
                405                 410                 415
```

```
Ala Val Val Thr Met Thr Thr Val Gly Tyr Gly Asp Met Pro Val Gly
            420                 425                 430
Val Trp Gly Lys Ile Val Gly Ser Leu Cys Ala Ile Ala Gly Val Leu
        435                 440                 445
Thr Ile Ala Leu Pro Val Pro Val Ile Val Ser Asn Phe Asn Tyr Phe
    450                 455                 460
Tyr His Arg Glu Thr Asp Gln Glu Glu Met Gln Ser Gln Asn Phe Asn
465                 470                 475                 480
His Val Thr Ser Cys Pro Tyr Leu Pro Gly Thr Leu Gly Gln His Met
            485                 490                 495
Lys Lys Ser Ser Leu Ser Glu Ser Ser Asp Leu Val Glu Leu Glu
        500                 505                 510
Glu Gly Leu Leu Val Thr Arg Asp Gln Leu Val Arg Lys Gln Asn Cys
        515                 520                 525
Asn Pro Arg His Asn Asn Asn Ile Asn Ala Met Ser Ile Glu Thr Asp
    530                 535                 540
Val
545

<210> SEQ ID NO 78
<211> LENGTH: 1743
<212> TYPE: DNA
<213> ORGANISM: Myzus persicae

<400> SEQUENCE: 78
atgtggcact cgggcggcat gggcagccac ggcggtggct ggatgaagct gatgggaatg      60
gtgcacaggg accggagatc ggcgcaacgg cacgtacagg acgccgctac agcattactg     120
gctcccatcg acaggtctct gccgaaactc agtacccaag acgaagacgg ctgtggtcca     180
ggggcaaatc ttgaacagg cctcacacac ggtcatcctc aacactgttc ggggagcgcg     240
acattcgaac cgataccgca cgaccacgac ttttgcgaaa gagtaacaat caacgtgagc     300
ggtatgaggt tcgagacgca gctgcggacg ttgaaccagt tcccggacac gctgctggga     360
gacccgtgtc ggaggatgcg gtacttcgat cctctgcgga cgagtacttt cttcgacagg     420
aaccggccga cgttcgacgc catactctac tattaccaga gcggtggccg gctgaggagg     480
ccaactacgg tgccgttgga cgtgttctcc gaggagatca agttctacga gctcggcgaa     540
ctggctacca ataaattag ggaagaagag ggttttataa agaagaaga gaaaccactg     600 ccaaagcctg agttccagcg gaaggtgtgg ctgctgttcg agtacccgga gctctcaa     660 gccgcccggg tggtggccat catatctgtg ttcgtcatac tgctgtccat cgttatattc     720
tgcctggaaa cgttgccaga gttcaaacac tacaaggtgt caacacgac gaccaatggt     780 accaagatcg aggaggatga ggtgcccgat atcaccgacc cgttcttctt gattgagacc     840
atttgtatcg tgtggttcac gttcgagctg tccgtccgct ttctcgcctg ccccaacaag     900
ttgcacttct tcaaagacgt gatgaacact atcgacataa tcgccataat accatacttc     960
atcacattag ccacggtgat tgccgaggag gaggacccaa cgatgaacct gcccaaggcg    1020
ccgcagaacc cgcaggacaa aagcaccaac caggccatgt cgttggccat acttagggtc    1080
atccggctcg tgagggtttt caggatattc aaattgtccc gacattccaa gggattgcaa    1140
attctcgggc gcaccctgaa agcctccatg cgagaactgg gattgctcat attttcttg    1200 tttatcggag tggtgctgtt ctcgagcacc gtgtacttcg ccgaggcggg ttccgatcag    1260 tcgttttca agtccatccc ggacgcgttc tggtgggccg tggtcaccat gacgacagtc    1320
```

-continued

```
ggatacggtg acatgagacc agtgggcgtg tggggaaaaa ttgtcggttc gctgtgcgcg    1380
attgccggcg tgctcacaat cgcactgccc gtgcccgtca tcgtgtccaa cttcaactat    1440
ttctatcaca gagagactga ccaagaagac atgcaatcgc agaacttcaa ccacgtcacc    1500
agctgccctt atcttcccgg tactttaggt caacacatgg tgaaatatcc gtcgggcggt    1560
gactcgacgt cggacctgat ggacttggag tcggccgaca attgtctgct ggacgcggag    1620
ctggacgaac cgccactgac gttgccgccg ccgcagcaac ccaaaaagtt caacagctgc    1680
gccaccgtgg tcaggctcaa caacaacagc atcaagaggt tcagtgtcga aactgacgtc    1740
tga                                                                  1743
```

<210> SEQ ID NO 79
<211> LENGTH: 580
<212> TYPE: PRT
<213> ORGANISM: Myzus persicae

<400> SEQUENCE: 79

```
Met Trp His Ser Gly Gly Met Gly Ser His Gly Gly Trp Met Lys
1               5                   10                  15

Leu Met Gly Met Val His Arg Asp Arg Arg Ser Ala Gln Arg His Val
                20                  25                  30

Gln Asp Ala Ala Thr Ala Leu Leu Ala Pro Ile Asp Arg Ser Leu Pro
            35                  40                  45

Lys Leu Ser Thr Gln Asp Glu Asp Gly Cys Gly Pro Gly Ala Asn Leu
        50                  55                  60

Gly Thr Gly Leu Thr His Gly His Pro Gln His Cys Ser Gly Ser Ala
    65                  70                  75                  80

Thr Phe Glu Pro Ile Pro His Asp His Asp Phe Cys Glu Arg Val Thr
                85                  90                  95

Ile Asn Val Ser Gly Met Arg Phe Glu Thr Gln Leu Arg Thr Leu Asn
            100                 105                 110

Gln Phe Pro Asp Thr Leu Leu Gly Asp Pro Cys Arg Arg Met Arg Tyr
        115                 120                 125

Phe Asp Pro Leu Arg Asn Glu Tyr Phe Phe Asp Arg Asn Arg Pro Thr
    130                 135                 140

Phe Asp Ala Ile Leu Tyr Tyr Tyr Gln Ser Gly Gly Arg Leu Arg Arg
145                 150                 155                 160

Pro Thr Thr Val Pro Leu Asp Val Phe Ser Glu Ile Lys Phe Tyr
                165                 170                 175

Glu Leu Gly Glu Leu Ala Thr Asn Lys Phe Arg Glu Glu Gly Phe
            180                 185                 190

Ile Lys Glu Glu Glu Lys Pro Leu Pro Lys Pro Glu Phe Gln Arg Lys
        195                 200                 205

Val Trp Leu Leu Phe Glu Tyr Pro Glu Ser Ser Gln Ala Ala Arg Val
    210                 215                 220

Val Ala Ile Ile Ser Val Phe Val Ile Leu Ser Ile Val Ile Phe
225                 230                 235                 240

Cys Leu Glu Thr Leu Pro Glu Phe Lys His Tyr Lys Val Phe Asn Thr
                245                 250                 255

Thr Thr Asn Gly Thr Lys Ile Glu Glu Asp Val Pro Asp Ile Thr
            260                 265                 270

Asp Pro Phe Phe Leu Ile Glu Thr Ile Cys Ile Val Trp Phe Thr Phe
        275                 280                 285

Glu Leu Ser Val Arg Phe Leu Ala Cys Pro Asn Lys Leu His Phe Phe
```

```
        290                 295                 300
Lys Asp Val Met Asn Thr Ile Asp Ile Ile Ala Ile Ile Pro Tyr Phe
305                 310                 315                 320

Ile Thr Leu Ala Thr Val Ile Ala Glu Glu Asp Pro Thr Met Asn
                325                 330                 335

Leu Pro Lys Ala Pro Gln Asn Pro Gln Asp Lys Ser Thr Asn Gln Ala
                340                 345                 350

Met Ser Leu Ala Ile Leu Arg Val Ile Arg Leu Val Arg Val Phe Arg
                355                 360                 365

Ile Phe Lys Leu Ser Arg His Ser Lys Gly Leu Gln Ile Leu Gly Arg
370                 375                 380

Thr Leu Lys Ala Ser Met Arg Glu Leu Gly Leu Leu Ile Phe Phe Leu
385                 390                 395                 400

Phe Ile Gly Val Val Leu Phe Ser Ser Thr Val Tyr Phe Ala Glu Ala
                405                 410                 415

Gly Ser Asp Gln Ser Phe Phe Lys Ser Ile Pro Asp Ala Phe Trp Trp
                420                 425                 430

Ala Val Val Thr Met Thr Thr Val Gly Tyr Gly Asp Met Arg Pro Val
                435                 440                 445

Gly Val Trp Gly Lys Ile Val Gly Ser Leu Cys Ala Ile Ala Gly Val
                450                 455                 460

Leu Thr Ile Ala Leu Pro Val Pro Val Ile Val Ser Asn Phe Asn Tyr
465                 470                 475                 480

Phe Tyr His Arg Glu Thr Asp Gln Glu Asp Met Gln Ser Gln Asn Phe
                485                 490                 495

Asn His Val Thr Ser Cys Pro Tyr Leu Pro Gly Thr Leu Gly Gln His
                500                 505                 510

Met Val Lys Tyr Pro Ser Gly Gly Asp Ser Thr Ser Asp Leu Met Asp
                515                 520                 525

Leu Glu Ser Ala Asp Asn Cys Leu Leu Asp Ala Glu Leu Asp Glu Pro
                530                 535                 540

Pro Leu Thr Leu Pro Pro Gln Gln Pro Lys Lys Phe Asn Ser Cys
545                 550                 555                 560

Ala Thr Val Val Arg Leu Asn Asn Asn Ser Ile Lys Arg Phe Ser Val
                565                 570                 575

Glu Thr Asp Val
            580

<210> SEQ ID NO 80
<211> LENGTH: 1743
<212> TYPE: DNA
<213> ORGANISM: Aphis gossypii

<400> SEQUENCE: 80
atgtggcact cgggcggcat gggcagccac ggcggtggct ggatgaaact gatgggcatg      60
gtacacaggg accggagatc agcgcaacgg catgtacagg acgccgctac agcattattg     120
gctcccatcg ataggtcact gccgaaactc agtacccaag acgaagacgg ctgtggtcca     180
ggggcaagtc ttggcacagg cctcacacac ggtcatcctc aacactgttc ggggagtgcg     240
acattcgaac cgataccgca cgatcacgac ttctgcgaaa gagtaacaat caacgtgagc     300
ggtatgaggt tcgaaacgca gctgcggacg ttgaaccagt tcccggacac gctgctggga     360
gacccgtgtc ggcggatgcg gtacttcgac ccactgcgca acgagtactt cttcgacagg     420
aaccggccga cgttcgatgc cattctctac tattaccaga gcggaggccg actgagaagg     480
```

-continued

```
ccaacaacgg tgccgttgga cgtgttctct gaagagatca agttctacga actcggtgaa    540
ctggccacca ataaatttag ggaagaagag ggttttataa agaagaagaa gaaaccactg    600
ccaaaacccg agttccaacg gaaggtatgg ctattgttcg aatacccgga gagctcacaa    660
gccgctcggg tggtggccat catatccgtg ttcgtcatat tgctgtccat cgtgatattc    720
tgtctggaaa cgttgccaga gtttaaacac tataaggtgt caacacgac gactaatggt     780
acgaagattg aagaggacga ggtgcctgac atcaccgatc cgttcttctt gattgagacc    840
atatgcatcg tgtggttcac gttcgagctg tccgtccgct ttctcgcctg ccctaataag    900
ttgcacttct tcaaagacgt gatgaataca atcgatataa tcgctattat accgtacttc    960
atcacgttgg ccacagtgat tgctgaggag gaggacccca cgatgaacct gcccaaggcg   1020
ccgcagaacc cgcaggataa gagcaccaac caggccatgt cactggccat actcagggtc   1080
atccggctcg tgagggtttt caggatattc aaactatccc gacattccaa gggattgcaa   1140
attcttgggc gcaccctaaa agcctccatg cgagaactgg gactgctcat atttttcttg   1200
tttatcggag tggtgctgtt ctcgagcacc gtgtacttcg ccgaggcggg ttccgatcag   1260
tcgttttttca gtccatccc ggacgcgttc tggtgggccg tggtcaccat gacgacagtc    1320
ggatacggtg atatgagacc agtgggcgtg tgggggaaaa ttgtcggttc actgtgcgcg   1380
attgccggcg tgctcacaat cgcactgccc gtgcccgtca tcgtgtccaa cttcaactat   1440
ttctatcaca gagagactga ccaagaagac atgcaatcgc agaacttcaa ccacgtcacc   1500
agctgccctt atcttcccgg tactttaggt caacacatgg tgaaatatcc gtcgggtggt   1560
gactcgacgt cggatctgat ggacttggag tcggccgaca attgtctgct ggacgcggag   1620
ctggacgaac cacctctgtc gttgccgccg ccgcagcaac ccaaaaagtt caacagctgt   1680
gccaccgtgg tcaggctcaa caacaacagc atcaagaggt tcagtgtcga aactgacgtc   1740
tga                                                                 1743
```

<210> SEQ ID NO 81
<211> LENGTH: 580
<212> TYPE: PRT
<213> ORGANISM: Aphis gossypii

<400> SEQUENCE: 81

```
Met Trp His Ser Gly Gly Met Gly Ser His Gly Gly Trp Met Lys
1               5                   10                  15

Leu Met Gly Met Val His Arg Asp Arg Arg Ser Ala Gln Arg His Val
            20                  25                  30

Gln Asp Ala Ala Thr Ala Leu Leu Ala Pro Ile Asp Arg Ser Leu Pro
        35                  40                  45

Lys Leu Ser Thr Gln Asp Glu Asp Gly Cys Gly Pro Gly Ala Ser Leu
    50                  55                  60

Gly Thr Gly Leu Thr His Gly His Pro Gln His Cys Ser Gly Ser Ala
65                  70                  75                  80

Thr Phe Glu Pro Ile Pro His Asp His Asp Phe Cys Glu Arg Val Thr
                85                  90                  95

Ile Asn Val Ser Gly Met Arg Phe Glu Thr Gln Leu Arg Thr Leu Asn
            100                 105                 110

Gln Phe Pro Asp Thr Leu Leu Gly Asp Pro Cys Arg Arg Met Arg Tyr
        115                 120                 125

Phe Asp Pro Leu Arg Asn Glu Tyr Phe Phe Asp Arg Asn Arg Pro Thr
    130                 135                 140
```

```
Phe Asp Ala Ile Leu Tyr Tyr Gln Ser Gly Gly Arg Leu Arg Arg
145                 150                 155                 160

Pro Thr Thr Val Pro Leu Asp Val Phe Ser Glu Ile Lys Phe Tyr
                165                 170                 175

Glu Leu Gly Glu Leu Ala Thr Asn Lys Phe Arg Glu Glu Gly Phe
            180                 185                 190

Ile Lys Glu Glu Lys Pro Leu Pro Lys Pro Glu Phe Gln Arg Lys
            195                 200                 205

Val Trp Leu Leu Phe Glu Tyr Pro Glu Ser Ser Gln Ala Ala Arg Val
    210                 215                 220

Val Ala Ile Ile Ser Val Phe Val Ile Leu Leu Ser Ile Val Ile Phe
225                 230                 235                 240

Cys Leu Glu Thr Leu Pro Glu Phe Lys His Tyr Lys Val Phe Asn Thr
                245                 250                 255

Thr Thr Asn Gly Thr Lys Ile Glu Glu Asp Glu Val Pro Asp Ile Thr
            260                 265                 270

Asp Pro Phe Phe Leu Ile Glu Thr Ile Cys Ile Val Trp Phe Thr Phe
        275                 280                 285

Glu Leu Ser Val Arg Phe Leu Ala Cys Pro Asn Lys Leu His Phe Phe
    290                 295                 300

Lys Asp Val Met Asn Thr Ile Asp Ile Ile Ala Ile Ile Pro Tyr Phe
305                 310                 315                 320

Ile Thr Leu Ala Thr Val Ile Ala Glu Glu Glu Asp Pro Thr Met Asn
                325                 330                 335

Leu Pro Lys Ala Pro Gln Asn Pro Gln Asp Lys Ser Thr Asn Gln Ala
            340                 345                 350

Met Ser Leu Ala Ile Leu Arg Val Ile Arg Leu Val Arg Val Phe Arg
    355                 360                 365

Ile Phe Lys Leu Ser Arg His Ser Lys Gly Leu Gln Ile Leu Gly Arg
    370                 375                 380

Thr Leu Lys Ala Ser Met Arg Glu Leu Gly Leu Leu Ile Phe Phe Leu
385                 390                 395                 400

Phe Ile Gly Val Val Leu Phe Ser Ser Thr Val Tyr Phe Ala Glu Ala
                405                 410                 415

Gly Ser Asp Gln Ser Phe Phe Lys Ser Ile Pro Asp Ala Phe Trp Trp
            420                 425                 430

Ala Val Val Thr Met Thr Thr Val Gly Tyr Gly Asp Met Arg Pro Val
            435                 440                 445

Gly Val Trp Gly Lys Ile Val Gly Ser Leu Cys Ala Ile Ala Gly Val
    450                 455                 460

Leu Thr Ile Ala Leu Pro Val Pro Val Ile Val Ser Asn Phe Asn Tyr
465                 470                 475                 480

Phe Tyr His Arg Glu Thr Asp Gln Glu Asp Met Gln Ser Gln Asn Phe
            485                 490                 495

Asn His Val Thr Ser Cys Pro Tyr Leu Pro Gly Thr Leu Gly Gln His
            500                 505                 510

Met Val Lys Tyr Pro Ser Gly Gly Asp Ser Thr Ser Asp Leu Met Asp
    515                 520                 525

Leu Glu Ser Ala Asp Asn Cys Leu Leu Asp Ala Glu Leu Asp Glu Pro
    530                 535                 540

Pro Leu Ser Leu Pro Pro Gln Gln Pro Lys Lys Phe Asn Ser Cys
545                 550                 555                 560
```

Ala Thr Val Val Arg Leu Asn Asn Asn Ser Ile Lys Arg Phe Ser Val
          565                 570                 575

Glu Thr Asp Val
        580

<210> SEQ ID NO 82
<211> LENGTH: 1743
<212> TYPE: DNA
<213> ORGANISM: Aphis fabae

<400> SEQUENCE: 82

| | | | |
|---|---|---|---|
| atgtggcact cgggcggcat gggcagccac ggcggtggct ggatgaaact gatgggcatg | 60 |
| gtacacaggg accggagatc agcgcaaagg catgtacagg acgctgctac agcattattg | 120 |
| gctcccatcg ataggtcact gccgaaactc agtacccaag acgaagacgg ctgtggtcca | 180 |
| ggggcaagtc ttggcacagg cctcacacac ggtcatcctc aacactgttc ggggagcgcg | 240 |
| acattcgaac cgataccgca cgatcacgac ttctgcgaaa gagtaacaat caacgtgagc | 300 |
| ggtatgaggt tcgagacgca gctgcggacg ttgaaccagt tcccggacac cctgctggga | 360 |
| gacccatgtc ggcggatgcg gtacttcgat ccactgcgca acgagtactt cttcgacagg | 420 |
| aaccggccga cgttcgatgc cattctctac tattaccaga gcggaggccg actgaggagg | 480 |
| ccaaccacgg tgccgttgga cgtgttctct gaggagatca agttctacga actcggtgaa | 540 |
| ctggccacca ataaatttag gaagaagag gttttataa agaagaaga gaaaccactg | 600 |
| ccaaaaccag agtttcaacg gaaggtgtgg ctactgttcg aatacccgga gagttcacaa | 660 |
| gccgctcggg tggtggccat catatccgtg ttcgtcatat tgctgtccat cgtgatattc | 720 |
| tgtctagaaa cgttgccaga gttcaaacac tataaagtgt tcaacacgac gactaatggt | 780 |
| acgaagattg aagaggacga ggtgcctgac atcaccgatc cgttcttctt gattgagacc | 840 |
| atatgtatcg tgtggttcac gttcgagctg tccgtccgct ttctcgcctg ccctaataag | 900 |
| ttgcacttct tcaaagacgt gatgaataca atcgatataa tcgctattat accgtacttc | 960 |
| atcacgttgg ccacagtgat tgctgaggag gaggacccca cgatgaacct gcccaaggcg | 1020 |
| ccgcagaatc cgcaggataa gagcaccaac caggccatgt cactggccat actcagggtc | 1080 |
| atccggctcg tgagggtttt caggatattc aaactgtccc gacattccaa gggattgcaa | 1140 |
| attcttgggc gcaccctaaa agcctccatg cgagaactgg gactgctcat atttttcttg | 1200 |
| tttatcggtg tggtgctatt ctcgagcgcg gtgtacttcg ccgaagccgg ctcagagaat | 1260 |
| tccttcttca gtccatccc ggacgcattc tggtgggctg ttgttaccat gacgactgtg | 1320 |
| ggctatggtg acatgacacc agtgggcgtg tgggggaaaa ttgtcggttc actgtgcgcg | 1380 |
| attgccggcg tgctcacaat cgcactgccc gtgcccgtca tcgtgtccaa cttcaactat | 1440 |
| ttctatcaca gagagactga ccaagaagac atgcaatcgc agaacttcaa ccacgtcacc | 1500 |
| agctgccctt atcttcccgg tactttaggt caacacatgg tgaaatatcc gtcgggtggt | 1560 |
| gactcgacgt cggatctgat ggacttggag tcggccgaca attgtctgct ggacgcggag | 1620 |
| ctggacgagc cacctctgtc gttgccgccg ccgcagcaac caaaaaagtt caacagctgt | 1680 |
| gccaccgtgg tcaggctcaa caacaacagc atcaagaggt tcagtgtcga aactgacgtc | 1740 |
| tga | 1743 |

<210> SEQ ID NO 83
<211> LENGTH: 580
<212> TYPE: PRT
<213> ORGANISM: Aphis fabae

<400> SEQUENCE: 83

Met Trp His Ser Gly Gly Met Gly Ser His Gly Gly Trp Met Lys
1               5                   10                  15

Leu Met Gly Met Val His Arg Asp Arg Arg Ser Ala Gln Arg His Val
                20                  25                  30

Gln Asp Ala Ala Thr Ala Leu Leu Ala Pro Ile Asp Arg Ser Leu Pro
            35                  40                  45

Lys Leu Ser Thr Gln Asp Glu Asp Gly Cys Gly Pro Gly Ala Ser Leu
    50                  55                  60

Gly Thr Gly Leu Thr His Gly His Pro Gln His Cys Ser Gly Ser Ala
65              70                  75                  80

Thr Phe Glu Pro Ile Pro His Asp His Asp Phe Cys Glu Arg Val Thr
                85                  90                  95

Ile Asn Val Ser Gly Met Arg Phe Glu Thr Gln Leu Arg Thr Leu Asn
            100                 105                 110

Gln Phe Pro Asp Thr Leu Leu Gly Asp Pro Cys Arg Arg Met Arg Tyr
        115                 120                 125

Phe Asp Pro Leu Arg Asn Glu Tyr Phe Phe Asp Arg Asn Arg Pro Thr
130                 135                 140

Phe Asp Ala Ile Leu Tyr Tyr Tyr Gln Ser Gly Gly Arg Leu Arg Arg
145                 150                 155                 160

Pro Thr Thr Val Pro Leu Asp Val Phe Ser Glu Ile Lys Phe Tyr
                165                 170                 175

Glu Leu Gly Glu Leu Ala Thr Asn Lys Phe Arg Glu Glu Gly Phe
            180                 185                 190

Ile Lys Glu Glu Glu Lys Pro Leu Pro Lys Pro Glu Phe Gln Arg Lys
        195                 200                 205

Val Trp Leu Leu Phe Glu Tyr Pro Glu Ser Ser Gln Ala Ala Arg Val
    210                 215                 220

Val Ala Ile Ile Ser Val Phe Val Ile Leu Leu Ser Ile Val Ile Phe
225                 230                 235                 240

Cys Leu Glu Thr Leu Pro Glu Phe Lys His Tyr Lys Val Phe Asn Thr
                245                 250                 255

Thr Thr Asn Gly Thr Lys Ile Glu Glu Asp Glu Val Pro Asp Ile Thr
            260                 265                 270

Asp Pro Phe Phe Leu Ile Glu Thr Ile Cys Ile Val Trp Phe Thr Phe
        275                 280                 285

Glu Leu Ser Val Arg Phe Leu Ala Cys Pro Asn Lys Leu His Phe Phe
290                 295                 300

Lys Asp Val Met Asn Thr Ile Asp Ile Ile Ala Ile Ile Pro Tyr Phe
305                 310                 315                 320

Ile Thr Leu Ala Thr Val Ile Ala Glu Glu Glu Asp Pro Thr Met Asn
                325                 330                 335

Leu Pro Lys Ala Pro Gln Asn Pro Gln Asp Lys Ser Thr Asn Gln Ala
            340                 345                 350

Met Ser Leu Ala Ile Leu Arg Val Ile Arg Leu Val Arg Val Phe Arg
        355                 360                 365

Ile Phe Lys Leu Ser Arg His Ser Lys Gly Leu Gln Ile Leu Gly Arg
370                 375                 380

Thr Leu Lys Ala Ser Met Arg Glu Leu Gly Leu Leu Ile Phe Phe Leu
385                 390                 395                 400

Phe Ile Gly Val Val Leu Phe Ser Ser Ala Val Tyr Phe Ala Glu Ala

```
            405                 410                 415
Gly Ser Glu Asn Ser Phe Phe Lys Ser Ile Pro Asp Ala Phe Trp Trp
            420                 425                 430

Ala Val Thr Met Thr Thr Val Gly Tyr Gly Asp Met Thr Pro Val
        435                 440                 445

Gly Val Trp Gly Lys Ile Val Gly Ser Leu Cys Ala Ile Ala Gly Val
    450                 455                 460

Leu Thr Ile Ala Leu Pro Val Pro Val Ile Val Ser Asn Phe Asn Tyr
465                 470                 475                 480

Phe Tyr His Arg Glu Thr Asp Gln Glu Asp Met Gln Ser Gln Asn Phe
                485                 490                 495

Asn His Val Thr Ser Cys Pro Tyr Leu Pro Gly Thr Leu Gly Gln His
            500                 505                 510

Met Val Lys Tyr Pro Ser Gly Gly Asp Ser Thr Ser Asp Leu Met Asp
        515                 520                 525

Leu Glu Ser Ala Asp Asn Cys Leu Leu Asp Ala Glu Leu Asp Glu Pro
    530                 535                 540

Pro Leu Ser Leu Pro Pro Pro Gln Gln Pro Lys Lys Phe Asn Ser Cys
545                 550                 555                 560

Ala Thr Val Val Arg Leu Asn Asn Asn Ser Ile Lys Arg Phe Ser Val
                565                 570                 575

Glu Thr Asp Val
            580

<210> SEQ ID NO 84
<211> LENGTH: 1164
<212> TYPE: DNA
<213> ORGANISM: Drosophila melanogaster

<400> SEQUENCE: 84
gccaccatgt gccgggctcc cattgcgtca ctcgactgta tggaggagtt cagtggtcgt    60
tcgatcagtt tgggctccaa tccggcgcta ccattgcgcc atggatccac accgacgccg   120
ggactgcggt acaagaatct gggcaagagc gggctgcgta tctcgaatgt gggattgggt   180
acttggccgg tattctcgcc gggcgtaagc gatgaccagg cggaggcaat cctaaagctg   240
gccatcgaga gcggtatcaa tctgttcgac atctcggagg cgcactcgga aacggagatc   300
ggcaagatac tgcagcgggc gggctggaag aggaccgcct atgtcatcac cacgaaggtc   360
tactggagca ccaagtcgga ggaacgtggt ctctcccgga acacatcat cgaatgtgtt    420
cgtgccagtt gcagcgatt gcagctgcag tacatcgata tcgtcatcat ccacaaggcg    480
gatcccatgt gtcccatgga ggaagtggtg cgcgccatga gctacgtgat acagcagggc   540
tgggcaatgt attgggcac cgctcgatgg agccaggtgg agatcatgga ggcctatacc   600
aactgccgcc agttcaactg catcacgccc attgtggagc agtccgagta ccatatgttc   660
tgtcgcgaaa agtgcgaact ctacctgccg gagatgtaca caagatcgg agtgggcctc   720
atggcctggg gtccactctc gatggccctc agcgacaccc agaatgggga caagcttttc   780
ctgcccaagg gctccttcaa gacgaagagc ttctcgtgga ccgaggacga gatcaatcgt   840
aatgccgctc tgtcgccgca gggcagttgg ggtaaggacc ggatcgatga ggggcgccgc   900
cactgcgacc gtctccgcga ccttgccgcc ctcgccgaga agctgggctg cagccccacc   960
cagctgtcca tcgcctggtc gctgaaacat gagccagtgc aatgcctgct ctgggcgcc   1020
acatcggcgg agcagctgca ccaaagtctg cagtcgttgc agctgctgcc acgactctca  1080
```

```
tcgagcgtta tactggagct ggaaaggata ttggaaaaca agccggtgcg gccgccgatg    1140
atctcgacct tggcgctccg gtga                                          1164
```

<210> SEQ ID NO 85
<211> LENGTH: 387
<212> TYPE: PRT
<213> ORGANISM: Drosophila melanogaster

<400> SEQUENCE: 85

```
Ala Thr Met Cys Arg Ala Pro Ile Ala Ser Leu Asp Cys Met Glu Glu
1               5                   10                  15

Phe Ser Gly Arg Ser Ile Ser Leu Gly Ser Asn Pro Ala Leu Pro Leu
            20                  25                  30

Arg His Gly Ser Thr Pro Thr Pro Gly Leu Arg Tyr Lys Asn Leu Gly
        35                  40                  45

Lys Ser Gly Leu Arg Ile Ser Asn Val Gly Leu Gly Thr Trp Pro Val
    50                  55                  60

Phe Ser Pro Gly Val Ser Asp Asp Gln Ala Glu Ala Ile Leu Lys Leu
65                  70                  75                  80

Ala Ile Glu Ser Gly Ile Asn Leu Phe Asp Ile Ser Glu Ala His Ser
                85                  90                  95

Glu Thr Glu Ile Gly Lys Ile Leu Gln Arg Ala Gly Trp Lys Arg Thr
            100                 105                 110

Ala Tyr Val Ile Thr Thr Lys Val Tyr Trp Ser Thr Lys Ser Glu Glu
        115                 120                 125

Arg Gly Leu Ser Arg Lys His Ile Ile Glu Cys Val Arg Ala Ser Leu
    130                 135                 140

Gln Arg Leu Gln Leu Gln Tyr Ile Asp Ile Val Ile His Lys Ala
145                 150                 155                 160

Asp Pro Met Cys Pro Met Glu Glu Val Val Arg Ala Met Ser Tyr Val
                165                 170                 175

Ile Gln Gln Gly Trp Ala Met Tyr Trp Gly Thr Ala Arg Trp Ser Gln
            180                 185                 190

Val Glu Ile Met Glu Ala Tyr Thr Asn Cys Arg Gln Phe Asn Cys Ile
        195                 200                 205

Thr Pro Ile Val Glu Gln Ser Glu Tyr His Met Phe Cys Arg Glu Lys
    210                 215                 220

Cys Glu Leu Tyr Leu Pro Glu Met Tyr Asn Lys Ile Gly Val Gly Leu
225                 230                 235                 240

Met Ala Trp Gly Pro Leu Ser Met Ala Leu Ser Asp Thr Gln Asn Gly
                245                 250                 255

Asp Lys Leu Phe Leu Pro Lys Gly Ser Phe Lys Thr Lys Ser Phe Ser
            260                 265                 270

Trp Thr Glu Asp Glu Ile Asn Arg Asn Ala Ala Leu Ser Pro Gln Gly
        275                 280                 285

Ser Trp Gly Lys Asp Arg Ile Asp Glu Gly Arg His Cys Asp Arg
    290                 295                 300

Leu Arg Asp Leu Ala Ala Leu Ala Glu Lys Leu Gly Cys Ser Pro Thr
305                 310                 315                 320

Gln Leu Ser Ile Ala Trp Ser Leu Lys His Glu Pro Val Gln Cys Leu
                325                 330                 335

Leu Leu Gly Ala Thr Ser Ala Glu Gln Leu His Gln Ser Leu Gln Ser
            340                 345                 350

Leu Gln Leu Leu Pro Arg Leu Ser Ser Ser Val Ile Leu Glu Leu Glu
```

355                 360                 365
Arg Ile Leu Glu Asn Lys Pro Val Arg Pro Met Ile Ser Thr Leu
        370                 375                 380

Ala Leu Arg
385

<210> SEQ ID NO 86
<211> LENGTH: 1188
<212> TYPE: DNA
<213> ORGANISM: Drosophila melanogaster

<400> SEQUENCE: 86
gccaccatgt gccgggctcc cattgcgtca ctcgactgta tggaggagtt cggtggtacg    60
ggcggtcatc ttgatttcgg tcgttcgatc agtttgggct ccaatccggc gctaccattg   120
cgccatggat ccacaccgac gccgggactg cggtacaaga atctgggcaa gagcgggctg   180
cgtatctcga atgtgggatt gggtacttgg ccggtattct cgccgggcgt aagcgatgac   240
caggcggagg caatcctaaa gctggccatc gagagcggta tcaatctgtt cgacatctcg   300
gaggcgcact cggaaacgga gatcggcaag atactgcagc gggcgggctg aagaggacc    360 gcctatgtca tcaccacgaa ggtctactgg agcaccaagt cggaggaacg tggtctctcc   420
cggaaacaca tcatcgaatg tgttcgtgcc agtttgcagc gattgcagct gcagtacatc   480
gatatcgtca tcatccacaa ggcggatccc atgtgtccca tggaggaagt ggtgcgcgcc   540
atgagctacg tgatacagca gggctgggca atgtattggg caccgctcga tggagccag    600 gtggagatca tggaggccta taccaactgc cgccagttca actgcatcac gcccattgtg   660
gagcagtccg agtaccatat gttctgtcgc gaaaagtgcg aactctacct gccggagatg   720
tacaacaaga tcggagtggg cctcatggcc tggggtccac tctcgatggc cctcagcgac   780
acccagaatg ggacaagct tttcctgccc aagggctcct tcaagacgaa gagcttctcg   840
tggaccgagg acgagatcaa tcgtaatgcc gctctgtcgc cgcagggcag ttggggtaag   900
gaccggatcg atgaggggcg ccgccactgc gaccgtctcc gcgaccttgc cgccctcgcc   960
gagaagctgg gctgcagccc cacccagctg tccatcgcct ggtcgctgaa acatgagcca  1020
gtgcaatgcc tgctgctggg cgccacatcg gcggagcagc tgcaccaaag tctgcagtcg  1080
ttgcagctgc tgccacgact ctcatcgagc gttatgctgg agctgaaag gatattggaa  1140 aacaagccgg tgcggccgcc gatgatctcg accttggcgc tccggtga                1188

<210> SEQ ID NO 87
<211> LENGTH: 395
<212> TYPE: PRT
<213> ORGANISM: Drosophila melanogaster

<400> SEQUENCE: 87

Ala Thr Met Cys Arg Ala Pro Ile Ala Ser Leu Asp Cys Met Glu Glu
1               5                   10                  15

Phe Gly Gly Thr Gly Gly His Leu Asp Phe Gly Arg Ser Ile Ser Leu
            20                  25                  30

Gly Ser Asn Pro Ala Leu Pro Leu Arg His Gly Ser Thr Pro Thr Pro
        35                  40                  45

Gly Leu Arg Tyr Lys Asn Leu Gly Lys Ser Gly Leu Arg Ile Ser Asn
    50                  55                  60

Val Gly Leu Gly Thr Trp Pro Val Phe Ser Pro Gly Val Ser Asp Asp
65                  70                  75                  80

-continued

```
Gln Ala Glu Ala Ile Leu Lys Leu Ala Ile Glu Ser Gly Ile Asn Leu
                 85                  90                  95

Phe Asp Ile Ser Glu Ala His Ser Glu Thr Glu Ile Gly Lys Ile Leu
            100                 105                 110

Gln Arg Ala Gly Trp Lys Arg Thr Ala Tyr Val Ile Thr Thr Lys Val
        115                 120                 125

Tyr Trp Ser Thr Lys Ser Glu Glu Arg Gly Leu Ser Arg Lys His Ile
    130                 135                 140

Ile Glu Cys Val Arg Ala Ser Leu Gln Arg Leu Gln Leu Gln Tyr Ile
145                 150                 155                 160

Asp Ile Val Ile His Lys Ala Asp Pro Met Cys Pro Met Glu Glu
                165                 170                 175

Val Val Arg Ala Met Ser Tyr Val Ile Gln Gln Gly Trp Ala Met Tyr
                180                 185                 190

Trp Gly Thr Ala Arg Trp Ser Gln Val Glu Ile Met Glu Ala Tyr Thr
            195                 200                 205

Asn Cys Arg Gln Phe Asn Cys Ile Thr Pro Ile Val Glu Gln Ser Glu
        210                 215                 220

Tyr His Met Phe Cys Arg Glu Lys Cys Glu Leu Tyr Leu Pro Glu Met
225                 230                 235                 240

Tyr Asn Lys Ile Gly Val Gly Leu Met Ala Trp Gly Pro Leu Ser Met
                245                 250                 255

Ala Leu Ser Asp Thr Gln Asn Gly Asp Lys Leu Phe Leu Pro Lys Gly
            260                 265                 270

Ser Phe Lys Thr Lys Ser Phe Ser Trp Thr Glu Asp Glu Ile Asn Arg
        275                 280                 285

Asn Ala Ala Leu Ser Pro Gln Gly Ser Trp Gly Lys Asp Arg Ile Asp
    290                 295                 300

Glu Gly Arg Arg His Cys Asp Arg Leu Arg Asp Leu Ala Ala Leu Ala
305                 310                 315                 320

Glu Lys Leu Gly Cys Ser Pro Thr Gln Leu Ser Ile Ala Trp Ser Leu
                325                 330                 335

Lys His Glu Pro Val Gln Cys Leu Leu Leu Gly Ala Thr Ser Ala Glu
            340                 345                 350

Gln Leu His Gln Ser Leu Gln Ser Leu Gln Leu Pro Arg Leu Ser
        355                 360                 365

Ser Ser Val Met Leu Glu Leu Glu Arg Ile Leu Glu Asn Lys Pro Val
370                 375                 380

Arg Pro Pro Met Ile Ser Thr Leu Ala Leu Arg
385                 390                 395

<210> SEQ ID NO 88
<211> LENGTH: 23
<212> TYPE: DNA
<213> ORGANISM: Artificial sequence
<220> FEATURE:
<223> OTHER INFORMATION: Primer

<400> SEQUENCE: 88
ccggtaccat ggccgccgtt gcc                                          23

<210> SEQ ID NO 89
<211> LENGTH: 22
<212> TYPE: DNA
<213> ORGANISM: Artificial sequence
<220> FEATURE:
<223> OTHER INFORMATION: Primer
```

```
<400> SEQUENCE: 89
ccggtctccg tagtcggcca cc                                                22

<210> SEQ ID NO 90
<211> LENGTH: 24
<212> TYPE: DNA
<213> ORGANISM: Artificial sequence
<220> FEATURE:
<223> OTHER INFORMATION: Primer

<400> SEQUENCE: 90
gccaccatgt tcgctggcgg aggt                                              24

<210> SEQ ID NO 91
<211> LENGTH: 22
<212> TYPE: DNA
<213> ORGANISM: Artificial sequence
<220> FEATURE:
<223> OTHER INFORMATION: Primer

<400> SEQUENCE: 91
tcattgatca ctgcaaacct cg                                                22

<210> SEQ ID NO 92
<211> LENGTH: 25
<212> TYPE: DNA
<213> ORGANISM: Artificial sequence
<220> FEATURE:
<223> OTHER INFORMATION: Primer

<400> SEQUENCE: 92
gccaccatgt ggcactcggg cggca                                             25

<210> SEQ ID NO 93
<211> LENGTH: 18
<212> TYPE: DNA
<213> ORGANISM: Artificial sequence
<220> FEATURE:
<223> OTHER INFORMATION: Primer

<400> SEQUENCE: 93
tcagacgtca gtttcgac                                                     18

<210> SEQ ID NO 94
<211> LENGTH: 25
<212> TYPE: DNA
<213> ORGANISM: Artificial sequence
<220> FEATURE:
<223> OTHER INFORMATION: Primer

<400> SEQUENCE: 94
gccaccatgt ggcactcggg cggca                                             25

<210> SEQ ID NO 95
<211> LENGTH: 18
<212> TYPE: DNA
<213> ORGANISM: Artificial sequence
<220> FEATURE:
<223> OTHER INFORMATION: Primer

<400> SEQUENCE: 95
tcagacgtca gtttcgac                                                     18

<210> SEQ ID NO 96
```

```
<211> LENGTH: 25
<212> TYPE: DNA
<213> ORGANISM: Artificial sequence
<220> FEATURE:
<223> OTHER INFORMATION: Primer

<400> SEQUENCE: 96
gccaccatgt ggcactcggg cggca                                   25

<210> SEQ ID NO 97
<211> LENGTH: 18
<212> TYPE: DNA
<213> ORGANISM: Artificial sequence
<220> FEATURE:
<223> OTHER INFORMATION: Primer

<400> SEQUENCE: 97
tcagacgtca gtttcgac                                           18

<210> SEQ ID NO 98
<211> LENGTH: 36
<212> TYPE: DNA
<213> ORGANISM: Artificial sequence
<220> FEATURE:
<223> OTHER INFORMATION: Primer

<400> SEQUENCE: 98
gccaccatgt gccgggctcc cattgcgtca ctcgac                       36

<210> SEQ ID NO 99
<211> LENGTH: 30
<212> TYPE: DNA
<213> ORGANISM: Artificial sequence
<220> FEATURE:
<223> OTHER INFORMATION: Primer

<400> SEQUENCE: 99
tcaccggagc gccaaggtcg agatcatcgg                              30

<210> SEQ ID NO 100
<211> LENGTH: 36
<212> TYPE: DNA
<213> ORGANISM: Artificial sequence
<220> FEATURE:
<223> OTHER INFORMATION: Primer

<400> SEQUENCE: 100
gccaccatgt gccgggctcc cattgcgtca ctcgac                       36

<210> SEQ ID NO 101
<211> LENGTH: 30
<212> TYPE: DNA
<213> ORGANISM: Artificial sequence
<220> FEATURE:
<223> OTHER INFORMATION: Primer

<400> SEQUENCE: 101
tcaccggagc gccaaggtcg agatcatcgg                              30

<210> SEQ ID NO 102
<211> LENGTH: 480
<212> TYPE: PRT
<213> ORGANISM: Artificial sequence
<220> FEATURE:
<223> OTHER INFORMATION: Consensus
<220> FEATURE:
<221> NAME/KEY: misc_feature
```

```
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(32)
<223> OTHER INFORMATION: Xaa can be any naturally occurring amino acid
<220> FEATURE:
<221> NAME/KEY: misc_feature
<222> LOCATION: (34)..(36)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (117)..(118)
<223> OTHER INFORMATION: Xaa can be any naturally occurring amino acid
<220> FEATURE:
<221> NAME/KEY: misc_feature
<222> LOCATION: (135)..(136)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (157)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
```

```
<221> NAME/KEY: misc_feature
<222> LOCATION: (163)..(164)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (256)..(257)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (297)..(298)
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (373)..(375)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid
<220> FEATURE:
<221> NAME/KEY: misc_feature
<222> LOCATION: (464)..(478)
<223> OTHER INFORMATION: Xaa can be any naturally occurring amino acid

<400> SEQUENCE: 102

Ser Leu Pro Lys Leu Xaa Xaa Gln Xaa Glu Xaa Xaa Xaa Xaa Xaa Xaa
```

```
1               5                   10                  15
Xaa Xaa Xaa Xaa Xaa Xaa Xaa Xaa Xaa Xaa Xaa Xaa Xaa Xaa
                20                  25                  30
Gly Xaa Xaa Xaa Phe Glu Pro Ile Xaa His Asp His Asp Phe Cys Glu
        35                  40                  45
Arg Val Xaa Ile Asn Val Ser Gly Xaa Xaa Phe Glu Thr Gln Leu Arg
    50                  55                  60
Thr Leu Asn Gln Phe Pro Xaa Thr Leu Leu Gly Asp Pro Xaa Arg Arg
65                  70                  75                  80
Xaa Arg Tyr Phe Asp Pro Leu Arg Asn Glu Tyr Phe Phe Asp Arg Xaa
            85                  90                  95
Arg Pro Xaa Phe Asp Ala Ile Leu Tyr Tyr Gln Ser Gly Gly Arg
            100                 105                 110
Leu Arg Arg Pro Xaa Xaa Val Pro Leu Asp Val Phe Ser Glu Glu Ile
            115                 120                 125
Lys Phe Tyr Glu Leu Gly Xaa Xaa Ala Xaa Asn Lys Phe Arg Glu Xaa
            130                 135                 140
Glu Gly Phe Ile Lys Glu Glu Xaa Pro Xaa Pro Xaa Xaa Glu Xaa
145                 150                 155                 160
Gln Arg Xaa Xaa Trp Leu Leu Phe Glu Tyr Pro Glu Ser Ser Gln Ala
            165                 170                 175
Ala Arg Val Val Ala Ile Ile Ser Val Phe Val Ile Leu Leu Ser Ile
            180                 185                 190
Val Ile Phe Cys Leu Glu Thr Leu Pro Glu Phe Lys His Tyr Lys Val
            195                 200                 205
Phe Asn Thr Thr Thr Asn Gly Thr Lys Ile Glu Glu Asp Glu Val Pro
            210                 215                 220
Asp Ile Thr Asp Pro Phe Phe Leu Ile Glu Thr Xaa Cys Ile Xaa Trp
225                 230                 235                 240
Phe Thr Phe Glu Leu Xaa Val Arg Phe Leu Ala Cys Pro Asn Lys Xaa
            245                 250                 255
Xaa Phe Xaa Xaa Asp Val Met Asn Xaa Ile Asp Ile Ile Ala Ile Ile
            260                 265                 270
Pro Tyr Phe Ile Thr Leu Ala Thr Val Xaa Ala Glu Glu Asp Xaa
            275                 280                 285
Thr Xaa Asn Leu Pro Xaa Ala Pro Xaa Xaa Pro Gln Xaa Lys Ser Xaa
    290                 295                 300
Asn Gln Ala Met Ser Leu Ala Ile Leu Arg Val Ile Arg Leu Val Arg
305                 310                 315                 320
Val Phe Arg Ile Phe Lys Leu Ser Arg His Ser Lys Gly Leu Gln Ile
            325                 330                 335
Leu Gly Arg Thr Leu Lys Ala Ser Met Arg Glu Leu Gly Leu Leu Ile
            340                 345                 350
Phe Phe Leu Phe Ile Gly Val Val Leu Phe Ser Ser Xaa Val Tyr Phe
            355                 360                 365
Ala Glu Ala Gly Xaa Xaa Xaa Ser Phe Phe Lys Ser Ile Pro Asp Ala
            370                 375                 380
Phe Trp Trp Ala Val Val Thr Met Thr Thr Val Gly Tyr Gly Asp Met
385                 390                 395                 400
Xaa Pro Val Gly Val Trp Gly Lys Ile Val Gly Ser Leu Cys Ala Ile
            405                 410                 415
Ala Gly Val Leu Thr Ile Ala Leu Pro Val Pro Val Ile Val Ser Asn
            420                 425                 430
```

```
Phe Asn Tyr Phe Tyr His Arg Glu Thr Asp Gln Glu Xaa Met Gln Ser
            435                 440                 445

Gln Asn Phe Asn His Val Thr Ser Cys Pro Tyr Leu Pro Gly Thr Xaa
450                 455                 460

Xaa Xaa Xaa Xaa Xaa Xaa Xaa Xaa Xaa Xaa Xaa Xaa Xaa Xaa Ser Asp
465                 470                 475                 480

<210> SEQ ID NO 103
<211> LENGTH: 395
<212> TYPE: PRT
<213> ORGANISM: Artificial sequence
<220> FEATURE:
<223> OTHER INFORMATION: Consensus
<220> FEATURE:
<221> NAME/KEY: misc_feature
<222> LOCATION: (18)..(26)
<223> OTHER INFORMATION: Xaa can be any naturally occurring amino acid
<220> FEATURE:
<221> NAME/KEY: misc_feature
<222> LOCATION: (372)..(372)
<223> OTHER INFORMATION: Xaa can be any naturally occurring amino acid

<400> SEQUENCE: 103

Ala Thr Met Cys Arg Ala Pro Ile Ala Ser Leu Asp Cys Met Glu Glu
1               5                   10                  15

Phe Xaa Xaa Xaa Xaa Xaa Xaa Xaa Xaa Gly Arg Ser Ile Ser Leu
            20                  25                  30

Gly Ser Asn Pro Ala Leu Pro Leu Arg His Gly Ser Thr Pro Thr Pro
            35                  40                  45

Gly Leu Arg Tyr Lys Asn Leu Gly Lys Ser Gly Leu Arg Ile Ser Asn
50                  55                  60

Val Gly Leu Gly Thr Trp Pro Val Phe Ser Pro Gly Val Ser Asp Asp
65                  70                  75                  80

Gln Ala Glu Ala Ile Leu Lys Leu Ala Ile Glu Ser Gly Ile Asn Leu
            85                  90                  95

Phe Asp Ile Ser Glu Ala His Ser Glu Thr Glu Ile Gly Lys Ile Leu
            100                 105                 110

Gln Arg Ala Gly Trp Lys Arg Thr Ala Tyr Val Ile Thr Thr Lys Val
            115                 120                 125

Tyr Trp Ser Thr Lys Ser Glu Glu Arg Gly Leu Ser Arg Lys His Ile
130                 135                 140

Ile Glu Cys Val Arg Ala Ser Leu Gln Arg Leu Gln Leu Gln Tyr Ile
145                 150                 155                 160

Asp Ile Val Ile Ile His Lys Ala Asp Pro Met Cys Pro Met Glu Glu
            165                 170                 175

Val Val Arg Ala Met Ser Tyr Val Ile Gln Gln Gly Trp Ala Met Tyr
            180                 185                 190

Trp Gly Thr Ala Arg Trp Ser Gln Val Glu Ile Met Glu Ala Tyr Thr
            195                 200                 205

Asn Cys Arg Gln Phe Asn Cys Ile Thr Pro Ile Val Glu Gln Ser Glu
            210                 215                 220

Tyr His Met Phe Cys Arg Glu Lys Cys Glu Leu Tyr Leu Pro Glu Met
225                 230                 235                 240

Tyr Asn Lys Ile Gly Val Gly Leu Met Ala Trp Gly Pro Leu Ser Met
            245                 250                 255

Ala Leu Ser Asp Thr Gln Asn Gly Asp Lys Leu Phe Leu Pro Lys Gly
            260                 265                 270
```

```
Ser Phe Lys Thr Lys Ser Phe Ser Trp Thr Glu Asp Glu Ile Asn Arg
            275                 280                 285

Asn Ala Ala Leu Ser Pro Gln Gly Ser Trp Lys Asp Arg Ile Asp
        290                 295                 300

Glu Gly Arg Arg His Cys Asp Arg Leu Arg Asp Leu Ala Ala Leu Ala
305                 310                 315                 320

Glu Lys Leu Gly Cys Ser Pro Thr Gln Leu Ser Ile Ala Trp Ser Leu
                325                 330                 335

Lys His Glu Pro Val Gln Cys Leu Leu Leu Gly Ala Thr Ser Ala Glu
                340                 345                 350

Gln Leu His Gln Ser Leu Gln Ser Leu Gln Leu Pro Arg Leu Ser
            355                 360                 365

Ser Ser Val Xaa Leu Glu Leu Glu Arg Ile Leu Glu Asn Lys Pro Val
        370                 375                 380

Arg Pro Pro Met Ile Ser Thr Leu Ala Leu Arg
385                 390                 395

<210> SEQ ID NO 104
<211> LENGTH: 5
<212> TYPE: PRT
<213> ORGANISM: Artificial sequence
<220> FEATURE:
<223> OTHER INFORMATION: Motif

<400> SEQUENCE: 104

Ser Leu Pro Lys Leu
1               5

<210> SEQ ID NO 105
<211> LENGTH: 4
<212> TYPE: PRT
<213> ORGANISM: Artificial sequence
<220> FEATURE:
<223> OTHER INFORMATION: Motif

<400> SEQUENCE: 105

Phe Glu Pro Ile
1

<210> SEQ ID NO 106
<211> LENGTH: 9
<212> TYPE: PRT
<213> ORGANISM: Artificial sequence
<220> FEATURE:
<223> OTHER INFORMATION: Motif

<400> SEQUENCE: 106

His Asp His Asp Phe Cys Glu Arg Val
1               5

<210> SEQ ID NO 107
<211> LENGTH: 5
<212> TYPE: PRT
<213> ORGANISM: Artificial sequence
<220> FEATURE:
<223> OTHER INFORMATION: Motif

<400> SEQUENCE: 107

Ile Asn Val Ser Gly
1               5

<210> SEQ ID NO 108
<211> LENGTH: 12
```

```
<212> TYPE: PRT
<213> ORGANISM: Artificial sequence
<220> FEATURE:
<223> OTHER INFORMATION: Motif

<400> SEQUENCE: 108

Phe Glu Thr Gln Leu Arg Thr Leu Asn Gln Phe Pro
1               5                   10

<210> SEQ ID NO 109
<211> LENGTH: 6
<212> TYPE: PRT
<213> ORGANISM: Artificial sequence
<220> FEATURE:
<223> OTHER INFORMATION: Motif

<400> SEQUENCE: 109

Thr Leu Leu Gly Asp Pro
1               5

<210> SEQ ID NO 110
<211> LENGTH: 14
<212> TYPE: PRT
<213> ORGANISM: Artificial sequence
<220> FEATURE:
<223> OTHER INFORMATION: Motif

<400> SEQUENCE: 110

Arg Tyr Phe Asp Pro Leu Arg Asn Glu Tyr Phe Phe Asp Arg
1               5                   10

<210> SEQ ID NO 111
<211> LENGTH: 17
<212> TYPE: PRT
<213> ORGANISM: Artificial sequence
<220> FEATURE:
<223> OTHER INFORMATION: Motif

<400> SEQUENCE: 111

Phe Asp Ala Ile Leu Tyr Tyr Tyr Gln Ser Gly Gly Arg Leu Arg Arg
1               5                   10                  15

Pro

<210> SEQ ID NO 112
<211> LENGTH: 16
<212> TYPE: PRT
<213> ORGANISM: Artificial sequence
<220> FEATURE:
<223> OTHER INFORMATION: Motif

<400> SEQUENCE: 112

Val Pro Leu Asp Val Phe Ser Glu Glu Ile Lys Phe Tyr Glu Leu Gly
1               5                   10                  15

<210> SEQ ID NO 113
<211> LENGTH: 5
<212> TYPE: PRT
<213> ORGANISM: Artificial sequence
<220> FEATURE:
<223> OTHER INFORMATION: Motif

<400> SEQUENCE: 113

Asn Lys Phe Arg Glu
1               5

<210> SEQ ID NO 114
```

```
<211> LENGTH: 8
<212> TYPE: PRT
<213> ORGANISM: Artificial sequence
<220> FEATURE:
<223> OTHER INFORMATION: Motif

<400> SEQUENCE: 114

Glu Gly Phe Ile Lys Glu Glu Glu
1               5

<210> SEQ ID NO 115
<211> LENGTH: 71
<212> TYPE: PRT
<213> ORGANISM: Artificial sequence
<220> FEATURE:
<223> OTHER INFORMATION: Motif

<400> SEQUENCE: 115

Trp Leu Leu Phe Glu Tyr Pro Glu Ser Ser Gln Ala Ala Arg Val Val
1               5                   10                  15

Ala Ile Ile Ser Val Phe Val Ile Leu Ser Ile Val Ile Phe Cys
            20                  25                  30

Leu Glu Thr Leu Pro Glu Phe Lys His Tyr Lys Val Phe Asn Thr Thr
            35                  40                  45

Thr Asn Gly Thr Lys Ile Glu Glu Asp Glu Val Pro Asp Ile Thr Asp
    50                  55                  60

Pro Phe Phe Leu Ile Glu Thr
65                  70

<210> SEQ ID NO 116
<211> LENGTH: 6
<212> TYPE: PRT
<213> ORGANISM: Artificial sequence
<220> FEATURE:
<223> OTHER INFORMATION: Motif

<400> SEQUENCE: 116

Trp Phe Thr Phe Glu Leu
1               5

<210> SEQ ID NO 117
<211> LENGTH: 9
<212> TYPE: PRT
<213> ORGANISM: Artificial sequence
<220> FEATURE:
<223> OTHER INFORMATION: Motif

<400> SEQUENCE: 117

Val Arg Phe Leu Ala Cys Pro Asn Lys
1               5

<210> SEQ ID NO 118
<211> LENGTH: 4
<212> TYPE: PRT
<213> ORGANISM: Artificial sequence
<220> FEATURE:
<223> OTHER INFORMATION: Motif

<400> SEQUENCE: 118

Asp Val Met Asn
1

<210> SEQ ID NO 119
<211> LENGTH: 16
<212> TYPE: PRT
```

```
<213> ORGANISM: Artificial sequence
<220> FEATURE:
<223> OTHER INFORMATION: Motif

<400> SEQUENCE: 119

Ile Asp Ile Ile Ala Ile Ile Pro Tyr Phe Ile Thr Leu Ala Thr Val
1               5                   10                  15

<210> SEQ ID NO 120
<211> LENGTH: 5
<212> TYPE: PRT
<213> ORGANISM: Artificial sequence
<220> FEATURE:
<223> OTHER INFORMATION: Motif

<400> SEQUENCE: 120

Ala Glu Glu Glu Asp
1               5

<210> SEQ ID NO 121
<211> LENGTH: 60
<212> TYPE: PRT
<213> ORGANISM: Artificial sequence
<220> FEATURE:
<223> OTHER INFORMATION: Motif

<400> SEQUENCE: 121

Asn Gln Ala Met Ser Leu Ala Ile Leu Arg Val Ile Arg Leu Val Arg
1               5                   10                  15

Val Phe Arg Ile Phe Lys Leu Ser Arg His Ser Lys Gly Leu Gln Ile
                20                  25                  30

Leu Gly Arg Thr Leu Lys Ala Ser Met Arg Glu Leu Gly Leu Leu Ile
            35                  40                  45

Phe Phe Leu Phe Ile Gly Val Val Leu Phe Ser Ser
        50                  55                  60

<210> SEQ ID NO 122
<211> LENGTH: 7
<212> TYPE: PRT
<213> ORGANISM: Artificial sequence
<220> FEATURE:
<223> OTHER INFORMATION: Motif

<400> SEQUENCE: 122

Val Tyr Phe Ala Glu Ala Gly
1               5

<210> SEQ ID NO 123
<211> LENGTH: 25
<212> TYPE: PRT
<213> ORGANISM: Artificial sequence
<220> FEATURE:
<223> OTHER INFORMATION: Motif

<400> SEQUENCE: 123

Ser Phe Phe Lys Ser Ile Pro Asp Ala Phe Trp Trp Ala Val Val Thr
1               5                   10                  15

Met Thr Thr Val Gly Tyr Gly Asp Met
                20                  25

<210> SEQ ID NO 124
<211> LENGTH: 43
<212> TYPE: PRT
<213> ORGANISM: Artificial sequence
<220> FEATURE:
```

<223> OTHER INFORMATION: Motif

<400> SEQUENCE: 124

```
Pro Val Gly Val Trp Gly Lys Ile Val Gly Ser Leu Cys Ala Ile Ala
1               5                   10                  15

Gly Val Leu Thr Ile Ala Leu Pro Val Pro Val Ile Val Ser Asn Phe
            20                  25                  30

Asn Tyr Phe Tyr His Arg Glu Thr Asp Gln Glu
        35                  40
```

<210> SEQ ID NO 125
<211> LENGTH: 18
<212> TYPE: PRT
<213> ORGANISM: Artificial sequence
<220> FEATURE:
<223> OTHER INFORMATION: Motif

<400> SEQUENCE: 125

```
Met Gln Ser Gln Asn Phe Asn His Val Thr Ser Cys Pro Tyr Leu Pro
1               5                   10                  15

Gly Thr
```

<210> SEQ ID NO 126
<211> LENGTH: 17
<212> TYPE: PRT
<213> ORGANISM: Artificial sequence
<220> FEATURE:
<223> OTHER INFORMATION: Motif

<400> SEQUENCE: 126

```
Ala Thr Met Cys Arg Ala Pro Ile Ala Ser Leu Asp Cys Met Glu Glu
1               5                   10                  15

Phe
```

<210> SEQ ID NO 127
<211> LENGTH: 345
<212> TYPE: PRT
<213> ORGANISM: Artificial sequence
<220> FEATURE:
<223> OTHER INFORMATION: Motif

<400> SEQUENCE: 127

```
Gly Arg Ser Ile Ser Leu Gly Ser Asn Pro Ala Leu Pro Leu Arg His
1               5                   10                  15

Gly Ser Thr Pro Thr Pro Gly Leu Arg Tyr Lys Asn Leu Gly Lys Ser
            20                  25                  30

Gly Leu Arg Ile Ser Asn Val Gly Leu Gly Thr Trp Pro Val Phe Ser
            35                  40                  45

Pro Gly Val Ser Asp Asp Gln Ala Glu Ala Ile Leu Lys Leu Ala Ile
        50                  55                  60

Glu Ser Gly Ile Asn Leu Phe Asp Ile Ser Glu Ala His Ser Glu Thr
65                  70                  75                  80

Glu Ile Gly Lys Ile Leu Gln Arg Ala Gly Trp Lys Arg Thr Ala Tyr
                85                  90                  95

Val Ile Thr Thr Lys Val Tyr Trp Ser Thr Lys Ser Glu Glu Arg Gly
            100                 105                 110

Leu Ser Arg Lys His Ile Ile Glu Cys Val Arg Ala Ser Leu Gln Arg
        115                 120                 125

Leu Gln Leu Gln Tyr Ile Asp Ile Val Ile His Lys Ala Asp Pro
        130                 135                 140
```

```
Met Cys Pro Met Glu Glu Val Val Arg Ala Met Ser Tyr Val Ile Gln
145                 150                 155                 160

Gln Gly Trp Ala Met Tyr Trp Gly Thr Ala Arg Trp Ser Gln Val Glu
            165                 170                 175

Ile Met Glu Ala Tyr Thr Asn Cys Arg Gln Phe Asn Cys Ile Thr Pro
        180                 185                 190

Ile Val Glu Gln Ser Gly Tyr His Met Phe Cys Arg Glu Lys Cys Glu
    195                 200                 205

Leu Tyr Leu Pro Glu Met Tyr Asn Lys Ile Gly Val Gly Leu Met Ala
210                 215                 220

Trp Gly Pro Leu Ser Met Ala Leu Ser Asp Thr Gln Asn Gly Asp Lys
225                 230                 235                 240

Leu Phe Leu Pro Lys Gly Ser Phe Lys Thr Lys Ser Phe Ser Trp Thr
                245                 250                 255

Glu Asp Glu Ile Asn Arg Asn Ala Ala Leu Ser Pro Gln Gly Ser Trp
            260                 265                 270

Gly Lys Asp Arg Ile Asp Glu Gly Arg Arg His Cys Asp Arg Leu Arg
        275                 280                 285

Asp Leu Ala Ala Leu Ala Glu Lys Leu Gly Cys Ser Pro Thr Gln Leu
    290                 295                 300

Ser Ile Ala Trp Ser Leu Lys His Glu Pro Val Gln Cys Leu Leu Leu
305                 310                 315                 320

Gly Ala Thr Ser Ala Glu Gln Leu His Gln Ser Leu Gln Ser Leu Gln
                325                 330                 335

Leu Leu Pro Arg Leu Ser Ser Ser Val
            340                 345

<210> SEQ ID NO 128
<211> LENGTH: 23
<212> TYPE: PRT
<213> ORGANISM: Artificial sequence
<220> FEATURE:
<223> OTHER INFORMATION: Motif

<400> SEQUENCE: 128

Leu Glu Leu Glu Arg Ile Leu Glu Asn Lys Pro Val Arg Pro Pro Met
1               5                   10                  15

Ile Ser Thr Leu Ala Leu Arg
            20

<210> SEQ ID NO 129
<211> LENGTH: 1527
<212> TYPE: DNA
<213> ORGANISM: Drosophila melanogaster

<400> SEQUENCE: 129
atgacgctac tgcagaggct tcaggccatg tcggccacca cgaccaggac aatactggag      60
ggcagcatca gcagttttgg tggcgggaca atgagcctc tggcgagcaa atacccgtt      120 ctggaggagt ccgcctcaca tgccagatat ttgaaattca ttgccgacgg gctcatcgac     180
gagggtctgg gcagtgcggt tggcagtggg agcagcatcg ccgtatccgt tgaagacgtg     240
gtcgccggac aggcgcagga catccaggcg agcgaaggat ccaccgacga cgccgacggc     300
agtagccatt tggcattagt cttcgtcaag tgtttcatta ttggtttcat catactggcc     360
gccatcctgg gcaacatgct ggtgattgtg tcggtcatgc ggcaccggaa attgcgcatc     420
attaccaact actttgtggt ctctctggcc gtcgccgaca tgctggtggc cctctgtgcg     480
```

```
atgacattta atgcttccgt catgatctcg ggcaagtgga tgtttggttc cgtgatgtgc    540
gacatgtgga acagcttcga cgtctacttc tccaccgcca gcatcatgca cctctgttgc    600
atatcggtcg acagatacta cgccattgtg cagccactgg actatccact aatcatgaca    660
cagcgacgcg tgttcatcat gctattgatg gtgtggctat cgccggcgct cctctcgttc    720
ctgcccatct gctcgggatg gtacacaacg accgagaact acaagtatct caaatcgaat    780
ccgcatatat gcgagttcaa agtgaacaag catacgcca tagtcagctc gtcgatgagc     840
ttctggattc ccggcatcgt aatgctgtcg atgtactacc gcatttacca ggaggccgac    900
cgacaggagc gtctggtgta cagatccaag gtggccgctc tgctgctgga aagcatctg     960 cagattagcc aaattcccaa gccccggccg agcattcagg tggagcagtc gaccatctcg   1020
acgatgcggc gtgagcggaa ggccgcccgc accctgggca tcatcatgag cgccttcctc   1080
atctgctggc tgccgttctt cctctggtac atcgtatcct cgctgtgcga tagttgcatc   1140
actccgcgcc tgctcgttgg catcctgttt tggatcggct acttcaactc ggccctgaac   1200
cccattattt atgcatactt caaccgcgac ttcagggccg ccttcaagaa gaccctcaag   1260
agtctgtttc cctacgcttt ctacttctgt cgacgtggca gggggcgaga cgatgaccgg   1320
gatctggagt tcggcggtcc cagccgacgg ggaaccaatg gagcccaacg gaccggatcc   1380
ggatccgccg agatggccaa ctgcgtcaac tccacggcct cgtcggagat acacatgagc   1440
gtgatgcgtg cccgccagta tgccgtcaat gtcacaccca ccacggacgc ccagatgcag   1500
cagctgcatc ccctgtacac caactaa                                       1527
```

<210> SEQ ID NO 130
<211> LENGTH: 508
<212> TYPE: PRT
<213> ORGANISM: Drosophila melanogaster

<400> SEQUENCE: 130

```
Met Thr Leu Leu Gln Arg Leu Gln Ala Met Ser Ala Thr Thr Thr Arg
1               5                   10                  15

Thr Ile Leu Glu Gly Ser Ile Ser Ser Phe Gly Gly Gly Thr Asn Glu
            20                  25                  30

Pro Leu Ala Ser Lys Ile Pro Val Leu Glu Glu Ser Ala Ser His Ala
        35                  40                  45

Arg Tyr Leu Lys Phe Ile Ala Asp Gly Leu Ile Asp Glu Gly Leu Gly
    50                  55                  60

Ser Ala Val Gly Ser Gly Ser Ile Ala Val Ser Val Glu Asp Val
65                  70                  75                  80

Val Ala Gly Gln Ala Gln Asp Ile Gln Ala Ser Glu Gly Ser Thr Asp
                85                  90                  95

Asp Ala Asp Gly Ser Ser His Leu Ala Leu Val Phe Val Lys Cys Phe
            100                 105                 110

Ile Ile Gly Phe Ile Ile Leu Ala Ala Ile Leu Gly Asn Met Leu Val
        115                 120                 125

Ile Val Ser Val Met Arg His Arg Lys Leu Arg Ile Ile Thr Asn Tyr
    130                 135                 140

Phe Val Val Ser Leu Ala Val Ala Asp Met Leu Val Ala Leu Cys Ala
145                 150                 155                 160

Met Thr Phe Asn Ala Ser Val Met Ile Ser Gly Lys Trp Met Phe Gly
                165                 170                 175

Ser Val Met Cys Asp Met Trp Asn Ser Phe Asp Val Tyr Phe Ser Thr
```

```
            180             185                 190
Ala Ser Ile Met His Leu Cys Cys Ile Ser Val Asp Arg Tyr Tyr Ala
        195                 200                 205

Ile Val Gln Pro Leu Asp Tyr Pro Leu Ile Met Thr Gln Arg Arg Val
    210                 215                 220

Phe Ile Met Leu Leu Met Val Trp Leu Ser Pro Ala Leu Leu Ser Phe
225                 230                 235                 240

Leu Pro Ile Cys Ser Gly Trp Tyr Thr Thr Thr Glu Asn Tyr Lys Tyr
                245                 250                 255

Leu Lys Ser Asn Pro His Ile Cys Glu Phe Lys Val Asn Lys Ala Tyr
            260                 265                 270

Ala Ile Val Ser Ser Ser Met Ser Phe Trp Ile Pro Gly Ile Val Met
        275                 280                 285

Leu Ser Met Tyr Tyr Arg Ile Tyr Gln Glu Ala Asp Arg Gln Glu Arg
    290                 295                 300

Leu Val Tyr Arg Ser Lys Val Ala Ala Leu Leu Glu Lys His Leu
305                 310                 315                 320

Gln Ile Ser Gln Ile Pro Lys Pro Arg Pro Ser Ile Gln Val Glu Gln
                325                 330                 335

Ser Thr Ile Ser Thr Met Arg Arg Glu Arg Lys Ala Ala Arg Thr Leu
            340                 345                 350

Gly Ile Ile Met Ser Ala Phe Leu Ile Cys Trp Leu Pro Phe Phe Leu
        355                 360                 365

Trp Tyr Ile Val Ser Ser Leu Cys Asp Ser Cys Ile Thr Pro Arg Leu
    370                 375                 380

Leu Val Gly Ile Leu Phe Trp Ile Gly Tyr Phe Asn Ser Ala Leu Asn
385                 390                 395                 400

Pro Ile Ile Tyr Ala Tyr Phe Asn Arg Asp Phe Arg Ala Ala Phe Lys
                405                 410                 415

Lys Thr Leu Lys Ser Leu Phe Pro Tyr Ala Phe Tyr Phe Cys Arg Arg
            420                 425                 430

Gly Arg Gly Arg Asp Asp Asp Arg Asp Leu Glu Phe Gly Gly Pro Ser
        435                 440                 445

Arg Arg Gly Thr Asn Gly Ala Gln Arg Thr Gly Ser Gly Ser Ala Glu
    450                 455                 460

Met Ala Asn Cys Val Asn Ser Thr Ala Ser Ser Glu Ile His Met Ser
465                 470                 475                 480

Val Met Arg Ala Arg Gln Tyr Ala Val Asn Val Thr Pro Thr Thr Asp
                485                 490                 495

Ala Gln Met Gln Gln Leu His Pro Leu Tyr Thr Asn
            500                 505

<210> SEQ ID NO 131
<211> LENGTH: 25
<212> TYPE: DNA
<213> ORGANISM: Artificial sequence
<220> FEATURE:
<223> OTHER INFORMATION: Primer

<400> SEQUENCE: 131
atgacgctac tgcagaggct tcagg                                   25

<210> SEQ ID NO 132
<211> LENGTH: 22
<212> TYPE: DNA
<213> ORGANISM: Artificial sequence
```

<220> FEATURE:
<223> OTHER INFORMATION: Primer

<400> SEQUENCE: 132
ttagttggtg tacaggggat gc    22

<210> SEQ ID NO 133
<211> LENGTH: 1185
<212> TYPE: DNA
<213> ORGANISM: Myzus persicae

<400> SEQUENCE: 133

```
atggacccgc agatgtggtg gtacgacgcg ggatttgtac caggcggtgt gcagatagct      60
gcagtcgtcg gtaacggcac gtgcggcgga ggtgtcggcg gcggtgtcgg tgtcgacgga     120
gacgccgccg tgggcccggt gctcgtcatc aaaacggtgg ccatgtgctc gataatattg     180
tgcgcggtgc tgggcaacgc tctggtggtg atcagcgtgg tacggcaccg gaagctccgc     240
atactcacca attactacgt cgtgtcgctg gccttcgccg acttcctggt ggcgctgtgc     300
gccatgtcgt tcaacgccag cgtcgagatc accggcaagt ggatgttcgg gtacgtcatg     360
tgtgacgtct ggaacagcct ggacgtgtac ttctccaccg cttccatact gcacctgtgc     420
tgcataagcg tggaccggta ctacgccatc gtcagccctc ttcagtaccc gatcaccatg     480
acgcagcgca ccgtcctgta catgctgctc aacgtgtgga cgctaccagc gctcatatcg     540
ttccttccga tattttcgg ttggtatacg acagccgagc accaggcttt ccgccggaag     600
aaccccatgt cgtgcgtgtt cgtcgtcaac cggtactacg cgatcatatc gtcgtctgtc     660
tcgttttgga tacccggcgt cgtcatgatc gtcatgtact acaggattta caaagaagcc     720
gttcgacaac ggcaagcctt gtcccggacg tccagtaata taattctgaa cagcatacat     780
caacacagga ttcaacacta tagtcataga ttacggcctc cagacagcga aaacatgtca     840
aatggaaacg ttacgacggc gaagaccagt acgagttgga ggaccgagca caaagctgct     900
cgcacgctgg gaatcattat gggcgtattc ctattgtgct ggttgccatt tttcctttgg     960
tatgtgatat cgacattatg cggagatcca tgtagcttcc cggaaacact cgtgaccgtg    1020
ttgtttggga ttggttattt caattcatca ctgaacccac tgatatatgc ctacttcaat    1080
agagacttca gggaagcatt caaaaatacg ctgcagtgtg tgttcccgtg ttgtcagtca    1140
tgttgtccaa aagaaagcga ctcgacagcc atgagctatg tttaa                    1185
```

<210> SEQ ID NO 134
<211> LENGTH: 394
<212> TYPE: PRT
<213> ORGANISM: Myzus persicae

<400> SEQUENCE: 134

Met Asp Pro Gln Met Trp Trp Tyr Asp Ala Gly Phe Val Pro Gly Gly
1               5                   10                  15

Val Gln Ile Ala Ala Val Val Gly Asn Gly Thr Cys Gly Gly Gly Val
            20                  25                  30

Gly Gly Gly Val Gly Val Asp Gly Asp Ala Ala Val Gly Pro Val Leu
        35                  40                  45

Val Ile Lys Thr Val Ala Met Cys Ser Ile Ile Leu Cys Ala Val Leu
    50                  55                  60

Gly Asn Ala Leu Val Val Ile Ser Val Val Arg His Arg Lys Leu Arg
65                  70                  75                  80

Ile Leu Thr Asn Tyr Tyr Val Val Ser Leu Ala Phe Ala Asp Phe Leu

```
            85                  90                  95
Val Ala Leu Cys Ala Met Ser Phe Asn Ala Ser Val Glu Ile Thr Gly
            100                 105                 110
Lys Trp Met Phe Gly Tyr Val Met Cys Asp Val Trp Asn Ser Leu Asp
            115                 120                 125
Val Tyr Phe Ser Thr Ala Ser Ile Leu His Leu Cys Cys Ile Ser Val
            130                 135                 140
Asp Arg Tyr Tyr Ala Ile Val Ser Pro Leu Gln Tyr Pro Ile Thr Met
145                 150                 155                 160
Thr Gln Arg Thr Val Leu Tyr Met Leu Leu Asn Val Trp Thr Leu Pro
                165                 170                 175
Ala Leu Ile Ser Phe Leu Pro Ile Phe Phe Gly Trp Tyr Thr Thr Ala
                180                 185                 190
Glu His Gln Ala Phe Arg Arg Lys Asn Pro Met Ser Cys Val Phe Val
                195                 200                 205
Val Asn Arg Tyr Tyr Ala Ile Ile Ser Ser Ser Val Ser Phe Trp Ile
                210                 215                 220
Pro Gly Val Val Met Ile Val Met Tyr Tyr Arg Ile Tyr Lys Glu Ala
225                 230                 235                 240
Val Arg Gln Arg Gln Ala Leu Ser Arg Thr Ser Ser Asn Ile Ile Leu
                245                 250                 255
Asn Ser Ile His Gln His Arg Ile Gln His Tyr Ser His Arg Leu Arg
                260                 265                 270
Pro Pro Asp Ser Glu Asn Met Ser Asn Gly Asn Val Thr Thr Ala Lys
                275                 280                 285
Thr Ser Thr Ser Trp Arg Thr Glu His Lys Ala Ala Arg Thr Leu Gly
                290                 295                 300
Ile Ile Met Gly Val Phe Leu Leu Cys Trp Leu Pro Phe Phe Leu Trp
305                 310                 315                 320
Tyr Val Ile Ser Thr Leu Cys Gly Asp Pro Cys Ser Phe Pro Glu Thr
                325                 330                 335
Leu Val Thr Val Leu Phe Trp Ile Gly Tyr Phe Asn Ser Ser Leu Asn
                340                 345                 350
Pro Leu Ile Tyr Ala Tyr Phe Asn Arg Asp Phe Arg Glu Ala Phe Lys
                355                 360                 365
Asn Thr Leu Gln Cys Val Phe Pro Cys Cys Gln Ser Cys Cys Pro Lys
                370                 375                 380
Glu Ser Asp Ser Thr Ala Met Ser Tyr Val
385                 390

<210> SEQ ID NO 135
<211> LENGTH: 26
<212> TYPE: DNA
<213> ORGANISM: Artificial sequence
<220> FEATURE:
<223> OTHER INFORMATION: Primer

<400> SEQUENCE: 135
gccaccatgg acccgcagat gtggtg                                      26

<210> SEQ ID NO 136
<211> LENGTH: 20
<212> TYPE: DNA
<213> ORGANISM: Artificial sequence
<220> FEATURE:
<223> OTHER INFORMATION: Primer
```

<400> SEQUENCE: 136

```
ttaaacatag ctcatggctg                                               20
```

<210> SEQ ID NO 137
<211> LENGTH: 1603
<212> TYPE: DNA
<213> ORGANISM: Tribolium castaneum

<400> SEQUENCE: 137

```
atgcttaggt gggtagtgga aattcgcgtt ttccataaga ggtcgcttgc ttcgccgcaa    60
agccgcgaaa agctccggag ttaccctaaa cagcacagtt tgccgcgcgt tgccgaccaa   120
aaactaccat cgtccggaaa actcaaagca aaacgtgcca acattttcga caactctttg   180
agacacagta accttttttt accataatgt ccaaaccacg ccaattcctc acttgaactc   240
agccatgaac gagatcctcg tcataaccga cttggtgact caagcctctc tgaagaactc   300
caccgacaat cccaacgaca cgtccgaggc gatccacata tccaacaact acgcgtactc   360
tctccagccg acatgggcga agaactcttg gctcctctgc ttcctgctga cggtcaagac   420
caccgtgatg gccctaatca taatcgccgc gttgttcggc aacctcctag tgatagtttc   480
agtgatgcgc atcggaagc tgcgcgttat caccaactat ttcgtcgtga gcttagctct   540
ggccgatatg ctggtcgcaa tttgggcgat gtgttttaat ttcagtgtgg agatcacggg   600
cggtagatgg atatttggct actttatgtg tgacgtgtgg aactctctgg acgtgtattt   660
ttcgacagcg tctatttac atttgtgttg tataagtgtg acagatact acgccatcgt    720
gcagccactc gactatccct tgatcatgac gaatgcaagg cttgcggtca tgctggccgt   780
cgtgtggtgc agtccggctt tagtgtcctt cttgcccata tttatggagt ggtacacgac   840
cgaggaacat ctacaattca ggaggaagca tccttacata tgcaccttca cagtcaacag   900
gacctattca gttatttctt cgagcgtcag cttctgggtg cccggcatgg tcatgatatt   960
catgtactac agaatttatg tggaagccga caggcaagag cggatgctct accggagtaa  1020
agtagcagca gccctgctca caaacacct gcaaatcaac ggaatatcgg caggactaac   1080
ggcgcttcgt caatcggtag acgcaggact cgaatccgaa aaaactcctg atcctggaac  1140
tagcagcaaa atgaaacgcg aaagaaaagc tgccaggacc ctaggcatca tcgtgtcggc  1200
ctttctagct tgctggcttc cctttttttct gtggtacgtg ataacgtctc tatgtggttc  1260
gaaacgttgc tacagtcccc cgtcggtgat cactttagtt ttctggatcg gttacttcaa  1320
ttcggctttg aatccactaa tctacgccta tttcaatcgc gaatttcggg tggctttcaa  1380
gaaaacgtta cagagttgct gccaactgag ctccaagttg gtctgttgga atggccgag   1440
gtcaagggc gatcatcagg tgaattacag caacgcgtcg agcgagatgc acgttaataa  1500
ccatctcagg actgacttac gagccgaggg tatggcgcaa agattcagct ataacatttc  1560
cgaaggtgaa attattaatt tgcaaagtga agacgctatt taa                     1603
```

<210> SEQ ID NO 138
<211> LENGTH: 452
<212> TYPE: PRT
<213> ORGANISM: Tribolium castaneum

<400> SEQUENCE: 138

```
Met Asn Glu Ile Leu Val Ile Thr Asp Leu Val Thr Gln Ala Ser Leu
1               5                   10                  15

Lys Asn Ser Thr Asp Asn Pro Asn Asp Thr Ser Glu Ala Ile His Ile
            20                  25                  30
```

```
Ser Asn Asn Tyr Ala Tyr Ser Leu Gln Pro Thr Trp Ala Lys Asn Ser
         35                  40                  45

Trp Leu Leu Cys Phe Leu Leu Thr Val Lys Thr Thr Val Met Ala Leu
     50                  55                  60

Ile Ile Ile Ala Ala Leu Phe Gly Asn Leu Leu Val Ile Val Ser Val
 65                  70                  75                  80

Met Arg His Arg Lys Leu Arg Val Ile Thr Asn Tyr Phe Val Val Ser
                 85                  90                  95

Leu Ala Leu Ala Asp Met Leu Val Ala Ile Trp Ala Met Cys Phe Asn
                100                 105                 110

Phe Ser Val Glu Ile Thr Gly Gly Arg Trp Ile Phe Gly Tyr Phe Met
         115                 120                 125

Cys Asp Val Trp Asn Ser Leu Asp Val Tyr Phe Ser Thr Ala Ser Ile
     130                 135                 140

Leu His Leu Cys Cys Ile Ser Val Asp Arg Tyr Tyr Ala Ile Val Gln
145                 150                 155                 160

Pro Leu Asp Tyr Pro Leu Ile Met Thr Asn Ala Arg Leu Ala Val Met
                165                 170                 175

Leu Ala Val Val Trp Cys Ser Pro Ala Leu Val Ser Phe Leu Pro Ile
            180                 185                 190

Phe Met Glu Trp Tyr Thr Thr Glu Glu His Leu Gln Phe Arg Arg Lys
         195                 200                 205

His Pro Tyr Ile Cys Thr Phe Thr Val Asn Arg Thr Tyr Ser Val Ile
     210                 215                 220

Ser Ser Ser Val Ser Phe Trp Val Pro Gly Met Val Met Ile Phe Met
225                 230                 235                 240

Tyr Tyr Arg Ile Tyr Val Glu Ala Asp Arg Gln Glu Arg Met Leu Tyr
                245                 250                 255

Arg Ser Lys Val Ala Ala Ala Leu Leu Asn Lys His Leu Gln Ile Asn
            260                 265                 270

Gly Ile Ser Ala Gly Leu Thr Ala Leu Arg Gln Ser Val Asp Ala Gly
         275                 280                 285

Leu Glu Ser Glu Lys Thr Pro Asp Pro Gly Thr Ser Ser Lys Met Lys
     290                 295                 300

Arg Glu Arg Lys Ala Ala Arg Thr Leu Gly Ile Ile Val Ser Ala Phe
305                 310                 315                 320

Leu Ala Cys Trp Leu Pro Phe Phe Leu Trp Tyr Val Ile Thr Ser Leu
                325                 330                 335

Cys Gly Ser Lys Arg Cys Tyr Ser Pro Ser Val Ile Thr Leu Val
            340                 345                 350

Phe Trp Ile Gly Tyr Phe Asn Ser Ala Leu Asn Pro Leu Ile Tyr Ala
         355                 360                 365

Tyr Phe Asn Arg Glu Phe Arg Val Ala Phe Lys Lys Thr Leu Gln Ser
     370                 375                 380

Cys Cys Gln Leu Ser Ser Lys Leu Val Cys Trp Lys Trp Pro Arg Ser
385                 390                 395                 400

Arg Gly Asp His Gln Val Asn Tyr Ser Asn Ala Ser Ser Glu Met His
                405                 410                 415

Val Asn Asn His Leu Arg Thr Asp Leu Arg Ala Glu Gly Met Ala Gln
            420                 425                 430

Arg Phe Ser Tyr Asn Ile Ser Glu Gly Glu Ile Ile Asn Leu Gln Ser
         435                 440                 445
```

Glu Asp Ala Ile
    450

<210> SEQ ID NO 139
<211> LENGTH: 30
<212> TYPE: DNA
<213> ORGANISM: Artificial sequence
<220> FEATURE:
<223> OTHER INFORMATION: Primer

<400> SEQUENCE: 139
atgcttaggt gggtagtgga aattcgcgtt                                       30

<210> SEQ ID NO 140
<211> LENGTH: 40
<212> TYPE: DNA
<213> ORGANISM: Artificial sequence
<220> FEATURE:
<223> OTHER INFORMATION: Primer

<400> SEQUENCE: 140
ttaaatagcg tcttcacttt gcaaattaat aatttcacct                            40

<210> SEQ ID NO 141
<211> LENGTH: 1329
<212> TYPE: DNA
<213> ORGANISM: Spodoptera eridania

<400> SEQUENCE: 141
atgaaactag aaatcgtttt ggaacctgac aattttactt ttgacatcgc tgatttatct      60
acatcaatgt atctgacgga tatttacgtt aacaagactt tggaagttaa tgagacgacg     120
aacgagttgg tgtactccaa tcaattcgaa gatgatgccc taatagtgtt tctggtgata     180
ctaaaatgtt tgataatgct ctttattata ctggctgcta tatttggcaa tttactcgta     240
atagtttcgg taatgagaca cagaaaactc agagtgatca caactatttt cgttgtgtct     300
ttagccctgg ctgatatgct tgtggcgata tgggcaatgt gtttcaactt cagtgtggaa     360
cttacaaacg gagaatggtt atttggctat ttcatgtgtg acgtatggaa ttccttggat     420
gtatactttt catcggcatc cattctccat ctatgctgca ttagcgtcga cagatattac     480
gccatcgtcc aacctctgga ctatcccctg ataatgacga ctgcaaaatt ggggattatg     540
ttggcagttg tgtggtgcag tccagcttta gtgtcgtttc tcccaatctt catgggttgg     600
tacacaactg aagatcattt gaactttaga aagcgtttcc caaatgtgtg cagttttact     660
gtgaataagg tttatgctgt ggtgtcaagt agtgttagtt tttggatacc gggagtcatc     720
atgctgtata tgtactacag aatttacttg gaagctgaac gacaggagag gatgttatac     780
aggagtaaag tagcagccct acttctggac aaacatctgc agatcaacgg atctcaatg     840 ggcgaggtaa tgcgagagag acagagcata caaatgcagc ccatggccag cagtaagatg     900
aaaagagaga gaaagcagc aaggacccct ggcatcatca tgtccgcttt cttagcgtgt     960
tggctgccat tcttttatg gtacataatc acagctctgt gtggagatgc ctgtccctcc    1020
ccaccacctg tggtagctgc tgtgttttgg gtgggatact tcaactcggc attaaacccc    1080
ctcatctacg catacttcaa cagggacttc agagctgcgt ttaggaagac cttggattct    1140
tgctgcaggt ctctctgcgg cgacattgca cgtcgctact gctgccagcg tcaacgtcgc    1200
gagcaacatc attccaacgc atcctcgac atccacatga caattgcgt taaatcaaca    1260 tccgcagatg tactgcgagc tcatcatgca tcctgctcca ggcctgaaga tatagtcttc    1320
ggaacgtag 1329

<210> SEQ ID NO 142
<211> LENGTH: 442
<212> TYPE: PRT
<213> ORGANISM: Spodoptera eridania

<400> SEQUENCE: 142

```
Met Lys Leu Glu Ile Val Leu Glu Pro Asp Asn Phe Thr Phe Asp Ile
1               5                   10                  15

Ala Asp Leu Ser Thr Ser Met Tyr Leu Thr Asp Ile Tyr Val Asn Lys
            20                  25                  30

Thr Leu Glu Val Asn Glu Thr Thr Asn Glu Leu Val Tyr Ser Asn Gln
        35                  40                  45

Phe Glu Asp Asp Ala Leu Ile Val Phe Leu Val Ile Leu Lys Cys Leu
    50                  55                  60

Ile Met Leu Phe Ile Ile Leu Ala Ala Ile Phe Gly Asn Leu Leu Val
65                  70                  75                  80

Ile Val Ser Val Met Arg His Arg Lys Leu Arg Val Ile Thr Asn Tyr
                85                  90                  95

Phe Val Val Ser Leu Ala Leu Ala Asp Met Leu Val Ala Ile Trp Ala
            100                 105                 110

Met Cys Phe Asn Phe Ser Val Glu Leu Thr Asn Gly Glu Trp Leu Phe
        115                 120                 125

Gly Tyr Phe Met Cys Asp Val Trp Asn Ser Leu Asp Val Tyr Phe Ser
    130                 135                 140

Ser Ala Ser Ile Leu His Leu Cys Cys Ile Ser Val Asp Arg Tyr Tyr
145                 150                 155                 160

Ala Ile Val Gln Pro Leu Asp Tyr Pro Leu Ile Met Thr Thr Ala Lys
                165                 170                 175

Leu Gly Ile Met Leu Ala Val Val Trp Cys Ser Pro Ala Leu Val Ser
            180                 185                 190

Phe Leu Pro Ile Phe Met Gly Trp Tyr Thr Thr Glu Asp His Leu Asn
        195                 200                 205

Phe Arg Lys Arg Phe Pro Asn Val Cys Ser Phe Thr Val Asn Lys Val
    210                 215                 220

Tyr Ala Val Val Ser Ser Val Ser Phe Trp Ile Pro Gly Val Ile
225                 230                 235                 240

Met Leu Tyr Met Tyr Tyr Arg Ile Tyr Leu Glu Ala Glu Arg Gln Glu
                245                 250                 255

Arg Met Leu Tyr Arg Ser Lys Val Ala Ala Leu Leu Leu Asp Lys His
            260                 265                 270

Leu Gln Ile Asn Gly Ile Ser Met Gly Glu Val Met Arg Glu Arg Gln
        275                 280                 285

Ser Ile Gln Met Gln Pro Met Ala Ser Ser Lys Met Lys Arg Glu Arg
    290                 295                 300

Lys Ala Ala Arg Thr Leu Gly Ile Ile Met Ser Ala Phe Leu Ala Cys
305                 310                 315                 320

Trp Leu Pro Phe Phe Leu Trp Tyr Ile Ile Thr Ala Leu Cys Gly Asp
                325                 330                 335

Ala Cys Pro Ser Pro Pro Val Val Ala Ala Val Phe Trp Val Gly
            340                 345                 350

Tyr Phe Asn Ser Ala Leu Asn Pro Leu Ile Tyr Ala Tyr Phe Asn Arg
        355                 360                 365
```

```
Asp Phe Arg Ala Ala Phe Arg Lys Thr Leu Asp Ser Cys Cys Arg Ser
    370                 375                 380

Leu Cys Gly Asp Ile Ala Arg Arg Tyr Cys Cys Gln Arg Gln Arg Arg
385                 390                 395                 400

Glu Gln His His Ser Asn Ala Ser Ser Asp Ile His Met Asn Asn Cys
                405                 410                 415

Val Lys Ser Thr Ser Ala Asp Val Leu Arg Ala His His Ala Ser Cys
            420                 425                 430

Ser Arg Pro Glu Asp Ile Val Phe Gly Thr
            435                 440
```

<210> SEQ ID NO 143
<211> LENGTH: 24
<212> TYPE: DNA
<213> ORGANISM: Artificial sequence
<220> FEATURE:
<223> OTHER INFORMATION: Primer

<400> SEQUENCE: 143
gccaccatga aactagaaat cgtt                                              24

<210> SEQ ID NO 144
<211> LENGTH: 22
<212> TYPE: DNA
<213> ORGANISM: Artificial sequence
<220> FEATURE:
<223> OTHER INFORMATION: Primer

<400> SEQUENCE: 144
ctacgttccg aagactatat ct                                                22

<210> SEQ ID NO 145
<211> LENGTH: 1560
<212> TYPE: DNA
<213> ORGANISM: Spodoptera eridania

<400> SEQUENCE: 145
atgcgctcac tgaacgaaac agcgtgccag gcgctgcttg aagacgtacg gtgggacgag        60
cccgtcagcc ttgtcagctt agcaatactc gcccttattg acgtgcttgt gatcgctggt       120
aactgcctgg tgatagcggc agtgctgtgc tcctctaagc tgcgcagtgt caccaatctg       180
ttcatcgtgt cgctcgcggt cgctgaccta ttggtcggcg ttgcagtact gcctttctca       240
gctactagag aagtgttcga ggtatggatc ttcggcgacg tctggtgttc agtatggcta       300
gcagtagacg tctggatgtg cacggcctcc atcctgaacc tctgtgccat ctccctggac       360
cgctacgtag ccgtcacaag acccgtcagt taccctagca tcatgagcag aaaaagggct       420
aaggctctta tagctggtct ctgggtgctg tcttttgtca tctgtttccc gccgctggtc       480
ggatggaagg ataaaaagcc tgaagaagca gacataaaag acggttgggt ccccaacccc       540
ccttgcgaat ggacctgtga gctgaccaac gatgctggct acgtcgtcta tcagctctc        600 ggttccttct acatccccat gttcgtgatg ctgttctttt attggaggat atacaaagcc       660
gctgttagaa ccaccaaagc aattaatcag ggttttagga ctacgaaagc ctgctctcaa       720
tttgcaggca aaggtatggg cagtcggttc gatgacaacc gactgacgct tcggatacat       780
cgtggtagag gatccaatcg acctcacggg tctccgctat cgaacgcctc caatcattct       840
acgagcacct cgcttagtgc gtccccagaa agattaagaa gacactcaag tgccaggcga       900
gctcatgaga aggtgaaaat ctccgtatcc tatccctcat cagaacaaat atgtccagct       960

```
cacgagaatt ccatgtcttc aagtagatct cccagtccat ctttatacgc agtccattat    1020
gaacgagatg ggagggaact gacagaaagc cggttaaggg ttcgagcttc acatcatttg    1080
gctccaggac cattgtatga tgagtatgat gataagccta ggactactag aaggatgggc    1140
aagaggaata ttaaagctca ggtcaaacgc ttccgtatgg agactaaagc agccaagacc    1200
ctcggcatca tagtcggagg cttcgtgttc tgctggcttc ccttcttcag cgtgtacgtt    1260
gtgagggcgt tctgtgggga ctgtgtcagt cccatcgtct tctccgtgct gttctggctg    1320
ggatactgca actctgccat caacccttg atttatgcgt tattctctaa ggactttaga    1380
ttcgcattca aacgcataat atgcaagtgt tctgcggcg gcggtggccc tagaagagag    1440
tcggacggtg aaggatcccg acggcagaac aaccgaccga ctcactccca ttcactggaa    1500
gaacatgacg cgaacaacca cacctccacc acgactagca ctagcgctgc agataggtga    1560
```

<210> SEQ ID NO 146
<211> LENGTH: 519
<212> TYPE: PRT
<213> ORGANISM: Spodoptera eridania

<400> SEQUENCE: 146

```
Met Arg Ser Leu Asn Glu Thr Ala Cys Gln Ala Leu Leu Glu Asp Val
1               5                   10                  15

Arg Trp Asp Glu Pro Val Ser Leu Val Ser Leu Ala Ile Leu Ala Leu
            20                  25                  30

Ile Asp Val Leu Val Ile Ala Gly Asn Cys Leu Val Ile Ala Ala Val
        35                  40                  45

Leu Cys Ser Ser Lys Leu Arg Ser Val Thr Asn Leu Phe Ile Val Ser
    50                  55                  60

Leu Ala Val Ala Asp Leu Leu Val Gly Val Ala Val Leu Pro Phe Ser
65                  70                  75                  80

Ala Thr Arg Glu Val Phe Glu Val Trp Ile Phe Gly Asp Val Trp Cys
                85                  90                  95

Ser Val Trp Leu Ala Val Asp Val Trp Met Cys Thr Ala Ser Ile Leu
            100                 105                 110

Asn Leu Cys Ala Ile Ser Leu Asp Arg Tyr Val Ala Val Thr Arg Pro
        115                 120                 125

Val Ser Tyr Pro Ser Ile Met Ser Arg Lys Arg Ala Lys Ala Leu Ile
    130                 135                 140

Ala Gly Leu Trp Val Leu Ser Phe Val Ile Cys Phe Pro Pro Leu Val
145                 150                 155                 160

Gly Trp Lys Asp Lys Lys Pro Glu Glu Ala Asp Ile Lys Asp Gly Trp
                165                 170                 175

Val Pro Asn Pro Pro Cys Glu Trp Thr Cys Glu Leu Thr Asn Asp Ala
            180                 185                 190

Gly Tyr Val Val Tyr Ser Ala Leu Gly Ser Phe Tyr Ile Pro Met Phe
        195                 200                 205

Val Met Leu Phe Phe Tyr Trp Arg Ile Tyr Lys Ala Ala Val Arg Thr
    210                 215                 220

Thr Lys Ala Ile Asn Gln Gly Phe Arg Thr Thr Lys Ala Cys Ser Gln
225                 230                 235                 240

Phe Ala Gly Lys Gly Met Gly Ser Arg Phe Asp Asp Asn Arg Leu Thr
                245                 250                 255

Leu Arg Ile His Arg Gly Arg Gly Ser Asn Arg Pro His Gly Ser Pro
            260                 265                 270
```

Leu Ser Asn Ala Ser Asn His Ser Thr Ser Thr Ser Leu Ser Ala Ser
            275                 280                 285

Pro Glu Arg Leu Arg Arg His Ser Ser Ala Arg Ala His Glu Lys
290                 295                 300

Val Lys Ile Ser Val Ser Tyr Pro Ser Ser Glu Gln Ile Cys Pro Ala
305                 310                 315                 320

His Glu Asn Ser Met Ser Ser Ser Arg Ser Pro Ser Pro Ser Leu Tyr
                325                 330                 335

Ala Val His Tyr Glu Arg Asp Gly Arg Glu Leu Thr Glu Ser Arg Leu
            340                 345                 350

Arg Val Arg Ala Ser His His Leu Ala Pro Gly Pro Leu Tyr Asp Glu
355                 360                 365

Tyr Asp Asp Lys Pro Arg Thr Thr Arg Arg Met Gly Lys Arg Asn Ile
370                 375                 380

Lys Ala Gln Val Lys Arg Phe Arg Met Glu Thr Lys Ala Ala Lys Thr
385                 390                 395                 400

Leu Gly Ile Ile Val Gly Gly Phe Val Phe Cys Trp Leu Pro Phe Phe
                405                 410                 415

Ser Val Tyr Val Val Arg Ala Phe Cys Gly Asp Cys Val Ser Pro Ile
            420                 425                 430

Val Phe Ser Val Leu Phe Trp Leu Gly Tyr Cys Asn Ser Ala Ile Asn
435                 440                 445

Pro Leu Ile Tyr Ala Leu Phe Ser Lys Asp Phe Arg Phe Ala Phe Lys
450                 455                 460

Arg Ile Ile Cys Lys Cys Phe Cys Gly Gly Gly Pro Arg Arg Glu
465                 470                 475                 480

Ser Asp Gly Glu Gly Ser Arg Arg Gln Asn Asn Arg Pro Thr His Ser
                485                 490                 495

His Ser Leu Glu Glu His Asp Ala Asn Asn His Thr Ser Thr Thr Thr
            500                 505                 510

Ser Thr Ser Ala Ala Asp Arg
        515

<210> SEQ ID NO 147
<211> LENGTH: 24
<212> TYPE: DNA
<213> ORGANISM: Artificial sequence
<220> FEATURE:
<223> OTHER INFORMATION: Primer

<400> SEQUENCE: 147
gccaccatgc gctcactgaa cgaa                                          24

<210> SEQ ID NO 148
<211> LENGTH: 22
<212> TYPE: DNA
<213> ORGANISM: Artificial sequence
<220> FEATURE:
<223> OTHER INFORMATION: Primer

<400> SEQUENCE: 148
tcacctatct gcagcgctag tg                                            22

<210> SEQ ID NO 149
<211> LENGTH: 1557
<212> TYPE: DNA
<213> ORGANISM: Tribolium castaneum

<400> SEQUENCE: 149

```
gccaccatgc gagaaacact caacgcatcc gcgtgtgcgg cgcttctcga tgctgtcaat    60
tgggggatc cccaattact tctctcctta tcaatcctag ctcttatcaa tgttatggtc   120
attgtgggca actgtttggt cattgctgcc gttttctgct cctccaaact gcgatcagtg   180
acgaacttgt tcatcgtttc tttggctgtt gccgatttac tagtcggagt tgcagttttg   240
cccttttcgg cgacttggga agttttaag gtctggatat tcggcgacgt ttggtgcaac   300
atgtggctgg ctttggacgt ctggatgtgc accgcttcca ttctcaattt gtgtgccatt   360
tctctggacc gttatgtggc cgtcacgcgt cccatcacat atcccagcat catgtcccat   420
tccagagcca agctcttaat cgctggctta tgggtgctca gttttgttat ctgttttccg   480
ccgctggtcg ggtggaaaga gactgaaaga cgttgtcctt ggaagtgcga actgactaac   540
gaggcagggt atgttgtgta ttcagcccct tggtagcttt acataccgat gtttgtcatg   600
ttgttcttct actggaggat ttatcgagcg gctataagaa ccaccagggc aattaaccaa   660
ggatttagga cgaccaaagg ttctcgcggt ttcggcaacc gtttcgacga gcaacgtctc   720
acgttgcgca ttcatcgagg ccgtggctct tcagacaaac gtccccacgg ctcccctcac   780
agcaacggca gcaacagcac caccacaagc agcgtcagcc ccagtccttc cactcgaggc   840
aaacacgagc gcgtcaaaat cagcgtcagt tatccctcca gcgaaaacct ttcgcctaat   900
ccaaacctcc tagctcctgc ctcacccaca cagttcgccg ttcattactc cgtgaacgga   960
aaggacacca ccacggcgtt gtacaaacgc gagaaccagc tgagagtgca gagactgagc  1020
tccaggagga gggcctccag gaggtcgagc agtggcgata cgaacgcgc accaagtccg  1080
agtccgagcg cttgtgaaga agggaagaag gtgatgtcga ggagaatggg caagaggaac  1140
atcaaggcgc aagtgaagag gtttcgcatg gagacaaagg cggccaaaac gctggcaatc  1200
atcgtcggag gttttatctt ctgttggctt ccgttttca ccatgtatct agtgcgggcg  1260
ttttgtcccg attgcattcc accgttgctc ttctccatac tcttctggct ggggtattgc  1320
aacagtgcca tcaatccgct catttatgcc ctcttctcca aagacttcag attcgccttc  1380
aagcgcatcg tctgcaagtg cttctgcaag gtcgcgatg gaggcggtcg tcgcggttcc  1440
gacggttcgc agctccaagg ccgccagttc cgatctccaa gctacaacgt gcagcagcag  1500
ggaaattcgc tcggagacga cagtgatcca ggcgcagatc cgtcggattc gaggtga     1557
```

<210> SEQ ID NO 150
<211> LENGTH: 518
<212> TYPE: PRT
<213> ORGANISM: Tribolium castaneum

<400> SEQUENCE: 150

Ala Thr Met Arg Glu Thr Leu Asn Ala Ser Ala Cys Ala Ala Leu Leu
1               5                   10                  15

Asp Ala Val Asn Trp Gly Asp Pro Gln Leu Leu Leu Ser Leu Ser Ile
            20                  25                  30

Leu Ala Leu Ile Asn Val Met Val Ile Val Gly Asn Cys Leu Val Ile
        35                  40                  45

Ala Ala Val Phe Cys Ser Ser Lys Leu Arg Ser Val Thr Asn Leu Phe
    50                  55                  60

Ile Val Ser Leu Ala Val Ala Asp Leu Leu Val Gly Val Ala Val Leu
65                  70                  75                  80

Pro Phe Ser Ala Thr Trp Glu Val Phe Lys Val Trp Ile Phe Gly Asp
                85                  90                  95

```
Val Trp Cys Asn Met Trp Leu Ala Leu Asp Val Trp Met Cys Thr Ala
            100                 105                 110
Ser Ile Leu Asn Leu Cys Ala Ile Ser Leu Asp Arg Tyr Val Ala Val
        115                 120                 125
Thr Arg Pro Ile Thr Tyr Pro Ser Ile Met Ser His Ser Arg Ala Lys
    130                 135                 140
Leu Leu Ile Ala Gly Leu Trp Val Leu Ser Phe Val Ile Cys Phe Pro
145                 150                 155                 160
Pro Leu Val Gly Trp Lys Glu Thr Glu Arg Arg Cys Pro Trp Lys Cys
                165                 170                 175
Glu Leu Thr Asn Glu Ala Gly Tyr Val Val Tyr Ser Ala Leu Gly Ser
            180                 185                 190
Phe Tyr Ile Pro Met Phe Val Met Leu Phe Phe Tyr Trp Arg Ile Tyr
        195                 200                 205
Arg Ala Ala Ile Arg Thr Thr Arg Ala Ile Asn Gln Gly Phe Arg Thr
    210                 215                 220
Thr Lys Gly Ser Arg Gly Phe Gly Asn Arg Phe Asp Glu Gln Arg Leu
225                 230                 235                 240
Thr Leu Arg Ile His Arg Gly Arg Gly Ser Ser Asp Lys Arg Pro His
                245                 250                 255
Gly Ser Pro His Ser Asn Gly Ser Asn Ser Thr Thr Thr Ser Ser Val
            260                 265                 270
Ser Pro Ser Pro Ser Thr Arg Gly Lys His Glu Arg Val Lys Ile Ser
        275                 280                 285
Val Ser Tyr Pro Ser Ser Glu Asn Leu Ser Pro Asn Pro Asn Leu Leu
    290                 295                 300
Ala Pro Ala Ser Pro Thr Gln Phe Ala Val His Tyr Ser Val Asn Gly
305                 310                 315                 320
Lys Asp Thr Thr Thr Ala Leu Tyr Lys Arg Glu Asn Gln Leu Arg Val
                325                 330                 335
Gln Arg Leu Ser Ser Arg Arg Ala Ser Arg Ser Ser Ser Gly
            340                 345                 350
Asp Ser Glu Arg Ala Pro Ser Pro Ser Pro Ser Ala Cys Glu Glu Gly
            355                 360                 365
Lys Lys Val Met Ser Arg Met Gly Lys Arg Asn Ile Lys Ala Gln
            370                 375                 380
Val Lys Arg Phe Arg Met Glu Thr Lys Ala Ala Lys Thr Leu Ala Ile
385                 390                 395                 400
Ile Val Gly Gly Phe Ile Phe Cys Trp Leu Pro Phe Phe Thr Met Tyr
                405                 410                 415
Leu Val Arg Ala Phe Cys Pro Asp Cys Ile Pro Pro Leu Leu Phe Ser
            420                 425                 430
Ile Leu Phe Trp Leu Gly Tyr Cys Asn Ser Ala Ile Asn Pro Leu Ile
        435                 440                 445
Tyr Ala Leu Phe Ser Lys Asp Phe Arg Phe Ala Phe Lys Arg Ile Val
    450                 455                 460
Cys Lys Cys Phe Cys Lys Gly Arg Asp Gly Gly Arg Arg Gly Ser
465                 470                 475                 480
Asp Gly Ser Gln Leu Gln Gly Arg Gln Phe Arg Ser Pro Ser Tyr Asn
                485                 490                 495
Val Gln Gln Gln Gly Asn Ser Leu Gly Asp Asp Ser Asp Pro Gly Ala
            500                 505                 510
Asp Pro Ser Asp Ser Arg
```

-continued

```
<210> SEQ ID NO 151
<211> LENGTH: 25
<212> TYPE: DNA
<213> ORGANISM: Artificial sequence
<220> FEATURE:
<223> OTHER INFORMATION: Primer

<400> SEQUENCE: 151
gccaccatgc gagaaacact caacg                                              25

<210> SEQ ID NO 152
<211> LENGTH: 24
<212> TYPE: DNA
<213> ORGANISM: Artificial sequence
<220> FEATURE:
<223> OTHER INFORMATION: Primer

<400> SEQUENCE: 152
tcacctcgaa tccgacggat ctgc                                               24

<210> SEQ ID NO 153
<211> LENGTH: 2118
<212> TYPE: DNA
<213> ORGANISM: Myzus persicae

<400> SEQUENCE: 153
atgaaccgga ccgagtgtca gacgctgcgc gactcgctgg tgtggagaga cgcgcaggtg        60
ttgagcaccc tggccggcct gtccttcatc gcgctcatcg tgaccgtcgg caacacgctt       120
gtcgtggccg ccgtattcaa cagttccaaa ctcaggtcac cgaccaacac gttcatcgtt       180
tcgctggccg tgtccgacct aatggtcggc gtggccgtgt tgccgttcag cgccacctgg       240
gaggtgttca aggtgtggct gttcggcgat tacctgtgct ccgtgtggct ggccgtggac       300
gtgtggatgt gcacggccag catcctgaac ctgtgcgcca tcgctggaca caggtacctg       360
gccgtaaccc ggccagtgca gtacccgagc ctgatgacca gtttccgggc caaggtgctg       420
gtggtgatcg tgtgggtgct gagcttcgtc atatgtctgc cgccgctggt ggctggcgg        480 gacactcaca taccggccga agcgtccacg gtgctgatcc ggaacgagct gtaccggaac       540
ggcaccggca gccggccgca gcaggaagag ctgccgccgt cgtgcccgtg gatatgcgag       600
ctgcccaaca acaagtggta cgtcgtgtac tcggcgctgg gctcgttcta cataccgatg       660
ttcgtgatgc tgttcttcta ctggcacatc tacaaggcgg ccgtgcacac cacccgtgcc       720
atcaaccagg gattccggac gatgcgcagc cgccggacgt ttggcaaccg gttcgacgaa       780
cagcgactca cgttgcgcat tcaccgcggc cgcggttcgt cactcaagca ctcggccgcc       840
accgcgtctc cgtcgtccgc cgccgtcatc gcggccaacg gcccgagcgg tgggtcgccg       900
gacgtgaacc ggccgccgaa cagccggcgg ccgtcggtcc ggcgcagcaa ccacgagcgg       960
atcaagatca gcgtcagcta cccgagttca gactgcataa gcgcagcggc ggccgccgcg      1020
gccgtggcca ccgtcaccac aaccaccacc tcggtggacg cgaacggcaa ctccccgccc      1080
gagacgctta gccaaaagtc gcggagctcg ttctcgtcca cgacgtcgcc gaccagctcc      1140
agtccactgt acgccgtcca ctacacggcg gccgagacgt accaacacca gcgggccgcc      1200
acggtccggt cggtggtcga cacgtccgcg tgtcagctgc gcgtggccgg tggcagccgg      1260
aaggaacacc gacggtgcag cgccggcgac acggcctcgc cccattcgcg tctcctgttg      1320
acgtcgtcac cgggcggcga ccatcaccac catcaccagc acagcggtgg aggaatagcg      1380
```

```
ggcgggcgac ccgcgtcctg ttccgtcgcg tccgtcaaag accaactgtc gccgtcgccg    1440
tcgtacgacg agtccactgg tggcggcggc ggtggcagta gtggcggggc gggcgcgagc    1500
gcgggtagcg acgtcgggct cggtcgcggc ggccttgggt cctcaaacag caagtccaag    1560
ttcgcgtcga agatgatggg cggtggcaag cggaacatca aggcccaggt gaagcggttc    1620
cggatggaga ccaaagcggc caagacgctg gcataatcg tcggcggttt catcgtgtgc     1680
tggctacctt tcttcaccat gtacctggta agggcttttt gccccacttg catacaaccc    1740
accctgttct ccgtcatgtt ctggttgggg tactgtaaca gcgccatcaa cccgatgatc    1800
tacgcgctgt tcagcaagga cttccggttc gcgttcaagc ggatcatatg tcggtggtgc    1860
tgttgggcgt ccgccggcga ctcgacggcc ggcatcggcg gaggacttac cgtcgccgac    1920 tacgccgcc gcaaggggtc ggacggttcc cagctgggcg ccgtggcca cggcggcgcg      1980 tcgccccgga acaggtacat cgtgacgggt tccggtgccg gggccgcggg ttccgacgag    2040
tgcagcacgc gcagcatgcg actgctccag tattcggaca gcgaaccgct caacgaaccg    2100
tgttcggacg acaggtga                                                  2118

<210> SEQ ID NO 154
<211> LENGTH: 705
<212> TYPE: PRT
<213> ORGANISM: Myzus persicae

<400> SEQUENCE: 154

Met Asn Arg Thr Glu Cys Gln Thr Leu Arg Asp Ser Leu Val Trp Arg
1               5                   10                  15

Asp Ala Gln Val Leu Ser Thr Leu Ala Gly Leu Ser Phe Ile Ala Leu
                20                  25                  30

Ile Val Thr Val Gly Asn Thr Leu Val Val Ala Ala Val Phe Asn Ser
            35                  40                  45

Ser Lys Leu Arg Ser Pro Thr Asn Thr Phe Ile Val Ser Leu Ala Val
        50                  55                  60

Ser Asp Leu Met Val Gly Val Ala Val Leu Pro Phe Ser Ala Thr Trp
65                  70                  75                  80

Glu Val Phe Lys Val Trp Leu Phe Gly Asp Tyr Leu Cys Ser Val Trp
                85                  90                  95

Leu Ala Val Asp Val Trp Met Cys Thr Ala Ser Ile Leu Asn Leu Cys
            100                 105                 110

Ala Ile Ser Leu Asp Arg Tyr Leu Ala Val Thr Arg Pro Val Gln Tyr
        115                 120                 125

Pro Ser Leu Met Thr Ser Phe Arg Ala Lys Val Leu Val Ile Val
    130                 135                 140

Trp Val Leu Ser Phe Val Ile Cys Leu Pro Pro Leu Val Gly Trp Arg
145                 150                 155                 160

Asp Thr His Ile Pro Ala Glu Ala Ser Thr Val Leu Ile Arg Asn Glu
                165                 170                 175

Leu Tyr Arg Asn Gly Thr Gly Ser Arg Pro Gln Gln Glu Glu Leu Pro
            180                 185                 190

Pro Ser Cys Pro Trp Ile Cys Glu Leu Pro Asn Asn Lys Trp Tyr Val
        195                 200                 205

Val Tyr Ser Ala Leu Gly Ser Phe Tyr Ile Pro Met Phe Val Met Leu
    210                 215                 220

Phe Phe Tyr Trp His Ile Tyr Lys Ala Ala Val His Thr Thr Arg Ala
225                 230                 235                 240
```

```
Ile Asn Gln Gly Phe Arg Thr Met Arg Ser Arg Arg Thr Phe Gly Asn
                245                 250                 255

Arg Phe Asp Glu Gln Arg Leu Thr Leu Arg Ile His Arg Gly Arg Gly
            260                 265                 270

Ser Ser Leu Lys His Ser Ala Ala Thr Ala Ser Pro Ser Ser Ala Ala
        275                 280                 285

Val Ile Ala Ala Asn Gly Pro Ser Gly Gly Ser Pro Asp Val Asn Arg
    290                 295                 300

Pro Pro Asn Ser Arg Arg Pro Ser Val Arg Arg Ser Asn His Glu Arg
305                 310                 315                 320

Ile Lys Ile Ser Val Ser Tyr Pro Ser Ser Asp Cys Ile Ser Ala Ala
                325                 330                 335

Ala Ala Ala Ala Ala Val Ala Thr Val Thr Thr Thr Thr Thr Ser Val
            340                 345                 350

Asp Ala Asn Gly Asn Ser Pro Pro Glu Thr Leu Ser Gln Lys Ser Arg
        355                 360                 365

Ser Ser Phe Ser Ser Thr Thr Ser Pro Thr Ser Ser Ser Pro Leu Tyr
    370                 375                 380

Ala Val His Tyr Thr Ala Ala Glu Thr Tyr Gln His Gln Arg Ala Ala
385                 390                 395                 400

Thr Val Arg Ser Val Val Asp Thr Ser Ala Cys Gln Leu Arg Val Ala
                405                 410                 415

Gly Gly Ser Arg Lys Glu His Arg Arg Cys Ser Ala Gly Asp Thr Ala
            420                 425                 430

Ser Pro His Ser Arg Leu Leu Leu Thr Ser Ser Pro Gly Gly Asp His
        435                 440                 445

His His His His Gln His Ser Gly Gly Ile Ala Gly Gly Arg Pro
    450                 455                 460

Ala Ser Cys Ser Val Ala Ser Val Lys Asp Gln Leu Ser Pro Ser Pro
465                 470                 475                 480

Ser Tyr Asp Glu Ser Thr Gly Gly Gly Gly Gly Ser Ser Gly Gly
                485                 490                 495

Ala Gly Ala Ser Ala Gly Ser Asp Val Gly Leu Gly Arg Gly Gly Leu
            500                 505                 510

Gly Ser Ser Asn Ser Lys Ser Lys Phe Ala Ser Lys Met Met Gly Gly
        515                 520                 525

Gly Lys Arg Asn Ile Lys Ala Gln Val Lys Arg Phe Arg Met Glu Thr
    530                 535                 540

Lys Ala Ala Lys Thr Leu Gly Ile Ile Val Gly Gly Phe Ile Val Cys
545                 550                 555                 560

Trp Leu Pro Phe Phe Thr Met Tyr Leu Val Arg Ala Phe Cys Pro Thr
                565                 570                 575

Cys Ile Gln Pro Thr Leu Phe Ser Val Met Phe Trp Leu Gly Tyr Cys
            580                 585                 590

Asn Ser Ala Ile Asn Pro Met Ile Tyr Ala Leu Phe Ser Lys Asp Phe
        595                 600                 605

Arg Phe Ala Phe Lys Arg Ile Ile Cys Arg Trp Cys Cys Trp Ala Ser
    610                 615                 620

Ala Gly Asp Ser Thr Ala Gly Ile Gly Gly Leu Thr Val Ala Asp
625                 630                 635                 640

Tyr Gly Arg Arg Lys Gly Ser Asp Gly Ser Gln Leu Gly Ala Gly Gly
                645                 650                 655
```

```
      His Gly Gly Ala Ser Pro Arg Asn Arg Tyr Ile Val Thr Gly Ser Gly
                      660                 665                 670

Ala Gly Ala Ala Gly Ser Asp Glu Cys Ser Thr Arg Ser Met Arg Leu
                  675                 680                 685

Leu Gln Tyr Ser Asp Ser Glu Pro Leu Asn Glu Pro Cys Ser Asp Asp
              690                 695                 700

Arg
      705

<210> SEQ ID NO 155
<211> LENGTH: 32
<212> TYPE: DNA
<213> ORGANISM: Artificial sequence
<220> FEATURE:
<223> OTHER INFORMATION: Primer

<400> SEQUENCE: 155
gccaccatga accggaccga gtgtcagacg ct                                      32

<210> SEQ ID NO 156
<211> LENGTH: 18
<212> TYPE: DNA
<213> ORGANISM: Artificial sequence
<220> FEATURE:
<223> OTHER INFORMATION: Primer

<400> SEQUENCE: 156
tcacctgtcg tccgaaca                                                      18

<210> SEQ ID NO 157
<211> LENGTH: 1618
<212> TYPE: DNA
<213> ORGANISM: Drosophila melanogaster

<400> SEQUENCE: 157
atgttgttgt gcgacggact tggcccggag ccaccgcggc aaaggcatcg aaatcgaacc        60
agtgccgcca ggattagaaa agaccgaaat gctgctgcg gcgatggcgg cagcggcaat       120
caggcggagc agcccggcgg datagttagc aacccaatta gttatggcca aagtctgaca      180
acattggcgc gggtcacggc ggccgcactg accacggcgg ccatgctgca cacaacgaat      240
gccctggctg ccaccggctc atccagcgca tccaactctt ccaccggcgg aatagcactg      300
ccgctgggca ctgccacacc tgccacacac gaactgaatg ccacacagcc gtttggcggc      360
acgggtctga agttcaacga aagcggcgct ggattaagtg accatcatca tcatcaacaa      420
cacaatcccg acgaggattg gctggacaac atcgtttggg tgttcaaggc ctttgtcatg      480
ctgctcatca tcattgcggc catctgcggc aatctgcttg ttattatttc tgtgatgcgt      540
gttagaaaat taagagttat aacgaattac tttgtagttt ccttagccat ggctgatata      600
atggtcgcta ttatggccat gacatttaac tttagtgtgc aagtaactgg gcggtggaac      660
ttcagcccct tcctgtgcga tttgtggaac agcctcgatg tctacttctc aacagcgagt      720
attttgcatt tatgctgcat atctgtggat agatactatg ctattgttaa gcccctcaag      780
tatccgatta gcatgacgaa acgcgtggtc ggcattatgc tgctaaacac atggatatcg      840
ccggcactgc tctccttctt gcccatcttc atcggctggt acaccacgcc gcagcaccag      900
cagttcgtca tccagaatcc gacgcaatgc tcgttcgtgg tgaacaagta ctacgccgtc      960
atctcgagct ccatatcgtt ctggataccc tgcaccatta tgatattcac ctacttggcc     1020
atcttccggg aagccaatcg gcaggagaag cagctgatga tgcggcacgg caatgccatg     1080
```

-continued

```
ctgatgcacc gaccatccat gcagccatca ggcgaggcgc tgagcggatc cgggtcgtcg    1140
aaaacattga cgctgcacga ggtcgagcag gagcacaccc ccactaagga caagcactta    1200
atcaaaatga agcgggagca caaggccgca cgcacgctgg gcatcatcat gggcaccttc    1260
atcctctgct ggctgccttt cttcctgtgg tacacactct ccatgacctg cgaggtgtgc    1320
caagtgccgg acatagtcgt ctcgatcctc ttctggatcg ggtacttcaa ctcaacgcta    1380 aaccgctga tctacgcgta ctttaaccgc gacttccggg aggcgttccg caacacgctg    1440
ctctgtctgt tctgcaattg gtggaaggat cgccacctgc tctggacat cgacatccgg     1500 cgctccagcc tacgctacga ccagcgggcg aagagcgtct actcggagag ctacctcaac    1560
tcgacaacgc cctcgcatcg ccgccagtct cagatggtgg acaacttagg gcgcgccc     1618
```

<210> SEQ ID NO 158
<211> LENGTH: 539
<212> TYPE: PRT
<213> ORGANISM: Drosophila melanogaster

<400> SEQUENCE: 158

```
Met Leu Leu Cys Asp Gly Leu Gly Pro Glu Pro Pro Arg Gln Arg His
1               5                   10                  15

Arg Asn Arg Thr Ser Ala Ala Arg Ile Arg Lys Arg Pro Lys Cys Cys
                20                  25                  30

Cys Gly Asp Gly Gly Ser Gly Asn Gln Ala Glu Gln Pro Gly Gly Ile
            35                  40                  45

Val Ser Asn Pro Ile Ser Tyr Gly Gln Ser Leu Thr Thr Leu Ala Arg
    50                  55                  60

Val Thr Ala Ala Ala Leu Thr Thr Ala Ala Met Leu His Thr Thr Asn
65                  70                  75                  80

Ala Leu Ala Ala Thr Gly Ser Ser Ala Ser Asn Ser Ser Thr Gly
                85                  90                  95

Gly Ile Ala Leu Pro Leu Gly Thr Ala Thr Pro Ala Thr His Glu Leu
            100                 105                 110

Asn Ala Thr Gln Pro Phe Gly Gly Thr Gly Leu Lys Phe Asn Glu Ser
        115                 120                 125

Gly Ala Gly Leu Ser Asp His His His Gln Gln His Asn Pro Asp
    130                 135                 140

Glu Asp Trp Leu Asp Asn Ile Val Trp Val Phe Lys Ala Phe Val Met
145                 150                 155                 160

Leu Leu Ile Ile Ile Ala Ala Ile Cys Gly Asn Leu Leu Val Ile Ile
                165                 170                 175

Ser Val Met Arg Val Arg Lys Leu Arg Val Ile Thr Asn Tyr Phe Val
            180                 185                 190

Val Ser Leu Ala Met Ala Asp Ile Met Val Ala Ile Met Ala Met Thr
        195                 200                 205

Phe Asn Phe Ser Val Gln Val Thr Gly Arg Trp Asn Phe Ser Pro Phe
    210                 215                 220

Leu Cys Asp Leu Trp Asn Ser Leu Asp Val Tyr Phe Ser Thr Ala Ser
225                 230                 235                 240

Ile Leu His Leu Cys Cys Ile Ser Val Asp Arg Tyr Tyr Ala Ile Val
                245                 250                 255

Lys Pro Leu Lys Tyr Pro Ile Ser Met Thr Lys Arg Val Val Gly Ile
            260                 265                 270

Met Leu Leu Asn Thr Trp Ile Ser Pro Ala Leu Leu Ser Phe Leu Pro
```

```
                275                 280                 285
Ile Phe Ile Gly Trp Tyr Thr Thr Pro Gln His Gln Gln Phe Val Ile
    290                 295                 300
Gln Asn Pro Thr Gln Cys Ser Phe Val Val Asn Lys Tyr Tyr Ala Val
305                 310                 315                 320
Ile Ser Ser Ser Ile Ser Phe Trp Ile Pro Cys Thr Ile Met Ile Phe
                325                 330                 335
Thr Tyr Leu Ala Ile Phe Arg Glu Ala Asn Arg Gln Glu Lys Gln Leu
            340                 345                 350
Met Met Arg His Gly Asn Ala Met Leu Met His Arg Pro Ser Met Gln
            355                 360                 365
Pro Ser Gly Glu Ala Leu Ser Gly Ser Gly Ser Ser Lys Thr Leu Thr
370                 375                 380
Leu His Glu Val Glu Gln Glu His Thr Pro Thr Lys Asp Lys His Leu
385                 390                 395                 400
Ile Lys Met Lys Arg Glu His Lys Ala Ala Arg Thr Leu Gly Ile Ile
                405                 410                 415
Met Gly Thr Phe Ile Leu Cys Trp Leu Pro Phe Phe Leu Trp Tyr Thr
            420                 425                 430
Leu Ser Met Thr Cys Glu Val Cys Gln Val Pro Asp Ile Val Val Ser
            435                 440                 445
Ile Leu Phe Trp Ile Gly Tyr Phe Asn Ser Thr Leu Asn Pro Leu Ile
    450                 455                 460
Tyr Ala Tyr Phe Asn Arg Asp Phe Arg Glu Ala Phe Arg Asn Thr Leu
465                 470                 475                 480
Leu Cys Leu Phe Cys Asn Trp Trp Lys Asp Arg His Leu Pro Leu Asp
                485                 490                 495
Ile Asp Ile Arg Arg Ser Ser Leu Arg Tyr Asp Gln Arg Ala Lys Ser
                500                 505                 510
Val Tyr Ser Glu Ser Tyr Leu Asn Ser Thr Thr Pro Ser His Arg Arg
            515                 520                 525
Gln Ser Gln Met Val Asp Asn Leu Gly Arg Ala
    530                 535

<210> SEQ ID NO 159
<211> LENGTH: 32
<212> TYPE: DNA
<213> ORGANISM: Artificial sequence
<220> FEATURE:
<223> OTHER INFORMATION: Primer

<400> SEQUENCE: 159
gccaccatgt tgttgtgcga cggacttggc cc                                  32

<210> SEQ ID NO 160
<211> LENGTH: 33
<212> TYPE: DNA
<213> ORGANISM: Artificial sequence
<220> FEATURE:
<223> OTHER INFORMATION: Primer

<400> SEQUENCE: 160
gggcgcgccc taagttgtcc accatctgag act                                 33

<210> SEQ ID NO 161
<211> LENGTH: 1236
<212> TYPE: DNA
<213> ORGANISM: Tribolium castaneum
```

<400> SEQUENCE: 161

```
atggacaact taacataccvt cagtacatcg acgacgcaaa tcaccaaaac ccccgaccaa      60
gaatggaccc attacctcat cgtgttcctg aaagccacca tcatgggttc gataatcgtc     120
gtatcgatat tcggcaacct ccttgttatc gtgtcggtga tgcggcatcg caaactccgc     180
atcatcacca actactacgt catctcgcta gccttcgccg acatgttggt ggcaatgttc     240
gccatgacgt ttaactttag cgtgcaaatc ttcgatacgt ggctgttcgg gtactttatg     300
tgcgacgtgt ggaactcttt agacgtttac ttttcgacgg tttcgatcct ccacctgtgc     360
tgtatcagtg tagatcgcta catcgccatc gtcaagccgc tcaaatacgc gctcagcatg     420
accaagaaca tcgtcgcgtt gatgctcctc gccacgtggg tgatgccagc cttttgagt     480
ttcctgccca tcttcatggg ctggtacgcg acggaggagc acctcaaaga ccggttcgat     540
catccggact cgtgcgagtt caaagtcaac aagttgtacg cgatcattag tagcagtatc     600
tcgttctgga ttccgtgcac gatcatgatc tacatgtacc tggcgatctt ccgcgaggcg     660
aacaagcagg aaaaagacat gtataatagg cagggggcgg ccttgctcct ccaccagaac     720
aacaccaacg tgatatgtt gtcgaactct ggtggttctt ccaaaacgct gactcttcac     780
gaaatcaacc aggatcttca ccacactccg accaaggagc ggaatctcaa caaaatgaag     840
cgcgagcaca aagccgcgag gactttgagt attatcatgg ggacgtttac gttgtgctgg     900
ttgccctttt tcctgtggta cgtctcgatc tcgttgtgca ccacgtgcga atgccccgac     960
atggtcgtgg ggatcttgtt ctggatcggg tacttcaatt cgacgctgaa tcccttgatt    1020
tatgcctatt caacaagga cttcagggaa gcgttcaaga acacgttgca gtgcgttttt    1080
tgtagtttgt gccgccgtcc gccatctgat ttagacaagt tcgatatcag aagaccgtcg    1140
ataaggtatg atgatagaac tagaagcatc tattcggaaa cttacttaaa acatattgat    1200
aggaggagga gttcggagtt tgggtcgagt ctctga                              1236
```

<210> SEQ ID NO 162
<211> LENGTH: 411
<212> TYPE: PRT
<213> ORGANISM: Tribolium castaneum

<400> SEQUENCE: 162

```
Met Asp Asn Leu Thr Tyr Leu Ser Thr Ser Thr Gln Ile Thr Lys
1               5                  10                  15

Thr Pro Asp Gln Glu Trp Thr His Tyr Leu Ile Val Phe Leu Lys Ala
            20                  25                  30

Thr Ile Met Gly Ser Ile Ile Val Ser Ile Phe Gly Asn Leu Leu
        35                  40                  45

Val Ile Val Ser Val Met Arg His Arg Lys Leu Arg Ile Ile Thr Asn
    50                  55                  60

Tyr Tyr Val Ile Ser Leu Ala Phe Ala Asp Met Leu Val Ala Met Phe
65                  70                  75                  80

Ala Met Thr Phe Asn Phe Ser Val Gln Ile Phe Asp Thr Trp Leu Phe
                85                  90                  95

Gly Tyr Phe Met Cys Asp Val Trp Asn Ser Leu Asp Val Tyr Phe Ser
            100                 105                 110

Thr Val Ser Ile Leu His Leu Cys Cys Ile Ser Val Asp Arg Tyr Ile
        115                 120                 125

Ala Ile Val Lys Pro Leu Lys Tyr Ala Leu Ser Met Thr Lys Asn Ile
    130                 135                 140
```

Val Ala Leu Met Leu Leu Ala Thr Trp Val Met Pro Ala Phe Leu Ser
145                 150                 155                 160

Phe Leu Pro Ile Phe Met Gly Trp Tyr Ala Thr Glu Glu His Leu Lys
            165                 170                 175

Asp Arg Phe Asp His Pro Asp Ser Cys Glu Phe Lys Val Asn Lys Leu
        180                 185                 190

Tyr Ala Ile Ile Ser Ser Ile Ser Phe Trp Ile Pro Cys Thr Ile
    195                 200                 205

Met Ile Tyr Met Tyr Leu Ala Ile Phe Arg Glu Ala Asn Lys Gln Glu
210                 215                 220

Lys Asp Met Tyr Asn Arg Gln Gly Ala Ala Leu Leu Leu His Gln Asn
225                 230                 235                 240

Asn Thr Asn Gly Asp Met Leu Ser Asn Ser Gly Gly Ser Ser Lys Thr
            245                 250                 255

Leu Thr Leu His Glu Ile Asn Gln Asp Leu His His Thr Pro Thr Lys
            260                 265                 270

Glu Arg Asn Leu Asn Lys Met Lys Arg Glu His Lys Ala Ala Arg Thr
        275                 280                 285

Leu Ser Ile Ile Met Gly Thr Phe Thr Leu Cys Trp Leu Pro Phe Phe
290                 295                 300

Leu Trp Tyr Val Ser Ile Ser Leu Cys Thr Thr Cys Glu Cys Pro Asp
305                 310                 315                 320

Met Val Val Gly Ile Leu Phe Trp Ile Gly Tyr Phe Asn Ser Thr Leu
            325                 330                 335

Asn Pro Leu Ile Tyr Ala Tyr Phe Asn Lys Asp Phe Arg Glu Ala Phe
            340                 345                 350

Lys Asn Thr Leu Gln Cys Val Phe Cys Ser Leu Cys Arg Arg Pro Pro
        355                 360                 365

Ser Asp Leu Asp Lys Phe Asp Ile Arg Arg Pro Ser Ile Arg Tyr Asp
370                 375                 380

Asp Arg Thr Arg Ser Ile Tyr Ser Glu Thr Tyr Leu Lys His Ile Asp
385                 390                 395                 400

Arg Arg Arg Ser Ser Glu Phe Gly Ser Ser Leu
            405                 410

<210> SEQ ID NO 163
<211> LENGTH: 40
<212> TYPE: DNA
<213> ORGANISM: Artificial sequence
<220> FEATURE:
<223> OTHER INFORMATION: Primer

<400> SEQUENCE: 163
atggacaact taacatacct cagtacatcg acgacgcaaa                    40

<210> SEQ ID NO 164
<211> LENGTH: 38
<212> TYPE: DNA
<213> ORGANISM: Artificial sequence
<220> FEATURE:
<223> OTHER INFORMATION: Primer

<400> SEQUENCE: 164
tcagagactc gacccaaact ccgaactcct cctcctga                      38

<210> SEQ ID NO 165
<211> LENGTH: 1410

```
<212> TYPE: DNA
<213> ORGANISM: Bemisia argentifolii

<400> SEQUENCE: 165
atgggcgccc tctccgacat gagcctcaat cccaacagct tcatgctcga cgcccccgga    60
ccggcccct gggcggggcc caccgccgca gccgccctcc gcaacctctc cgccgccaac    120
ctcaacgtca ctagcaattt tacctcagac gagttttgga tggacccgga ggacgtggag    180
gactgggcga gcgtggtgct gtgggtgctg cggacgatgg tgatggcgac gatcatcctg    240
gcggccatct tcgggaacct cctcgtcatc gtgagtgtga tgcggcaccg gaagctccgg    300
gtcatcacca actacttcgt cgtgagcctg cccctcgccg acatgctcgt cgccatggtc    360
gccatgacct tcaacatgag cgtccaggtc accggcaagt ggctcttcgg cgccttcatc    420
tgcgacgtct ggaacgccct cgacgtctac ttctccaccg cctccattat ccatctctgt    480
tgcatctcgg tcgataggta ctacgccatt gtaaagccac tcaagtaccc gatcaagatg    540
acgaaacgga agtggccat catgctcttg ctgacgtgga tctcgccggc cattatctcg    600
ttcgttccta ttttctgtgg ttggtatacg acggaagagc acaagcacta ccgcaacaac    660
cacccccgatg aatgtcaatt tgaggtcaac aaattatacg ccctcatttc atcatcgata    720
tccttttgga tcccttgtac aatcatgatt tttacctact tagcaatttt caaagaagcc    780
aaccggcaag aaaaacaaat tcacgcacgg ataggcaatc aacttttaca aaaccataat    840
agagaattat attcaaatac taatggagat gtattaagca atagcggcgg ttcgagcaaa    900
aacttgaccg tcaatgaagt cggggcggtg cactcgaccc cgacgaaaga cgggagcttc    960
atcaaaatga agagagagca caaagcagcc cgaacgttag gcataataat gggcaccttc   1020
atgctctgtt ggctccccctt tttcttgtgg tacgtgatca cctcgatctg cggggacccg   1080
tgtcacttct cgaacggggt ggtggccgtg ttcttctgga tcgggtactc caactcgacg   1140
ctgaacccgg tgatctacgc ctacttcaac cgggacttcc gggaggccta ccgcaacacc   1200
ctccagtgcg ccttctgctc cctctgccgg cggccgccct ccgacctgga ggccctcgac   1260
cgggacgctc gccgcgcctc cctcacctac gcccccgcct ccggctacga cgaccgcgat   1320
cgggcccgca gcacccggag catccactcc gacacctact tcaagcacgt cgaccgccgc   1380
cgctccagcc agttcggcag ctccttatga                                     1410

<210> SEQ ID NO 166
<211> LENGTH: 469
<212> TYPE: PRT
<213> ORGANISM: Bemisia argentifolii

<400> SEQUENCE: 166

Met Gly Ala Leu Ser Asp Met Ser Leu Asn Pro Asn Ser Phe Met Leu
1               5                   10                  15

Asp Ala Pro Gly Pro Ala Pro Trp Ala Gly Pro Thr Ala Ala Ala
            20                  25                  30

Leu Arg Asn Leu Ser Ala Ala Asn Leu Asn Val Thr Ser Asn Phe Thr
        35                  40                  45

Ser Asp Glu Phe Trp Met Asp Pro Glu Asp Val Glu Asp Trp Ala Ser
    50                  55                  60

Val Val Leu Trp Val Leu Arg Thr Met Val Met Ala Thr Ile Ile Leu
65                  70                  75                  80

Ala Ala Ile Phe Gly Asn Leu Leu Val Ile Val Ser Val Met Arg His
                85                  90                  95
```

Arg Lys Leu Arg Val Ile Thr Asn Tyr Phe Val Ser Leu Ala Leu
                100                 105                 110

Ala Asp Met Leu Val Ala Met Val Ala Met Thr Phe Asn Met Ser Val
            115                 120                 125

Gln Val Thr Gly Lys Trp Leu Phe Gly Ala Phe Ile Cys Asp Val Trp
        130                 135                 140

Asn Ala Leu Asp Val Tyr Phe Ser Thr Ala Ser Ile Ile His Leu Cys
145                 150                 155                 160

Cys Ile Ser Val Asp Arg Tyr Tyr Ala Ile Val Lys Pro Leu Lys Tyr
                165                 170                 175

Pro Ile Lys Met Thr Lys Arg Lys Val Ala Ile Met Leu Leu Leu Thr
            180                 185                 190

Trp Ile Ser Pro Ala Ile Ile Ser Phe Val Pro Ile Phe Cys Gly Trp
        195                 200                 205

Tyr Thr Thr Glu Glu His Lys His Tyr Arg Asn Asn His Pro Asp Glu
    210                 215                 220

Cys Gln Phe Glu Val Asn Lys Leu Tyr Ala Leu Ile Ser Ser Ser Ile
225                 230                 235                 240

Ser Phe Trp Ile Pro Cys Thr Ile Met Ile Phe Thr Tyr Leu Ala Ile
                245                 250                 255

Phe Lys Glu Ala Asn Arg Gln Glu Lys Gln Ile His Ala Arg Ile Gly
            260                 265                 270

Asn Gln Leu Leu Gln Asn His Asn Arg Glu Leu Tyr Ser Asn Thr Asn
        275                 280                 285

Gly Asp Val Leu Ser Asn Ser Gly Gly Ser Ser Lys Asn Leu Thr Val
    290                 295                 300

Asn Glu Val Gly Ala Val His Ser Thr Pro Thr Lys Asp Gly Ser Phe
305                 310                 315                 320

Ile Lys Met Lys Arg Glu His Lys Ala Ala Arg Thr Leu Gly Ile Ile
                325                 330                 335

Met Gly Thr Phe Met Leu Cys Trp Leu Pro Phe Phe Leu Trp Tyr Val
            340                 345                 350

Ile Thr Ser Ile Cys Gly Asp Pro Cys His Phe Ser Asn Gly Val Val
        355                 360                 365

Ala Val Phe Phe Trp Ile Gly Tyr Ser Asn Ser Thr Leu Asn Pro Val
    370                 375                 380

Ile Tyr Ala Tyr Phe Asn Arg Asp Phe Arg Glu Ala Tyr Arg Asn Thr
385                 390                 395                 400

Leu Gln Cys Ala Phe Cys Ser Leu Cys Arg Arg Pro Pro Ser Asp Leu
                405                 410                 415

Glu Ala Leu Asp Arg Asp Ala Arg Ala Ser Leu Thr Tyr Ala Pro
            420                 425                 430

Ala Ser Gly Tyr Asp Asp Arg Asp Arg Ala Arg Ser Thr Arg Ser Ile
        435                 440                 445

His Ser Asp Thr Tyr Phe Lys His Val Asp Arg Arg Ser Ser Gln
    450                 455                 460

Phe Gly Ser Ser Leu
465

<210> SEQ ID NO 167
<211> LENGTH: 24
<212> TYPE: DNA
<213> ORGANISM: Artificial sequence
<220> FEATURE:
<223> OTHER INFORMATION: Primer

<400> SEQUENCE: 167
gccaccatgg gcgccctctc cgac    24

<210> SEQ ID NO 168
<211> LENGTH: 22
<212> TYPE: DNA
<213> ORGANISM: Artificial sequence
<220> FEATURE:
<223> OTHER INFORMATION: Primer

<400> SEQUENCE: 168
tcataaggag ctgccgaact gg    22

<210> SEQ ID NO 169
<211> LENGTH: 1305
<212> TYPE: DNA
<213> ORGANISM: Tribolium castaneum

<400> SEQUENCE: 169
atggcttcat tctcagcaac attgacggca acatcgacga acctcccgag cgtcctccaa    60
aacggcacat caaacgatac aaacgtcgcc accgtgggca accctcatcc gcactggacg    120
gagttgctct tgctgatcgt gaaagggttt attttcggaa cgataatcgt gagtgccgtg    180
ttgggcaacg ctctagtgat aataagcgtc catcgacaca gaaaactaag agtgatcacg    240
aattactacg tggtgagctt ggcgatggcc gatatgctgg tagcactgtg cgcgatgact    300
ttcaacgcta gcgtggagct aacgggggc aaatggctgt tcgggtattt catgtgtgac    360
gtgtggaact ctctcgatgt gtacttttcc accgcctcga ttttacatct gtgttgtatc    420
agtgtggaca ggtactacgc catcgtgcgg ccgttggaat atcccataac catgacccat    480
cggacggttt cgttcatgct agccaacgtc tggactctac cagcgttgat cagcttcaca    540
cccatcttcc ttgggtggta cacaacggag gatcatatcg atttcagaaa accaatccc    600
aatgtttgta aatttgttgt caaccaatac tacgcactta tcagcagttc cataagtttc    660
tggatacctg ggatagtgat ggtaacaatg tactgcagga tacaaaaga agcgatccgg    720
caacgcaaag ctttatccag gacttcctca aatatcatcc tgaactcaat ccaccaacac    780
agaacttcct acagagacag atacggagac catttcttgc atccttccga tggcgaattg    840
accacagtcg gcaaatcaa tggccggaga agtacaagtt cgggatcagc agtatcgtac    900
ggaactacca aaccgaatt caatacagca atgaacagca gagacaacag taaagccgca    960
accgaactca atatgaacgg cacttccatt cgccagcagt ccaaaagctg gagagccgag    1020
cacaaggccg cccgcacctt gggcataata atgggtgctt tcatgttatg ttggcttcct    1080
tttttcttat ggtatgtgat aacgacgctt tgtggcgacg acttgtgtcc gacacccgac    1140
tggctgatcg gcatgttgtt ctgggttggc tacttcaact cggccctgaa tccgctgatt    1200
tacgcctatt ttaacagaga cttccgggaa gctttcaaag cacccctgct ctgcgcgatg    1260
ccgtgctgct tcacgtgttg gaaaaatcct gcaaggttcc tttag    1305

<210> SEQ ID NO 170
<211> LENGTH: 434
<212> TYPE: PRT
<213> ORGANISM: Tribolium castaneum

<400> SEQUENCE: 170

Met Ala Ser Phe Ser Ala Thr Leu Thr Ala Thr Ser Thr Asn Leu Pro
1               5                   10                  15

```
Ser Val Leu Gln Asn Gly Thr Ser Asn Asp Thr Asn Val Ala Thr Val
         20                  25                  30

Gly Asn Pro His Pro His Trp Thr Glu Leu Leu Leu Ile Val Lys
         35                  40                  45

Gly Phe Ile Phe Gly Thr Ile Ile Val Ser Ala Val Leu Gly Asn Ala
 50                  55                  60

Leu Val Ile Ile Ser Val His Arg His Arg Lys Leu Arg Val Ile Thr
 65                  70                  75                  80

Asn Tyr Tyr Val Val Ser Leu Ala Met Ala Asp Met Leu Val Ala Leu
                 85                  90                  95

Cys Ala Met Thr Phe Asn Ala Ser Val Glu Leu Thr Gly Gly Lys Trp
             100                 105                 110

Leu Phe Gly Tyr Phe Met Cys Asp Val Trp Asn Ser Leu Asp Val Tyr
             115                 120                 125

Phe Ser Thr Ala Ser Ile Leu His Leu Cys Cys Ile Ser Val Asp Arg
130                 135                 140

Tyr Tyr Ala Ile Val Arg Pro Leu Glu Tyr Pro Ile Thr Met Thr His
145                 150                 155                 160

Arg Thr Val Ser Phe Met Leu Ala Asn Val Trp Thr Leu Pro Ala Leu
                 165                 170                 175

Ile Ser Phe Thr Pro Ile Phe Leu Gly Trp Tyr Thr Thr Glu Asp His
                 180                 185                 190

Ile Asp Phe Arg Lys Thr Asn Pro Asn Val Cys Lys Phe Val Val Asn
             195                 200                 205

Gln Tyr Tyr Ala Leu Ile Ser Ser Ile Ser Phe Trp Ile Pro Gly
210                 215                 220

Ile Val Met Val Thr Met Tyr Cys Arg Ile Tyr Lys Glu Ala Ile Arg
225                 230                 235                 240

Gln Arg Lys Ala Leu Ser Arg Thr Ser Ser Asn Ile Ile Leu Asn Ser
                 245                 250                 255

Ile His Gln His Arg Thr Ser Tyr Arg Asp Arg Tyr Gly Asp His Phe
                 260                 265                 270

Leu His Pro Ser Asp Gly Glu Leu Thr Thr Val Gly Gln Ile Asn Gly
             275                 280                 285

Arg Arg Ser Thr Ser Ser Gly Ser Ala Val Ser Tyr Gly Thr Thr Thr
290                 295                 300

Thr Glu Phe Asn Thr Ala Met Asn Ser Arg Asp Asn Ser Lys Ala Ala
305                 310                 315                 320

Thr Glu Leu Asn Met Asn Gly Thr Ser Ile Arg Gln Gln Ser Lys Ser
                 325                 330                 335

Trp Arg Ala Glu His Lys Ala Arg Thr Leu Gly Ile Ile Met Gly
             340                 345                 350

Ala Phe Met Leu Cys Trp Leu Pro Phe Phe Leu Trp Tyr Val Ile Thr
             355                 360                 365

Thr Leu Cys Gly Asp Asp Leu Cys Pro Thr Pro Asp Trp Leu Ile Gly
370                 375                 380

Met Leu Phe Trp Val Gly Tyr Phe Asn Ser Ala Leu Asn Pro Leu Ile
385                 390                 395                 400

Tyr Ala Tyr Phe Asn Arg Asp Phe Arg Glu Ala Phe Lys Asp Thr Leu
                 405                 410                 415

Leu Cys Ala Met Pro Cys Cys Phe Thr Cys Trp Lys Asn Pro Ala Arg
                 420                 425                 430
```

Phe Leu

<210> SEQ ID NO 171
<211> LENGTH: 36
<212> TYPE: DNA
<213> ORGANISM: Artificial sequence
<220> FEATURE:
<223> OTHER INFORMATION: Primer

<400> SEQUENCE: 171
atggcttcat tctcagcaac attgacggca acatcg          36

<210> SEQ ID NO 172
<211> LENGTH: 39
<212> TYPE: DNA
<213> ORGANISM: Artificial sequence
<220> FEATURE:
<223> OTHER INFORMATION: Primer

<400> SEQUENCE: 172
ctaaaggaac cttgcaggat ttttccaaca cgtgaagca       39

<210> SEQ ID NO 173
<211> LENGTH: 7285
<212> TYPE: DNA
<213> ORGANISM: Artificial sequence
<220> FEATURE:
<223> OTHER INFORMATION: OA2-GFP fusion sequence

<400> SEQUENCE: 173

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt ccagtgtggt ggaattcgcc | 960 |
| accatgacgc tactgcagag gcttcaggcc atgtcggcca ccacgaccag gacaatactg | 1020 |
| gagggcagca tcagcagttt tggtggcggg acaaatgagc ctctggcgag caaaataccc | 1080 |
| gttctggagg agtccgcctc acatgccaga tatttgaaat tcattgccga cgggctcatc | 1140 |
| gacgagggtc tgggcagtgc ggttggcagt gggagcagca tcgccgtatc cgttgaagac | 1200 |
| gtggtcgccg gacaggcgca ggacatccag gcgagcgaag gatccaccga cgacgccgac | 1260 |
| ggcagtagcc atttggcatt agtcttcgtc aagtgtttca ttattggttt catcatactg | 1320 |

-continued

```
gccgccatcc tgggcaacat gctggtgatt gtgtcggtca tgcggcaccg gaaattgcgc   1380
atcattacca actactttgt ggtctctctg gccgtcgccg acatgctggt ggccctctgt   1440
gcgatgacat ttaatgcttc cgtcatgatc tcgggcaagt ggatgtttgg ttccgtgatg   1500
tgcgacatgt ggaacagctt cgacgtctac ttctccaccg ccagcatcat gcacctctgt   1560
tgcatatcgg tcgacagata ctacgccatt gtgcagccac tggactatcc actaatcatg   1620
acacagcgac gcgtgttcat catgctattg atggtgtggc tatcgccggc gctcctctcg   1680
ttcctgccca tctgctcggg atggtacaca acgaccgaga actacaagta tctcaaatcg   1740
aatccgcata tatgcgagtt caaagtgaac aaggcatacg ccatagtcag ctcgtcgatg   1800
agcttctgga ttcccggcat cgtaatgctg tcgatgtact accgcattta ccaggaggcc   1860
gaccgacagg agcgtctggt gtacagatcc aaggtggccg ctctgctgct ggagaagcat   1920
ctgcagatta gccaaattcc caagcccccgg ccagcattc aggtggagca gtcgaccatc   1980
tcgacgatgc ggcgtgagcg gaaggccgcc cgcaccctgg gcatcatcat gagcgccttc   2040
ctcatctgct ggctgccgtt cttcctctgg tacatcgtat cctcgctgtg cgatagttgc   2100
atcactccgc gcctgctcgt tggcatcctg ttttggatcg gctacttcaa ctcggccctg   2160
aaccccatta tttatgcata cttcaaccgc gacttcaggg ccgccttcaa gaagaccctc   2220
aagagtctgt ttccctacgc tttctacttc tgtcgacgtg gcaggggcg agacgatgac   2280
cgggatctgg agttcggcgg tcccagccga cggggaacca atggagccca acggaccgga   2340
tccggatccg ccgagatggc caactgcgtc aactccacgg cctcgtcgga gatacacatg   2400
agcgtgatgc gtgcccgcca gtatgccgtc aatgtcacac ccaccacgga cgcccagatg   2460
cagcagctgc atcccctgta caccaacggc gcgcccatgg tgagcaaggg cgccgagctg   2520
ttcaccggca tcgtgcccat cctgatcgag ctgaatggcg atgtgaatgg ccacaagttc   2580
agcgtgagcg gcgagggcga gggcgatgcc acctacggca agctgaccct gaagttcatc   2640
tgcaccaccg gcaagctgcc tgtgccctgg cccaccctgg tgaccaccct gagctacggc   2700
gtgcagtgct tctcacgcta ccccgatcac atgaagcagc acgacttctt caagagcgcc   2760
atgcctgagg gctacatcca ggagcgcacc atcttcttcg aggatgacgg caactacaag   2820
tcgcgcgccg aggtgaagtt cgagggcgat accctggtga atcgcatcga gctgaccggc   2880
accgatttca aggaggatgg caacatcctg ggcaataaga tggagtacaa ctacaacgcc   2940
cacaatgtgt acatcatgac cgacaaggcc aagaatggca tcaaggtgaa cttcaagatc   3000
cgccacaaca tcgaggatgg cagcgtgcag ctggccgacc actaccagca gaataccccc   3060
atcggcgatg gccctgtgct gctgcccgat aaccactacc tgtccaccca gagcgccctg   3120
tccaaggacc ccaacgagaa gcgcgatcac atgatctact cggcttcgt gaccgccgcc   3180
gccatcaccc acggcatgga tgagctgtac aagtgaaggg cgaattctgc agatatccag   3240
cacagtggcg gccgctcgag tctagagggc ccgtttaaac ccgctgatca gcctcgactg   3300
tgccttctag ttgccagcca tctgttgttt gcccctcccc cgtgccttcc ttgaccctgg   3360
aaggtgccac tcccactgtc ctttcctaat aaaatgagga aattgcatcg cattgtctga   3420
gtaggtgtca ttctattctg gggggtgggg tgggcagga cagcaagggg gaggattggg   3480
aagacaatag caggcatgct ggggatgcgg tgggctctat ggcttctgag gcggaaagaa   3540
ccagctgggg ctctaggggg tatccccacg cgccctgtag cggcgcatta agcgcggcgg   3600
gtgtggtggt tacgcgcagc gtgaccgcta cacttgccag cgccctagcg cccgctcctt   3660
```

```
tcgctttctt cccttcctttt ctcgccacgt tcgccggctt tccccgtcaa gctctaaatc    3720
ggggcatccc tttagggttc cgatttagtg ctttacggca cctcgacccc aaaaaacttg    3780
attagggtga tggttcacgt agtgggccat cgccctgata gacggttttt cgccctttga    3840
cgttggagtc cacgttcttt aatagtggac tcttgttcca aactgaaaca acactcaacc    3900
ctatctcggt ctattctttt gatttataag ggattttggg gatttcggcc tattggttaa    3960
aaaatgagct gatttaacaa aaatttaacg cgaattaatt ctgtggaatg tgtgtcagtt    4020
agggtgtgga aagtccccag gctccccagg caggcagaag tatgcaaagc atgcatctca    4080
attagtcagc aaccaggtgt ggaaagtccc caggctcccc agcaggcaga gtatgcaaa    4140 gcatgcatct caattagtca gcaaccatag tcccgcccct aactccgccc atcccgcccc    4200
taactccgcc cagttccgcc cattctccgc cccatggctg actaatttttt tttatttatg    4260 cagaggccga ggccgcctct gcctctgagc tattccagaa gtagtgagga ggcttttttg    4320
gaggcctagg cttttgcaaa aagctcccgg gagcttgtat atccattttc ggatctgatc    4380
agcacgtgtt gacaattaat catcggcata gtatatcggc atagtataat acgacaaggt    4440
gaggaactaa accatggcca agttgaccag tgccgttccg gtgctcaccg cgcgcgacgt    4500
cgccggagcg gtcgagttct ggaccgaccg gctcgggttc tcccgggact cgtggagga    4560 cgacttcgcc ggtgtggtcc gggacgacgt gaccctgttc atcagcgcgg tccaggacca    4620
ggtggtgccg gacaacaccc tggcctgggt gtgggtgcgc ggcctggacg agctgtacgc    4680
cgagtggtcg gaggtcgtgt ccacgaactt ccgggacgcc tccgggccgg ccatgaccga    4740
gatcggcgag cagccgtggg ggcgggagtt cgccctgcgc gacccggccg gcaactgcgt    4800
gcacttcgtg gccgaggagc aggactgaca cgtgctacga gatttcgatt ccaccgccgc    4860
cttctatgaa aggttgggct tcggaatcgt tttccgggac gccggctgga tgatcctcca    4920
gcgcggggat ctcatgctgg agttcttcgc ccaccccaac ttgtttattg cagcttataa    4980
tggttacaaa taaagcaata gcatcacaaa tttcacaaat aaagcatttt tttcactgca    5040
ttctagttgt ggtttgtcca aactcatcaa tgtatcttat catgtctgta taccgtcgac    5100
ctctagctag agcttggcgt aatcatggtc atagctgttt cctgtgtgaa attgttatcc    5160
gctcacaatt ccacacaaca tacgagccgg aagcataaag tgtaaagcct ggggtgccta    5220
atgagtgagc taactcacat taattgcgtt gcgctcactg cccgctttcc agtcgggaaa    5280
cctgtcgtgc cagctgcatt aatgaatcgg ccaacgcgcg gggagaggcg gtttgcgtat    5340
tgggcgctct tccgcttcct cgctcactga ctcgctgcgc tcggtcgttc ggctgcggcg    5400
agcggtatca gctcactcaa aggcggtaat acggttatcc acagaatcag gggataacgc    5460
aggaaagaac atgtgagcaa aaggccagca aaaggccagg aaccgtaaaa aggccgcgtt    5520
gctggcgttt ttccataggc tccgcccccc tgacgagcat cacaaaaatc gacgctcaag    5580
tcagaggtgg cgaaacccga caggactata aagataccag gcgtttcccc ctggaagctc    5640
cctcgtgcgc tctcctgttc cgaccctgcc gcttaccgga tacctgtccg cctttctccc    5700
ttcgggaagc gtggcgcttt ctcaatgctc acgctgtagg tatctcagtt cggtgtaggt    5760
cgttcgctcc aagctgggct gtgtgcacga accccccgtt cagcccgacc gctgcgcctt    5820
atccggtaac tatcgtcttg agtccaaccc ggtaagacac gacttatcgc cactggcagc    5880
agccactggt aacaggatta gcagagcgag gtatgtaggc ggtgctacag agttcttgaa    5940
gtggtggcct aactacggct acactagaag gacagtattt ggtatctgcg ctctgctgaa    6000
gccagttacc ttcggaaaaa gagttggtag ctcttgatcc ggcaaacaaa ccaccgctgg    6060
```

```
tagcggtggt ttttttgttt gcaagcagca gattacgcgc agaaaaaaag gatctcaaga      6120
agatcctttg atcttttcta cggggtctga cgctcagtgg aacgaaaact cacgttaagg      6180
gattttggtc atgagattat caaaaaggat cttcacctag atccttttaa attaaaaatg      6240
aagttttaaa tcaatctaaa gtatatatga gtaaacttgg tctgacagtt accaatgctt      6300
aatcagtgag gcacctatct cagcgatctg tctatttcgt tcatccatag ttgcctgact      6360
ccccgtcgtg tagataacta cgatacggga gggcttacca tctggcccca gtgctgcaat      6420
gataccgcga gacccacgct caccggctcc agatttatca gcaataaacc agccagccgg      6480
aagggccgag cgcagaagtg gtcctgcaac tttatccgcc tccatccagt ctattaattg      6540
ttgccgggaa gctagagtaa gtagttcgcc agttaatagt ttgcgcaacg ttgttgccat      6600
tgctacaggc atcgtggtgt cacgctcgtc gtttggtatg gcttcattca gctccggttc      6660
ccaacgatca aggcgagtta catgatcccc catgttgtgc aaaaaagcgg ttagctcctt      6720
cggtcctccg atcgttgtca gaagtaagtt ggccgcagtg ttatcactca tggttatggc      6780
agcactgcat aattctctta ctgtcatgcc atccgtaaga tgcttttctg tgactggtga      6840
gtactcaacc aagtcattct gagaatagtg tatgcggcga ccgagttgct cttgcccggc      6900
gtcaatacgg gataataccg cgccacatag cagaacttta aaagtgctca tcattggaaa      6960
acgttcttcg gggcgaaaac tctcaaggat cttaccgctg ttgagatcca gttcgatgta      7020
acccactcgt gcacccaact gatcttcagc atcttttact ttcaccagcg tttctgggtg      7080
agcaaaaaca ggaaggcaaa atgccgcaaa aaagggaata agggcgacac ggaaatgttg      7140
aatactcata ctcttccttt ttcaatatta ttgaagcatt tatcagggtt attgtctcat      7200
gagcggatac atatttgaat gtatttagaa aaataaacaa ataggggttc cgcgcacatt      7260
tccccgaaaa gtgccacctg acgtc                                            7285
```

<210> SEQ ID NO 174
<211> LENGTH: 750
<212> TYPE: PRT
<213> ORGANISM: Artificial sequence
<220> FEATURE:
<223> OTHER INFORMATION: OA2-GFP fusion sequence

<400> SEQUENCE: 174

```
Met Thr Leu Leu Gln Arg Leu Gln Ala Met Ser Ala Thr Thr Thr Arg
1               5                  10                  15

Thr Ile Leu Glu Gly Ser Ile Ser Ser Phe Gly Gly Gly Thr Asn Glu
            20                  25                  30

Pro Leu Ala Ser Lys Ile Pro Val Leu Glu Glu Ser Ala Ser His Ala
        35                  40                  45

Arg Tyr Leu Lys Phe Ile Ala Asp Gly Leu Ile Asp Glu Gly Leu Gly
    50                  55                  60

Ser Ala Val Gly Ser Gly Ser Ser Ile Ala Val Ser Val Glu Asp Val
65                  70                  75                  80

Val Ala Gly Gln Ala Gln Asp Ile Gln Ala Ser Glu Gly Ser Thr Asp
                85                  90                  95

Asp Ala Asp Gly Ser Ser His Leu Ala Leu Val Phe Val Lys Cys Phe
            100                 105                 110

Ile Ile Gly Phe Ile Ile Leu Ala Ala Ile Leu Gly Asn Met Leu Val
        115                 120                 125

Ile Val Ser Val Met Arg His Arg Lys Leu Arg Ile Ile Thr Asn Tyr
    130                 135                 140
```

```
Phe Val Val Ser Leu Ala Val Ala Asp Met Leu Val Ala Leu Cys Ala
145                 150                 155                 160

Met Thr Phe Asn Ala Ser Val Met Ile Ser Gly Lys Trp Met Phe Gly
                165                 170                 175

Ser Val Met Cys Asp Met Trp Asn Ser Phe Asp Val Tyr Phe Ser Thr
            180                 185                 190

Ala Ser Ile Met His Leu Cys Cys Ile Ser Val Asp Arg Tyr Tyr Ala
        195                 200                 205

Ile Val Gln Pro Leu Asp Tyr Pro Leu Ile Met Thr Gln Arg Arg Val
210                 215                 220

Phe Ile Met Leu Leu Met Val Trp Leu Ser Pro Ala Leu Leu Ser Phe
225                 230                 235                 240

Leu Pro Ile Cys Ser Gly Trp Tyr Thr Thr Thr Glu Asn Tyr Lys Tyr
                245                 250                 255

Leu Lys Ser Asn Pro His Ile Cys Glu Phe Lys Val Asn Lys Ala Tyr
            260                 265                 270

Ala Ile Val Ser Ser Ser Met Ser Phe Trp Ile Pro Gly Ile Val Met
        275                 280                 285

Leu Ser Met Tyr Tyr Arg Ile Tyr Gln Glu Ala Asp Arg Gln Glu Arg
290                 295                 300

Leu Val Tyr Arg Ser Lys Val Ala Ala Leu Leu Glu Lys His Leu
305                 310                 315                 320

Gln Ile Ser Gln Ile Pro Lys Pro Arg Pro Ser Ile Gln Val Glu Gln
                325                 330                 335

Ser Thr Ile Ser Thr Met Arg Arg Glu Arg Lys Ala Ala Arg Thr Leu
            340                 345                 350

Gly Ile Ile Met Ser Ala Phe Leu Ile Cys Trp Leu Pro Phe Phe Leu
        355                 360                 365

Trp Tyr Ile Val Ser Ser Leu Cys Asp Ser Cys Ile Thr Pro Arg Leu
370                 375                 380

Leu Val Gly Ile Leu Phe Trp Ile Gly Tyr Phe Asn Ser Ala Leu Asn
385                 390                 395                 400

Pro Ile Ile Tyr Ala Tyr Phe Asn Arg Asp Phe Arg Ala Ala Phe Lys
                405                 410                 415

Lys Thr Leu Lys Ser Leu Phe Pro Tyr Ala Phe Tyr Phe Cys Arg Arg
            420                 425                 430

Gly Arg Gly Arg Asp Asp Arg Asp Leu Glu Phe Gly Gly Pro Ser
        435                 440                 445

Arg Arg Gly Thr Asn Gly Ala Gln Arg Thr Gly Ser Gly Ser Ala Glu
450                 455                 460

Met Ala Asn Cys Val Asn Ser Thr Ala Ser Ser Glu Ile His Met Ser
465                 470                 475                 480

Val Met Arg Ala Arg Gln Tyr Ala Val Asn Val Thr Pro Thr Thr Asp
                485                 490                 495

Ala Gln Met Gln Gln Leu His Pro Leu Tyr Thr Asn Gly Ala Pro Met
            500                 505                 510

Val Ser Lys Gly Ala Glu Leu Phe Thr Gly Ile Val Pro Ile Leu Ile
        515                 520                 525

Glu Leu Asn Gly Asp Val Asn Gly His Lys Phe Ser Val Ser Gly Glu
530                 535                 540

Gly Glu Gly Asp Ala Thr Tyr Gly Lys Leu Thr Leu Lys Phe Ile Cys
545                 550                 555                 560
```

```
Thr Thr Gly Lys Leu Pro Val Pro Trp Pro Thr Leu Val Thr Thr Leu
            565                 570                 575
Ser Tyr Gly Val Gln Cys Phe Ser Arg Tyr Pro Asp His Met Lys Gln
        580                 585                 590
His Asp Phe Phe Lys Ser Ala Met Pro Glu Gly Tyr Ile Gln Glu Arg
    595                 600                 605
Thr Ile Phe Glu Asp Asp Gly Asn Tyr Lys Ser Arg Ala Glu Val
610                 615                 620
Lys Phe Glu Gly Asp Thr Leu Val Asn Arg Ile Glu Leu Thr Gly Thr
625                 630                 635                 640
Asp Phe Lys Glu Asp Gly Asn Ile Leu Gly Asn Lys Met Glu Tyr Asn
            645                 650                 655
Tyr Asn Ala His Asn Val Tyr Ile Met Thr Asp Lys Ala Lys Asn Gly
        660                 665                 670
Ile Lys Val Asn Phe Lys Ile Arg His Asn Ile Glu Asp Gly Ser Val
    675                 680                 685
Gln Leu Ala Asp His Tyr Gln Gln Asn Thr Pro Ile Gly Asp Gly Pro
690                 695                 700
Val Leu Leu Pro Asp Asn His Tyr Leu Ser Thr Gln Ser Ala Leu Ser
705                 710                 715                 720
Lys Asp Pro Asn Glu Lys Arg Asp His Met Ile Tyr Phe Gly Phe Val
            725                 730                 735
Thr Ala Ala Ala Ile Thr His Gly Met Asp Glu Leu Tyr Lys
        740                 745                 750
```

<210> SEQ ID NO 175
<211> LENGTH: 41
<212> TYPE: DNA
<213> ORGANISM: Artificial sequence
<220> FEATURE:
<223> OTHER INFORMATION: Primer

<400> SEQUENCE: 175
ctgcatcccc tgtacaccaa cggcgcgccc atggtgagca a          41

<210> SEQ ID NO 176
<211> LENGTH: 45
<212> TYPE: DNA
<213> ORGANISM: Artificial sequence
<220> FEATURE:
<223> OTHER INFORMATION: Primer

<400> SEQUENCE: 176
ggatatctgc agaattcgcc cttcacttgt acagctcatc catgc      45

<210> SEQ ID NO 177
<211> LENGTH: 331
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

```
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (59)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(106)
```

```
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (113)..(118)
<223> OTHER INFORMATION: Xaa can be any naturally occurring amino acid
<220> FEATURE:
<221> NAME/KEY: misc_feature
<222> LOCATION: (121)..(122)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (136)..(138)
<223> OTHER INFORMATION: Xaa can be any naturally occurring amino acid
<220> FEATURE:
<221> NAME/KEY: misc_feature
<222> LOCATION: (143)..(152)
<223> OTHER INFORMATION: Xaa can be any naturally occurring amino acid
<220> FEATURE:
<221> NAME/KEY: misc_feature
<222> LOCATION: (154)..(155)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (162)..(163)
<223> OTHER INFORMATION: Xaa can be any naturally occurring amino acid
<220> FEATURE:
<221> NAME/KEY: misc_feature
<222> LOCATION: (165)..(167)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (178)..(179)
<223> OTHER INFORMATION: Xaa can be any naturally occurring amino acid
<220> FEATURE:
<221> NAME/KEY: misc_feature
<222> LOCATION: (181)..(182)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(192)
<223> OTHER INFORMATION: Xaa can be any naturally occurring amino acid
<220> FEATURE:
<221> NAME/KEY: misc_feature
<222> LOCATION: (195)..(199)
<223> OTHER INFORMATION: Xaa can be any naturally occurring amino acid
<220> FEATURE:
<221> NAME/KEY: misc_feature
```

```
<222> LOCATION: (201)..(206)
<223> OTHER INFORMATION: Xaa can be any naturally occurring amino acid
<220> FEATURE:
<221> NAME/KEY: misc_feature
<222> LOCATION: (208)..(210)
<223> OTHER INFORMATION: Xaa can be any naturally occurring amino acid
<220> FEATURE:
<221> NAME/KEY: misc_feature
<222> LOCATION: (212)..(254)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (266)..(268)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (281)..(284)
<223> OTHER INFORMATION: Xaa can be any naturally occurring amino acid
<220> FEATURE:
<221> NAME/KEY: misc_feature
<222> LOCATION: (287)..(290)
<223> OTHER INFORMATION: Xaa can be any naturally occurring amino acid
<220> FEATURE:
<221> NAME/KEY: misc_feature
<222> LOCATION: (292)..(293)
<223> OTHER INFORMATION: Xaa can be any naturally occurring amino acid
<220> FEATURE:
<221> NAME/KEY: misc_feature
<222> LOCATION: (295)..(301)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (328)..(329)
<223> OTHER INFORMATION: Xaa can be any naturally occurring amino acid

<400> SEQUENCE: 177

Lys Xaa Xaa Xaa Xaa Xaa Xaa Ile Ile Xaa Xaa Ala Xaa Xaa Gly Asn
1               5                   10                  15

Xaa Leu Val Xaa Xaa Ser Val Xaa Arg His Arg Lys Leu Arg Xaa Xaa
            20                  25                  30

Thr Asn Tyr Xaa Val Val Ser Leu Ala Xaa Ala Asp Xaa Leu Val Ala
        35                  40                  45

Xaa Xaa Ala Met Xaa Phe Asn Xaa Ser Val Xaa Xaa Xaa Xaa Gly Xaa
    50                  55                  60

Trp Xaa Phe Gly Xaa Xaa Met Cys Asp Xaa Trp Asn Ser Xaa Asp Val
65                  70                  75                  80
```

```
Tyr Phe Ser Xaa Ala Ser Ile Xaa His Leu Cys Cys Ile Ser Val Asp
                85              90                  95

Arg Tyr Tyr Ala Ile Val Xaa Pro Leu Xaa Tyr Pro Xaa Xaa Met Thr
            100             105             110

Xaa Xaa Xaa Xaa Xaa Xaa Met Leu Xaa Xaa Val Trp Xaa Xaa Pro Ala
            115             120             125

Leu Xaa Ser Phe Leu Pro Ile Xaa Xaa Xaa Trp Tyr Thr Thr Xaa Xaa
    130             135             140

Xaa Xaa Xaa Xaa Xaa Xaa Xaa Pro Xaa Xaa Cys Xaa Phe Xaa Val
145             150             155             160

Asn Xaa Xaa Tyr Xaa Xaa Xaa Ser Ser Xaa Ser Phe Trp Xaa Pro
            165             170             175

Gly Xaa Xaa Met Xaa Xaa Met Tyr Tyr Arg Ile Tyr Xaa Glu Ala Xaa
            180             185             190

Arg Gln Xaa Xaa Xaa Xaa Xaa Arg Xaa Xaa Xaa Xaa Xaa Leu Xaa
        195             200             205

Xaa Xaa His Xaa Xaa Xaa Xaa Xaa Xaa Xaa Xaa Xaa Xaa Xaa Xaa
    210             215             220

Xaa Xaa Xaa Xaa Xaa Xaa Xaa Xaa Xaa Xaa Xaa Xaa Xaa Xaa Xaa
225             230             235             240

Xaa Xaa Xaa Xaa Xaa Xaa Xaa Xaa Xaa Xaa Xaa Xaa Glu Xaa
            245             250             255

Lys Ala Ala Arg Thr Leu Gly Ile Ile Xaa Xaa Xaa Phe Leu Xaa Cys
            260             265             270

Trp Leu Pro Phe Phe Leu Trp Tyr Xaa Xaa Xaa Xaa Leu Cys Xaa Xaa
            275             280             285

Xaa Xaa Cys Xaa Xaa Pro Xaa Xaa Xaa Xaa Xaa Xaa Phe Trp Xaa
            290             295             300

Gly Tyr Phe Asn Ser Xaa Leu Asn Pro Xaa Ile Tyr Ala Tyr Phe Asn
305             310             315             320

Arg Xaa Phe Arg Xaa Ala Phe Xaa Xaa Thr Leu
            325             330
```

<210> SEQ ID NO 178
<211> LENGTH: 653
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (15)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(25)

```
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (90)..(91)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
```

```
<222> LOCATION: (132)..(134)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(143)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (159)..(193)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (203)..(205)
<223> OTHER INFORMATION: Xaa can be any naturally occurring amino acid
<220> FEATURE:
<221> NAME/KEY: misc_feature
<222> LOCATION: (228)..(228)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (234)..(235)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (247)..(258)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (264)..(265)
<223> OTHER INFORMATION: Xaa can be any naturally occurring amino acid
<220> FEATURE:
<221> NAME/KEY: misc_feature
<222> LOCATION: (278)..(299)
<223> OTHER INFORMATION: Xaa can be any naturally occurring amino acid
<220> FEATURE:
<221> NAME/KEY: misc_feature
<222> LOCATION: (301)..(308)
<223> OTHER INFORMATION: Xaa can be any naturally occurring amino acid
<220> FEATURE:
<221> NAME/KEY: misc_feature
<222> LOCATION: (310)..(318)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
```

-continued

```
<221> NAME/KEY: misc_feature
<222> LOCATION: (324)..(325)
<223> OTHER INFORMATION: Xaa can be any naturally occurring amino acid
<220> FEATURE:
<221> NAME/KEY: misc_feature
<222> LOCATION: (335)..(364)
<223> OTHER INFORMATION: Xaa can be any naturally occurring amino acid
<220> FEATURE:
<221> NAME/KEY: misc_feature
<222> LOCATION: (366)..(383)
<223> OTHER INFORMATION: Xaa can be any naturally occurring amino acid
<220> FEATURE:
<221> NAME/KEY: misc_feature
<222> LOCATION: (385)..(388)
<223> OTHER INFORMATION: Xaa can be any naturally occurring amino acid
<220> FEATURE:
<221> NAME/KEY: misc_feature
<222> LOCATION: (393)..(416)
<223> OTHER INFORMATION: Xaa can be any naturally occurring amino acid
<220> FEATURE:
<221> NAME/KEY: misc_feature
<222> LOCATION: (420)..(481)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid
<220> FEATURE:
<221> NAME/KEY: misc_feature
<222> LOCATION: (485)..(529)
<223> OTHER INFORMATION: Xaa can be any naturally occurring amino acid
<220> FEATURE:
<221> NAME/KEY: misc_feature
<222> LOCATION: (532)..(533)
<223> OTHER INFORMATION: Xaa can be any naturally occurring amino acid
<220> FEATURE:
<221> NAME/KEY: misc_feature
<222> LOCATION: (555)..(555)
<223> OTHER INFORMATION: Xaa can be any naturally occurring amino acid
<220> FEATURE:
<221> NAME/KEY: misc_feature
<222> LOCATION: (562)..(563)
<223> OTHER INFORMATION: Xaa can be any naturally occurring amino acid
<220> FEATURE:
<221> NAME/KEY: misc_feature
<222> LOCATION: (570)..(571)
<223> OTHER INFORMATION: Xaa can be any naturally occurring amino acid
<220> FEATURE:
<221> NAME/KEY: misc_feature
<222> LOCATION: (573)..(573)
<223> OTHER INFORMATION: Xaa can be any naturally occurring amino acid
<220> FEATURE:
<221> NAME/KEY: misc_feature
<222> LOCATION: (579)..(580)
<223> OTHER INFORMATION: Xaa can be any naturally occurring amino acid
<220> FEATURE:
<221> NAME/KEY: misc_feature
<222> LOCATION: (582)..(583)
<223> OTHER INFORMATION: Xaa can be any naturally occurring amino acid
<220> FEATURE:
<221> NAME/KEY: misc_feature
<222> LOCATION: (585)..(586)
<223> OTHER INFORMATION: Xaa can be any naturally occurring amino acid
<220> FEATURE:
<221> NAME/KEY: misc_feature
<222> LOCATION: (589)..(590)
<223> OTHER INFORMATION: Xaa can be any naturally occurring amino acid
<220> FEATURE:
<221> NAME/KEY: misc_feature
<222> LOCATION: (603)..(603)
<223> OTHER INFORMATION: Xaa can be any naturally occurring amino acid
<220> FEATURE:
<221> NAME/KEY: misc_feature
<222> LOCATION: (620)..(620)
<223> OTHER INFORMATION: Xaa can be any naturally occurring amino acid
<220> FEATURE:
<221> NAME/KEY: misc_feature
<222> LOCATION: (622)..(624)
<223> OTHER INFORMATION: Xaa can be any naturally occurring amino acid
```

```
<220> FEATURE:
<221> NAME/KEY: misc_feature
<222> LOCATION: (626)..(645)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid
<220> FEATURE:
<221> NAME/KEY: misc_feature
<222> LOCATION: (649)..(650)
<223> OTHER INFORMATION: Xaa can be any naturally occurring amino acid

<400> SEQUENCE: 178

Asn Xaa Xaa Xaa Cys Xaa Xaa Leu Xaa Xaa Xaa Xaa Trp Xaa Xaa
1               5                   10                  15

Xaa Xaa Xaa Leu Xaa Xaa Leu Xaa Xaa Leu Xaa Xaa Ile Xaa Xaa
            20                  25                  30

Val Xaa Xaa Gly Asn Xaa Leu Val Xaa Ala Ala Val Xaa Xaa Ser Ser
        35                  40                  45

Lys Leu Arg Ser Xaa Thr Asn Xaa Phe Ile Val Ser Leu Ala Val Xaa
50                  55                  60

Asp Leu Xaa Val Gly Val Ala Val Leu Pro Phe Ser Ala Thr Xaa Glu
65                  70                  75                  80

Val Phe Xaa Val Trp Xaa Phe Gly Asp Xaa Xaa Cys Xaa Xaa Trp Leu
                85                  90                  95

Ala Xaa Asp Val Trp Met Cys Thr Ala Ser Ile Leu Asn Leu Cys Ala
            100                 105                 110

Ile Ser Leu Asp Arg Tyr Xaa Ala Val Thr Arg Pro Xaa Xaa Tyr Pro
            115                 120                 125

Ser Xaa Met Xaa Xaa Xaa Arg Ala Lys Xaa Leu Xaa Xaa Xaa Xaa Trp
        130                 135                 140

Val Leu Ser Phe Val Ile Cys Xaa Pro Pro Leu Val Gly Trp Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Cys Xaa Trp Xaa Cys Glu Leu Xaa Asn Xaa Xaa Xaa Tyr Val Val
        195                 200                 205

Tyr Ser Ala Leu Gly Ser Phe Tyr Ile Pro Met Phe Val Met Leu Phe
        210                 215                 220

Phe Tyr Trp Xaa Ile Tyr Xaa Ala Ala Xaa Xaa Thr Thr Xaa Ala Ile
225                 230                 235                 240

Asn Gln Gly Phe Arg Thr Xaa Xaa Xaa Xaa Xaa Xaa Xaa Xaa Xaa
                245                 250                 255

Xaa Xaa Gly Xaa Arg Phe Asp Xaa Xaa Arg Leu Thr Leu Arg Ile His
        260                 265                 270

Arg Gly Arg Gly Ser Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Ser Xaa Xaa Xaa Xaa
        290                 295                 300

Xaa Xaa Xaa Xaa Pro Xaa Xaa Xaa Xaa Xaa Xaa Xaa Xaa Arg Xaa
305                 310                 315                 320

Xaa His Glu Xaa Xaa Lys Ile Ser Val Ser Tyr Pro Ser Ser Xaa Xaa
        325                 330                 335

Xaa Xaa Xaa Xaa Xaa Xaa Xaa Xaa Xaa Xaa Xaa Xaa Xaa Xaa Xaa
```

-continued

```
                340                 345                 350
Xaa Xaa Xaa Xaa Xaa Xaa Xaa Xaa Xaa Xaa Glu Xaa Xaa Xaa
            355                 360                 365

Xaa Xaa Xaa Xaa Xaa Xaa Xaa Xaa Xaa Xaa Xaa Xaa Xaa Ser
        370                 375                 380

Xaa Xaa Xaa Xaa Ala Val His Tyr Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa
            405                 410                 415

Leu Arg Val Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa
465                 470                 475                 480

Xaa Pro Xaa Pro Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa
            515                 520                 525

Xaa Met Gly Xaa Xaa Lys Arg Asn Ile Lys Ala Gln Val Lys Arg Phe
        530                 535                 540

Arg Met Glu Thr Lys Ala Ala Lys Thr Leu Xaa Ile Ile Val Gly Gly
545                 550                 555                 560

Phe Xaa Xaa Cys Trp Leu Pro Phe Phe Xaa Xaa Tyr Xaa Val Arg Ala
            565                 570                 575

Phe Cys Xaa Xaa Cys Xaa Xaa Pro Xaa Xaa Phe Ser Xaa Xaa Phe Trp
        580                 585                 590

Leu Gly Tyr Cys Asn Ser Ala Ile Asn Pro Xaa Ile Tyr Ala Leu Phe
            595                 600                 605

Ser Lys Asp Phe Arg Phe Ala Phe Lys Arg Ile Xaa Cys Xaa Xaa Xaa
        610                 615                 620

Cys Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Gly Xaa Arg Xaa Xaa Ser Asp Gly
            645                 650

<210> SEQ ID NO 179
<211> LENGTH: 398
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
```

```
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (103)..(105)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
```

-continued

```
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (124)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (138)..(139)
<223> OTHER INFORMATION: Xaa can be any naturally occurring amino acid
<220> FEATURE:
<221> NAME/KEY: misc_feature
<222> LOCATION: (141)..(147)
<223> OTHER INFORMATION: Xaa can be any naturally occurring amino acid
<220> FEATURE:
<221> NAME/KEY: misc_feature
<222> LOCATION: (149)..(150)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (192)..(195)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (199)..(201)
```

```
<223> OTHER INFORMATION: Xaa can be any naturally occurring amino acid
<220> FEATURE:
<221> NAME/KEY: misc_feature
<222> LOCATION: (203)..(214)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (230)..(231)
<223> OTHER INFORMATION: Xaa can be any naturally occurring amino acid
<220> FEATURE:
<221> NAME/KEY: misc_feature
<222> LOCATION: (233)..(239)
<223> OTHER INFORMATION: Xaa can be any naturally occurring amino acid
<220> FEATURE:
<221> NAME/KEY: misc_feature
<222> LOCATION: (244)..(248)
<223> OTHER INFORMATION: Xaa can be any naturally occurring amino acid
<220> FEATURE:
<221> NAME/KEY: misc_feature
<222> LOCATION: (261)..(261)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (279)..(283)
<223> OTHER INFORMATION: Xaa can be any naturally occurring amino acid
<220> FEATURE:
<221> NAME/KEY: misc_feature
<222> LOCATION: (285)..(287)
<223> OTHER INFORMATION: Xaa can be any naturally occurring amino acid
<220> FEATURE:
<221> NAME/KEY: misc_feature
<222> LOCATION: (289)..(293)
<223> OTHER INFORMATION: Xaa can be any naturally occurring amino acid
<220> FEATURE:
<221> NAME/KEY: misc_feature
<222> LOCATION: (296)..(298)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (324)..(325)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
```

```
<222> LOCATION: (331)..(331)
<223> OTHER INFORMATION: Xaa can be any naturally occurring amino acid
<220> FEATURE:
<221> NAME/KEY: misc_feature
<222> LOCATION: (334)..(346)
<223> OTHER INFORMATION: Xaa can be any naturally occurring amino acid
<220> FEATURE:
<221> NAME/KEY: misc_feature
<222> LOCATION: (348)..(350)
<223> OTHER INFORMATION: Xaa can be any naturally occurring amino acid
<220> FEATURE:
<221> NAME/KEY: misc_feature
<222> LOCATION: (353)..(353)
<223> OTHER INFORMATION: Xaa can be any naturally occurring amino acid
<220> FEATURE:
<221> NAME/KEY: misc_feature
<222> LOCATION: (355)..(362)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (367)..(373)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
<222> LOCATION: (378)..(379)
<223> OTHER INFORMATION: Xaa can be any naturally occurring amino acid
<220> FEATURE:
<221> NAME/KEY: misc_feature
<222> LOCATION: (381)..(388)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (393)..(397)
<223> OTHER INFORMATION: Xaa can be any naturally occurring amino acid

<400> SEQUENCE: 179

Met Xaa Xaa Ile Ile Xaa Xaa Xaa Ile Xaa Gly Asn Leu Leu Val Ile
1               5                   10                  15

Xaa Ser Val Met Arg Xaa Arg Lys Leu Arg Xaa Ile Thr Asn Tyr Xaa
                20                  25                  30

Val Xaa Ser Leu Ala Xaa Ala Asp Xaa Xaa Val Ala Xaa Xaa Ala Met
            35                  40                  45

Thr Phe Asn Xaa Ser Val Gln Xaa Xaa Xaa Trp Xaa Phe Xaa Xaa
    50                  55                  60

Phe Xaa Cys Asp Xaa Trp Asn Xaa Leu Asp Val Tyr Phe Ser Thr Xaa
65                  70                  75                  80

Ser Ile Xaa His Leu Cys Cys Ile Ser Val Asp Arg Tyr Xaa Ala Ile
                85                  90                  95

Val Lys Pro Leu Lys Tyr Xaa Xaa Xaa Met Thr Lys Xaa Xaa Val Xaa
                100                 105                 110

Xaa Met Leu Leu Xaa Thr Trp Xaa Xaa Pro Ala Xaa Xaa Ser Phe Xaa
            115                 120                 125

Pro Ile Phe Xaa Gly Trp Tyr Xaa Thr Xaa Xaa His Xaa Xaa Xaa Xaa
        130                 135                 140

Xaa Xaa Xaa Pro Xaa Xaa Cys Xaa Phe Xaa Val Asn Lys Xaa Tyr Ala
145                 150                 155                 160
```

```
Xaa Ile Ser Ser Ser Ile Ser Phe Trp Ile Pro Cys Thr Ile Met Ile
                165                 170                 175

Xaa Xaa Tyr Leu Ala Ile Phe Xaa Glu Ala Asn Xaa Gln Glu Lys Xaa
            180                 185                 190

Xaa Xaa Xaa Arg Xaa Gly Xaa Xaa Xaa Leu Xaa Xaa Xaa Xaa Xaa Xaa
        195                 200                 205

Xaa Xaa Xaa Xaa Xaa Xaa Gly Xaa Xaa Leu Ser Xaa Ser Gly Xaa Ser
    210                 215                 220

Ser Lys Xaa Leu Thr Xaa Xaa Glu Xaa Xaa Xaa Xaa Xaa Xaa Xaa Thr
225                 230                 235                 240

Pro Thr Lys Xaa Xaa Xaa Xaa Xaa Lys Met Lys Arg Glu His Lys Ala
                245                 250                 255

Ala Arg Thr Leu Xaa Ile Ile Met Gly Thr Phe Xaa Leu Cys Trp Leu
            260                 265                 270

Pro Phe Phe Leu Trp Tyr Xaa Xaa Xaa Xaa Cys Xaa Xaa Xaa Xaa Cys
            275                 280                 285

Xaa Xaa Xaa Xaa Xaa Val Val Xaa Xaa Xaa Phe Trp Ile Gly Tyr Xaa
        290                 295                 300

Asn Ser Thr Leu Asn Pro Xaa Ile Tyr Ala Tyr Phe Asn Xaa Asp Phe
305                 310                 315                 320

Arg Glu Ala Xaa Xaa Asn Thr Leu Xaa Cys Xaa Phe Cys Xaa Xaa Xaa
                325                 330                 335

Xaa Xaa Xaa Xaa Xaa Xaa Xaa Xaa Asp Xaa Xaa Xaa Arg Arg
        340                 345                 350

Xaa Ser Xaa Xaa Xaa Xaa Xaa Tyr Asp Xaa Arg Xaa Xaa
        355                 360                 365

Xaa Xaa Xaa Xaa Xaa Ser Xaa Xaa Ser Xaa Xaa Tyr Xaa Xaa Xaa Xaa
        370                 375                 380

Xaa Xaa Xaa Xaa Arg Arg Xaa Ser Xaa Xaa Xaa Xaa Leu
385                 390                 395

<210> SEQ ID NO 180
<211> LENGTH: 6
<212> TYPE: PRT
<213> ORGANISM: Artificial
<220> FEATURE:
<223> OTHER INFORMATION: Motif

<400> SEQUENCE: 180

Arg His Arg Lys Leu Arg
1               5

<210> SEQ ID NO 181
<211> LENGTH: 5
<212> TYPE: PRT
<213> ORGANISM: Artificial
<220> FEATURE:
<223> OTHER INFORMATION: Motif

<400> SEQUENCE: 181

Val Val Ser Leu Ala
1               5

<210> SEQ ID NO 182
<211> LENGTH: 5
<212> TYPE: PRT
<213> ORGANISM: Artificial
<220> FEATURE:
<223> OTHER INFORMATION: Motif
```

```
<400> SEQUENCE: 182

Asp Val Tyr Phe Ser
1               5

<210> SEQ ID NO 183
<211> LENGTH: 14
<212> TYPE: PRT
<213> ORGANISM: Artificial
<220> FEATURE:
<223> OTHER INFORMATION: Motif

<400> SEQUENCE: 183

His Leu Cys Cys Ile Ser Val Asp Arg Tyr Tyr Ala Ile Val
1               5                   10

<210> SEQ ID NO 184
<211> LENGTH: 5
<212> TYPE: PRT
<213> ORGANISM: Artificial
<220> FEATURE:
<223> OTHER INFORMATION: Motif

<400> SEQUENCE: 184

Ser Phe Leu Pro Ile
1               5

<210> SEQ ID NO 185
<211> LENGTH: 4
<212> TYPE: PRT
<213> ORGANISM: Artificial
<220> FEATURE:
<223> OTHER INFORMATION: Motif

<400> SEQUENCE: 185

Trp Tyr Thr Thr
1

<210> SEQ ID NO 186
<211> LENGTH: 6
<212> TYPE: PRT
<213> ORGANISM: Artificial
<220> FEATURE:
<223> OTHER INFORMATION: Motif

<400> SEQUENCE: 186

Met Tyr Tyr Arg Ile Tyr
1               5

<210> SEQ ID NO 187
<211> LENGTH: 9
<212> TYPE: PRT
<213> ORGANISM: Artificial
<220> FEATURE:
<223> OTHER INFORMATION: Motif

<400> SEQUENCE: 187

Lys Ala Ala Arg Thr Leu Gly Ile Ile
1               5

<210> SEQ ID NO 188
<211> LENGTH: 9
<212> TYPE: PRT
<213> ORGANISM: Artificial
<220> FEATURE:
<223> OTHER INFORMATION: Motif

<400> SEQUENCE: 188
```

```
Cys Trp Leu Pro Phe Phe Leu Trp Tyr
1               5

<210> SEQ ID NO 189
<211> LENGTH: 5
<212> TYPE: PRT
<213> ORGANISM: Artificial
<220> FEATURE:
<223> OTHER INFORMATION: Motif

<400> SEQUENCE: 189

Gly Tyr Phe Asn Ser
1               5

<210> SEQ ID NO 190
<211> LENGTH: 7
<212> TYPE: PRT
<213> ORGANISM: Artificial
<220> FEATURE:
<223> OTHER INFORMATION: Motif

<400> SEQUENCE: 190

Ile Tyr Ala Tyr Phe Asn Arg
1               5

<210> SEQ ID NO 191
<211> LENGTH: 6
<212> TYPE: PRT
<213> ORGANISM: Artificial
<220> FEATURE:
<223> OTHER INFORMATION: Motif

<400> SEQUENCE: 191

Ser Ser Lys Leu Arg Ser
1               5

<210> SEQ ID NO 192
<211> LENGTH: 7
<212> TYPE: PRT
<213> ORGANISM: Artificial
<220> FEATURE:
<223> OTHER INFORMATION: Motif

<400> SEQUENCE: 192

Phe Ile Val Ser Leu Ala Val
1               5

<210> SEQ ID NO 193
<211> LENGTH: 11
<212> TYPE: PRT
<213> ORGANISM: Artificial
<220> FEATURE:
<223> OTHER INFORMATION: Motif

<400> SEQUENCE: 193

Val Gly Val Ala Val Leu Pro Phe Ser Ala Thr
1               5                   10

<210> SEQ ID NO 194
<211> LENGTH: 20
<212> TYPE: PRT
<213> ORGANISM: Artificial
<220> FEATURE:
<223> OTHER INFORMATION: Motif

<400> SEQUENCE: 194
```

```
Asp Val Trp Met Cys Thr Ala Ser Ile Leu Asn Leu Cys Ala Ile Ser
1               5                   10                  15

Leu Asp Arg Tyr
            20

<210> SEQ ID NO 195
<211> LENGTH: 5
<212> TYPE: PRT
<213> ORGANISM: Artificial
<220> FEATURE:
<223> OTHER INFORMATION: Motif

<400> SEQUENCE: 195

Ala Val Thr Arg Pro
1               5

<210> SEQ ID NO 196
<211> LENGTH: 8
<212> TYPE: PRT
<213> ORGANISM: Artificial
<220> FEATURE:
<223> OTHER INFORMATION: Motif

<400> SEQUENCE: 196

Trp Val Leu Ser Phe Val Ile Cys
1               5

<210> SEQ ID NO 197
<211> LENGTH: 6
<212> TYPE: PRT
<213> ORGANISM: Artificial
<220> FEATURE:
<223> OTHER INFORMATION: Motif

<400> SEQUENCE: 197

Pro Pro Leu Val Gly Trp
1               5

<210> SEQ ID NO 198
<211> LENGTH: 22
<212> TYPE: PRT
<213> ORGANISM: Artificial
<220> FEATURE:
<223> OTHER INFORMATION: Motif

<400> SEQUENCE: 198

Tyr Val Val Tyr Ser Ala Leu Gly Ser Phe Tyr Ile Pro Met Phe Val
1               5                   10                  15

Met Leu Phe Phe Tyr Trp
            20

<210> SEQ ID NO 199
<211> LENGTH: 8
<212> TYPE: PRT
<213> ORGANISM: Artificial
<220> FEATURE:
<223> OTHER INFORMATION: Motif

<400> SEQUENCE: 199

Ala Ile Asn Gln Gly Phe Arg Thr
1               5

<210> SEQ ID NO 200
<211> LENGTH: 12
<212> TYPE: PRT
<213> ORGANISM: Artificial
```

```
<220> FEATURE:
<223> OTHER INFORMATION: Motif

<400> SEQUENCE: 200

Arg Leu Thr Leu Arg Ile His Arg Gly Arg Gly Ser
1               5                   10

<210> SEQ ID NO 201
<211> LENGTH: 9
<212> TYPE: PRT
<213> ORGANISM: Artificial
<220> FEATURE:
<223> OTHER INFORMATION: Motif

<400> SEQUENCE: 201

Lys Ile Ser Val Ser Tyr Pro Ser Ser
1               5

<210> SEQ ID NO 202
<211> LENGTH: 4
<212> TYPE: PRT
<213> ORGANISM: Artificial
<220> FEATURE:
<223> OTHER INFORMATION: Motif

<400> SEQUENCE: 202

Ala Val His Tyr
1

<210> SEQ ID NO 203
<211> LENGTH: 21
<212> TYPE: PRT
<213> ORGANISM: Artificial
<220> FEATURE:
<223> OTHER INFORMATION: Motif

<400> SEQUENCE: 203

Lys Arg Asn Ile Lys Ala Gln Val Lys Arg Phe Arg Met Glu Thr Lys
1               5                   10                  15

Ala Ala Lys Thr Leu
            20

<210> SEQ ID NO 204
<211> LENGTH: 6
<212> TYPE: PRT
<213> ORGANISM: Artificial
<220> FEATURE:
<223> OTHER INFORMATION: Motif

<400> SEQUENCE: 204

Ile Ile Val Gly Gly Phe
1               5

<210> SEQ ID NO 205
<211> LENGTH: 6
<212> TYPE: PRT
<213> ORGANISM: Artificial
<220> FEATURE:
<223> OTHER INFORMATION: Motif

<400> SEQUENCE: 205

Cys Trp Leu Pro Phe Phe
1               5

<210> SEQ ID NO 206
<211> LENGTH: 5
```

```
<212> TYPE: PRT
<213> ORGANISM: Artificial
<220> FEATURE:
<223> OTHER INFORMATION: Motif

<400> SEQUENCE: 206

Val Arg Ala Phe Cys
1               5

<210> SEQ ID NO 207
<211> LENGTH: 12
<212> TYPE: PRT
<213> ORGANISM: Artificial
<220> FEATURE:
<223> OTHER INFORMATION: Motif

<400> SEQUENCE: 207

Phe Trp Leu Gly Tyr Cys Asn Ser Ala Ile Asn Pro
1               5                   10

<210> SEQ ID NO 208
<211> LENGTH: 16
<212> TYPE: PRT
<213> ORGANISM: Artificial
<220> FEATURE:
<223> OTHER INFORMATION: Motif

<400> SEQUENCE: 208

Ile Tyr Ala Leu Phe Ser Lys Asp Phe Arg Phe Ala Phe Lys Arg Ile
1               5                   10                  15

<210> SEQ ID NO 209
<211> LENGTH: 6
<212> TYPE: PRT
<213> ORGANISM: Artificial
<220> FEATURE:
<223> OTHER INFORMATION: Motif

<400> SEQUENCE: 209

Gly Asn Leu Leu Val Ile
1               5

<210> SEQ ID NO 210
<211> LENGTH: 4
<212> TYPE: PRT
<213> ORGANISM: Artificial
<220> FEATURE:
<223> OTHER INFORMATION: Motif

<400> SEQUENCE: 210

Ser Val Met Arg
1

<210> SEQ ID NO 211
<211> LENGTH: 4
<212> TYPE: PRT
<213> ORGANISM: Artificial
<220> FEATURE:
<223> OTHER INFORMATION: Motif

<400> SEQUENCE: 211

Arg Lys Leu Arg
1

<210> SEQ ID NO 212
<211> LENGTH: 4
<212> TYPE: PRT
```

```
<213> ORGANISM: Artificial
<220> FEATURE:
<223> OTHER INFORMATION: Motif

<400> SEQUENCE: 212

Ile Thr Asn Tyr
1

<210> SEQ ID NO 213
<211> LENGTH: 5
<212> TYPE: PRT
<213> ORGANISM: Artificial
<220> FEATURE:
<223> OTHER INFORMATION: Motif

<400> SEQUENCE: 213

Ala Met Thr Phe Asn
1               5

<210> SEQ ID NO 214
<211> LENGTH: 7
<212> TYPE: PRT
<213> ORGANISM: Artificial
<220> FEATURE:
<223> OTHER INFORMATION: Motif

<400> SEQUENCE: 214

Leu Asp Val Tyr Phe Ser Thr
1               5

<210> SEQ ID NO 215
<211> LENGTH: 10
<212> TYPE: PRT
<213> ORGANISM: Artificial
<220> FEATURE:
<223> OTHER INFORMATION: Motif

<400> SEQUENCE: 215

His Leu Cys Cys Ile Ser Val Asp Arg Tyr
1               5                   10

<210> SEQ ID NO 216
<211> LENGTH: 8
<212> TYPE: PRT
<213> ORGANISM: Artificial
<220> FEATURE:
<223> OTHER INFORMATION: Motif

<400> SEQUENCE: 216

Ala Ile Val Lys Pro Leu Lys Tyr
1               5

<210> SEQ ID NO 217
<211> LENGTH: 15
<212> TYPE: PRT
<213> ORGANISM: Artificial
<220> FEATURE:
<223> OTHER INFORMATION: Motif

<400> SEQUENCE: 217

Ile Ser Ser Ser Ile Ser Phe Trp Ile Pro Cys Thr Ile Met Ile
1               5                   10                  15

<210> SEQ ID NO 218
<211> LENGTH: 5
<212> TYPE: PRT
<213> ORGANISM: Artificial
```

```
<220> FEATURE:
<223> OTHER INFORMATION: Motif

<400> SEQUENCE: 218

Tyr Leu Ala Ile Phe
1               5

<210> SEQ ID NO 219
<211> LENGTH: 4
<212> TYPE: PRT
<213> ORGANISM: Artificial
<220> FEATURE:
<223> OTHER INFORMATION: Motif

<400> SEQUENCE: 219

Thr Pro Thr Lys
1

<210> SEQ ID NO 220
<211> LENGTH: 12
<212> TYPE: PRT
<213> ORGANISM: Artificial
<220> FEATURE:
<223> OTHER INFORMATION: Motif

<400> SEQUENCE: 220

Lys Met Lys Arg Glu His Lys Ala Ala Arg Thr Leu
1               5                   10

<210> SEQ ID NO 221
<211> LENGTH: 6
<212> TYPE: PRT
<213> ORGANISM: Artificial
<220> FEATURE:
<223> OTHER INFORMATION: Motif

<400> SEQUENCE: 221

Ile Ile Met Gly Thr Phe
1               5

<210> SEQ ID NO 222
<211> LENGTH: 10
<212> TYPE: PRT
<213> ORGANISM: Artificial
<220> FEATURE:
<223> OTHER INFORMATION: Motif

<400> SEQUENCE: 222

Leu Cys Trp Leu Pro Phe Phe Leu Trp Tyr
1               5                   10

<210> SEQ ID NO 223
<211> LENGTH: 5
<212> TYPE: PRT
<213> ORGANISM: Artificial
<220> FEATURE:
<223> OTHER INFORMATION: Motif

<400> SEQUENCE: 223

Phe Trp Ile Gly Tyr
1               5

<210> SEQ ID NO 224
<211> LENGTH: 6
<212> TYPE: PRT
<213> ORGANISM: Artificial
<220> FEATURE:
```

<223> OTHER INFORMATION: Motif

<400> SEQUENCE: 224

Asn Ser Thr Leu Asn Pro
1               5

<210> SEQ ID NO 225
<211> LENGTH: 6
<212> TYPE: PRT
<213> ORGANISM: Artificial
<220> FEATURE:
<223> OTHER INFORMATION: Motif

<400> SEQUENCE: 225

Ile Tyr Ala Tyr Phe Asn
1               5

<210> SEQ ID NO 226
<211> LENGTH: 5
<212> TYPE: PRT
<213> ORGANISM: Artificial
<220> FEATURE:
<223> OTHER INFORMATION: Motif

<400> SEQUENCE: 226

Asp Phe Arg Glu Ala
1               5

<210> SEQ ID NO 227
<211> LENGTH: 1722
<212> TYPE: DNA
<213> ORGANISM: Drosophila melanogaster

<400> SEQUENCE: 227

```
atgaaaacac cttccattgc gaaccgggaa cagatctcat ctggatgcaa cgaagaagcg    60
gccgaggcac tagtgggtat ccactcagac taccctaggt atatggaaga cgtgctctt   120 actggcggca atacgtccag gaagccatca acaaactcgg ccaaacacaa acccaatgtg   180
ggctatcgcc tgggaaagag gaaagccctc ttcgagaagc gcaaacggat cagcgattac   240
gccctggtca tgggcatgtt cgggatcatc gtgatggtta tcgaaaacga actgagcagt   300
gccggtgtct acacaaaggc atcgttctac tcgacagcgt taaaaacctt aatatctgtt   360
tcgactgtga ttctttagg acttatagta gcttaccatg ctttggaagt gcagttattc   420
atgatagata actgcgctga cgattggagg atcgcaatga catggcaacg aattagtcaa   480
atagggttag aactttttat atgcgctata catccaattc ctggcgaata ctatttccag   540
tggacgacga aattggccaa taagaataaa acaattggca ccgaaatggt gccatatgac   600
gtagctttat cattacctat gttccttcga ttatatttaa tctgccgcgt aatgctgctg   660
cattcaaagc tattcacaga tgcatcatca cggagcattg gcgctctcaa taggattaat   720
tttaacacaa gattcgtttt aaaaactcta atgacaaat gtccgggaac ggttctattg   780
gtcttcatgg tctcgctgtg gatcatcgca tcgtggacgc tgcgtcagtg cgaaagattt   840
catgatgaag aacacgcgaa tctttttgaat gcaatgtggc tgatagcgat aacattttg   900 agtgttggtt tcggtgatat tgttccgaat acgtactgtg acgtggtat cgctgtcagt   960 acaggaataa tgggcgccgg ctgtacggct ctactggtgg ccgtagtctc tcggaaactg  1020
gagctgaccc gtgctgagaa gcatgtgcac aacttcatga tggacacgca gttgacgaaa  1080
cggctgaaaa atgctgcggc gaatgttctg cgtgaaactt ggctcattta caaacataca  1140
```

-continued

```
agactagtaa aacgggttaa tcccggccgt gtaagaaccc accaaagaaa gttccttcta    1200
gctatatatg cgttgcgaaa agttaaaatg gatcagcgca aactaatgga taatgcaaac    1260
acaataactg acatggctaa gacacaaaac acggtctacg agataatatc ggacatgtct    1320
agccgtcagg atgccatcga agagcgttta accaacctag aggacaaaat gcagagcata    1380
caagagcaca tggaaagcct tccagaccta ttgtctcgat gtctgaccca gcaccaggag    1440
cggatcgagc agcggcggaa cttttttacat cctgacacag ctgcagttgc ccccattcaa    1500
gcgccaacgc cccaatcgat gttcaatgca gcgcccatgc tgtttccaca ttctagaagt    1560
gttccctcat ccaataacgc cgctgctact taccattggc caacaagccc tattttgcca    1620
cctatatcta gtagaacacc acatttagtg cctgatactc acatgccatc aaatggatct    1680
gcagttaata gctacgcatc ttccaacaaa tacggcagct ga                       1722
```

<210> SEQ ID NO 228
<211> LENGTH: 573
<212> TYPE: PRT
<213> ORGANISM: Drosophila melanogaster

<400> SEQUENCE: 228

```
Met Lys Thr Pro Ser Ile Ala Asn Arg Glu Gln Ile Ser Ser Gly Cys
1               5                   10                  15

Asn Glu Glu Ala Ala Glu Ala Leu Val Gly Ile His Ser Asp Tyr Pro
            20                  25                  30

Arg Tyr Met Glu Glu Arg Ala Leu Thr Gly Gly Asn Thr Ser Arg Lys
        35                  40                  45

Pro Ser Thr Asn Ser Ala Lys His Lys Pro Asn Val Gly Tyr Arg Leu
    50                  55                  60

Gly Lys Arg Lys Ala Leu Phe Glu Lys Arg Lys Arg Ile Ser Asp Tyr
65                  70                  75                  80

Ala Leu Val Met Gly Met Phe Gly Ile Ile Val Met Val Ile Glu Asn
                85                  90                  95

Glu Leu Ser Ser Ala Gly Val Tyr Thr Lys Ala Ser Phe Tyr Ser Thr
            100                 105                 110

Ala Leu Lys Thr Leu Ile Ser Val Ser Thr Val Ile Leu Leu Gly Leu
        115                 120                 125

Ile Val Ala Tyr His Ala Leu Glu Val Gln Leu Phe Met Ile Asp Asn
    130                 135                 140

Cys Ala Asp Asp Trp Arg Ile Ala Met Thr Trp Gln Arg Ile Ser Gln
145                 150                 155                 160

Ile Gly Leu Glu Leu Phe Ile Cys Ala Ile His Pro Ile Pro Gly Glu
                165                 170                 175

Tyr Tyr Phe Gln Trp Thr Thr Lys Leu Ala Asn Lys Asn Lys Thr Ile
            180                 185                 190

Gly Thr Glu Met Val Pro Tyr Asp Val Ala Leu Ser Leu Pro Met Phe
        195                 200                 205

Leu Arg Leu Tyr Leu Ile Cys Arg Val Met Leu Leu His Ser Lys Leu
    210                 215                 220

Phe Thr Asp Ala Ser Ser Arg Ser Ile Gly Ala Leu Asn Arg Ile Asn
225                 230                 235                 240

Phe Asn Thr Arg Phe Val Leu Lys Thr Leu Met Thr Ile Cys Pro Gly
                245                 250                 255

Thr Val Leu Leu Val Phe Met Val Ser Leu Trp Ile Ile Ala Ser Trp
            260                 265                 270
```

```
Thr Leu Arg Gln Cys Glu Arg Phe His Asp Glu His Ala Asn Leu
            275                 280                 285
Leu Asn Ala Met Trp Leu Ile Ala Ile Thr Phe Leu Ser Val Gly Phe
    290                 295                 300
Gly Asp Ile Val Pro Asn Thr Tyr Cys Gly Arg Gly Ile Ala Val Ser
305                 310                 315                 320
Thr Gly Ile Met Gly Ala Gly Cys Thr Ala Leu Leu Val Ala Val Val
                325                 330                 335
Ser Arg Lys Leu Glu Leu Thr Arg Ala Glu Lys His Val His Asn Phe
            340                 345                 350
Met Met Asp Thr Gln Leu Thr Lys Arg Leu Lys Asn Ala Ala Ala Asn
    355                 360                 365
Val Leu Arg Glu Thr Trp Leu Ile Tyr Lys His Thr Arg Leu Val Lys
370                 375                 380
Arg Val Asn Pro Gly Arg Val Arg Thr His Gln Arg Lys Phe Leu Leu
385                 390                 395                 400
Ala Ile Tyr Ala Leu Arg Lys Val Lys Met Asp Gln Arg Lys Leu Met
                405                 410                 415
Asp Asn Ala Asn Thr Ile Thr Asp Met Ala Lys Thr Gln Asn Thr Val
            420                 425                 430
Tyr Glu Ile Ile Ser Asp Met Ser Ser Arg Gln Asp Ala Ile Glu Glu
    435                 440                 445
Arg Leu Thr Asn Leu Glu Asp Lys Met Gln Ser Ile Gln Glu His Met
450                 455                 460
Glu Ser Leu Pro Asp Leu Leu Ser Arg Cys Leu Thr Gln His Gln Glu
465                 470                 475                 480
Arg Ile Glu Gln Arg Arg Asn Phe Leu His Pro Asp Thr Ala Ala Val
                485                 490                 495
Ala Pro Ile Gln Ala Pro Thr Pro Gln Ser Met Phe Asn Ala Ala Pro
            500                 505                 510
Met Leu Phe Pro His Ser Arg Ser Val Pro Ser Ser Asn Asn Ala Ala
    515                 520                 525
Ala Thr Tyr His Trp Pro Thr Ser Pro Ile Leu Pro Pro Ile Ser Ser
530                 535                 540
Arg Thr Pro His Leu Val Pro Asp Thr His Met Pro Ser Asn Gly Ser
545                 550                 555                 560
Ala Val Asn Ser Tyr Ala Ser Ser Asn Lys Tyr Gly Ser
                565                 570

<210> SEQ ID NO 229
<211> LENGTH: 1878
<212> TYPE: DNA
<213> ORGANISM: Myzus persicae

<400> SEQUENCE: 229
atgcttctgt gttatatcaa aagtacagag ctgcgaaagc acacgtcatc gacattgtcg      60
atcactagtg ggatgaaggt tagcggttca ggtggccgag gcgatagcgg cgtagtgggc     120
gaggaagccg gcatagcatt ggttagcata cattccgact atccccgcta caccgaagaa     180
cgtaccgggt tggtgtgcaa gggtaccagc ttagtaggtt ccagtggtaa tataactggc     240
agtaaacaca aaccaaacgt cggatacaga ctgggtaggc gtaaaacact tttcgaaaaa     300
cgaaaaagaa tcagtgatta cgctctagtg atgggaatgt ttggaattat aatcatggtc     360
atcgagaatg agttggccag tgcaggagta tactcgaaaa cgtcattcta ttctacgtca     420
```

```
ctgaaaacgc tcatatccgt atccaccatc attctgctgg gtttgatcat ggcctaccac    480
gcgctcgaag tacagttgtt catgatcgac aattgcgcgg acgactggcg gatcgcgatg    540
acgtggcagc ggattgccac catcacgatg gagctggtga tctgcgcgat ccacccgatc    600
cctggcgagt attacttcga gtggaaaacc aagctggcca acaagcacgg gaagctggag    660
actcggtggg tgccgtacga tgtgccactg tcgctaccga tgttcttccg gctgtacctc    720
atctgccggg tcatgttgct tcacagcaag ctgttcacgg acgcatcgtc ccgcagcatc    780
ggcgccctga accggatcaa cttcaacacg aggttcgtgc tgaagacgct catgaccata    840
tgcccgggca cggtgctact cgtgttcatg gtgtccctgt ggataatcgc cagctggacg    900
ctcagacagt gcgagaggtt ccacgacgag gaccacgcca attacttgaa ctcgatgtgg    960
ctgatagcca tcacgttact cagtgtaggc tacggagaca ttgtaccaaa cacgtactgc   1020
ggacgaggca tcacgctctc ctgcggtatt atgggtgccg ggtgcacagc tcttctagtg   1080
gctgttgtgt cacgaaagat ggaactgtct agggcagaga acatgtcca taatttcatg   1140
atggacactc aacttacaaa acgactgaaa acgctgcgg ccaacgtcct tagagagacg   1200
tggctgatct acaaacacac cagactggtg aaaagggtga atgcaggcag ggttcgaaca   1260
caccaacgaa aattcttgtt ggccatatac gcgttgagaa aagtaaaaat ggaccaaaga   1320
aaattaatgg acaacgcaaa tacaataaca gacatggcca aaaacacagt ttatgaaatt   1380
gtatccgaca tgagtaatcg atatgatgcg tttgaagaac gtttggtgaa tctcgaagat   1440
aaactggtag ccttacaaga acagctggag ctgttgccgg agatcctgac ccggtgcata   1500
gcgcagaacc agcagaacca gcagaacacc agcaacctgt cgtcgacgac ggagtccagg   1560
cgcaatttcc tgcacccgga atctgcggcc gcggtggcca ccggcggtct gatgcaaccg   1620
tccgtctcgt ctccggcggg cagcatgacc ggcgtcggcg aaacccgct gatgttcccg   1680
tcgtcctcgg gcgccgcgag cggcggcatg atgttggcca tgggtaacgg atcgacggtc   1740
atgtcccact cgcgcagcgt gccaccgacc ggtgccggcg gcgcgtccca ttaccactgg   1800
cccaccagtc ccatattgcc gccaatcagc agccggacgc cgcatttagt gcccgagccc   1860
atccagccgt ccagctga                                                 1878
```

<210> SEQ ID NO 230
<211> LENGTH: 625
<212> TYPE: PRT
<213> ORGANISM: Myzus persicae

<400> SEQUENCE: 230

```
Met Leu Leu Cys Tyr Ile Lys Ser Thr Glu Leu Arg Lys His Thr Ser
1               5                   10                  15

Ser Thr Leu Ser Ile Thr Ser Gly Met Lys Val Ser Gly Ser Gly Gly
            20                  25                  30

Arg Gly Asp Ser Gly Val Val Gly Glu Glu Ala Gly Ile Ala Leu Val
        35                  40                  45

Ser Ile His Ser Asp Tyr Pro Arg Tyr Thr Glu Glu Arg Thr Gly Leu
    50                  55                  60

Val Cys Lys Gly Thr Ser Leu Val Gly Ser Gly Asn Ile Thr Gly
65                  70                  75                  80

Ser Lys His Lys Pro Asn Val Gly Tyr Arg Leu Gly Arg Arg Lys Thr
                85                  90                  95

Leu Phe Glu Lys Arg Lys Arg Ile Ser Asp Tyr Ala Leu Val Met Gly
            100                 105                 110
```

```
Met Phe Gly Ile Ile Ile Met Val Ile Glu Asn Glu Leu Ala Ser Ala
            115                 120                 125

Gly Val Tyr Ser Lys Thr Ser Phe Tyr Ser Thr Ser Leu Lys Thr Leu
            130                 135                 140

Ile Ser Val Ser Thr Ile Ile Leu Leu Gly Leu Ile Met Ala Tyr His
145                 150                 155                 160

Ala Leu Glu Val Gln Leu Phe Met Ile Asp Asn Cys Ala Asp Asp Trp
                165                 170                 175

Arg Ile Ala Met Thr Trp Gln Arg Ile Ala Thr Ile Thr Met Glu Leu
            180                 185                 190

Val Ile Cys Ala Ile His Pro Ile Pro Gly Glu Tyr Tyr Phe Glu Trp
            195                 200                 205

Lys Thr Lys Leu Ala Asn Lys His Gly Lys Leu Glu Thr Arg Trp Val
            210                 215                 220

Pro Tyr Asp Val Pro Leu Ser Leu Pro Met Phe Phe Arg Leu Tyr Leu
225                 230                 235                 240

Ile Cys Arg Val Met Leu Leu His Ser Lys Leu Phe Thr Asp Ala Ser
                245                 250                 255

Ser Arg Ser Ile Gly Ala Leu Asn Arg Ile Asn Phe Asn Thr Arg Phe
            260                 265                 270

Val Leu Lys Thr Leu Met Thr Ile Cys Pro Gly Thr Val Leu Leu Val
            275                 280                 285

Phe Met Val Ser Leu Trp Ile Ile Ala Ser Trp Thr Leu Arg Gln Cys
            290                 295                 300

Glu Arg Phe His Asp Glu Asp His Ala Asn Tyr Leu Asn Ser Met Trp
305                 310                 315                 320

Leu Ile Ala Ile Thr Leu Leu Ser Val Gly Tyr Gly Asp Ile Val Pro
                325                 330                 335

Asn Thr Tyr Cys Gly Arg Gly Ile Thr Leu Ser Cys Gly Ile Met Gly
            340                 345                 350

Ala Gly Cys Thr Ala Leu Leu Val Ala Val Ser Arg Lys Met Glu
            355                 360                 365

Leu Ser Arg Ala Glu Lys His Val His Asn Phe Met Met Asp Thr Gln
370                 375                 380

Leu Thr Lys Arg Leu Lys Asn Ala Ala Ala Asn Val Leu Arg Glu Thr
385                 390                 395                 400

Trp Leu Ile Tyr Lys His Thr Arg Leu Val Lys Arg Val Asn Ala Gly
                405                 410                 415

Arg Val Arg Thr His Gln Arg Lys Phe Leu Leu Ala Ile Tyr Ala Leu
            420                 425                 430

Arg Lys Val Lys Met Asp Gln Arg Lys Leu Met Asp Asn Ala Asn Thr
            435                 440                 445

Ile Thr Asp Met Ala Lys Asn Thr Val Tyr Glu Ile Val Ser Asp Met
450                 455                 460

Ser Asn Arg Tyr Asp Ala Phe Glu Glu Arg Leu Val Asn Leu Glu Asp
465                 470                 475                 480

Lys Leu Val Ala Leu Gln Glu Gln Leu Glu Leu Leu Pro Glu Ile Leu
                485                 490                 495

Thr Arg Cys Ile Ala Gln Asn Gln Asn Gln Asn Gln Thr Ser Asn
            500                 505                 510

Leu Ser Ser Thr Thr Glu Ser Arg Arg Asn Phe Leu His Pro Glu Ser
            515                 520                 525

Ala Ala Ala Val Ala Thr Gly Gly Leu Met Gln Pro Ser Val Ser Ser
```

|  | 530 |  |  | 535 |  |  | 540 |  |  |
|---|---|---|---|---|---|---|---|---|---|

Pro Ala Gly Ser Met Thr Gly Val Gly Gly Asn Pro Leu Met Phe Pro
545                     550                     555                     560

Ser Ser Ser Gly Ala Ala Ser Gly Gly Met Met Leu Ala Met Gly Asn
            565                     570                     575

Gly Ser Thr Val Met Ser His Ser Arg Ser Val Pro Pro Thr Gly Ala
        580                     585                     590

Gly Gly Ala Ser His Tyr His Trp Pro Thr Ser Pro Ile Leu Pro Pro
        595                     600                     605

Ile Ser Ser Arg Thr Pro His Leu Val Pro Glu Pro Ile Gln Pro Ser
    610                     615                     620

Ser
625

<210> SEQ ID NO 231
<211> LENGTH: 2166
<212> TYPE: DNA
<213> ORGANISM: Tribolium castaneum

<400> SEQUENCE: 231

| atgaatgccg aagtgaaagc tcaaaggact gcaaaaactc caattagtca caggattctg | 60 |
|---|---|
| acagctaacc gaagttccag taagaagatg agtagccaag acgagactgc tggcctgctg | 120 |
| gtagcgcaac cgtctctcac gagcacttct tctccggcaa actgctccaa accggtgctg | 180 |
| atgcgccaag aatgcacgac attcttggtg tcgtcgcacc atcctcagct ttcagtgttt | 240 |
| tctgacagcg aggaagacgg atctctttgc ttggaggaga cagcactcg ctcggtgccg | 300 |
| gacattgaac ttcactgcag gctggacgtg aaaggatgca agcagaactt gtcgtcgaac | 360 |
| atcccgacgc ggaacaggag ttcatcaaat gcatttcagc ttgcgccgta cacgtcgtcg | 420 |
| ccgcggggt tattggagag agaacgtcc cagactccgg cgtcgaccct gaaaatcgtg | 480 |
| cgctccgtgt caagagagag cgtgcggtcc attcaccatt gtacttgtcc gtgcctcaat | 540 |
| gcgccgctac gaaagcccgt ctcgactctc tccgtccccg gagcggtgaa gaactcgagc | 600 |
| agggactctg ccggcggaag gatgcagcag gaggagccgg gagtcgccct cgtgggacac | 660 |
| gtggactacc cccggtacat ggaggacagg actataggaa gcggcgtcta caagggcct | 720 |
| tcgtctggaa gtctcaagca caaacccaac gtgggctatc ggttaggccg cgcaaggcg | 780 |
| cttttttgaaa agaggagaag gattagtgat tacgctcttg ttatggggat gtttgggatt | 840 |
| attgttatgg ttatagaaaa tgaactctca agtgctggcg tttatcgcaa agacgatttt | 900 |
| tactcaattg cgctcaaaac tctgatatct gtttcgactg tgattctttt aggcctcatt | 960 |
| gtggcctatc atgctttaga agtgcagctt tttatgatag acaactgcgc ggacgattgg | 1020 |
| cggatcgcga tgacctggca gaggatctgc caaatcacca tggaactagt catatgtgca | 1080 |
| gtgcatccga ttcctggaca ctatcggttc gtgtggacga ctaaattatc caatcacaag | 1140 |
| gacggggga tcggatcaaa gtgtgtaccg tacgacgtgc ccttatcttt accgatgttc | 1200 |
| cttcggcttt acttaatctg cagagtgatg ttactgcata gtaagttgtt cacggacgca | 1260 |
| tcgtcgcgca gcataggagc tcttaatcga attaattta atacgcggtt tgtcttaaaa | 1320 |
| actctcatga ccatctgccc cgggacagtg ctcttagttt ttatggtttc cttgtggatt | 1380 |
| atcgccagtt ggacattgcg ccagtgcgaa aggttccacg atgaagaaca cgcaaacctg | 1440 |
| cttaatgcta tgtggctgat agcgatcact ttcctgagcg ttggcttcgg agatattgtt | 1500 |
| cctaacacgt actgtggaag gggcattgcg gtcagcacag gcatcatggg ggctggttgc | 1560 |

-continued

```
acggccttac tcgtggctgt ggtgtcgagg aagctggaat tgactcgagc ggaaaagcac    1620
gtgcataatt ttatgatgga cacccaacta acaaaacggc taaaaaacgc cgccgccaac    1680
gttttacgag aaacttggtt aatttacaaa cacacaaggc tagtgaaaag ggtgaaccct    1740
ggcagagttc ggactcatca aagaaaattt ttactcgcaa tttacgcgtt acgtaaagtt    1800
aaaatggacc aacgcaaatt aatggacaat gccaacacca taacggatat ggcgaagacg    1860
caaaacaccg tgtatgagat agtttccgat atgagcacga ggcaagacac cttggaagat    1920
cgcttgacga cgatggaaga taagatcgta gcacttcagg agcagctaga tttgctacct    1980
gatctcattg ctactagaat ccaagctcag gcggagaaaa tggagcaaag acgcaacttt    2040
ttgcatcctg aatccgcggc tggtcttcaa caggcgcgta gcgtgccccc tggatgccct    2100
tggcccggtc ctgctttagc tcctgctgga aagcaatctg ctgcctcttc aaacgcacag    2160
agttga                                                                2166
```

<210> SEQ ID NO 232
<211> LENGTH: 721
<212> TYPE: PRT
<213> ORGANISM: Tribolium castaneum

<400> SEQUENCE: 232

```
Met Asn Ala Glu Val Lys Ala Gln Arg Thr Ala Lys Thr Pro Ile Ser
1               5                   10                  15

His Arg Ile Leu Thr Ala Asn Arg Ser Ser Lys Lys Met Ser Ser
                20                  25                  30

Gln Asp Glu Thr Ala Gly Leu Leu Val Ala Gln Pro Ser Leu Thr Ser
            35                  40                  45

Thr Ser Ser Pro Ala Asn Cys Ser Lys Pro Val Leu Met Arg Gln Glu
        50                  55                  60

Cys Thr Thr Phe Leu Val Ser Ser His His Pro Gln Leu Ser Val Phe
65                  70                  75                  80

Ser Asp Ser Glu Glu Asp Gly Ser Leu Cys Leu Glu Glu Asn Ser Thr
                85                  90                  95

Arg Ser Val Pro Asp Ile Glu Leu His Cys Arg Leu Asp Val Lys Gly
            100                 105                 110

Cys Lys Gln Asn Leu Ser Ser Asn Ile Pro Thr Arg Asn Arg Ser Ser
        115                 120                 125

Ser Asn Ala Phe Gln Leu Ala Pro Tyr Thr Ser Ser Pro Arg Gly Leu
    130                 135                 140

Leu Glu Arg Arg Thr Ser Gln Thr Pro Ala Ser Thr Leu Lys Ile Val
145                 150                 155                 160

Arg Ser Val Ser Arg Glu Ser Val Arg Ser Ile His His Cys Thr Cys
                165                 170                 175

Pro Cys Leu Asn Ala Pro Leu Arg Lys Pro Val Ser Thr Leu Ser Val
            180                 185                 190

Pro Gly Ala Val Lys Asn Ser Ser Arg Asp Ser Ala Gly Gly Arg Met
        195                 200                 205

Gln Gln Glu Glu Pro Gly Val Ala Leu Val Gly His Val Asp Tyr Pro
    210                 215                 220

Arg Tyr Met Glu Asp Arg Thr Ile Gly Ser Gly Val Tyr Lys Gly Pro
225                 230                 235                 240

Ser Ser Gly Ser Leu Lys His Lys Pro Asn Val Gly Tyr Arg Leu Gly
                245                 250                 255
```

```
Arg Arg Lys Ala Leu Phe Glu Lys Arg Arg Ile Ser Asp Tyr Ala
            260                 265                 270
Leu Val Met Gly Met Phe Gly Ile Ile Val Met Val Ile Glu Asn Glu
        275                 280                 285
Leu Ser Ser Ala Gly Val Tyr Arg Lys Asp Asp Phe Tyr Ser Ile Ala
        290                 295                 300
Leu Lys Thr Leu Ile Ser Val Ser Thr Val Ile Leu Leu Gly Leu Ile
305                 310                 315                 320
Val Ala Tyr His Ala Leu Glu Val Gln Leu Phe Met Ile Asp Asn Cys
                325                 330                 335
Ala Asp Asp Trp Arg Ile Ala Met Thr Trp Gln Arg Ile Cys Gln Ile
                340                 345                 350
Thr Met Glu Leu Val Ile Cys Ala Val His Pro Ile Pro Gly His Tyr
        355                 360                 365
Arg Phe Val Trp Thr Thr Lys Leu Ser Asn His Lys Asp Gly Gly Ile
        370                 375                 380
Gly Ser Lys Cys Val Pro Tyr Asp Val Pro Leu Ser Leu Pro Met Phe
385                 390                 395                 400
Leu Arg Leu Tyr Leu Ile Cys Arg Val Met Leu Leu His Ser Lys Leu
                405                 410                 415
Phe Thr Asp Ala Ser Ser Arg Ser Ile Gly Ala Leu Asn Arg Ile Asn
                420                 425                 430
Phe Asn Thr Arg Phe Val Leu Lys Thr Leu Met Thr Ile Cys Pro Gly
                435                 440                 445
Thr Val Leu Leu Val Phe Met Val Ser Leu Trp Ile Ile Ala Ser Trp
450                 455                 460
Thr Leu Arg Gln Cys Glu Arg Phe His Asp Glu His Ala Asn Leu
465                 470                 475                 480
Leu Asn Ala Met Trp Leu Ile Ala Ile Thr Phe Leu Ser Val Gly Phe
                485                 490                 495
Gly Asp Ile Val Pro Asn Thr Tyr Cys Gly Arg Gly Ile Ala Val Ser
                500                 505                 510
Thr Gly Ile Met Gly Ala Gly Cys Thr Ala Leu Leu Val Ala Val Val
        515                 520                 525
Ser Arg Lys Leu Glu Leu Thr Arg Ala Glu Lys His Val His Asn Phe
530                 535                 540
Met Met Asp Thr Gln Leu Thr Lys Arg Leu Lys Asn Ala Ala Ala Asn
545                 550                 555                 560
Val Leu Arg Glu Thr Trp Leu Ile Tyr Lys His Thr Arg Leu Val Lys
                565                 570                 575
Arg Val Asn Pro Gly Arg Val Arg Thr His Gln Arg Lys Phe Leu Leu
                580                 585                 590
Ala Ile Tyr Ala Leu Arg Lys Val Lys Met Asp Gln Arg Lys Leu Met
                595                 600                 605
Asp Asn Ala Asn Thr Ile Thr Asp Met Ala Lys Thr Gln Asn Thr Val
            610                 615                 620
Tyr Glu Ile Val Ser Asp Met Ser Arg Gln Asp Thr Leu Glu Asp
625                 630                 635                 640
Arg Leu Thr Thr Met Glu Asp Lys Ile Val Ala Leu Gln Glu Gln Leu
                645                 650                 655
Asp Leu Leu Pro Asp Leu Ile Ala Thr Arg Ile Gln Ala Gln Ala Glu
                660                 665                 670
Lys Met Glu Gln Arg Arg Asn Phe Leu His Pro Glu Ser Ala Ala Gly
```

```
              675                 680                 685
Leu Gln Gln Ala Arg Ser Val Pro Pro Gly Cys Pro Trp Pro Gly Pro
        690                 695                 700

Ala Leu Ala Pro Ala Gly Lys Gln Ser Ala Ala Ser Ser Asn Ala Gln
705                 710                 715                 720

Ser
```

```
<210> SEQ ID NO 233
<211> LENGTH: 20
<212> TYPE: DNA
<213> ORGANISM: Artificial
<220> FEATURE:
<223> OTHER INFORMATION: forward primer DM

<400> SEQUENCE: 233
atgaaaacac cttccattgc                                              20

<210> SEQ ID NO 234
<211> LENGTH: 20
<212> TYPE: DNA
<213> ORGANISM: Artificial
<220> FEATURE:
<223> OTHER INFORMATION: reverse primer DM

<400> SEQUENCE: 234
tcagctgccg tatttgttgg                                              20

<210> SEQ ID NO 235
<211> LENGTH: 39
<212> TYPE: DNA
<213> ORGANISM: Artificial
<220> FEATURE:
<223> OTHER INFORMATION: forward primer MP

<400> SEQUENCE: 235
gccaccatgc ttctgtgtta tatcaaaagt acagagctg                         39

<210> SEQ ID NO 236
<211> LENGTH: 23
<212> TYPE: DNA
<213> ORGANISM: Artificial
<220> FEATURE:
<223> OTHER INFORMATION: reverse primer MP

<400> SEQUENCE: 236
tcagctggac ggctggatgg gct                                          23

<210> SEQ ID NO 237
<211> LENGTH: 40
<212> TYPE: DNA
<213> ORGANISM: Artificial
<220> FEATURE:
<223> OTHER INFORMATION: forward primer TC

<400> SEQUENCE: 237
atgaatgccg aagtgaaagc tcaaaggact gcaaaaactc                        40

<210> SEQ ID NO 238
<211> LENGTH: 40
<212> TYPE: DNA
<213> ORGANISM: Artificial
<220> FEATURE:
<223> OTHER INFORMATION: reverse primer TC

<400> SEQUENCE: 238
```
tcaactctgt gcgtttgaag aggcagcaga ttgctttcca        40

<210> SEQ ID NO 239
<211> LENGTH: 448
<212> TYPE: PRT
<213> ORGANISM: Artificial
<220> FEATURE:
<223> OTHER INFORMATION: consensus
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid
<220> FEATURE:

```
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (136)..(143)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (265)..(266)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (335)..(335)
<223> OTHER INFORMATION: Xaa can be any naturally occurring amino acid
<220> FEATURE:
<221> NAME/KEY: misc_feature
<222> LOCATION: (375)..(376)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (388)..(388)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
```

```
<220> FEATURE:
<221> NAME/KEY: misc_feature
<222> LOCATION: (392)..(393)
<223> OTHER INFORMATION: Xaa can be any naturally occurring amino acid
<220> FEATURE:
<221> NAME/KEY: misc_feature
<222> LOCATION: (395)..(395)
<223> OTHER INFORMATION: Xaa can be any naturally occurring amino acid
<220> FEATURE:
<221> NAME/KEY: misc_feature
<222> LOCATION: (398)..(400)
<223> OTHER INFORMATION: Xaa can be any naturally occurring amino acid
<220> FEATURE:
<221> NAME/KEY: misc_feature
<222> LOCATION: (404)..(407)
<223> OTHER INFORMATION: Xaa can be any naturally occurring amino acid
<220> FEATURE:
<221> NAME/KEY: misc_feature
<222> LOCATION: (410)..(413)
<223> OTHER INFORMATION: Xaa can be any naturally occurring amino acid
<220> FEATURE:
<221> NAME/KEY: misc_feature
<222> LOCATION: (416)..(439)
<223> OTHER INFORMATION: Xaa can be any naturally occurring amino acid
<220> FEATURE:
<221> NAME/KEY: misc_feature
<222> LOCATION: (441)..(441)
<223> OTHER INFORMATION: Xaa can be any naturally occurring amino acid

<400> SEQUENCE: 239

Lys His Lys Pro Asn Val Gly Tyr Arg Leu Gly Xaa Arg Lys Xaa Leu
1               5                   10                  15

Phe Glu Lys Arg Xaa Arg Ile Ser Asp Tyr Ala Leu Val Met Gly Met
            20                  25                  30

Phe Gly Ile Ile Xaa Met Val Ile Glu Asn Glu Leu Xaa Ser Ala Gly
        35                  40                  45

Val Tyr Xaa Lys Xaa Xaa Phe Tyr Ser Xaa Xaa Leu Lys Thr Leu Ile
    50                  55                  60

Ser Val Ser Thr Xaa Ile Leu Leu Gly Leu Ile Xaa Ala Tyr His Ala
65                  70                  75                  80

Leu Glu Val Gln Leu Phe Met Ile Asp Asn Cys Ala Asp Asp Trp Arg
                85                  90                  95

Ile Ala Met Thr Trp Gln Arg Ile Xaa Xaa Ile Xaa Xaa Glu Leu Xaa
            100                 105                 110

Ile Cys Ala Xaa His Pro Ile Pro Gly Xaa Tyr Xaa Phe Xaa Trp Xaa
        115                 120                 125

Thr Lys Leu Xaa Asn Xaa Lys Xaa Xaa Xaa Xaa Xaa Xaa Xaa Xaa Val
    130                 135                 140

Pro Tyr Asp Val Xaa Leu Ser Leu Pro Met Phe Xaa Arg Leu Tyr Leu
145                 150                 155                 160

Ile Cys Arg Val Met Leu Leu His Ser Lys Leu Phe Thr Asp Ala Ser
                165                 170                 175

Ser Arg Ser Ile Gly Ala Leu Asn Arg Ile Asn Phe Asn Thr Arg Phe
            180                 185                 190

Val Leu Lys Thr Leu Met Thr Ile Cys Pro Gly Thr Val Leu Leu Val
        195                 200                 205

Phe Met Val Ser Leu Trp Ile Ile Ala Ser Trp Thr Leu Arg Gln Cys
    210                 215                 220

Glu Arg Phe His Asp Glu Xaa His Ala Asn Xaa Leu Asn Xaa Met Trp
225                 230                 235                 240

Leu Ile Ala Ile Thr Xaa Leu Ser Val Gly Xaa Gly Asp Ile Val Pro
                245                 250                 255
```

-continued

```
Asn Thr Tyr Cys Gly Arg Gly Ile Xaa Xaa Ser Xaa Gly Ile Met Gly
            260                 265                 270

Ala Gly Cys Thr Ala Leu Leu Val Ala Val Ser Arg Lys Xaa Glu
        275                 280                 285

Leu Xaa Arg Ala Glu Lys His Val His Asn Phe Met Met Asp Thr Gln
    290                 295                 300

Leu Thr Lys Arg Leu Lys Asn Ala Ala Ala Asn Val Leu Arg Glu Thr
305                 310                 315                 320

Trp Leu Ile Tyr Lys His Thr Arg Leu Val Lys Arg Val Asn Xaa Gly
                325                 330                 335

Arg Val Arg Thr His Gln Arg Lys Phe Leu Leu Ala Ile Tyr Ala Leu
            340                 345                 350

Arg Lys Val Lys Met Asp Gln Arg Lys Leu Met Asp Asn Ala Asn Thr
        355                 360                 365

Ile Thr Asp Met Ala Lys Xaa Xaa Asn Thr Val Tyr Glu Ile Xaa Ser
    370                 375                 380

Asp Met Ser Xaa Arg Xaa Asp Xaa Xaa Glu Xaa Arg Leu Xaa Xaa Xaa
385                 390                 395                 400

Glu Asp Lys Xaa Xaa Xaa Xaa Gln Glu Xaa Xaa Xaa Xaa Leu Pro Xaa
            405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Glu Xaa Arg Arg Asn Phe Leu His Pro
    435                 440                 445

<210> SEQ ID NO 240
<211> LENGTH: 11
<212> TYPE: PRT
<213> ORGANISM: Artificial
<220> FEATURE:
<223> OTHER INFORMATION: motif

<400> SEQUENCE: 240

Lys His Lys Pro Asn Val Gly Tyr Arg Leu Gly
1               5                   10

<210> SEQ ID NO 241
<211> LENGTH: 15
<212> TYPE: PRT
<213> ORGANISM: Artificial
<220> FEATURE:
<223> OTHER INFORMATION: motif

<400> SEQUENCE: 241

Arg Ile Ser Asp Tyr Ala Leu Val Met Gly Met Phe Gly Ile Ile
1               5                   10                  15

<210> SEQ ID NO 242
<211> LENGTH: 9
<212> TYPE: PRT
<213> ORGANISM: Artificial
<220> FEATURE:
<223> OTHER INFORMATION: motif

<400> SEQUENCE: 242

Leu Lys Thr Leu Ile Ser Val Ser Thr
1               5

<210> SEQ ID NO 243
<211> LENGTH: 6
<212> TYPE: PRT
```

```
<213> ORGANISM: Artificial
<220> FEATURE:
<223> OTHER INFORMATION: motif

<400> SEQUENCE: 243

Ile Leu Leu Gly Leu Ile
1               5

<210> SEQ ID NO 244
<211> LENGTH: 28
<212> TYPE: PRT
<213> ORGANISM: Artificial
<220> FEATURE:
<223> OTHER INFORMATION: motif

<400> SEQUENCE: 244

Ala Tyr His Ala Leu Glu Val Gln Leu Phe Met Ile Asp Asn Cys Ala
1               5                   10                  15

Asp Asp Trp Arg Ile Ala Met Thr Trp Gln Arg Ile
            20                  25

<210> SEQ ID NO 245
<211> LENGTH: 6
<212> TYPE: PRT
<213> ORGANISM: Artificial
<220> FEATURE:
<223> OTHER INFORMATION: motif

<400> SEQUENCE: 245

Leu Ser Leu Pro Met Phe
1               5

<210> SEQ ID NO 246
<211> LENGTH: 74
<212> TYPE: PRT
<213> ORGANISM: Artificial
<220> FEATURE:
<223> OTHER INFORMATION: motif

<400> SEQUENCE: 246

Arg Leu Tyr Leu Ile Cys Arg Val Met Leu Leu His Ser Lys Leu Phe
1               5                   10                  15

Thr Asp Ala Ser Ser Arg Ser Ile Gly Ala Leu Asn Arg Ile Asn Phe
            20                  25                  30

Asn Thr Arg Phe Val Leu Lys Thr Leu Met Thr Ile Cys Pro Gly Thr
        35                  40                  45

Val Leu Leu Val Phe Met Val Ser Leu Trp Ile Ala Ser Trp Thr
    50                  55                  60

Leu Arg Gln Cys Glu Arg Phe His Asp Glu
65                  70

<210> SEQ ID NO 247
<211> LENGTH: 7
<212> TYPE: PRT
<213> ORGANISM: Artificial
<220> FEATURE:
<223> OTHER INFORMATION: motif

<400> SEQUENCE: 247

Met Trp Leu Ile Ala Ile Thr
1               5

<210> SEQ ID NO 248
<211> LENGTH: 13
```

```
<212> TYPE: PRT
<213> ORGANISM: Artificial
<220> FEATURE:
<223> OTHER INFORMATION: motif

<400> SEQUENCE: 248

Gly Asp Ile Val Pro Asn Thr Tyr Cys Gly Arg Gly Ile
1               5                   10

<210> SEQ ID NO 249
<211> LENGTH: 18
<212> TYPE: PRT
<213> ORGANISM: Artificial
<220> FEATURE:
<223> OTHER INFORMATION: motif

<400> SEQUENCE: 249

Gly Ile Met Gly Ala Gly Cys Thr Ala Leu Leu Val Ala Val Val Ser
1               5                   10                  15

Arg Lys

<210> SEQ ID NO 250
<211> LENGTH: 44
<212> TYPE: PRT
<213> ORGANISM: Artificial
<220> FEATURE:
<223> OTHER INFORMATION: motif

<400> SEQUENCE: 250

Arg Ala Glu Lys His Val His Asn Phe Met Met Asp Thr Gln Leu Thr
1               5                   10                  15

Lys Arg Leu Lys Asn Ala Ala Ala Asn Val Leu Arg Glu Thr Trp Leu
                20                  25                  30

Ile Tyr Lys His Thr Arg Leu Val Lys Arg Val Asn
            35                  40

<210> SEQ ID NO 251
<211> LENGTH: 39
<212> TYPE: PRT
<213> ORGANISM: Artificial
<220> FEATURE:
<223> OTHER INFORMATION: motif

<400> SEQUENCE: 251

Gly Arg Val Arg Thr His Gln Arg Lys Phe Leu Leu Ala Ile Tyr Ala
1               5                   10                  15

Leu Arg Lys Val Lys Met Asp Gln Arg Lys Leu Met Asp Asn Ala Asn
                20                  25                  30

Thr Ile Thr Asp Met Ala Lys
            35

<210> SEQ ID NO 252
<211> LENGTH: 6
<212> TYPE: PRT
<213> ORGANISM: Artificial
<220> FEATURE:
<223> OTHER INFORMATION: motif

<400> SEQUENCE: 252

Asn Thr Val Tyr Glu Ile
1               5

<210> SEQ ID NO 253
<211> LENGTH: 7
```

```
<212> TYPE: PRT
<213> ORGANISM: Artificial
<220> FEATURE:
<223> OTHER INFORMATION: motif

<400> SEQUENCE: 253

Arg Arg Asn Phe Leu His Pro
1               5
```